(12) United States Patent
Shi et al.

(10) Patent No.: US 11,319,315 B2
(45) Date of Patent: *May 3, 2022

(54) CYCLOHEXYL ACID TRIAZOLE AZOLES AS LPA ANTAGONISTS

(71) Applicant: BRISTOL-MYERS SQUIBB COMPANY, Princeton, NJ (US)

(72) Inventors: Yan Shi, Flourtown, PA (US); Peter Tai Wah Cheng, Princeton, NJ (US); Ying Wang, Belle Mead, NJ (US); Jun Li, Pittsburgh, PA (US); Tianan Fang, Newtown, PA (US); James R. Corte, Yardley, PA (US); Jun Shi, Pennington, NJ (US); Hao Zhang, Belle Mead, NJ (US); Lawrence J. Kennedy, Titusville, NJ (US); Shiwei Tao, Hillsborough, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/772,842

(22) PCT Filed: Dec. 18, 2018

(86) PCT No.: PCT/US2018/066123
§ 371 (c)(1),
(2) Date: Jun. 15, 2020

(87) PCT Pub. No.: WO2019/126094
PCT Pub. Date: Jun. 27, 2019

(65) Prior Publication Data
US 2021/0163470 A1    Jun. 3, 2021

Related U.S. Application Data

(60) Provisional application No. 62/607,488, filed on Dec. 19, 2017.

(51) Int. Cl.
C07D 401/14 (2006.01)
C07D 403/14 (2006.01)
C07D 417/14 (2006.01)
C07D 413/14 (2006.01)

(52) U.S. Cl.
CPC ......... *C07D 417/14* (2013.01); *C07D 401/14* (2013.01); *C07D 403/14* (2013.01); *C07D 413/14* (2013.01)

(58) Field of Classification Search
CPC ............................ C07D 401/14; C07D 403/14
See application file for complete search history.

(56) References Cited

U.S. PATENT DOCUMENTS

| | | | |
|---|---|---|---|
| 10,071,078 B2 | 9/2018 | Cheng et al. | |
| 10,576,062 B2 | 5/2020 | Cheng et al. | |
| 10,662,172 B2 | 5/2020 | Shi et al. | |
| 2014/0031353 A1 | 1/2014 | An et al. | |
| 2014/0329871 A1 | 11/2014 | Mishira et al. | |
| 2017/0360759 A1 | 12/2017 | Cheng et al. | |
| 2020/0138789 A1 | 5/2020 | Cheng et al. | |
| 2020/0148665 A1 | 5/2020 | Shi et al. | |

FOREIGN PATENT DOCUMENTS

| | | |
|---|---|---|
| WO | WO2002062389 A1 | 8/2002 |
| WO | WO2011017350 A2 | 2/2011 |
| WO | WO2011041461 A2 | 4/2011 |
| WO | WO2011041694 A2 | 4/2011 |
| WO | WO2012078593 A2 | 6/2012 |
| WO | WO2012138648 A1 | 10/2012 |
| WO | WO2013070879 A1 | 5/2013 |
| WO | WO2013189864 A1 | 12/2013 |
| WO | WO2013189865 A1 | 12/2013 |
| WO | WO2017/223016 A1 | 12/2017 |

OTHER PUBLICATIONS

U.S. Appl. No. 16/772,825, filed Jun. 15, 2020, Shi et al.
U.S. Appl. No. 16/954,221, filed Jun. 16, 2020, Cheng et al.
U.S. Appl. No. 16/954,310, filed Jun. 16, 2020, Shi et al.
U.S. Appl. No. 16/954,320, filed Jun. 16, 2020, Shi et al.
U.S. Appl. No. 16/954,325, filed Jun. 16, 2020, Shi et al.
U.S. Appl. No. 16/954,546, filed Jun. 17, 2020, Cheng et al.
U.S. Appl. No. 16/954,550, filed Jun. 17, 2020, Cheng et al.
U.S. Appl. No. 16/954,552, filed Jun. 17, 2020, Shi et al.
U.S. Appl. No. 16/954,556, filed Jun. 17, 2020, Cheng et al.

(Continued)

*Primary Examiner* — Samira J Jean-Louis

(74) *Attorney, Agent, or Firm* — Jing G. Sun

(57) ABSTRACT

The present invention provides compounds of Formula (I): Formula (I) or a stereoisomer, tautomer, or pharmaceutically acceptable salt or solvate thereof, wherein all the variables are as defined herein. These compounds are selective LPA receptor inhibitors.

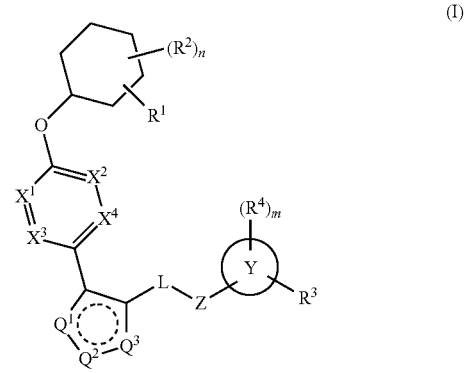

30 Claims, No Drawings

(56) References Cited

OTHER PUBLICATIONS

Amishima, et al., "Expression of Epidermal Growth Factor and Epidermal Growth Factor Receptor Immunoreactivity in the Asthmatic Human Airway", Am. J. Respir. Critical Care Medicine, vol. 157, pp. 1907-1912 (1998).
Boucharaba, et al., "Platelet-derived lysophosphatidic acid supports the progression of osteolytic bone metastases in breast cancer", J. Clin. Invest., vol. 114(12), pp. 1714-1725 (2004).
Boucharaba, et al., "The type 1 lysophosphatidic acid receptor is a target for therapy in bone metastases", PNAS, vol. 103(25), pp. 9643-9648 (2006).
Chen, et al., "Specific receptor subtype mediation of LPA-induced dual effects incardiac fibroblasts", FEBS Letters, vol. 580(19), pp. 4737-4745 (2006).
Choi, et al., "Biological roles of lysophospholipid receptors revealed by genetic null mice: An update", Biochemica et Biophysica Acta, vol. 1781, pp. 531-539 (2008).
Contos, et al., "Lysophosphatidic Acid Receptors", Mol. Pharmacology, vol. 58(6), pp. 1188-1196 (2000).
Ediger, et al., "Transcription factor activation and mitogenic synergism in airway smooth muscle cells", Eur Respir Journal, vol. 21, pp. 759-769 (2003).
Gardell, et al., "Emerging medicinal roles for lysophospholipid signaling", Trends in Molecular Medicine, vol. 12(2), pp. 65-75 (2006).
Geoetzl, et al., "Lysophosphatidic Acid and Sphingosine 1-PhosphateProtection of T Cells from Apoptosis in Association with Suppression of Bax1", Journal of Immunology, vol. 162, pp. 2049-2056 (1999).
Guo, et al., "Mitogenic Signaling in Androgen Sensitive and Insensitive Prostate Cancer Cell Lines", Journal of Urology, vol. 163(3), pp. 1027-1032 (2000).
Hashimoto, et al., "Lysophosphatidic Acid (LPA) Induces Plasma Exudation and Histamine Release in Mice via LPA Receptors", J Pharmacol Science, vol. 100, pp. 82-87 (2006).
Holtsberg, et al., "Lysophosphatidic Acid Induces Necrosis and Apoptosis in Hippocampal Neurons", J. Neurochemistry, vol. 70, pp. 66-76 (1998).
Imamura, "Induction of In Vitro Tumor cell invasion of cellular monolayers by lysophosphatidic acid or phospholupase D", Biochem Biophys Res Commun., vol. 193(2), pp. 497-503 (1993).
Inoue, et al., "Initiation of neuropathic pain require lysophosphatidic acid receptor signaling" Nature Medicine, vol. 10, pp. 712-718 (2004).
Inoue, et al., "Lysophosphatidic acid and mesangial cells: implications for renal diseases", Clinical Science, vol. 96(4), pp. 431-436 (1999).
Ishii, et al., "Lysophospholipid Receptors:Signaling and Biology", Annu Rev Biochemistry, vol. 73, pp. 321-354 (2004).
Kantarci, et al., "Epithelial and connective tissue cell CTGF/CCN2 expression in gingival fibrosis", J Pathol., vol. 210, pp. 59-66 (2006).
Koh, et al., "Lysophosphatidic Acid Is a Major Serum Noncytokine Survival Factor for Murine Macrophages Which Acts via the Phosphatidylinositol 3-Kinase Signaling Pathway", J Clin Invest., vol. 102, pp. 716-727 (1998).
Kropp, et al., "Characterization of Cultured Bladder Smooth Muscle Cells: Assessment of In Vitro Contractility", Journal of Urology, vol. 162(5), pp. 1779-1784 (1999).
Kuroda, et al., "Phospholipid Concentration in Lung Lavage Fluid as Biomarker for Pulmonary Fibrosis", Inhalation Toxicology, vol. 18(5), pp. 389-393 (2006).
Lin, et al., "Lysophosphatidic acid regulates inflammation-related genes in human endothelial cells through LPA1 and LPA3", Biochem Biophys Res Communication, vol. 363(4), pp. 1001-1008, (2007).
Maguire, et al., "Regulation of vascular reactivity by established and emerging GPCRs", Trends in Pharmacological Sciences, vol. 26(9), pp. 448-454 (2005).
Mills, et al., "The Emerging Role of Lysophosphatidic Acid in Cancer", Nat Rev Cancer, vol. 3, pp. 582-591 (2003).
Moolenaar, "Lysophosphatidic acid signalling", Curr. Opin. Cell Biology, vol. 7, pp. 203-210 (1995).
Mototani, et al., "A functional SNP in EDG2 increases susceptibility to knee osteoarthritis in Japanese", Hum. Mol. Genetics, vol. 17(12), pp. 1790-1797 (2008).
Munger, et al., "The Integrin avb6 Binds and Activates Latent TGFb1:A Mechanism for Regulating Pulmonary Inflammation and Fibrosis", Cell, vol. 96, pp. 319-328 (1999).
Murph, et al., "Sharpening the edges of understanding the structure/function of the LPA1 receptor: Expression in cancer and mechanisms of regulation", Biochimica et Biophysica Acta, vol. 1781, pp. 547-557 (2008).
Nakagawa, et al. "Molecular Liver Cancer Prevention in Cirrhosis by Organ Transcriptome Analysis and Lysophosphatidic Acid Pathway Inhibition" Cancer Cell, vol. 30, pp. 879-890 (2016).
Osborne, et al., "Lipid Receptors in Cardiovascular Development", Annual Rev. Physiol., vol. 65, pp. 23-43 (2003).
Palmer, et al. "Randomized, Double-Blind, Placebo Controlled, Phase 2 Trial of BMS-986020, a Lysophosphatidic Acid Receptor Antagonist for the Treatment of Idiopathic Pulmonary Fibrosis" Chest, vol. 154, pp. 1061-1069 (2018).
Pradere, et al. "LPA1 Receptor Activation Promotes Renal Interstitial Fibrosis", J Am Soc Nephrol, vol. 18, pp. 3110-3118 (2007).
Pradere, et al., "Lysophosphatidic acid and renal fibrosis", Biochimica et Biophysica Acta, vol. 1781, pp. 582-587 (2008).
Rother, et al., "Subtype-Selective Antagonists of Lysophosphatidic Acid Receptors Inhibit Platelet Activation Triggered by the LipidCore of Atherosclerotic Plaques", Circulation, vol. 108, pp. 741-747 (2003).
Saunders, et al., "Identification of small-molecule inhibitors of autotaxin that inhibit melanoma cell migration and invasion", Mol Cancer Ther., vol. 7(10), pp. 3352-3362 (2008).
Siess, "Athero- and thrombogenic actions of lysophosphatidic acid and sphingosine-1-phosphate", Biochimica et Biophysica Acta, vol. 1582, pp. 204-215 (2002).
Simon, et al., "Lysophosphatidic Acid 1 Receptor-dependent Down-regulation of Peroxisome Proliferator-activated Receptor γ" J. Biol. Chemistry, vol. 280(15) pp. 14656-14662 (2005).
Smalheiser, "Acute Neurite Retraction Elicited by Diverse Agents Is Prevented by Genistein, a Tyrosine Kinase Inhibitor", J. Neurochemistry, vol. 61(1), pp. 340-343 (1993).
Sutphen, et al., "Lysophospholipids Are Potential Biomarkers of Ovarian Cancer", Cancer Epidemiol. Biomarkers Prev. 13, pp. 1185-1191 (2004).
Tager, et al., The lysophosphatidic acid receptor LPA1 links pulmonary fibrosis to lung injury by mediating fibroblast recruitment and vascular leak, Nature Medicine, vol. 14, pp. 45-54 (2008).
Watanabe, et al., "Both Plasma Lysophosphatidic Acid and Serum Autotaxin Levels are Increased in Chronic Hepatitis C", J Clinical Gastroenterology, vol. 41, pp. 616-623 (2007).
Watanabe, et al., "Plasma lysophosphatidic acid level and serum autotaxin activity are increased in liver injury in rats in relation to its severity", Life Science, vol. 81, pp. 1009-1015 (2007).
Wiedmaier, et al., "Bacteria induce CTGF and CYR61 expression in epithelial cells in a lysophosphatidic acid receptor-dependent manner", Int J Med Microbiology, vol. 298(3-4), pp. 231-243 (2008).
Xu, et al.,"Lysophosphatidic Acid Induces αvβ6 Integrin-Mediated TGF-β Activation via the LPA2 Receptor and the Small G Protein Gαq", Am J Pathology, vol. 174(4), pp. 1264-1279 (2009).
Yamada, et al., "Lysophosphatidic Acid (LPA) in Malignant Ascites Stimulates Motility of Human Pancreatic Cancer Cells through LPA1", J Biol Chemistry, vol. 279, pp. 6596-6605 (2004).
Yamada, et al., "Lysophosphatidic acid stimulates the proliferation and motility of malignant pleural mesothelioma cells through lysophosphatidic acid receptors, LPA1 and LPA2", Cancer Science, vol. 99(8), pp. 1603-1610 (2008).
Yasuda, et al., "Phospholipid Analysis of Alveolar Macrophages and Bronchoalveolar Lavage Fluid Following Bleomycin Administration to Rabbits", Lung, vol. 172, pp. 91-102 (1994).
Zhao, et al., "Regulation of Lysophosphatidic Acid Receptor Expression and Function in Human Synoviocytes: Implications for Rheumatoid Arthritis" Mol. Pharmacology, vol. 73(2), pp. 587-600 (2008).

CYCLOHEXYL ACID TRIAZOLE AZOLES AS LPA ANTAGONISTS

CROSS-REFERENCE TO RELATED APPLICATIONS

This application is a 371 of International Application No. PCT/US2018/066123 filed on Dec. 18, 2018, which claims the priority benefit of U.S. Provisional Application 62/607,488, filed Dec. 19, 2017; each of which is incorporated herein by reference in its entirety.

FIELD OF THE INVENTION

The present invention relates to novel substituted triazole compounds, compositions containing them, and methods of using them, for example, for the treatment of disorders associated with one or more of the lysophosphatidic acid (LPA) receptors.

BACKGROUND OF THE INVENTION

Lysophospholipids are membrane-derived bioactive lipid mediators, of which one of the most medically important is lysophosphatidic acid (LPA). LPA is not a single molecular entity but a collection of endogenous structural variants with fatty acids of varied lengths and degrees of saturation (Fujiwara et al., *J Biol. Chem.*, 2005, 280, 35038-35050). The structural backbone of the LPAs is derived from glycerol-based phospholipids such as phosphatidylcholine (PC) or phosphatidic acid (PA).

The LPAs are bioactive lipids (signaling lipids) that regulate various cellular signaling pathways by binding to the same class of 7-transmembrane domain G protein-coupled (GPCR) receptors (Chun, J., Hla, T., Spiegel, S., Moolenaar, W., Editors, *Lysophospholipid Receptors: Signaling and Biochemistry*, 2013, Wiley; ISBN: 978-0-470-56905-4 & Zhao, Y. et al, *Biochim. Biophys. Acta (BBA)-Mol. Cell Biol. Of Lipids*, 2013, 1831, 86-92). The currently known LPA receptors are designated as $LPA_1$, $LPA_2$, $LPA_3$, $LPA_4$, $LPA_5$ and $LPA_6$ (Choi, J. W., *Annu. Rev. Pharmacol. Toxicol.*, 2010, 50, 157-186; Kihara, Y., et al, *Br. J. Pharmacol.*, 2014, 171, 3575-3594).

The LPAs have long been known as precursors of phospholipid biosynthesis in both eukaryotic and prokaryotic cells, but the LPAs have emerged only recently as signaling molecules that are rapidly produced and released by activated cells, notably platelets, to influence target cells by acting on specific cell-surface receptors (see, e.g., Moolenaar et al., *BioEssays*, 2004, 26, 870-881, and van Leewen et al., *Biochem. Soc. Trans.*, 2003, 31, 1209-1212). Besides being synthesized and processed to more complex phospholipids in the endoplasmic reticulum, LPAs can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotaxin (lysoPLD/NPP2), may be the product of an oncogene, as many tumor types up-regulate autotaxin (Brindley, D., *J. Cell Biochem.* 2004, 92, 900-12). The concentrations of LPAs in human plasma & serum as well as human bronchoalveolar lavage fluid (BALF) have been reported, including determinations made using sensitive and specific LC/MS & LC/MS/MS procedures (Baker et al. *Anal. Biochem.*, 2001, 292, 287-295; Onorato et al., *J. Lipid Res.*, 2014, 55, 1784-1796).

LPA influences a wide range of biological responses, ranging from induction of cell proliferation, stimulation of cell migration and neurite retraction, gap junction closure, and even slime mold chemotaxis (Goetzl, et al., *Scientific World J.*, 2002, 2, 324-338; Chun, J., Hla, T., Spiegel, S., Moolenaar, W., Editors, *Lysophospholipid Receptors: Signaling and Biochemistry*, 2013, Wiley; ISBN: 978-0-470-56905-4). The body of knowledge about the biology of LPA continues to grow as more and more cellular systems are tested for LPA responsiveness. For instance, it is now known that, in addition to stimulating cell growth and proliferation, LPAs promote cellular tension and cell-surface fibronectin binding, which are important events in wound repair and regeneration (Moolenaar et al., *BioEssays*, 2004, 26, 870-881). Recently, anti-apoptotic activity has also been ascribed to LPA, and it has recently been reported that PPARγ is a receptor/target for LPA (Simon et al., *J. Biol. Chem.*, 2005, 280, 14656-14662).

Fibrosis is the result of an uncontrolled tissue healing process leading to excessive accumulation and insufficient resorption of extracellular matrix (ECM) which ultimately results in end-organ failure (Rockey, D. C., et al., *New Engl. J. Med.*, 2015, 372, 1138-1149). The $LPA_1$ receptor has been reported to be over-expressed in idiopathic pulmonary fibrosis (IPF) patients. $LPA_1$ receptor knockout mice were protected from bleomycin-induced lung fibrosis (Tager et al., *Nature Med.*, 2008, 14, 45-54). The $LPA_1$ antagonist BMS-986020 was shown to significantly reduce the rate of FVC (forced vital capacity) decline in a 26-week clinical trial in IPF patients (Palmer et al., *Chest*, 2018, 154, 1061-1069). LPA pathway inhibitors (e.g. an $LPA_1$ antagonist) were shown to be chemopreventive anti-fibrotic agents in the treatment of hepatocellular carcinoma in a rat model (Nakagawa et al., *Cancer Cell*, 2016, 30, 879-890).

Thus, antagonizing the $LPA_1$ receptor may be useful for the treatment of fibrosis such as pulmonary fibrosis, hepatic fibrosis, renal fibrosis, arterial fibrosis and systemic sclerosis, and thus the diseases that result from fibrosis (pulmonary fibrosis-Idiopathic Pulmonary Fibrosis [IPF], hepatic fibrosis-Non-alcoholic Steatohepatitis [NASH], renal fibrosis-diabetic nephropathy, systemic sclerosis-scleroderma, etc.).

SUMMARY OF THE INVENTION

The present invention provides novel substituted triazole compounds including stereoisomers, tautomers, and pharmaceutically acceptable salts or solvates thereof, which are useful as antagonists against one or more of the lysophosphatidic acid (LPA) receptors, especially the LPA1 receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts or solvates thereof.

The compounds of the invention may be used in the treatment of conditions in which LPA plays a role.

The compounds of the present invention may be used in therapy.

The compounds of the present invention may be used for the manufacture of a medicament for the treatment of a condition in which inhibition of the physiological activity of LPA is useful, such as diseases in which an LPA receptor participates, is involved in the etiology or pathology of the disease, or is otherwise associated with at least one symptom of the disease.

In another aspect, the present invention is directed to a method of treating fibrosis of organs (liver, kidney, lung, heart and the like as well as skin), liver diseases (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease [cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like], inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like).

In another aspect, the present invention is directed to a method of treating diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology.

In another aspect, the present invention is directed to a method of treating renal fibrosis, pulmonary fibrosis, hepatic fibrosis, arterial fibrosis and systemic sclerosis comprising administering to a patient in need of such treatment a compound of the present invention as described above.

In one aspect, the present invention provides methods, compounds, pharmaceutical compositions, and medicaments described herein that comprise antagonists of LPA receptors, especially antagonists of LPA1.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

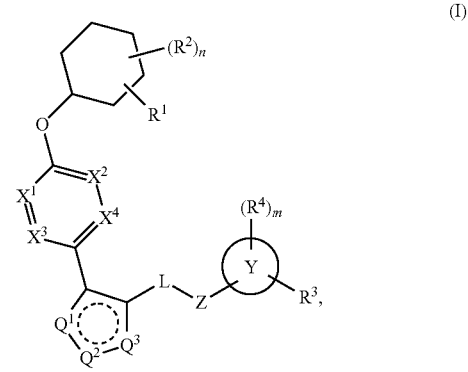

or a stereoisomer, tautomer, or pharmaceutically acceptable salt or solvate thereof, wherein $X^1$, $X^2$, $X^3$, and $X^4$ are each independently $CR^5$ or N; provided that no more than two of $X^1$, $X^2$, $X^3$, or $X^4$ are N;

one of $Q^1$, $Q^2$, and $Q^3$ is $NR^6$, and the other two are N; and the dashed circle denotes optional bonds forming an aromatic ring;

L is a covalent bond or $C_{1-4}$ alkylene substituted with 0 to 4 $R^7$;

Z is $CHR^{8a}$, $NR^{8b}$ or O;

the Y ring is an azole moiety or 5-membered heterocyclyl which contains one nitrogen atom (as part of the ring) and at least one other heteroatom (as part of the ring) selected from nitrogen, oxygen, and sulfur; and the term "azole" refers to a 5-membered heteroaryl containing one nitrogen atom (as part of the ring) and at least one other heteroatom (as part of the ring) selected from nitrogen, oxygen, and sulfur;

$R^1$ is $(-CH_2)_aR^9$;

a is an integer of 0 or 1;

$R^2$ is each independently halo, cyano, hydroxyl, amino, $C_{1-6}$ alkyl, $C_{3-6}$ cycloalkyl, 4- to 6-membered heterocyclyl, alkylamino, haloalkyl, hydroxyalkyl, aminoalkyl, alkoxy, alkoxyalkyl, haloalkoxyalkyl, or haloalkoxy;

n is an integer of 0, 1, or 2;

$R^3$ is halo, cyano, hydroxyl, amino, oxo, $-OR^a$, $-SR^a$, =S, $-NR^cR^c$, =NH, =N-OH, $-NR^a$, =N-$OR^a$, $-NO_2$, $-S(O)_2R^a$, $-S(O)_2NHR^b$, $-S(O)_2NR^cR^c$, $-S(O)_2OR^b$, $-OS(O)_2R^b$, $-OS(O)_2OR^b$, $-P(O)(OR^b)(OR^b)$, $-C(O)R^b$, $-C(NR^b)R^b$, $-C(O)OR^b$, $-C(O)NR^cR^c$, $-C(NR^b)NR^cR^c$, $-OC(O)R^b$, $-NR^bC(O)R^b$, $-OC(O)OR^b$, $-NR^bC(O)OR^b$, $-OC(O)NR^cR^c$, $-NR^bC(O)NR^cR^c$, $-NR^bC(NR^b)R^b$, $-NR^bC(NR^b)NR^cR^c$, $C_{1-6}$ alkyl, $C_{1-6}$ deuterated alkyl (fully or partially deuterated), $C_{2-6}$ alkenyl, $C_{1-6}$ haloalkyl, $C_{1-6}$ heteroalkyl, 6- to 10-membered aryl, arylalkyl, 5- to 10-membered heteroaryl, heteroarylalkyl, 3- to 8-membered carbocyclyl substituted with 0 to 1=$CH_2$, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^a$ is selected from $C_{1-6}$ alkyl, $C_{1-6}$ deuterated alkyl (fully or partially deuterated), haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, =S, —$NR^cR^c$, =NH, =N—OH, —$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$NR^bC(O)NR^cR^c$, —$NR^bC(NR^b)R^b$, and —$NR^bC(NR^b)NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety;

$R^4$ is each independently halo, hydroxyl, amino, cyano, —$C(O)NH_2$, —$C(O)NR^{12a}R^{12b}$, $C(O)OR^{12a}$, $C_{1-4}$ alkyl, $C_{1-4}$ haloalkyl, $C_{2-6}$ alkoxyalkyl, $C_{1-4}$ alkoxy, oxo (=O), or imino (=NH); or alternatively $R^3$ and $R^4$, taken together with the atoms to which they are attached, form a cyclic moiety (carbocyclyl or heterocyclyl);

m is an integer of 0, 1, or 2;

$R^5$ is hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^6$ is hydrogen, $C_{1-6}$ alkyl, alkylamino, haloalkyl, hydroxyalkyl, aminoalkyl, alkoxyalkyl, haloalkoxyalkyl, alkoxy, or haloalkoxy;

$R^7$ is halo, oxo, cyano, hydroxyl, amino, $C_{1-6}$ alkyl, $C_{3-6}$ cycloalkyl, 4- to 6-membered heterocyclyl, alkylamino, haloalkyl, hydroxyalkyl, aminoalkyl, alkoxyalkyl, haloalkoxyalkyl, alkoxy, or haloalkoxy;

$R^{8a}$ is hydrogen, halo, cyano, or $C_{1-4}$ alkyl;

$R^{8b}$ is hydrogen or $C_{1-4}$ alkyl;

$R^9$ is selected from —CN, —$C(O)OR^{10}$, —$C(O)NR^{11a}R^{11b}$,

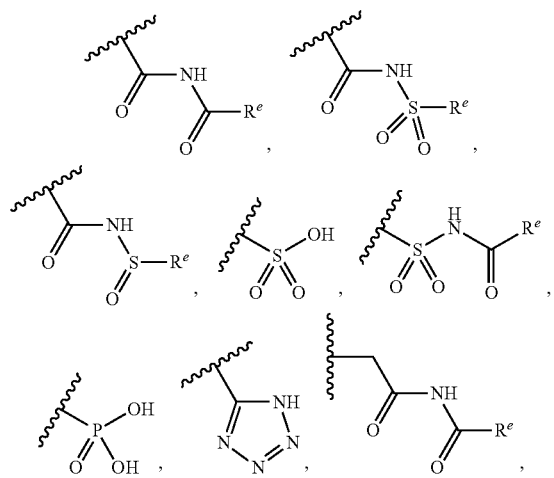

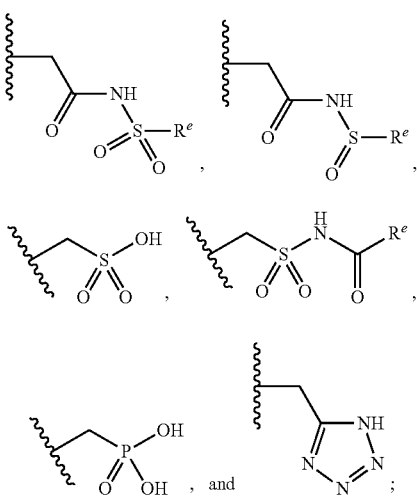

$R^e$ is $C_{1-6}$ alkyl, haloalkyl, hydroxyalkyl, aminoalkyl, alkoxyalkyl, or haloalkoxyalkyl;

$R^{10}$ is hydrogen or $C_{1-10}$ alkyl;

$R^{11a}$ and $R^{11b}$ are each independently hydrogen, $C_{1-6}$ alkyl, $C_{3-6}$ cycloalkyl, 4- to 6-membered heterocyclyl, alkylamino, haloalkyl, hydroxyalkyl, aminoalkyl, alkoxyalkyl, haloalkoxyalkyl, alkoxy, or haloalkoxy;

$R^{12a}$ is $C_{1-4}$ alkyl; and $R^{12b}$ is hydrogen or $C_{1-4}$ alkyl.

In one embodiment of Formula (I), $R^3$ is halo, cyano, hydroxyl, amino, oxo, —$OR^a$, —$SR^a$, =S, —$NR^cR^c$, =NH, =N—OH, —$NR^a$, =N—$OR^a$, —$NO_2$, —$S(O)_2R^a$, —$S(O)_2NHR^b$, —$S(O)_2NR^cR^c$, —$S(O)_2OR^b$, —$OS(O)_2R^b$, —$OS(O)_2OR^b$, —$P(O)(OR^b)(OR^b)$, —$C(O)R^b$, —$C(NR^b)R^b$, —$C(O)OR^b$, —$C(O)NR^cR^c$, —$C(NR^b)NR^cR^c$, —$OC(O)R^b$, —$NR^bC(O)R^b$, —$OC(O)OR^b$, —$NR^bC(O)OR^b$, —$OC(O)NR^cR^c$, —$NR^bC(O)NR^cR^c$, —$NR^bC(NR^b)R^b$, —$NR^bC(NR^b)NR^cR^c$, $C_{1-6}$ alkyl, $C_{1-6}$ deuterated alkyl (fully or partially deuterated), $C_{1-6}$ haloalkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$.

In one embodiment of Formula (I), $X^2$ is $CR^5$, where $R^5$ is hydrogen or $C_{1-4}$ alkyl (e.g., methyl).

In any one of the preceding embodiments of Formula (I), $R^6$ is hydrogen or $C_{1-6}$ alkyl.

In any one of the preceding embodiments of Formula (I), the

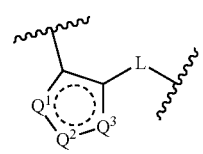

moiety is

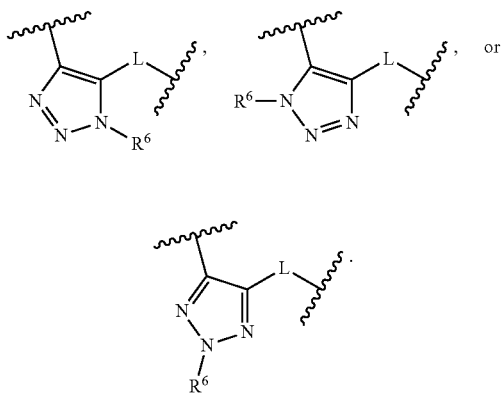

In any one of the preceding embodiments of Formula (I), the

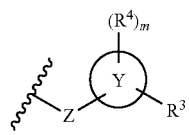

moiety is

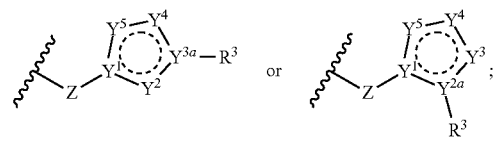

$Y^1$, $Y^{2a}$, and Va are each independently selected from C or N; and the dashed circle denotes optional bonds; wherein the 5-member ring formed by ($Y^1$, $Y^2$, $Y^{3a}$, $Y^4$, and $Y^5$) or ($Y^1$, $Y^{2a}$, $Y^3$, $Y^4$, and $Y^5$) can be either aromatic or nonaromatic;

$Y^2$, $Y^3$, $Y^4$, and $Y^5$ are each independently selected from C, $CR^{4a}$, N, $NR^{4b}$, S, or O; with the provisos that (1) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is N or $NR^{4b}$, and (2) at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is C or $CR^{4a}$;

$R^{4a}$ is each independently hydrogen, halo, oxo, imino, $C_{1-4}$ alkyl, $C_{1-4}$ haloalkyl, $C_{2-6}$ alkoxyalkyl, $C_{1-4}$ alkoxy; and $R^{4b}$ is each independently hydrogen or $C_{1-4}$ alkyl.

In any one of the preceding embodiments of Formula (I), $R^3$ is halo, cyano, hydroxyl, amino, $-OR^a$, $-SR^a$, $-NR^cR^c$, $C_{1-6}$ alkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$, $R^a$ is selected from $C_{1-6}$ alkyl, $C_{1-6}$ deuterated alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl;

$R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, $-OR^a$, $-SR^a$, and $-NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety.

In any one of the preceding embodiments of Formula (I), the compound is represented by Formula (IIa) or (IIb):

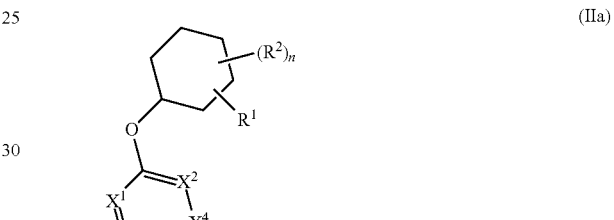

(IIa)

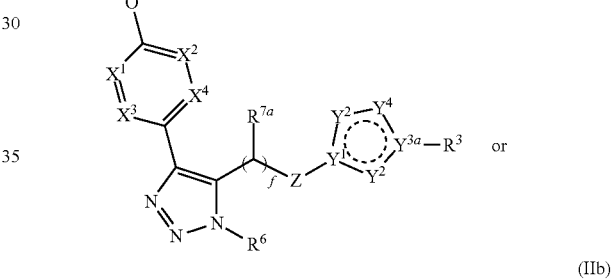

(IIb)

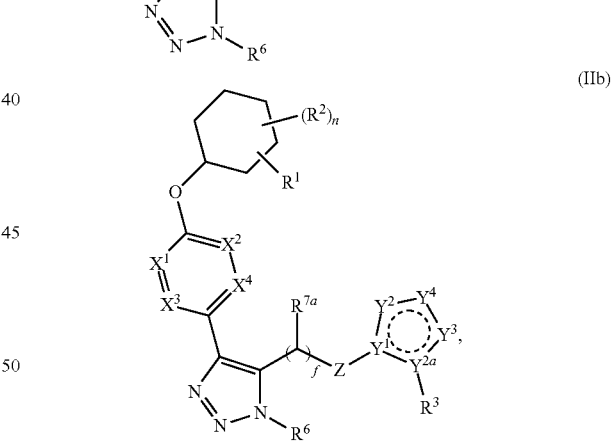

$Y^1$, $Y^{2a}$, and Va are each independently selected from C or N;

$Y^2$, $Y^3$, $Y^4$, and $Y^5$ are each independently selected from C, $CR^{4a}$, N, $NR^{4b}$, S, or O; with the proviso that at least one of ($Y^1$, $Y^2$, $Y^{3a}$, $Y^4$, and $Y^5$) or at least one of ($Y^1$, $Y^{2a}$, $Y^3$, $Y^4$, and $Y^5$) is N or $NR^{4b}$; and the dashed circle denotes optional bonds; wherein the 5-member ring formed by ($Y^1$, $Y^2$, $Y^{3a}$, $Y^4$, and $Y^5$) or ($Y^1$, $Y^{2a}$, $Y^3$, $Y^4$, and $Y^5$) can be either aromatic or nonaromatic;

$R^{4a}$ is each independently hydrogen, halo, hydroxyl, cyano, $-C(O)NH_2$, $-C(O)NR^{12a}R^{12b}$, $C(O)OR^{12a}$, $C_{1-4}$ alkyl, $C_{1-4}$ haloalkyl, $C_{2-6}$ alkoxyalkyl, $C_{1-4}$ alkoxy, oxo, or imino; or alternatively, $R^3$ and $R^{4a}$, taken together with the atoms to which they are attached, form a cyclic moiety (either carbocyclyl or heterocyclyl);

$R^{12a}$ is CM alkyl;

$R^{12b}$ is hydrogen or CM alkyl;

$R^{4b}$ is each independently hydrogen or CM alkyl;

$R^{7a}$ is each independently hydrogen, halo, cyano, hydroxyl, amino, $C_{1-6}$ alkyl, $C_{3-6}$ cycloalkyl, alkylamino, haloalkyl, hydroxyalkyl, aminoalkyl, alkoxyalkyl, haloalkoxyalkyl, alkoxy, or haloalkoxy;

f is an integer of 0, 1, or 2;

Z is $CH_2$ or $NR^{8b}$; with the proviso that when Z is $NR^{8b}$, $Y^1$ is C;

n is 0 or 1;

$R^6$ is $C_{1-4}$ alkyl; and $R^1$, $R^2$, n, $R^3$, $R^6$, $R^{8b}$, $X^1$, $X^2$, $X^3$, and $X^4$ are the same as defined above.

In one embodiment of Formula (IIa) or (IIb), $X^1$ is $CR^5$, where $R^5$ is hydrogen or $C_{1-4}$ alkyl.

In any one of the preceding embodiments of Formula (IIa) or (IIb), $X^3$ is N.

In any one of the preceding embodiments of Formula (IIa) or (IIb), the

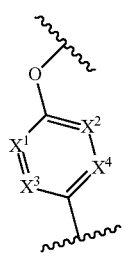

moiety is selected from

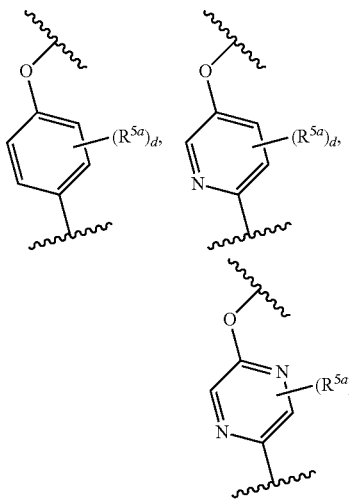

$R^{5a}$ is each independently halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; and d is an integer of 0, 1, or 2.

In any one of the preceding embodiments of Formula (IIa) or (IIb), the

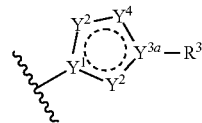

moiety is

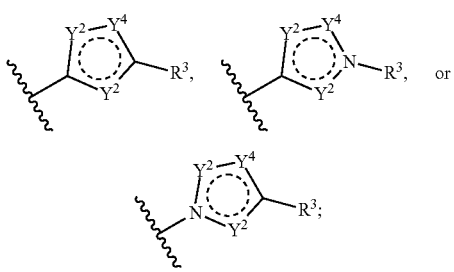

and $Y^2$, $Y^4$, and $Y^5$ are each independently C, $CR^{4a}$, N, O or S.

In any one of the preceding embodiments of Formula (IIa) or (IIb), the

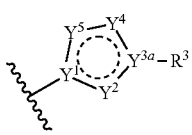

moiety is

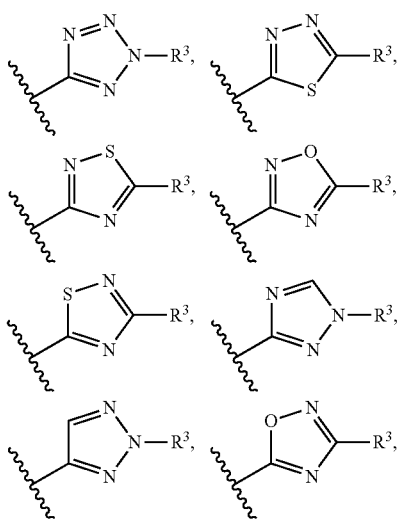

-continued

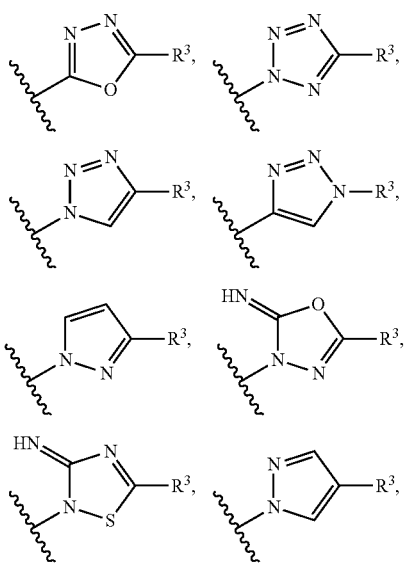

$R^4$ is methyl, Cl, or F.

In any one of the preceding embodiments of Formula (IIa) or (IIb),
the

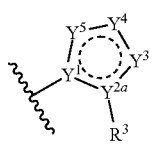

moiety is

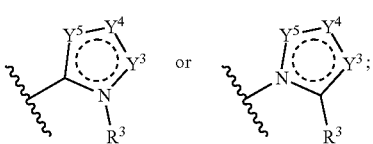

and $Y^3$, $Y^4$, and $Y^5$ are each independently C, N, O or S.

In any one of the preceding embodiments of Formula (IIa) or (IIb),
the

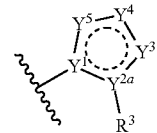

moiety is

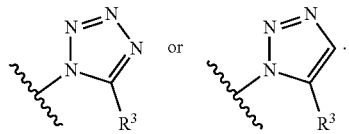

In any one of the preceding embodiments of Formula (IIa) or (IIb),
the

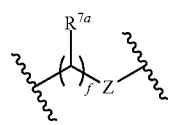

moiety is

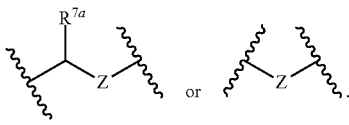

In any one of the preceding embodiments of Formula (IIa) or (IIb), $R^{7a}$ is hydrogen.

In any one of the preceding embodiments of Formula (IIa) or (IIb), $R^1$ is $CO_2H$.

In any one of the preceding embodiments of Formula (IIa) or (IIb), $R^2$ is hydrogen.

In any one of the preceding embodiments of Formula (IIa) or (IIb), the compound is represented by Formula (IIIa) or (IIIb):

(IIIa)

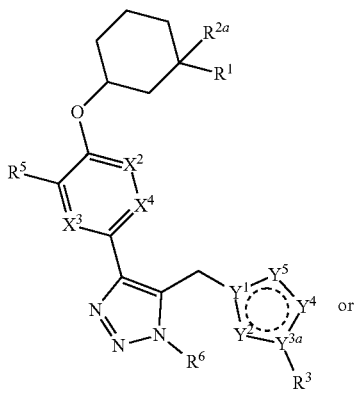

-continued (IIIb)

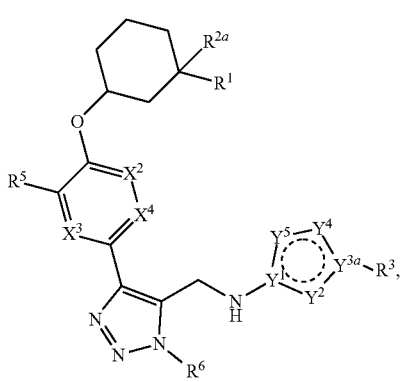

Y¹ and Va are each independently selected from C or N;

Y², Y⁴, and Y⁵ are each independently selected from C, $CR^{4a}$, N, S, or O; with the proviso that at least one of Y¹, Y², $Y^{3a}$, Y⁴, and Y⁵ is N or $NR^{4b}$; and the dashed circle denotes optional bonds forming an aromatic ring;

$R^{2a}$ is hydrogen, chloro, fluoro, or $C_{1-4}$ alkyl;

$R^{4a}$ is each independently hydrogen, halo, hydroxyl, cyano, —$C(O)NH_2$, —C(O)NHR, C(O)OR, $C_{1-4}$ alkyl, $C_{1-4}$ haloalkyl, $C_{2-6}$ alkoxyalkyl, or $C_{1-4}$ alkoxy;

$R^{4b}$ is each independently hydrogen or $C_{1-4}$ alkyl;

$R^5$ is hydrogen or $C_{1-4}$ alkyl; and $R^6$ is $C_{1-4}$ alkyl (e.g., methyl); and $R^1$, $R^3$, $X^2$, $X^3$, and $X^4$ are the same as defined above.

In one embodiment of Formula (IIIa) or (IIIb), two $R^d$, when attached to a cycloalkyl or heterocyclyl, taken together with the atoms to which they are attached, form a bridge moiety.

In another embodiment of Formula (IIIa) or (IIIb), $R^3$ and $R^{4a}$, together with the atoms to which they are attached, form a monocyclic or bicyclic moiety. In one embodiment, the bicyclic moiety is heterocyclyl.

In any one of the preceding embodiments of Formula (IIIa) or (IIIb), the

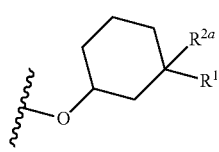

moiety is selected from

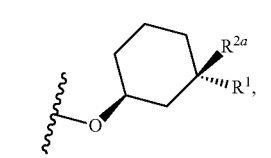

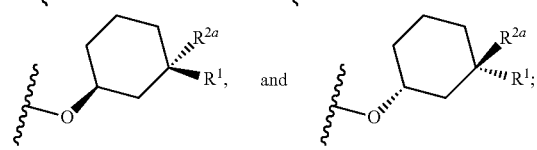

wherein wedges represent bonds towards the viewed and dashed lines represent bonds away from the viewer.

In any one of the preceding embodiments of Formula (IIIa) or (IIIb), $R^1$ is $CO_2H$.

In any one of the preceding embodiments of Formula (IIIa) or (IIIb), the

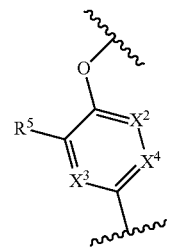

moiety is

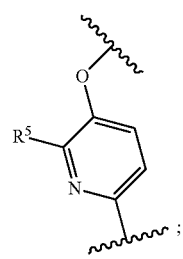

and $R^5$ is hydrogen, methyl, or ethyl.

In any one of the preceding embodiments of Formula (IIIa) or (IIIb), the

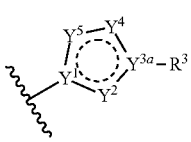

moiety is

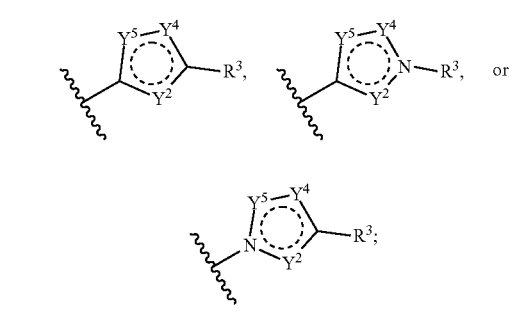

and

Y², Y⁴, and Y⁵ are each independently C, N, O or S.

In any one of the preceding embodiments of Formula (IIIa) or (IIIb), the

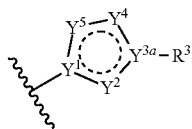

moiety is

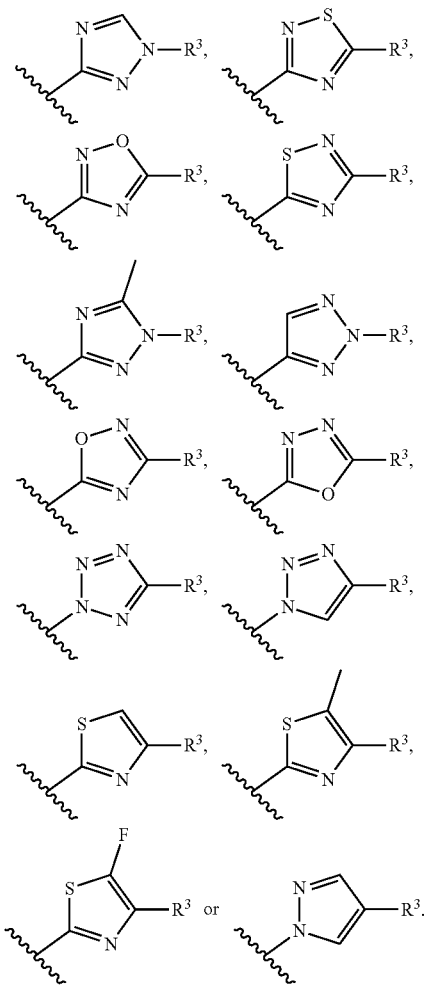

In any one of the preceding embodiments of Formula (IIIa) or (IIIb), $R^3$ is halo, cyano, hydroxyl, amino, —OR$^a$, —SR$^a$, —NR$^c$R$^c$, $C_{1-6}$ alkyl, $C_{1-6}$ deuterated alkyl, $C_{1-6}$ haloalkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and R$^a$, by themselves or as part of another group, are each independently substituted with 0 to 5 R$^d$;

R$^a$ is selected from $C_{1-6}$ alkyl, $C_{1-6}$ deuterated alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

R$^b$ is each independently hydrogen or R$^a$;

R$^c$ is each independently R$^b$; or alternatively, two R$^c$, taken together with the nitrogen atom to which they are attached, form a 4- to 7-membered heterocyclyl;

R$^d$ is each independently selected from R$^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —OR$^a$, —SR$^a$, and —NR$^c$R$^c$; or alternatively one or two R$^d$ on alkyl, heteroalkyl, aryl, heteroaryl, carbocyclyl, or heterocyclyl, taken together with the atoms to which the R$^d$ is attached, form a cyclic or bridge moiety.

In any one of the preceding embodiments of Formula (IIIa) or (IIIb), R$^3$ is $C_{1-6}$ alkyl, $C_{1-6}$ haloalkyl, $C_{1-6}$ alkoxy, deuterated $C_{1-6}$ alkoxy, $C_{1-6}$ haloalkoxy, —S—($C_{1-6}$ alkyl), $C_{3-6}$ cycloalkyl, 4- to 6-membered heterocyclyl, phenyl, (a 5 or 6-membered heteroaryl containing 1 to 3 heteroatoms each of which is independently selected from N, O, and S), —($C_{1-3}$ alkylene)-($C_{3-6}$ cycloalkyl), —($C_{1-3}$ alkylene)-(phenyl), —($C_{1-3}$ alkylene)-(4 to 6-membered heterocyclyl), —O—($C_{3-6}$ cycloalkyl), —O-(4 to 6-membered heterocyclyl), —O-phenyl, —O-(5 or 6-membered heteroaryl containing 1 to 3 heteroatoms each of which is independently selected from N, O, and S), —O—($C_{1-3}$ alkylene)-(phenyl), —O—($C_{1-3}$ alkylene)-($C_{3-6}$ cycloalkyl), —NH—($C_{1-3}$ alkylene)-(phenyl), —NH—($C_{1-6}$ alkyl), —NH—($C_{1-6}$ haloalkyl), —NH-phenyl, —NH—($C_{3-6}$ cycloalkyl), —NH—($C_{1-3}$ alkylene)-($C_{3-6}$ cycloalkyl), and —N($C_{1-6}$ alkyl)$_2$; and the alkyl, alkylene, cycloalkyl, phenyl, heterocyclyl, and heteroaryl, by themselves or as part of another group, are each independently substituted with 0 to 3 R$^d$; R$^d$ is halo, cyano, hydroxyl, amino, $C_{1-6}$ alkyl, $C_{1-6}$ alkoxy, $C_{3-6}$ cycloalkyl, or 4- to 6-membered heterocyclyl; R$^{4a}$ is hydrogen, fluoro, chloro, $C_{1-4}$ alkyl, $C_{1-4}$ haloalkyl, $C_{2-6}$ alkoxyalkyl, or $C_{1-4}$ alkoxy; and R$^{4b}$ is hydrogen.

In any one of the preceding embodiments of Formula (IIIa) or (IIIb), R$^3$ is $C_{1-6}$ alkyl, $C_{1-6}$ haloalkyl, $C_{1-6}$ alkoxy, deuterated $C_{1-6}$ alkoxy, $C_{1-6}$ haloalkoxy, —S—($C_{1-6}$ alkyl), $C_{3-6}$ cycloalkyl, phenyl, pyridyl, —($C_{1-3}$ alkylene)-($C_{3-6}$ cycloalkyl), —($C_{1-3}$ alkylene)-(phenyl), —O—($C_{3-6}$ cycloalkyl), —O-phenyl, —NH—($C_{1-3}$ alkylene)-(phenyl), —NH—($C_{1-6}$ alkyl), —N($C_{1-6}$ alkyl)$_2$; and the alkyl, alkylene, cycloalkyl, phenyl, and pyridyl, by themselves or as part of another group, are each independently substituted with 0 to 3 R$^d$.

In one embodiment of the present invention, the compound is selected from any one of the Examples as described in the specification, or a stereoisomer, a tautomer, or a pharmaceutically acceptable salt or solvate thereof.

In another embodiment of the present invention, the compound is selected from Examples 1 to 412 as described in the specification, or a stereoisomer, a tautomer, or a pharmaceutically acceptable salt or solvate thereof.

In another embodiment of the present invention, the compound is selected from Examples 1 to 114 as described in the specification, or a stereoisomer, a tautomer, or a pharmaceutically acceptable salt or solvate thereof.

In one embodiment of the present invention, the compound is selected from:
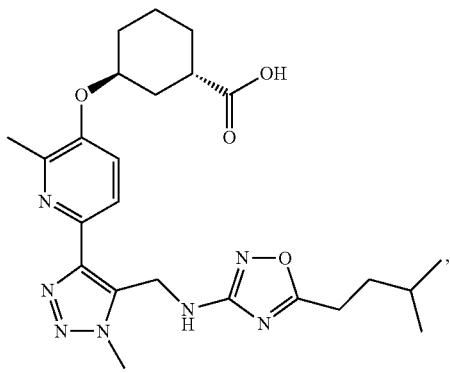
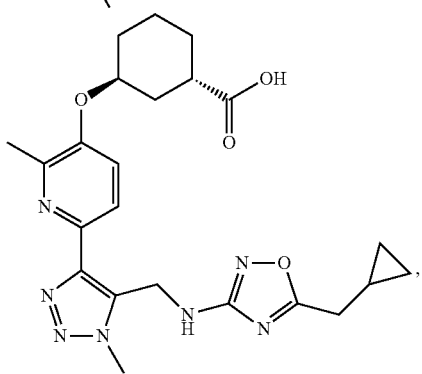
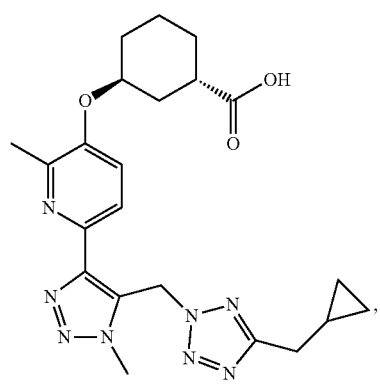
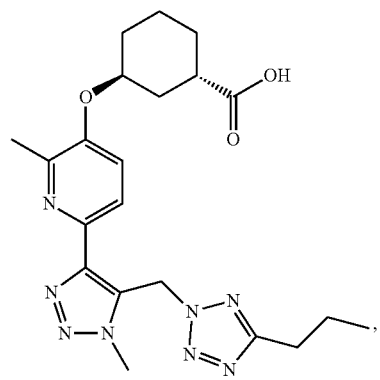
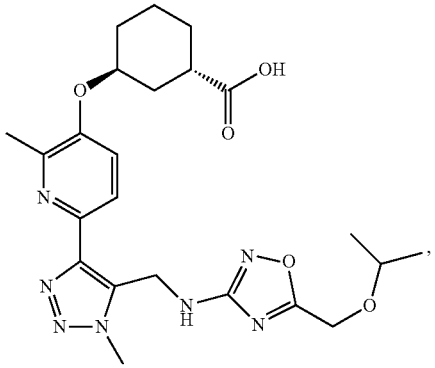
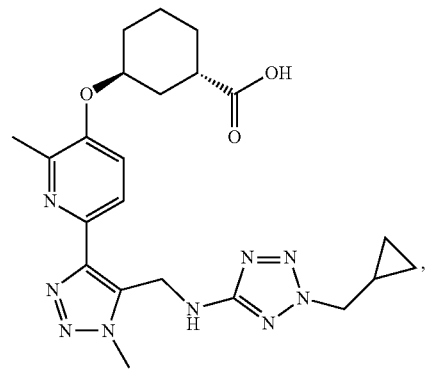
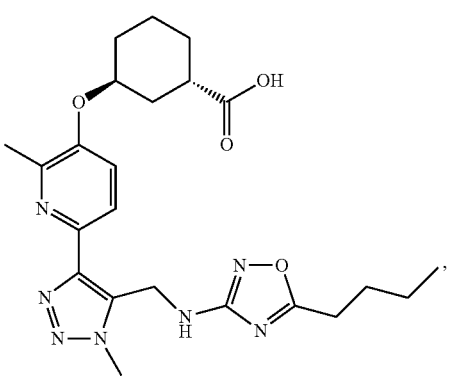
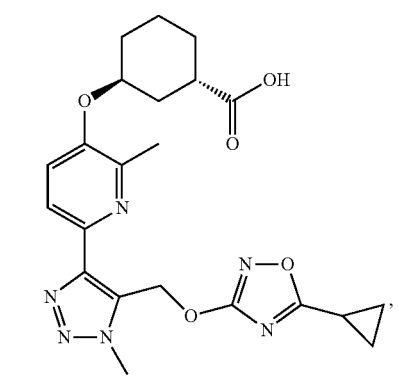

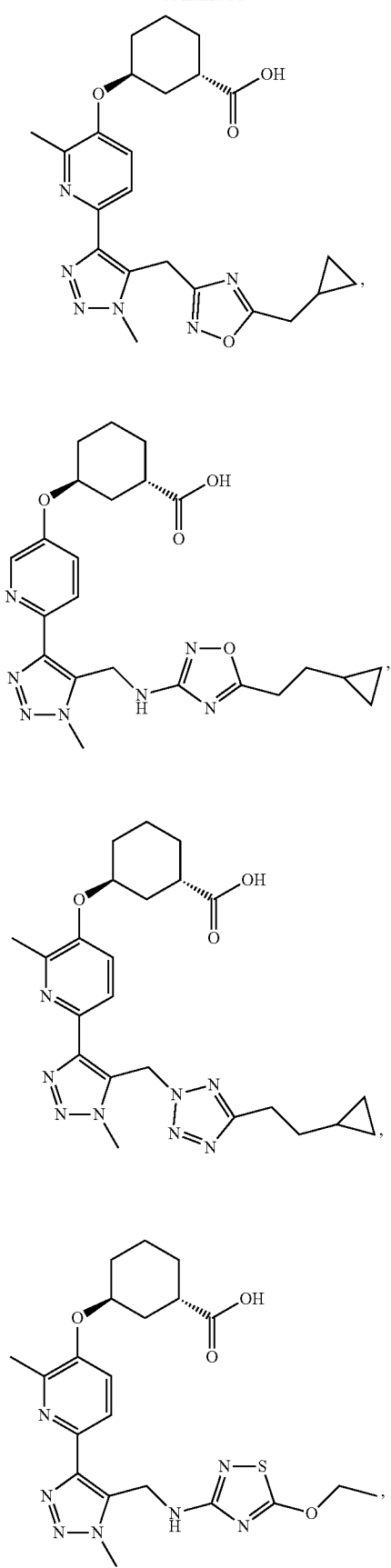
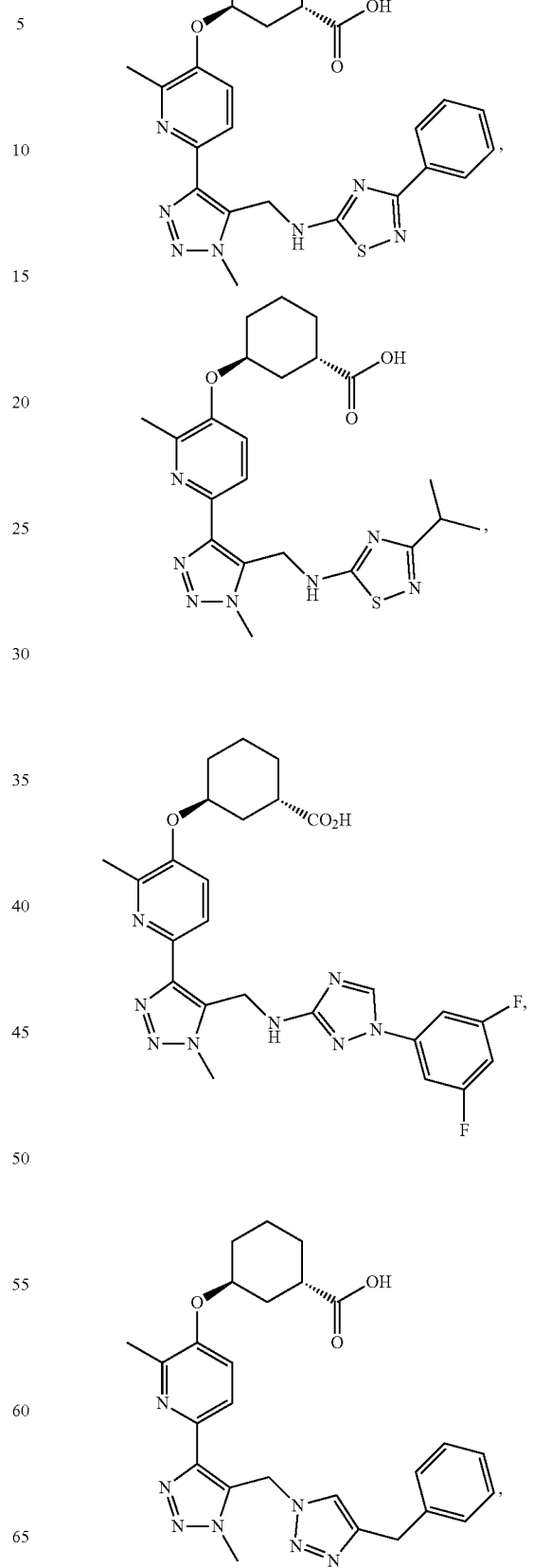

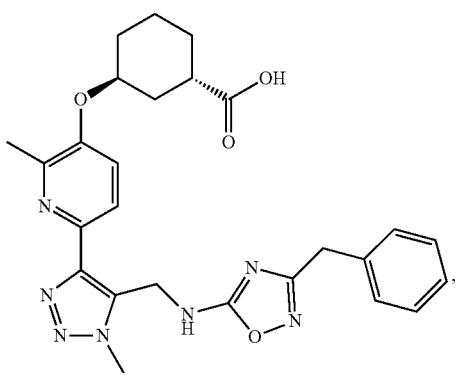
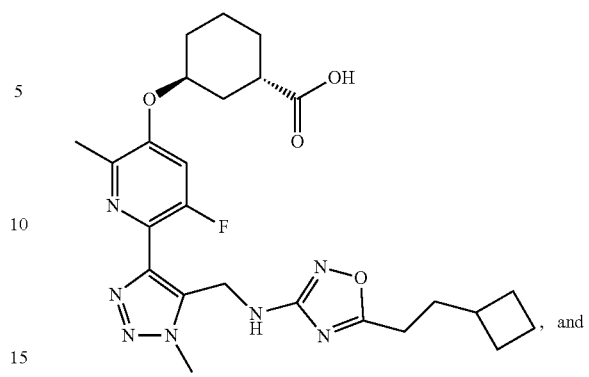, and
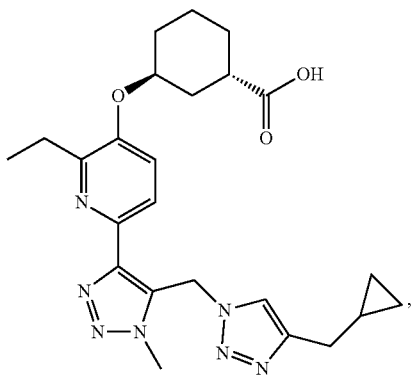
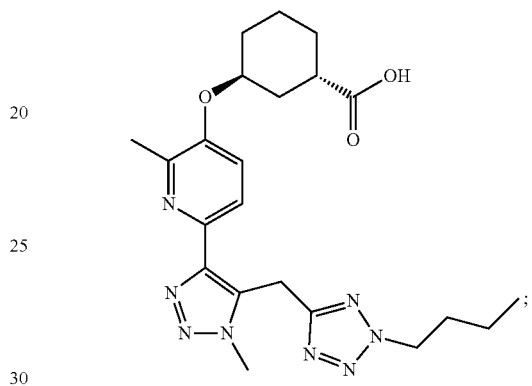
or a pharmaceutically acceptable salt or solvate thereof.
In another embodiment of the present invention, the compound is selected from:
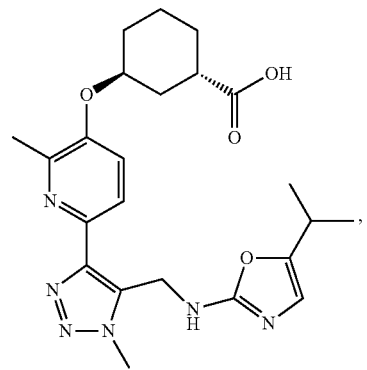
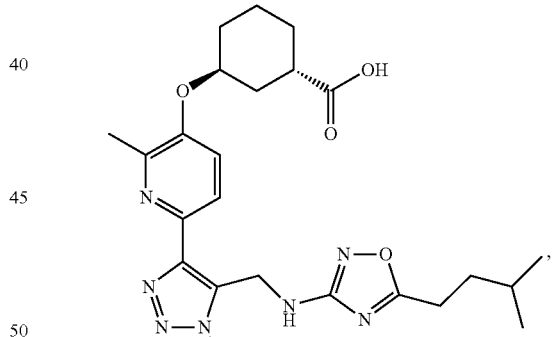
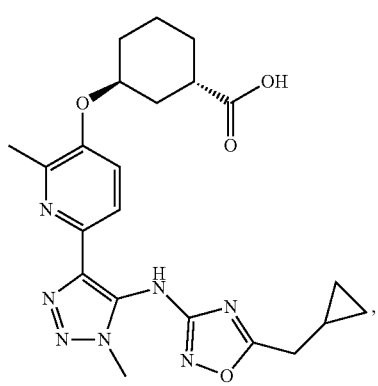
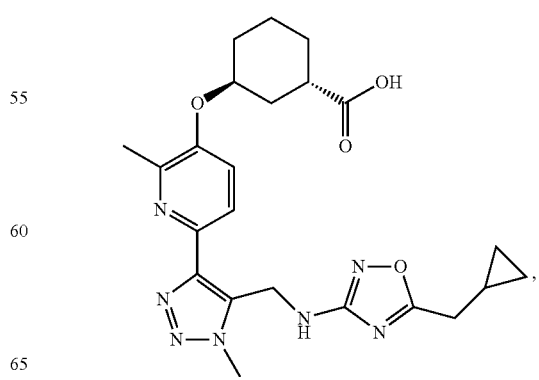

-continued
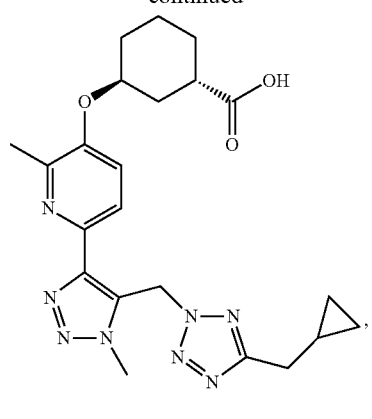
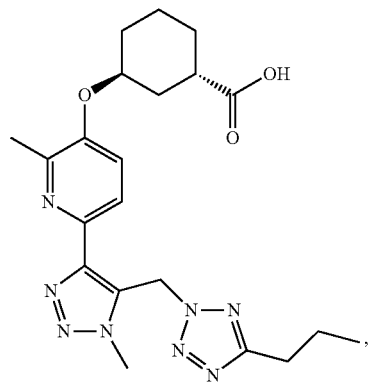
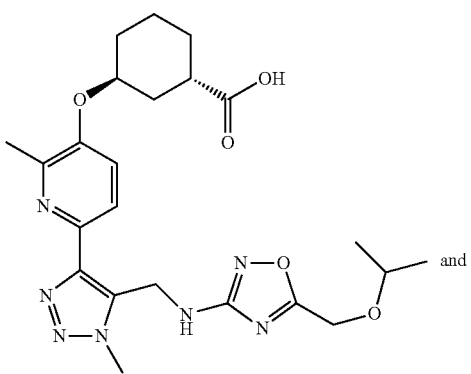
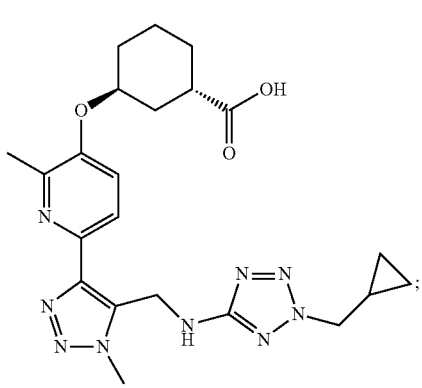
or a pharmaceutically acceptable salt or solvate thereof.
In another embodiment of the present invention, the compound is selected from:
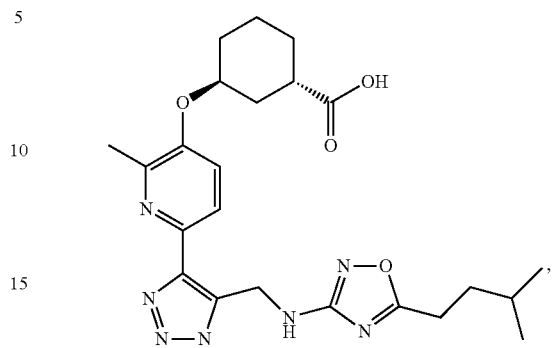
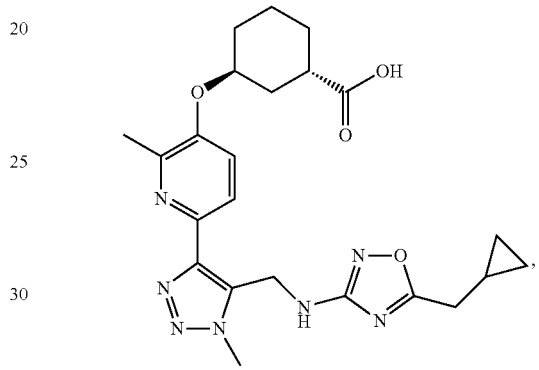
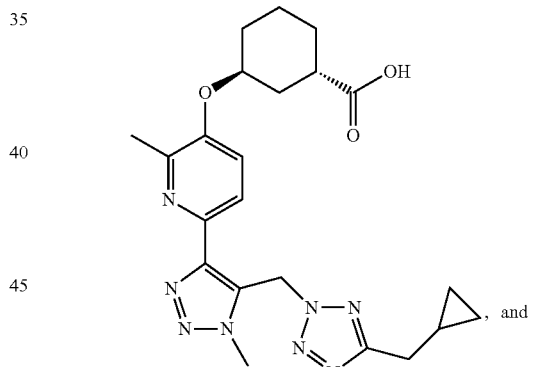
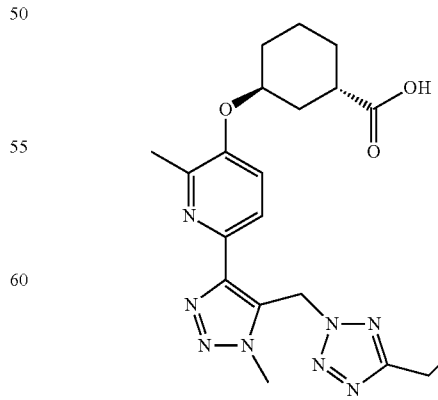
or a pharmaceutically acceptable salt or solvate thereof.

In another embodiment of the present invention, the compound is selected from:
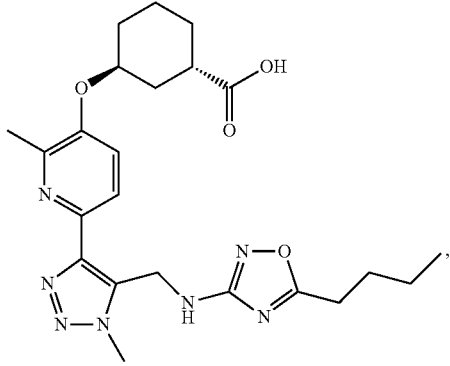
,
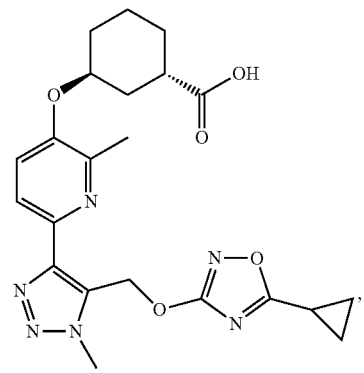
,
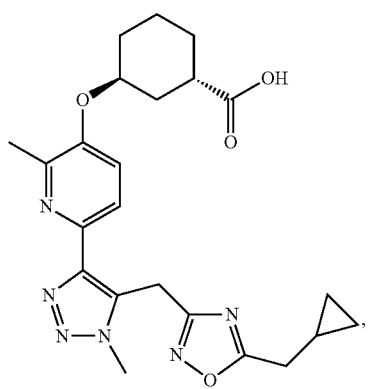
,
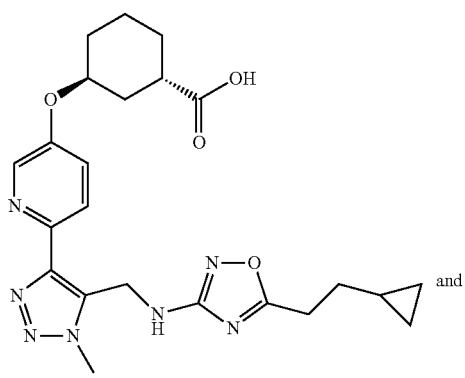
and
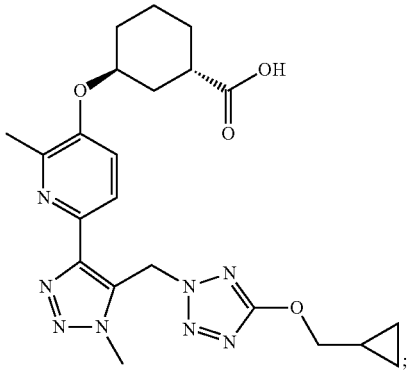 [SMILES: Cc1nc(-c2nnn(C)c2Cn2nnc(OCC3CC3)n2)ccc1O[C@H]1CCC[C@H](C(=O)O)C1]
;
or a pharmaceutically acceptable salt or solvate thereof.
In another embodiment of the present invention, the compound is selected from:
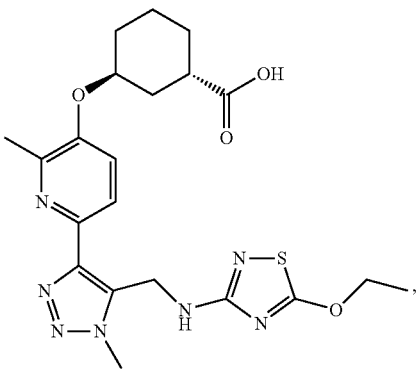
,
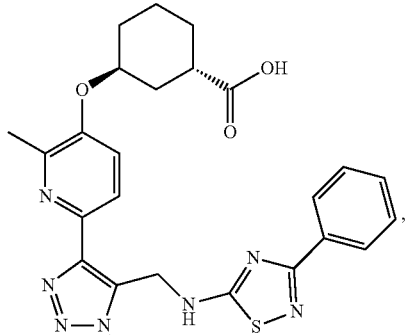
,
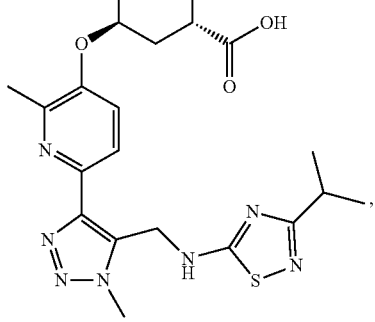
, 27
-continued
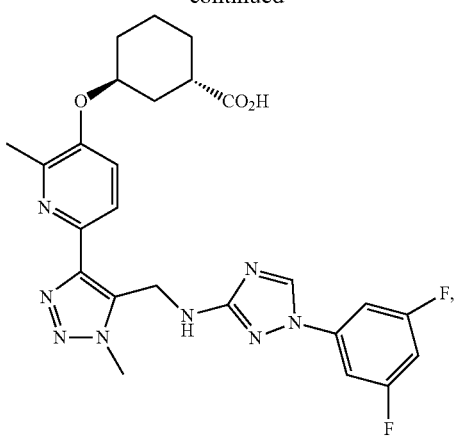
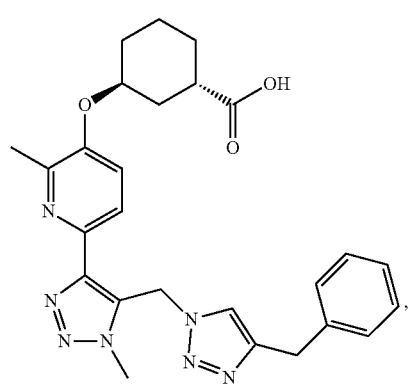
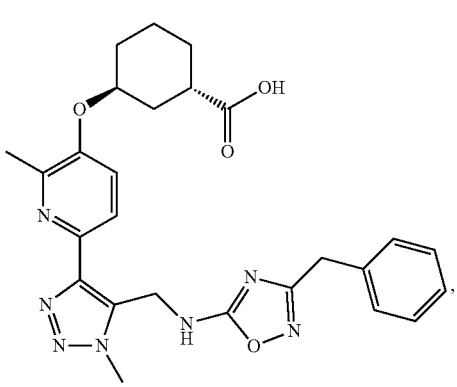
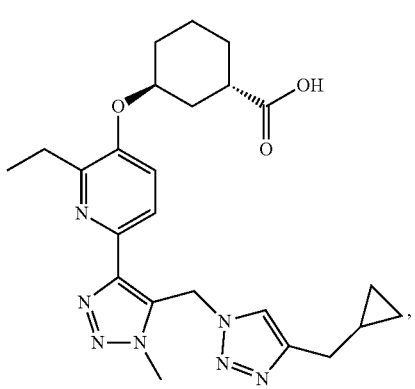
28
-continued
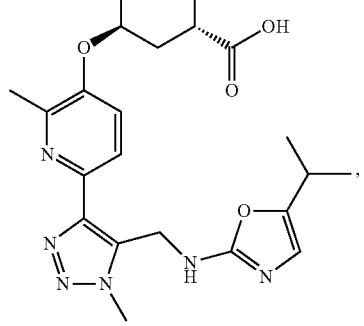
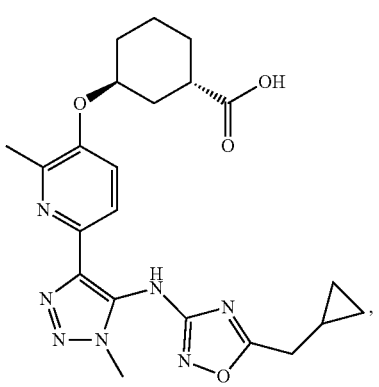
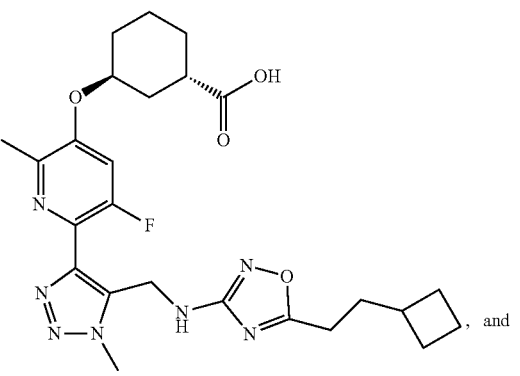, and
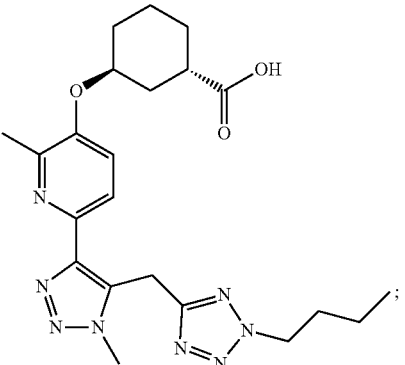
or a pharmaceutically acceptable salt or solvate thereof.

In another embodiment of the present invention, the compound is selected from:
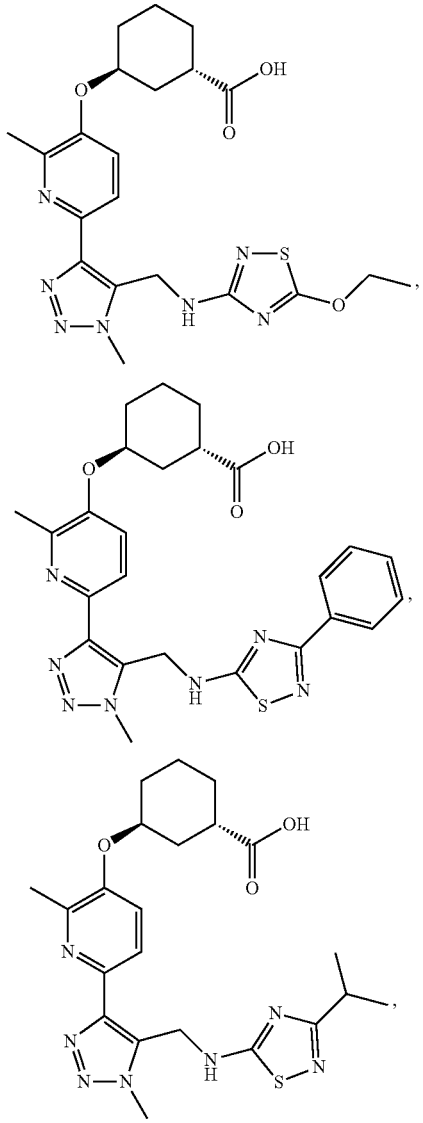
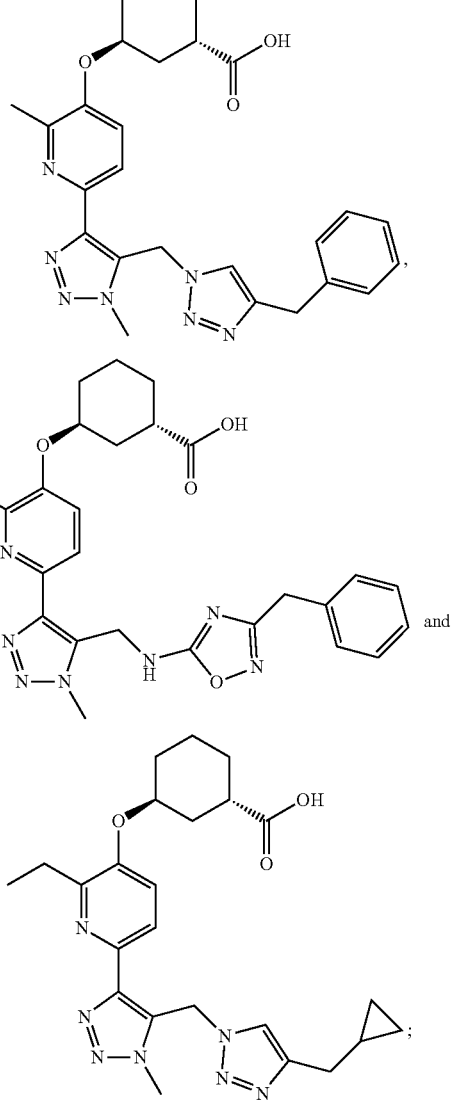
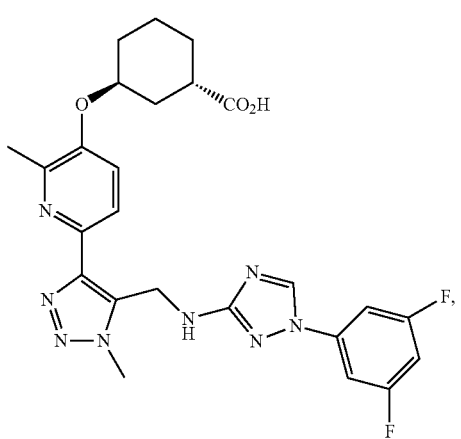
or a pharmaceutically acceptable salt or solvate thereof.
In another embodiment of the present invention, the compound is selected from:
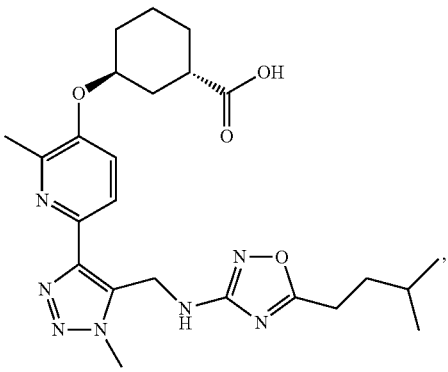

31
-continued
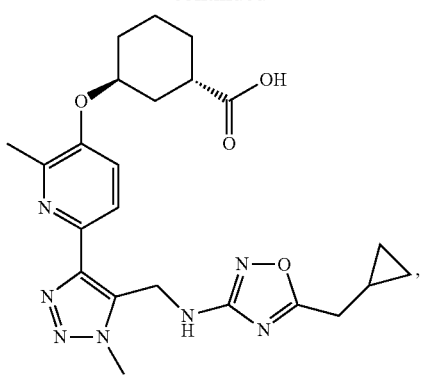
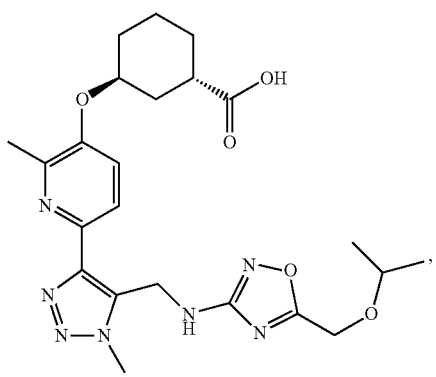
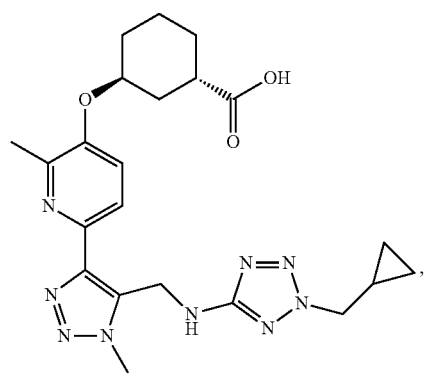
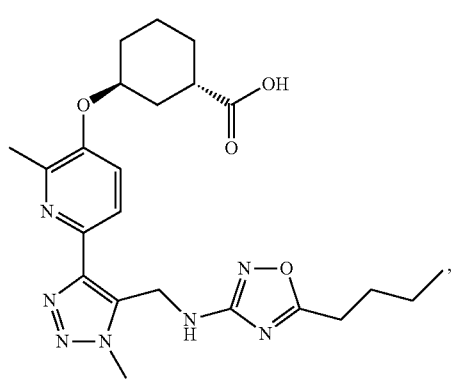
32
-continued
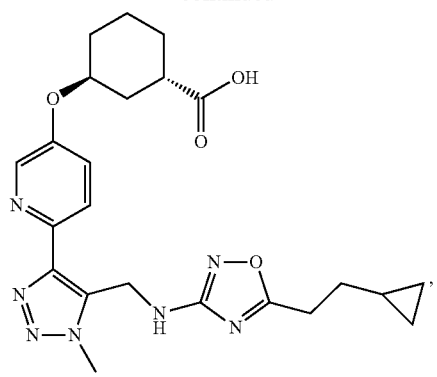
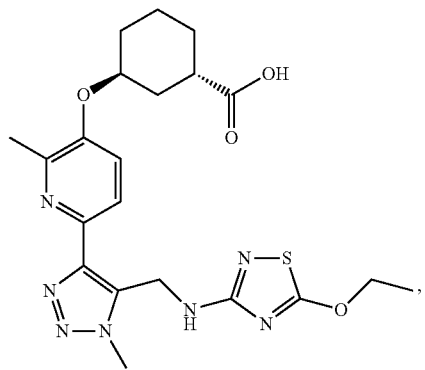
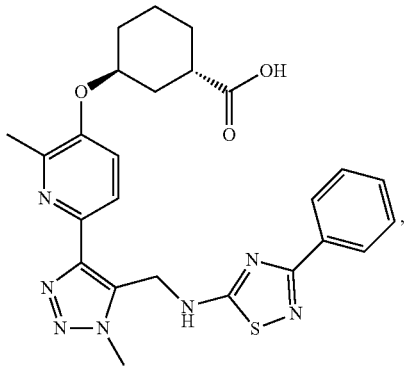
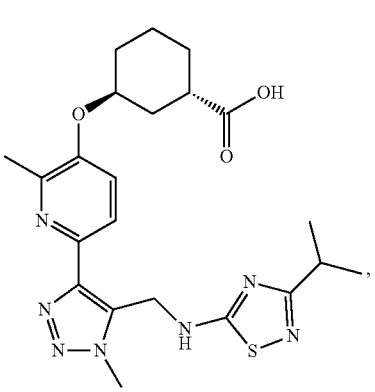

-continued
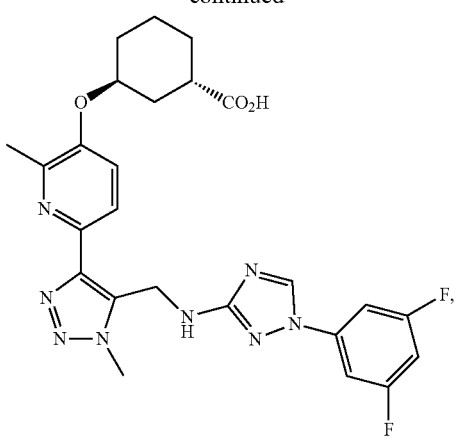
In another embodiment of the present invention, the compound is selected from:
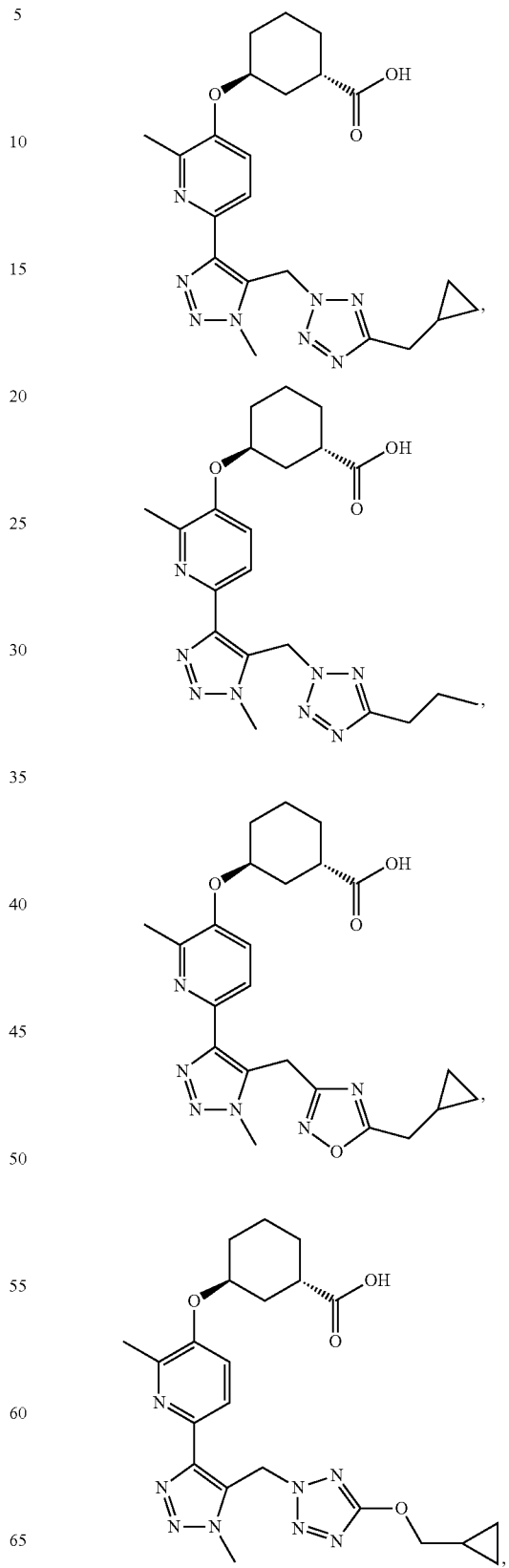
or a pharmaceutically acceptable salt or solvate thereof.

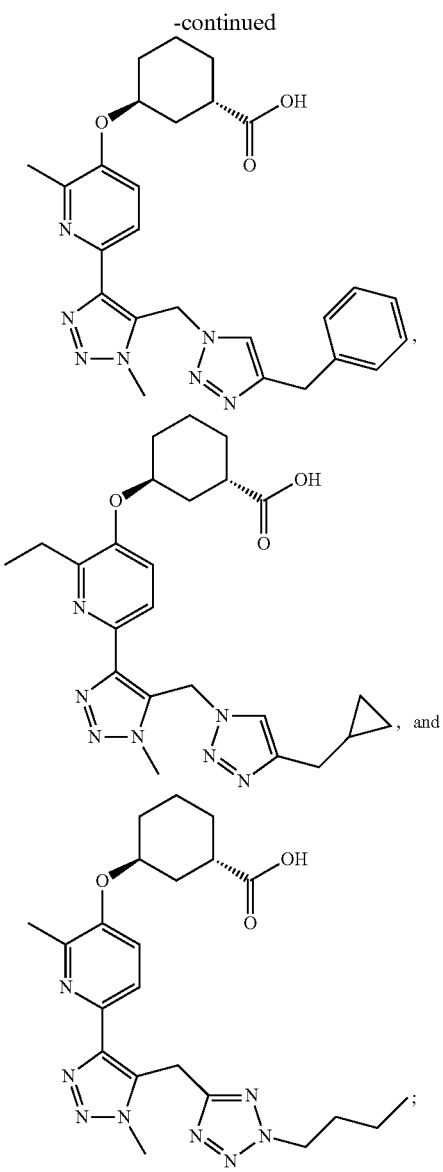

or a pharmaceutically acceptable salt or solvate thereof.

In one embodiment, the compounds of the present invention have hLPA$_1$ IC$_{50}$ values ≤5000 nM, using the LPA$_1$ functional antagonist assay; in another embodiment, the compounds of the present invention have hLPA$_1$ IC$_{50}$ values ≤1000 nM; in another embodiment, the compounds of the present invention have hLPA$_1$ IC$_{50}$ values ≤500 nM; in another embodiment, the compounds of the present invention have hLPA$_1$ IC$_{50}$ values ≤200 nM; in another embodiment, the compounds of the present invention have hLPA$_1$ IC$_{50}$ values ≤100 nM; in another embodiment, the compounds of the present invention have hLPA$_1$ IC$_{50}$ values ≤50 nM.

II. Other Embodiments of the Invention

In some embodiments, the compound of Formulas (I), or a pharmaceutically acceptable salt thereof, is an antagonist of at least one LPA receptor. In some embodiments, the compound of Formula (I), or a pharmaceutically acceptable salt thereof, is an antagonist of LPA$_1$. In some embodiments, the compound of Formula (I), or a pharmaceutically acceptable salt thereof, is an antagonist of LPA$_2$. In some embodiments, the compound of Formula (I), or a pharmaceutically acceptable salt thereof, is an antagonist of LPA$_3$.

In some embodiments, presented herein are compounds selected from active metabolites, tautomers, pharmaceutically acceptable salts or solvates of a compound of Formula (I).

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment of a condition associated with LPA receptor mediated fibrosis, comprising administering to a patient in need of such treatment a therapeutically effective amount of at least one of the compounds of the present invention or a stereoisomer, a tautomer, a pharmaceutically acceptable salt, or a solvate thereof. As used herein, the term "patient" encompasses all mammalian species.

In another embodiment, the present invention provides a method of treating a disease, disorder, or condition associated with dysregulation of lysophosphatidic acid receptor 1 (LPA$_1$) in a patient in need thereof, comprising administering a therapeutically effective amount of a compound of the present invention, or a stereoisomer, a tautomer, or a pharmaceutically acceptable salt or solvate thereof, to the patient. In one embodiment of the method, the disease, disorder, or condition is related to pathological fibrosis, transplant rejection, cancer, osteoporosis, or inflammatory disorders. In one embodiment of the method, the pathological fibrosis is pulmonary, liver, renal, cardiac, dermal, ocular, or pancreatic fibrosis. In one embodiment of the method, the disease, disorder, or condition is idiopathic pulmonary fibrosis (IPF), non-alcoholic steatohepatitis (NASH), non-alcoholic fatty liver disease (NAFLD), chronic kidney disease, diabetic kidney disease, and systemic sclerosis. In one embodiment of the method, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In another embodiment, the present invention provides a method of treating fibrosis in a mammal comprising administering a therapeutically effective amount of a compound of the present invention, or a stereoisomer, a tautomer, or a pharmaceutically acceptable salt or solvate thereof, to the mammal in need thereof. In one embodiment of the method, the fibrosis is idiopathic pulmonary fibrosis (IPF), nonalcoholic steatohepatitis (NASH), chronic kidney disease, diabetic kidney disease, and systemic sclerosis.

In another embodiment, the present invention provides a method of treating lung fibrosis (idiopathic pulmonary fibrosis), asthma, chronic obstructive pulmonary disease (COPD), renal fibrosis, acute kidney injury, chronic kidney disease, liver fibrosis (non-alcoholic steatohepatitis), skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, cancer pain, tumor metastasis, transplant organ rejection, scleroderma, ocular fibrosis, age related macular degeneration (AMD), diabetic retinopathy, collagen vascular disease, atherosclerosis, Raynaud's phenomenon, or neuropathic pain in a mammal comprising administering a therapeutically effective amount of a compound of the present invention, or a stereoisomer, a tautomer, or a pharmaceutically acceptable salt or solvate thereof, to the mammal in need thereof.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state. As used herein, "treating" or "treatment" also include the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for such protective therapy based on factors that are known to increase risk of suffering a clinical disease state compared to the general population. For protective treatment, conditions of the clinical disease state may or may not be presented yet. The protective treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_3$ to $C_{10}$ alkyl" or "$C_{1-10}$ alkyl" is intended to include $C_3$, $C_2$, $C_3$, $C_4$, $C_5$, $C_6$, $C_7$, $C_8$, $C_9$, and $C_{10}$ alkyl groups. "$C_3$ to $C_{10}$ alkylene" or "$C_{1-10}$ alkylene", is intended to include $C_3$, $C_2$, $C_3$, $C_4$, $C_5$, $C_6$, $C_7$, $C_8$, $C_9$, and $C_{10}$ alkylene groups. Additionally, for example, "$C_3$ to $C_6$ alkyl" or "$C_{1-6}$ alkyl" denotes alkyl having 1 to 6 carbon atoms; and "$C_3$ to $C_6$ alkylene" or "$C_{1-6}$ alkylene" denotes alkylene having 1 to 6 carbon atoms; and "$C_3$ to $C_4$ alkyl" or "$C_{1-4}$ alkyl" denotes alkyl having 1 to 4 carbon atoms; and "$C_3$ to $C_4$ alkylene" or "$C_{1-4}$ alkylene" denotes alkylene having 1 to 4 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. Furthermore, the term "alkyl", by itself or as part of another group, such as alkylamino, haloalkyl, hydroxyalkyl, aminoalkyl, alkoxy, alkoxyalkyl, haloalkoxyalkyl, and haloalkoxy, can be an alkyl having 1 to 4 carbon atoms, or 1 to 6 carbon atoms, or 1 to 10 carbon atoms.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$. "Benzyl" can also be represented by formula "Bn".

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_3$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^{c1}$R$^{c2}$, wherein R$^{c1}$ and R$^{c2}$ are independently H or $C_{1-6}$ alkyl; or alternatively, R$^{c1}$ and R$^{c2}$, taken together with the atoms to which they are attached, form a 3- to 8-membered heterocyclic ring which is optionally substituted with one or more group selected from halo, cyano, hydroxyl, amino, oxo, $C_{1-6}$ alkyl, alkoxy, and aminoalkyl. When R$^{c1}$ or R$^{c2}$ (or both of them) is $C_{1-6}$ alkyl, the amino group can also be referred to as alkylamino. Examples of alkylamino group include, without limitation, methylamino, ethylamino, propylamino, isopropylamino and the like. In one embodiment, amino is —$NH_2$.

The term "aminoalkyl" refers to an alkyl group on which one of the hydrogen atoms is replaced by an amino group. For example, aminoalkyl may be represented by N(R$^{c1}$R$^{c2}$)-alkylene-. "$C_1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or $C_1$, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or $C_1$, preferably F, such as polyfluoroalkoxy, for example, $CF_3CH_2O$, $CF_3O$ or $CF_3CF_2CH_2O$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_8$ cycloalkyl" or "$C_{3-8}$ cycloalkyl" is intended to include $C_3$, $C_4$, $C_5$, $C_6$, $C_7$, and $C_8$ cycloalkyl groups, including monocyclic, bicyclic, and polycyclic rings. Example cycloalkyl groups include, but are not limited to, cyclopropyl, cyclobutyl, cyclopentyl, cyclohexyl, and norbornyl. Branched cycloalkyl groups such as 1-methyl cyclopropyl and 2-methyl cyclopropyl and spiro and bridged cycloalkyl groups are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

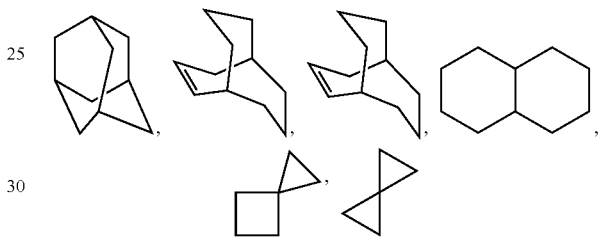

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, C$_1$, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl also include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heteroaryl include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl. In some embodiments, the heteroaryl are selected from benzthiazolyl, imidazolpyridinyl, pyrrolopyridinyl, quinolinyl, and indolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings), for example,

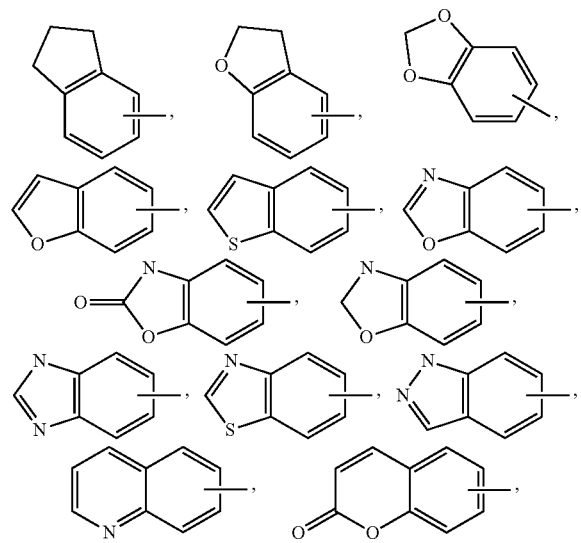

and may be optionally substituted through available carbon or nitrogen atoms (as applicable) with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, aryl carbonyl oxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkoxy, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryl oxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as 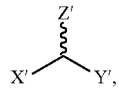 as used in structural formulas herein, depicts the bond that is the point of attachment of the moiety or substituent to the core or backbone structure.

In accordance with a convention used in the art, a wavy or squiggly bond in a structural formula, such as

is used to depict a stereogenic center of the carbon atom to which X', Y', and Z' are attached and is intended to represent both enantiomers in a single figure. That is, a structural formula with such as wavy bond denotes each of the enantiomers individually, such as

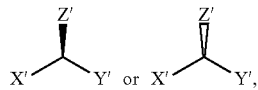

as well as a racemic mixture thereof. When a wavy or squiggly bond is attached to a double bond (such as C=C or C=N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to give other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

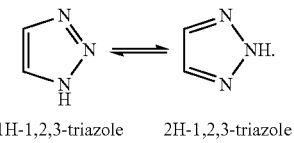

1H-1,2,3-triazole    2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, compounds of Formula (I) may have prodrug forms. Any compound that will be converted in vivo to provide the bioactive agent (i.e., a compound of formula I) is a prodrug within the scope and spirit of the invention.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Such esters may be prepared by conventional techniques known in the art.

Preparation of prodrugs is well known in the art and described in, for example, King, F. D., ed., *Medicinal Chemistry; Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

ABBREVIATIONS

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "γ", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum trichloride
AIBN Azobis-isobutyronitrile
BBr$_3$ boron tribromide
BCl$_3$ boron trichloride BEMP 2-tert-butylimino-2-di ethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or $CH_2Cl_2$ dichloromethane
$CH_3CN$ or ACN acetonitrile
$CDCl_3$ deutero-chloroform
$CHCl_3$ chloroform
mCPBA or m-CPBA meta-chloroperbenzoic acid
$Cs_2CO_3$ cesium carbonate
$Cu(OAC)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DEA Diethylamine
DEAD Diethyl azodicarboxylate
Dess-Martin 1,1,1-tris(acetyloxy)-1,1-dihydro-1,2-benziodoxol-3-(1H)-one
DIAD Diisopropyl azodicarboxylate
DIC or DIPCDI diisopropylcarbodiimide
DIEA, DIPEA or diisopropylethylamine
Hunig's base
DMAP 4-dimethylaminopyridine
DME 1,2-dimethoxy ethane
DMF dimethyl formamide
DMSO dimethyl sulfoxide
cDNA complementary DNA
Dppp (R)-(+)-1,2-bis(di phenyl phosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyl-uronium hexafluorophosphate
HEPES 4-(2-hydroxyethyl)piperaxine-1-ethanesulfonic acid
Hex hexane
HOBt or HOBT 1-hydroxybenzotriazole
$H_2O_2$ hydrogen peroxide
IBX 2-iodoxybenzoic acid
$H_2SO_4$ sulfuric acid
Jones reagent $CrO_3$ in aqueous $H_2SO_4$, 2 M solution
$K_2CO_3$ potassium carbonate
$K_2HPO_4$ potassium phosphate dibasic (potassium hydrogen phosphate)
KOAc potassium acetate
$K_3PO_4$ potassium phosphate tribasic
LAH lithium aluminum hydride
LG leaving group
LiOH lithium hydroxide
MeOH methanol
$MgSO_4$ magnesium sulfate
MsOH or MSA methylsulfonic acid/methanesulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
$NH_4^+HCO_2^-$ ammonium formate
NMM N-methylmorpholine
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PPTS pyridinium p-toluenesulfonate
i-PrOH or IPA isopropanol
PS Polystyrene
RT or rt room temperature
SEM-$C_{1-2}$-(trimethysilyl)ethoxymethyl chloride
$SiO_2$ silica oxide
$SnCl_2$ tin(II) chloride
TBAF tetra-n-butylammonium fluoride
TBAI tetra-n-butylammonium iodide
TFA trifluoroacetic acid
THF tetrahydrofuran
THP tetrahydropyran
$TMSCHN_2$ Trimethylsilyldiazomethane
$TMSCH_2N_3$ Trimethylsilylmethyl azide
T3P propane phosphonic acid anhydride
TRIS tris (hydroxymethyl) aminomethane
pTsOH p-toluenesulfonic acid IV. Biology Lysophospholipids are membrane-derived bioactive lipid mediators. Lysophospholipids include, but are not limited to, lysophosphatidic acid (1-acyl-2-hydroxy-sn-glycero-3-phosphate; LPA), sphingosine 1-phosphate (SIP), lysophosphatidylcholine (LPC), and sphingosylphosphorylcholine (SPC). Lysophospholipids affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

Lysophospholipids, such as LPA, are quantitatively minor lipid species compared to their major phospholipid counterparts (e.g., phosphatidylcholine, phosphatidylethanolamine, and sphingomyelin). LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors ($LPA_1$, $LPA_2$, $LPA_3$, $LPA_4$, $LPA_5$, $LPA_6$) with LPA mediates a range of downstream signaling cascades. These include, but are not limited to, mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include, but are not limited to, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (INK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C (PKC), ras-related C3 botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. $LPA_1$, $LPA_2$, and $LPA_3$ share high amino acid sequence similarity.

LPA is produced from activated platelets, activated adipocytes, neuronal cells, and other cell types. Serum LPA is produced by multiple enzymatic pathways that involve monoacylglycerol kinase, phospholipase $A_1$, secretory phospholipase $A_2$, and lysophospholipase D (lysoPLD), including autotaxin. Several enzymes are involved in LPA degradation: lysophospholipase, lipid phosphate phosphatase, and LPA acyl transferase such as endophilin. LPA concentrations in human serum are estimated to be 1-5 µM. Serum LPA is bound to albumin, low-density lipoproteins, or other proteins, which possibly protect LPA from rapid degradation. LPA molecular species with different acyl chain lengths and saturation are naturally occurring, including 1-palmitoyl (16:0), 1-palmitoleoyl (16:1), 1-stearoyl (18:0), 1-oleoyl (18:1), 1-linoleoyl (18:2), and 1-arachidonyl (20:4) LPA. Quantitatively minor alkyl LPA has biological activities similar to acyl LPA, and different LPA species activate LPA receptor subtypes with varied efficacies.

LPA Receptors $LPA_1$ (previously called VZG-1/EDG-2/mrec1.3) couples with three types of G proteins, $G_{i/o}$, $G_q$, and $G_{12/13}$. Through activation of these G proteins, LPA induces a range of cellular responses through $LPA_1$ including but not limited to: cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Wide expression of $LPA_1$ is observed in adult mice, with clear presence in testis, brain, heart, lung, small intestine, stomach, spleen, thymus, and skeletal muscle. Similarly, human tissues also express $LPA_1$; it is present in brain, heart, lung, placenta, colon, small intestine, prostate, testis, ovary, pancreas, spleen, kidney, skeletal muscle, and thymus.

$LPA_2$ (EDG-4) also couples with three types of G proteins, $G_{i/o}$, $G_q$, and $G_{12/13}$, to mediate LPA-induced cellular signaling. Expression of $LPA_2$ is observed in the testis, kidney, lung, thymus, spleen, and stomach of adult mice and in the human testis, pancreas, prostate, thymus, spleen, and peripheral blood leukocytes. Expression of $LPA_2$ is upregulated in various cancer cell lines, and several human $LPA_2$ transcriptional variants with mutations in the 3'-untranslated region have been observed. Targeted deletion of $LPA_2$ in mice has not shown any obvious phenotypic abnormalities, but has demonstrated a significant loss of normal LPA signaling (e.g., PLC activation, $Ca^{2+}$ mobilization, and stress fiber formation) in primary cultures of mouse embryonic fibroblasts (MEFs). Creation of lpa1(–/–) lpa2 (–/–) double-null mice has revealed that many LPA-induced responses, which include cell proliferation, AC inhibition, PLC activation, $Ca^{2+}$ mobilization, INK and Akt activation, and stress fiber formation, are absent or severely reduced in double-null MEFs. All these responses, except for AC inhibition (AC inhibition is nearly abolished in $LPA_1$ (–/–) MEFs), are only partially affected in either $LPA_1$ (–/–) or $LPA_2$ (–/–) MEFs. $LPA_2$ contributes to normal LPA-mediated signaling responses in at least some cell types (Choi et al, *Biochemica et Biophysica Acta* 2008, 1781,p 531-539).

$LPA_3$ (EDG-7) is distinct from $LPA_1$ and $LPA_2$ in its ability to couple with $G_{i/o}$ and $G_q$ but not $G_{12/13}$ and is much less responsive to LPA species with saturated acyl chains. $LPA_3$ can mediate pleiotropic LPA-induced signaling that includes PLC activation, $Ca^{2+}$ mobilization, AC inhibition/activation, and MAPK activation. Overexpression of $LPA_3$ in neuroblastoma cells leads to neurite elongation, whereas that of $LPA_1$ or $LPA_2$ results in neurite retraction and cell rounding when stimulated with LPA. Expression of $LPA_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala).

$LPA_4$ ($p2y_9$/GPR23) is of divergent sequence compared to $LPA_1$, $LPA_2$, and $LPA_3$ with closer similarity to the platelet-activating factor (PAF) receptor. $LPA_4$ mediates LPA induced $Ca^{2+}$ mobilization and cAMP accumulation, and functional coupling to the G protein Gs for AC activation, as well as coupling to other G proteins. The $LPA_4$ gene is expressed in the ovary, pancreas, thymus, kidney and skeletal muscle.

$LPA_5$ (GPR92) is a member of the purinocluster of GPCRs and is structurally most closely related to $LPA_4$. $LPA_5$ is expressed in human heart, placenta, spleen, brain, lung and gut. $LPA_5$ also shows very high expression in the CD8+ lymphocyte compartment of the gastrointestinal tract.

$LPA_6$ (p2y5) is a member of the purinocluster of GPCRs and is structurally most closely related to $LPA_4$. $LPA_6$ is an LPA receptor coupled to the G12/13-Rho signaling pathways and is expressed in the inner root sheaths of human hair follicles.

Illustrative Biological Activity

Wound Healing

Normal wound healing occurs by a highly coordinated sequence of events in which cellular, soluble factors and matrix components act in concert to repair the injury. The healing response can be described as taking place in four broad, overlapping phases-hemostasis, inflammation, proliferation, and remodeling. Many growth factors and cytokines are released into a wound site to initiate and perpetuate wound healing processes.

When wounded, damaged blood vessels activate platelets. The activated platelets play pivotal roles in subsequent repair processes by releasing bioactive mediators to induce cell proliferation, cell migration, blood coagulation, and angiogenesis. LPA is one such mediator that is released from activated platelets; this induces platelet aggregation along with mitogenic/migration effects on the surrounding cells, such as endothelial cells, smooth muscle cells, fibroblasts, and keratinocytes.

Topical application of LPA to cutaneous wounds in mice promotes repair processes (wound closure and increased neoepithelial thickness) by increasing cell proliferation/migration without affecting secondary inflammation.

Activation of dermal fibroblasts by growth factors and cytokines leads to their subsequent migration from the edges of the wound into the provisional matrix formed by the fibrin clot whereupon the fibroblasts proliferate and start to restore the dermis by secreting and organizing the characteristic dermal extracellular matrix (ECM). The increasing number of fibroblasts within the wound and continuous precipitation of ECM enhances matrix rigidity by applying small tractional forces to the newly formed granulation tissue. The increase in mechanical stress, in conjunction with transforming growth factor β (TGFβ), induces α-smooth muscle actin (α-SMA) expression and the subsequent transformation of fibroblasts into myofibroblasts. Myofibroblasts facilitate granulation tissue remodeling via myofibroblast contraction and through the production of ECM components.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing, such as epithelial and endothelial cells (EC), macrophages, keratinocytes, and fibroblasts. A role for $LPA_1$ in LPA-induced proliferation was provided by the observation that LPA-stimulated proliferation of fibroblasts isolated from $LPA_1$ receptor null mice was attenuated (Mills et al, Nat Rev. Cancer 2003; 3: 582-591). LPA induces cytoskeletal changes that are integral to fibroblast adhesion, migration, differentiation and contraction.

Fibrosis

Tissue injury initiates a complex series of host wound-healing responses; if successful, these responses restore normal tissue structure and function. If not, these responses can lead to tissue fibrosis and loss of function.

For the majority of organs and tissues the development of fibrosis involves a multitude of events and factors. Molecules involved in the development of fibrosis include proteins or peptides (profibrotic cytokines, chemokines, metalloproteinases etc.) and phospholipids. Phospholipids involved in the development of fibrosis include platelet activating factor (PAF), phosphatidyl choline, sphingosine-1 phosphate (SIP) and lysophosphatidic acid (LPA).

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF (J. P. Pradere, et al., $LPA_1$ receptor activation promotes renal interstitial fibrosis, J. Am. Soc. Nephrol. 18 (2007) 3110-3118; N. Wiedmaier, et al., Int J Med Microbiol, 298(3-4):231-43, 2008). CTGF is a profibrotic cytokine, signaling down-stream and in parallel with TGFβ.

CTGF expression by gingival epithelial cells, which are involved in the development of gingival fibromatosis, was found to be exacerbated by LPA treatment (A. Kantarci, et al., J. Pathol. 210 (2006) 59-66).

LPA is associated with the progression of liver fibrosis. In vitro, LPA induces stellate cell and hepatocyte proliferation. These activated cells are the main cell type responsible for the accumulation of ECM in the liver. Furthermore, LPA plasma levels rise during $CCl_4$-induced liver fibrosis in rodents, or in hepatitis C virus-induced liver fibrosis in humans (N. Watanabe, et al., Plasma lysophosphatidic acid level and serum autotaxin activity are increased in liver injury in rats in relation to its severity, Life Sci. 81 (2007) 1009-1015; N. Watanabe, et al., J. Clin. Gastroenterol. 41 (2007) 616-623).

An increase of phospholipid concentrations in the bronchoalveolar lavage fluid in rabbits and rodents injected with bleomycin has been reported (K. Kuroda, et al., Phospholipid concentration in lung lavage fluid as biomarker for pulmonary fibrosis, Inhal. Toxicol 18 (2006) 389-393; K. Yasuda, et al., Lung 172 (1994) 91-102).

LPA is associated with heart disease and mycocardial remodeling. Serum LPA levels are increased after myocardial infarction in patients and LPA stimulates rat cardiac fibroblast proliferation and collagen production (Chen et al. FEBS Lett. 2006 Aug. 21; 580(19):4737-45).

Pulmonary Fibrosis

In the lung, aberrant wound healing responses to injury contribute to the pathogenesis of fibrotic lung diseases. Fibrotic lung diseases, such as idiopathic pulmonary fibrosis (IPF), are associated with high morbidity and mortality.

LPA is an important mediator of fibroblast recruitment in pulmonary fibrosis. LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The $LPA$-$LPA_1$ pathway has a role in mediating fibroblast migration and vascular leakage in IPF. The end result is the aberrant healing process that characterizes this fibrotic condition.

The $LPA_1$ receptor is the LPA receptor most highly expressed on fibroblasts obtained from patients with IPF. Furthermore, BAL obtained from IPF patients induced chemotaxis of human foetal lung fibroblasts that was blocked by the dual $LPA_1$-$LPA_3$ receptor antagonist Ki16425. In an experimental bleomycin-induced lung injury mouse model, it was shown that LPA levels were high in bronchoalveolar lavage samples compared with unexposed controls. $LPA_1$ knockout mice are protected from fibrosis after bleomycin challenge with reduced fibroblast accumulation and vascular leakage. In human subjects with IPF, high LPA levels were observed in bronchoalveolar lavage samples compared with healthy controls. Increased fibroblast chemotactic activity in these samples was inhibited by the Ki16425 indicating that fibroblast migration is mediated by the LPA-LPA receptor(s) pathway (Tager et al. Nature Medicine, 2008, 14, 45-54).

The $LPA$-$LPA_1$ pathway is crucial in fibroblast recruitment and vascular leakage in pulmonary fibrosis.

Activation of latent TGF-β by the αvβ6 integrin plays a critical role in the development of lung injury and fibrosis (Munger et al. Cell, vol. 96, 319-328, 1999). LPA induces αvβ6-mediated TGF-β activation on human lung epithelial cells (Xu et al. *Am. J. Pathology,* 2009, 174, 1264-1279). The LPA-induced αvβ6-mediated TGF-β activation is mediated by the $LPA_2$ receptor. Expression of the $LPA_2$ receptor is increased in epithelial cells and mesenchymal cells in areas of lung fibrosis from IPF patients compared to normal human lung tissue. The $LPA$-$LPA_2$ pathway contributes to the activation of the TGF-β pathway in pulmonary fibrosis. In some embodiments, compounds that inhibit $LPA_2$ show efficacy in the treatment of lung fibrosis. In some embodiments, compounds that inhibit both $LPA_1$ and $LPA_2$ show improved efficacy in the treatment of lung fibrosis compared to compounds which inhibit only $LPA_1$ or $LPA_2$.

The $LPA_1$ antagonist BMS-986020 was shown to significantly reduce the rate of FVC (forced vital capacity) decline in a 26-week clinical trial in IPF patients (Palmer et al., *Chest,* 2018, 154, 1061-1069).

Renal Fibrosis

LPA and $LPA_1$ are involved in the etiology of kidney fibrosis. LPA has effects on both proliferation and contraction of glomerular mesangial cells and thus has been implicated in proliferative glomerulonephritis (C. N. Inoue, et al., *Clin. Sci.* (Colch.) 1999, 96, 431-436). In an animal model of renal fibrosis [unilateral ureteral obstruction (UUO)], it was found that renal LPA receptors are expressed under basal conditions with an expression order of $LPA_2$>$LPA_3$=$LPA_1$>>$LPA_4$. This model mimics in an accelerated manner the development of renal fibrosis including renal inflammation, fibroblast activation and accumulation of extracellular matrix in the tubulointerstitium. UUO significantly induced $LPA_1$-receptor expression. This was paralleled by renal LPA production (3.3 fold increase) in conditioned media from kidney explants. Contra-lateral kidneys exhibited no significant changes in LPA release and LPA-receptors expression. This shows that a prerequisite for an action of LPA in fibrosis is met: production of a ligand (LPA) and induction of one of its receptors (the $LPA_1$ receptor) (J. P. Pradere et al., *Biochimica et Biophysica Acta,* 2008, 1781, 582-587).

In mice where the $LPA_1$ receptor was knocked out ($LPA_1$ (−/−), the development of renal fibrosis was significantly attenuated. UUO mice treated with the LPA receptor antagonist Ki16425 closely resembled the profile of $LPA_1$ (−/−) mice.

LPA can participate in intraperitonial accumulation of monocyte/macrophages and LPA can induce expression of the profibrotic cytokine CTGF in primary cultures of human fibroblasts (J. S. Koh, et al., *J. Clin. Invest.,* 1998, 102, 716-727).

LPA treatment of a mouse epithelial renal cell line, MCT, induced a rapid increase in the expression of the profibrotic cytokine CTGF. CTGF plays a crucial role in UUO-induced tubulointerstitial fibrosis (TIF), and is involved in the profibrotic activity of TGFβ. This induction was almost completely suppressed by co-treatment with the LPA-receptor antagonist Ki16425. In one aspect, the profibrotic activity of LPA in kidney results from a direct action of LPA on kidney cells involving induction of CTGF.

Hepatic Fibrosis

LPA is implicated in liver disease and fibrosis. Plasma LPA levels and serum autotaxin (enzyme responsible for LPA production) are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

Ocular Fibrosis

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA and its homologues are present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells Cardiac Fibrosis LPA is implicated in myocardial infarction and cardiac fibrosis. Serum LPA levels are increased in patients following mycocardial infarction (MI) and LPA stimulates proliferation and collagen production (fibrosis) by rat cardiac fibroblasts. Both $LPA_1$ and $LPA_3$ receptors are highly expressed in human heart tissue.

Treatment of Fibrosis

In one aspect, a compound of Formula (I), or a pharmaceutically acceptable salt thereof, is used to treat or prevent fibrosis in a mammal. In one aspect, a compound of Formulas (I), or a pharmaceutically acceptable salt thereof, is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formulas (I), or a pharmaceutically acceptable salt thereof. In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of Formula (I), or a pharmaceutically acceptable salt thereof, is administered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formula (I), or a pharmaceutically acceptable salt thereof: atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of Formula (I), or a pharmaceutically acceptable salt thereof, is administered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppressants. In one aspect, the one or more agents include B-cell antagonists. In one aspect, the one or more agents include uteroglobin.

In one aspect, a compound of Formula (I), or a pharmaceutically acceptable salt thereof, is used to treat a dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria. In one aspect, a compound of Formula (I), or a pharmaceutically acceptable salt thereof, is used to treat systemic sclerosis.

Pain

Since LPA is released following tissue injury, $LPA_1$ plays an important role in the initiation of neuropathic pain. $LPA_1$, unlike $LPA_2$ or $LPA_3$, is expressed in both dorsal root ganglion (DRG) and dorsal root neurons. Using the antisense oligodeoxynucleotide (AS-ODN) for $LPA_1$ and $LPA_1$-null mice, it was found that LPA-induced mechanical allodynia and hyperalgesia is mediated in an $LPA_1$-dependent manner. $LPA_1$ and downstream Rho-ROCK activation play a role in the initiation of neuropathic pain signaling. Pretreatment with *Clostridium botulinum* C3 exoenzyme (BoTXC3, Rho inhibitor) or Y-27632 (ROCK inhibitor) completely abolished the allodynia and hyperalgesia in nerve-injured mice. LPA also induced demyelination of the dorsal root, which was prevented by BoTXC3. The dorsal root demyelination by injury was not observed in $LPA_1$-null mice or AS-ODN injected wild-type mice. LPA signaling appears to induce important neuropathic pain markers such as protein kinase Cγ (PKCγ) and a voltage-gated calcium channel α2δ1 subunit (Caα2δ1) in an $LPA_1$ and Rho-dependent manner (M. Inoue, et al., Initiation of neuropathic pain requires lysophosphatidic acid receptor signaling, *Nat. Med.* 10 (2004) 712-718).

In one aspect, a compound of Formula (I), or a pharmaceutically acceptable salt thereof, is used in the treatment of pain in a mammal. In one aspect, the pain is acute pain or chronic pain. In another aspect, the pain is neuropathic pain.

In one aspect, a compound of Formula (I), or a pharmaceutically acceptable salt thereof, is used in the treatment of fibromylagia. In one aspect, fibromyalgia stems from the formation of fibrous scar tissue in contractile (voluntary) muscles. Fibrosis binds the tissue and inhibits blood flow, resulting in pain.

Cancer

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers. The initiation, progression and metastasis of cancer involve several concurrent and sequential processes including cell proliferation and growth, survival and anti-apoptosis, migration of cells, penetration of foreign cells into defined cellular layers and/or organs, and promotion of angiogenesis. The control of each of these processes by LPA signaling in physiological and pathophysiological conditions underscores the potential therapeutic usefulness of modulating LPA signaling pathways for the treatment of cancer, especially at the level of the LPA receptors or ATX/lysoPLD. Autotaxin (ATX) is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 µM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA receptors ($LPA_2$ and $LPA_3$) are also overexpressed in ovarian cancer cells as compared to normal ovarian surface epithelial cells. LPA stimulates Cox-2 expression through transcriptional activation and post-transcriptional enhancement of Cox-2 mRNA in ovarian cancer cells. Prostaglandins produced by Cox-2 have been implicated in a number of human cancers and pharmacological inhibition of Cox-2 activity reduces colon cancer development and decreases the size and number of adenomas in patients with familial adenomatous polyposis. LPA has also been implicated in the initiation or progression of prostate cancer, breast cancer, melanoma, head and neck cancer, bowel cancer (colorectal cancer), thyroid cancer and other cancers (Gardell et al. *Trends in Molecular Medicine*, vol. 12, no. 2, p 65-75, 2006; Ishii et al, *Annu. Rev. Biochem*, 73, 321-354, 2004; Mills et al., *Nat. Rev. Cancer*, 3, 582-591, 2003; Murph et al., *Biochimica et Biophysica Acta*, 1781, 547-557, 2008).

The cellular responses to LPA are mediated through the lysophosphatidic acid receptors. For example, LPA receptors mediate both migration of and invasion by pancreatic cancer cell lines: an antagonist of $LPA_1$ and $LPA_3$ (Ki16425) and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signaling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. The genetic or pharmacological manipulation of LPA metabolism, specific blockade of receptor signaling, and/or inhibition of downstream signal transduction pathways, represent approaches for cancer therapies.

It has been reported that LPA and other phospholipids stimulate expression of interleukin-8 (IL-8) in ovarian cancer cell lines. In some embodiments, high concentrations of IL-8 in ovarian cancer correlate with poor initial response to chemotherapy and with poor prognosis, respectively. In animal models, expression of IL-8 and other growth factors such as vascular endothelial growth factor (VEGF) is associated with increased tumorigenicity, ascites formation, angiogenesis, and invasiveness of ovarian cancer cells. In some aspects, IL-8 is an important modulator of cancer progression, drug resistance, and prognosis in ovarian cancer. In some embodiments, a compound of Formula (I) inhibits or reduces IL-8 expression in ovarian cancer cell lines.

In one aspect, a compound of Formula (I), or a pharmaceutically acceptable salt thereof, is used in the treatment of cancer. In one aspect, a compound of Formula (I), or a pharmaceutically acceptable salt thereof, is used in the treatment of malignant and benign proliferative disease. In one aspect, a compound of Formula (I), or a pharmaceutically acceptable salt thereof, is used to prevent or reduce proliferation of tumor cells, invasion and metastasis of carcinomas, pleural mesothelioma (Yamada, *Cancer Sci.*, 2008, 99(8), 1603-1610) or peritoneal mesothelioma, cancer pain, bone metastases (Boucharaba et al, *J. Clin. Invest.*, 2004, 114(12), 1714-1725; Boucharaba et al. *Proc. Natl. acad. Sci.*, 2006, 103(25) 9643-9648). In one aspect is a method of treating cancer in a mammal, the method comprising administering to the mammal a compound of Formula (I), or a pharmaceutically acceptable salt thereof, and a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The increased concentrations of LPA and vesicles in ascites from ovarian cancer patients and breast cancer effusions indicate that it could be an early diagnostic marker, a prognostic indicator or an indicator of response to therapy (Mills et al, *Nat. Rev. Cancer.*, 3, 582-591, 2003; Sutphen et al., *Cancer Epidemiol. Biomarkers Prev.* 13, 1185-1191, 2004). LPA concentrations are consistently higher in ascites samples than in matched plasma samples.

LPA pathway inhibitors (e.g. an $LPA_1$ antagonist) were recently shown to be chemopreventive anti-fibrotic agents in the treatment of hepatocellular carcinoma in a rat model (Nakagawa et al., *Cancer Cell,* 2016, 30, 879-890).

Respiratory and Allergic Disorders

In one aspect, LPA is a contributor to the pathogenesis of respiratory diseases. In one aspect the respiratory disease is asthma. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and 11-8 has been shown to exacerbate airway inflammation and airway remodeling of asthmatics. $LPA_1$, $LPA_2$ and $LPA_3$ receptors have all been shown to contribute to the LPA-induced IL-8 production. Studies cloning multiple GPCRs that are activated by LPA allowed the demonstration of the presence of mRNA for the $LPA_1$, $LPA_2$ and $LPA_3$ in the lung (J. J. A. Contos, et al., *Mol. Pharmacol.* 58, 1188-1196, 2000).

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, LPA contributes to these structural changes in the airway. In one aspect, LPA is involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In addition to the cellular responses mediated by LPA, several of the LPA signaling pathway components leading to these responses are relevant to asthma. EGF receptor upregulation is induced by LPA and is also seen in asthmatic airways (M. Amishima, et al., *Am. J. Respir. Crit. Care Med.* 157, 1907-1912, 1998). Chronic inflammation is a contributor to asthma, and several of the transcription factors that are activated by LPA are known to be involved in inflammation (Ediger et al., *Eur Respir J* 21:759-769, 2003).

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006). In one aspect, plasma exudation induced by LPA is mediated by histamine release from mast cells via one or more LPA receptors. In one aspect, the LPA receptor(s) include $LPA_1$ and/or $LPA_3$. In one aspect, a compound of Formula (I), or a pharmaceutically acceptable salt thereof, is used in the treatment of various allergic disorders in a mammal. In one aspect, a compound of Formula (I), or a pharmaceutically acceptable salt thereof, is used in the treatment of respiratory diseases, disorders or conditions in a mammal. In one aspect, a compound of Formula (I), or a pharmaceutically acceptable salt thereof, is used in the treatment of asthma in a mammal. In one aspect, a compound of Formula (I), or a pharmaceutically acceptable salt thereof, is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of Formula (I), or a pharmaceutically acceptable salt thereof, in the treatment or prevention of chronic obstructive pulmonary disease in a mammal comprising administering to the mammal at least once an effective amount of at least one compound of Formula (I), or a pharmaceutically acceptable salt thereof. In addition, chronic obstructive pulmonary disease includes, but is not limited to, chronic bronchitis or emphysema, pulmonary hypertension, interstitial lung fibrosis and/or airway inflammation, and cystic fibrosis.

Nervous System

The nervous system is a major locus for $LPA_1$ expression; there it is spatially and temporally regulated throughout brain development. Oligodendrocytes, the myelinating cells in the central nervous system (CNS), express $LPA_1$ in mammals. In addition, Schwann cells, the myelinating cells of the peripheral nervous system, also express $LPA_1$, which is involved in regulating Schwann cell survival and morphology. These observations identify important functions for receptor-mediated LPA signaling in neurogenesis, cell survival, and myelination.

Exposure of peripheral nervous system cell lines to LPA produces a rapid retraction of their processes resulting in cell rounding, which was, in part, mediated by polymerization of the actin cytoskeleton. In one aspect, LPA causes neuronal degeneration under pathological conditions when the blood-brain barrier is damaged and serum components leak into the brain (Moolenaar, Curr. Opin. Cell Biol. 7:203-10, 1995). Immortalized CNS neuroblast cell lines from the cerebral cortex also display retraction responses to LPA exposure through Rho activation and actomyosin interactions. In one aspect, LPA is associated with post-ischemic neural damage (J. Neurochem. 61, 340, 1993; J. Neurochem., 70:66, 1998).

In one aspect, provided is a compound of Formula (I), or a pharmaceutically acceptable salt thereof, for use in the treatment or prevention of a nervous system disorder in a mammal. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In one aspect, provided is a compound of Formula (I), or a pharmaceutically acceptable salt thereof, for use in the treatment or prevention of a CNS disorder in a mammal. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Cardiovascular Disorders

Cardiovascular phenotypes observed after targeted deletion of lysophospholipid receptors reveal important roles for lysophospholipid signaling in the development and maturation of blood vessels, formation of atherosclerotic plaques and maintenance of heart rate (Ishii, I. et al. Annu. Rev. Biochem. 73, 321-354, 2004). Angiogenesis, the formation of new capillary networks from pre-existing vasculature, is normally invoked in wound healing, tissue growth and myocardial angiogenesis after ischemic injury. Peptide growth factors (e.g. vascular endothelial growth factor (VEGF)) and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy (Osborne, N. and Stainier, D. Y. Annu. Rev. Physiol. 65, 23-43, 2003).

Downstream signaling pathways evoked by lysophospholipid receptors include Rac-dependent lamellipodia formation (e.g. $LPA_1$) and Rho-dependent stress-fiber formation (e.g. $LPA_1$), which is important in cell migration and adhesion. Dysfunction of the vascular endothelium can shift the balance from vasodilatation to vasoconstriction and lead to hypertension and vascular remodeling, which are risk factors for atherosclerosis (Maguire, J. J. et al., Trends Pharmacol. Sci. 26, 448-454, 2005).

LPA contributes to both the early phase (barrier dysfunction and monocyte adhesion of the endothelium) and the late phase (platelet activation and intra-arterial thrombus formation) of atherosclerosis, in addition to its overall progression. In the early phase, LPA from numerous sources accumulates in lesions and activates its cognate GPCRs ($LPA_1$ and $LPA_3$) expressed on platelets (Siess, W. Biochim. Biophys. Acta 1582, 204-215, 2002; Rother, E. et al, Circulation 108, 741-747, 2003). This triggers platelet shape change and aggregation, leading to intra-arterial thrombus formation and, potentially, myocardial infarction and stroke. In support of its atherogenic activity, LPA can also be a mitogen and motogen to VSMCs and an activator of endothelial cells and macrophages. In one aspect, mammals with cardiovascular disease benefit from LPA receptor antagonists that prevent thrombus and neointima plaque formation.

In one aspect, a compound of Formula (I), or a pharmaceutically acceptable salt thereof, is used to treat or prevent cardiovascular disease in mammal.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formula (I), or a pharmaceutically acceptable salt thereof, or pharmaceutical composition or medicament which includes a compound of Formula (I), or a pharmaceutically acceptable salt thereof.

In one aspect, provided herein are methods for reducing cardiac reperfusion injury following myocardial ischemia and/or endotoxic shock comprising administering at least once to the mammal an effective amount of at least one compound of Formula (I), or a pharmaceutically acceptable salt thereof.

In one aspect, provided herein are methods for reducing the constriction of blood vessels in a mammal comprising administering at least once to the mammal an effective amount of at least one compound of Formula (I), or a pharmaceutically acceptable salt thereof.

In one aspect, provided herein are methods for lowering or preventing an increase in blood pressure of a mammal comprising administering at least once to the mammal an effective amount of at least one compound of Formula (I), or a pharmaceutically acceptable salt thereof.

Inflammation

LPA has been shown to regulate immunological responses by modulating activities/functions of immune cells such as T-/B-lymphocytes and macrophages. In activated T cells, LPA activates IL-2 production/cell proliferation through $LPA_1$ (Gardell et al, *TRENDS in Molecular Medicine* Vol. 12 No. 2 Feb. 2006). Expression of LPA-induced inflammatory response genes is mediated by $LPA_1$ and $LPA_3$ (*Biochem Biophys Res Commun.* 363(4): 1001-8, 2007). In addition, LPA modulates the chemotaxis of inflammatory cells (*Biochem Biophys Res Commun.*, 1993, 15; 193(2), 497). The proliferation and cytokine-secreting activity in response to LPA of immune cells (*J. Imuunol.* 1999, 162, 2049), platelet aggregation activity in response to LPA, acceleration of migration activity in monocytes, activation of NF-κB in fibroblast, enhancement of fibronectin-binding to the cell surface, and the like are known. Thus, LPA is associated with various inflammatory/immune diseases.

In one aspect, a compound of Formula (I), or a pharmaceutically acceptable salt thereof, is used to treat or prevent inflammation in a mammal. In one aspect, antagonists of $LPA_1$ and/or $LPA_3$ find use in the treatment or prevention of inflammatory/immune disorders in a mammal. In one aspect, the antagonist of $LPA_1$ is a compound of Formula (I), or a pharmaceutically acceptable salt thereof.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Other Diseases, Disorders or Conditions

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formula (I), or a pharmaceutically acceptable salt thereof. In certain embodiments, the subject already has a LPA-dependent or LPA-mediated disease or condition at the time of administration, or is at risk of developing a LPA-dependent or LPA-mediated disease or condition.

In certain aspects, the activity of $LPA_1$ in a mammal is directly or indirectly modulated by the administration of (at least once) a therapeutically effective amount of at least one compound of Formula (I), or a pharmaceutically acceptable salt thereof. Such modulation includes, but is not limited to, reducing and/or inhibiting the activity of $LPA_1$. In additional aspects, the activity of LPA in a mammal is directly or indirectly modulated, including reducing and/or inhibiting, by the administration of (at least once) a therapeutically effective amount of at least one compound of Formula (I), or a pharmaceutically acceptable salt thereof. Such modulation includes, but is not limited to, reducing and/or inhibiting the amount and/or activity of a LPA receptor. In one aspect, the LPA receptor is $LPA_1$.

In one aspect, LPA has a contracting action on bladder smooth muscle cell isolated from bladder, and promotes growth of prostate-derived epithelial cell (*J. Urology,* 1999, 162, 1779-1784; *J. Urology,* 2000, 163, 1027-1032). In another aspect, LPA contracts the urinary tract and prostate in vitro and increases intraurethral pressure in vivo (WO 02/062389).

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formula (I), or a pharmaceutically acceptable salt thereof.

In certain aspects, are methods for the treatment of cystitis, including, e.g., interstitial cystitis, comprising administering at least once to the mammal a therapeutically effective amount of at least one compound of Formula (I), or a pharmaceutically acceptable salt thereof.

In accordance with one aspect, methods described herein include the diagnosis or determination of whether or not a patient is suffering from a LPA-dependent or LPA-mediated disease or condition by administering to the subject a therapeutically effective amount of a compound of Formula (I), or a pharmaceutically acceptable salt thereof, and determining whether or not the patient responds to the treatment.

In one aspect provided herein are compounds of Formula (I), pharmaceutically acceptable salts, pharmaceutically acceptable prodrugs, and pharmaceutically acceptable solvates thereof, which are antagonists of $LPA_1$, and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, ult respiratory distress syndrome, myocardial infarction, aneurysm, stroke, and cancer.

In one aspect, a compound of Formula (I), or a pharmaceutically acceptable salt thereof, is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of a compound of Formula (I), or a pharmaceutically acceptable salt thereof, in the treatment or prevention of ocular inflammation and allergic conjunctivitis, vernal keratoconjunctivitis, and papillary conjunctivitis in a mammal comprising administering at least once to the mammal an effective amount of at least one compound of Formula (I), or a pharmaceutically acceptable salt thereof.

In one aspect, presented herein is the use of a compound of Formula (I), or a pharmaceutically acceptable salt thereof, in the treatment or prevention of Sjogren disease or inflammatory disease with dry eyes in a mammal comprising administering at least once to the mammal an effective amount of at least one compound of Formula (I), or a pharmaceutically acceptable salt thereof.

In one aspect, LPA and LPA receptors (e.g. $LPA_1$) are involved in the pathogenesis of osteoarthritis (Kotani et al, *Hum. Mol. Genet.*, 2008, 77, 1790-1797). In one aspect, presented herein is the use of a compound of Formula (I), or a pharmaceutically acceptable salt thereof, in the treatment or prevention of osteoarthritis in a mammal comprising administering at least once to the mammal an effective amount of at least one compound of Formula (I), or a pharmaceutically acceptable salt thereof.

In one aspect, LPA receptors (e.g. $LPA_1$, $LPA_3$) contribute to the pathogenesis of rheumatoid arthritis (Zhao et al. *Mol. Pharmacol.*, 2008, 73(2), 587-600). In one aspect, presented herein is the use of a compound of Formula (I), or a pharmaceutically acceptable salt thereof, in the treatment or prevention of rheumatoid arthritis in a mammal comprising administering at least once to the mammal an effective amount of at least one compound of Formula (I), or a pharmaceutically acceptable salt thereof.

In one aspect, LPA receptors (e.g. $LPA_1$) contribute to adipogenesis. (Simon et al, *J. Biol. Chem.*, 2005, vol. 280, no. 15, p. 14656). In one aspect, presented herein is the use of a compound of Formula (I), or a pharmaceutically acceptable salt thereof, in the promotion of adipose tissue formation in a mammal comprising administering at least once to the mammal an effective amount of at least one compound of Formula (I), or a pharmaceutically acceptable salt thereof.

a. In Vitro Assays

The effectiveness of compounds of the present invention as $LPA_1$ inhibitors can be determined in an $LPA_1$ functional antagonist assay as follows:

Chinese hamster ovary cells overexpressing human $LPA_1$ were plated overnight (15,000 cells/well) in poly-D-lysine coated 384-well microplates (Greiner bio-one, Cat #781946) in DMEM/F12 medium (Gibco, Cat #11039). Following overnight culture, cells were loaded with calcium indicator dye (AAT Bioquest Inc, Cat #34601) for 30 minutes at 37° C. The cells were then equilibrated to room temperature for 30 minutes before the assay. Test compounds solubilized in DMSO were transferred to 384 well non-binding surface plates (Corning, Cat #3575) using the Labcyte Echo acoustic dispense and diluted with assay buffer [IX HBSS with calcium/magnesium (Gibco Cat #14025-092), 20 mM HEPES (Gibco Cat #15630-080) and 0.1% fatty acid free BSA (Sigma Cat #A9205)] to a final concentration of 0.5% DMSO. Diluted compounds were added to the cells by FDSS6000 (Hamamatsu) at final concentrations ranging from 0.08 nM to 5 μM. and were then incubated for 20 min at room temperature at which time LPA (Avanti Polar Lipids Cat #857130C) was added at final concentrations of 10 nM to stimulate the cells. The compound $IC_{50}$ value was defined as the concentration of test compound which inhibited 50% of the calcium flux induced by LPA alone. $IC_{50}$ values were determined by fitting data to a 4-parameter logistic equation (GraphPad Prism, San Diego Calif.).

b. In Vivo Assays

LPA Challenge with Plasma Histamine Evaluation.

Compound is dosed orally p.o. 2 hours to CD-1 female mice prior to the LPA challenge. The mice are then dosed via tail vein (IV) with 0.15 mL of LPA in 0.1% BSA/PBS (2 μg/μL). Exactly 2 minutes following the LPA challenge, the mice are euthanized by decapitation and the trunk blood is collected. These samples are collectively centrifuged and individual 75 μL samples are frozen at −20° C. until the time of the histamine assay.

The plasma histamine analysis was run by standard EIA (Enzyme Immunoassay) methods. Plasma samples were thawed and diluted 1:30 in 0.1% BSA in PBS. The EIA protocol for histamine analysis as outlined by the manufacturer was followed (Histamine EIA, Oxford Biomedical Research, EA #31).

The LPA used in the assay is formulated as follows: LPA (l-oleoyl-2-hydroxy-sn-glycero-3-phosphate (sodium salt), 857130P, Avanti Polar Lipids) is prepared in 0.1% BSA/PBS for total concentration of 2 μg/μL. 13 mg of LPA is weighed and 6.5 mL 0.1% BSA added, vortexed and sonicated for 1 hour until a clear solution is achieved.

V. Pharmaceutical Compositions, Formulations and Combinations

In some embodiments, provided is a pharmaceutical composition comprising a therapeutically effective amount of a compound of Formula (I), or a pharmaceutically acceptable salt thereof. In some embodiments, the pharmaceutical composition also contains at least one pharmaceutically acceptable inactive ingredient.

In some embodiments, provided is a pharmaceutical composition comprising a therapeutically effective amount of a compound of Formula (I), or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents selected from: corticosteroids (e.g., dexamethasone or fluticasone), immunosuppresants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacyl glycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g., TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the pharmaceutical composition further comprises one or more additional anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9,Met(O2) 11]-Substance P, pentoxifylline, mercaptamine bitartrate, obeticholic acid, aramchol, GFT-505, eicosapentaenoic acid ethyl ester, metformin, metreleptin, muromonab-CD3, oltipraz, IMM-124-E, MK-4074, PX-102, RO-5093151. In some embodiments, provided is a method comprising administering a compound of Formula (I), or a pharmaceutically acceptable salt thereof, to a human with a LPA-dependent or LPA-mediated disease or condition. In some embodiments, the human is already being administered one or more additional therapeutically active agents other than a compound of Formula (I), or a pharmaceutically acceptable salt thereof. In some embodiments, the method further comprises administering one or more additional therapeutically active agents other than a compound of Formula (I), or a pharmaceutically acceptable salt thereof.

In some embodiments, the one or more additional therapeutically active agents other than a compound of Formula (I), or a pharmaceutically acceptable salt thereof, are selected from: corticosteroids (e.g., dexamethasone or fluticasone), immunosuppresants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g. TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the one or more additional therapeutically active agents other than a compound of Formula (I), or a pharmaceutically acceptable salt thereof, are other anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9,Met(O2)11]-Substance P, pentoxifylline, mercaptamine bitartrate, obeticholic acid, aramchol, GFT-505, eicosapentyl ethyl ester, metformin, metreleptin, muromonab-CD3, oltipraz, IMM-124-E, MK-4074, PX-102, RO-5093151.

In some embodiments, the one or more additional therapeutically active agents other than a compound of Formula (I), or a pharmaceutically acceptable salt thereof, are selected from ACE inhibitors, ramipril, AII antagonists, irbesartan, anti-arrythmics, dronedarone, PPARα activators, PPARγ activators, pioglitazone, rosiglitazone, prostanoids, endothelin receptor antagonists, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, PDE inhibitors, PDE5 inhibitors, NO donors, *digitalis* drugs, ACE/NEP inhibitors, statins, bile acid reuptake inhibitors, PDGF antagonists, vasopressin antagonists, aquaretics, NHE1 inhibitors, Factor Xa antagonists, Factor XIIIa antagonists, anticoagulants, anti-thrombotics, platelet inhibitors, profibrotics, thrombin-activatable fibrinolysis inhibitors (TAFI), PAI-1 inhibitors, coumarins, heparins, thromboxane antagonists, serotonin antagonists, COX inhibitors, aspirin, therapeutic antibodies, GPIIb/IIIa antagonists, ER antagonists, SERMs, tyrosine kinase inhibitors, RAF kinase inhibitors, p38 MAPK inhibitors, pirfenidone, multi-kinase inhibitors, nintedanib, sorafenib.

In some embodiments, the one or more additional therapeutically active agents other than a compound of Formula (I), or a pharmaceutically acceptable salt thereof, are selected from Gremlin-1 mAb, PAI-1 mAb, Promedior (PRM-151; recombinant human Pentraxin-2); FGF21, TGFβ antagonists, αvβ6 & αvβ pan-antagonists; FAR inhibitors, TG2 inhibitors, LOXL2 inhibitors, NOX4 inhibitors, MGAT2 inhibitors, GPR120 agonists.

Pharmaceutical formulations described herein are administrable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), or a pharmaceutically acceptable salt thereof, is administered orally.

In some embodiments, the compound of Formula (I), or a pharmaceutically acceptable salt thereof, is administered topically. In such embodiments, the compound of Formula (I), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of Formula (I), or a pharmaceutically acceptable salt thereof, is administered topically to the skin.

In another aspect, the compound of Formula (I), or a pharmaceutically acceptable salt thereof, is administered by inhalation. In one embodiment, the compound of Formula (I), or a pharmaceutically acceptable salt thereof, is administered by inhalation that directly targets the pulmonary system.

In another aspect, the compound of Formula (I), or a pharmaceutically acceptable salt thereof, is formulated for intranasal administration. Such formulations include nasal sprays, nasal mists, and the like.

In another aspect, the compound of Formula (I), or a pharmaceutically acceptable salt thereof, is formulated as eye drops.

In another aspect is the use of a compound of Formula (I), or a pharmaceutically acceptable salt thereof, in the manufacture of a medicament for treating a disease, disorder or conditions in which the activity of at least one LPA receptor contributes to the pathology and/or symptoms of the disease or condition. In one embodiment of this aspect, the LPA is selected from $LPA_1$, $LPA_2$, $LPA_3$, $LPA_4$, $LPA_5$ and $LPA_6$. In one aspect, the LPA receptor is $LPA_1$. In one aspect, the disease or condition is any of the diseases or conditions specified herein.

In any of the aforementioned aspects are further embodiments in which: (a) the effective amount of the compound of Formula (I), or a pharmaceutically acceptable salt thereof, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of inhibiting the physiological activity of LPA in a mammal comprising administering a therapeutically effective amount of a compound of Formula (I) or a pharmaceutically acceptable salt thereof to the mammal in need thereof.

In one aspect, provided is a medicament for treating a LPA-dependent or LPA-mediated disease or condition in a mammal comprising a therapeutically effective amount of a compound of Formula (I), or a pharmaceutically acceptable salt thereof.

In some cases disclosed herein is the use of a compound of Formula (I), or a pharmaceutically acceptable salt thereof, in the manufacture of a medicament for the treatment of a LPA-dependent or LPA-mediated disease or condition.

In some cases disclosed herein is the use of a compound of Formula (I), or a pharmaceutically acceptable salt thereof, in the treatment or prevention of a LPA-dependent or LPA-mediated disease or condition.

In one aspect, is a method for treating or preventing a LPA-dependent or LPA-mediated disease or condition in a mammal comprising administering a therapeutically effective amount of a compound of Formula (I), or a pharmaceutically acceptable salt thereof.

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In one aspect, the LPA-dependent or LPA-mediated disease or condition is a respiratory disease or condition. In some embodiments, the respiratory disease or condition is asthma, chronic obstructive pulmonary disease (COPD), pulmonary fibrosis, pulmonary arterial hypertension or acute respiratory distress syndrome.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, the LPA-dependent or LPA-mediated disease or condition is described herein.

In one aspect, provided is a method for the treatment or prevention of organ fibrosis in a mammal comprising administering a therapeutically effective amount of a compound of Formula (I) or a pharmaceutically acceptable salt thereof to a mammal in need thereof.

In one aspect, the organ fibrosis comprises lung fibrosis, renal fibrosis, or hepatic fibrosis.

In one aspect, provided is a method of improving lung function in a mammal comprising administering a therapeutically effective amount of a compound of Formula (I), or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NAFLD, NASH), metabolic and auto-immune disease.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formula (I), or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of at least one LPA receptor, or for the treatment, prevention or amelioration of one or more symptoms of a disease or condition that would benefit from inhibition of the activity of at least one LPA receptor, are provided.

VI. General Synthesis Including Schemes

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

The compounds of Formula (I) may be prepared by the exemplary processes described in the following schemes and working examples, as well as relevant published literature procedures that are used by one skilled in the art. Exemplary reagents and procedures for these reactions appear herein after and in the working examples. Protection and deprotection in the processes below may be carried out by procedures generally known in the art (see, for example, Wuts, P. G. M., *Greene's Protective Groups in Organic Synthesis*, 5th Edition, Wiley (2014)). General methods of organic synthesis and functional group transformations are found in: Trost, B. M. et al., Eds., *Comprehensive Organic Synthesis; Selectivity, Strategy & Efficiency in Modern Organic Chemistry*, Pergamon Press, New York, N.Y. (1991); Smith, M. B. et al., *March's Advanced Organic Chemistry*; Reactions, Mechanisms, and Structure. 7th Edition, Wiley, New York, N.Y. (2013); Katritzky, A. R. et al., Eds., *Comprehensive Organic Functional Group Transformations II*, 2nd Edition, Elsevier Science Inc., Tarrytown, N.Y. (2004); Larock, R. C., *Comprehensive Organic Transformations*, $2^{nd}$ Edition, Wiley-VCH, New York, N.Y. (1999), and references therein.

Scheme 1 describes the synthesis of amino-azole methyl triazole-aryloxy cyclohexyl acids 16. A dihalo (preferably dibromo) phenyl or azine (e.g. pyridine) derivative 1 is coupled with an appropriately protected (e.g. as a tetrahydropyranyl ether) propargyl alcohol 2 under Sonogashira conditions (e.g. Alper, P. et al, WO 2008097428) to give the corresponding bromo-aryl or bromo-heteroaryl protected propargyl alcohol 3. Thermal reaction of alkyne 3 with an alkyl azide 4 (with or without an appropriate catalyst; Qian, Y. et al, *J. Med. Chem.*, 2012, 55, 7920-7939 or Boren, B. C., et al., *J. Am. Chem. Soc.*, 2008, 130, 8923-8930) provides the corresponding protected hydroxylmethyl-triazole regioisomers, from which the desired triazole regioisomer 5 can be isolated. Reaction of the bromoaryl- or bromoheteroaryl-triazoles 5 with pinacol diboronate in the presence of an appropriate transition metal catalyst (e.g. palladium, for instance Ishiyama, T. et al, *J. Org. Chem.* 1995, 60, 7508-7510) provides the corresponding pinacol boronate 6, which is then oxidized with hydrogen peroxide to give the corresponding phenol or hydroxyheteroarene 7 (e.g. Fukumoto, S. et al, WO 2012137982). Reaction of phenol/hydroxyheteroarene 7 with a 3-hydroxy cycloalkyl ester 8 under Mitsunobu reaction conditions (Kumara Swamy, K. C., *Chem. Rev.*, 2009, 109, 2551-2651) furnishes the corresponding triazole cycloalkyl ether ester 9. Deprotection of the hydoxy-triazole 9 provides the triazole alcohol 10, which is then reacted with $PBr_3$ (or another mild brominating agent such as $CBr_4/Ph_3P$) to give the corresponding bromide 11. Displacement of bromide 11 with $NaN_3$ (or other azide equivalent reagents) gives azide 12 which undergoes reduction (e.g. Staudinger reduction with Ph₃P/water) to give amine 13. Amine 13 is then reacted with an appropriate halo-azole 14 in the presence of an appropriate base (nucleophilic aromatic substitution reaction) or via Pd-catalyzed amination to give triazole amino-azoles 15, which then undergoes ester deprotection to give the desired triazole-azole aryloxy cycloalkyl acids 16.
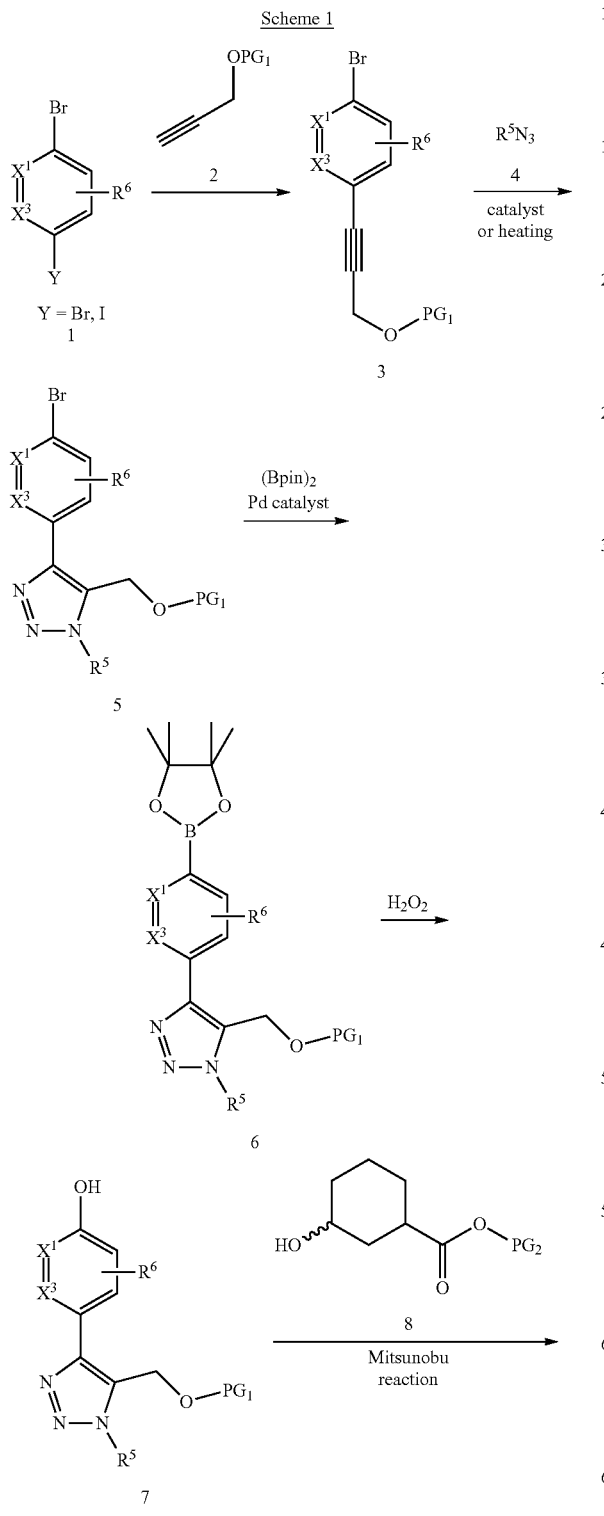
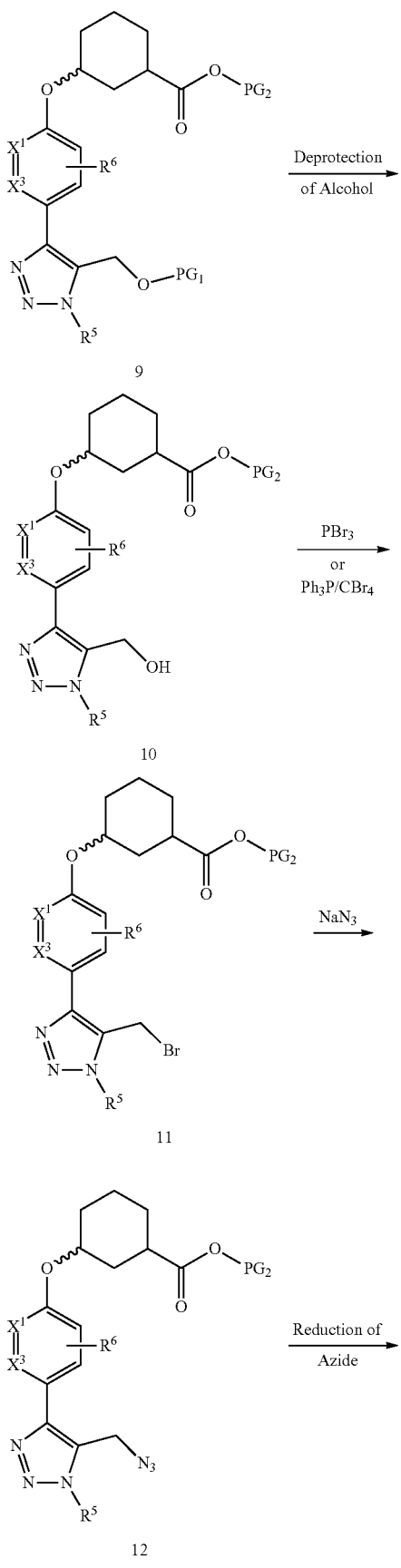

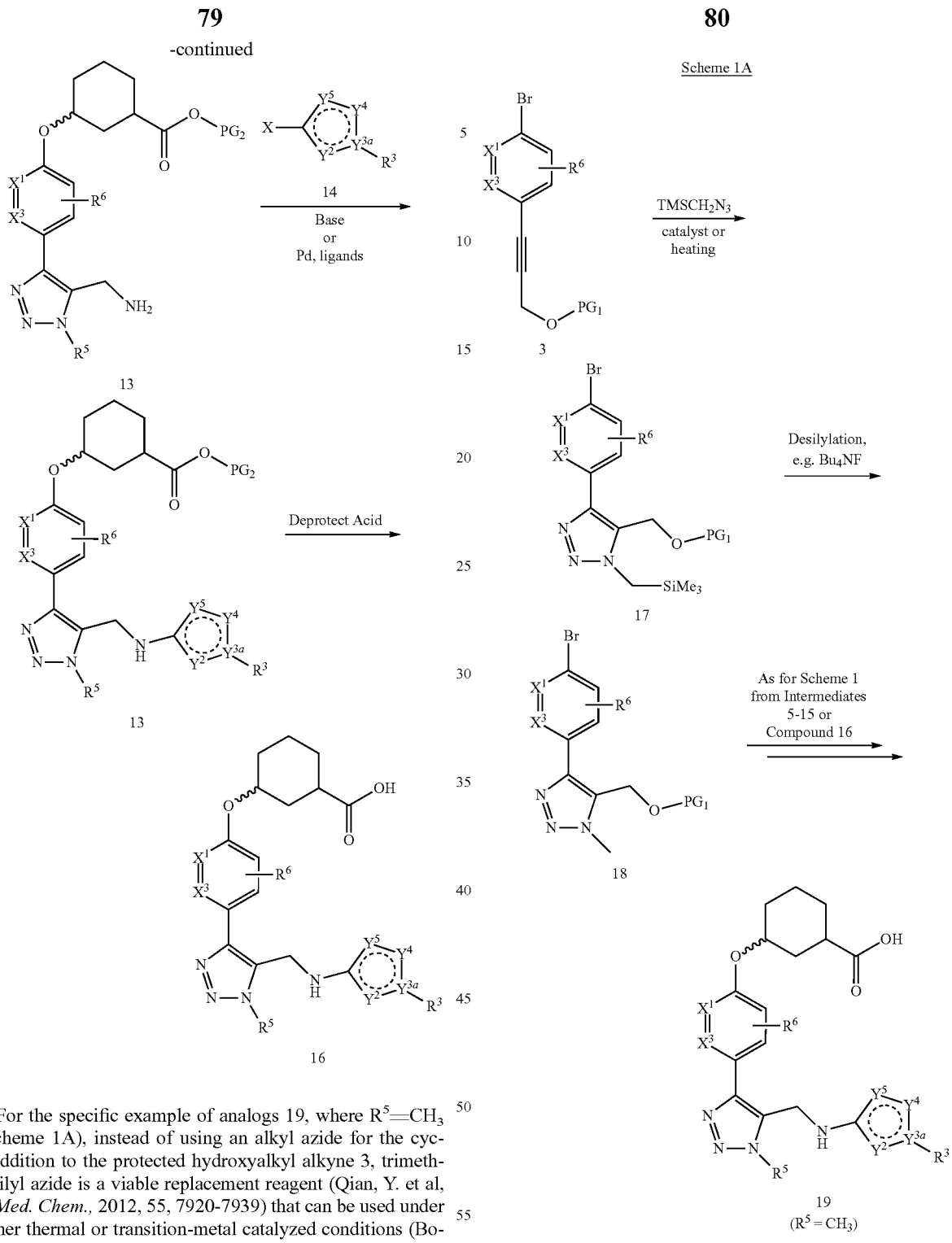

Scheme 1A

For the specific example of analogs 19, where $R^5$=$CH_3$ (Scheme 1A), instead of using an alkyl azide for the cycloaddition to the protected hydroxyalkyl alkyne 3, trimethylsilyl azide is a viable replacement reagent (Qian, Y. et al, *J. Med. Chem.*, 2012, 55, 7920-7939) that can be used under either thermal or transition-metal catalyzed conditions (Boren, B. C. et. al., *J. Am. Chem. Soc.*, 2008, 130, 8923-8930). Under these conditions, the desired triazole regioisomer 17 is obtained as the major product of the 1,3-dipolar cycloaddition reaction, and the trimethylsilyl group is subsequently removed under standard desilylation conditions (e.g. $Bu_4NF$, as in Qian, Y. et al, *J. Med. Chem.*, 2012, 55, 7920-7939) to give the methyl triazole 18. This intermediate 18 is then carried through the same synthetic sequence as described for the synthesis of amino-azole triazole acids 16 from triazole intermediate 5 in Scheme 1 to give the methyl-triazole amino-azole acids 19.

Scheme 2 describes an alternative synthetic route to the amino-pyridyl/pyrimidinyl methyl triazole-aryloxy cyclohexyl acids 16. A dihalo (preferably dibromo) phenyl or azine (e.g. pyridine) derivative 1 is coupled with propargyl alcohol under Sonogashira conditions (Alper, P. et al, WO 2008097428) to give the corresponding bromo-aryl or bromo-heteroaryl propargyl alcohol 20. Thermal reaction of alkyne 20 with an alkyl azide 4 (with or without an appropriate catalyst, Qian, Y. et al, *J. Med. Chem.*, 2012, 55, 7920-7939; Boren, B. C. et. al., *J. Am. Chem. Soc.*, 2008, 130, 8923-8930) provides the corresponding regioisomeric hydroxymethyl-triazoles, from which the desired triazole regioisomer 21 can be isolated. Triazole alcohol 21 is then reacted with PBr$_3$ to give the corresponding bromide 22. Displacement of bromide 22 with NaN$_3$ (or other azide reagents) gave azide 23 which is subjected to reduction to give amine 24. Protection of the primary amine 24 provides intermediate 25. The bromo-aryl/heteroaryl triazole 25 is then converted to the hydroxyaryl or hydroxy-heteroaryl triazole 26 via the corresponding boronate using the 2 step sequence [B(pin)$_2$/Pd-catalysis followed by treatment with H$_2$O$_2$] described in Scheme 1. Reaction of hydroxy-aryl/heteroaryl triazole 26 with a 3-hydroxy cycloalkyl ester 8 under Mitsunobu reaction conditions furnishes the corresponding triazole cycloalkyl ether ester 27. Deprotection of the aminomethyl triazole 27 provides the triazole amine 28, which is then reacted with an appropriate halo-azole 14 (as described in Scheme 1) to give the desired triazole-azole aryloxy cycloalkyl acids 16.

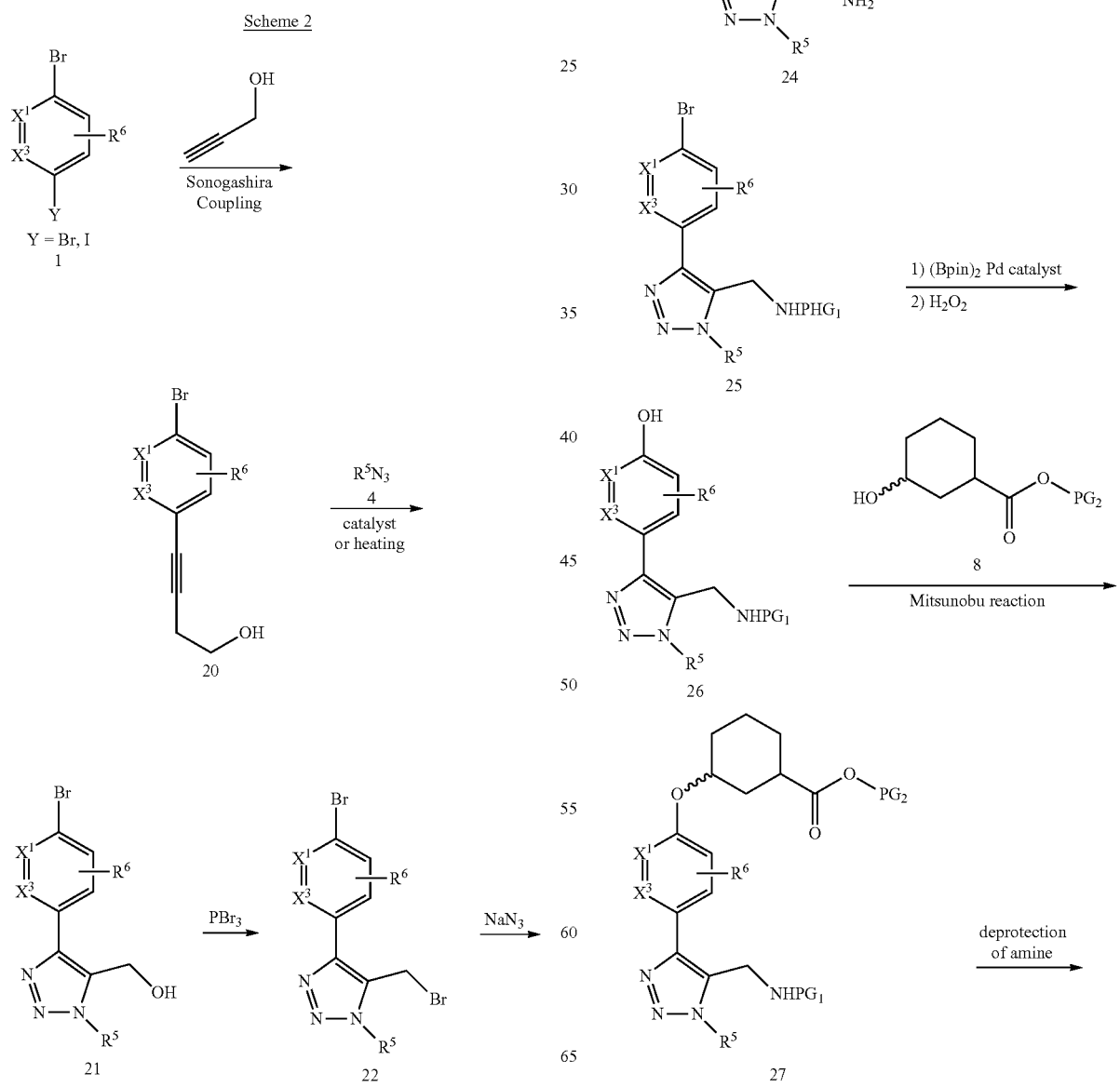

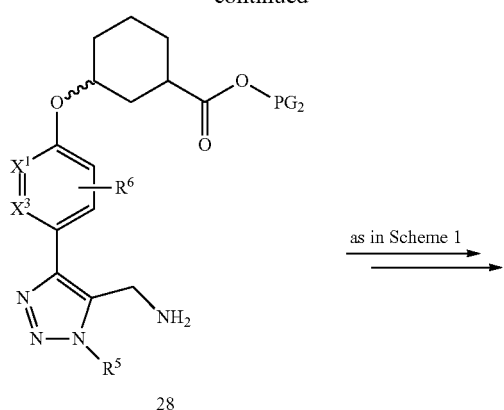

28

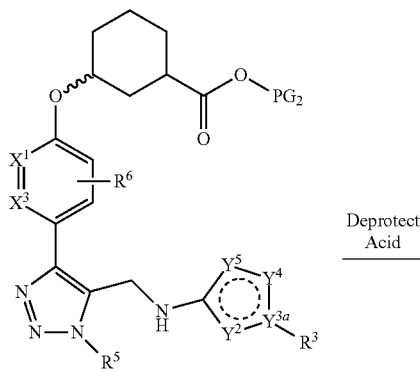

15 as in Scheme 1

Deprotect Acid

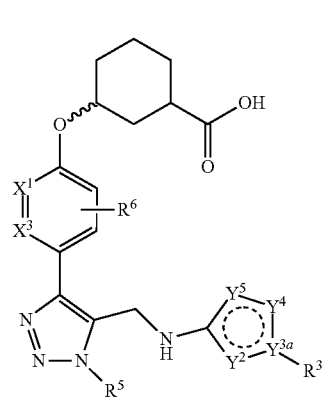

16

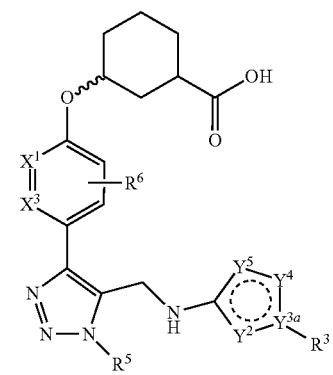

16

Scheme 3 describes an alternative synthesis of amino-azole triazole acids 16. Triazole-bromide 11 can be reacted with an appropriate amino-azole 29 either under basic conditions (nucleophilic substitution reaction of amino-azole with bromide) or under transition-metal catalysis (e.g. palladium catalyst in the presence of appropriate ligands) to give the triazole amino-azole cyclohexyl ester 15. Subsequent deprotection of ester 15 provides the triazole-amino-azole cyclohexyl acids 16.

Scheme 4 describes an alternative synthesis of amino-azole triazole acids 16. Triazole-alcohol 10 is oxidized to the triazole-aldehyde 30 (e.g. with Dess-Martin periodinane or Swern oxidation). Aldehyde 30 can then undergo reductive amination with an appropriate amino-azole 29 (e.g. with sodium triacetoxyborohydride, ref. Abdel-Magid, A. F., et. al., $J.$ $Org.$ $Chem.$ 1996, 61, 3849-3862) to give the triazole amino-azole cyclohexyl ester 15. Subsequent deprotection of ester 15 provides the triazole-amino-azole cyclohexyl acids 16.

Scheme 3

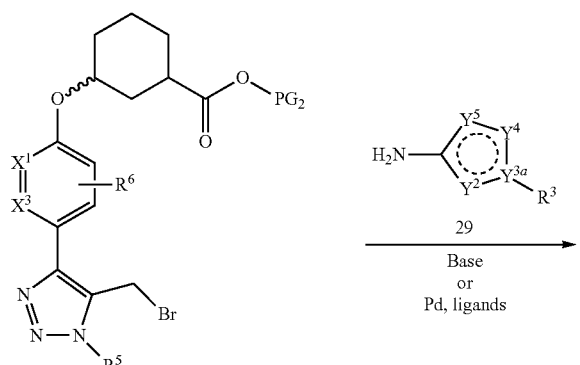

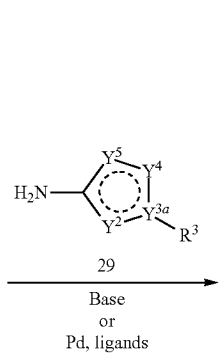
29
Base or Pd, ligands

Scheme 4

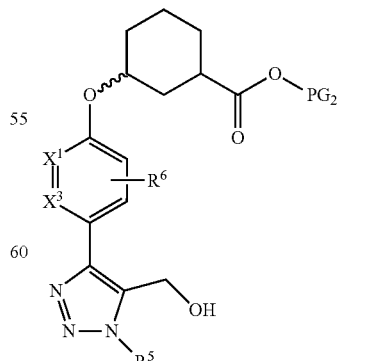

Oxidation

11

10

-continued

Scheme 5

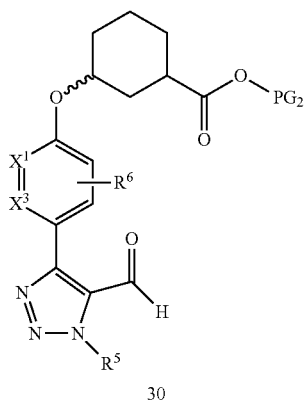
30

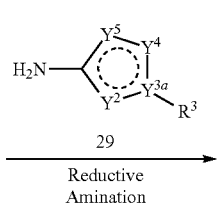
29
Reductive Amination

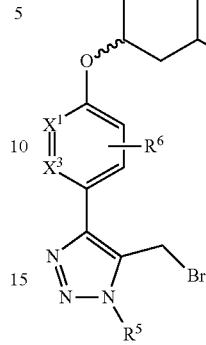
11

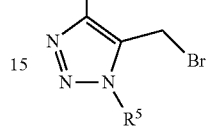

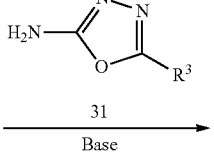
31
Base

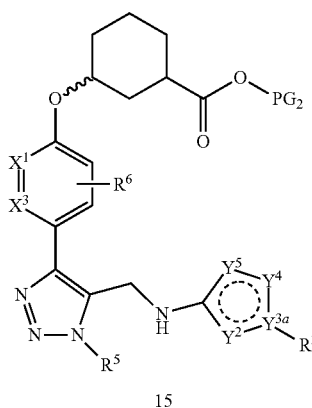
15

Deprotect
Acid

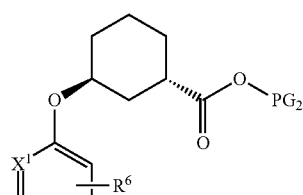
+
32

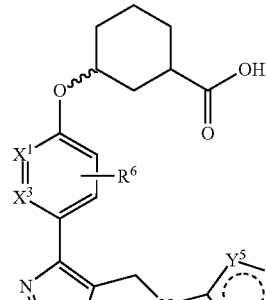
16

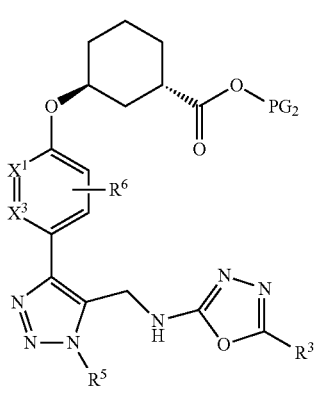
33

Deprotection of Acid

Scheme 5 describes the case where an appropriately substituted 2-amino-1,3,4-oxadiazole is deprotonated with a base (e.g. sodium hydride), which subsequently undergoes reaction with triazole bromide 11. In addition to the direct displacement of the bromide by the 2-amino-1,3,4-oxadiazole to give the triazole-amino-oxadiazole 33, the product resulting from reaction at the nitrogen at the 3-position of the oxadiazole (the triazole 1,3,4-oxadiazol-2(3H)-imine 32) is also generated. Both the triazole 2-amino-1,3,4-oxadiazole esters 33 as well as the triazole 1,3,4-oxadiazol-2(3H)-imine esters 32 are then deprotected to give the corresponding triazole 2-amino-1,3,4-oxadiazole cyclohexyl acids 35 as well as the triazole 1,3,4-oxadiazol-2(3H)-imine cyclohexyl acids 34.

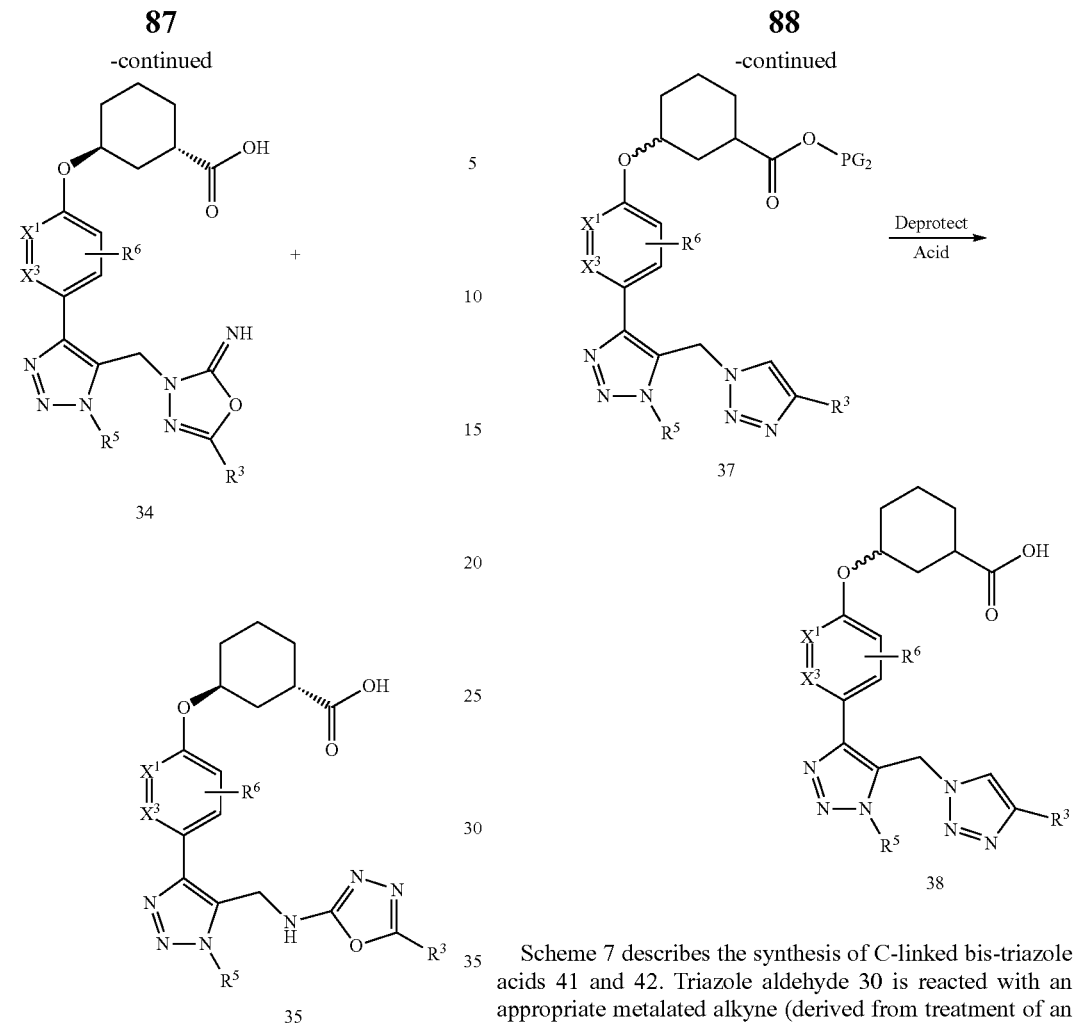

Scheme 6 describes the synthesis of N-linked bis-triazole cyclohexyl acids 37. Triazole azide 12 undergoes Cu-mediated [3+2] cycloaddition (e.g. Haldon, E., *Org. Biomol. Chem.*, 2015, 13, 9528-9550) with an appropriately substituted alkyne 36 to give the 1,2,3-triazole ester 37, which is deprotected to provide bis-triazole cyclohexyl acids 37.

Scheme 7 describes the synthesis of C-linked bis-triazole acids 41 and 42. Triazole aldehyde 30 is reacted with an appropriate metalated alkyne (derived from treatment of an alkyne 39 with an appropriate base, e.g. n-BuLi or t-BuLi) to give the triazole alkyne-alcohol 39. The triazole alkyne-alcohol is then reacted with an appropriate alkyl/aryl azide to give the corresponding 1,2,3-triazole alcohol 40. Deprotection of bis-triazole cyclohexyl ester furnishes the hydroxyl-bis-triazole cyclohexyl acids 41. Alternatively, the 1,2,3-triazole alcohol 40 can be deoxygenated (e.g. Herrmann, J. M. et al, *Eur. J. Org. Chem.*, 2013, 7017-7027), after which deprotection of the bis-triazole cyclohexyl ester intermediate provides bis-triazole cyclohexyl acids 42.

Scheme 6

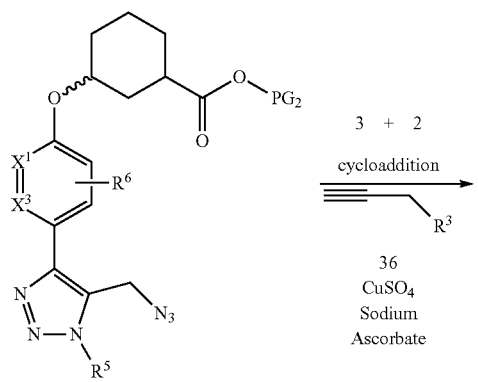

Scheme 7

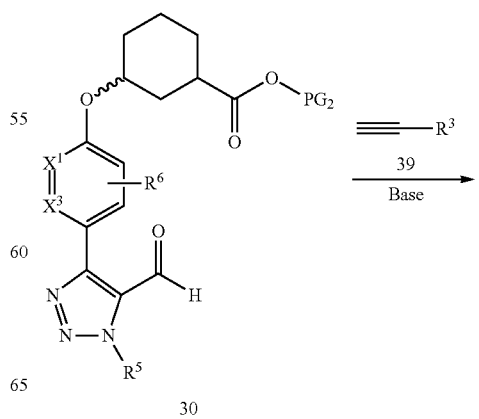

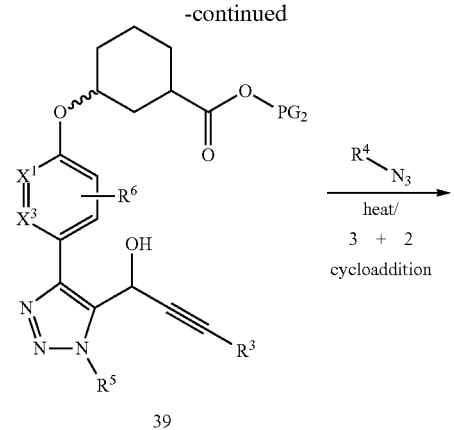

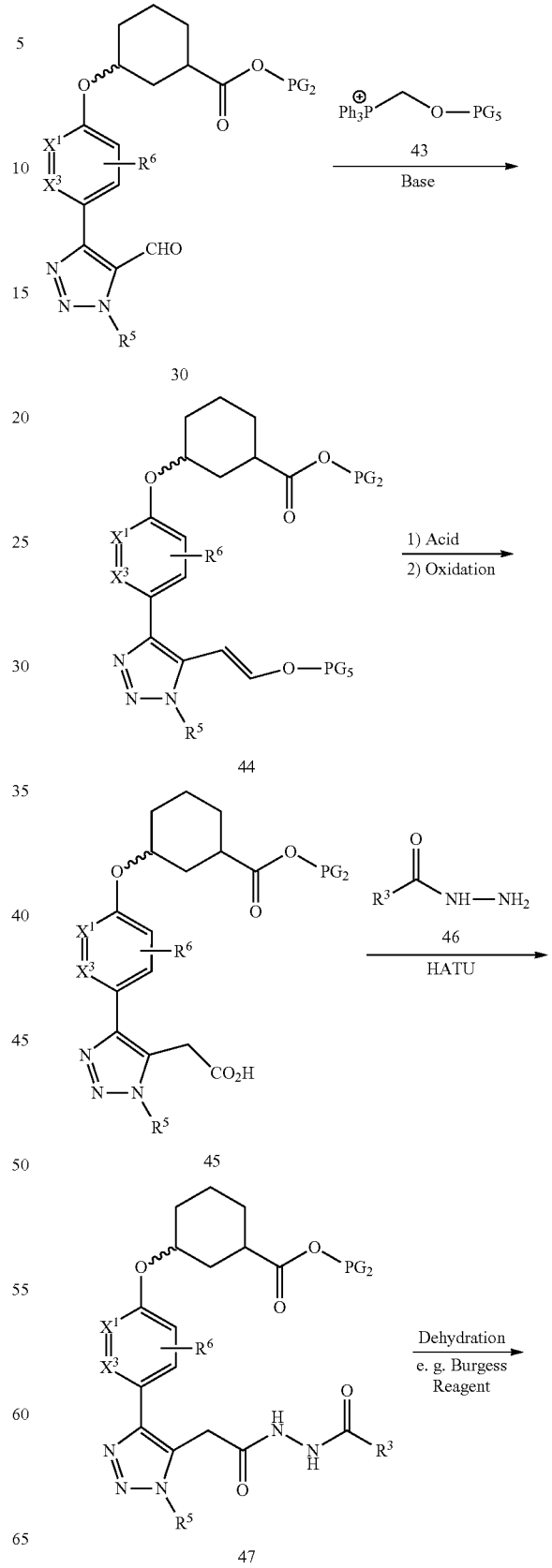

Scheme 8

Scheme 8 describes the synthesis of triazole 1,2,4-oxadiazole cyclohexyl acids 49. Triazole aldehyde 30 is reacted with a Wittig reagent (e.g. 43) to give the triazole enol ether 44, which undergoes acid-mediated hydrolysis to give the homologated aldehyde of 30, followed by oxidation to the corresponding acid 45 (e.g. with $NaClO_2$, ref. Lindgren, B. O., Acta Chem. Scand. 1973, 27, 888). Coupling of triazole acid 45 with an appropriate hydrazide 46 (e.g. with HATU) provides the triazole acyl hydrazide 47, which undergoes reaction with an appropriate dehydrating agent (e.g. Burgess reagent) to give the triazole 1,2,4-oxadiazole 48. Deprotection of triazole ester 48 furnishes the triazole 1,2,4-oxadiazole cyclohexyl acids 49.

91
-continued

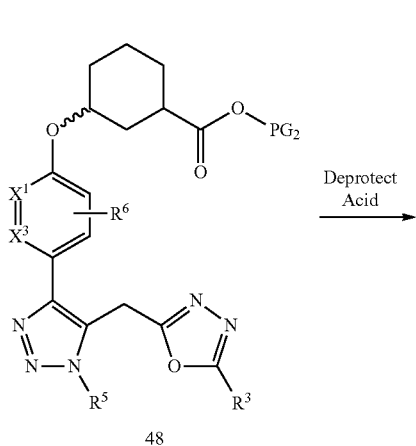
48

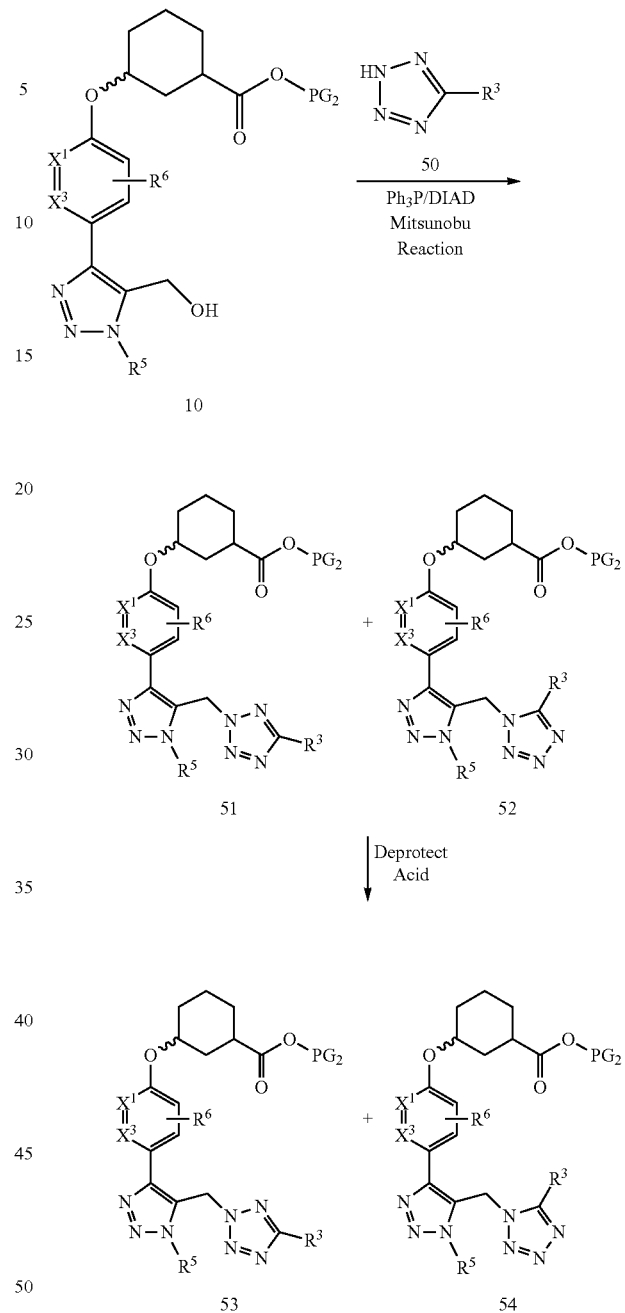

92
-continued

Scheme 9 describes the synthesis of tetrazole cyclohexyl acids 53 and 54. A nitrile ($R^3$=alkyl, aryl, heteroaryl) is reacted under microwave conditions with NaN3 in the presence of a Lewis acid (e.g. $ZnBr_2$) to provide the corresponding substituted tetrazoles 50. Tetrazole 50 is reacted with cyclohexyl ester triazole alcohol 10 under Mitsunobu conditions to provide the regioisomeric tetrazoles 51 and 52. Deprotection of cyclohexyl esters 51 and 52 provide the regioisomeric tetrazole-triazole cyclohexyl acids 53 and 54.

Scheme 10 describes the synthesis of heteroaryloxy-triazole-pyridyloxy-cyclohexane containing acids 56. The cyclohexanecarboxylic acid alkyl ester 10 is deprotected to give the corresponding hydroxymethyl triazole-cyclohexyl carboxylic acid 55. $S_NAr$ reaction of the anion of 55 with heteroaryl halide 14 and then acidification provides the desired heteroaryloxy-methyl triazole-pyridyloxy-cyclohexanecarboxylic acids 56.

Scheme 9

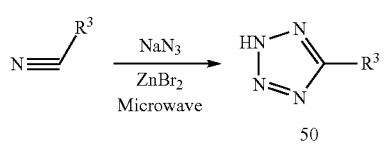
50

Alternatively, the ester-alcohol 10 can react with heteroaryl halide 14 under transition metal-catalysis conditions (e.g. Pd-ligand-mediated) to give the heteroaryloxy methyl triazole 57, which upon ester deprotection and then acidification provides the desired heteroaryloxy-methyl triazole-pyridyloxy-cyclohexanecarboxylic acids 56.

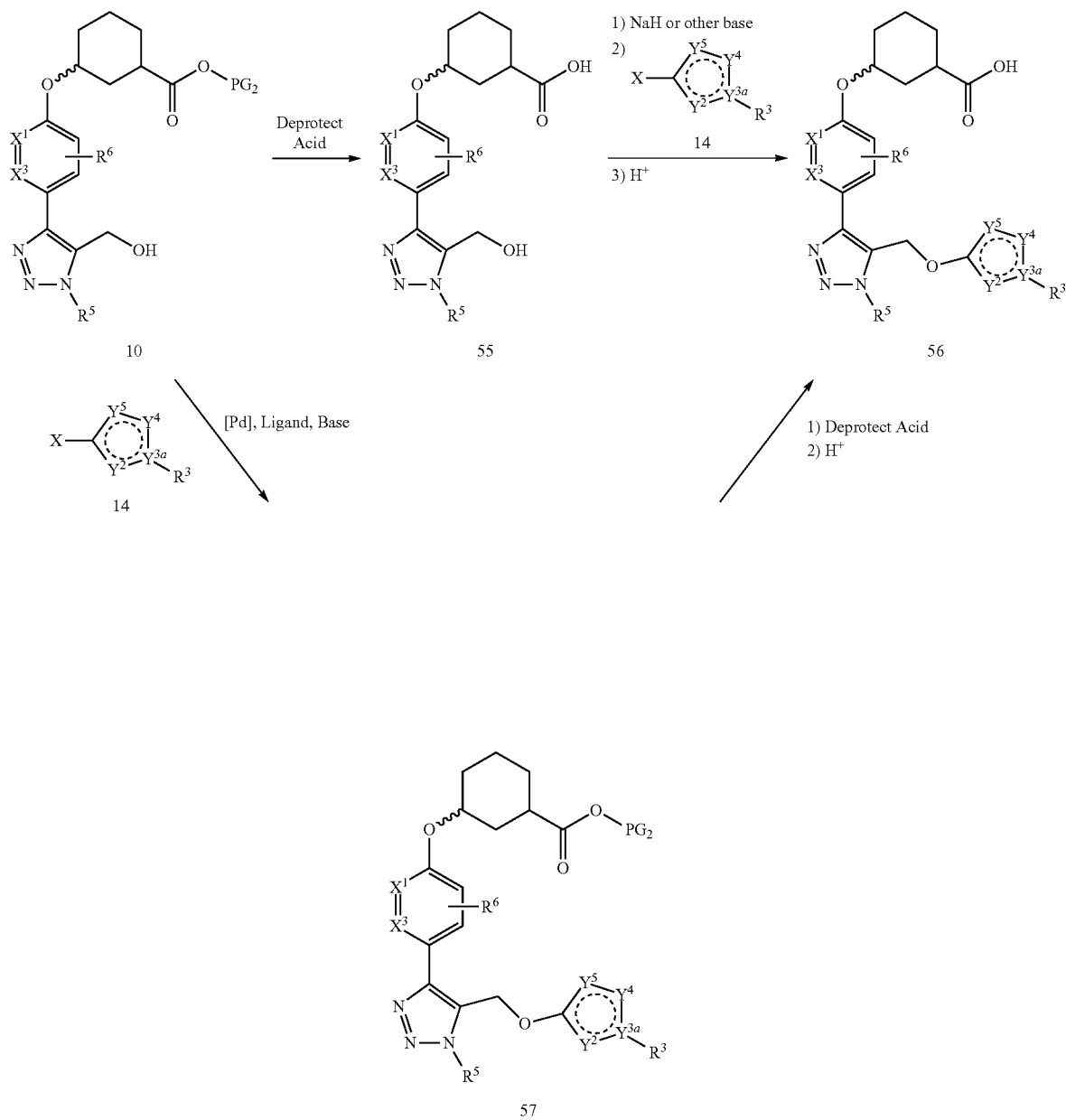

Scheme 11 describes an alternate synthesis of heteroaryloxy-triazole-pyridyloxy-cyclohexane containing acids 56. The ester-alcohol 10 can react with heteroaryl hydroxy compounds 14 under Mitsunobu reaction conditions to give the heteroaryloxy methyl triazole 57, which upon ester deprotection and then acidification provides the desired heteroaryloxy-methyl triazole-pyridyloxy-cyclohexanecarboxylic acids 56.

Scheme 11

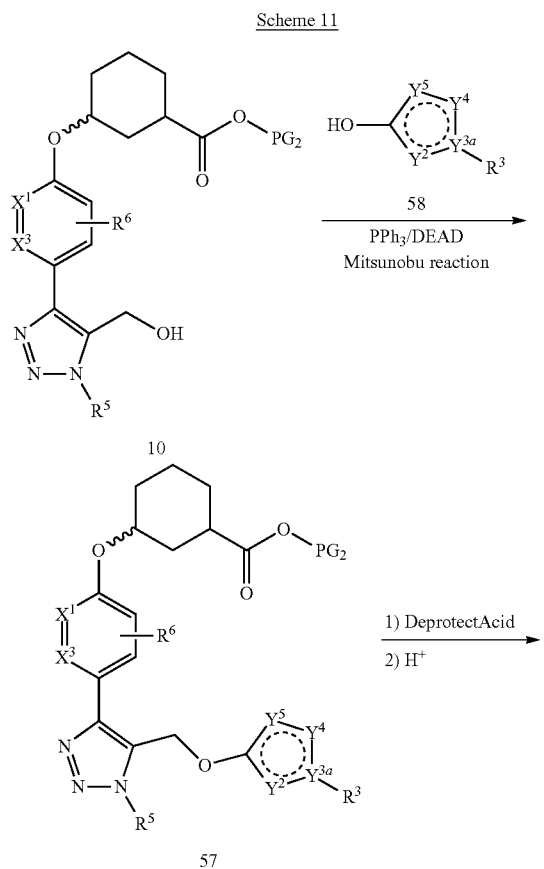

Scheme 12

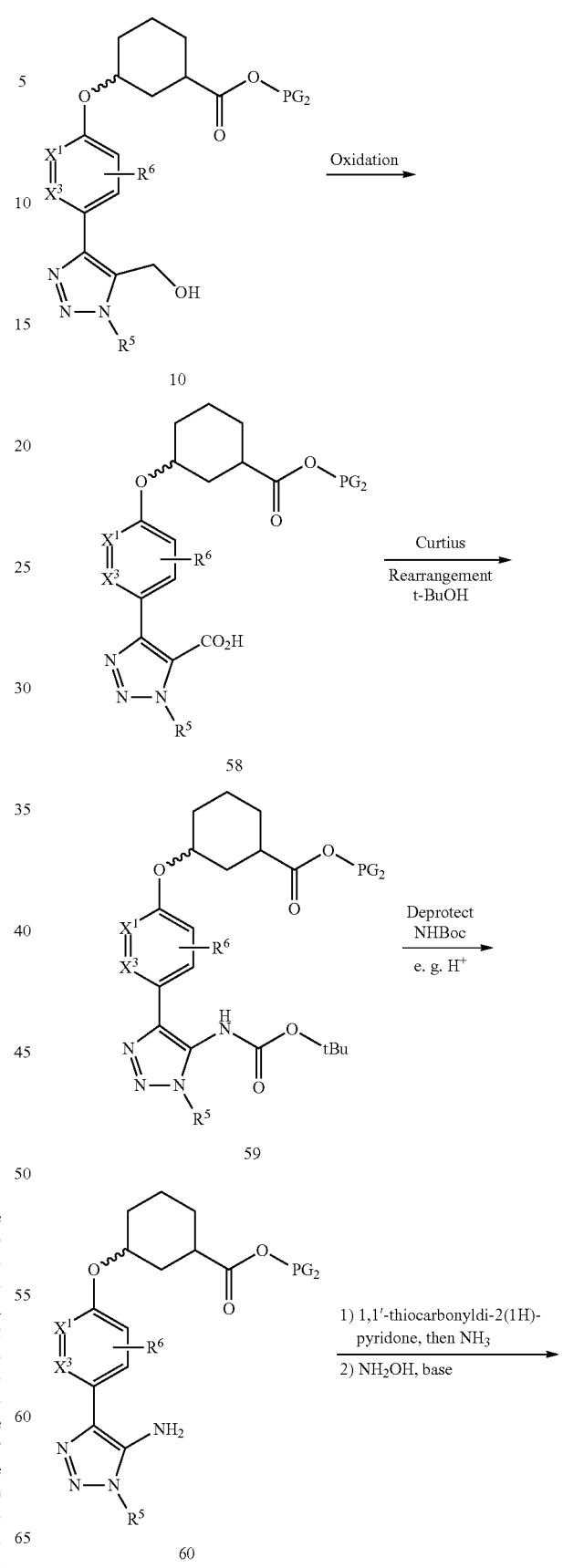

Scheme 12 describes the synthesis of triazole amino-azole acids 63. Cyclohexyl ether triazole-alcohol 10 is oxidized to the carboxylic acid 58 (e.g. directly to the acid with pyridinium dichromate or via a 2-step procedure via the aldehyde [Swern oxidation or Dess-Martin periodinane followed by $NaClO_2$ oxidation to the acid, e.g. Lindgren, B. O., *Acta Chem. Scand.* 1973, 27, 888]). Curtius rearrangement of 58 in the presence of t-butanol provides the triazole NH-Boc-carbamate 59. Deprotection of the triazole NH-Boc carbamate 59 under acidic conditions provides the triazole amine 60. The triazole-amine 60 is converted to the hydroxy guanidine 61 in two steps. Coupling of hydroxy guanidine 60 with an appropriate carboxylic acid (e.g. with HATU) followed by acid-mediated dehydration with heating provides the amino oxadiazole 62. Deprotection of ester 62 furnishes the desired triazole-amino-oxadiazole cyclohexyl acids 63.

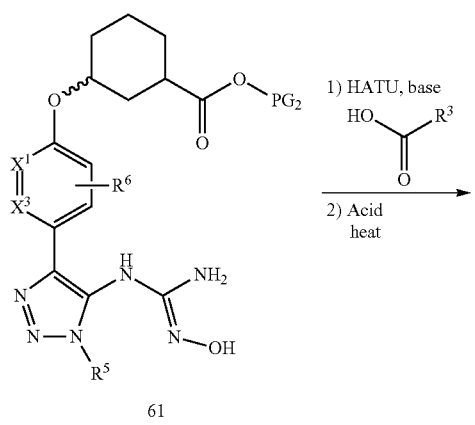

61

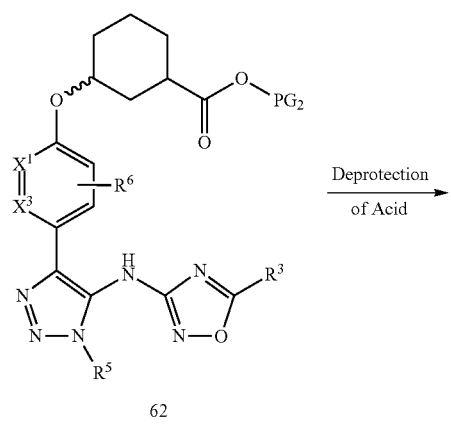

62

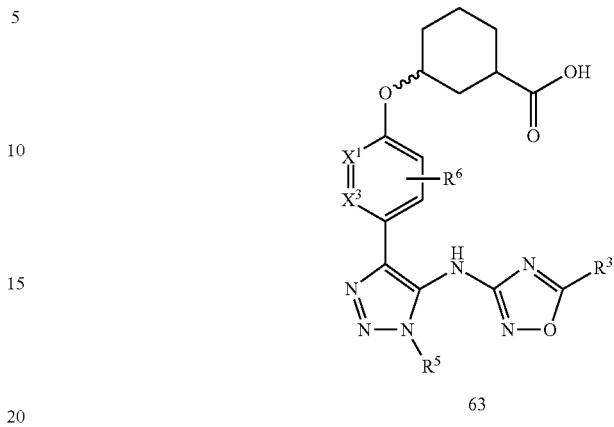

63

Scheme 13 describes the synthesis of triazole amino-oxadiazole acids 65 and 68. Triazole-amine 60 is reacted with phosgene followed by the addition of an appropriately substituted hydrazide. Subsequent dehydration (e.g. with T3P) with heating provides the triazole amino-oxadiazole 64. Deprotection of ester 63 furnishes the desired triazole-amino-oxadiazole cyclohexyl acids 65. Alternatively, the triazole-amine 60 undergoes a transition metal-catalyzed cross-coupling reaction with an appropriately substituted halo-oxadiazole 66 to give amino-oxadiazole 67, which then undergoes ester deprotection to give the desired triazole-amino-oxadiazole cyclohexyl acids 68.

Scheme 13

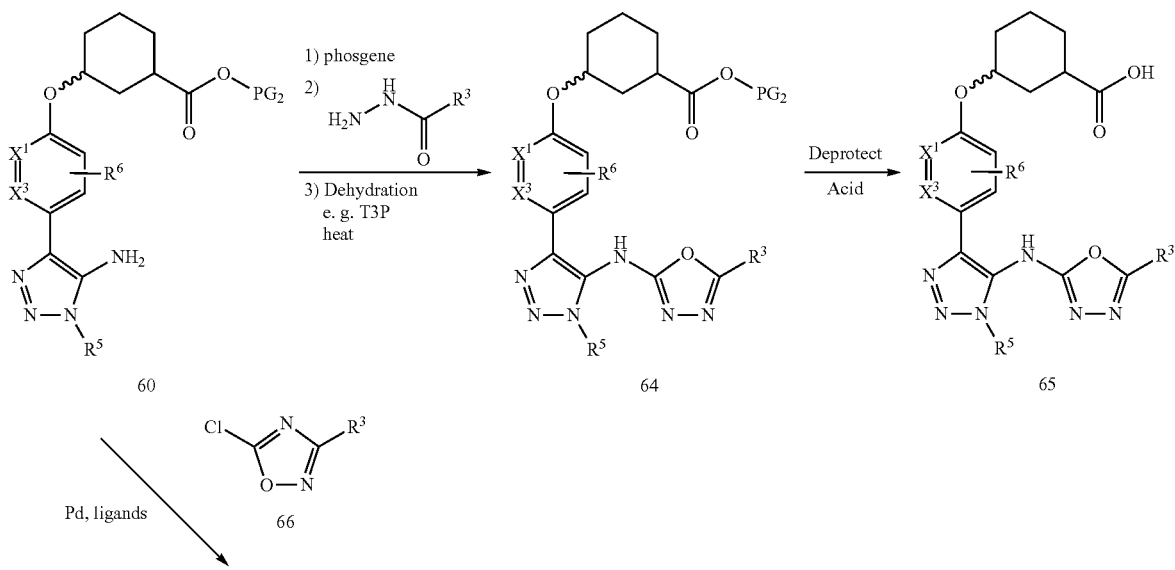

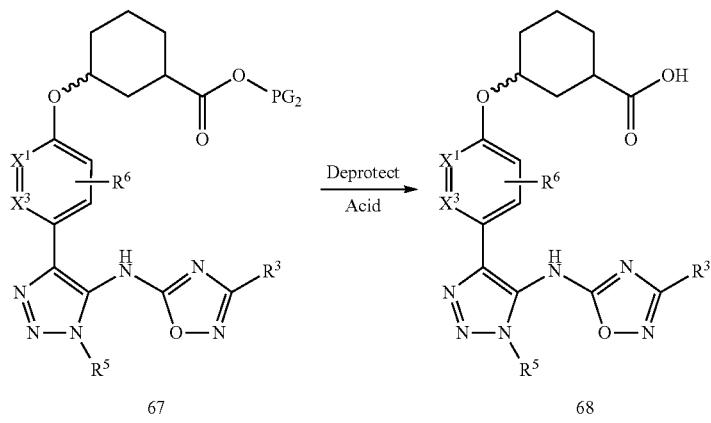

Scheme 14 describes the synthesis of triazole-tetrazole cyclohexyl acids 71 and 72. Reaction of triazole bromide 11 with cyanide provides nitrile 69, which is then subjected to a dialkyl tin oxide-mediated cycloaddition reaction with TMSN₃ (Wittenberger, S., et al, *J. Org. Chem.,* 1993, 58, 4139-4141) to provide triazole-tetrazole 70. Reaction of tetrazole 70 with an appropriate alcohol under Mitsunobu reaction conditions followed by ester deprotection provides the desired triazole-alkyl-tetrazole cyclohexyl acids 71. Reaction of tetrazole 70 with aryl or heteroaryl boronic acids under Chan-Lam cross-coupling reaction conditions (Qiao, J. X., et al, *Synthesis,* 2011, 829-856) followed by ester deprotection provides the desired triazole-aryl/heteroaryl-tetrazole cyclohexyl acids 72.

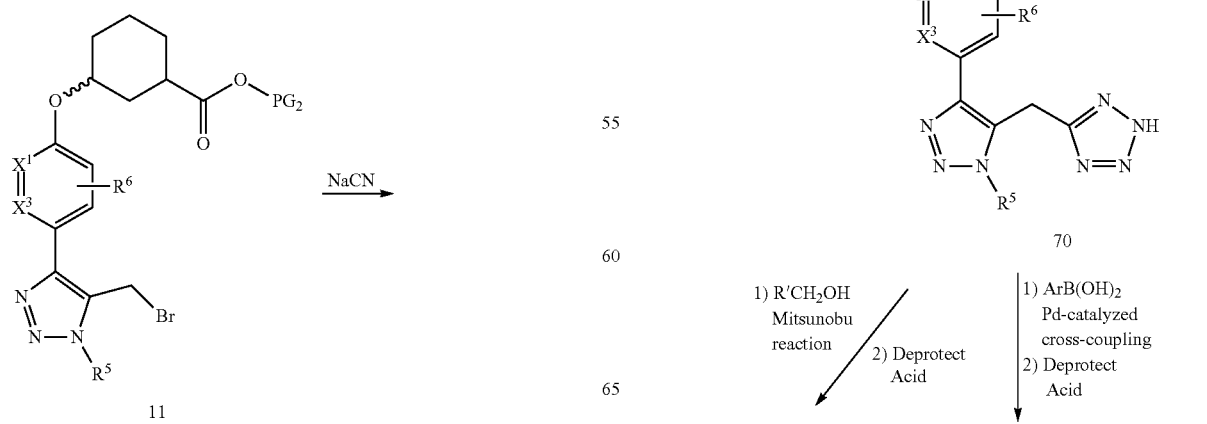

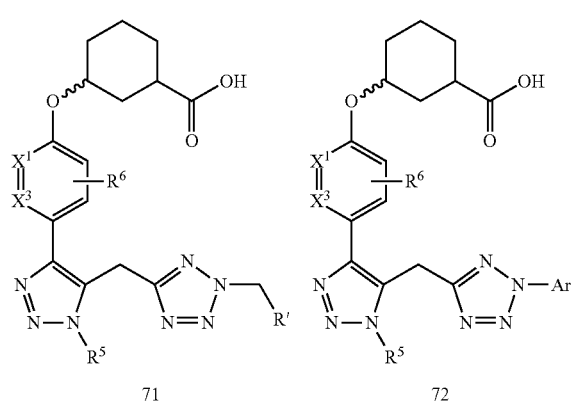

71        72

Scheme 15 describes the synthesis of triazole-amino-tetrazole cyclohexyl acids 75 and 76. Reductive amination (e.g. with NaBH(OAc)₃) of triazole aldehyde 30 with protected amino tetrazole 73 followed by deprotection of the tetrazole provides triazole amino-tetrazole 74. Reaction of tetrazole 74 with an appropriate alcohol under Mitsunobu reaction conditions followed by ester deprotection provides the desired triazole-alkyl-tetrazole cyclohexyl acids 75. Reaction of tetrazole 74 with aryl or heteroaryl boronic acids under Chan-Lam cross-coupling reaction conditions (Qiao, J. X., et al, *Synthesis,* 2011, 829-856) followed by ester deprotection provides the desired triazole-aryl/heteroaryl-tetrazole cyclohexyl acids 76.

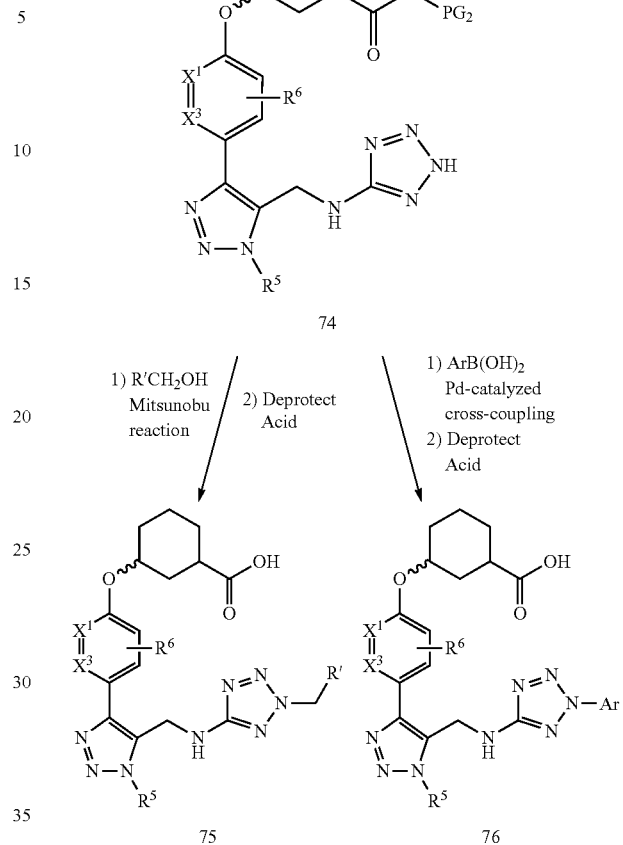

75        76

Scheme 16 describes the synthesis of triazole-alkoxy-tetrazole cyclohexyl acids 79. Triazole bromide 11 is reacted with 5-(methylthio)-2H-tetrazole 77 to give the triazole-tetrazole sulfide, which undergoes oxidation (e.g. Oxone®) to the tetrazole sulfone 78. Deprotection of the ester 78 followed by displacement of the sulfone with an appropriate alkoxide (from treatment of alcohol $R^3$—OH with an appropriate base, e.g. KN(TMS)₂) provides the desired triazole-alkoxy-tetrazole cyclohexyl acids 79.

Scheme 15

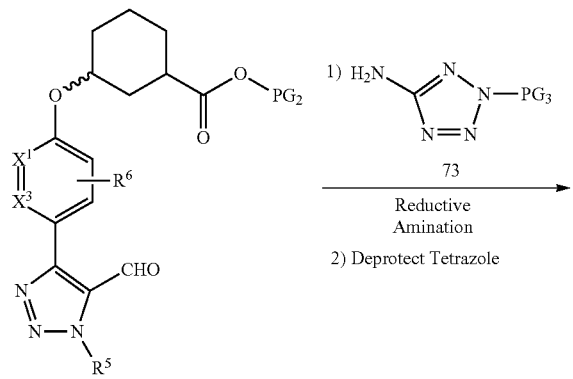

30

Scheme 16

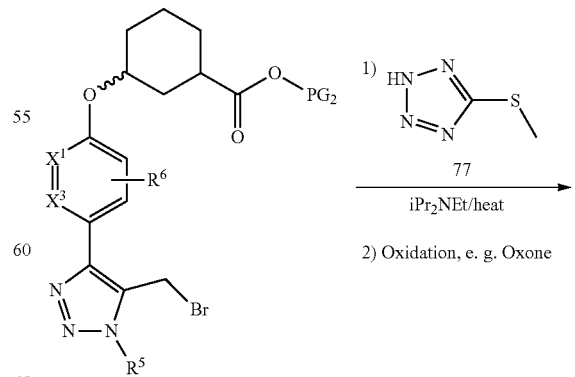

11

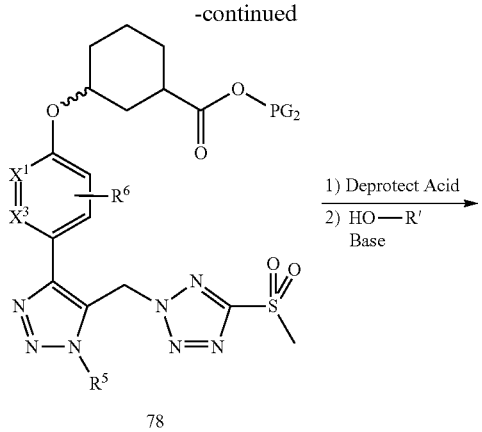

78

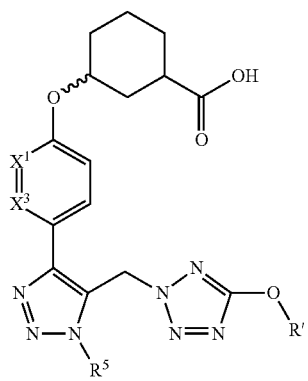

79

VII. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

Microwave reactions were carried out using a 400W Biotage Initiator instrument in microwave reaction vessels under microwave (2.5 GHz) irradiation.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

In the examples where $^1$H NMR spectra were collected in $d_6$-DMSO, a water-suppression sequence is often utilized. This sequence effectively suppresses the water signal and any proton peaks in the same region usually between 3.30-3.65 ppm which will affect the overall proton integration.

The term HPLC refers to a Shimadzu high performance liquid chromatography instrument with one of following methods:

HPLC-1: Sunfire C18 column (4.6×150 mm) 3.5 μm, gradient from 10 to 100% B:A for 12 min, then 3 min hold at 100% B.

Mobile phase A: 0.05% TFA in water:CH$_3$CN (95:5)

Mobile phase B: 0.05% TFA in CH$_3$CN:water (95:5)

TFA Buffer pH=2.5; Flow rate: 1 mL/min; Wavelength: 254 nm, 220 nm.

HPLC-2: XBridge Phenyl (4.6×150 mm) 3.5 μm, gradient from 10 to 100% B:A for 12 min, then 3 min hold at 100% B.

Mobile phase A: 0.05% TFA in water:CH$_3$CN (95:5)

Mobile phase B: 0.05% TFA in CH$_3$CN:water (95:5)

TFA Buffer pH=2.5; Flow rate: 1 mL/min; Wavelength: 254 nm, 220 nm.

HPLC-3: Chiralpak AD-H, 4.6×250 mm, 5 μm.

Mobile Phase: 30% EtOH-heptane (1:1)/70% CO$_2$

Flow rate=40 mL/min, 100 Bar, 35° C.; Wavelength: 220 nm

HPLC-4: Waters Acquity UPLC BEH C18, 2.1×50 mm, 1.7-μm particles;

Mobile Phase A: 5:95 CH$_3$CN:water with 10 mM NH$_4$OAc;

Mobile Phase B: 95:5 CH$_3$CN:water with 10 mM NH$_4$OAc;

Temperature: 50° C.; Gradient: 0-100% B over 3 min, then a 0.75-min hold at 100% B;

Flow: 1.11 mL/min; Detection: UV at 220 nm.

HPLC-5: Waters Acquity UPLC BEH C18, 2.1×50 mm, 1.7-μm particles;

Mobile Phase A: 5:95 CH$_3$CN:water with 0.1% TFA;

Mobile Phase B: 95:5 CH$_3$CN:water with 0.1% TFA;

Temperature: 50° C.; Gradient: 0-100% B over 3 min, then a 0.75-min hold at 100% B; Flow: 1.11 mL/min; Detection: UV at 220 nm.

Intermediate 1. Isopropyl (1 S,3S)-3-((6-(5-(hydroxymethyl)-1-methyl-1H-1,2,3-triazol-4-yl)-2-methylpyridin-3-yl)oxy)cyclohexane-1-carboxylate

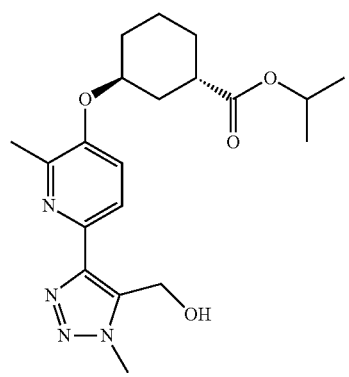 [SMILES: Cc1nc(-c2nnn(C)c2CO)ccc1O[C@H]1CCC[C@H](C(=O)OC(C)C)C1]

Intermediate 1A. 3-Bromo-2-methyl-6-(3-((tetrahydro-2H-pyran-2-yl)oxy)prop-1-yn-1-yl)pyridine

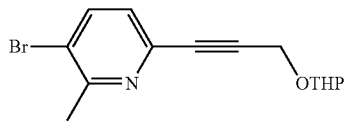

To a solution of 2,5-dibromo-6-methyl-pyridine (5 g, 21.11 mmol) and 2-(prop-2-yn-1-yloxy) tetrahydro-2H-pyran (4.44 g, 31.7 mmol) in MeCN (42.2 mL) was added Et$_3$N (8.83 mL, 63.3 mmol). The solution was degassed under N$_2$, then (Ph$_3$P)$_2$PdCl$_2$ (0.74 g, 1.06 mmol) and CuI (0.20 g, 1.06 mmol) were added. The reaction was stirred at RT for 14 h, after which the reaction mixture was filtered through a plug of Celite® and the plug was washed with EtOAc (2×10 mL). The combined filtrates were concentrated in vacuo; the residue was chromatographed (SiO$_2$; continuous gradient from 0% to 100% EtOAc in hexanes over 20 min) to give the title compound as a white solid (6.0 g, 20.3 mmol, 96% yield). $^1$H NMR (400 MHz, CDCl$_3$) δ 8.65 (d, J=2.0 Hz, 1H), 7.80 (dd, 2.3 Hz, 1H), 7.35 (dd, J=8.4, 0.4 Hz, 1H), 4.91 (t, J=3.3 Hz, 1H), 4.61-4.45 (m, 2H), 3.98-3.81 (m, 1H), 3.66-3.44 (m, 1H), 1.92-1.73 (m, 2H), 1.72-1.52 (m, 2H). LCMS, [M+H]$^+$=298.0.

Intermediate 1B. 3-Bromo-2-methyl-6-(1-methyl-5-(((tetrahydro-2H-pyran-2-yl)oxy)methyl)-1H-1,2,3-triazol-4-yl)pyridine

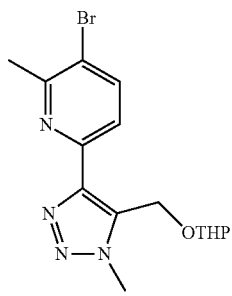

A solution of Intermediate 1A (6.0 g, 20.3 mmol) in toluene (20 mL) and TMSCH$_2$N$_3$ (7.85 g, 60.8 mmol) was heated at 90° C. under Ar for 15 h, then was cooled to RT. Volatiles were removed in vacuo and the residue was dissolved in THF (20 mL). To the mixture was added TBAF (20.3 mL of a 1 M solution in THF, 20.3 mmol) at 0° C. After stirring for 10 min, the reaction was complete as determined by analytical HPLC. Volatiles were removed in vacuo and the residue was chromatographed (SiO$_2$; continuous gradient from 0% to 100% EtOAc in hexanes over 20 min) to give the title compound (2.1 g, 29% yield) as a white solid. $^1$H NMR (400 MHz, CDCl$_3$) δ 7.85 (d, J=8.4 Hz, 1H), 7.13 (d, J=8.4 Hz, 1H), 6.03 (br. s., 1H), 5.39-5.23 (m, 4H), 4.81-4.76 (m, 1H), 4.17 (s, 3H), 3.91 (ddd, J11.3, 7.9, 3.3 Hz, 1H), 3.65-3.48 (m, 1H), 2.54 (s, 3H), 1.88-1.68 (m, 2H), 1.56 (br. s., 2H).

Intermediate 1C. 2-methyl-6-(1-methyl-5-(((tetrahydro-2H-pyran-2-yl)oxy)methyl)-1H-1,2,3-triazol-4-yl)pyridin-3-ol

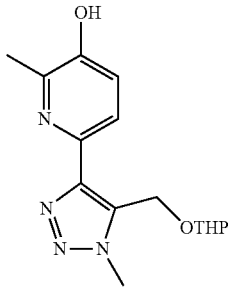

To a degassed solution (sparged with Ar 3X) of Intermediate 1B (213 mg, 0.60 mmol), bis(pinacolato)diboron (230 mg, 0.91 mmol) and KOAc (178 mg, 1.81 mmol) in THF was added Pd(dppf)Cl$_2$ (22 mg, 0.03 mmol). The reaction mixture was heated in a sealed tube at 80° C. for 16 h, then was cooled to RT and partitioned between water and EtOAc. The aqueous layer was extracted with EtOAc (3×20 mL). The combined organic extracts were washed with brine, dried (MgSO$_4$), filtered and concentrated in vacuo. The crude pinacol boronate product was carried on to the next step without further purification. To a solution of the crude pinacol boronate product (241 mg, 0.603 mmol) in EtOAc (2 mL) was added H$_2$O$_2$ (0.19 mL of a 30% aq. solution, 6.0 mmol). The reaction mixture was stirred at RT for 1 h, then was cooled to 0° C. and quenched by slowly adding satd aq. Na$_2$S$_2$O$_3$. The aqueous layer was extracted with EtOAc (3×20 mL). The combined organic extracts were washed with brine, dried (MgSO$_4$) and concentrated in vacuo. The residue was chromatographed (SiO$_2$; continuous gradient from 0% to 100% EtOAc in hexanes over 20 min) to give the title compound (150 mg, 86%) as a white solid. $^1$H NMR (400 MHz, CDCl$_3$) δ 8.27 (d, J=2.6 Hz, 1H), 8.06 (d, J=8.6 Hz, 1H), 7.29-7.21 (m, 1H), 5.33 (s, 1H), 5.28 (d, J=2.4 Hz, 2H), 4.76 (s, 1H), 4.18 (s, 3H), 3.90 (s, 1H), 3.63-3.48 (m, 1H), 1.72 (s, 2H), 1.65-1.51 (m, 2H). LCMS, [M+H]$^+$=291.2.

Intermediate 1D. Isopropyl (1S,3S)-3-((2-methyl-6-(1-methyl-5-(((tetrahydro-2H-pyran-2-yl)oxy)methyl)-1H-1,2,3-triazol-4-yl)pyridin-3-yl)oxy)cyclohexane-1-carboxylate

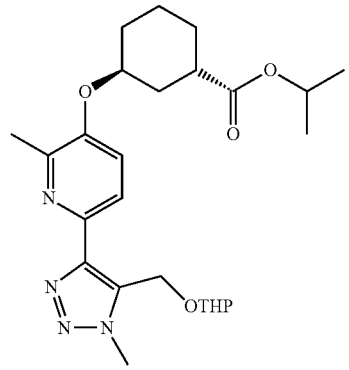

To a solution of Intermediate 1C (1.18 g, 4.06 mmol) and (1S, 3R)-isopropyl 3-hydroxycyclo-hexane carboxylate (synthesized according to the procedure described in US2007/0197788A1, 1.51 g, 8.13 mmol) in toluene (81 mL) was added Bu₃P (3.17 mL, 12.2 mmol). To this stirred mixture was added (E)-diazene-1,2-diylbis(piperidin-1-yl-methanone) (3.08 g, 12.2 mmol) portionwise, and the reaction mixture was heated at 50° C. for 120 min, then was cooled to RT. At this point an LCMS of the reaction mixture showed the desired product. The mixture was filtered and the filtrate was concentrated in vacuo. The residue was chromatographed (SiO₂; continuous gradient from 0% to 100% EtOAc in hexanes over 20 min) to give the title compound (1.2 g, 2.62 mmol, 64.4% yield) as a white foam. ¹H NMR (400 MHz, CDCl₃) δ 7.95 (d, J=8.6 Hz, 1H), 7.22 (d, J=8.6 Hz, 1H), 5.45-5.24 (m, 2H), 5.04 (dt, J=12.5, 6.3 Hz, 1H), 4.83-4.64 (m, 2H), 4.16 (s, 3H), 3.91 (ddd, J=11.2, 7.9, 3.1 Hz, 1H), 3.64-3.48 (m, 1H), 2.93-2.71 (m, 1H), 2.52 (s, 3H), 2.23-1.45 (m, 14H), 1.26 (dd, J=6.4, 2.0 Hz, 6H).

Intermediate 1

To a solution of Intermediate 1D (1.7 g, 3.71 mmol) in MeOH (37 mL) added PPTS (0.932 g, 3.71 mmol). The reaction mixture was heated to 60° C. for 2 h, then was cooled to RT, diluted with water and sat. aq. NaHCO₃, then was extracted with EtOAc (3×10 mL). The combined organic extracts were concentrated in vacuo and chromatographed (SiO₂; continuous gradient from 0% to 100% EtOAc in Hexanes, 20 min) to give the title compound as a white foam (1.36 g, 3.63 mmol, 98% yield). ¹H NMR (400 MHz, CDCl₃) δ 8.01 (d, J=8.6 Hz, 1H), 7.46 (d, J=5.1 Hz, 1H), 7.27-7.15 (m, 1H), 4.96 (dt, J=12.5, 6.3 Hz, 1H), 4.74 (s, 2H), 4.66-4.59 (m, 1H), 4.00 (s, 3H), 2.80-2.64 (m, 1H), 2.46 (s, 3H), 2.07-1.50 (m, 8H), 1.18 (dd, J=6.4, 2.2 Hz, 6H).

Intermediate 2. (1S,3S)-Isopropyl 3-((6-(5-(bromomethyl)-1-methyl-1H-1,2,3-triazol-4-yl)-2-methylpyridin-3-yl)oxy)cyclohexanecarboxylate

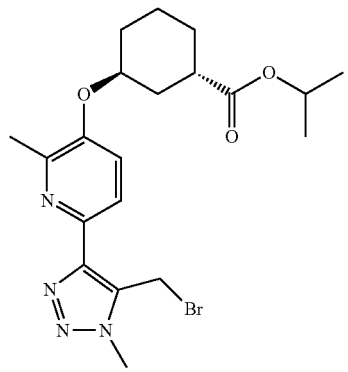 [SMILES: Cc1nc(-c2nnn(C)c2CBr)ccc1O[C@H]1CCC[C@H](C(=O)OC(C)C)C1]

To a 0° C. solution of Intermediate 1 (0.28 g, 0.721 mmol) in DME (7 mL) was added PBr₃ (0.17 mL, 1.802 mmol). The reaction was stirred overnight at RT, then was cooled to 0° C. and neutralized with satd aq. NaHCO₃ to pH~7. The mixture was partitioned between EtOAc (50 mL) and water (5 mL), and the aqueous layer was extracted with EtOAc (3×10 mL). The combined organic extracts were dried (MgSO₄) and concentrated in vacuo. The residue was chromatographed (12 g SiO₂; continuous gradient from 0% to 50% of EtOAc in hexanes over 25 min) to give the title compound (300 mg, 0.665 mmol, 92% yield) as a white solid. LCMS, [M+H]⁺=451.2. ¹H NMR (500 MHz, CDCl₃) δ 7.99 (d, J=8.5 Hz, 1H), 7.22 (d, J=8.5 Hz, 1H), 5.26 (d, J=1.4 Hz, 2H), 5.03 (spt, J=6.3 Hz, 1H), 4.75-4.63 (m, 1H), 4.12 (s, 3H), 2.82-2.74 (m, 1H), 2.54 (s, 3H), 2.14-2.07 (m, 1H), 1.99-1.88 (m, 3H), 1.81-1.59 (m, 4H), 1.27-1.24 (m, 6H).

Intermediate 3. (1S,3S)-Isopropyl 3-((6-(5-(aminomethyl)-1-methyl-1H-1,2,3-triazol-4-yl)-2-methylpyridin-3-yl)oxy)cyclohexanecarboxylate

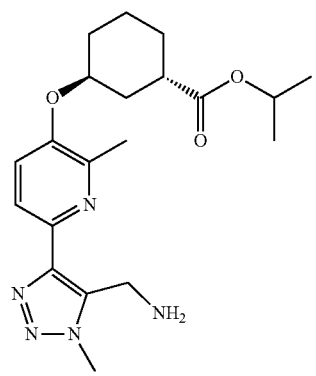 [SMILES: Cc1nc(-c2nnn(C)c2CN)ccc1O[C@H]1CCC[C@H](C(=O)OC(C)C)C1]

Intermediate 3A. (1S,3S)-Isopropyl 3-((6-(5-(azidomethyl)-1-methyl-1H-1,2,3-triazol-4-yl)-2-methylpyridin-3-yl)oxy)cyclohexanecarboxylate

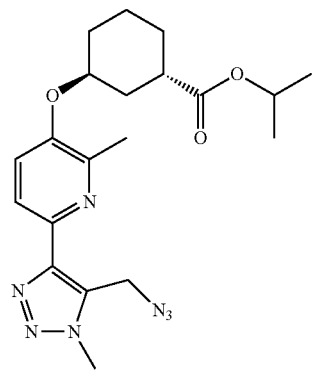 [SMILES: Cc1nc(-c2nnn(C)c2CN=[N+]=[N-])ccc1O[C@H]1CCC[C@H](C(=O)OC(C)C)C1]

To a solution of Intermediate 2 (100 mg, 0.22 mmol) in DMF (1.5 mL) was added NaN₃ (36 mg, 0.55 mmol) and the reaction mixture was stirred at 80° C. for 1 h; at this point LCMS analysis indicated that the reaction was complete. The reaction mixture was cooled to RT, partitioned between EtOAc and water (10 mL each), and the resulting mixture was stirred at RT. After 15 min, the organic layer was dried (Na₂SO₄) and concentrated in vacuo. The crude title compound was used in the next step without further purification. LCMS, [M+H]⁺=414.3.

Intermediate 3

To a solution of Intermediate 3A (92 mg, 0.22 mmol) in THF (1 mL) and H₂O (0.3 mL) was added Ph₃P (58 mg, 0.22 mmol). The reaction mixture was stirred at RT overnight, then was taken up in EtOAc and water (10 mL each). The mixture was stirred at RT for 15 min. The separated organic layer was dried (Na$_2$SO$_4$) and concentrated in vacuo. The residue was chromatographed (12 g SiO$_2$; 100% EtOAc for 10 min, then a continuous gradient from 0% to 10% MeOH in CH$_2$Cl$_2$ over 20 min; flow rate=30 mL/min) to give the title compound (81 mg, 0.21 mmol, 94% yield) as a beige oil. LCMS, [M+H]$^+$=388.3.

Intermediate 4. Methyl (1S,3S)-3-((6-(5-(hydroxymethyl)-1-methyl-1H-1,2,3-triazol-4-yl)-2-methylpyridin-3-yl)oxy)cyclohexane-1-carboxylate

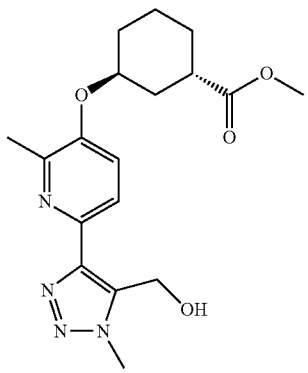

Intermediate 4 was synthesized from (1S, 3R)-methyl 3-hydroxycyclohexane carboxylate and Intermediate 1C (using the same synthetic sequence that was used to synthesize Intermediate 1 from (1S, 3R)-isopropyl 3-hydroxy cyclohexanecarboxylate and Intermediate 1C). $^1$H NMR (400 MHz, CDCl$_3$) δ 8.09 (d, J=8.7 Hz, 1H), 7.29 (d, J=8.6 Hz, 1H), 4.81 (s, 2H), 4.72 (dp, J=5.1, 2.7 Hz, 1H), 4.07 (s, 3H), 3.69 (s, 3H), 2.82 (tt, J=10.2, 3.9 Hz, 1H), 2.53 (s, 3H), 2.19-1.54 (m, 8H). LCMS, [M+H]+=361.2.

Intermediate 5. Methyl (1S,3S)-3-((6-(5-(bromomethyl)-1-methyl-1H-1,2,3-triazol-4-yl)-2-methylpyridin-3-yl)oxy)cyclohexane-1-carboxylate

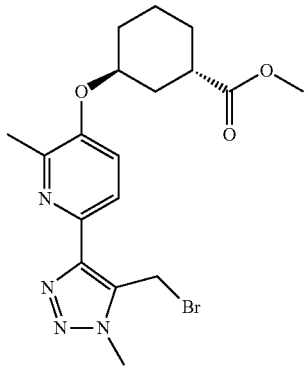

Intermediate 5 was synthesized from Intermediate 4 (using the same procedure that was used to synthesize Intermediate 2 from Intermediate 1). $^1$H NMR (500 MHz, CDCl$_3$) δ 8.01 (d, J=8.6 Hz, 1H), 7.22 (d, J=8.6 Hz, 1H), 5.32-5.22 (m, 2H), 4.73 (dp, J=4.7, 2.6 Hz, 1H), 4.14 (s, 3H), 3.72 (s, 3H), 2.86 (tt, J=10.6, 4.0 Hz, 1H), 2.55 (s, 3H), 2.21-1.60 (m, 8H). LCMS, [M+H]$^+$=423.1.

Intermediate 6. Methyl (1 S,3 S)-3-((6-(5-(azidomethyl)-1-methyl-1H-1,2,3-triazol-4-yl)-2-methylpyridin-3-yl)oxy)cyclohexane-1-carboxylate

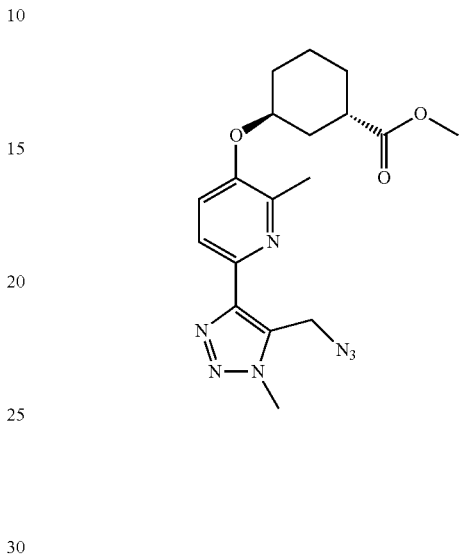

Intermediate 6 was synthesized from Intermediate 5 (using the same procedure that was used to synthesize Intermediate 3A from Intermediate 2). LCMS, [M+H]$^+$=386.1.

Intermediate 7. Methyl (1 S,3 S)-3-((6-(5-(aminomethyl)-1-methyl-1H-1,2,3-triazol-4-yl)-2-methylpyridin-3-yl)oxy)cyclohexane-1-carboxylate

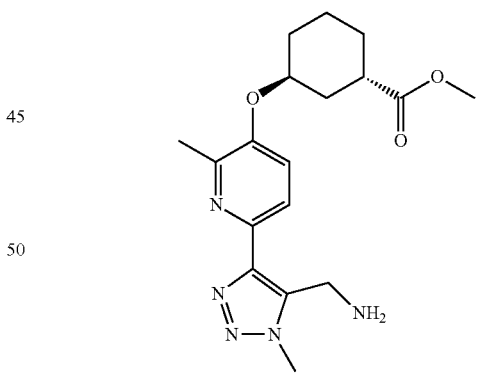

Intermediate 7 was synthesized from Intermediate 5 (using the same synthetic sequence that was used to synthesize Intermediate 3 from Intermediate 3A). $^1$H NMR (400 MHz, CDCl$_3$) δ 7.98 (d, J=8.6 Hz, 1H), 7.21 (d, J=8.6 Hz, 1H), 4.70 (dp, J=5.1, 2.7 Hz, 1H), 4.17 (s, 2H), 4.09 (s, 3H), 3.69 (s, 3H), 2.83 (tt, J=10.5, 3.9 Hz, 1H), 2.51 (s, 3H), 2.19-1.56 (m, 8H). LCMS, [M+H]$^+$=360.1.

Intermediate 8. Methyl (1S,3S)-3-((6-(5-formyl-1-methyl-1H-1,2,3-triazol-4-yl)-2-methylpyridin-3-yl)oxy)cyclohexane-1-carboxylate

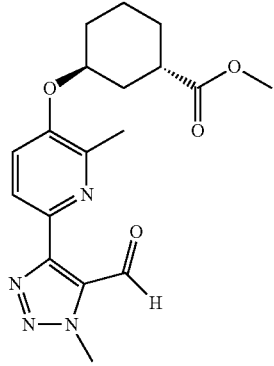 [SMILES: COC(=O)[C@H]1CCC[C@H](Oc2ccc(-c3nnn(C)c3C=O)nc2C)C1]

To a solution of Intermediate 4 (0.37 g, 1.03 mmol) in CH$_2$Cl$_2$ (6 mL) were successively added NaHCO$_3$ (0.43 g, 5.13 mmol) and Dess-Martin periodinane (0.52 g, 1.23 mmol). The reaction was stirred at RT for 1 h, after which TLC (hexanes/EtOAc=1/3) showed disappearance of starting material and appearance of product. The white solid was filtered off through Celite, which was rinsed with EtOAc. The filtrate was washed with sat. aq. NaHCO$_3$, water and brine, dried (Na$_2$SO$_4$) and concentrated in vacuo. The crude product was chromatographed (40 g SiO$_2$; continuous gradient from 0%-80% EtOAc/hexanes over 20 min) to give the title compound (365 mg, 1.02 mmol, 99% yield) as a white solid. LCMS, [M+H]$^+$=359.1.

Intermediate 9. Isopropyl (1S,3S)-3-((6-(5-formyl-1-methyl-1H-1,2,3-triazol-4-yl)-2-methylpyridin-3-yl)oxy)cyclohexane-1-carboxylate

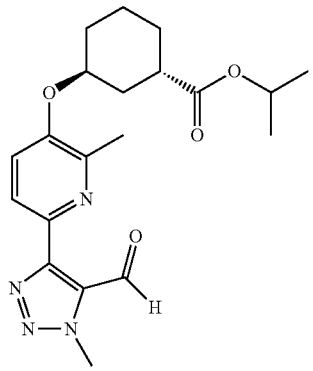 [SMILES: Cc1nc(-c2nnn(C)c2C=O)ccc1O[C@H]1CCC[C@H](C(=O)OC(C)C)C1]

Intermediate 9 was synthesized from intermediate 1 in the same way as Intermediate 8 was synthesized from Intermediate 4. [M+H]$^+$=387.1; $^1$H NMR (400 MHz, CDCl3) δ 10.96 (s, 1H), 8.08 (d, J=8.6 Hz, 1H), 7.27-7.23 (m, 1H), 5.03 (dt, J=12.5, 6.3 Hz, 1H), 4.75-4.70 (m, 1H), 4.35 (s, 3H), 2.83-2.72 (m, 1H), 2.51 (s, 3H), 2.13-2.03 (m, 1H), 2.02-1.87 (m, 3H), 1.85-1.57 (m, 4H), 1.25 (dd, J=6.2, 2.0 Hz, 6H).

Intermediate 10. 5-Isopentyl-1,2,4-oxadiazol-3-amine

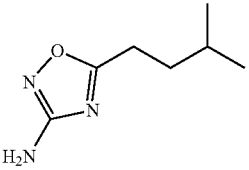

To a 0° C. suspension of sodium hydrogen cyanamide (NaHNCN; 1.43 g, 22.3 mmol) in THF (14.9 mL) was added dropwise 4-methylpentanoyl chloride (1.0 mL, 7.43 mmol). The reaction was allowed to warm to RT and stirred at RT for 18 h, then was concentrated in vacuo. The resulting yellow solid was dissolved in H$_2$O (20 mL) and the pH was adjusted to 6.5 with 10% aq. HCl. The mixture was extracted with EtOAc (2×20 mL). The aqueous layer was acidified to pH 1.5 with 10% aq. HCl and extracted with DCM (3×20 mL). The combined organic extracts were dried (Na$_2$SO$_4$) and concentrated in vacuo to give N-cyano-4-methylpentanamide (0.95 g, 91%) as a colorless liquid.

To a solution of N-cyano-4-methylpentanamide (0.95 g, 6.78 mmol) in EtOH (10 mL) was added NH$_2$OH·HCl (0.706 g, 10.2 mmol), followed by pyridine (2.19 mL, 27.1 mmol). The reaction was stirred at RT for 18 h, then was concentrated in vacuo. The residue was partitioned between DCM and water. The aqueous layer was extracted with DCM (2×). The combined organic extracts were dried (Na$_2$SO$_4$) and concentrated in vacuo to give the title compound (0.89 g, 85%) as a white solid. LCMS, [M+H]$^+$=156.1. $^1$H NMR (500 MHz, CDCl$_3$) δ 4.51 (br s, 2H), 2.86-2.68 (m, 2H), 1.76-1.55 (m, 3H), 0.96 (d, J=6.3 Hz, 6H).

Intermediate 11. 5-(Cyclobutylmethyl)-1,2,4-oxadiazol-3-amine

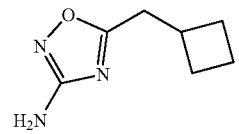

To a 0° C. solution of 2-cyclobutylacetic acid (0.194 g, 1.70 mmol) in DMF (3.4 mL) were successively added NaHNCN (0.109 g, 1.70 mmol), DIEA (1.48 mL, 8.50 mmol) and HATU (0.776 g, 2.04 mmol). The reaction was allowed to warm to RT and stirred at RT for 18 h, then was concentrated in vacuo. The residue was suspended in EtOH (2 mL), then NH$_2$OH·HCl (0.177 g, 2.55 mmol) was added, followed by pyridine (0.550 mL, 6.80 mmol). The reaction was stirred at RT for 18 h, then was concentrated in vacuo. The residue was partitioned between DCM and water; the aqueous layer was extracted with DCM (2×). The combined organic layers were dried (Na$_2$SO$_4$) and concentrated in vacuo. The crude product was chromatographed (12 g SiO$_2$, continuous gradient from 0-100% EtOAc:Hex) to give the title compound (0.14 g, 54%) as a white solid. LCMS, [M+H]$^+$=154.1. $^1$H NMR (400 MHz, CDCl$_3$) δ 4.61-4.26 (m, 2H), 2.87-2.66 (m, 3H), 2.21-2.10 (m, 2H), 1.95-1.66 (m, 4H).

Intermediate 12: (1S,3S)-3-((6-(5-(hydroxymethyl)-1-methyl-1H-1,2,3-triazol-4-yl)-2-methylpyridin-3-yl)oxy)cyclohexane-1-carboxylic acid

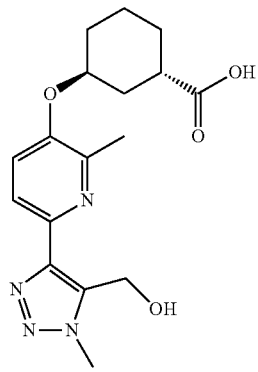 [SMILES: Cc1nc(-c2nnn(C)c2CO)ccc1O[C@H]1CCC[C@H](C(=O)O)C1]

To a solution of Intermediate 1 (0.62 g, 1.596 mmol) in MeOH (2 mL) was added KOH (0.448 g, 7.98 mmol) in water (2 mL) at RT dropwise. The reaction mixture was stirred at RT overnight, then was concentrated in vacuo and acidified with conc. HCl to pH~3. The solids were filtered off, washed with water and dried at RT to give the title compound (0.45 g, 1.30 mmol, 81% yield) as a white solid. LCMS, [M+H]$^+$=347.1. $^1$H NMR (500 MHz, DMSO-d$_6$) δ 7.83 (d, J=8.5 Hz, 1H), 7.49 (d, J=8.7 Hz, 1H), 4.96 (s, 2H), 4.77 (s, 1H), 4.03 (s, 3H), 2.64-2.57 (m, 1H), 2.42 (s, 3H), 2.05-1.40 (m, 8H).

Intermediate 13. 5-(3-Methylenecyclobutyl)-1,2,4-oxadiazol-3-amine

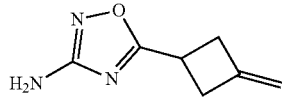

To a solution of 3-methylenecyclobutane-1-carboxylic acid (1.22 g, 10.88 mmol) in DCM (9.1 mL) was added DMF (0.042 mL, 0.544 mmol) followed by oxalyl chloride (0.95 mL, 10.88 mmol). The reaction was stirred at RT for 4 h. The reaction mixture was added dropwise to a cooled (0° C.) suspension of sodium hydrogencyanamide (2.09 g, 32.6 mmol) in THF (21.8 mL). Following the addition, the reaction was allowed to warm to RT. After 18 h, the reaction was concentrated. The resulting yellow solid was dissolved in distilled water (25 mL) and the alkaline solution was adjusted to pH 6.5 with 10% HCl. The mixture was then extracted with EtOAc (2×25 mL). The aqueous layer was acidified to pH 1.5 with 10% HCl and extracted with DCM (3×25 mL). The DCM layers were combined, dried (Na$_2$SO$_4$), filtered and concentrated in vacuo to give N-cyano-3-methylenecyclobutane-1-carboxamide (1.48 g, 100%) as a yellow liquid.

To a solution of N-cyano-3-methylenecyclobutane-1-carboxamide (1.48 g, 10.88 mmol) in EtOH (43.5 mL) was added hydroxylamine hydrochloride (1.13 g, 16.32 mmol) followed by pyridine (3.5 mL, 43.5 mmol). The reaction was stirred at RT for 18 h and then the reaction was concentrated. The residue was partitioned between DCM and water and then the layers were separated. The aqueous layer was extracted with DCM (2×). The organic layers were combined, dried (Na$_2$SO$_4$), filtered, and concentrated. The crude product was purified by normal phase chromatography (40 g SiO$_2$ column, eluting with 0-100% EtOAc/Hex) to give the title compound (1.2 g, 73%) as a white solid. LCMS, [M+H]$^+$=152.0. $^1$H NMR (500 MHz, CDCl$_3$) δ 4.96-4.85 (m, 2H), 4.40 (br s, 2H), 3.64 (quin, J=8.3 Hz, 1H), 3.21-3.05 (m, 4H).

Intermediate 14. 5-(3-Methylcyclobutyl)-1,2,4-oxadiazol-3-amine

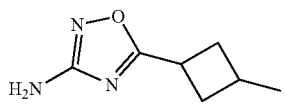

To a solution of 5-(3-methylenecyclobutyl)-1,2,4-oxadiazol-3-amine (50 mg, 0.331 mmol) in EtOH (2 mL) was added 10% palladium on carbon (35.2 mg, 0.033 mmol). Hydrogen gas (balloon) was bubbled through the reaction mixture for a few minutes, then the reaction was stirred under a hydrogen balloon for 2 h. The reaction mixture was filtered through a pad of Celite®, rinsing with MeOH. The filtrate was concentrated to give the title compound (50 mg, 99%) as a white solid. LCMS, [M+H]$^+$=153.9. The material was carried onto the next step without further purification.

Intermediate 15. 5-((1R,3R)-3-Fluoro-3-methylcyclobutyl)-1,2,4-oxadiazol-3-amine

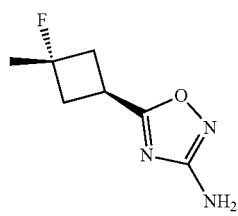

5-(Cis-3-Fluoro-3-methylcyclobutyl)-1,2,4-oxadiazol-3-amine

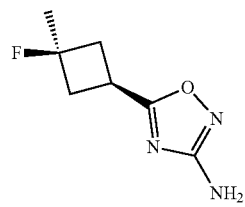

A 0° C. yellow suspension of Fe(III) oxalate hexahydrate (726 mg, 1.50 mmol) in water (30 mL) was degassed by bubbling N$_2$ through the reaction mixture for 10 min. Selectfluor (531 mg, 1.50 mmol) and MeCN (15 mL) were added, followed by a solution of 5-(3-methylenecyclo-butyl)-1,2,4-oxadiazol-3-amine (113 mg, 0.75 mmol) in MeCN (15 mL). Finally, NaBH₄ (91 mg, 2.40 mmol) was added, and the reaction mixture was stirred for 2 min, after which more NaBH₄ (91 mg, 2.40 mmol) was added. The reaction mixture was stirred for 30 min, then was quenched by the addition of 30% aq. NH₄OH (12 mL) and extracted with 10% MeOH in DCM (2×). The combined organic extracts were dried (Na₂SO₄) and concentrated in vacuo. The crude product was chromatographed (12 g SiO₂, continuous gradient from 0-100% EtOAc in hexanes) to give the title compound (38 mg, 30%) as a white solid. LCMS, [M+H]⁺=172.0. ¹H NMR (500 MHz, CDCl₃) δ 4.58 (br s, 2H), 3.72 (tt, J=9.8, 6.8 Hz, 1H), 2.92-2.76 (m, 2H), 2.63-2.45 (m, 2H), 1.54 (d, J=22.3 Hz, 3H). In addition, 5-((Trans-3-fluoro-3-methylcyclobutyl)-1,2,4-oxadiazol-3-amine (38 mg, 30%) was also obtained as a white solid. LCMS, [M+H]⁺=172.0. ¹H NMR (500 MHz, CDCl₃) δ 4.59 (br s, 2H), 3.16-3.08 (m, 1H), 2.84-2.72 (m, 2H), 2.63-2.52 (m, 2H), 1.57 (d, J=21.7 Hz, 3H). [The cis/trans isomers were assigned according to the ¹H NMR (trans methine adjacent to the oxadiazole further down field) in WO2013/134298].

Intermediate 16.
3-Chloro-5-isopentyl-1,2,4-oxadiazole

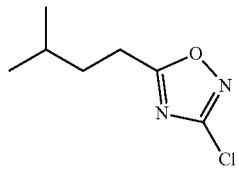

To a cooled (0° C.) solution of 5-isopentyl-1,2,4-oxadiazol-3-amine (400 mg, 2.58 mmol) in 37% HCl (25.8 mL) was added dropwise a solution of sodium nitrite (445 mg, 6.44 mmol) in water (2 mL). The reaction was stirred for 2 h at 0° C. The reaction mixture was diluted with water and then extracted with DCM (3×). The organic layers were combined, washed with brine, dried (Na₂SO₄), filtered and concentrated. The crude product was chromatographed (12 g SiO₂ column, eluting with 0-100% EtOAc in n-hexanes) to give the title compound (320 mg, 71%) as a yellow oil. ¹H NMR (500 MHz, CDCl₃) δ 2.92 (t, J=7.8 Hz, 2H), 1.79-1.61 (m, 3H), 0.98 (d, J=6.3 Hz, 6H). The material was carried onto the next step without further purification.

Intermediate 17.
5-(3-Fluorobutyl)-1,2,4-oxadiazol-3-amine

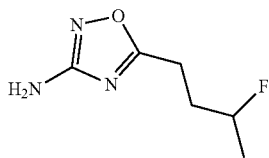

5-(3-fluorobutyl)-1,2,4-oxadiazol-3-amine (38 mg, 32%, white solid) was prepared from 5-(but-3-en-1-yl)-1,2,4-oxadiazol-3-amine (104 mg, 0.75 mmol) according to the procedure described for the synthesis of 5-((1R,3R)-3-fluoro-3-methylcyclobutyl)-1,2,4-oxadiazol-3-amine. LCMS, [M+H]⁺=160.0. ¹H NMR (500 MHz, CDCl₃) δ 4.88-4.64 (m, 1H), 4.48 (br s, 2H), 3.06-2.81 (m, 2H), 2.17-1.97 (m, 2H), 1.44-1.35 (m, 3H).

Intermediate 18. Methyl (1 S,3 S)-3-((6-(5-amino-1-methyl-1H-1,2,3-triazol-4-yl)-2-methylpyridin-3-yl)oxy)cyclohexane-1-carboxylate

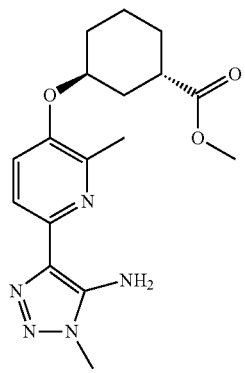

Intermediate 18A. 4-(5-(((1 S,3 S)-3-(methoxycarbonyl)cyclohexyl)oxy)-6-methylpyridin-2-yl)-1-methyl-1H-1,2,3-triazole-5-carboxylic acid

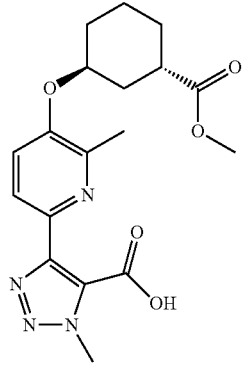 [SMILES: COC(=O)[C@H]1CCC[C@H](Oc2ccc(-c3nnn(C)c3C(=O)O)nc2C)C1]

To a mixture of Intermediate 8 (2.36 g, 6.58 mmol), NaH₂PO₄ (3.95 g, 32.9 mmol), 2-methyl-2-butene, (26.35 ml of a 2M solution in THF; 52.7 mmol), water (1.7 mL), and t-BuOH (8.4 mL) at RT was added NaClO₂ (1.489 g, 13.17 mmol). The reaction mixture was stirred at RT for 3 h, then was poured into brine and extracted with EtOAc (3×). The combined organic extracts were dried (Na₂SO₄) and concentrated in vacuo to give the crude title compound (2.40 g, 97%) as a white solid. This crude acid was used in the next reaction without further purification. LC-MS, [M+H]⁺=375.0. ¹H NMR (500 MHz, CDCl₃) δ 8.52-8.19 (m, 1H), 7.67-7.40 (m, 1H), 4.85-4.75 (m, 1H), 4.52-4.40 (m, 3H), 3.78-3.63 (m, 3H), 2.90-2.77 (m, 1H), 2.67-2.53 (m, 3H), 1.99-1.83 (m, 3H), 1.80-1.62 (m, 5H).

117

Intermediate 18B. Methyl (1S,3S)-3-((6-(5-(((tert-butoxycarbonyl)amino)-1-methyl-1H-1,2,3-triazol-4-yl)-2-methylpyridin-3-yl)oxy)cyclohexane-1-carboxylate

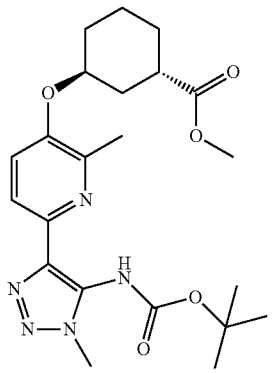 [SMILES: COC(=O)[C@H]1CCC[C@H](Oc2ccc(-c3nnn(C)c3NC(=O)OC(C)(C)C)nc2C)C1]

A mixture of Intermediate 18A (0.60 g, 1.6 mmol), (PhO)₂PON₃ (0.63 mL, 2.9 mmol), t-butanol (0.46 mL, 2.4 mmol), TEA (0.89 mL, 6.4 mmol) in toluene (5.3 mL) was stirred at 80° C. for 1 h, then was cooled to RT and concentrated in vacuo. The crude product was chromatographed (40 g SiO₂; continuous gradient from 0% to 60% EtOAc in n-hexanes) to afford the title compound (0.44 g, 62%) as a white foam. LC-MS, [M+H]⁺=446.4.

Intermediate 18

A solution of Intermediate 18B (0.44 g, 0.99 mmol) in CH₂Cl₂ (9 mL) and TFA (1 mL) was stirred at RT for 16 h, then was concentrated in vacuo. The crude product was dissolved in DCM, washed with satd aq. NaHCO₃ and brine, dried (Na₂SO₄), and concentrated in vacuo. The crude product was chromatographed (24 g SiO₂; continuous gradient from 0% to 100% EtOAc in hexane for 30 min and 100% EtOAc for 20 min) to give the title compound (0.20 g, 59%) as a white solid. LCMS, [M+H]⁺=346.2. ¹H NMR (400 MHz, CDCl₃) δ 7.87 (d, J=8.6 Hz, 1H), 7.20 (d, J=8.7 Hz, 1H), 5.29 (br s, 2H), 4.69-4.64 (m, 1H), 3.85 (s, 3H), 3.69 (s, 3H), 2.83 (tt, J=10.5, 3.9 Hz, 1H), 2.49 (s, 3H), 2.18-2.10 (m, 1H), 2.00-1.84 (m, 3H), 1.81-1.69 (m, 1H), 1.66-1.54 (m, 3H).

Intermediate 19.
2,5-dibromo-3-fluoro-6-methylpyridine

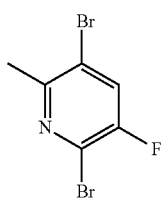

118

Intermediate 19A.
3-fluoro-6-methylpyridin-2-amine

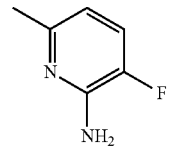

To a solution of 2-bromo-3-fluoro-6-methylpyridine (5.0 g, 26.3 mmol) in ethylene glycol (50 mL) and aq. 28% NH₄OH (63 mL; 450 mmol) were added Cu₂O (0.19 g, 1.32 mmol), K₂CO₃ (0.73 g, 5.26 mmol), and N1, N1-dimethylethane-1,2-diamine (0.29 mL, 2.63 mmol). The reaction mixture was purged with N₂, then was heated at 80° C. overnight in a sealed tube, after which it was cooled to RT and extracted with CH₂Cl₂ (3×). The combined organic extracts were dried (Na₂SO₄), and concentrated in vacuo. The residue was chromatographed (SiO₂; continuous gradient from 0-100% EtOAc in hexanes) to give the title compound (2.81 g, 85% yield). ¹H NMR (500 MHz, CDCl₃) δ 7.11 (dd, J=10.6, 8.1 Hz, 1H), 6.47 (dd, J=8.0, 3.0 Hz, 1H), 4.55 (br s, 2H), 2.38 (s, 3H).

Intermediate 19B.
5-bromo-3-fluoro-6-methylpyridin-2-amine

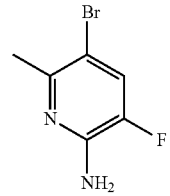

To a 0° C. solution of Intermediate 19A (3.91 g, 31.0 mmol) in CH₃CN (100 mL) was added portionwise NBS (5.52 g, 31.0 mmol) while maintaining the reaction temperature at ≤5° C. The reaction mixture was stirred at RT for 30 min, then was concentrated in vacuo. The residue was chromatographed (SiO₂; isocratic 30% EtOAc in hexanes) to give the title compound (6.14 g, 97% yield). ¹H NMR (500 MHz, CDCl₃) δ 7.37 (d, J=9.6 Hz, 1H), 4.59 (br s, 2H), 2.48 (d, J=1.1 Hz, 3H).

Intermediate 19

To a 0° C. solution of aq. 48% HBr (23.7 mL, 210 mmol, 48%) was added slowly portionwise Intermediate 19B (6.14 g, 29.9 mmol). Br₂ (3.09 mL, 59.9 mmol) was added dropwise while maintaining the reaction temperature at ≤5° C. The reaction mixture was stirred at 0° C. for 30 min, after which a solution of NaNO₂ (5.17 g, 74.9 mmol) in water (10 mL) was added dropwise while maintaining the reaction temperature at ≤5° C. The reaction mixture was stirred for 30 min at 0° C., then was poured into ice water, basified with 50% aq. NaOH and extracted with EtOAc (2×). The combined organic extracts were washed with aq. 10% Na₂S₂O₃, brine, dried (Na₂SO₄), and concentrated in vacuo. The residue was chromatographed (SiO₂; continuous gradient from 0-25% EtOAc in hexanes) to give the title compound (3.90 g, 48% yield). $^1$H NMR (500 MHz, CDCl$_3$) δ 7.60 (d, J=6.6 Hz, 1H), 2.64 (d, J=1.4 Hz, 3H).

Intermediate 20. Isopropyl (1 S,3S)-3-((5-fluoro-6-(5-formyl-1-methyl-1H-1,2,3-triazol-4-yl)-2-methylpyridin-3-yl)oxy)cyclohexane-1-carboxylate

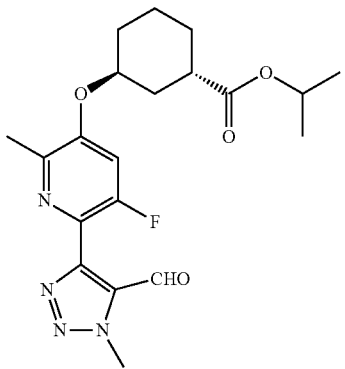 [SMILES: Cc1nc(-c2nnn(C)c2C=O)c(F)cc1O[C@H]1CCC[C@H](C(=O)OC(C)C)C1]

The title compound was synthesized using the same procedure that was used to synthesize Intermediate 9 except that Intermediate 19 was used instead of 2,5-dibromo-6-methyl-pyridine (as described for the preparation of Intermediate 1A). LCMS, [M+H]$^+$=405, $^1$H NMR (400 MHz, CDCl$_3$) δ 10.59 (s, 1H), 7.12 (d, J=11.7 Hz, 1H), 5.05 (quin, J=6.2 Hz, 1H), 4.68 (m, 1H), 4.38 (s, 3H), 2.78 (m, 1H), 2.49 (d, J=0.9 Hz, 3H), 2.05 (m, 2H), 1.96-1.88 (m, 2H), 1.81-1.61 (m, 4H), 1.27 (m, 6H)

Intermediate 21. Methyl (1 S,3 S)-3-((6-(5-formyl-1-methyl-1H-1,2,3-triazol-4-yl)pyridin-3-yl) oxy) cyclohexane-1-carboxylate

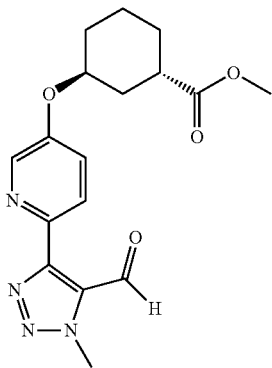 [SMILES: COC(=O)[C@H]1CCC[C@H](Oc2ccc(-c3nnn(C)c3C=O)nc2)C1]

To a solution of methyl (1 S,3 S)-3-((6-(5-(hydroxymethyl)-1-methyl-1H-1,2,3-triazol-4-yl)pyridin-3-yl)oxy)cyclohexane-1-carboxylate (prepared in the same way as Intermediate 4 except that 2,5-dibromopyridine was used instead of 2,5-dibromo-6-methylpyridine as starting material; 660 mg, 1.90 mmol) in DCM (10 mL) was added NaHCO$_3$ (800 mg, 9.53 mmol) followed by Dess-Martin periodinane (970 mg, 2.29 mmol). The reaction mixture was stirred at RT for 1 h, then was filtered through a plug of Celite®, which was washed with EtOAc (2×3 mL). The combined filtrates were partitioned between satd aq. NaHCO$_3$ and EtOAc. The aqueous layer was extracted with EtOAc (3×5 mL). The combined organic extracts were washed with water, brine, dried (MgSO$_4$) and concentrated in vacuo. The residue was chromatographed (SiO$_2$; continuous gradient from 0% to 100% EtOAc in hexanes for 20 min) to give the title compound (650 mg, 99% yield). LCMS [M+H]$^+$=345.1; $^1$H NMR (400 MHz, CDCl$_3$) δ 10.89 (s, 1H), 8.36 (d, J=3.1 Hz, 1H), 8.25 (d, J=8.8 Hz, 1H), 7.38 (dd, J=8.8, 3.1 Hz, 1H), 4.87-4.69 (m, 1H), 4.38 (s, 3H), 3.73 (s, 3H), 3.01-2.79 (m, 1H), 2.17-2.08 (m, 1H), 2.03-1.91 (m, 3H), 1.82-1.61 (m, 4H).

Example 1. (1 S,3 S)-3-((6-(5-(((5-Cyclopropyl-1,2,4-thiadiazol-3-yl)amino)methyl)-1-methyl-1H-1,2,3-triazol-4-yl)-2-methylpyridin-3-yl)oxy)cyclohexane-1-carboxylic acid

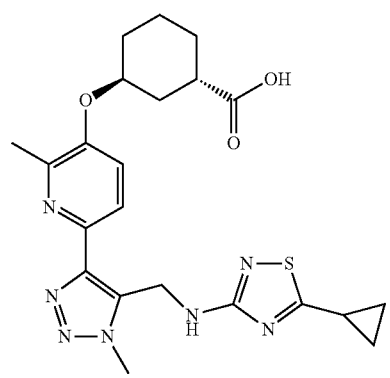 [SMILES: Cc1nc(-c2nnn(C)c2CNc2nsc(C3CC3)n2)ccc1O[C@H]1CCC[C@H](C(=O)O)C1]

To a solution of Intermediate 8 (15 mg, 0.04 mmol), 5-cyclopropyl-1,2,4-thiadiazol-3-amine (8.9 mg, 0.06 mmol) in MeOH (0.8 mL) was added HOAc (0.01 mL, 0.21 mmol), and the reaction was warmed to 65° C. for 2 h, then cooled to RT, and NaBH$_3$CN (5.3 mg, 0.08 mmol) was added. The mixture was stirred at RT for 2 h, after which sat. aq. NaHCO$_3$ was added. The aqueous layer was extracted with EtOAc. The organic layer was washed with brine, dried (MgSO$_4$) and concentrated in vacuo. The residue was purified by reverse phase HPLC (Phenomenex Luna Axis 5u 30×100 mm; flow rate 40 mL/min.; detection 220 nm; gradient elution 0% B to 100% B over 12 min.) (A=10% MeCN, 90% H$_2$O, 0.1% TFA & B=90% MeCN, 10% H$_2$O, 0.1% TFA) to give methyl (1 S,3 S)-3-((6-(5-(((5-cyclopropyl-1,2,4-thiadiazol-3-yl)amino)methyl)-1-methyl-1H-1,2,3-triazol-4-yl)-2-methylpyridin-3-yl)oxy) cyclohexane-1-carboxylate as a colorless solid. This material was dissolved in THF (0.8 mL)/MeOH (0.4 mL)/H$_2$O (0.4 mL). LiOH·H$_2$O (5 mg, 0.12 mmol) was added to the reaction at RT and the reaction was stirred at RT overnight. Volatiles were removed in vacuo and the residue was taken up in H$_2$O (5 mL). The pH was adjusted to ~5 with 1N aq. HCl and the mixture was extracted with EtOAc (3×5 mL). The combined organic extracts were washed with brine (2 mL), dried (MgSO$_4$) and concentrated in vacuo. The crude product was purified by reverse phase HPLC (Sunfire 5u 30×100 mm; flow rate 40 mL/min.; detection 220 nm; gradient elution 0% B to 100% B over 12 min.) (A=10% MeCN, 90% H$_2$O, 0.1% TFA & B=90% MeCN, 10% H$_2$O, 0.1% TFA) to give the title compound (7.1 mg, 0.02 mmol, 60% yield) as an oil. LCMS, [M+H]$^+$=470.1. $^1$H NMR (500 MHz, CDCl$_3$) δ 8.09 (d, J=8.8 Hz, 1H), 7.72 (d, J=8.8 Hz, 1H), 4.92 (s, 2H), 4.88-4.82 (m, 1H), 4.25 (s, 3H), 2.97-2.90 (m, 1H), 2.78 (s, 3H), 2.19-1.67 (m, 9H), 1.23-1.16 (m, 2H), 1.05-0.99 (m, 2H). hLPA$_1$ IC$_{50}$=1184 nM.

Example 2. (1 S,3S)-3-((2-Methyl-6-(1-methyl-5-(((5-propyl-1,3,4-thiadiazol-2-yl)amino)methyl)-1H-1,2,3-triazol-4-yl)pyridin-3-yl)oxy)cyclohexanecarboxylic acid

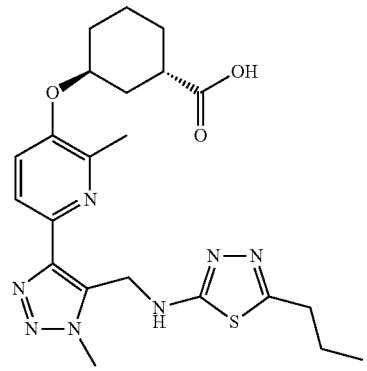 [SMILES: CCCc1nnc(NCc2c(-c3ccc(O[C@H]4CCC[C@H](C(=O)O)C4)c(C)n3)nnn2C)s1]

To a solution of 5-propyl-1,3,4-thiadiazol-2-amine (6.4 mg, 0.04 mmol) in THF (0.5 mL) was added NaH (1.3 mg of a 60% dispersion in oil, 0.03 mmol); the mixture was stirred at RT for 30 min. A solution of Intermediate 5 (10 mg, 0.02 mmol) in THF (0.2 mL) was added and the mixture was stirred at RT for 4 h. LCMS at this point indicated the formation of the product. To the reaction were successively added THF (0.8 mL)/H$_2$O (0.4 mL)/MeOH (0.4 mL) and LiOH·H$_2$O (5 mg, 0.11 mmol) at RT. The mixture was stirred at RT overnight, after which solvents were removed in vacuo and the residue was taken up in H$_2$O (5 mL). The pH of the mixture was adjusted to ~5 with 1N aq. HCl to ~5 and extracted with EtOAc (3×5 mL). The combined organic extracts were washed with brine (2 mL), dried (MgSO$_4$) and concentrated in vacuo. The crude product was purified via preparative LC/MS: (Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 18-58% B over 20 min, then a 5-min hold at 100% B; Flow: 20 mL/min) to provide the title compound (2.9 mg, 5.8 μmol, 26% yield) as an oil: LCMS, [M+H]$^+$=472.0. $^1$H NMR (500 MHz, DMSO-d$_6$) δ 7.85 (br d, J=8.5 Hz, 1H), 7.48 (br d, J=8.7 Hz, 1H), 5.00 (br d, J=4.0 Hz, 2H), 4.81-4.72 (m, 1H), 4.13 (s, 3H), 2.75 (br t, J=7.3 Hz, 2H), 2.62 (br t, J=10.4 Hz, 1H), 2.41 (s, 3H), 2.05-1.42 (m, 10H), 0.89 (br t, J=7.3 Hz, 3H). hLPA$_1$ IC$_{50}$=185 nM.

Example 3. (1 S,3 S)-3-((6-(5-(((3-(tert-Butyl)-1,2,4-thiadiazol-5-yl)amino)methyl)-1-methyl-1H-1,2,3-triazol-4-yl)-2-methylpyridin-3-yl)oxy)cyclohexanecarboxylic acid

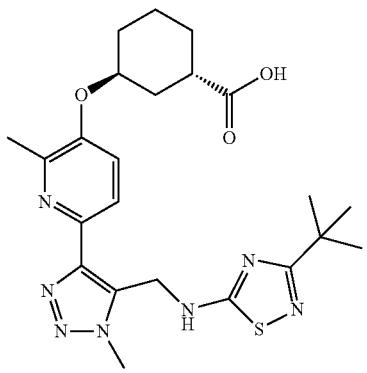 [SMILES: Cc1nc(-c2nnn(C)c2CNc2nc(C(C)(C)C)ns2)ccc1O[C@H]1CCC[C@H](C(=O)O)C1]

To a solution of Intermediate 7 (5 mg, 0.01 mmol) in n-BuOH (0.7 mL) were added 3-(tert-butyl)-5-chloro-1,2,4-thiadiazole (3.7 mg, 0.02 mmol) and iPr$_2$NEt (5 μl, 0.03 mmol) at RT. The mixture was stirred 180° C. for 80 min, then was cooled to RT. THF (0.8 mL)/H$_2$O (0.4 mL)/MeOH (0.4 mL) and LiOH·H$_2$O (3 mg, 0.07 mmol) were added and the mixture was stirred at RT overnight. Solvents were removed in vacuo; the residue was taken up in H$_2$O (5 mL), the pH was adjusted to ~5 with 1N aq. HCl and extracted with EtOAc (3×5 mL). The combined organic extracts were washed with brine (2 mL), dried (MgSO$_4$) and concentrated in vacuo. The crude product was purified via preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 15-55% B over 20 min, then a 5-min hold at 100% B; Flow: 20 mL/min. Fractions containing the desired product were combined and concentrated via centrifugal evaporation to provide the title compound as an oil (6.5 mg, 0.013 mmol, 96% yield). LCMS, [M+H]$^+$=486.1. 1H NMR (500 MHz, DMSO-d$_6$) δ 7.84 (br d, J=8.5 Hz, 1H), 7.50 (br d, J=8.8 Hz, 1H), 5.10 (br d, J=4.5 Hz, 2H), 4.79-4.73 (m, 1H), 4.17 (s, 3H), 2.58-2.55 (m, 1H), 2.43 (s, 3H), 2.00-1.45 (m, 8H), 1.19 (s, 9H). hLPA$_1$ IC$_{50}$=236 nM.

The Examples in Table 1 below were synthesized according to the procedures described above.

TABLE 1

| Ex # | Structure & Name | Analytical & Biological Data | Method |
|---|---|---|---|
| 4 | 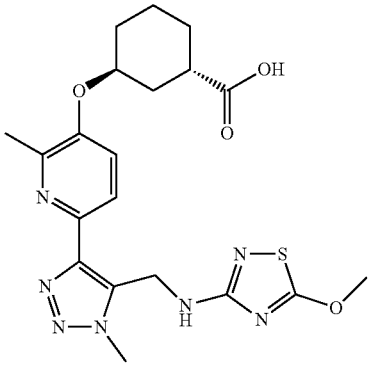<br>(1S,3S)-3-((6-(5-(((5-methoxy-1,2,4-thiadiazol-3-yl)amino)methyl)-1-methyl-1H-1,2,3-triazol-4-yl)-2-methylpyridin-3-yl)oxy)cyclohexane-1-carboxylic acid | LCMS, $[M + H]^+$ = 460.1; $^1$H NMR (500 MHz, CDCl$_3$) δ 8.08 (d, J = 8.8 Hz, 1H), 7.81 (d, J = 9.1 Hz, 1H), 4.89-4.83 (m, 1H), 4.80 (s, 2H), 4.26 (s, 3H), 4.14 (s, 3H), 2.95-2.89 (m, 1H), 2.75 (s, 3H), 2.21-1.65 (m, 8H); hLPA$_1$ IC$_{50}$ =1121 nM. | Example 1 |
| 5 | 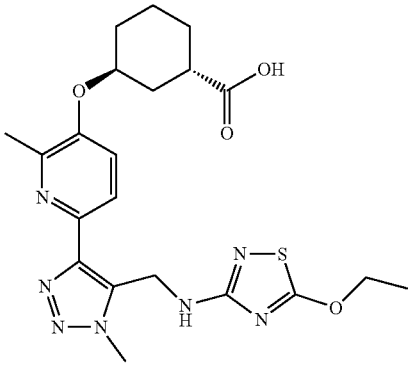<br>(1S,3S)-3-((6-(5-(((5-methoxy-1,2,4-thiadiazol-3-yl)amino)methyl)-1-methyl-1H-1,2,3-triazol-4-yl)-2-methylpyridin-3-yl)oxy)cyclohexane-1-carboxylic acid | LCMS, $[M + H]^+$ = 474.1; $^1$H NMR (500 MHz, DMSO-d$_6$) δ 7.85 (d, J = 8.5 Hz, 1H), 7.50 (d, J = 8.5 Hz, 1H), 4.85 (br d, J = 5.8 Hz, 2H), 4.81-4.75 (m, 1H), 4.35 (q, J = 7.0 Hz, 2H), 4.11 (s, 3H), 2.67-2.59 (m, 1H), 2.45 (s, 3H), 2.07-1.44 (m, 8H), 1.33 (t, J = 7.0 Hz, 3H); hLPA$_1$ IC$_{50}$ = 28 nM. | Example 1 |
| 6 | 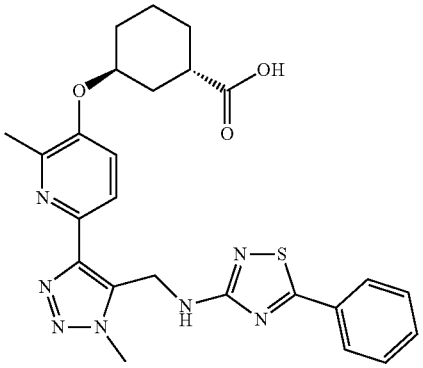<br>(1S,3S)-3-((2-methyl-6-(1-methyl-5-(((5-phenyl-1,2,4-thiadiazol-3-yl)amino)methyl)-1H-1,2,3-triazol-4-yl)pyridin-3-yl)oxy)cyclohexane carboxylic acid | LCMS, $[M + H]^+$ = 506.3. $^1$H NMR (500 MHz, DMSO-d$_6$) δ 7.95-7.90 (m, 1H), 7.85-7.76 (m, 3H), 7.59-7.45 (m, 4H), 4.96 (br d, J = 5.7 Hz, 2H), 4.78-4.70 (m, 1H), 4.14 (s, 3H), 2.58-2.55 (m, 1H), 2.44 (s, 3H), 1.96-1.42 (m, 8H). hLPA$_1$ IC$_{50}$ = 18 nM. | Example 2 |

TABLE 1-continued

| Ex # | Structure & Name | Analytical & Biological Data | Method |
|---|---|---|---|
| 7 | (1S,3S)-3-((6-(5-(((5-methoxy-1,3,4-thiadiazol-2-yl)amino)methyl)-1-methyl-1H-1,2,3-triazol-4-yl)-2-methylpyridin-3-yl)oxy)cyclohexane-1-carboxylic acid | LCMS, [M + H]$^+$ = 470.2; $^1$H NMR (500 MHz, DMSO-d$_6$) δ 7.84 (d, J = 8.5 Hz, 1H), 7.49 (br d, J = 8.5 Hz, 1H), 4.98 (br d, J = 3.7 Hz, 2H0, 4.79-4.73 (m, 1H), 4.13 (s, 3H), 2.61-2.57 (m, 1H), 2.41 (s, 3H), 2.23-2.11 (m, 1H), 2.01-1.44 (m, 8H), 1.05-0.97 (m, 2H), 0.83-0.77 (m, 2H); hLPA$_1$ IC$_{50}$ = 2241 nM. | Example 1 |
| 8 | (1S,3S)-3-((6-(5-(((5-isobutyl-1,3,4-thiadiazol-2-yl)amino)methyl)-1-methyl-1H-1,2,3-triazol-4-yl)-2-methylpyridin-3-yl)oxy)cyclohexane carboxylic acid | LCMS, [M + H]$^+$ = 485.9; $^1$H NMR (500 MHz, DMSO-d$_6$) δ 7.85 (br d, J = 8.4 Hz, 1H), 7.52 (br d, J = 8.7 Hz, 1H), 4.97 (s, 2H), 4.82-4.75 (m, 1H), 4.12 (s, 3H), 2.66 (br d, J = 7.1 Hz, 2H), 2.63-2.57 (m, 1H), 2.42 (s, 3H), 2.05-1.40 (m, 9H), 0.87 (d, J = 6.6 Hz, 6H); hLPA$_1$ IC$_{50}$ = 455 nM. | Example 2 |
| 9 | (1S,3S)-3-((2-methyl-6-(1-methyl-5-(((3-phenyl-1,2,4-thiadiazol-5-yl) amino)methyl)-1H-1,2,3-triazol-4-yl)pyridin-3-yl)oxy)cyclohexane carboxylic acid | LCMS, [M + H]$^+$ = 506.3; $^1$H NMR (500 MHz, DMSO-d$_6$) δ 7.95 (br d, J = 7.3 Hz, 2H), 7.86 (br d, J = 8.5 Hz, 1H), 7.52 (br d, J = 8.5 Hz, 1H), 7.45-7.39 (m, 3H), 5.22 (br d, J = 4.6 Hz, 2H), 4.81-4.72 (m, 1H), 4.19 (s, 3H), 2.60-2.56 (m, 1H), 2.43 (s, 3H), 2.00-1.44 (m, 8H); hLPA$_1$ IC$_{50}$ = 38 nM. | Example 3 |

TABLE 1-continued

| Ex # | Structure & Name | Analytical & Biological Data | Method |
|---|---|---|---|
| 10 | (1S,3S)-3-((6-(5-(((3-isopropyl-1,2,4-thiadiazol-5-yl)amino)methyl)-1-methyl-1H-1,2,3-triazol-4-yl)-2-methylpyridin-3-yl)oxy)cyclohexane carboxylic acid | LCMS, [M + H]$^+$ = 472.0; $^1$H NMR (500 MHz, DMSO-$d_6$) δ 7.84 (br d, J = 8.5 Hz, 1H), 7.49 (br d, J = 8.5 Hz, 1H), 5.06 (br d, J = 5.2 Hz, 2H), 4.81-4.70 (m, 1H), 4.16 (s, 3H), 2.88-2.81 (m, 1H), 2.59-2.55 (m, 1H), 2.42 (s, 3H), 1.97-1.42 (m, 8H), 1.15 (d, J = 6.7 Hz, 6H); hLPA$_1$ IC$_{50}$ = 71 nM. | Example 3 |
| 11 | (1S,3S)-3-((2-methyl-6-(1-methyl-5-(((1-propyl-1H-1,2,3-triazol-4-yl) amino)methyl)-1H-1,2,3-triazol-4-yl)pyridin-3-yl)oxy)cyclohexane carboxylic acid | LCMS, [M + H]$^+$ = 455.3; $^1$H NMR (500 MHz, DMSO-$d_6$) δ 7.85 (br d, J = 8.6 Hz, 1H), 7.50 (br d, J = 8.5 Hz, 1H), 7.27 (s, 1H), 4.82-4.74 (m, 1H), 4.68 (br d, J = 6.2 Hz, 2H), 4.15-4.04 (m, 5H), 2.67-2.57 (m, 1H), 2.04-1.42 (m, 10H), 0.74 (br t, J = 7.3 Hz, 3H); hLPA$_1$ IC$_{50}$ = 705 nM. | Example 2 |
| 12 | (1S,3S)-3-((6-(5-(((4-isopropyl-thiazol-2-yl)amino)methyl)-1-methyl-1H-1,2,3-triazol-4-yl)-2-methyl-pyridin-3-yl)oxy)cyclohexane-1-carboxylic acid | LCMS, [M + H]$^+$ = 470.9; $^1$H NMR (500 MHz, DMSO-$d_6$) δ 7.83 (br d, J = 8.9 Hz, 1H), 7.59 (br d, J = 8.5 Hz, 1H), 6.16 (s, 1H), 4.97 (br d, J = 6.1 Hz, 2H), 4.74-4.68 (m, 1H), 4.17 (s, 3H), 3.40-3.34 (m, 1H), 2.43 (s, 3H), 2.35-2.26 (m, 1H), 1.99-1.46 (m, 8H), 1.12 (d, J = 6.7 Hz, 6H). hLPA$_1$ IC$_{50}$ = 745 nM. | Example 1 |

TABLE 1-continued

| Ex # | Structure & Name | Analytical & Biological Data | Method |
|---|---|---|---|
| 13 | (1S,3S)-3-((6-(5-(((4-cyclobutylthiazol-2-yl)amino)methyl)-1-methyl-1H-1,2,3-triazol-4-yl)-2-methyl-pyridin-3-yl)oxy)cyclohexanecarboxylic acid | LCMS, [M + H]$^+$ = 482.9; $^1$H NMR (500 MHz, DMSO-d$_6$) δ 7.82 (br d, J = 8.5 Hz, 1H), 7.51 (br d, J = 8.6 Hz, 1H), 6.19 (s, 1H), 4.96 (br d, J = 4.7 Hz, 2H), 4.76-4.69 (m, 1H), 4.16 (s, 3H), 3.33-3.23 (m, 1H), 2.48-2.38 (m, 4H), 2.16-1.44 (m, 14H); hLPA$_1$ IC$_{50}$ = 13 nM. | Example 2 |
| 14 | (1S,3S)-3-((2-methyl-6-(1-methyl-5-(((4-phenylthiazol-2-yl(amino) methyl)-1H-1,2,3-triazol-4-yl)-pyri-dine-3-yl)oxy)cyclohexane-1-carboxylic acid | LCMS, [M + H]$^+$ = 505.1; $^1$H NMR (500 MHz, DMSO-d$_6$) δ 7.85 (br d, J = 8.2 Hz, 1H), 7.68 (br d, J = 7.6 Hz, 2H), 7.51 (br d, J = 8.5 Hz, 1H), 7.34-7.28 (m, 2H), 7.27-7.21 (m, 1H), 7.08-7.03 (m, 1H), 5.14 (br d, J = 4.6 Hz, 2H), 4.83-4.75 (m, 1H), 4.16 (s, 3H), 2.69-2.59 (m, 1H), 2.44 (s, 3H), 2.08-1.44 (m, 8H); hLPA$_1$ IC$_{50}$ = 130 nM. | Example 3 |
| 15 | (1S,3S)-3-((6-(5-(((5-isopropyl thiazol-2-yl)amino)methyl)-1-methyl-1H-1,2,3-triazol-4-yl)-2-methyl-pyridin-3-yl)oxy)cyclohexane-1-carboxylic acid | LCMS, [M + H]$^+$ = 471.3; $^1$H NMR (500 MHz, DMSO-d$_6$) δ 7.99 (br d, J = 8.6 Hz, 1H), 7.72 (d, J = 8.2 Hz, 1H), 6.76 (s, 1H), 4.94 (s, 2H), 4.79-4.76 (m, 1H), 4.12 (s, 3H), 2.63-2.58 (m, 1H), 2.46 (s, 3H), 2.09-1.52 (m, 8H), 1.18 (d, J = 6.7 Hz, 6H), (The isopropyl C-H is not observed due to water-suppression); hLPA$_1$ IC$_{50}$ = 55 nM. | Example 1 |

TABLE 1-continued

| Ex # | Structure & Name | Analytical & Biological Data | Method |
|---|---|---|---|
| 16 | 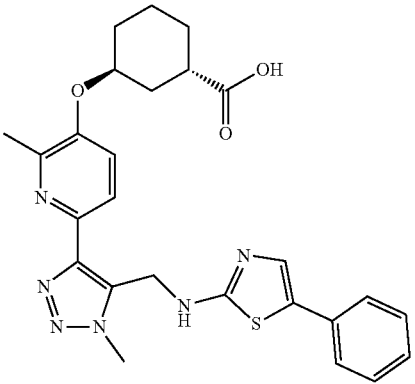<br>(1S,3S)-3-((2-methyl-6-(1-methyl-5-(((5-phenylthiazol-2-yl)amino) methyl)-1H-1,2,3-triazol-4-yl)pyridin-3-yl)oxy)cyclohexane-1-carboxylic acid | LCMS, [M + H]$^+$ = 505.2; $^1$H NMR (500 MHz, DMSO-$d_6$) δ 7.89-7.82 (m, 1H), 7.52-7.48 (m, 1H), 7.42-7.37 (m, 2H), 7.33 (br t, J = 7.8 Hz, 2H), 7.22-7.16 (m, 1H), 7.03 (s, 1H), 5.05 (br s, 2H), 4.82-4.74 (m, 1H), 4.14 (s, 3H), 2.67-2.59 (m, 1H), 2.45 (s, 3H), 2.08-1.43 (m, 8H); hLPA$_1$ IC$_{50}$ = 67 nM. | Example 3 |
| 17 | 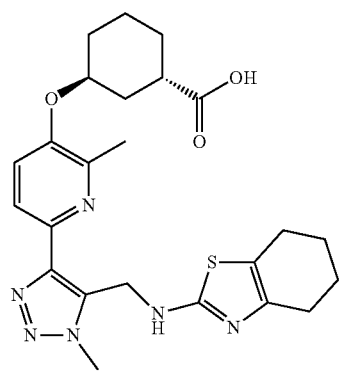<br>(1S,3S)-3-((2-methyl-6-(1-methyl-5-(((4,5,6,7-tetrahydrobenzo[d]thiazol-2-yl)amino)methyl)-1H-1,2,3-triazol-4-yl)pyridin-3-yl)oxy)cyclohexane carboxylic acid | LCMS, [M + H]$^+$ = 483.1; $^1$H NMR (500 MHz, DMSO-$d_6$) δ 7.82 (br d, J = 8.5 Hz, 1H), 7.48 (br d, J = 8.7 Hz, 1H), 4.86 (br s, 2H), 4.78-4.72 (m, 1H), 4.11 (s, 3H), 2.58-2.55 (m, 1H), 2.45-2.35 (m, 7H), 2.00-1.36 (m, 12H); hLPA$_1$ IC$_{50}$ = 1197 nM. | Example 2 |
| 18 | 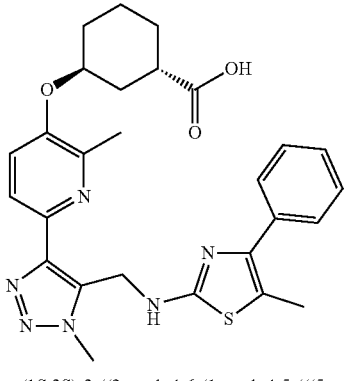<br>(1S,3S)-3-((2-methyl-6-(1-methyl-5-(((5-methyl-4-phenylthiazol-2-yl)amino)methyl)-1H-1,2,3-triazol-4-yl)pyridin-3-yl)oxy)cyclohexane carboxylic acid | LCMS, [M + H]$^+$ = 519.2; $^1$H NMR (500 MHz, DMSO-$d_6$) δ 7.84 (br d, J = 8.6 Hz, 1H), 7.48 (br d, J = 7.4 Hz, 3H), 7.36 (br t, J = 7.5 Hz, 2H), 7.30-7.24 (m, 1H), 5.00 (br d, J = 4.8 Hz, 2H), 4.80-4.73 (m, 1H), 4.12 (s, 3H), 2.66-2.57 (m, 1H), 2.44 (s, 3H), 2.29 (s, 3H), 2.06-1.42 (m, 8H); hLPA$_1$ IC$_{50}$ = 15 nM. | Example 2 |

TABLE 1-continued

| Ex # | Structure & Name | Analytical & Biological Data | Method |
|---|---|---|---|
| 19 | 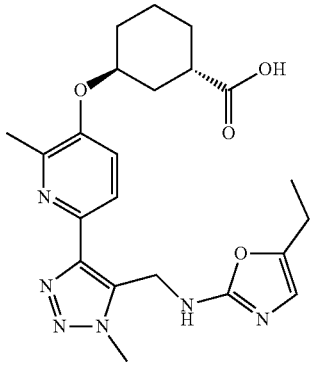<br>(1S,3S)-3-((6-(5-(((5-ethyloxazol-2-yl)amino)methyl)-1-methyl-1H-1,2,3-triazol-4-yl)-2-methylpyridin-3-yl)oxy)cyclohexane-1-carboxylic acid | LCMS, [M + H]$^+$ = 441.3; $^1$H NMR (500 MHz, DMSO-d$_6$) δ 7.85 (d, J = 8.2 Hz, 1H), 7.52 (br d, J = 8.5 Hz, 1H), 7.37 (br s, 1H), 6.38 (s, 1H), 4.87-4.74 (m, 3H), 4.13 (s, 3H), 2.64-2.57 (m, 1H), 2.48-2.39 (m, 5H), 2.02-1.45 (m, 8H), 1.05 (t, J = 7.5 Hz, 3H); hLPA$_1$ IC$_{50}$ = 106 nM. | Example 1 |
| 20 | 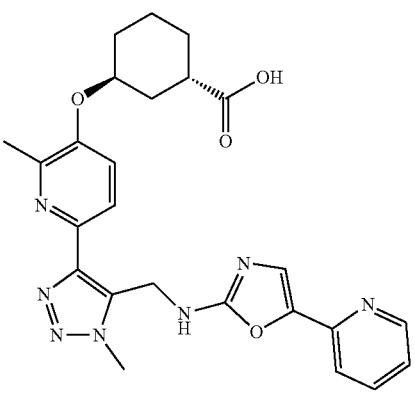<br>(1S,3S)-3-((2-methyl-6-(1-methyl-5-(((5-(pyridin-2-yl)oxazol-2-yl)amino) methyl)-1H-1,2,3-triazol-4-yl)pyridin-3-yl)oxy)cyclohexane carboxylic acid | LCMS, [M + H]$^+$ = 490.0; $^1$H NMR (500 MHz, DMSO-d$_6$) δ 8.46 (br d, J = 4.2 Hz, 1H), 8.12 (br s, 1H), 7.87 (br d, J = 8.5 Hz, 1H), 7.71 (br t, J = 7.7 Hz, 1H), 7.52 (br d, J = 8.6 Hz, 1H), 7.42 (2, 1H), 7.25 (br d, J = 8.0 Hz, 1H), 7.20-7.13 (m, 1H), 5.02 (br d, J = 5.0 Hz, 2H), 4.85-4.70 (m, 1H), 4.14 (s, 3H), 2.63-2.56 (m, 1H), 2.43 (s, 3H), 2.02-1.43 (m, 8H); hLPA$_1$ IC$_{50}$ = 99 nM. | Example 3 |

Example 21. (1 S,3 S)-3-((6-(5-(((5-fluoro-4-phenylthiazol-2-yl)amino)methyl)-1-methyl-1H-1,2,3-triazol-4-yl)-2-methylpyridin-3-yl)oxy)cyclohexane-1-carboxylic acid

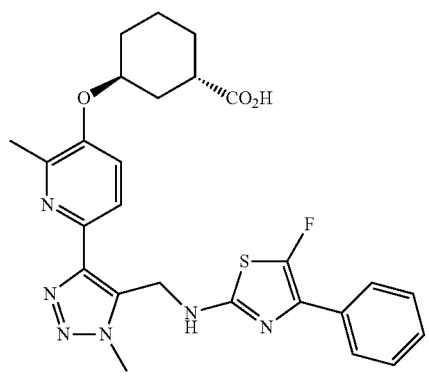 [SMILES: Cc1nc(-c2nnn(C)c2CNc2nc(-c3ccccc3)c(F)s2)ccc1O[C@H]1CCC[C@H](C(=O)O)C1]

21A. 5-fluoro-4-phenylthiazol-2-amine

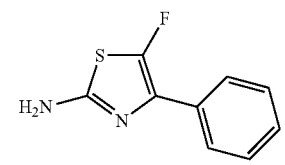 [SMILES: Nc1nc(-c2ccccc2)c(F)s1]

1-Chloromethyl-4-fluoro-1,4-diazoniabicyclo[2.2.2]octane bis(tetrafluoroborate) (1.17 g, 3.29 mmol) was added to a stirred solution of 4-phenylthiazol-2-amine (580 mg, 3.29 mmol) in anhydrous MeCN (20 mL) at 0° C. The reaction mixture was allowed to warm to RT and stirred overnight at RT, then was concentrated in vacuo and taken up in CH$_2$Cl$_2$ (15 mL). The precipitated quinuclidine salts were filtered off and the combined filtrates and CH$_2$Cl$_2$ rinses were concentrated in vacuo. The residual crude product was chromatographed (40 g SiO$_2$; continuous gradient from 0% to 20% EtOAc in hexane over 20 min) to give the title compound (300 mg, 1.55 mmol, 46.9% yield) as a light pink solid. $^1$H NMR (500 MHz, CDCl$_3$) δ 7.81 (d, J=7.7 Hz, 2H), 7.44 (t, J=7.7 Hz, 2H), 7.36-7.30 (m, 1H), 5.07 (br s, 2H); $^{19}$F NMR (471 MHz, CDCl$_3$) δ −153.50 (s, F) 21B. (1 S,3S)-3-((6-(5-formyl-1-methyl-1H-1,2,3-triazol-4-yl)-2-methylpyridin-3-yl)oxy)cyclo-hexane-1-carboxylic acid

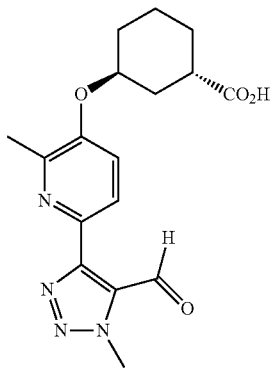 [SMILES: Cc1nc(-c2nnn(C)c2C=O)ccc1O[C@H]1CCC[C@H](C(=O)O)C1]

A mixture of Intermediate 9 (149 mg, 0.386 mmol) and 1.0 N aq. NaOH (1.16 mL, 1.16 mmol) in THF (2 mL)/MeOH (1 mL) was stirred at RT for 18 h, then was acidified with TFA (0.089 mL, 1.16 mmol). The solution was purified by preparative HPLC (Sunfire C18 30×100 mm-regenerated column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the title compound (TFA salt; 125 mg, 0.273 mmol, 70.7% yield) as a white solid. LCMS, [M+H]$^+$=345.2; $^1$H NMR (500 MHz, CDCl$_3$) δ 10.89 (s, 1H), 8.11 (d, J=8.5 Hz, 1H), 7.35-7.30 (m, 1H), 4.79 (br s, 1H), 4.40 (s, 3H), 2.97-2.88 (m, 1H), 2.57 (s, 3H), 2.20 (br d, J=13.2 Hz, 1H), 2.09-1.62 (m, 7H).

Example 21

To an RT solution of 21B (TFA salt; 60 mg; 0.13 mmol), TFA (40 mg, 0.087 mmol), 5-fluoro-4-phenylthiazol-2-amine (25 mg, 0.13 mmol) in DCM (1 mL) was added Ti(OiPr)$_3$Cl (0.071 mL, 0.262 mmol). The mixture was stirred at RT for 2 h, after which NaBH(OAc)$_3$ (37.0 mg, 0.175 mmol) and TFA (0.03 mL) were added portionwise. The reaction mixture was stirred at RT for 5 days, then was concentrated under N$_2$. The residue was dissolved in MeCN (1 mL), quenched with TFA and water, then was concentrated in vacuo. The residue was purified by preparative HPLC (Sunfire C18 30×100 mm-regenerated column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the title compound (TFA salt; 5 mg, 7.7 μmol, 8.8% yield) as a yellowish oil. LCMS, [M+H]$^+$=523.2; $^1$H NMR (500 MHz, CDCl$_3$) δ 8.11 (d, J=8.8 Hz, 1H), 7.65 (br d, J=8.8 Hz, 1H), 7.39-7.21 (m, 5H), 5.01 (s, 2H), 4.79 (br s, 1H), 4.27 (s, 3H), 2.87-2.76 (m, 1H), 2.11-1.62 (m, 11H); $^{19}$F NMR (471 MHz, CDCl$_3$) δ −75.90 (s, TFA), −154.94 (s, F). hLPA$_1$ IC$_{50}$=18 nM.

Example 22. (1 S,3 S)-3-((6-(5-(((2-isobutyl-2H-1,2,3-triazol-4-yl)amino)methyl)-1-methyl-1H-1,2,3-triazol-4-yl)-2-methylpyridin-3-yl)oxy)cyclohexane-1-carboxylic acid

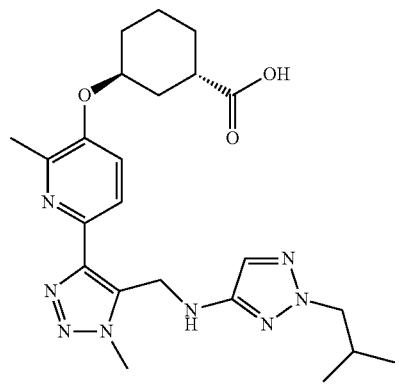 [SMILES: Cc1nc(-c2nnn(C)c2CNc2cnn(CC(C)C)n2)ccc1O[C@H]1CCC[C@H](C(=O)O)C1]

22A & 22B. (2-isobutyl-4-nitro-2H-1,2,3-triazole and 1-isobutyl-4-nitro-1H-1,2,3-triazole

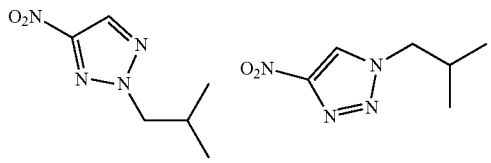

A mixture of 4-nitro-1,2,3-triazole (0.50 g, 4.38 mmol), 2-methyl-1-propanol (0.61 mL, 6.58 mmol), Ph$_3$P (1.73 g, 6.58 mmol), and DIAD (1.28 mL, 6.58 mmol) in THF (10 mL) was stirred at RT for 18 h, then was concentrated in vacuo. The crude oil was chromatographed (reverse ISCO C18 100 g Gold column; detection at 220 nm; flow rate=60 mL/min; continuous gradient from 0% B to 100% B over 20 min+5 min hold time at 100% B, where A=95:5:0.05 H$_2$O:MeCN:TFA and B=95:5:0.05 MeCN:H$_2$O:TFA) to give the two separated N-isobutyl-triazole regioisomers: 1-isobutyl-4-nitro-1H-1,2,3-triazole 22A (0.10 g, 0.588 mmol, 13.4% yield) ($^1$H NMR (400 MHz, CDCl$_3$) δ 8.28 (s, 1H), 4.28 (d, J=7.0 Hz, 2H), 2.30 (dt, J=13.6, 6.8 Hz, 1H), 1.01 (d, J=6.6 Hz, 6H)) and 2-isobutyl-4-nitro-2H-1,2,3-triazole 22B (0.40 g, 2.35 mmol, 53.6% yield) ($^1$H NMR (400 MHz, CDCl$_3$) δ 8.18 (s, 1H), 4.33 (d, J=7.3 Hz, 2H), 2.42 (dt, J=13.7, 6.9 Hz, 1H), 0.98 (d, J=6.6 Hz, 6H)).

22C. 2-isobutyl-2H-1,2,3-triazol-4-amine

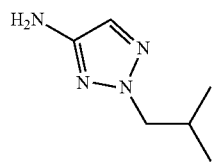

A mixture of 2-isobutyl-4-nitro-2H-1,2,3-triazole (0.40 g, 2.35 mmol), and 10% Pd/C (0.025 g, 0.24 mmol) in MeOH (10 mL) was stirred under an atmosphere of $H_2$ at RT for 3 h, after which the catalyst was filtered off. The filtrate was concentrated in vacuo to give the title compound (0.32 g, 2.283 mmol, 97% yield) as a clear oil. LCMS, $[M+H]^+$=141.2; $^1$H NMR (400 MHz, CDCl$_3$) δ 6.96 (s, 1H), 4.02 (d, J=7.3 Hz, 2H), 3.62 (br s, 2H), 2.26 (dt, J=13.7, 6.9 Hz, 1H), 0.91 (d, J=6.8 Hz, 6H).

22D. Isopropyl (1 S,3 S)-3-((6-(5-(((2-isobutyl-2H-1,2,3-triazol-4-yl)amino)methyl)-1-methyl-1H-1,2,3-triazol-4-yl)-2-methylpyridin-3-yl)oxy)cyclohexane-1-carboxylate

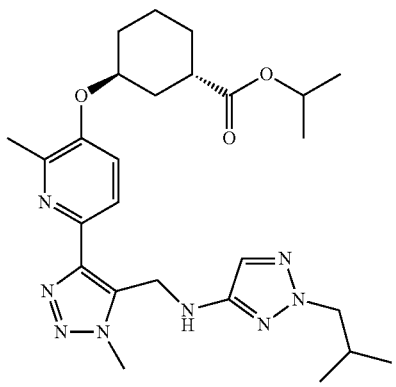 [SMILES: Cc1nc(-c2nnn(C)c2CNc2cnn(CC(C)C)n2)ccc1O[C@H]1CCC[C@H](C(=O)OC(C)C)C1]

To a RT solution of Intermediate 9 (60 mg, 0.155 mmol), 22C (33 mg, 0.23 mmol) in DCM (0.5 mL) was added Ti(OiPr)$_3$Cl (0.126 mL, 0.47 mmol). After 2 h stirring at RT, NaBH(OAc)$_3$ (66 mg, 0.31 mmol) and TFA (0.05 mL) were successively added to the mixture portionwise. The reaction mixture was stirred for 18 h at RT, after which satd aq. NaHCO$_3$ was added. The aqueous layer was extracted with EtOAc (3×). The combined organic extracts were washed with brine, dried (MgSO$_4$) and concentrated in vacuo. The crude product was chromatographed (4 g SiO$_2$; continuous gradient from 0% to 50% EtOAc/hexane over 10 min) to give the title compound (60 mg, 0.117 mmol, 76% yield) as a light yellowish oil. $^1$H NMR (500 MHz, CDCl$_3$) δ 8.03 (d, J=8.5 Hz, 1H), 7.34-7.22 (m, 1H), 5.04 (dt, J=12.4, 6.3 Hz, 1H), 4.71 (br s, 1H), 4.62 (s, 2H), 4.26 (s, 3H), 4.01 (d, J=7.2 Hz, 2H), 2.84-2.74 (m, 1H), 2.56 (s, 3H), 2.24 (dquin, J=13.8, 6.9 Hz, 1H), 2.15-2.06 (m, 1H), 2.02-1.88 (m, 3H), 1.82-1.59 (m, 4H), 1.32-1.21 (m, 7H), 0.88 (d, J=6.9 Hz, 6H).

Example 22

A mixture of 22D (60 mg, 0.117 mmol) and 1.0 M aq. NaOH (0.47 mL, 0.47 mmol) in THF (0.5 mL)/MeOH (0.5 mL) was stirred at RT for 18 h, then was concentrated in vacuo. The crude product was purified by preparative HPLC (Sunfire C18 30×100 mm column; detection at 220 nm; flow rate=40 mL/min; continuous gradient from 30% B to 100% B over 10 min+2 min hold time at 100% B, where A=90:10:0.1 H$_2$O:MeCN:TFA and B=90:10:0.1 MeCN:H$_2$O:TFA) to give the title compound (bis-TFA salt; 61 mg, 0.086 mmol, 73.0% yield) as an oil. LCMS, $[M+H]^+$=469.1; $^1$H NMR (500 MHz, CDCl$_3$) δ 8.28 (d, J=8.8 Hz, 1H), 7.80 (d, J=8.8 Hz, 1H), 7.23 (s, 1H), 4.82 (br s, 1H), 4.75 (s, 2H), 4.26 (s, 3H), 4.01 (d, J=7.2 Hz, 2H), 2.92-2.81 (m, 1H), 2.68 (s, 3H), 2.22-2.08 (m, 2H), 2.04-1.73 (m, 6H), 1.68 (br s, 1H), 0.85 (d, J=6.9 Hz, 6H). hLPA$_1$ IC$_{50}$=42 nM.

Example 23. (1 S,3 S)-3-((6-(5-(((1-isobutyl-1H-1,2,3-triazol-4-yl)amino)methyl)-1-methyl-1H-1,2,3-triazol-4-yl)-2-methylpyridin-3-yl)oxy)cyclohexane-1-carboxylic acid

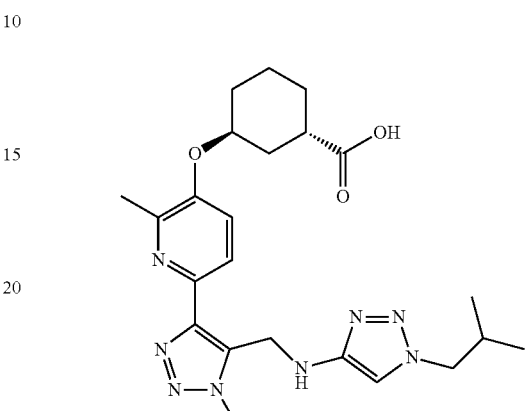

23A. 1-isobutyl-4-nitro-1H-1,2,3-triazole

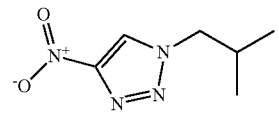

23B. 2-isobutyl-4-nitro-2H-1,2,3-triazole

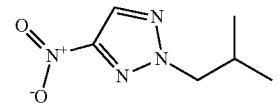

A mixture of 4-nitro-1,2,3-triazole (0.5 g, 4.38 mmol), 2-methyl-1-propanol (0.61 mL, 6.58 mmol), Ph$_3$P (1.73 g, 6.58 mmol), and DIAD (1.28 mL, 6.58 mmol) in THF (10 mL) was stirred at RT for 18 h, then was concentrated in vacuo. The crude oil was purified by preparative HPLC (C18 100 g RediSep gold column; detection at 214/254 nm; flow rate=60 mL/min; continuous gradient from 0% B to 100% B over 20 min+5 min hold time at 100% B, where A=95:5:0.05 H$_2$O:MeCN:TFA and B=95:5:0.05 MeCN:H$_2$O:TFA) to give Example 23A (0.10 g, 0.59 mmol, 13.4% yield); $^1$H NMR (400 MHz, CDCl$_3$) δ 8.28 (s, 1H), 4.28 (d, J=7.0 Hz, 2H), 2.30 (dt, J=13.6, 6.8 Hz, 1H), 1.01 (d, J=6.6 Hz, 6H)) and Example 23B (0.40 g, 2.35 mmol, 53.6% yield); $^1$H NMR (400 MHz, CDCl$_3$) δ 8.18 (s, 1H), 4.33 (d, J=7.3 Hz, 2H), 2.42 (dt, J=13.7, 6.9 Hz, 1H), 0.98 (d, J=6.6 Hz, 6H). Both compounds were obtained as white solids.

23C. 1-isobutyl-1H-1,2,3-triazol-4-amine

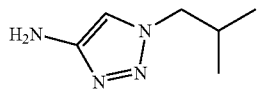

A mixture of Example 23A (0.1 g, 0.588 mmol) in MeOH (5 mL) was stirred under an atmosphere of H$_2$ at RT for 3 h, then was filtered. The filtrate was concentrated in vacuo to give the title compound (80 mg, 0.571 mmol, 97% yield) as a white solid. $^1$H NMR (400 MHz, CDCl$_3$) δ 6.92 (s, 1H), 4.03 (d, J=7.3 Hz, 2H), 3.72 (br s, 2H), 2.16 (dt, J=13.5, 6.9 Hz, 1H), 0.93 (d, J=6.6 Hz, 6H); [M+H]$^+$=141.3.

23D. Isopropyl (1 S,3 S)-3-((6-(5-(((1-isobutyl-1H-1,2,3-triazol-4-yl)amino)methyl)-1-methyl-1H-1,2,3-triazol-4-yl)-2-methylpyridin-3-yl)oxy)cyclohexane-1-carboxylate

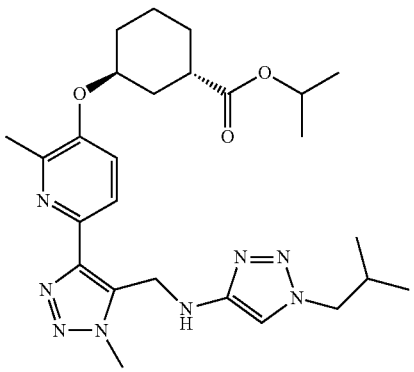 [SMILES: Cc1nc(-c2nnn(C)c2CNc2cn(CC(C)C)nn2)ccc1O[C@H]1CCC[C@H](C(=O)OC(C)C)C1]

To a solution of Intermediate 9 (30 mg, 0.078 mmol) and Example 23C (16.3 mg, 0.116 mmol) in DCM (0.5 mL) was added Ti(OiPr)$_3$Cl (0.07 mL, 0.233 mmol). The reaction was stirred at RT for 2 h, after which NaBH(OAc)$_3$ (33 mg, 0.155 mmol) was added portionwise, followed by TFA (0.1 mL) portionwise. The reaction mixture was stirred at RT for 18 h, then was quenched with satd aq. NaHCO$_3$ (5 mL). The aqueous layer was extracted with EtOAc. The organic layer was washed with brine, dried (MgSO$_4$) and concentrated in vacuo. The crude product was chromatographed (4 g SiO$_2$; continuous gradient from 0% to 50% EtOAc in hexane over 10 min) to give the title compound (24 mg, 0.047 mmol, 60.5% yield) as a light yellow oil. [M+H]$^+$=511.1.

Example 23

A mixture of Example 23D (24 mg, 0.047 mmol) and 1.0 M aq. NaOH (0.19 mL, 0.188 mmol) in THF/MeOH (0.5 mL each) was stirred at RT for 18 h, then was concentrated in vacuo. The residue was purified by preparative HPLC (Sunfire C18 30×100 mm column; detection at 220 nm; flow rate=40 mL/min; continuous gradient from 30% B to 100% B over 10 min+2 min hold time at 100% B, where A=90:10:0.1 H$_2$O:MeCN:TFA and B=90:10:0.1 MeCN:H$_2$O:TFA) to give the title compound (24 mg, 0.034 mmol, 72.6% yield) as an oil. LCMS, [M+H]$^+$=469.1; $^1$H NMR (500 MHz, CDCl$_3$) δ 8.14 (d, J=8.8 Hz, 1H), 7.92 (d, J=8.8 Hz, 1H), 7.37 (s, 1H), 4.91 (br s, 1H), 4.70 (s, 2H), 4.24 (s, 3H), 4.09 (d, J=7.2 Hz, 2H), 2.98-2.88 (m, 1H), 2.85 (s, 3H), 2.30-1.64 (m, 9H), 0.96 (d, J=6.6 Hz, 6H); hLPA$_1$ IC$_{50}$=435 nM.

Example 24. (1 S,3 S)-3-((6-(5-(((2-(cyclobutylmethyl)-2H-1,2,3-triazol-4-yl)amino)methyl)-1-methyl-1H-1,2,3-triazol-4-yl)-2-methylpyridin-3-yl)oxy)cyclohexane-1-carboxylic acid

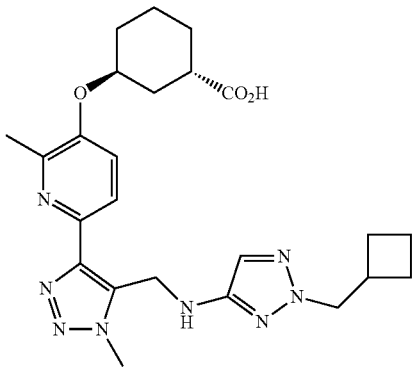 [SMILES: Cc1nc(-c2nnn(C)c2CNc2cnn(CC3CCC3)n2)ccc1O[C@H]1CCC[C@H](C(=O)O)C1]

24A. 2-(cyclobutylmethyl)-4-nitro-2H-1,2,3-triazole

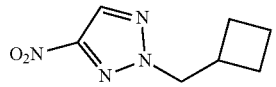 [SMILES: O=[N+]([O-])c1cnn(CC2CCC2)n1]

A mixture of 4-nitro-1,2,3-triazole (0.43 g, 3.77 mmol), (bromomethyl)cyclo-butane (0.847 mL, 7.54 mmol), and K$_2$CO$_3$ (2.084 g, 15.08 mmol) in MeCN (20 mL) was stirred at 60° C. for 18 h, then was cooled to RT and taken up in DCM (20 mL) and filtered. The filtrate was concentrated in vacuo. The residue was chromatographed (40 g SiO$_2$; continuous gradient from 0% to 30% EtOAc in Hexane over 20 min) to give the title compound (222 mg, 1.22 mmol, 32.3% yield) as a clear oil. $^1$H NMR (400 MHz, CDCl$_3$) δ 8.15 (s, 1H), 4.52 (d, J=7.5 Hz, 2H), 3.18-2.85 (m, 1H), 2.23-1.76 (m, 6H).

24B. 2-(cyclobutylmethyl)-2H-1,2,3-triazol-4-amine

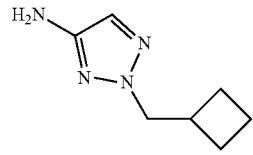 [SMILES: Nc1cnn(CC2CCC2)n1]

A mixture of 24A (0.22 g, 1.208 mmol), and 10% Pd/C (0.013 g, 0.121 mmol) in MeOH (10 mL) was stirred under an atmosphere of H₂ at RT for 3 h, after which the catalyst was filtered off. The filtrate was concentrated in vacuo to give the title compound (0.18 g, 1.18 mmol, 98% yield) as a light yellowish oil. LCMS, [M+H]⁺=153.2; ¹H NMR (400 MHz, CDCl₃) δ 6.95 (s, 1H), 4.22 (d, J=7.5 Hz, 2H), 2.96-2.78 (m, 1H), 2.14-2.01 (m, 2H), 1.97-1.76 (m, 4H).

Example 24

To a solution of Intermediate 9 (25 mg, 0.065 mmol), 24B (15 mg, 0.097 mmol) in DCM (0.5 mL) was added Ti(OiPr)₃Cl (0.053 mL, 0.194 mmol). After 2 h, NaBH(OAc)₃ (27 mg, 0.13 mmol) was added to the mixture portionwise, followed by TFA (0.05 mL) portionwise. The mixture was stirred for 18 h at RT, after which satd aq NaHCO₃ was added. The aqueous layer was extracted with EtOAc. The organic layer was washed with brine, dried (MgSO₄) and concentrated in vacuo. The crude residue was chromatographed (4 g SiO₂; continuous gradient from 0% to 100% EtOAc in Hexane over 10 min) to give the aminotriazole cyclohexyl ester as a clear oil. This crude product was stirred with 1.0 M aq. NaOH (0.54 mL, 0.54 mmol) in THF (1 mL)/MeOH (0.2 mL) at RT for 18 h, then was concentrated in vacuo. The crude product was purified by preparative HPLC (Sunfire C18 30×100 mm-column; detection at 220 nm; flow rate=40 mL/min; continuous gradient from 10% B to 100% B over 10 min+2 min hold time at 100% B, where A=90:10:0.1 H₂O:MeCN:TFA and B=90:10:0.1 MeCN:H₂O:TFA) to give the title compound (bis-TFA salt; 18 mg, 0.025 mmol, 38.5% yield) as a light yellowish oil. LCMS, [M+H]⁺=481.1; ¹H NMR (500 MHz, CDCl₃) δ 8.25 (d, J=8.8 Hz, 1H), 7.77 (d, J=9.1 Hz, 1H), 7.19 (s, 1H), 4.82 (br s, 1H), 4.73 (s, 2H), 4.27 (s, 3H), 4.20 (d, J=7.2 Hz, 2H), 2.95-2.84 (m, 1H), 2.76 (dt, J=15.2, 7.7 Hz, 1H), 2.67 (s, 3H), 2.18-1.61 (m, 15H). hLPA₁ IC₅₀=33 nM.

Example 25. (1 S,3 S)-3-((6-(5-(((1-isobutyl-1H-1,2,4-triazol-3-yl)amino)methyl)-1-methyl-1H-1,2,3-triazol-4-yl)-2-methylpyridin-3-yl)oxy)cyclohexane-1-carboxylic acid

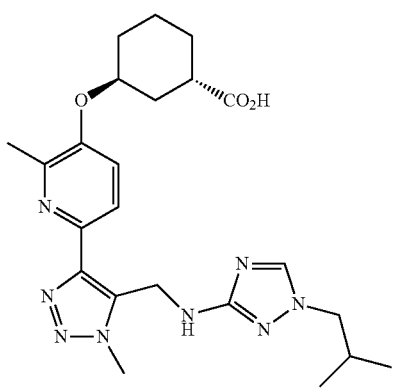 [SMILES: Cc1nc(-c2nnn(C)c2CNc2ncn(CC(C)C)n2)ccc1O[C@H]1CCC[C@H](C(=O)O)C1]

25A. 1-isobutyl-1H-1,2,4-triazol-3-amine

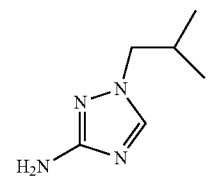

A solution of NaOMe in MeOH was generated by dissolving sodium (1.37 g, 59.5 mmol) in MeOH (100 mL). N,1-diisobutyl-1H-1,2,4-triazol-3-amine (5 g, 59.5 mmol) was added and the resulting solution was stirred for 10 min at 25° C., after which 1-bromo-2-methylpropane (6.49 mL, 59.5 mmol) was added. The resulting solution was heated under reflux for 24 h, then was cooled to RT and concentrated in vacuo. The residue was taken up in EtOAc (50 mL), washed with brine (2×50 mL), dried (MgSO₄) and concentrated in vacuo. The resulting solid was chromatographed (80 g SiO₂; continuous gradient from 0% to 10% MeOH/DCM over 20 min) to give the title compound (1.80 g, 12.8 mmol, 22% yield) as white solid. ¹H NMR (500 MHz, CDCl₃) δ 7.66 (s, 1H), 4.80 (br s, 2H), 3.75-3.70 (m, 2H), 2.21-2.12 (m, 1H), 0.93-0.86 (m, 6H); ¹³C NMR (126 MHz, CDCl₃) δ 163.8, 142.2, 56.5, 28.4, 19.6.

Example 25

To a solution of Intermediate 9 (25 mg, 0.065 mmol), 1-isobutyl-1H-1,2,4-triazol-3-amine (13.60 mg, 0.097 mmol) in DCM (0.5 mL) was added Ti(OiPr)₃Cl (0.053 mL, 0.194 mmol). After 2 h, NaBH(OAc)₃ (27.4 mg, 0.129 mmol) and TFA (0.02 mL) were successively added to the mixture portionwise. The mixture was stirred for 18 h at RT, after which sat aq. NaHCO₃ was added. The aqueous layer was extracted with EtOAc. The organic layer was washed with brine, dried (MgSO₄) and concentrated in vacuo. This crude ester product was stirred with 1.0 M aq. NaOH (0.54 mL, 0.54 mmol) in THF (1 mL)/MeOH (0.2 mL) at RT for 18 h, then was concentrated in vacuo. The crude product was purified by preparative HPLC (Sunfire C18 30×100 mm-column; detection at 220 nm; flow rate=40 mL/min; continuous gradient from 10% B to 100% B over 10 min+2 min hold time at 100% B, where A=90:10:0.1 H₂O:MeCN:TFA and B=90:10:0.1 MeCN:H₂O:TFA) to give the title compound (bis-TFA salt; 24 mg, 0.034 mmol, 86% yield) as an oil. LCMS, [M+H]⁺=469.0; ¹H NMR (400 MHz, CDCl₃) δ 8.37 (s, 1H), 7.94 (d, J=8.8 Hz, 1H), 7.71 (d, J=9.0 Hz, 1H), 4.85-4.73 (m, 3H), 4.23 (s, 3H), 3.81 (d, J=7.3 Hz, 2H), 2.93-2.85 (m, 1H), 2.71 (s, 3H), 2.23-1.60 (m, 9H), 0.92 (d, J=6.6 Hz, 6H). hLPA₁ IC₅₀=125 nM The Examples in Table 2 below were synthesized by the same procedures exemplified by Examples 21-25.

TABLE 2

| Ex # | Structure & Name | Analytical & Biological Data | Method |
|---|---|---|---|
| 26 | (1S,3S)-3-((6-(5-(((4,5-dimethylthiazol-2-yl)amino)methyl)-1-methyl-1H-1,2,3-triazol-4-yl)-2-methylpyridin-3-yl)oxy)cyclohexane-1-carboxylic acid | LCMS, $[M + H]^+$ = 457.0; $^1$H NMR (500 MHz, CDCl$_3$) δ 7.96 (br d, J = 8.8 Hz, 1H), 7.78 (br d, J = 8.8 Hz, 1H), 4.99 (s, 2H), 4.95-4.83 (m, 1H), 4.19 (s, 3H), 2.94-2.83 (m, 1H), 2.71 (s, 3H), 2.23-1.64 (m, 14H); hLPA$_1$ IC$_{50}$ = 3650 nM. | Example 21 |
| 27 | (1S,3S)-3-((6-(5-(((2-cyclohexyl-2H-1,2,3-triazol-4-yl)amino)methyl)-1-methyl-1H-1,2,3-triazol-4-yl)-2-methylpyridin-3-yl)oxy)cyclohexane-1-carboxylic acid | LCMS, $[M + H]^+$ = 495.2; $^1$H NMR (400 MHz, CDCl$_3$) δ 8.11 (d, J = 8.8 Hz, 1H), 7.52 (d, J = 8.8 Hz, 1H), 7.03 (s, 1H), 4.75 (br s, 1H), 4.67 (s, 2H), 4.25 (s, 3H), 4.19 (tt, J = 11.4, 3.9 Hz, 1H), 2.92-2.82 (m, 1H), 2.61 (s, 3H), 2.13-1.58 (m, 15H), 1.47-1.17 (m, 3H); hLPA$_1$ IC$_{50}$ = 100 nM | Example 22 |
| 28 | (1S,3S)-3-((6-(5-(((2-cyclopentyl-2H-1,2,3-triazol-4-yl)amino)methyl)-1-methyl-1H-1,2,3-triazol-4-yl)-2-methylpyridin-3-yl)oxy)cyclohexane-1-carboxylic acid | LCMS, $[M + H]^+$ = 481.2; $^1$H NMR (400 MHz, CDCl$_3$) δ 8.32 (d, J = 8.8 Hz, 1H), 7.88 (d, J = 9.2 Hz, 1H), 7.25 (s, 1H), 4.82 (br s, 1H), 4.78-4.69 (m, 3H), 4.24 (s, 3H), 2.85 (dt, J = 7.8, 3.8 Hz, 1H), 2.66 (s, 3H), 2.18-1.58 (m, 16H); hLPA$_1$ IC$_{50}$ = 39 nM. | Example 22 |

TABLE 2-continued

| Ex # | Structure & Name | Analytical & Biological Data | Method |
|---|---|---|---|
| 29 | (1S,3S)-3-((2-methyl-6-(1-methyl-5-(((2-propyl-2H-1,2,3-triazol-4-yl)amino)methyl)-1H-1,2,3-triazol-4-yl)pyridin-3-yl)oxy)cyclohexane-1-carboxylic acid | LCMS, [M + H]$^+$ = 455.2; $^1$H NMR (400 MHz, CDCl$_3$) δ 8.17 (d, J = 8.8 Hz, 1H), 7.67 (d, J = 9.0 Hz, 1H), 7.12 (s, 1H), 4.77 (br s, 1H), 4.69 (s, 2H), 4.24 (s, 3H), 4.14 (t, J = 7.0 Hz, 2H), 2.93-2.80 (m, 1H), 2.63 (s, 3H), 2.17-1.57 (m, 10H), 0.84 (t, J = 7.4 Hz, 3H); hLPA$_1$ IC$_{50}$ = 297 nM. | Example 22 |
| 30 | (1S,3S)-3-((6-(5-(((2-cyclobutyl-2H-1,2,3-triazol-4-yl)amino)methyl)-1-methyl-1H-1,2,3-triazol-4-yl)-2-methylpyridin-3-yl)oxy)cyclohexane-1-carboxylic acid | LCMS, [M + H]$^+$ = 467.2; $^1$H NMR (400 MHz, CDCl$_3$) δ 8.29 (d, J = 8.8 Hz, 1H), 7.82 (d, J = 9.0 Hz, 1H), 4.86-4.79 (m, 2H), 4.75 (s, 2H), 4.28 (s, 3H), 2.88 (dt, J = 8.1, 3.9 Hz, 1H), 2.67 (s, 3H), 2.52-2.35 (m, 4H), 2.18-2.08 (m, 1H), 2.03-1.58 (m, 10H); hLPA$_1$ IC$_{50}$ = 91 nM. | Example 22 |
| 31 | (1S,3S)-3-((6-(5-(((2-cyclopropyl-methyl)-2H-1,2,3-triazol-4-yl)amino) methyl)-1-methyl-1H-1,2,3-triazol-4-yl)-2-methyl-pyridin-3-yl)oxy) cyclohexane-1-carboxylic acid | LCMS, [M + H]$^+$ = 467.2; $^1$H NMR (500 MHz, CDCl$_3$) δ 8.26 (d, J = 9.1 Hz, 1H), 7.80 (d, J = 9.1 Hz, 1H), 7.23 (s, 1H), 4.82 (br s, 1H), 4.75 (s, 2H), 4.27 (s, 3H), 4.05 (d, J = 7.2 Hz, 2H), 2.94-2.83 (m, 1H), 2.68 (s, 3H), 2.21-1.57 (m, 9H), 1.29-1.15 (m, 1H), 0.60-0.54 (m, 2H), 0.35-0.29 (m, 2H); hLPA$_1$ IC$_{50}$ = 54 nM. | Example 22 |

TABLE 2-continued

| Ex # | Structure & Name | Analytical & Biological Data | Method |
|---|---|---|---|
| 32 | (1S,3S)-3-((2-methyl-6-(1-methyl-5-(((2-propyl-2H-1,2,3-triazol-4-yl) amino)methyl)-1H-1,2,3-triazol-4-yl) pyridin-3-yl)oxy)cyclohexane-1-carboxylic acid | LCMS, [M + H]$^+$ = 489.0; $^1$H NMR (400 MHz, CDCl$_3$) δ 8.22 (d, J = 9.0 Hz, 1H), 7.80 (d, J = 9.0 Hz, 1H), 7.72 (dd, J = 8.6, 1.1 Hz, 2H), 7.46-7.36 (m, 3H), 7.30-7.24 (m, 1H), 4.87-4.74 (m, 3H), 4.30 (s, 3H), 2.94-2.82 (m, 1H), 2.66 (s, 3H), 2.18-2.05 (m, 1H), 2.01-1.57 (m, 8H); hLPA$_1$ IC$_{50}$ = 10 nM. | Example 22 |
| 34 | (1S,3S)-3-((6-(5-(((1-benzyl-1H-1,2,4-triazol-3-yl)amino)methyl)-1-methyl-1H-1,2,3-triazol-4-yl)-2-methylpyridin-3-yl)oxy)cyclohexane-1-carboxylic acid | LCMS, [M + H]$^+$ = 503.0; $^1$H NMR (400 MHz, CDCl$_3$) δ 8.33 (s, 1H), 7.88 (d, J = 8.8 Hz, 1H), 7.71 (d, J = 9.0 Hz, 1H), 7.46-7.37 (m, 3H), 7.27-7.24 (m, 2H), 5.15 (s, 2H), 4.84-4.70 (m, 3H), 4.12 (s, 3H), 2.91-2.82 (m, 1H), 2.71 (s, 3H), 2.17-1.61 (m, 9H); hLPA$_1$ IC$_{50}$ = 332 nM. | Example 25 |
| 35 | (1S,3S)-3-((2-methyl-6-(1-methyl-5-(((1-propyl-1H-1,2,4-triazol-3-yl) amino)methyl)-1H-1,2,3-triazol-4-yl) pyridin-3-yl)oxy)cyclohexane-1-carboxylic acid | LCMS, [M + H]$^+$ = 455.1; $^1$H NMR (400 MHz, CD$_3$CN) δ 8.31 (s, 1H), 8.12-7.99 (m, 2H), 5.03-4.97 (m, 1H), 4.65 (s, 2H), 4.18 (s, 3H), 3.98 (t, J = 6.9 Hz, 2H), 2.88-2.79 (m, 1H), 2.74 (s, 3H), 2.19-2.09 (m, 1H), 2.03-1.90 (m, 4H), 1.86-1.58 (m, 6H), 0.88 (t, J = 7.4 Hz, 3H); hLPA$_1$ IC$_{50}$ = 309 nM. | Example 25 |

TABLE 2-continued

| Ex # | Structure & Name | Analytical & Biological Data | Method |
|---|---|---|---|
| 36 | 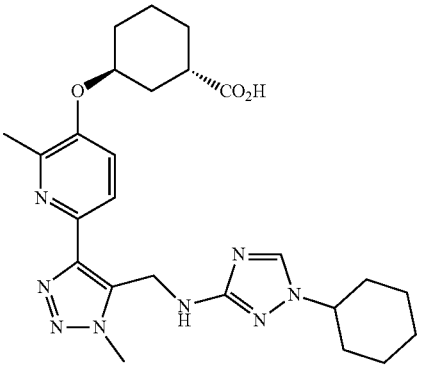<br>(1S,3S)-3-((6-(5-(((1-cyclohexyl-1H-1,2,4-triazol-3-yl)amino)methyl)-1-methyl-1H-1,2,3-triazol-4-yl)-2-methylpyridin-3-yl)oxy)cyclohexane-1-carboxylic acid | LCMS, [M + H]$^+$ = 495.2; $^1$H NMR (400 MHz, CDCl$_3$) δ 8.35 (s, 1H), 7.95 (d, J = 8.8 Hz, 1H), 7.51 (br dd, J = 6.5, 2.1 Hz, 1H), 4.81 (d, J = 2.6 Hz, 2H), 4.74 (br s, 1H), 4.24 (s, 3H), 3.98 (tt, J = 11.5, 3.7 Hz, 1H), 2.91-2.82 (m, 1H), 2.65 (s, 3H), 2.17-1.53 (m, 15H), 1.47-1.33 (m, 2H), 1.29-1.16 (m, 1H); hLPA$_1$ IC$_{50}$ = 147 nM. | Example 25 |
| 37 | 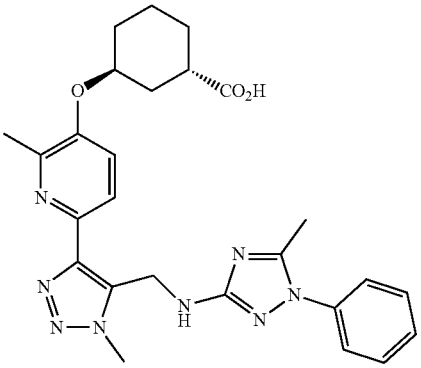<br>(1S,3S)-3-((2-methyl-6-(1-methyl-5-(((5-methyl-1-phenyl-1H-1,2,4-triazol-3-yl)amino)methyl)-1H-1,2,3-triazol-4-yl)pyridin-3-yl)oxy) cyclohexane-1-carboxylic acid | LCMS, [M + H]$^+$ = 503.2; $^1$H NMR (500 MHz, CDCl$_3$) δ 7.98 (d, J = 8.8 Hz, 1H), 7.67-7.53 (m, 4H), 7.35 (dd, J = 6.5, 3.2 Hz, 2H), 4.82 (s, 2H), 4.76 (br s, 1H), 4.24 (s, 3H), 2.88 (br s, 1H), 2.59 (s, 3H), 2.54 (s, 3H), 2.13-1.63 (m, 8H); hLPA$_1$ IC$_{50}$ = 46 nM. | Example 25 |
| 38 | 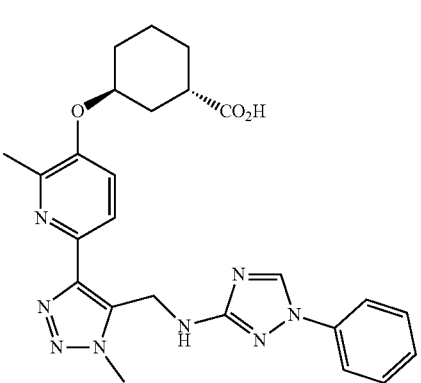<br>(1S,3S)-3-((2-methyl-6-(1-methyl-5-(((1-phenyl-1H-1,2,4-triazol-3-yl)amino)methyl)-1H-1,2,3-triazol-4-yl)pyridin-3-yl)oxy)cyclohexane-1-carboxylic acid | LCMS, [M + H]$^+$ = 489.1; $^1$H NMR (500 MHz, CDCl$_3$) δ 8.67 (s, 1H), 8.03 (d, J = 8.8 Hz, 1H), 7.81 (d, J = 9.1 Hz, 1H), 7.60-7.31 (m, 5H), 4.94-4.77 (m, 3H), 4.29 (s, 3H), 4.21-4.01 (m, 1H), 2.90 (br dd, J = 7.8, 4.0 Hz, 1H), 2.69 (s, 3H), 2.61-2.43 (m, 1H), 2.25-1.62 (m, 7H); hLPA$_1$ IC$_{50}$ = 34 nM. | Example 25 |

TABLE 2-continued

| Ex # | Structure & Name | Analytical & Biological Data | Method |
|---|---|---|---|
| 39 | 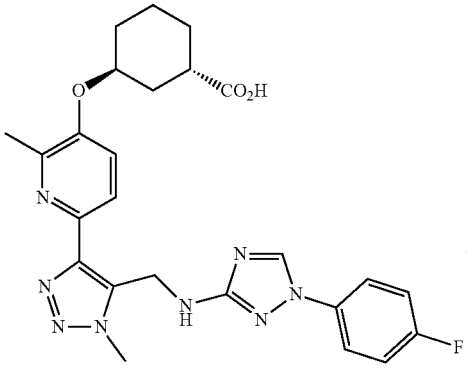<br>(1S,3S)-3-((6-(5-(((1-(4-fluoro-phenyl)-1H-1,2,4-triazol-3-yl)amino) methyl)-1-methyl-1H-1,2,3-triazol-4-yl)-2-methylpyridin-3-yl)oxy) cyclohexane-1-carboxylic acid | LCMS, [M + H]$^+$ = 507.1; $^1$H NMR (400 MHz, CDCl$_3$) δ 8.37 (s, 1H), 7.99 (d, J = 8.6 Hz, 1H), 7.56-7.45 (m, 3H), 7.23-7.11 (m, 2H), 4.81 (s, 2H), 4.78-4.71 (m, 1H), 4.28 (s, 3H), 2.96-2.85 (m, 1H), 2.67 (s, 3H), 2.13-1.62 (m, 8H); $^{19}$F NMR (377 MHz, CDCl$_3$) δ -75.93 (s, TFA), -112.06 (s, F); hLPA$_1$ IC$_{50}$ = 61 nM. | Example 25 |
| 40 | 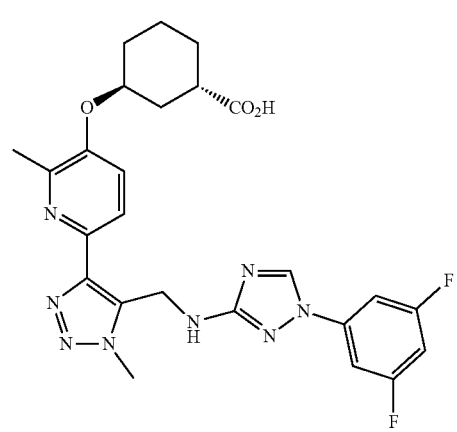<br>(1S,3S)-3-((6-(5-(((1-(3,5-difluoro-phenyl)-1H-1,2,4-triazol-3-yl)amino) methyl)-1-methyl-1H-1,2,3-triazol-4-yl)-2-methylpyridin-3-yl)oxy) cyclohexane-1-carboxylic acid | LCMS, [M + H]$^+$ = 525.2; $^1$H NMR (400 MHz, CDCl$_3$) δ 8.29 (s, 1H), 7.99 (d, J = 8.8 Hz, 1H), 7.39 (d, J = 8.6 Hz, 1H), 7.11 (dd, J = 7.7, 2.2 Hz, 2H), 6.78 (tt, J = 8.6, 2.3 Hz, 1H), 4.78 (s, 2H), 4.73 (br s, 1H), 4.30 (s, 3H), 2.94-2.85 (m, 1H), 2.65 (s, 3H), 2.17-1.60 (m, 8H); $^{19}$F NMR (377 MHz, CDCl$_3$) δ -75.97 (s, TFA), -106.31 (s, F); hLPA$_1$ IC$_{50}$ = 46 nM. | Example 25 |

Example 33. (1S,3S)-3-((6-(5-(((2-(4-fluorophenyl)-2H-1,2,3-triazol-4-yl)amino)methyl)-1-methyl-1H-1,2,3-triazol-4-yl)-2-methyl pyridin-3-yl)oxy) cyclohexane-1-carboxylic acid

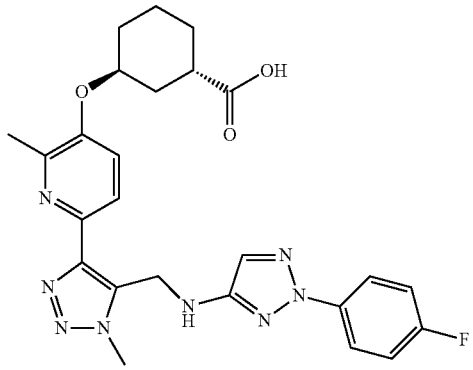 [SMILES: Cc1nc(-c2nnn(C)c2CNc2cnn(-c3ccc(F)cc3)n2)ccc1O[C@H]1CCC[C@H](C(=O)O)C1]

Example 33A.
2-(4-fluorophenyl)-4-nitro-2H-1,2,3-triazole

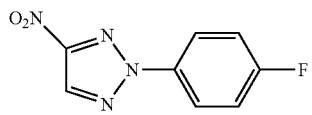

A mixture of 5-nitro-1H-1,2,3-triazole (140 mg, 1.23 mmol), (4-fluorophenyl)boronic acid (172 mg, 1.23 mmol), Cu(OAc)$_2$ (268 mg, 1.47 mmol), TEA (0.34 mL, 2.46 mmol), pyridine (1 ml, 12.3 mmol), and 4A molecular sieves (1 g) in DCM (5 mL) was stirred under air at RT for 4 days, then was filtered. The filtrate was concentrated in vacuo. The crude product was dissolved in EtOAc (5 mL), which was washed with 1N aq. HCl and water, then was concentrated in vacuo. The residue was chromatographed (24 g SiO$_2$; continuous gradient from 0% to 30% EtOAc in hexane over 10 min) to give Example 33A (50 mg, 0.240 mmol, 19.6% yield; $^1$H NMR (400 MHz, CDCl$_3$) δ 8.71 (s, 1H), 7.83-7.75

(m, 2H), 7.36-7.28 (m, 2H); $^{19}$F NMR (377 MHz, CDCl$_3$) δ −108.80 (s, F)) and Example XXB (140 mg, 0.673 mmol, 54.8% yield)($^1$H NMR (400 MHz, CDCl$_3$) δ 8.37 (s, 1H), 8.16-8.08 (m, 2H), 7.28-7.19 (m, 2H); $^{19}$F NMR (377 MHz, CDCl$_3$) δ −110.50 (s, F)) as white solids.

33B. 2-(4-fluorophenyl)-2H-1,2,3-triazol-4-amine

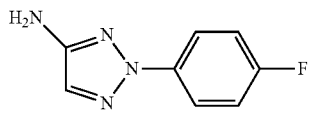 [SMILES: Nc1cnn(-c2ccc(F)cc2)n1]

A mixture of Example 33A (140 mg, 0.673 mmol), and 10% Pd/C (72 mg, 0.067 mmol) in AcOH (5 mL) was stirred under an atmosphere of H$_2$ at RT for 18 h, then was filtered. The filtrate was concentrated in vacuo to give the title compound (60 mg, 0.337 mmol, 50.1% yield) as a white solid. $^1$H NMR (500 MHz, MeOH-d$_4$) δ 7.93-7.79 (m, 2H), 7.24 (s, 1H), 7.21-7.09 (m, 2H); $^{19}$F NMR (471 MHz, MeOH-d$_4$) δ −119.17 (s, 1F); MS (ESI) m/z: 179.2 (M+H)$^+$ Example 33

A mixture of Intermediate 2 (30 mg, 0.066 mmol), Example 33B (18 mg, 0.10 mmol), and DIPEA (35 μL, 0.199 mmol) in DMF (1 mL) was heated at 150° C. in a microwave reactor for 15 min, then was cooled to RT and concentrated in vacuo. The residue was stirred with 1.0 M aq. NaOH (0.2 mL, 0.2 mmol) in THF/MeOH (0.5 mL each) at RT for 18 h, then was concentrated in vacuo. The crude oil was purified by preparative HPLC (Sunfire C18 30×100 mm column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the tile compound (13.9 mg, 0.018 mmol, 27.7% yield) as a clear oil. LCMS, [M+H]$^+$=507.4; $^1$H NMR (500 MHz, DMSO-d$_6$) δ 7.86 (br d, J=8.5 Hz, 1H), 7.69 (br dd, J=8.9, 4.9 Hz, 2H), 7.53 (d, J=8.5 Hz, 1H), 7.40 (s, 1H), 7.26 (br t, J=8.7 Hz, 2H), 4.90 (s, 2H), 4.80 (br s, 1H), 4.16 (s, 3H), 2.64 (br t, J=10.4 Hz, 1H), 2.45 (s, 3H), 2.09-1.99 (m, 1H), 1.91-1.44 (m, 7H); hLPA$_1$ IC$_{50}$=84 nM Example 41. (1S,3S)-3-((6-(5-((5-Benzyl-2-imino-1,3,4-oxadiazol-3(2H)-yl)methyl)-1-methyl-1H-1,2,3-triazol-4-yl)-2-methylpyridin-3-yl)oxy)cyclohexane-1-carboxylic acid, bis TFA salt

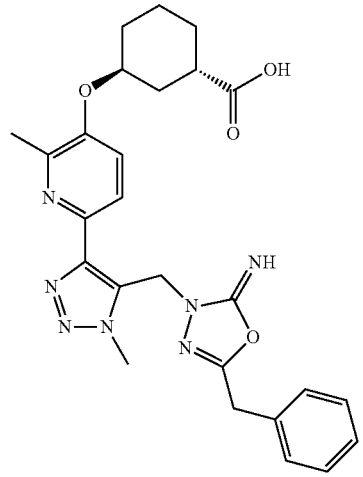 [SMILES: Cc1nc(-c2nnn(C)c2Cn2nc(Cc3ccccc3)oc2=N)ccc1O[C@H]1CCC[C@H](C(=O)O)C1]

41A. Methyl (1S,3S)-3-((6-(5-((5-benzyl-2-imino-1,3,4-oxadiazol-3(2H)-yl)methyl)-1-methyl-1H-1,2,3-triazol-4-yl)-2-methylpyridin-3-yl)oxy)cyclohexane-1-carboxylate, bis TFA salt

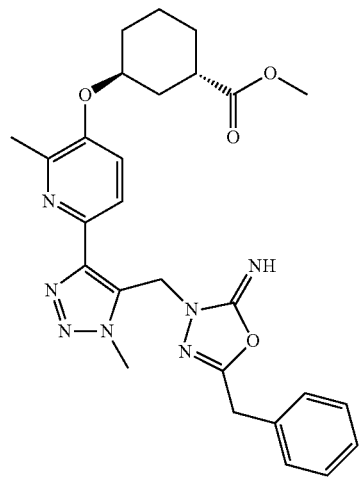 [SMILES: COC(=O)[C@H]1CCC[C@H](Oc2ccc(-c3nnn(C)c3Cn3nc(Cc4ccccc4)oc3=N)nc2C)C1]

A solution of Intermediate 5 (28 mg, 0.066 mmol), 5-benzyl-1,3,4-oxadiazol-2-amine (34.8 mg, 0.198 mmol) and DIEA (0.035 mL, 0.198 mmol) in DMF (1 mL) was microwaved at 150° C. for 15 min, then was cooled to RT and concentrated in vacuo. The crude product was purified by preparative HPLC: Column: Sunfire Prep C18 OBD 30×100 mm, 5-μm particles; Mobile Phase A: 10:90 MeCN:H$_2$O with 0.1% TFA; Mobile Phase B: 90:10 MeCN:H$_2$O with 0.1% TFA; Gradient: 20-100% B over 12 min; Flow: 40 mL/min. Fractions containing the desired product were combined and dried via centrifugal evaporation to give the title compound (9 mg, 18%). LCMS, [M+H]$^+$=518.1. $^1$H NMR (400 MHz, CD$_3$OD) δ 7.94 (d, J=8.4 Hz, 1H), 7.61 (d, J=8.8 Hz, 1H), 7.42-7.30 (m, 5H), 5.70 (s, 2H), 4.91-4.87 (m, 1H), 4.22-4.17 (m, 5H), 3.70 (s, 3H), 2.90-2.79 (m, 1H), 2.53 (s, 3H), 2.19-2.08 (m, 1H), 2.03-1.90 (m, 3H), 1.83-1.61 (m, 4H).

Example 41

To a solution of intermediate 41A (9 mg, 0.012 mmol) in THF (1 mL)/water (0.5 mL) was added 2M aq. LiOH (0.030 mL, 0.060 mmol). The mixture was stirred at RT for 18 h, after which the pH was adjusted with 1N aq. HCl to ~4 and extracted with EtOAc (3×5 mL). The combined organic extracts were washed with brine, dried (Na$_2$SO$_4$) and concentrated in vacuo. The crude material was purified via preparative HPLC: Column: XBridge C18, 19×200 mm, 5-μm particles; Mobile Phase A: 5:95 MeCN:H$_2$O with 0.1% TFA; Mobile Phase B: 95:5 MeCN:H$_2$O with 0.1% TFA; Gradient: 12-52% B over 20 min, then a 5-min hold at 100% B; Flow: 20 mL/min. Fractions containing the desired product were combined and dried via centrifugal evaporation to give the title compound (4 mg, 45%). LCMS, [M+H]$^+$=504.3. $^1$H NMR (500 MHz, DMSO-d$_6$) δ 7.90 (d, J=8.5 Hz, 1H), 7.60 (d, J=8.9 Hz, 1H), 7.40-7.27 (m, 5H), 5.68 (s, 2H), 4.83 (br s, 1H), 4.19 (s, 2H), 4.14 (s, 3H), 2.68-2.59 (m, 1H), 2.43 (s, 3H), 2.09-2.00 (m, 1H), 1.93-1.77 (m, 3H), 1.71-1.47 (m, 4H). hLPA$_1$ IC$_{50}$=221 nM.

Example 42. (1S,3S)-3-((6-(5-(((5-Isopropyl-1,3,4-oxadiazol-2-yl)amino)methyl)-1-methyl-1H-1,2,3-triazol-4-yl)-2-methylpyridin-3-yl)oxy)cyclohexane-1-carboxylic acid, 2 TFA salt

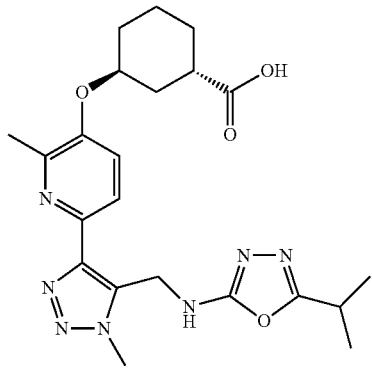 [SMILES: Cc1nc(-c2nnn(C)c2CNc2nnc(C(C)C)o2)ccc1O[C@H]1CCC[C@H](C(=O)O)C1]

42A. Methyl (1S,3S)-3-((6-(5-(((5-isopropyl-1,3,4-oxadiazol-2-yl)amino)methyl)-1-methyl-1H-1,2,3-triazol-4-yl)-2-methylpyridin-3-yl)oxy)cyclohexane-1-carboxylate, bis TFA salt

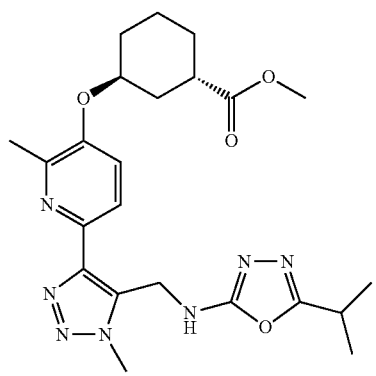 [SMILES: COC(=O)[C@H]1CCC[C@H](Oc2ccc(-c3nnn(C)c3CNc3nnc(C(C)C)o3)nc2C)C1]

To a solution of Intermediate 8 (35 mg, 0.098 mmol), 5-isopropyl-1,3,4-oxadiazol-2-amine (19 mg, 0.146 mmol) in MeOH (1.1 mL) was added HOAc (0.028 mL, 0.488 mmol). The reaction was stirred in a sealed vial at 65° C. for 2 h, then was cooled to RT. NaBH$_3$CN (12 mg, 0.195 mmol) was added, and the reaction was stirred at RT for 2 h, then was quenched with satd aq. NaHCO$_3$. The aqueous layer was extracted with EtOAc. The organic layer was washed with brine, dried (Na$_2$SO$_4$) and concentrated in vacuo. The crude material was purified via preparative HPLC: Column: Sunfire Prep C18 OBD, 30×100 mm, 5-μm particles; Mobile Phase A: 10:90 MeCN:H$_2$O with 0.1% TFA; Mobile Phase B: 90:10 MeCN:H$_2$O with 0.1% TFA; Gradient: 20-100% B over 12 min, then a 3-min hold at 100% B; Flow: 40 mL/min. Fractions containing the desired product were combined and dried via centrifugal evaporation to give the title compound (10 mg, 15%). LCMS, [M+H]$^+$=470.2. $^1$H NMR (400 MHz, CD$_3$OD) δ 8.17-8.07 (m, 2H), 5.09-5.00 (m, 1H), 4.85-4.81 (m, 2H), 4.24 (s, 3H), 3.71 (s, 3H), 3.09 (quin, J=6.9 Hz, 1H), 2.91-2.79 (m, 4H), 2.18 (dt, J=14.0, 4.4 Hz, 1H), 2.09-1.95 (m, 3H), 1.89-1.65 (m, 4H), 1.34 (d, J=7.0 Hz, 6H).

Example 42

The title compound was prepared from intermediate 42A according to the procedure described for the synthesis of Example 41. LCMS, [M+H]$^+$=456.1. $^1$H NMR (500 MHz, DMSO-d$_6$) δ 7.95-7.80 (m, 1H), 7.48 (br d, J=8.5 Hz, 1H), 4.91 (br d, J=4.3 Hz, 2H), 4.76 (br s, 1H), 4.12 (s, 3H), 2.97-2.87 (m, 1H), 2.67-2.59 (m, 1H), 2.41 (br s, 3H), 2.08-1.95 (m, 1H), 1.90-1.76 (m, 3H), 1.70-1.38 (m, 4H), 1.14 (d, J=7.0 Hz, 6H). hLPA$_1$ IC$_{50}$=1410 nM.

Example 43. (1S,3S)-3-((6-(5-(((3-Butyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt

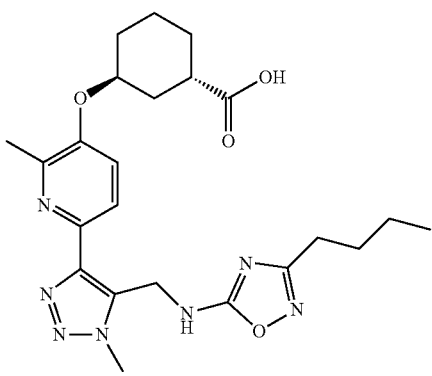 [SMILES: CCCCc1noc(NCc2c(-c3ccc(O[C@H]4CCC[C@H](C(=O)O)C4)c(C)n3)nnn2C)n1]

43A. 3-Butyl-5-(trichloromethyl)-1,2,4-oxadiazole

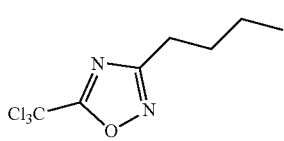

To a cooled (0° C.) solution of (Z)—N'-hydroxypentanimidamide (166 mg, 1.43 mmol) and pyridine (0.14 mL, 1.72 mmol) in dioxane (6 mL) was added dropwise 2,2,2-trichloroacetyl chloride (0.19 mL, 1.72 mmol). The reaction was allowed to warm to RT and stirred at RT for 18 h, then was filtered to remove the pyridine-HCl. The filtrate was concentrated in vacuo. The residue was dissolved in EtOAc and washed with aq. satd. NaHCO₃ (2×), water (2×), dried (MgSO₄) and concentrated in vacuo to give the title compound (300 mg, 86%) as a colorless oil. LCMS, [M+H]⁺=242.9. ¹H NMR (400 MHz, CDCl₃) δ 2.87-2.77 (m, 2H), 1.86-1.72 (m, 2H), 1.44 (dq, J=15.0, 7.4 Hz, 2H), 0.97 (t, J=7.4 Hz, 3H).

43B. Methyl (1S,3S)-3-((6-(5-(((3-butyl-1,2,4-oxadiazol-5-yl)amino)methyl)-1-methyl-1H-1,2,3-triazol-4-yl)-2-methylpyridin-3-yl)oxy)cyclohexane-1-carboxylate, 2 TFA salt

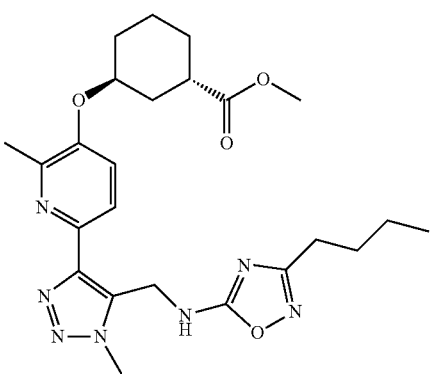 [SMILES: CCCCc1noc(NCc2c(-c3ccc(O[C@H]4CCC[C@H](C(=O)OC)C4)c(C)n3)nnn2C)n1]

To a solution of methyl (1S,3S)-3-((6-(5-(aminomethyl)-1-methyl-1H-1,2,3-triazol-4-yl)-2-methylpyridin-3-yl)oxy)cyclohexane-1-carboxylate (31 mg, 0.086 mmol) and 43A (25 mg, 0.10 mmol) in DMF (1 mL) was added Cs₂CO₃ (56 mg, 0.17 mmol). The reaction was stirred at RT for 18 h, then was concentrated in vacuo. The crude product was purified via preparative HPLC: Column: Sunfire Prep C18 OBD, 30×100 mm; 5-μm particles; Mobile Phase A: 10:90 MeCN:H₂O with 0.1% TFA; Mobile Phase B: 90:10 MeCN:H₂O with 0.1% TFA; Gradient: 20-100% B over 12 min, then a 3-min hold at 100% B; Flow: 40 mL/min. Fractions containing the desired product were combined and dried via centrifugal evaporation to give the title compound (26 mg, 42%) as a brown solid. LCMS, [M+H]⁺=484.3. ¹H NMR (500 MHz, CD₃OD) δ 8.06 (br d, J=8.5 Hz, 1H), 7.92 (br d, J=8.5 Hz, 1H), 4.99-4.92 (m, 3H), 4.24 (s, 3H), 3.70 (s, 3H), 2.90-2.83 (m, 1H), 2.68 (s, 3H), 2.51 (t, J=7.4 Hz, 2H), 2.19-2.09 (m, 1H), 2.06-1.91 (m, 3H), 1.85-1.53 (m, 6H), 1.40-1.28 (m, 2H), 0.92 (t, J=7.4 Hz, 3H).

Example 43

The title compound was prepared from intermediate 43B according to the procedure described for the synthesis of Example 41. LCMS, [M+H]$^+$=470.3. $^1$H NMR (500 MHz, DMSO-d$_6$) δ 8.48-8.42 (m, 1H), 7.85 (d, J=8.5 Hz, 1H), 7.47 (d, J=8.6 Hz, 1H), 5.02 (br d, J=5.1 Hz, 2H), 4.76 (br s, 1H), 4.10 (s, 3H), 2.70-2.61 (m, 1H), 2.47-2.39 (m, 5H), 2.07-1.97 (m, 1H), 1.90-1.77 (m, 3H), 1.70-1.48 (m, 6H), 1.37-1.27 (m, 2H), 0.88 (t, J=7.4 Hz, 3H). hLPA$_1$ IC$_{50}$=76 nM.

Example 44. (1S,3S)-3-((6-(5-(((3-Cyclobutyl-1,2,4-oxadiazol-5-yl)amino)methyl)-1-methyl-1H-1,2,3-triazol-4-yl)-2-methylpyridin-3-yl)oxy)cyclohexane-1-carboxylic acid, 2 TFA salt

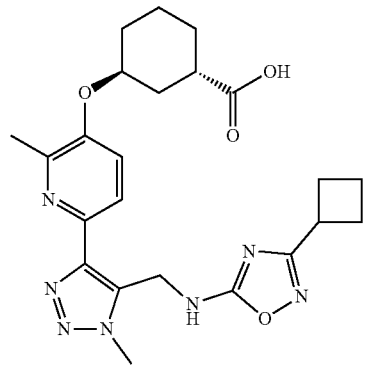 [SMILES: Cc1nc(-c2nnn(C)c2CNc2nc(C3CCC3)no2)ccc1O[C@H]1CCC[C@H](C(=O)O)C1]

44A. Methyl (1S,3S)-3-((6-(5-(((3-cyclobutyl-1,2,4-oxadiazol-5-yl)amino)methyl)-1-methyl-1H-1,2,3-triazol-4-yl)-2-methylpyridin-3-yl)oxy)cyclohexane-1-carboxylate

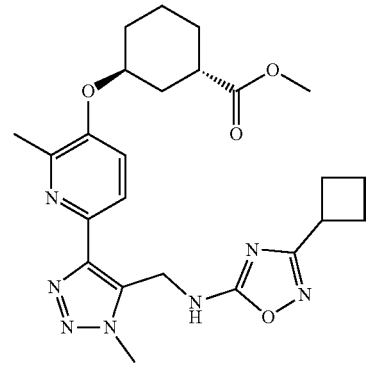 [SMILES: COC(=O)[C@H]1CCC[C@H](Oc2ccc(-c3nnn(C)c3CNc3nc(C4CCC4)no3)nc2C)C1]

A solution of Intermediate 7 (20 mg, 0.056 mmol), 5-chloro-3-cyclobutyl-1,2,4-oxadiazole (13 mg, 0.083 mmol) and iPr$_2$NEt (0.029 mL, 0.167 mmol) in EtOH (1 mL) was microwaved at 80° C. for 15 min, then was cooled to RT and concentrated in vacuo. The crude product was used in the next step without further purification. LCMS, [M+H]$^+$=482.2.

Example 44

The title compound was prepared from intermediate 44A according to the procedure described for the synthesis of Example 41. LCMS, [M+H]$^+$=468.3. $^1$H NMR (500 MHz, DMSO-d$_6$) δ 8.57 (br t, J=5.0 Hz, 1H), 7.85 (d, J=8.5 Hz, 1H), 7.49 (d, J=8.5 Hz, 1H), 5.06 (br d, J=4.9 Hz, 2H), 4.78 (br s, 1H), 4.12 (s, 3H), 2.69-2.60 (m, 1H), 2.41 (s, 3H), 2.25-2.12 (m, 4H), 2.06-1.95 (m, 2H), 1.91-1.74 (m, 4H), 1.68-1.44 (m, 4H). note: 2 of 29 protons not observed due to water suppression or solvent interference. hLPA$_1$ IC$_{50}$=105 nM.

The examples in Table 3 below were synthesized according to the same procedures described for Examples 41 to 44.

TABLE 3

| Ex # | Structure & Name | Analytical & Biological Data | Method |
|---|---|---|---|
| 45 | (1S,3S)-3-((6-(5-((5-Cyclopenyl-2-imino-1,3,4-oxadiazol-3(2H)-yl)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 482.1; $^1$H NMR (400 MHz CD$_3$OD) δ 7.94 (d, J = 8.6 Hz, 1H), 7.63 (d, J = 8.8 Hz, 1H), 5.70 (s, 2H), 4.92-4.87 (m, 1H), 4.24 (s, 3H), 3.31-3.26 (m, 1H), 2.84-2.74 (m, 1H), 2.59 (s, 3H), 2.18-2.07 (m, 3H), 2.02-1.88 (m, 5H), 1.88-1.65 (m, 8H); hLPA$_1$ IC$_{50}$ = 228 nM. | Example 41 |

TABLE 3-continued

| Ex # | Structure & Name | Analytical & Biological Data | Method |
|---|---|---|---|
| 46 | (1S,3S)-3-((6-(5-(((5-Cyclopenyl-2-imino-1,3,4-oxadiazol-3(2H)-yl)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 468.1; $^1$H NMR (400 MHz, CD$_3$OD) δ 7.94 (d, J = 8.8 Hz, 1H), 7.63 (d, J = 8.8 Hz, 1H), 5.72 (s, 2H), 4.93-4.89 (m, 1H), 4.24 (s, 3H), 3.70 (quind, J = 8.4, 1.0 Hz, 1H), 2.85-2.75 (m, 1H), 2.59 (s, 3H), 2.51-2.39 (m, 4H), 2.26-1.90 (m, 6H), 1.83-1.63 (m, 4H); hLPA$_1$ IC$_{50}$ = 137 nM. | Example 41 |
| 47 | (1S,3S)-3-((2-Methyl-6-(1-methyl-5-(((5-(trifluoromethyl-1,3,4-oxadiazol-2-yl)amino)methyl)-1H-1,2,3-triazol-4-yl)pyridin-3-yl)oxy)cyclohexane-1-carboxylic acid, bis TFA salt | LCMS, [M + H]$^+$ = 482.2; $^1$H NMR (500 MHz, DMSO-d$_6$) δ 8.89-8.81 (m, 1H), 7.87 (d, J = 8.5 Hz, 1H), 7.50 (d, J = 8.5 Hz, 1H), 5.10 (br d, J = 4.9 Hz, 2H), 4.79 (br s, 1H), 4.13 (s, 3H), 2.68-2.60 (m, 1H), 2.40 (s, 3H), 2.10-1.98 (m, 1H), 1.90-1.75 (m, 3H), 1.69-1.44 (m, 4H); hLPA$_1$ IC$_{50}$ = 595 nM. | Example 42 |
| 48 | (1S,3S)-3-((6-(5-(((5-Cyclopenyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 482.1; $^1$H NMR (400 MHz, CD$_3$OD) δ 8.14-8.04 (m, 2H), 5.07-4.99 (m, 1H), 4.83 (s, 2H), 4.24 (s, 3H), 3.28-3.19 (m, 1H), 2.88-2.78 (m, 4H), 2.21-1.94 (m, 6H), 1.92-1.66 (m, 10H); hLPA$_1$ IC$_{50}$ = 209 nM. | Example 42 |

TABLE 3-continued

| Ex # | Structure & Name | Analytical & Biological Data | Method |
|---|---|---|---|
| 49 | (1S,3S)-3-((2-Methyl-6-(1-methyl-5-(((5-phenyl-1,3,4-oxadiazol-2-yl)amino)methyl)-1H-1,2,3-triazol-4-yl)pyridin-3-yl)oxy)cyclohexane-1-carboxylic acid, bis TFA salt | LCMS, [M + H]$^+$ = 490.2; $^1$H NMR (500 MHz, DMSO-$d_6$) δ 7.88 (d, J = 8.6 Hz, 1H), 7.80-7.65 (m, 2H), 7.53-7.45 (m, 4H), 5.05 (br s, 2H), 4.77 (br s, 1H), 4.15 (s, 3H), 2.71-2.61 (m, 1H), 2.43 (s, 3H), 2.07-1.99 (m, 1H), 1.91-1.76 (m, 3H), 1.71-1.46 (m, 4H); hLPA$_1$ IC$_{50}$ = 180 nM. | Example 42 |
| 50 | (1S,3S)-3-((6-(5-(((5-Benzyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 503.9; $^1$H NMR (500 MHz, DMSO-$d_6$) δ 7.84 (d, J = 8.5 Hz, 1H), 7.48 (d, J = 8.5 Hz, 1H), 7.35-7.21 (m, 5H), 4.89 (br d, J = 4.6 Hz, 2H), 4.77 (br s, 1H), 4.09 (s, 3H), 4.01 (s, 2H), 2.67-2.59 (m, 1H), 2.36 (s, 3H), 2.05-1.96 (m, 1H), 1.90-1.72 (m, 3H), 1.66-1.44 (m, 4H); hLPA$_1$ IC$_{50}$ = 96 nM. | Example 42 |
| 51 | (1S,3S)-3-((6-(5-(((5-Cyclobutyl-1,3,4-oxadiazol-2-yl)amino)methyl)-1-methyl-1H-1,2,3-triazol-4-yl)-2-methylpyridin-3-yl)oxy)cyclohexane-1-carboxylic acid | LCMS, [M + H]$^+$ = 468.0; $^1$H NMR (500 MHz, DMSO-$d_6$) δ 7.86 (d, J = 8.6 Hz, 1H), 7.48 (d, J = 8.6 Hz, 1H), 4.92 (br d, J = 4.5 Hz, 2H), 4.76 (br s, 1H), 4.12 (s, 3H), 3.61-3.37 (m, 1H), 2.70-2.60 (m, 1H), 2.43 (s, 3H), 2.29-2.10 (m, 4H), 2.06-1.93 (m, 2H), 1.91-1.75 (m, 4H), 1.70-1.45 (m, 4H); hLPA$_1$ IC$_{50}$ = 59 nM. | Example 42 |

TABLE 3-continued

| Ex # | Structure & Name | Analytical & Biological Data | Method |
|---|---|---|---|
| 52 | (1S,3S)-3-((2-Methyl-6-(1-methyl-5-(((5-propyl-1,3,4-oxadiazol-2-yl)amino)methyl)-1H-1,2,3-triazol-4-yl)pyridin-3-yl)oxy)cyclohexane-1-carboxylic acid, 2 TFA salt | LCMS, [M + H]$^+$ = 456.3; $^1$H NMR (500 MHz, DMSO-d$_6$) δ 7.93-7.88 (m, 1H), 7.83 (br d, J = 8.4 Hz, 1H), 7.47 (br d, J = 8.6 Hz, 1H), 4.91-4.85 (m, 2H), 4.76 (br s, 1H), 4.10 (s, 3H), 2.70-2.57 (m, 3H), 2.40 (s, 3H), 2.05-1.96 (m, 1H), 1.89-1.70 (m, 3H), 1.66-1.43 (m, 6H), 0.84 (t, J = 7.4 Hz, 3H); hLPA$_1$ IC$_{50}$ = 396 nM. | Example 42 |
| 53 | (1S,3S)-3-((6-(5-(((5-Butyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 470.1; $^1$H NMR (500 MHz, DMSO-d$_6$) δ 7.86 (br d, J = 8.2 Hz, 1H), 7.50 (d, J = 8.5 Hz, 1H), 4.92 (br d, J = 5.2 Hz, 2H), 4.78 (br s, 1H), 4.12 (s, 3H), 2.67-2.57 (m, 3H), 2.42 (s, 3H), 2.08-1.98 (m, 1H), 1.92-1.75 (m, 3H), 1.69-1.45 (m, 6H), 1.33-1.23 (m, 2H), 0.86 (t, J = 7.5 Hz, 3H); hLPA$_1$ IC$_{50}$ = 297 nM. | Example 42 |
| 54 | (1S,3S)-3-((6-(5-(((5-Isobutyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 470.2; $^1$H NMR (500 MHz, DMSO-d$_6$) δ 7.86 (d, J = 8.5 Hz, 1H), 7.49 (d, J = 8.5 Hz, 1H), 4.92 (br d, J = 5.2 Hz, 2H), 4.78 (br s, 1H), 4.12 (s, 3H), 2.69-2.58 (m, 1H), 2.49-2.45 (m, 2H), 2.42 (s, 3H), 2.08-1.98 (m, 1H), 1.93-1.75 (m, 4H), 1.45 (m 4H), 0.88 (d, J = 6.4 Hz, 6H); hLPA$_1$ IC$_{50}$ = 191 nM. | Example 42 |

TABLE 3-continued

| Ex # | Structure & Name | Analytical & Biological Data | Method |
|---|---|---|---|
| 55 | (1S,3S)-3-((6-(5-(((5-Isobutyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M +H]$^+$ = 484.2; $^1$H NMR (500 MHz, DMSO-d$_6$) δ 7.88 (d, J = 8.5 Hz, 1H), 7.56 (d, J = 8.5 Hz, 1H), 4.90 (s, 2H), 4.80 (br s, 1H), 4.12 (s, 3H), 2.67-2.57 (m, 3H), 2.45 (s, 3H), 2.08-1.99 (m, 1H), 1.90-1.74 (m, 3H), 1.67-1.39 (m, 7H), 0.85 (d, J = 6.4 Hz, 6H); hLPA$_1$ IC$_{50}$ = 45 nM. | Example 42 |
| 56 | (1S,3S)-3-((6-(5-(((5-(Cyclopropylmethyl)-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 468.3; $^1$H NMR (500 MHz, DMSO-d$_6$) δ 7.99-7.77 (m, 1H), 7.48 (br d, J = 8.5 Hz, 1H), 4.90 (br s, 2H), 4.76 (br s, 1H), 4.12 (s, 3H), 3.57-3.31 (m, 2H), 2.70-2.60 (m, 1H), 2.41 (br s, 3H), 2.09-1.94 (m, 1H), 1.91-1.75 (m, 3H), 1.70-1.44 (m, 4H), 1.01-0.88 (m, 1H), 0.46 (br d, J = 7.7 Hz, 2H), 0.16 (br d, J = 4.7 Hz, 2H); hLPA$_1$ IC$_{50}$ = 136 nM. | Example 42 |
| 57 | (1S,3S)-3-((6-(5-(((5-Cyclohexyl-1,3,4-oxadiazol-2-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 496.3; $^1$H NMR (500 MHz, DMSO-d$_6$) δ 7.97-7.77 (m, 1H), 7.47 (br d, J = 8.7 Hz, 1H), 4.90 (br s, 2H), 4.80-4.71 (m, 1H), 4.11 (s, 3H), 2.70-2.59 (m, 2H), 2.42 (s, 3H), 2.06-1.98 (m, 1H), 1.90-1.76 (m, 3H), 1.71-1.46 (m, 7H), 1.41-1.13 (m, 7H); hLPA$_1$ IC$_{50}$ = 204 nM. | Example 42 |

TABLE 3-continued

| Ex # | Structure & Name | Analytical & Biological Data | Method |
|---|---|---|---|
| 58 | (1S,3S)-3-((6-(5-(((3-Cyclopropyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 454.1; $^1$H NMR (400 MHz, DMSO-$d_6$) δ 8.56 (t, J = 5.3 Hz, 1H), 7.84 (d, J = 8.6 Hz, 1H), 7.50 (d, J = 8.8 Hz, 1H), 4.99 (d, J = 5.3 Hz, 2H), 4.79 (br s, 1H), 4.09 (s, 3H), 2.70-2.60 (m, 1H), 2.41 (s, 3H), 2.07-1.97 (m, 1H), 1.92-1.75 (m, 4H), 1.69-1.45 (m, 4H), 0.95-0.86 (m, 2H), 0.75-0.68 (m, 2H); hLPA$_1$ IC$_{50}$ = 316 nM. | Example 43 |
| 59 | (1S,3S)-3-((6-(5-(((3-Isopropyl-1,2,4-oxadiazol-5-yl)amino)methyl)-1-methyl-1H-1,2,3-triazol-4-yl)-2-methylpyridin-3-yl)oxy)cyclohexane-1-carboxylic acid | LCMS, [M = H]$^+$ = 456.2; $^1$H NMR (500 MHz, DMSO-$d_6$) δ 8.44 (br t, J = 4.8 Hz, 1H), 7.84 (d, J = 8.5 Hz, 1H), 7.47 (d, J = 8.7 Hz, 1H), 5.01 (d, J = 5.1 Hz, 2H), 4.76 (br s, 1H), 4.11 (s, 3H), 2.85-2.75 (m, 1H), 2.68-2.60 (m, 1H), 2.41 (s, 3H), 2.06-1.97 (m, 1H), 1.92-1.77 (m, 3H), 1.69-1.46 (m, 4H), 1.16 (d, J = 6.9 Hz, 6H); hLPA$_1$ IC$_{50}$ = 495 nM. | Example 43 |
| 60 | (1S,3S)-3-((6-(5-(((3-(tert-Butyl)-1,2,4-oxadiazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 470.3; $^1$H NMR (500 MHz, DMSO-$d_6$) δ 8.52 (br t, J = 5.2 Hz, 1H), 7.82 (br d, J = 4.6 Hz, 1H), 7.47 (br s, 1H), 4.99 (br d, J = 5.2 Hz, 2H), 4.77 (br s, 1H), 4.11 (s, 3H), 2.72-2.59 (m, 1H), 2.39 (br s, 3H), 2.08-1.40 (m, 8H), 1.15 (s, 9H); hLPA$_1$ IC$_{50}$ = 478 nM. | Example 43 |

TABLE 3-continued

| Ex # | Structure & Name | Analytical & Biological Data | Method |
|---|---|---|---|
| 61 | (1S,3S)-3-((2-Methyl-6-(1-methyl-5-(((3-phenyl-1,2,4-oxadiazol-5-yl)amino)methyl)-1H-1,2,3-triazol-4-yl)pyridin-3-yl)oxy)cyclohexane-1-carboxylic acid, bis TFA salt | LCMS, [M + H]$^+$ = 490.0; $^1$H NMR (500 MHz, DMSO-d$_6$) δ 8.86 (br t, J = 5.0 Hz, 1H), 7.90-7.83 (m, 3H), 7.57-7.47 (m, 4H), 5.16 (br d, J = 49 Hz 2H) 479 (br s, 1H), 4.17 (s, 3H), 2.74-2.58 (m, 1H), 2.41 (s, 3H), 2.03 (br d, J = 13.4 Hz, 1H), 1.91-1.75 (m, 3H) 1.69-1.43 (m 4H); hLPA$_1$ IC$_{50}$ = 26 nM. | Example 44 |
| 62 | (1S,3S)-3-((6-(5-(((3-Cyclopentyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 482.4; $^1$H NMR (500 MHz, DMSO-d$_6$) δ 8.56-8.51 (m, 1H), 7.83 (br d, J = 8.5 Hz, 1H), 7.47 (br d, J = 8.5 Hz, 1H), 5.01 (br d, J = 5.2 Hz, 2H), 4.77 (br s, 1H), 4.10 (s, 3H), 2.96-2.89 (m, 1H), 2.66-2.59 (m, 1H), 2.39 (s, 3H), 2.08-1.98 (m, 1H), 1.90-1.74 (m, 5H), 1.69-1.45 (m, 10H); hLPA$_1$ IC$_{50}$ = 43 nM. | Example 43 |
| 63 | (1S,3S)-3-((6-(5-(((3-Benzyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M +H]$^+$ = 504.1; $^1$H NMR (500 MHz, DMSO-d$_6$) δ 8.61 (t, J = 5.2 Hz, 1H), 7.84 (d, J = 8.5 Hz, 1H), 7.47 (d, J = 8.5 Hz, 1H), 7.34-7.22 (m, 5H), 4.99 (br d, J = 5.2 Hz, 2H), 4.77 (br s, 1H), 4.04 (s, 3H), 3.81 (s, 2H), 2.67-2.59 (m, 1H), 2.33 (s, 3H), 2.09-1.98 (m, 1H), 1.92-1.74 (m, 3H), 1.68-1.45 (m, 4H); hLPA$_1$ IC$_{50}$ = 38 nM. | Example 43 |

TABLE 3-continued

| Ex # | Structure & Name | Analytical & Biological Data | Method |
|---|---|---|---|
| 64 | 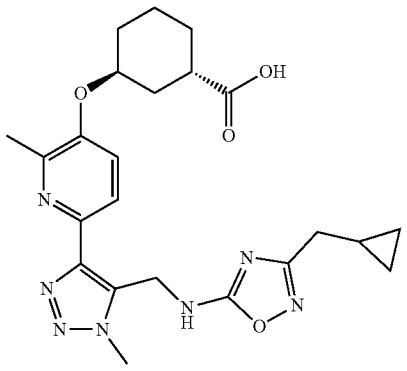<br>(1S,3S)-3-((6-(5-(((3-Cyclopropylmethyl)-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 468.2; $^1$H NMR (500 MHz, CD$_3$OD) δ 7.88 (d, J = 8.5 Hz, 1H), 7.48 (d, J = 8.8 Hz, 1H), 5.04 (s, 2H), 4.84-4.81 (m, 1H), 4.24 (s, 3H), 2.84-2.76 (m, 1H), 2.54 (s, 3H), 2.45 (d, J = 7.2 Hz, 2H), 2.17-2.09 (m, 1H), 2.01-1.91 (m, 3H), 1.86-1.62 (m, 4H), 1.13-1.04 (m, 1H), 0.59-0.53 (m, 2H), 0.27-0.22 (m, 2H); hLPA$_1$ IC$_{50}$ = 105 nM. | Example 43 |
| 65 | 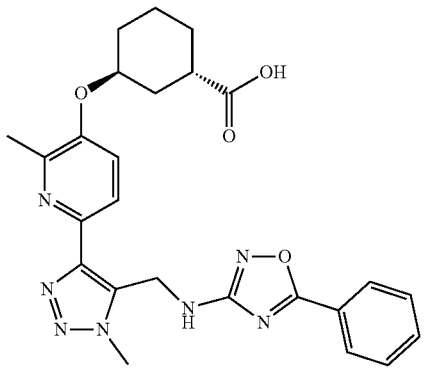<br>(1S,3S)-3-((2-Methyl-6-(1-methyl-5-(((5-phenyl-1,3,4-oxadiazol-3-yl)amino)methyl)-1H-1,2,3-triazol-4-yl)pyridin-3-yl)oxy)cyclohexane-1-carboxylic acid, bis TFA salt | LCMS, [M + H]$^+$ = 490.3; $^1$H NMR (500 MHz, DMSO-d$_6$) δ 7.96 (br d, J = 7.6 Hz, 2H), 7.86 (br d, J = 7.9 Hz, 1H), 7.69-7.63 (m, 1H), 7.61-7.55 (m, 2H), 7.49 (br d, J = 8.5 Hz, 1H), 4.87 (br d, J = 5.2 Hz, 2H), 4.78 (br s, 1H), 4.14 (s, 3H), 2.67-2.58 (m, 1H), 2.44 (s, 3H), 2.07-1.97 (m, 1H), 1.91-1.74 (m, 3H), 1.68-1.43 (m, 4H); hLPA$_1$ IC$_{50}$ = 23 nM. | Example 42 |
| 66 | <br>(1S,3S)-3-((6-(5-(((5-Butyl-1,2,4-oxadiazol-3-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 470.3; $^1$H NMR (500 MHz, DMSO-d$_6$) δ 7.89 (br s, 1H), 7.53 (br d, J = 8.2 Hz, 1H), 4.80 (br s, 3H), 4.13 (s, 3H), 2.73 (br t, J = 7.5 Hz, 2H), 2.69-2.63 (m, 1H), 2.46 (br s, 3H), 2.10-1.97 (m, 1H), 1.95-1.75 (m, 3H), 1.71-1.49 (m, 6H), 1.39-1.23 (m, 2H), 0.89 (t, J = 7.3 Hz, 3H); hLPA$_1$ IC$_{50}$ = 15 nM. | Example 42 |

TABLE 3-continued

| Ex # | Structure & Name | Analytical & Biological Data | Method |
| --- | --- | --- | --- |
| 67 | 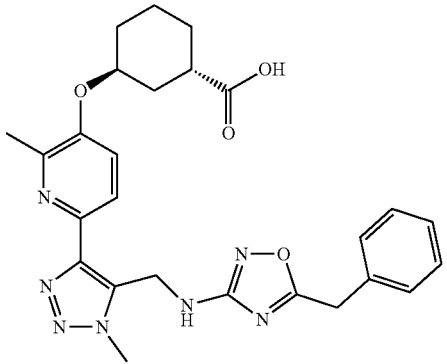<br>(1S,3S)-3-((6-(5-(((5-Butyl-1,2,4-oxadiazol-3-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 504.3; $^1$H NMR (500 MHz, DMSO-d$_6$) δ 7.85 (br d, J = 8.5 Hz, 1H), 7.50 (br d, J = 8.9 Hz, 1H), 7.36-7.24 (m, 5H), 4.81-4.72 (m, 3H), 4.13 (s, 2H), 4.07 (s, 3H), 2.67-2.60 (m, 1H), 2.40 (s, 3H), 2.08-1.95 (m, 1H), 1.92-1.74 (m, 3H), 1.68-1.46 (m, 4H); hLPA$_1$ IC$_{50}$ = 14 nM. | Example 42 |
| 68 | 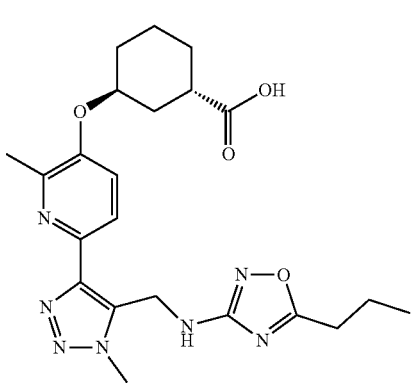<br>(1S,3S)-3-((2-Methyl-6-(1-methyl-5-(((5-propyl-1,2,4-oxadiazol-3-yl) amino) methyl)-1H-1,2,3-triazol-4-yl) pyridin-3-yl)oxy)cyclohexane-1-carboxylic acid | LCMS, [M + H]$^+$ = 456.3; $^1$H NMR (500 MHz, DMSO-d$_6$) δ 7.85 (d, J = 8.5 Hz, 1H), 7.51-7.46 (m, 1H), 7.13 (br t, J = 5.8 Hz, 1H), 4.80-4.73 (m, 3H), 4.10 (s, 3H), 2.72-2.60 (m, 3H), 2.44 (s, 3H), 2.08-1.97 (m, 1H), 1.90-1.77 (m, 3H), 1.72-1.46 (m, 6H), 0.91 (t, J = 7.4 Hz, 3H); hLPA$_1$ IC$_{50}$ = 42 nM. | Example 42 |
| 69 | 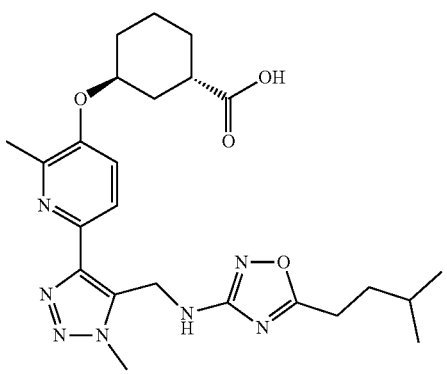<br>(1S,3S)-3-((6-(5-(((5-Isopentyl-1,2,4-oxadiazol-3-yl)amino)methyl)-1-methyl-1H-1,2,3-triazol-4-yl)-2-methylpyridin-3-yl)oxy)cyclohexane-1-carboxylic acid | LCMS, [M + H]$^+$ = 484.3; $^1$H NMR (500 MHz, DMSO-d$_6$) δ 7.85 (br d, J = 8.5 Hz, 1H), 7.49 (d, J = 8.5 Hz, 1H), 4.81-4.72 (m, 3H), 4.10 (s, 3H), 2.70 (br t, J = 7.2 Hz, 2H), 2.63 (br t, J = 10.5 Hz, 1H), 2.43 (s, 3H), 2.06-1.98 (m, 1H), 1.89-1.74 (m, 3H), 1.68-1.45 (m, 7H), 0.85 (br d, J = 5.8 Hz, 6H); hLPA$_1$ IC$_{50}$ = 15 nM. | Example 42 |

TABLE 3-continued

| Ex # | Structure & Name | Analytical & Biological Data | Method |
|---|---|---|---|
| 70 | (1S,3S)-3-((6-(5-(((5-(Cyclopropyl-methyl)-1,2,4-oxadiazol-3-yl)amino)methyl)-1-methyl-1H-1,2,3-triazol-4-yl)-2-methylpyridin-3-yl)oxy) cyclohexane-1-carboxylic acid, bis TFA salt | LCMS, [M + H]$^+$ = 468.4; $^1$H NMR (500 MHz, CD$_3$OD) δ 8.08 (d, J = 8.8 Hz, 1H), 8.03 (d, J = 8.8 Hz, 1H), 5.04-4.97 (m, 1H), 4.73 (s, 2H), 4.26 (s, 3H), 2.88-2.79 (m, 1H), 2.75 (s, 3H), 2.67 (d, J = 7.2 Hz, 2H), 2.18-2.10 (m, 1H), 2.08-1.93 (m, 3H), 1.86-1.67 (m, 4H), 1.14-1.06 (m, 1H), 0.64-0.54 (m 2H) 0.32-0.23 (m, 2H); hLPA$_1$ IC$_{50}$ = 15 nM, acute in vivo histamine assay in CD-1 mice: −39% histamine at a 1 mg/kg dose of Example 70. | Example 42 |
| 71 | (1S,3S)-3-((6-(5-(((5-Isopentyl-1,2,4-oxadiazol-3-yl)amino)methyl)-1-methyl-1H-1,2,3-triazol-4-yl)-2-methylpyridin-3-yl)oxy)cyclohexane-1-carboxylic | LCMS, [M + H]$^+$ = 470.4; $^1$H NMR (500 MHz, METHANOL-d$_4$) δ 8.10-8.02 (m, 2H), 5.04-4.97 (m, 1H), 4.73 (s, 2H), 4.25 (s, 3H), 2.88-2.79 (m, 1H), 2.75) (s, 3H), 2.64 (d, J = 7.2 Hz, 2H), 2.20-1.93 (m, 5H), 1.86-1.67 (m, 4H), 0.99 (d, J = 6.6 Hz, 6H); hLPA$_1$ IC$_{50}$ = 33 nM. | Example 42 |
| 72 | (1S,3S)-3-((6-(5-(((5-(Cyclobutylmethyl)-1,2,4-oxadiazol-3-yl)amino) methyl)-1-methyl-1H-1,2,3-triazol-4-yl)-2-methyl-pyridin-3-yl)oxy)cyclohexane-1-carboxylic acid, bis TFA salt | LCMS, [M + H]$^+$ = 482.3; $^1$H NMR (500 MHz, DMSO-d$_6$) δ 7.84 (d, J = 8.5 Hz, 1H), 7.48 (d, J = 8.9 Hz, 1H), 7.21 (br t, J = 5.8 Hz, 1H), 4.78-4.71 (m, 3H), 4.09 (s, 3H), 2.79 (d, J = 7.3 Hz, 2H), 2.66-2.57 (m, 2H), 2.42 (s, 3H), 2.04-1.97 (m, 3H) 1.87-1.74 (m, 5H), 1.72-1.42 (m, 6H); hLPA$_1$ IC$_{50}$ = 4 nM | Example 42 |

Example 73. (1 S,3 S)-3-((6-(5-((5-benzyl-1,3,4-oxadiazol-2-yl)methyl)-1-methyl-1H-1,2,3-triazol-4-yl)-2-methylpyridin-3-yl)oxy)cyclohexane-1-carboxylic acid min, followed by addition of Intermediate 9 (900 mg, 2.51 mmol) in THF (10 mL). The reaction was stirred at 0° C. for 30 min, then was warmed to RT and stirred at RT for 1 h, after which it was quenched by addition of sat. aq. NH$_4$Cl at 0° C., then was warmed to RT. EtOAc was added and the aqueous layer was extracted with EtOAc. The combined organic layers were washed with brine, dried (Na$_2$SO$_4$), and concentrated in vacuo. The crude product was chromatographed (80 g SiO$_2$; continuous gradient from 0% to 80% EtOAc in hexanes for 30 min and 80% EtOAc in hexanes for 20 min) to give the title compound (650 mg, 1.38 mmol, 55% yield) as an oil. LCMS, [M+H]$^+$=463.2.

73B. Methyl (1 S,3 S)-3-((2-methyl-6-(1-methyl-5-(2-oxoethyl)-1H-1,2,3-triazol-4-yl)pyridin-3-yl)oxy)cyclohexane-1-carboxylate

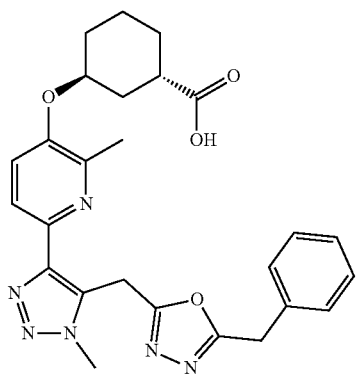 [SMILES: Cc1nc(-c2nnn(C)c2Cc2nnc(Cc3ccccc3)o2)ccc1O[C@H]1CCC[C@H](C(=O)O)C1]

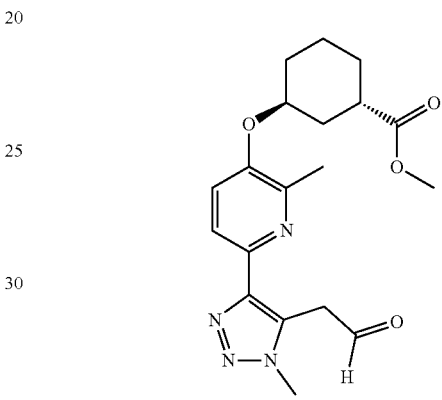

73A. Methyl (1 S,3S)-3-((2-methyl-6-(1-methyl-5-((E)-2-((trimethylsilyl)oxy)vinyl)-1H-1,2,3-triazol-4-yl)pyridin-3-yl)oxy)cyclohexane-1-carboxylate A solution of intermediate 73A (600 mg, 1.269 mmol) in CH$_2$Cl$_2$ (12 mL)/TFA (1.15 mL) at 23° C. was stirred at RT for 16 h, then was concentrated in vacuo to give the crude title compound, which was used in the following step without further purification. LCMS, [M+H]$^+$=373.1

73C. 2-(4-(5-(((1 S,3 S)-3-(methoxycarbonyl)cyclohexyl)oxy)-6-methylpyridin-2-yl)-1-methyl-1H-1,2,3-triazol-5-yl)acetic acid

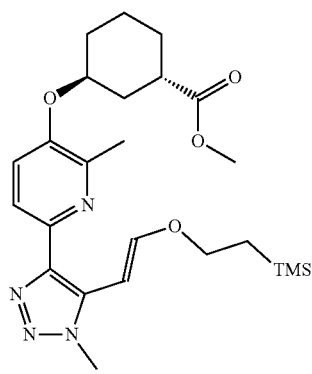 [SMILES: COC(=O)[C@H]1CCC[C@H](Oc2ccc(-c3nnn(C)c3/C=C/OCC[Si](C)(C)C)nc2C)C1]

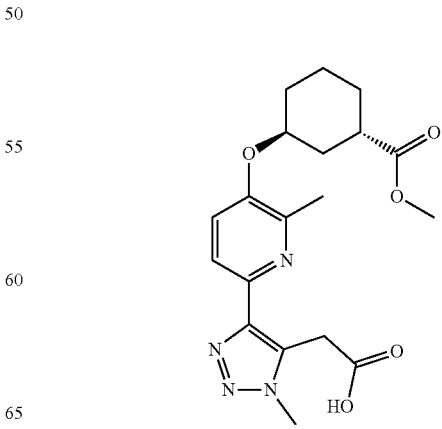

To triphenyl((2-(trimethylsilyl)ethoxy)methyl)phosphonium chloride (1.62 g, 3.77 mmol) in THF (25 mL) at 0° C. was added KOtBu (338 mg, 3.01 mmol) and stirred for 30

To a mixture of crude intermediate 73B (43 mg, 0.115 mmol), NaH₂PO₄ (69 mg, 0.577 mmol), 2-methyl-2-butene, 2.0 M in THF (0.10 mL, 0.20 mmol), water (0.2 mL), and t-BuOH (2 mL) at RT was added NaClO₂ (21 mg, 0.23 mmol). The reaction mixture was stirred at RT for 3 h, then was poured into brine and extracted with EtOAc (3×). The combined organic extracts were dried (Na₂SO₄) and concentrated in vacuo. The crude title compound was used in the next reaction without further purification. LCMS, [M+H]⁺=389.1.

73D. Methyl (1 S,3S)-3-((2-methyl-6-(1-methyl-5-(2-oxo-2-(2-(2-phenylacetyl)hydrazineyl) ethyl)-1H-1,2,3-triazol-4-yl)pyridin-3-yl)oxy)cyclohexane-1-carboxylate

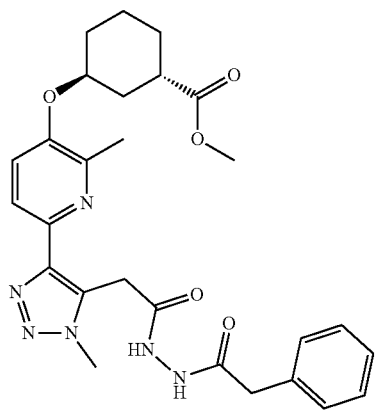 [SMILES: COC(=O)[C@H]1CCC[C@H](Oc2ccc(-c3nnn(C)c3CC(=O)NNC(=O)Cc3ccccc3)nc2C)C1]

To a solution of Intermediate 73C (16 mg, 0.041 mmol) and 2-phenylacetohydrazide (6 mg, 0.041 mmol) in MeCN (0.82 mL) added HATU (19 mg, 0.049 mmol) and N-ethyl-N-isopropylpropan-2-amine (7.3 μL, 0.041 mmol). The mixture was stirred at RT for 3 h, then was concentrated in vacuo. The crude product was chromatographed (12 g SiO₂; continuous gradient from 0% to 80% EtOAc in hexanes for 30 min and at 80% EtOAc in hexanes for 20 min) to give the title compound (16 mg, 0.031 mmol, 74.6% yield). LCMS, [M+H]⁺=521.1.

73E. Methyl (1 S,3 S)-3-((6-(5-((5-benzyl-1,3,4-oxadiazol-2-yl)methyl)-1-methyl-1H-1,2,3-triazol-4-yl)-2-methylpyridin-3-yl)oxy)cyclohexane-1-carboxylate A mixture of Intermediate 73D (16 mg, 0.03 mmol), DCM (1 mL), and Burgess reagent (15 mg, 0.06 mmol) was heated at 40 C for 4 h, then was cooled to RT. The reaction mixture was concentrated in vacuo. The crude product was chromatographed (12 g SiO₂; continuous gradient from 0% to 80% EtOAc in hexanes for 30 min and at 80% EtOAc in hexanes for 20 min) to give the crude title compound as an oil (10 mg, 0.020 mmol, 64.7% yield).

Example 73

To a stirred solution of Intermediate 73E (10 mg, 0.020 mmol) in THF (1.5 mL), MeOH (0.100 mL) and water (0.15 mL) at RT was added 2.0 M aq LiOH (0.030 mL, 0.060 mmol). The reaction mixture was stirred at 50° C. for 1 h, after which LCMS showed no starting material remaining. The reaction mixture was cooled to RT and acidified to pH 2.3 by dropwise addition of 1M aq. HCl. The mixture was concentrated in vacuo, and the crude product was purified by preparative HPLC ((Sunfire C18 (150×19) mm; 5 μm; mobile phase A: 10 mM NH₄OAc in water (pH: 4.5); mobile phase B: MeCN, flow rate: 15 mL/min; time (min)/% B: 0/20, 25/60; retention time: 15.19 min)) to give the title compound (TFA salt; 2 mg, 3.32 μmol, 16.7% yield). LCMS, [M+H]⁺=489.0. ¹H NMR (500 MHz, CD₃CN) S 7.97-7.87 (m, 1H), 7.58-7.50 (m, 1H), 7.40-7.23 (m, 5H), 4.86-4.80 (m, 1H), 4.78-4.69 (m, 2H), 4.21-4.16 (m, 2H), 4.11-4.02 (m, 3H), 2.85-2.74 (m, 1H), 2.47-2.41 (m, 3H), 2.15-2.06 (m, 1H), 1.92-1.85 (m, 3H), 1.79-1.56 (m, 5H). hLPA₁ IC₅₀=55 nM.

The Examples in Table 4 below were synthesized by the same methods exemplified by the preparation of Example 73.

TABLE 4

| Ex # | Structure & Name | Analytical & Biological Data |
|---|---|---|
| 74 | 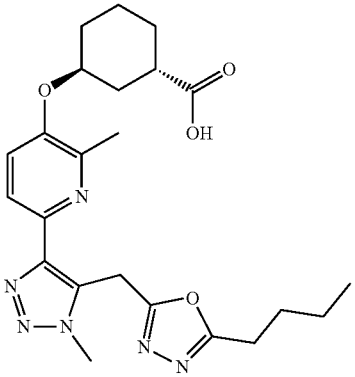<br>(1S,3S)-3-((6-(5-((5-butyl-1,3,4-oxadiazol-2-yl)methyl)-1-methyl-1H-1,2,3-triazol-4-yl)-2-methylpyridin-3-yl)oxy)cyclohexane-1-carboxylic acid | LCMS, $[M + H]^+ = 455.1$;<br>$^1$H NMR (500 MHz, DMSO-$d_6$) δ 7.89-7.75 (m, 1H), 7.59-7.47 (m, 1H), 4.99-4.87 (m, 2H), 4.78-4.64 (m, 1H), 4.27-4.01 (m, 3H), 2.95-2.71 (m, 2H), 2.62-2.54 (m, 2H), 2.39-2.26 (m, 3H), 2.02-1.49 (m, 9H), 1.37-1.19 (m, 2H), 1.00-0.78 (m, 3H);<br>hLPA$_1$ IC$_{50}$ = 227 nM. |
| 75 | 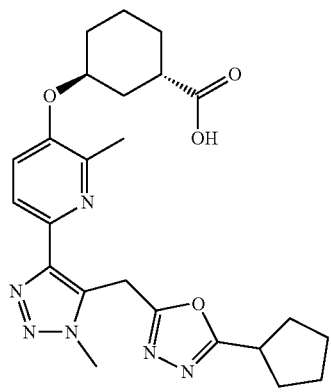<br>(1S,3S)-3-((6-(5-((5-cyclopentyl-1,3,4-oxadiazol-2-yl)methyl)-1-methyl-1H-1,2,3-triazol-4-yl)-2-methylpyridin-3-yl)oxy)cyclohexane-1-carboxylic acid | LCMS, $[M + H]^+ = 467.1$;<br>$^1$H NMR (500 MHz, DMSO-$d_6$) δ 7.88-7.73 (m, 1H), 7.59-7.44 (m, 1H), 5.01-4.81 (m, 2H), 4.75-4.60 (m, 1H), 4.20-4.03 (m, 3H), 2.57-2.55 (m, 1H), 2.43-2.25 (m, 4H), 2.10-1.90 (m, 3H), 1.86-1.45 (m, 13H);<br>hLPA$_1$ IC$_{50}$ = 289 nM. |
| 76 | 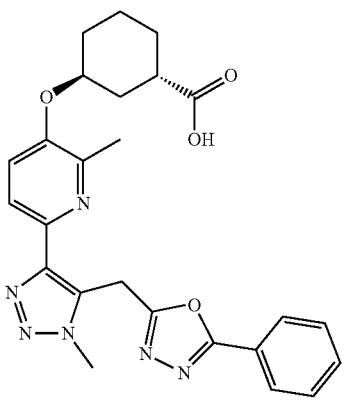<br>(1S,3S)-3-((2-methyl-6-(1-methyl-5-((5-phenyl-1,3,4-oxadiazol-2-yl)methyl)-1H-1,2,3-triazol-4-yl)pyridin-3-yl)oxy)cyclohexane-1-carboxylic acid | LCMS, $[M + H]^+ = 475.0$;<br>$^1$H NMR (500 MHz, DMSO-$d_6$) δ 8.00-7.78 (m, 3H), 7.69-7.46 (m, 4H), 5.21-4.89 (m, 2H), 4.76-4.54 (m, 1H), 4.27-4.02 (m, 3H), 2.67-2.54 (m, 3H), 2.42-2.23 (m, 2H), 2.09-1.42 (m, 8H);<br>hLPA$_1$ IC$_{50}$ = 290 nM. |

TABLE 4-continued

| Ex # | Structure & Name | Analytical & Biological Data |
|---|---|---|
| 77 | 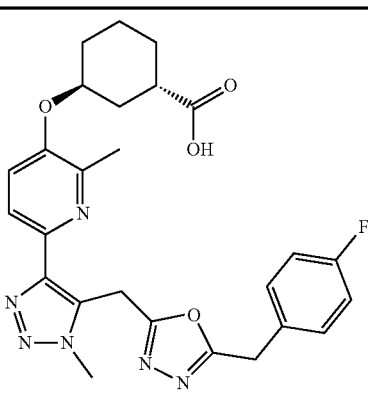<br>(1S,3S)-3-((6-(5-((5-(4-fluoro-benzyl)-1,3,4-oxadiazol-2-yl)methyl)-1-methyl-1H-1,2,3-triazol-4-yl)-2-methylpyridin-3-yl)oxy)cyclohexane-1-carboxylic acid | LCMS, $[M + H]^+ = 507.0$;<br>$^1$H NMR (500 MHz, DMSO-$d_6$) δ 7.91-7.69 (m, 1H), 7.63-7.46 (m, 1H), 7.39-7.26 (m, 2H), 7.19-7.03 (m, 2H), 5.01-4.81 (m, 2H), 4.76-4.59 (m, 1H), 4.36-4.11 (m, 2H), 4.13-3.94 (m, 3H), 2.61-2.55 (m, 1H), 2.44-2.32 (m, 1H), 2.27-2.16 (m, 2H), 2.02-1.85 (m, 3H), 1.85-1.46 (m, 5H);<br>hLPA$_1$ IC$_{50}$ = 260 nM. |

Example 78. (1 S,3 S)-3-((6-(5-((1-benzyl-1H-1,2,3-triazol-4-yl)(hydroxy)methyl)-1-methyl-1H-1,2,3-triazol-4-yl)-2-methylpyridin-3-yl)oxy)cyclohexane-1-carboxylic acid

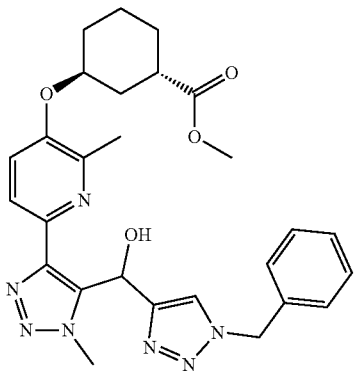 [SMILES: COC(=O)[C@H]1CCC[C@H](Oc2ccc(-c3nnn(C)c3C(O)c3cn(Cc4ccccc4)nn3)nc2C)C1]

78A. Methyl (1 S,3S)-3-((6-(5-(1-hydroxyprop-2-yn-1-yl)-1-methyl-1H-1,2,3-triazol-4-yl)-2-methylpyridin-3-yl)oxy)cyclohexane-1-carboxylate

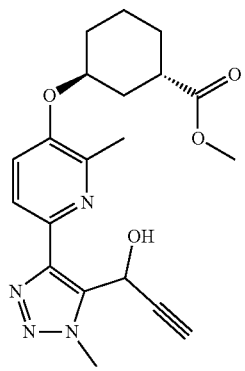 [SMILES: C#CC(O)c1c(-c2ccc(O[C@H]3CCC[C@H](C(=O)OC)C3)c(C)n2)nnn1C]

To a solution of Intermediate 8 (100 mg, 0.279 mmol) in THF (2.79 mL) at −78° C. was added ethynylmagnesium bromide (558 μL of a 0.5 M solution in THF; 0.279 mmol). The reaction was allowed to warm to 0° C. and stirred at 0° C. for 30 min, then was allowed to warm to RT and stirred at RT for 1 h. The reaction was then quenched by addition of sat. aq. NH$_4$Cl at 0° C., then was warmed to RT. EtOAc was added and the aqueous layer was extracted with EtOAc (2×). The combined organic layers were combined and washed with brine, dried (Na$_2$SO$_4$) and concentrated in vacuo. The crude product was chromatographed (12 g SiO$_2$; continuous gradient from 0% to 80% EtOAc in hexanes for 30 min and 80% EtOAc in hexanes for 20 min) to give the title compound (86 mg, 0.22 mmol, 80% yield). $^1$H NMR (400 MHz, CDCl$_3$) δ 9.90-9.37 (m, 1H), 8.24-8.05 (m, 1H), 7.36-7.30 (m, 1H), 5.82-5.49 (m, 1H), 4.83-4.66 (m, 1H), 4.13-4.11 (m, 3H), 3.78-3.64 (m, 3H), 2.93-2.75 (m, 1H), 2.64-2.51 (m, 3H), 2.48-2.43 (m, 1H), 2.21-2.10 (m, 1H), 2.02-1.84 (m, 3H), 1.81-1.48 (m, 4H).

78B. Methyl (1 S,3S)-3-((6-(5-((1-benzyl-1H-1,2,3-triazol-4-yl)(hydroxy)methyl)-1-methyl-1H-1,2,3-triazol-4-yl)-2-methylpyridin-3-yl)oxy)cyclohexane-1-carboxylate

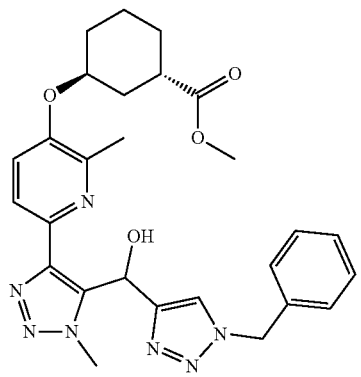 [SMILES: COC(=O)[C@H]1CCC[C@H](Oc2ccc(-c3nnn(C)c3C(O)c3cn(Cc4ccccc4)nn3)nc2C)C1]

To a mixture of 78A (63 mg, 0.164 mmol) and (azidomethyl)benzene (144 mg, 1.081 mmol), sodium ascorbate (1.966 mg, 0.016 mmol) in tBuOH (0.5 mL) in H$_2$O (0.5 mL) at RT was added CuSO$_4$ (3 mg, 0.016 mmol). The reaction mixture was stirred at 40° C. for 18 h, then was cooled to RT and concentrated in vacuo. The crude product was chromatographed (12 g SiO$_2$; continuous gradient from 0% to 80% EtOAc in hexanes for 30 min and 80% EtOAc in hexanes for 20 min) to give the title compound (28 mg, 0.054 mmol, 33% yield). $^1$H NMR (400 MHz, CDCl$_3$) δ 9.76-9.49 (m, 1H), 8.14 (dd, 1.7 Hz, 1H), 7.46-7.38 (m, 1H), 7.38-7.31 (m, 2H), 7.30-7.25 (m, 2H), 7.23-7.12 (m, 2H), 6.29-6.14 (m, 1H), 5.60-5.34 (m, 2H), 4.77-4.64 (m, 1H), 4.26 (s, 3H), 3.76-3.67 (m, 3H), 2.93-2.73 (m, 1H), 2.44-2.35 (m, 3H), 2.21-2.07 (m, 1H), 2.04-1.87 (m, 3H), 1.81-1.63 (m, 4H).

Example 78

To a stirred solution of intermediate 78B (20 mg, 0.039 mmol) in THF (1.5 mL), MeOH (0.10 mL) and water (0.15 mL) at RT was added 2.0 M aq LiOH (0.058 mL, 0.116 mmol). The reaction mixture was stirred at 50° C. for 1 h, then was cooled to RT and acidified to pH 2.3 by dropwise addition of 1M aq. HCl. The mixture was concentrated in vacuo and the residual crude product was purified by preparative HPLC ((Sunfire C18 (150×19) mm; 5 μm; mobile phase A: 10 mM NH$_4$OAc in H$_2$O(pH: 4.5); mobile phase B: MeCN, flow rate: 15 mL/min; time (min)/% B: 0/20, 25/60; retention time: 15.19 min)) to give the title compound (TFA salt; 20 mg, 0.032 mmol, 84% yield). LCMS, [M+H]$^+$=504.1; $^1$H NMR (400 MHz, CDCl$_3$) δ 8.54-8.33 (m, 1H), 7.95-7.80 (m, 2H), 7.44-7.34 (m, 3H), 7.32-7.29 (m, 2H), 6.71-6.59 (m, 1H), 6.37-5.82 (m, 2H), 5.58-5.45 (m, 2H), 4.95-4.74 (m, 1H), 4.11 (d, J=1.5 Hz, 3H), 3.00-2.81 (m, 1H), 2.70-2.59 (m, 3H), 2.30-2.10 (m, 1H), 2.04-1.62 (m, 7H).); hLPA$_1$ IC$_{50}$=88 nM.

Example 79. (1 S,3 S)-3-((6-(5-((4-butyl-1H-1,2,3-triazol-1-yl)methyl)-1-methyl-1H-1,2,3-triazol-4-yl)-2-methylpyridin-3-yl)oxy)cyclohexane-1-carboxylic acid

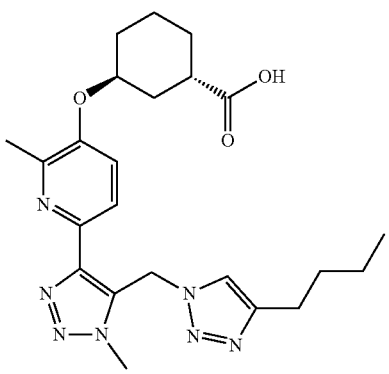 [SMILES: CCCCc1cn(Cc2c(-c3ccc(O[C@H]4CCC[C@H](C(=O)O)C4)c(C)n3)nnn2C)nn1]

A solution of azide Intermediate 6 (25 mg, 0.065 mmol) and hex-1-yne (27 mg, 0.32 mmol) in 1:1 tBuOH/H$_2$O (0.65 mL) was treated with sodium ascorbate (3 mg, 0.013 mmol) and CuSO$_4$.5H$_2$O (2 mg, 6.5 μmol). The reaction mixture was heated to 37° C. for 3 h (after which LCMS indicated that the reaction was complete), then was cooled to RT and extracted with EtOAc (2×). The combined organic extracts were concentrated in vacuo and the residual crude product was added to a solution of aq. LiOH (162 μL, 0.649 mmol) in THF/MeOH (0.5 mL/0.1 mL). The reaction was stirred overnight at RT, after which LC/MS indicated that the reaction was complete. The reaction was filtered and concentrated in vacuo. The residual crude product was purified by preparative HPLC (PHENOMENEX®, Axia 5μ C18 30×100 mm column; detection at 220 nm; flow rate=40 mL/min; continuous gradient from 0% B to 100% B over 10 min+2 min hold time at 100% B, where A=90:10:0.1 H/2O:MeOH:TFA and B=90:10:0.1 MeOH:H$_2$O:TFA), to give the title compound (18 mg, 0.038 mmol, 58.2% yield) as an oil. [M+H]$^+$=454.1; $^1$H NMR (500 MHz, DMSO-d$_6$) δ 7.95 (s, 1H), 7.89 (d, J=8.5 Hz, 1H), 7.51 (d, J=8.9 Hz, 1H), 6.17 (s, 2H), 4.80 (br s, 1H), 4.14 (s, 3H), 2.58 (br t, J=7.5 Hz, 3H), 2.49 (s, 3H), 2.03 (br d, J=13.7 Hz, 1H), 1.91-1.76 (m, 3H), 1.70-1.45 (m, 6H), 1.27 (sxt, J=7.4 Hz, 2H), 0.86 (t, J=7.3 Hz, 3H); hLPA$_1$ IC$_{50}$=44 nM.

Example 80. (1 S,3 S)-3-((6-(5-((4-benzyl-1H-pyrazol-1-yl)methyl)-1-methyl-1H-1,2,3-triazol-4-yl)-2-methylpyridin-3-yl)oxy)cyclohexane-1-carboxylic acid

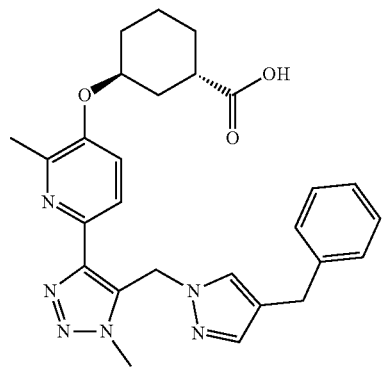 [SMILES: Cc1nc(-c2nnn(C)c2Cn2cc(Cc3ccccc3)cn2)ccc1O[C@H]1CCC[C@H](C(=O)O)C1]

4-benzyl-1H-pyrazole (17 mg, 0.11 mmol) was added to a solution of Intermediate 5 (30 mg, 0.071 mmol) in DMF (1 mL) at RT, followed by addition of NaH (6 mg of a 60% dispersion in oil, 0.11 mmol). The reaction was stirred overnight at RT, after which LCMS indicated that reaction was complete. The reaction was quenched with water (3 mL), then was partitioned between EtOAc and water and extracted with EtOAc (3×8 mL). The combined organic extracts were dried (MgSO$_4$) and concentrated in vacuo. The residue was mixed with aq. LiOH (177 μL, 0.709 mmol) in THF/MeOH (0.5 mL/0.1 mL) and stirred for 2 h at RT, after which LCMS indicated that the reaction was complete. The reaction was filtered, concentrated in vacuo and purified by preparative HPLC (PHENOMENEX®, Axia 5μ C18 30×100 mm column; detection at 220 nm; flow rate=40 mL/min; continuous gradient from 0% B to 100% B over 10 min+2 min hold time at 100% B, where A=90:10:0.1 H$_2$O:MeOH:TFA and B=90:10:0.1 MeOH:H$_2$O:TFA), to give the title compound (11 mg, 30.4% yield). LCMS, [M+H]$^+$=487.0; $^1$H NMR (DMSO-d$_6$) δ: 7.87 (br d, J=8.9 Hz, 1H), 7.65 (br d, J=6.1 Hz, 1H), 7.44-7.58 (m, 2H), 7.10-7.34 (m, 6H), 5.87 (s, 2H), 4.79 (br s, 1H), 4.34-4.52 (m, 1H), 4.14 (s, 3H), 3.72 (s, 2H), 2.59-2.72 (m, 1H), 2.33-2.43 (m, 3H), 1.21-2.18 (m, 8H); hLPA$_1$ IC$_{50}$=15 nM.

The Examples in Table 5 below were synthesized by the same methods exemplified by the preparation of the Examples as indicated.

TABLE 5

| Ex # | Structure & Name | Analytical & Biological Data | Method |
|---|---|---|---|
| 81 | 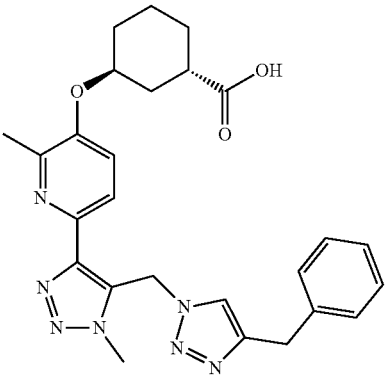<br>(1S,3S)-3-((6-(5-((4-benzyl-1H-1,2,3-triazol-1-yl)methyl)-1-methyl-1H-1,2,3-triazol-4-yl)-2-methylpyridin-3-yl)oxy)cyclohexane-1-carboxylic acid | LCMS, [M + H]$^+$ = 488.0; $^1$H NMR (DMSO-d$_6$) δ: 7.93-7.99 (m, 1H), 7.88 (d, J =8.2 Hz, 1H), 7.50 (d, J = 8.5 Hz, 1H), 7.10-7.36 (m, 5H), 6.14 (s, 2H), 4.79 (br s, 1H), 4.15 (s, 3H), 3.97 (s, 2H), 2.64 (br t, J = 10.7 Hz, 1H), 2.37 (s, 3H), 1.43-2.13 (m, 8H); hLPA$_1$ IC$_{50}$ = 37 nM. | Example 79 |
| 82 | 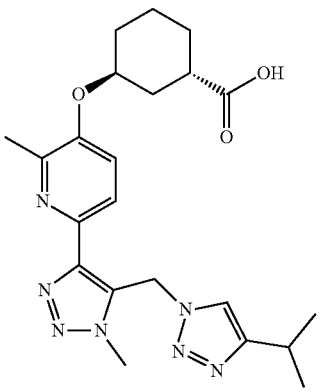<br>(1S,3S)-3-((6-(5-((4-isopropyl-1H-1,2,3-triazol-1-yl)methyl)-1-methyl-1H-1,2,3-triazol-4-yl)-2-methyl-pyridin-3-yl)oxy)cyclohexane-1-carboxylic acid | LCMS, [M + H]$^+$ = 440.1; $^1$H NMR (DMSO-d$_6$) δ: 7.99 (s, 1H), 7.89 (d, J = 8.5 Hz, 1H), 7.51 (d, J = 8.5 Hz, 1H), 6.14 (s, 2H), 4.80 (br s, 1H), 4.15 (s, 3H), 2.83-3.09 (m, 1H), 2.60-2.72 (m, 1H), 2.49 (s, 3H), 1.41-2.16 (m, 8H), 1.19 (d, J = 7.0 Hz, 5H); hLPA$_1$ IC$_{50}$ = 821 nM. | Example 79 |
| 83 | 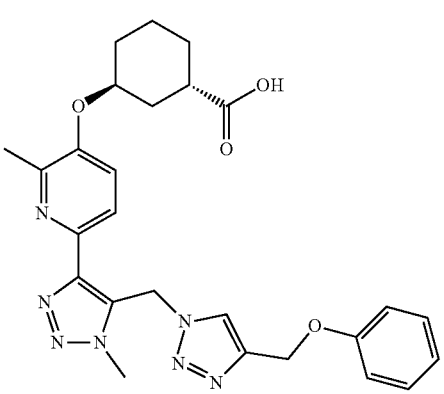<br>(1S,3S)-3-((2-methyl-6-(1-methyl-5-((4-(phenoxymethyl)-1H-1,2,3-triazol-1-yl)methyl)-1H-1,2,3-triazol-4-yl)pyridin-3-yl)oxy)cyclohexane-1-carboxylic acid | LCMS, [M + H]$^+$ = 504.3; $^1$H NMR (DMSO-d$_6$) δ: 8.33 (s, 1H), 7.90 (d, J = 8.9 Hz, 1H), 7.51 (d, J = 8.5 Hz, 1H), 7.27 (t, J = 7.9 Hz, 2H), 6.99 (br d, J = 8.2 Hz, 2H), 6.94 (t, J = 7.3 Hz, 1H), 6.23 (s, 2H), 5.13 (s, 2H), 4.80 (br s, 1H), 4.17 (s, 3H), 2.64 (br t, J = 10.2 Hz, 1H), 2.46 (s, 3H), 1.42-2.20 (m, 8H); hLPA$_1$ IC$_{50}$ = 135 nM. | Example 79 |

TABLE 5-continued

| Ex # | Structure & Name | Analytical & Biological Data | Method |
|---|---|---|---|
| 84 | 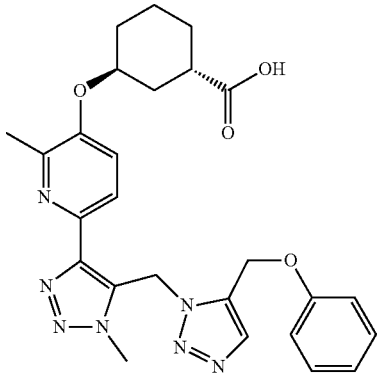<br>(1S,3S)-3-((2-methyl-6-(1-methyl-5-((5-(phenoxymethyl)-1H-1,2,3-triazol-1-yl)methyl)-1H-1,2,3-triazol-4-yl)pyridin-3-yl)oxy)cyclohexane-1-carboxylic acid | LCMS, [M + H]$^+$ = 504.2; $^1$H NMR (DMSO-d$_6$) δ: 8.34 (s, 1H), 7.90 (d, J = 8.2 Hz, 1H), 7.52 (br d, J = 8.5 Hz, 1H), 7.28 (br t, J = 7.9 Hz, 3H), 7.00 (br d, J = 7.9 Hz, 2H), 6.94 (t, J = 7.2 Hz, 1H), 6.24 (s, 2H), 5.13 (s, 2H), 4.80 (br s, 1H), 4.18 (s, 3H), 2.59-2.74 (m, 1H), 2.47 (s, 3H), 1.43-2.17 (m, 8H); hLPA$_1$ IC$_{50}$ = 172 nM. | Example 79 |
| 85 | 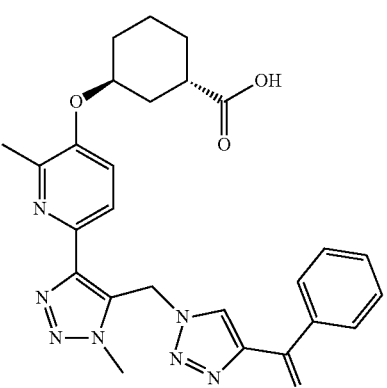<br>(1S,3S)-3-((6-(5-((4-benzyl-1H-1,2,3-triazol-1-yl)methyl)-1-methyl-1H-1,2,3-triazol-4-yl)-2-methyl-pyridin-3-yl)oxy)cyclohexane-1-carboxylic acid | LCMS, [M + H]$^+$ = 1003.3; $^1$H NMR (500 MHz, DMSO-d$_6$) δ 9.01 (s, 1H), 8.18 (br d, J = 7.6 Hz, 2H), 7.90 (d, J = 8.5 Hz, 1H), 7.76-7.65 (m, 1H), 7.61-7.47 (m, 3H), 6.30 (s, 2H), 4.79 (br s, 1H), 4.23 (s, 3H), 2.63 (br t, J = 10.5 Hz, 1H), 2.46 (s, 3H), 2.02 (br d, J = 14.0 Hz, 1H), 1.91-1.74 (m, 3H), 1.69-1.42 (m, 4H); hLPA$_1$ IC$_{50}$ = 241 nM. | Example 79 |
| 86 | 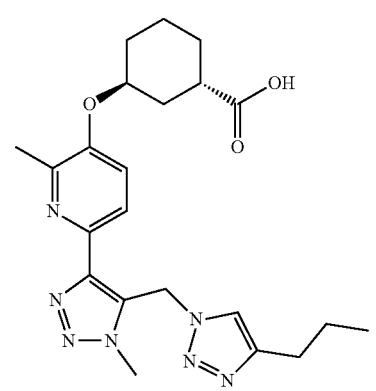<br>(1S,3S)-3-((2-methyl-6-(1-methyl-5-((4-propyl-1H-1,2,3-triazol-1-yl) methyl)-1H-1,2,3-triazol-4-yl) pyridin-3-yl)oxy)cyclohexane-1-carboxylic acid | LCMS, [M + H]$^+$ = 440.3; $^1$H NMR (DMSO-d$_6$) δ: 7.87-8.22 (m, 2H), 7.43-7.74 (m, 1H), 6.13-6.40 (m, 2H), 4.75-5.05 (m, 1H), 4.11-4.39 (m, 3H), 2.78 (br d, J = 9.8 Hz, 1H), 2.63-2.68 (m, 5H), 1.42-2.29 (m, 10H), 0.82-1.12 (m, 3H); hLPA$_1$ IC$_{50}$ = 187 nM. | Example 79 |

TABLE 5-continued

| Ex # | Structure & Name | Analytical & Biological Data | Method |
|---|---|---|---|
| 87 | 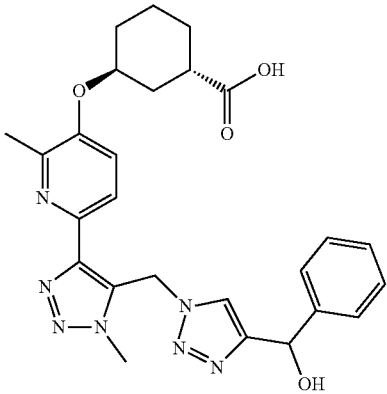<br>(1S,3S)-3-((6-(5-(((4-hydroxyl-(phenyl)methyl)-1H-1,2,3-triazol-1-yl)methyl)-1-methyl-1H-1,2,3-triazol-4-yl)-2-methylpyridin-3-yl)oxy)cyclohexane-1-carboxylic acid | LCMS, [M + H]$^+$ = 504.2;<br>$^1$H NMR (DMSO-d$_6$) δ: 8.00 (s, 1H), 7.88 (d, J = 8.2 Hz, 1H), 7.50 (br d, J = 8.5 Hz, 1H), 7.18-7.40 (m, 6H), 6.13 (br s, 2H), 5.78 (br d, J = 4.3 Hz, 1H), 4.78 (br s, 1H), 4.16 (s, 2H), 2.65 (br s, 1H), 2.38 (s, 3H), 1.20-2.14 (m, 8H);<br>hLPA$_1$ IC$_{50}$ = 363 nM. | Example 79 |
| 88 | 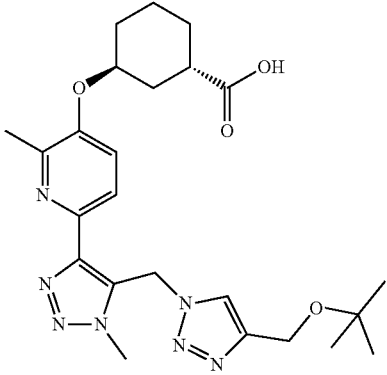<br>(1S,3S)-3-((6-(5-(((4-(tert-butoxy-methyl)-1H-1,2,3-triazol-1-yl)-methyl)-1-methyl-1H-1,2,3-triazol-4-yl)-2-methylpyridin-3-yl)oxy)-cyclohexane-1-carboxylic acid | LCMS, [M + H]$^+$ = 484.2;<br>$^1$H NMR (DMSO-d$_6$) δ: 8.13 (s, 1H), 7.89 (d, J = 8.5 Hz, 1H), 7.50 (d, J = 8.5 Hz, 1H), 6.16 (s, 2H), 4.79 (br s, 1H), 4.41 (s, 2H), 4.17 (s, 3H), 2.58-2.70 (m, 1H), 2.49 (s, 3H), 1.43-2.11 (m, 8H), 1.15 (s, 9H);<br>hLPA$_1$ IC$_{50}$ = 2928 nM. | Example 79 |
| 89 | 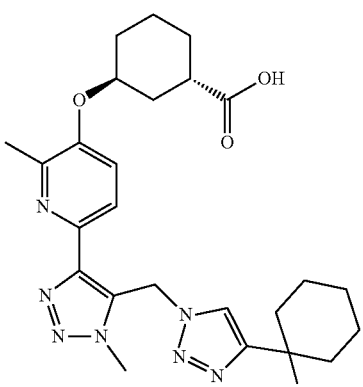<br>(1S,3S)-3-((6-(5-(((4-(1-hydroxyl-cyclohexyl)-1H-1,2,3-triazol-1-yl)methyl)-1-methyl-1H-1,2,3-triazol-4-yl)-2-methylpyridin-3-yl)oxy) cyclohexane-1-carboxylic acid | LCMS, [M + H]$^+$ = 496.2;<br>$^1$H NMR (DMSO-d$_6$) δ: 8.04 (s, 1H), 7.90 (br d, J = 7.9 Hz, 1H), 7.53 (br d, J = 7.6 Hz, 1H), 6.18 (s, 2H), 4.80 (br s, 1H), 4.16 (s, 3H), 2.58-2.77 (m, 1H), 2.48-2.51 (m, 3H), 1.09-2.14 (m, 18H);<br>hLPA$_1$ IC$_{50}$ = 3270 nM. | Example 79 |

TABLE 5-continued

| Ex # | Structure & Name | Analytical & Biological Data | Method |
|---|---|---|---|
| 90 | 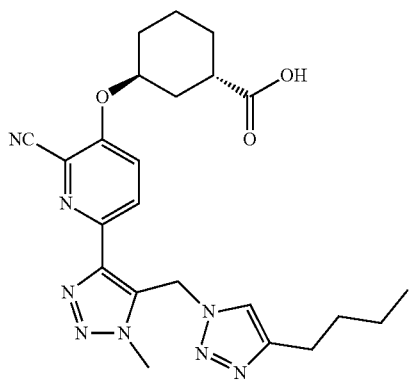<br>(1S,3S)-3-((6-(5-((4-butyl-1H-1,2,3-triazol-1-yl)methyl)-1-methyl-1H-1,2,3-triazol-4-yl)-2-cyanopyridin-3-yl)oxy)cyclohexane-1-carboxylic acid | LCMS, [M + H]$^+$ = 465.4;<br>$^1$H NMR (DMSO-d$_6$) δ: 8.32 (d, J = 8.9 Hz, 1H), 7.99 (br d, J = 9.2 Hz, 1H), 7.94 (s, 1H), 6.07 (s, 2H), 5.02 (br s, 1H), 4.17 (s, 3H), 2.67 (br d, J = 13.7 Hz, 1H), 2.56-2.61 (m, 2H), 1.18-2.13 (m, 12H), 0.86 (t, J = 7.3 Hz, 3H);<br>hLPA$_1$ IC$_{50}$ = 78 nM. | Example 79 |
| 91 | 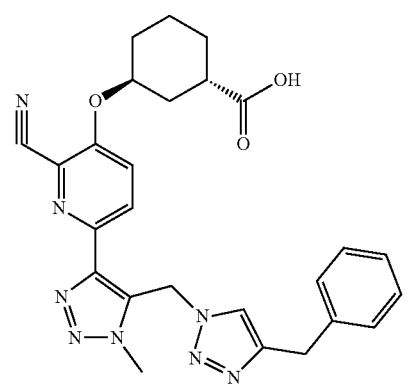<br>(1S,3S)-3-((6-(5-((4-benzyl-1H-1,2,3-triazol-1-yl)methyl)-1-methyl-1H-1,2,3-triazol-4-yl)-2-cyano-pyridin-3-yl)oxy)cyclohexane-1-carboxylic acid | LCMS, [M + H]$^+$ = 499.3;<br>$^1$H NMR (DMSO-d$_6$) δ: 8.31 (d, J = 8.9 Hz, 1H), 7.90-8.01 m, 2H), 7.03-7.34 (m, 5H), 6.08 (s, 2H), 5.02 (br s, 1H), 4.15 (s, 3H), 3.96 (s, 2H), 2.60-2.76 (m, 1H), 1.39-2.15 (m, 8H);<br>hLPA$_1$ IC$_{50}$ = 109 nM. | Example 79 |
| 92 | 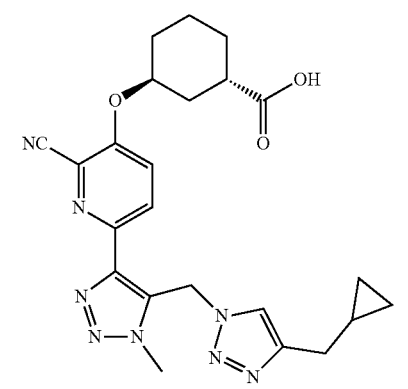<br>(1S,3S)-3-((6-(5-((4-(cyclopropyl-methyl)-1H-1,2,3-triazol-1-yl) methyl)-1-methyl-1H-1,2,3-triazol-4-yl)-2-cyanopyridin-3-yl)oxy) cyclohexane-1-carboxylic acid | LCMS, [M + H]$^+$ = 463.3;<br>$^1$H NMR (DMSO-d$_6$) δ: 8.19 (d, J = 8.9 Hz, 1H), 7.89 (s, 1H), 7.86 (d, J = 9.2 Hz, 1H), 5.94 (s, 2H), 4.89 (br s, 1H), 4.06 (s, 3H), 2.52 (br t, J = 10.8 Hz, 1H), 2.38-2.40 (m, 2H), 1.24-2.03 (m, 8H), 0.72-0.87 (m, 1H), 0.31 (br d, J = 6.7 Hz, 2H), 0.01 (br d, J = 4.6 Hz, 2H);<br>hLPA$_1$ IC$_{50}$ = 110 nM. | Example 79 |

TABLE 5-continued

| Ex # | Structure & Name | Analytical & Biological Data | Method |
|---|---|---|---|
| 93 | 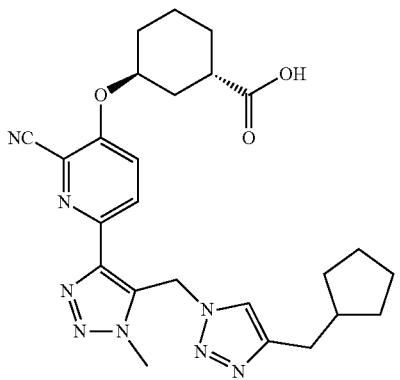<br>(1S,3S)-3-((6-(5-((4-(cyclopropyl-methyl)-1H-1,2,3-triazol-1-yl) methyl)-1-methyl-1H-1,2,3-triazol-4-yl)-2-cyanopyridin-3-yl)oxy) cyclohexane-1-carboxylic acid | LCMS, [M + H]$^+$ = 491.2; $^1$H NMR (DMSO-d$_6$) δ: 8.32 (d, J = 9.2 Hz, 1H), 7.99 (d, J = 9.2 Hz, 1H), 7.95 (s, 1H), 6.07 (s, 2H), 5.02 (br s, 1H), 4.17 (s, 3H), 2.62-2.72 (m, 1H), 2.58 (d, J = 7.3 Hz, 2H), 1.04-2.19 (m, 17H); hLPA$_1$ IC$_{50}$ = 60 nM. | Example 79 |
| 94 | 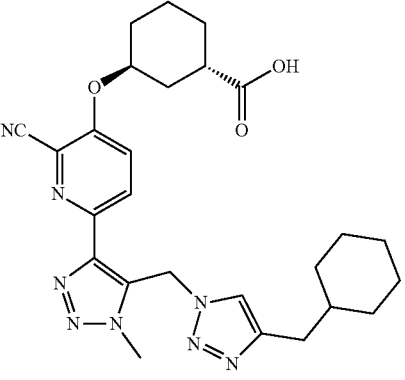<br>(1S,3S)-3-((6-(5-((4-(cyclopropyl-methyl)-1H-1,2,3-triazol-1-yl) methyl)-1-methyl-1H-1,2,3-triazol-4-yl)-2-cyanopyridin-3-yl)oxy) cyclohexane-1-carboxylic acid | LCMS, [M + H]$^+$ = 505.3; $^1$H NMR (DMSO-d$_6$) δ: 8.30 (d, J = 8.9 Hz, 1H), 7.93 (br d, J = 8.9 Hz, 1H), 7.90 (s, 1H), 6.01 (s, 2H), 4.99 (br s, 1H), 4.18 (s, 3H), 2.58-2.69 (m, 1H), 2.46 (br d, J = 6.7 Hz, 2H), 0.77-2.12 (m, 19H); hLPA$_1$ IC$_{50}$ = 54 nM. | Example 79 |
| 95 | 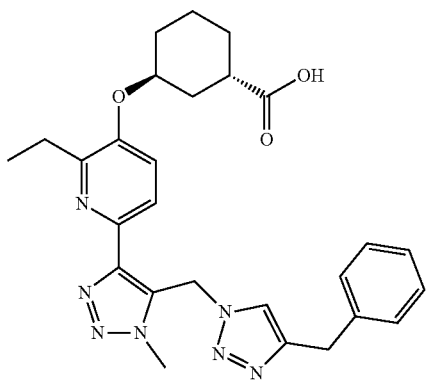<br>(1S,3S)-3-((6-(5-((4-benzyl-1H-1,2,3-triazol-1-yl) methyl)-1-methyl-1H-1,2,3-triazol-4-yl)-2-ethylpyridin-3-yl)oxy)cyclohexane-1-carboxylic acid | LCMS, [M + H]$^+$ = 502.3; $^1$H NMR (500 MHz, DMSO-d$_6$) δ 7.87 (d, J = 8.6 Hz, 1H), 7.77 (s, 1H), 7.46 (d, J = 8.6 Hz, 1H), 7.22 (t, J = 6.8 Hz, 2H), 7.16 (br d, J = 6.6 Hz, 3H), 6.15 (s, 2H), 4.75 (br s, 1H), 4.08 (s, 3H), 3.93 (s, 2H), 3.65 (br s, 1H), 2.74 (q, J = 7.4 Hz, 2H), 2.61 (br t, J = 10.4 Hz, 1H), 2.01 (br d, J = 17.4 Hz, 1H), 1.92-1.72 (m, 3H), 1.63 (br d, J = 9.8 Hz, 2H), 1.59-1.45 (m, 2H), 1.10 (t, J = 7.5 Hz, 3H); hLPA$_1$ IC$_{50}$ = 7 nM. | Example 79 |

TABLE 5-continued

| Ex # | Structure & Name | Analytical & Biological Data | Method |
|---|---|---|---|
| 96 | 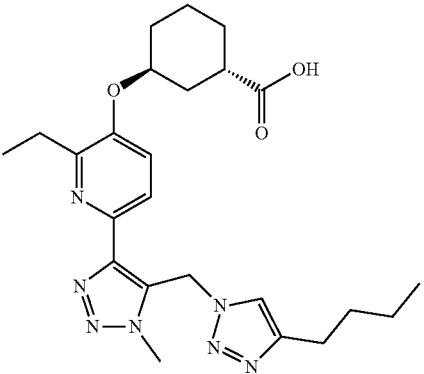<br>(1S,3S)-3-((6-(5-((4-benzyl-1H-1,2,3-triazol-1-yl)methyl)-1-methyl-1H-1,2,3-triazol-4-yl)-2-ethylpyridin-3-yl)oxy)cyclohexane-1-carboxylic acid | LCMS, [M + H]$^+$ = 468.3; $^1$H NMR (500 MHz, DMSO-$d_6$) δ 7.89 (br d, J = 8.5 Hz, 1H), 7.83 (s, 1H), 7.48 (br d, J = 8.5 Hz, 1H), 6.18 (s, 2H), 4.77 (br s, 1H), 4.07 (s, 3H), 3.55 (br s, 1H), 2.83 (q, J = 7.3 Hz, 2H), 2.60 (t, J = 10.4 Hz, 1H), 2.07-1.93 (m, 1H), 1.85 (br d, J = 11.9 Hz, 1H), 1.82-1.71 (m, 2H), 1.60 (br s, 2H), 1.55 (br s, 1H), 1.52-1.43 (m, 3H), 1.27-1.13 (m, 6H), 0.82 (br t, J = 7.3 Hz, 3H); hLPA$_1$ IC$_{50}$ = 9 nM. | Example 79 |
| 97 | 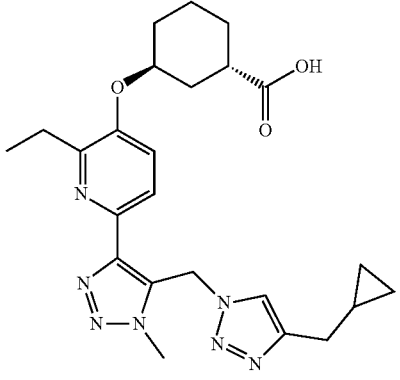<br>(1S,3S)-3-((6-(5-((4-(cyclopropyl-methyl)-1H-1,2,3-triazol-1-yl)methyl)-1-methyl-1H-1,2,3-triazol-4-yl)-2-ethylpyridin-3-yl)oxy)cyclohexane-1-carboxylic acid | LCMS, [M + H]$^+$ = 466.3; $^1$H NMR (500 MHz, DMSO-$d_6$) δ 7.87 (d, J = 8.6 Hz, 1H), 7.77 (s, 1H), 7.46 (d, J = 8.6 Hz, 1H), 7.22 (t, J = 6.8 Hz, 2H), 7.16 (br d, J = 6.6 Hz, 3H), 6.15 (s, 2H), 4.75 (br s, 1H), 4.08 (s, 3H), 3.93 (s, 2H), 3.65 (br s, 2H), 2.74 (q, J = 7.4 Hz, 2H), 2.61 (br t, J = 10.4 Hz, 1H), 2.01 (br d, J = 17.4 Hz, 1H), 1.92-1.72 (m, 3H), 1.63 (br d, J = 9.8 Hz, 2H), 1.59-1.45 (m, 2H), 1.10 (t, J = 7.5 Hz, 3H); hLPA$_1$ IC$_{50}$ = 8 nM. | Example 79 |
| 98 | 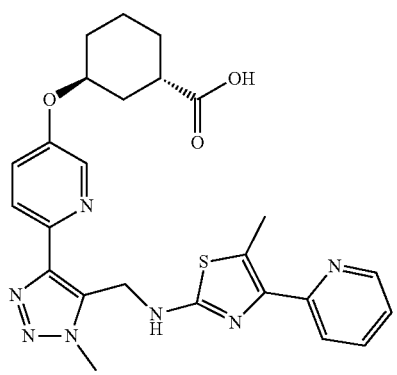<br>(1S,3S)-3-((6-(1-Methyl-5-(((5-methyl)-4-(pyridin-2-yl)thiazol-2-yl)amino)methyl)-1H-1,2,3-triazol-4-yl)pyridin-3-yl)oxy)cyclohexane-1-carboxylic acid | LCMS, M + H]$^+$ = 506.0; $^1$H NMR (500 MHz, DMSO-$d_6$) δ 8.53 (d, J = 4.8 Hz, 1H), 8.41 (d, J = 2.7 Hz, 1H), 8.01 (d, J = 8.7 Hz, 1H), 7.66 (t, J = 7.7 Hz, 1H), 7.57 (d, J = 8.2 Hz, 2H), 7.26-7.12 (m, 1H), 5.07 (d, J = 5.3 Hz, 2H), 4.79 (s, 1H), 4.15 (s, 3H), 2.73-2.63 (m, 1H), 2.59 (s, 3H), 2.03-1.44 (m, 8H); hLPA$_1$ IC$_{50}$ = 1050 nM. | Example 2 (aminothiazole-NaH) |

TABLE 5-continued

| Ex # | Structure & Name | Analytical & Biological Data | Method |
|---|---|---|---|
| 99 | 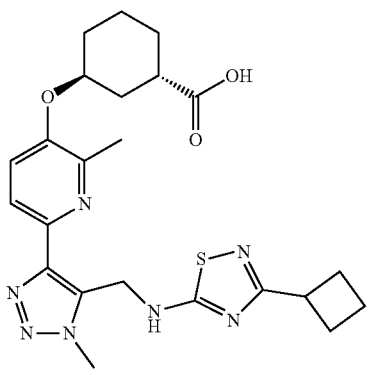<br>(1S,3S)-3-((6-(5-(((3-cyclobutyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, M + H]$^+$ = 484.1; $^1$H NMR (500 MHz, DMSO-d$_6$) δ 7.83 (d, J = 8.6 Hz, 1H), 7.46 (d, J 8.6 Hz, 1H), 5.07 (d, J = 4.3 Hz, 2H), 4.71 (br s, 1H), 4.15 (s, 3H), 2.43 (d, J = 7.6 Hz, 3H), 2.18 (td, J = 8.6, 6.0 Hz, 4H), 1.98-1.42 (m, 10H). (The proton α to acid and the methine proton on the cyclobutyl are not observed due to water-suppression); hLPA$_1$ IC$_{50}$ = 73 nM. | Example 3 (Cl-hetero-aryl i-Pr$_2$Net 180° C., 2h) |
| 100 | 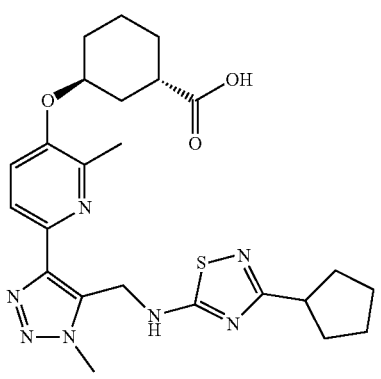<br>(1S,3S)-3-((6-(5-(((3-cyclobutyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 498.2; $^1$H NMR (500 MHz, DMSO-d$_6$) δ 7.86 (d, J = 8.5 Hz, 1H), 7.50 (d, J = 8.7 Hz, 1H), 5.09 (d, J = 5.5 Hz, 2H), 4.77 (s, 1H), 4.17 (s, 3H), 3.09-2.93 (m, 1H), 2.66-2.58 (m, 1H), 2.44 (s, 3H), 2.02-1.19 (m, 16H); hLPA$_1$ IC$_{50}$ = 77 nM. | Example 3 |
| 101 | 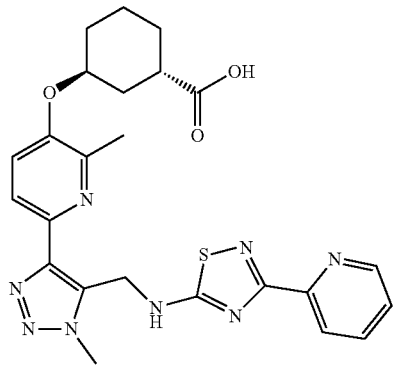<br>(1S,3S)-3-((2-methyl-6-(1-methyl-5-(((3-(pyridin-2-yl)-1,2,4-thiadiazol-5-yl)amino)methyl)1H-1,2,3-triazol-4-yl)pyridin-3-yl)oxy)cyclohexane-1-carboxylic acid | LCMS, [M +H]$^+$ = 507.2; $^1$H NMR (500 MHz, DMSO-d$_6$) δ 8.68 (s, 1H), 8.04 (s, 1H), 7.93 (t, J = 7.7 Hz, 1H), 7.89 (d, J = 8.7 Hz, 1H), 7.52 (d, J = 8.8 Hz, 2H), 5.21 (d, J = 5.0 Hz, 2H), 4.80 (s, 1H), 4.27 (s, 3H), 2.68-2.59 (m, 1H), 2.46 (s, 3H), 2.07-1.43 (m, 8H); hLPA$_1$ IC$_{50}$ = 483 nM. | Example 3 |

TABLE 5-continued

| Ex # | Structure & Name | Analytical & Biological Data | Method |
|---|---|---|---|
| 102 | (1S,3S)-3-((6-(5-(((3-isobutyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 485.9; $^1$H NMR (500 MHz, DMSO-d$_6$) δ 7.86 (d, J = 8.5 Hz, 1H), 7.51 (d, J = 8.7 Hz, 1H), 5.09 (d, J = 5.3 Hz, 2H), 4.78 (s, 1H), 2.63-2.57 (m, 1H), 2.45 (m, 3H), 2.09-1.46 (m, 9H), 0.88 (d, J = 6.6 Hz, 6H). (The —CH$_2$— off the thiadiazole are not observed due to water-suppression); hLPA$_1$ IC$_{50}$ = 98 nM. | Example 3 |
| 103 | (1S,3S)-3-((6-(5-(((3-cyclopropyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, M + H]$^+$ = 470.1; $^1$H NMR (500 MHz, DMSO-d$_6$) δ 8.61 (s, 1H), 7.86 (d, J = 8.5 Hz, 1H), 7.50 (d, J = 8.7 Hz, 1H), 5.07 (d, J = 5.5 Hz, 2H), 4.80 (s, 1H), 2.69-2.60 (m, 1H), 2.45 (s, 3H), 2.07-1.45 (m, 8H), 0.86 (br s, 2H), 0.78 (br s, 2H). (The methine proton on the cyclopropyl is not observed due to water-suppression); hLPA$_1$ IC$_{50}$ = 510 nM. | Example 3 |
| 104 | (1S,3S)-3-((2-methyl-6-(1-methyl-5-(((3-propyl-1,2,4-thiadiazol-5-yl)amino)methyl) 1H-1,2,3-triazol-4-yl)pyridin-3-yl)oxy)cyclohexane-1-carboxylic acid | LCMS, [M + H]$^+$ = 472.2; $^1$H NMR (500 MHz, DMSO-d$_6$) δ 7.84 (d, J = 8.5 Hz, 1H), 7.48 (d, J = 8.6 Hz, 1H), 5.06 (d, J = 3.1 Hz, 2H), 4.75 (s, 1H), 4.14 (s, 3H), 2.62-2.57 (m, 1H), 2.43 (s, 3H), 2.00-1.44 (m, 10H), 0.87 (t, J = 7.4 Hz, 3H). (The —CH$_2$— off the thiadiazole are not observed due to water-suppression) hLPA$_1$ IC$_{50}$ = 109 nM. | Example 3 |

Example 105. (1S,3S)-3-((6-(5-((5-(cyclopropylmethyl)-2H-tetrazol-2-yl)methyl)-1-methyl-1H-1,2,3-triazol-4-yl)-2-methylpyridin-3-yl)oxy)cyclohexane-1-carboxylic acid

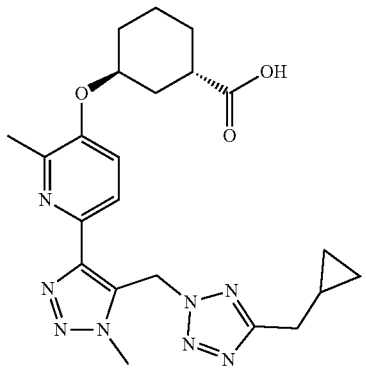 [SMILES: Cc1nc(-c2nnn(C)c2Cn2nnc(CC3CC3)n2)ccc1O[C@H]1CCC[C@H](C(=O)O)C1]

Example 106. (1S,3S)-3-((6-(5-((5-(cyclopropylmethyl)-1H-tetrazol-1-yl)methyl)-1-methyl-1H-1,2,3-triazol-4-yl)-2-methylpyridin-3-yl)oxy)cyclohexane-1-carboxylic acid

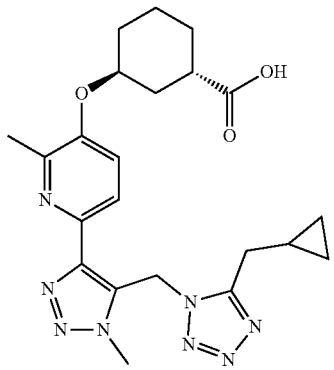 [SMILES: Cc1nc(-c2nnn(C)c2Cn2nnnc2CC2CC2)ccc1O[C@H]1CCC[C@H](C(=O)O)C1]

105A. 5-(cyclopropylmethyl)-2H-tetrazole

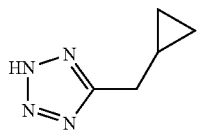

A mixture of 2-cyclopropylacetonitrile (0.225 mL, 2.47 mmol), NaN$_3$ (0.176 g, 2.71 mmol) and ZnBr$_2$ (0.555 g, 2.47 mmol) in water (4 mL) was heated in a microwave reactor at 150 C for 3 h, then was cooled to RT. Aq. 6 N HCl and EtOAc (10 mL) were added, and the mixture was stirred vigorously until all solids were dissolved and the aqueous layer had a pH of 1. The organic layer was separated; the aqueous layer was extracted with EtOAc (2×10 mL). The combined organic extracts were washed with brine, dried (Na$_2$SO$_4$) and concentrated in vacuo to give the crude title compound (0.16 g, 1.29 mmol, 52.3% yield), which was used in the next step without further purification.

Examples 105 and 106

To a solution of Intermediate 4 (26 mg, 0.072 mmol) in DCM (721 µL) was added 105A (18 mg, 0.14 mmol) and Ph$_3$P (38 mg, 0.14 mmol), followed by DIAD (29 mg, 0.14 mmol). The reaction mixture was stirred at RT overnight, after which LCMS indicated that the reaction was complete. The reaction mixture was concentrated in vacuo, and the residue was chromatographed (4 g SiO$_2$; continuous gradient from 0%-100% EtOAc in hexane) to give two regioisomeric tetrazole isomers. The first isomer to elute was methyl (1S,3S)-3-((6-(5-((5-(cyclopropylmethyl)-2H-tetrazol-2-yl)methyl)-1-methyl-1H-1,2,3-triazol-4-yl)-2-methylpyridin-3-yl)oxy)cyclo-hexane-1-carboxylate (20 mg, 0.034 mmol, 47.5% yield). The second isomer to elute was methyl (1S,3S)-3-((6-(5-((5-(cyclopropylmethyl)-1H-tetrazol-1-yl)methyl)-1-methyl-1H-1,2,3-triazol-4-yl)-2-methylpyridin-3-yl)oxy)cyclohexane-1-carboxylate (30 mg crude), which was mixed with Ph$_3$PO; this material was used in the next step without further purification.

To a solution of methyl (1S,3S)-3-((6-(5-((5-(cyclopropylmethyl)-2H-tetrazol-2-yl)methyl)-1-methyl-1H-1,2,3-triazol-4-yl)-2-methylpyridin-3-yl)oxy)cyclohexane-1-carboxylate (20 mg, 0.034 mmol) in THF (0.5 mL) was added MeOH (0.1 mL), followed by aq. LiOH (0.047 mL, 0.189 mmol). The reaction mixture was stirred at RT overnight; at this point LCMS indicated that the reaction was complete. The reaction was filtered and concentrated in vacuo. The residue was purified by preparative HPLC (Phenomenex®, Axia 5µ C18 30×100 mm column; detection at 220 nm; flow rate=40 mL/min; continuous gradient from 0% B to 100% B over 10 min+2 min hold time at 100% B, where A=90:10:0.1 H$_2$O:MeOH:TFA and B=90:10:0.1 MeOH:H$_2$O:TFA) to give Example 105 (4.6 mg, 9.9 µmol, 21% yield). LCMS, [M+H]$^+$=453.1. $^1$H NMR (DMSO-d$_6$) δ: 7.70 (d, J=8.5 Hz, 1H), 7.31 (d, J=8.5 Hz, 1H), 6.36 (s, 2H), 4.61 (br s, 1H), 4.00 (s, 3H), 2.56 (d, J=7.0 Hz, 2H), 2.44-2.50 (m, 1H), 2.22 (s, 3H), 0.72-1.95 (m, 9H), 0.20-0.42 (m, 2H), −0.06-0.12 (m, 2H). LCMS, [M+H]$^+$=453.1; hLP$_1$ IC$_{50}$=29 nM To a solution of methyl (1S,3S)-3-((6-(5-((5-(cyclopropyl-methyl)-1H-tetrazol-1-yl)methyl)-1-methyl-1H-1,2,3-triazol-4-yl)-2-methylpyridin-3-yl)oxy) cyclohexane-1-carboxylate (30 mg, with impurity of Ph$_3$PO) in THF (0.5 mL) was added MeOH (0.1 mL), followed by aq. LiOH (0.043 mL, 0.171 mmol). The reaction mixture was stirred at RT overnight; at this point LCMS indicated that the reaction was complete. The reaction mixture was concentrated in vacuo. The residue was purified by preparative HPLC (PHENOMENEX®, Axia 5µ C18 30×100 mm column; detection at 220 nm; flow rate=40 mL/min; continuous gradient from 0% B to 100% B over 10 min+2 min hold time at 100% B, where A=90:10:0.1 H$_2$O:MeOH:TFA and B=90:10:0.1 MeOH:H$_2$O:TFA) to give Example 106 (17.5 mg, 0.033 mmol, 77% yield). LCMS, [M+H]$^+$=453.3. 1H NMR (DMSO-d$_6$) δ: 7.77 (d, J=8.5 Hz, 1H), 7.40 (d, J=8.5 Hz, 1H), 6.17 (s, 2H), 4.67 (br s, 1H), 4.03 (s, 3H), 2.76 (d, J=7.0 Hz, 2H), 2.50 (br t, J=10.4 Hz, 1H), 2.29 (s, 3H), 0.80-1.98 (m, 9H), 0.34 (br d, J=7.3 Hz, 2H), 0.01 (br d, J=4.6 Hz, 2H). [M+H]$^+$=453.3; hLP$_1$ IC$_{50}$=147 nM.

The Examples in Table 7 below were synthesized by the same methods exemplified by the preparation of Examples 105 and 106.

TABLE 7

| Ex # | Structure & Name | Analytical & Biological Data |
| --- | --- | --- |
| 107 | 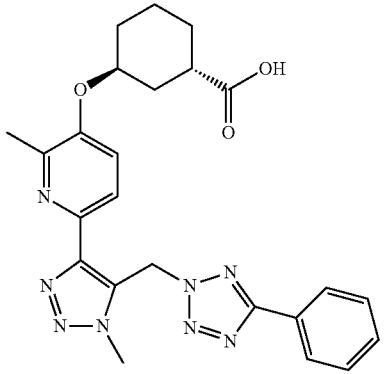<br>(1S,3S)-3-((2-methyl-6-(1-methyl-5-((5-phenyl-2H-tetrazol-2-yl)methyl)-1H-1,2,3-triazol-4-yl)pyridin-3-yl)oxy) cyclohexane-1-carboxylic acid | LCMS, [M + H]$^+$ = 475.3;<br>$^1$H NMR (DMSO-d$_6$) δ: 7.98-8.10 (m, 2H), 7.88 (d, J = 8.2 Hz, 1H), 7.50-7.62 (m, 3H), 7.46 (d, J = 8.5 Hz, 1H), 6.61 (br s, 2H), 4.75 (br s, 1H), 4.24 (s, 3H), 2.58-2.67 (m, 1H), 2.38 (s, 3H), 1.37-2.07 (m, 8H);<br>hLPA$_1$ IC$_{50}$ = 42 nM. |
| 108 | 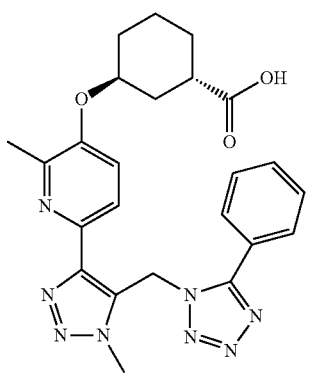<br>(1S,3S)-3-((2-methyl-6-(1-methyl-5-((5-phenyl-1H-tetrazol-1-yl)methyl)-1H-1,2,3-triazol-4-yl)pyridin-3-yl)oxy) cyclohexane-1-carboxylic acid | LCMS, [M + H]$^+$ = 475.3;<br>$^1$H NMR (DMSO-d$_6$) δ: 7.83 (br d, J = 7.9 Hz, 2H), 7.77 (d, J = 8.4 Hz, 1H), 7.53-7.67 (m, 3H), 7.38 (br d, J = 8.5 Hz, 1H), 6.40 (s, 2H), 4.70 (br s, 1H), 4.16 (s, 3H), 2.57-2.64 (m, 1H), 1.88 (s, 3H), 1.38-2.09 (m, 8H);<br>hLPA$_1$ IC$_{50}$ = 239 nM. |
| 109 | 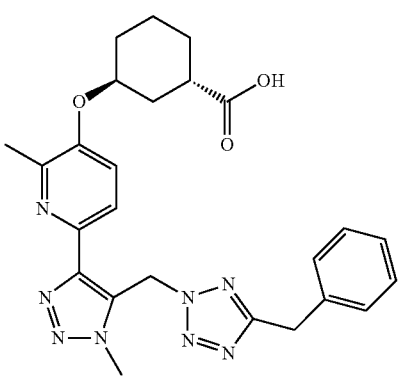<br>(1S,3S)-3-((6-(5-((5-benzyl-2H-tetrazol-2-yl)methyl)-1-methyl-1H-1,2,3-triazol-4-yl)-2-methylpyridin-3-yl)oxy)cyclohexane-1-carboxylic acid | LCMS, [M + H]$^+$ = 489.2;<br>$^1$H NMR (DMSO-d$_6$) δ: 7.84 (d, J = 8.5 Hz, 1H), 7.42 (d, J = 8.6 Hz, 1H), 7.12-7.32 (m, 5H), 6.47 (s, 2H), 4.73 (br s, 1H), 4.16 (s, 2H), 4.12 (s, 3H), 2.58-2.71 (m, 1H), 2.30 (s, 3H), 1.37-2.11 (m, 8H);<br>hLPA$_1$ IC$_{50}$ = 14 nM. |

TABLE 7-continued

| Ex # | Structure & Name | Analytical & Biological Data |
|---|---|---|
| 110 | (1S,3S)-3-((6-(5-((5-benzyl-1H-tetrazol-1-yl)methyl)-1-methyl-1H-1,2,3-triazol-4-yl)-2-methylpyridin-3-yl)oxy) cyclohexane-1-carboxylic acid | LCMS, [M + H]$^+$ = 489.2; $^1$H NMR (DMSO-d$_6$) δ: 7.85 (d, J = 8.5 Hz, 1H), 7.47 (br d, J = 8.5 Hz, 1H), 7.17-7.33 (m, 3H), 7.07 (br d, J = 6.7 Hz, 2H), 6.31 (br s, 2H), 4.75 (br s, 1H), 4.42 (s, 2H), 4.07 (s, 3H), 2.56-2.62 (m, 1H), 2.29 (s, 3H), 1.36-2.06 (m, 8H); hLPA$_1$ IC$_{50}$ = 207 nM. |
| 111 | (1S,3S)-3-((6-(5-((5-butyl-2H-tetrazol-2-yl)methyl)-1-methyl-1H-1,2,3-triazol-4-yl)-2-methylpyridin-3-yl)oxy) cyclohexane-1-carboxylic acid | LCMS, [M + H]$^+$ = 455.1; $^1$H NMR (DMSO-d$_6$) δ: 7.85 (br d, J = 8.2 Hz, 1H), 7.45 (d, J = 8.5 Hz, 1H), 6.48 (s, 2H), 4.75 (br s, 1H), 4.13 (s, 3H), 2.70-2.83 (m, 2H), 2.59 (br d, J = 10.1 Hz, 1H), 2.35 (s, 3H), 1.14-2.08 (m, 12H), 0.82 (t, J = 7.3 Hz, 3H); hLPA$_1$ IC$_{50}$ = 34 nM. |
| 112 | (1S,3S)-3-((6-(5-((5-butyl-1H-tetrazol-1-yl)methyl)-1-methyl-1H-1,2,3-triazol-4-yl)-2-methylpyridin-3-yl)oxy) cyclohexane-1-carboxylic acid | LCMS, [M + H]$^+$ = 455.1; $^1$H NMR (DMSO-d$_6$) δ: 7.90 (d, J = 8.5 Hz, 1H), 7.51 (br d, J = 8.5 Hz, 1H), 6.30 (s, 2H), 4.79 (br s, 1H), 4.12 (s, 3H), 2.86 (br t, J = 7.8 Hz, 2H), 2.62 (br t, J = 10.7 Hz, 1H), 2.42 (s, 3H), 1.07-2.11 (m, 12H), 0.78 (t, J = 7.3 Hz, 3H); hLPA$_1$ IC$_{50}$ = 176 nM. |

TABLE 7-continued

| Ex # | Structure & Name | Analytical & Biological Data |
|---|---|---|
| 113 | (1S,3S)-3-((2-methyl-6-(1-methyl-5-((5-propyl-2H-tetrazol-2-yl)methyl)-1H-1,2,3-triazol-4-yl)pyridin-3-yl)oxy) cyclohexane-1-carboxylic acid | LCMS, [M + H]⁺ = 441.2; $^1$H NMR (DMSO-$d_6$) δ: 7.86 (d, J = 8.5 Hz, 1H), 7.47 (d, J = 8.9 Hz, 1H), 6.51 (s, 2H), 4.77 (br s, 1H), 4.15 (s, 3H), 2.75 (t, J = 7.3 Hz, 2H), 2.62 (br t, J = 10.5 Hz, 1H), 2.37 (s, 3H), 1.38-2.10 (m, 10H), 0.86 (t, J = 7.3 Hz, 3H); hLPA$_1$ IC$_{50}$ = 30 nM. |
| 114 | (1S,3S)-3-((2-methyl-6-(1-methyl-5-((5-propyl-1H-tetrazol-1-yl)methyl)-1H-1,2,3-triazol-4-yl)pyridin-3-yl)oxy) cyclohexane-1-carboxylic acid | LCMS, [M + H]$^{1+}$ = 441.2; $^1$H NMR (DMSO-$d_6$) δ: 7.90 (br d, J = 8.5 Hz, 1H), 7.52 (br d, J = 8.5 Hz, 1H), 6.28 (s, 2H), 4.79 (br s, 1H), 4.13 (s, 3H), 2.87 (br t, J = 7.6 Hz, 2H), 2.59 (br d, J = 10.1 Hz, 1H), 2.42 (s, 3H), 1.38-2.13 (m, 10H), 0.82 (t, J = 7.3 Hz, 3H); hLPA$_1$ IC$_{50}$ = 125 nM. |

Example 115. (1S,3S)-3-((2-methyl-6-(1-methyl-5-(((1-phenyl-1H-1,2,4-triazol-3-yl)oxy) methyl)-1H-1,2,3-triazol-4-yl)pyridin-3-yl)oxy)cyclohexane-1-carboxylic acid

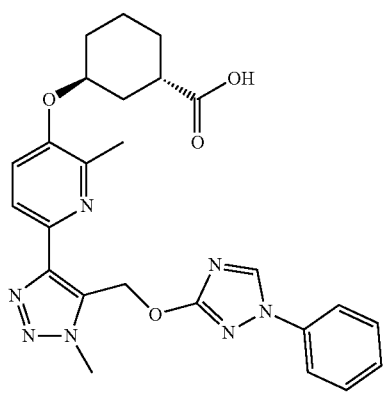 [SMILES: Cc1nc(-c2nnn(C)c2COc2ncn(-c3ccccc3)n2)ccc1O[C@H]1CCC[C@H](C(=O)O)C1]

To a RT solution of Intermediate 4 (20 mg, 0.055 mmol), 1-phenyl-1H-1,2,4-triazol-3-ol (9 mg, 0.055 mmol), and Ph$_3$P (29 mg, 0.111 mmol) in DCM (0.3 mL) was added DEAD (0.018 mL, 0.111 mmol). The reaction mixture was stirred at RT for 16 h, then was concentrated in vacuo. The residue was chromatographed (4 g SiO$_2$; continuous gradient from 0 to 100% EtOAc in hexanes over 13 min, then hold at 100% EtOAc for 5 min) to give the impure product as an oil. The impure product was dissolved in THF and water (0.5 mL each). LiOH·H$_2$O (12 mg, 0.28 mmol) was added and the reaction was stirred for 3 h at RT, then was concentrated in vacuo. The residue was dissolved in EtOAc (2 mL)/water (1 mL), and adjusted to pH~5 with 1N aq. HCl and extracted with EtOAC (3×5 mL). The combined organic extracts were dried (MgSO$_4$) and concentrated in vacuo. The crude product was purified by preparative LC/MS: Column: XBridge C18, 200 mm×19 mm, 5-μm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 11% B, 11-51% B over 20 min, then a 6-min hold at 100% B; Flow Rate: 20 mL/min; Column Temperature: 25 C. Fraction collection was triggered by MS signals. Fractions containing the desired product were combined and dried via centrifugal evaporation to give the title compound (14.4 mg, purity by LCMS=99%). LCMS, [M+H]⁺=490.4. $^1$H NMR (500 MHz, DMSO-$d_6$) δ 9.00 (s, 1H), 7.85 (d, J=8.5 Hz, 1H), 7.64 (d, J=8.0 Hz, 2H), 7.48 (t, J=7.9 Hz, 3H), 7.35 (t, J=7.5 Hz, 1H), 6.04 (s, 2H), 4.76 (s, 1H), 4.15 (s, 3H), 2.61-2.56 (m, 1H), 2.33 (s, 3H), 2.01-1.42 (m, 8H). hLPA$_1$ IC$_{50}$=47 nM.

Example 116. (1S,3S)-3-((6-(5-(((3-cyclopropyl-1,2,4-thiadiazol-5-yl)oxy)methyl)-1-methyl-1H-1,2,3-triazol-4-yl)-2-methylpyridin-3-yl)oxy)cyclohexane-1-carboxylic acid

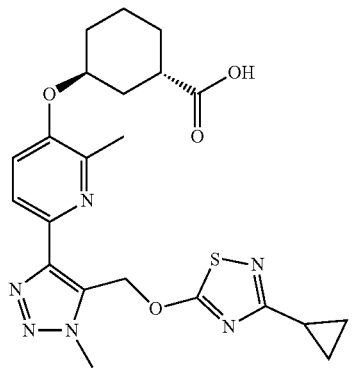 [SMILES: Cc1nc(-c2nnn(C)c2COc2nc(C3CC3)ns2)ccc1O[C@H]1CCC[C@H](C(=O)O)C1]

To a solution of Intermediate 12 (25 mg, 0.072 mmol) in 1,4-dioxane (1.5 mL) was added NaH (17 mg of a 60% dispersion in oil, 0.43 mmol). The mixture was stirred at RT for 10 min, then 5-chloro-3-cyclopropyl-1,2,4-thiadiazole (23 mg, 0.14 mmol) was added. The reaction was stirred at 160° C. in a microwave reactor for 1 h, then was cooled to RT and concentrated in vacuo. The crude product was dissolved in EtOAc (2 mL)/water (1 mL), and adjusted to pH~5 with 1N aq. HCl. The mixture was extracted with EtOAc (3×2 mL). The combined organic extracts were dried (MgSO$_4$) and concentrated in vacuo. The crude product was purified by preparative LC/MS: Column: XBridge C18, 200 mm×19 mm, 5-µm particles; Mobile Phase A: 5:95 MeCN:H$_2$O with 0.1% TFA; Mobile Phase B: 95:5 MeCN:H$_2$O with 0.1% TFA; Gradient: a 0-min hold at 19% B, 19-59% B over 20 min, then a 4-min hold at 100% B; Flow Rate: 20 mL/min; Column Temperature: 25° C. Fraction collection was triggered by MS signals. Fractions containing the desired product were combined and dried via centrifugal evaporation to give the title compound (bis-TFA salt; 4.2 mg, 8% yield; purity by LCMS=97%). LCMS, [M+H]$^+$=471.2. $^1$H NMR (500 MHz, DMSO-d$_6$) δ 7.79 (d, J=8.7 Hz, 1H), 7.45 (d, J=8.6 Hz, 1H), 5.70 (s, 2H), 4.75 (s, 1H), 3.98 (s, 3H), 2.64-2.56 (m, 1H), 2.39 (s, 3H), 2.05-1.40 (m, 9H), 0.77-0.71 (m, 2H), 0.53 (dd, J=8.3, 2.8 Hz, 2H). hLPA$_1$ IC$_{50}$=405 nM.

Example 117. (1S,3S)-3-((6-(5-(((5-(cyclopropylmethyl)-1,2,4-oxadiazol-3-yl)oxy)methyl)-1-methyl-1H-1,2,3-triazol-4-yl)-2-methylpyridin-3-yl)oxy)cyclohexane-1-carboxylic acid

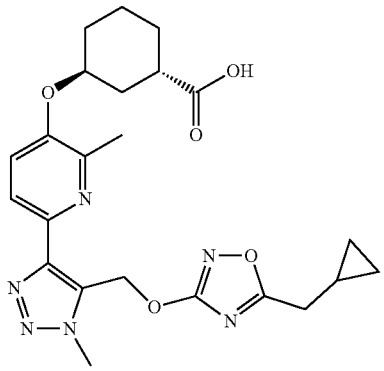 [SMILES: Cc1nc(-c2nnn(C)c2COc2noc(CC3CC3)n2)ccc1O[C@H]1CCC[C@H](C(=O)O)C1]

A mixture of BrettPhos (0.8 mg, 1.665 µmol) and NaOtBu (11 mg, 0.12 mmol) was evacuated and backfilled with N$_2$ (repeated 3×), after which Intermediate 4 (30 mg, 0.083 mmol) and 3-bromo-5-(cyclopropylmethyl)-1,2,4-oxadiazole (17 mg, 0.083 mmol) were added. A second flask was charged with the Pd precatalyst t-Bu-BrettPhos Pd G3 (1.4 mg, 1.67 µmol), which was evacuated and backfilled with Ar (repeated 3×), after which 1,4-dioxane (0.3 mL) was added; the mixture was stirred at RT until it became a homogeneous solution. This precatalyst solution was added dropwise to the reaction mixture, which was quickly evacuated and back-filled with Ar, then was stirred at RT for 18 h. THF/water (0.5 mL each) and LiOH·H$_2$O (18 mg, 0.43 mmol) were then added to the reaction mixture, which was stirred for 18 h at RT, then was concentrated in vacuo. The residue was taken up in EtOAc (2 mL)/water (1 mL), and adjusted to pH ~5 with 1N aq. HCl. The mixture was extracted with EtOAc (3×2 mL). The combined organic extracts were dried (MgSO$_4$) and concentrated in vacuo. The crude product was purified by preparative LC/MS: Column: XBridge C18, 200 mm×19 mm, 5-µm particles; Mobile Phase A: 5:95 MeCN:H$_2$O with 0.1% TFA; Mobile Phase B: 95:5 MeCN:H$_2$O with 0.1% TFA; Gradient: a 0-min hold at 10% B, 10-70% B over 20 min, then a 4-min hold at 100% B; Flow Rate: 20 mL/min; Column Temperature: 25° C. Fraction collection was triggered by MS signals. Fractions containing the desired product were combined and dried via centrifugal evaporation. This material was further purified via preparative LC/MS: Column: XBridge C18, 200 mm×19 mm, 5-µm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 15% B, 15-40% B over 35 min, then a 4-min hold at 100% B; Flow Rate: 20 mL/min; Column Temperature: 25° C. Fraction collection was triggered by MS signals. Fractions containing the desired product were combined and dried via centrifugal evaporation to give the title compound (3.4 mg, 9% yield; purity by LCMS analysis=100%). Injection 1 conditions: Column: Waters XBridge C18, 2.1 mm×50 mm, 1.7 μm particles; Mobile Phase A: 5:95 MeCN:H₂O with 10 mM aq. NH₄OAc; Mobile Phase B: 95:5 MeCN:H₂O with 10 mM aq. NH₄OAc; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 469.23; Retention Time: 1.45 min. Injection 2 conditions: Column: Waters XBridge C18, 2.1 mm×50 mm, 1.7 μm particles; Mobile Phase A: 5:95 MeCN:H₂O with 0.1% TFA; Mobile Phase B: 95:5 MeCN:H₂O with 0.1% TFA; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 469.23; Retention Time: 1.67 min. LCMS, [M+H]⁺=469.2; ¹H NMR (500 MHz, DMSO-d₆) δ 7.87 (d, J=8.5 Hz, 1H), 7.53 (d, J=8.6 Hz, 1H), 5.99 (s, 2H), 4.74 (s, 1H), 4.15 (s, 3H), 2.78 (d, J=7.1 Hz, 2H), 2.49-2.44 (m, 1H), 2.31 (s, 3H), 1.90-1.48 (m, 8H), 1.11-1.03 (m, 1H), 0.53 (dd, J=7.9, 1.8 Hz, 2H), 0.26 (d, J=5.0 Hz, 2H). hLPA₁ IC₅₀=11 nM.

The Examples in the following table were synthesized by the procedures described for the preparation of Examples 1-5.

| Ex # | Structure & Name | Analytical & Biological Data | Method |
|---|---|---|---|
| 118 | 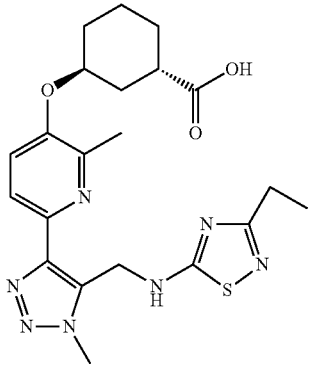<br>(1S,3S)-3-((6-(5-(((3-ethyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, [M + H]⁺ = 458.2; ¹H NMR (500 MHz, DMSO-d₆) δ 7.85 (d, J = 8.6 Hz, 1H), 7.48 (d, J = 8.6 Hz, 1H), 5.06 (s, 2H), 4.76 (s, 1H), 4.15 (s, 3H), 2.68-2.61 (m, 1H), 2.58 (q, J = 7.6 Hz, 2H), 2.44 (s, 3H), 2.06-1.42 (m, 8H), 1.16 (td, J = 7.6 Hz, 3H); hLPA₁ IC₅₀ = 919 nM. | Example 3 180° C., 2 h |
| 119 | 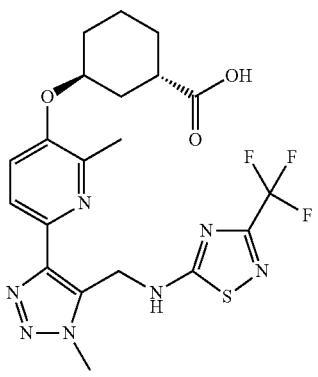<br>(1S,3S)-3-((2-methyl-6-(1-methyl-5-(((3-(trifluoromethyl)-1,2,4-thiadiazol-5-yl)amino)methyl)-1H-1,2,3-triazol-4-yl)pyridin-3-yl)oxy)cyclohexane-1-carboxylic acid | LCMS, [M + H]⁺ = 498.1; ¹H NMR (500 MHz, DMSO-d₆) δ 7.87 (d, J = 8.4 Hz, 1H), 7.48 (d, J = 8.6 Hz, 1H), 5.14 (s, 2H), 4.76 (s, 1H), 4.16 (s, 3H), 2.66-2.57 (m, 1H), 2.42 (s, 3H), 2.04-1.47 (m, 8H); hLPA₁ IC₅₀ = 60 nM. | Example 3 180° C., 2 h |

| Ex # | Structure & Name | Analytical & Biological Data | Method |
|---|---|---|---|
| 120 | 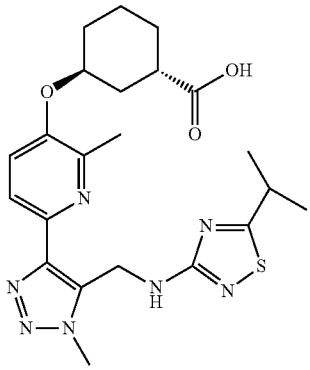<br>(1S,3S)-3-((6-(5-(((5-isopropyl-1,2,4-thiadiazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 472.1; $^1$H NMR (500 MHz, DMSO-$d_6$) δ 7.84 (d, J = 8.5 Hz, 1H), 7.67 (t, J = 6.0 Hz, 1H), 7.48 (d, J = 8.6 Hz, 1H), 4.87 (d, J = 6.0 Hz, 2H), 4.76 (s, 1H), 4.12 (s, 3H), 3.24-3.15 (m, 1H), 2.67-2.57 (m, 1H), 2.44 (s, 3H), 2.03-1.42 (m, 8H), 1.24 (d, J = 6.9 Hz, 6H); hLPA$_1$ IC$_{50}$ = 25 nM | Example 3 180° C., 4 h |
| 121 | 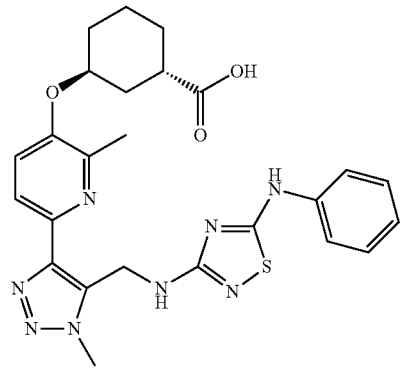<br>(1S,3S)-3-((2-methyl-6-(1-methyl-5-(((5-(phenylamino)-1,2,4-thiadiazol-3-yl)amino)methyl)-1H-1,2,3-triazol-4-yl)pyridin-3-yl)oxy)cyclohexane-1-carboxylic acid | LCMS, [M + H]$^+$ = 521.1; $^1$H NMR (500 MHz, DMSO-$d_6$) δ 7.86 (d, J = 8.5 Hz, 1H), 7.50 (d, J = 8.7 Hz, 1H), 7.45 (d, J = 8.0 Hz, 2H), 7.37 (t, J = 6.1 Hz, 1H), 7.32 (t, J = 7.8 Hz, 2H), 7.03 (t, J = 7.4 Hz, 1H), 4.86 (d, J = 6.0 Hz, 2H), 4.76 (s, 1H), 4.12 (s, 3H), 2.65-2.57 (m, 1H), 2.48 (s, 3H), 2.01-1.48 (m, 8H); hLPA$_1$ IC$_{50}$ = 470 nM. | Example 1 |
| 122 | 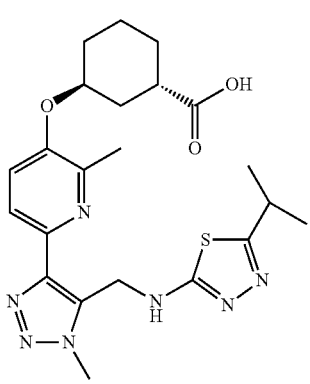<br>(1S,3S)-3-((6-(5-(((5-isopropyl-1,3,4-thiadiazol-2-yl)amino)methyl)-1-methyl-1H-1,2,3-triazol-4-yl)-2-methylpyridin-3-yl)oxy)cyclohexane-1-carboxylic acid | LCMS, [M + H]$^+$ = 472.0; $^1$H NMR (500 MHz, DMSO-$d_6$) δ 7.86 (d, J = 8.6 Hz, 1H), 7.50 (d, J = 8.7 Hz, 1H), 5.01 (d, J = 4.2 Hz, 2H), 4.78 (s, 1H), 4.15 (s, 3H), 3.14 (p, J = 6.9 Hz, 1H), 2.66-257 (m, 1H), 2.43 (s, 3H), 2.09-1.45 (m, 8H), 1.24 (d, J = 6.8 Hz, 6H); hLPA$_1$ IC$_{50}$ = 555 nM. | Example 1 |

| Ex # | Structure & Name | Analytical & Biological Data | Method |
|---|---|---|---|
| 123 | 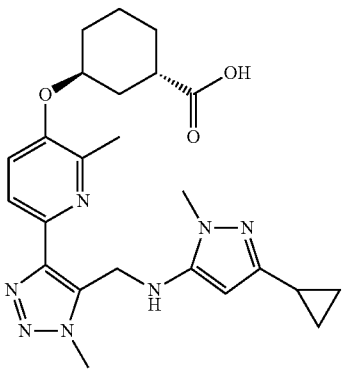<br>(1S,3S)-3-((6-(5-(((3-cyclopropyl-1-methyl-1H-pyrazol-5-yl)amino)methyl)-1-methyl-1H-1,2,3-triazol-4-yl)-2-methylpyridin-3-yl)oxy)cyclohexane-1-carboxylic acid | LCMS, $[M + H]^+ = 466.2$; $^1$H NMR (rotamers) (500 MHz, DMSO-$d_6$) δ 7.88-7.80 (m, 1H), 7.56-7.49 (m, 1H), 4.79 (br s, 2H), 4.78 (s, 1H) 4.27 (s, 1H), 4.08 (s, 3H), 3.92 (s, 3H), 2.73-2.62 (m, 1H), 2.48 (s, 1.3H), 2.46 (s, 1.7H), 2.09-1.46 (m, 9H), 0.76-0.61 (m, 3H), 0.37 (dt, J = 6.3, 3.1 Hz, 1H); hLPA$_1$ IC$_{50}$ = 1287 nM. | Example 1 |
| 124 | 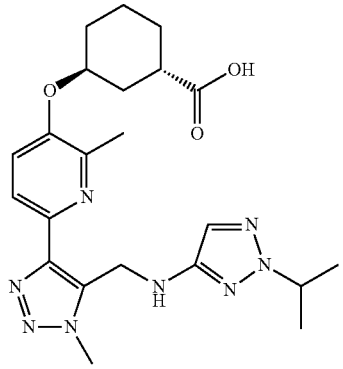<br>(1S,3S)-3-((6-(5-(((2-isopropyl-2H-1,2,3-triazol-4-yl)amino)methyl)-1-methyl-1H-1,2,3-triazol-4-yl)-2-methylpyridin-3-yl)oxy)cyclohexane-1-carboxylic acid | LCMS, $[M + H]^+ = 455.4$; $^1$H NMR (500 MHz, DMSO-$d_6$) δ 7.85 (d, J = 8.5 Hz, 1H), 7.48 (d, J = 8.6 Hz, 1H), 6.98 (s, 1H), 4.77 (s, 1H), 4.73 (d, J = 1.7 Hz, 2H), 4.49 (sep, J = 8.4 Hz, 1H), 4.13 (s, 3H), 2.67 (t, J = 11.9 Hz, 1H), 2.46 (s, 3H), 2.07-1.46 (m, 8H), 1.35 (d, J = 8.4 Hz, 6H); hLPA$_1$ IC$_{50}$ = 337 nM. | Example 1 |
| 125 | 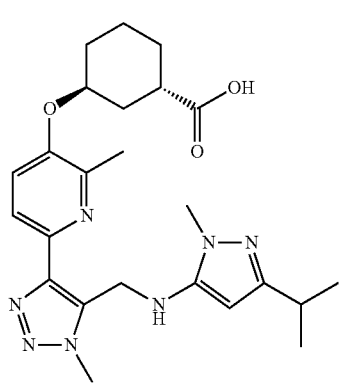<br>(1S,3S)-3-((6-(5-(((3-isopropyl-1-methyl-1H-pyrazol-5-yl)amino)methyl)-1-methyl-1H-1,2,3-triazol-4-yl)-2-methylpyridin-3-yl)oxy)cyclohexane-1-carboxylic acid | LCMS, $[M + H]^+ = 468.2$; $^1$H NMR (rotamers) (500 MHz, DMSO-$d_6$) δ 7.88 (d, J = 8.5 Hz, 0.6H), 7.81 (d, J = 8.6 Hz, 0.4H), 7.57 (d, J = 8.7 Hz, 0.4H), 7.53 (d, J = 8.7 Hz, 0.6H), 5.65 (s, 0.8H), 4.96 (s, 1.2H), 4.81 (s, 1H), 4.27 (s, 0.6H), 4.09 (s, 1.8H), 3.88 (s, 1.2H), 3.62 (s, 0.4H), 2.74-2.67 (m, 1H), 2.66-2.58 (s, 1H), 2.46 (s, 3H), 2.13-1.42 (m, 8H), 1.05 (d, J = 6.9 Hz, 2.4H), 1.00 (d, J = 7.0 Hz, 3.6H); (pyrazole N—CH$_3$ not observed due to water-suppression). hLPA$_1$ IC$_{50}$ = 627 nM. | Example 1 |

| Ex # | Structure & Name | Analytical & Biological Data | Method |
|---|---|---|---|
| 126 | (1S,3S)-3-((6-(((1-isopropyl-1H-1,2,4-triazol-3-yl)amino)methyl)-1-methyl-1H-1,2,3-triazol-4-yl)-2-methylpyridin-3-yl)oxy)cyclohexane-1-carboxylic acid | LCMS, [M + H]$^+$ = 455.1; $^1$H NMR (500 MHz, DMSO-d$_6$) δ 8.00 (s, 1H), 7.85 (d, J = 8.5 Hz, 1H), 7.50 (d, J = 8.7 Hz, 1H), 6.40 (t, J = 6.8 Hz, 1H), 4.78 (s, 1H), 4.64 (d, J = 6.7 Hz, 2H), 4.29 (sep, J = 6.6 Hz, 1H), 4.18 (s, 3H), 2.67-2.59 (m, 1H), 2.48 (s, 3H), 2.06-1.44 (m, 8H), 1.31 (d, J = 6.6 Hz, 6H); hLPA$_1$ IC$_{50}$ = 1488 nM. | Example 1 |
| 127 | (1S,3S)-3-((2-methyl-6-(1-methyl-5-(((3-propyl-1,2,4-thiadiazol-5-yl)oxy)methyl)-1H-1,2,3-triazol-4-yl)pyridin-3-yl)oxy)cyclohexane-1-carboxylic acid | LCMS, [M + H]$^+$ = 473.1; $^1$H NMR (500 MHz, DMSO-d$_6$) δ 7.85 (d, J = 8.5 Hz, 1H), 7.51 (d, J = 8.6 Hz, 1H), 5.66 (s, 2H), 4.80 (s, 1H), 3.99 (s, 3H), 2.66-2.57 (m, 1H), 2.44 (s, 3H), 2.40 (t, J = 8.0 Hz, 2H), 2.07-1.39 (m, 10H), 0.60 (t, J = 7.3 Hz, 3H); hLPA$_1$ IC$_{50}$ = 425 nM. | Example 5 160° C. 0.5 h |
| 128 | (1S,3S)-3-((6-(5-(((3-isopropyl-1,2,4-thiadiazol-5-yl)oxy)methyl)-1-methyl-1H-1,2,3-triazol-4-yl)-2-methylpyridin-3-yl)oxy)cyclohexane-1-carboxylic acid | LCMS, [M + H]$^+$ = 473.3; $^1$H NMR (500 MHz, DMSO-d$_6$) δ 7.84 (d, J = 8.6 Hz, 1H), 7.51 (d, J = 8.6 Hz, 1H), 5.70 (s, 2H), 4.80 (s, 1H), 3.98 (s, 3H), 2.66-2.57 (m, 1H), 2.43 (s, 3H), 2.25-1.09 (m, 9H), 0.98-0.90 (m, 6H); hLPA$_1$ IC$_{50}$ = 98 nM. | Example 5 160° C. 1 h |

| Ex # | Structure & Name | Analytical & Biological Data | Method |
|---|---|---|---|
| 129 | 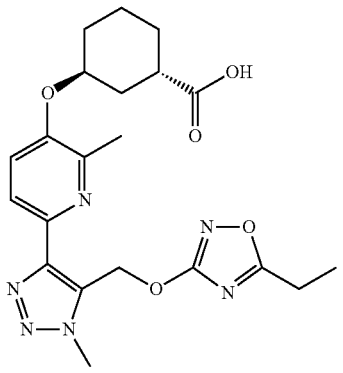<br>(1S,3S)-3-((6-(5-(((5-ethyl-1,2,4-oxadiazol-3-yl)oxy)methyl)-1-methyl-1H-1,2,3-triazol-4-yl)-2-methylpyridin-3-yl)oxy)cyclohexane-1-carboxylic acid | LCMS, [M + H]$^+$ = 443.4;<br>$^1$H NMR (500 MHz, CDCl$_3$) δ 8.05 (d, J = 8.5 Hz, 1H), 7.76 (d, J = 8.7 Hz, 1H), 5.77 (s, 2H), 4.86 (s, 1H), 4.27 (s, 3H), 2.97-2.90 (m, 1H), 2.83 (q, J = 7.6 Hz, 2H), 2.75 (s, 3H), 2.18-1.65 (m, 8H), 1.37 (t, J = 7.7 Hz, 3H); hLPA$_1$ IC$_{50}$ = 41 nM. | Example 5<br>160° C. 3 h |
| 130 | 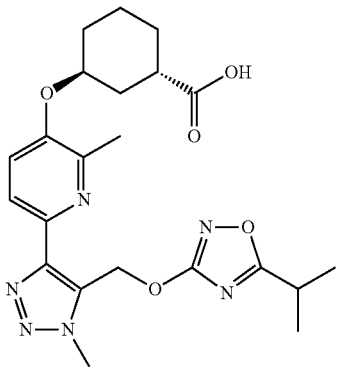<br>(1S,3S)-3-((6-(5-(((5-isopropyl-1,2,4-oxadiazol-3-yl)oxy)methyl)-1-methyl-1H-1,2,3-triazol-4-yl)-2-methylpyridin-3-yl)oxy)cyclohexane-1-carboxylic acid | LCMS, [M + H]$^+$ = 457.3;<br>$^1$H NMR (500 MHz, DMSO-d$_6$) δ 7.88 (d, J = 8.5 Hz, 1H), 7.48 (d, J = 8.6 Hz, 1H), 5.99 (s, 2H), 4.78 (s, 1H), 4.14 (s, 3H), 3.23-3.08 (m, 1H), 2.65-2.58 (m, 1H), 2.31 (s, 3H), 2.06-1.40 (m, 8H), 1.26 (d, J = 7.0 Hz, 6H); hLPA$_1$ IC$_{50}$ = 26 nM. | Example 5<br>160° C. 3 h |
| 131 | 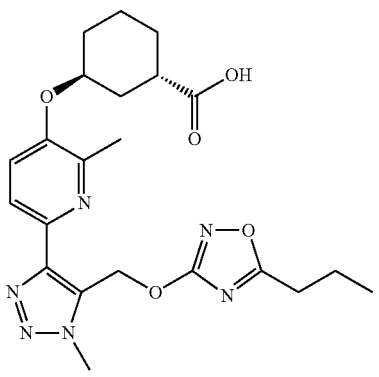<br>(1S,3S)-3-((2-methyl-6-(1-methyl-5-(((5-propyl-1,2,4-oxadiazol-3-yl)oxy)methyl)-1H-1,2,3-triazol-4-yl)pyridin-3-yl)oxy)cyclohexane-1-carboxylic acid | LCMS, [M + H]$^+$ = 457.5;<br>$^1$H NMR (500 MHz, DMSO-d$_6$) δ 7.88 (d, J = 8.5 Hz, 1H), 7.48 (d, J = 8.7 Hz, 1H), 5.98 (s, 2H), 4.78 (s, 1H), 4.14 (s, 3H), 2.82 (t, J = 7.3 Hz, 2H), 2.66-2.58 (m, 1H), 2.31 (s, 3H), 2.05-1.43 (m, 10H), 0.93 (t, J = 7.4 Hz, 3H); hLPA$_1$ IC$_{50}$ = 19 nM. | Example 5<br>100° C. 6 h |

| Ex # | Structure & Name | Analytical & Biological Data | Method |
|---|---|---|---|
| 132 | 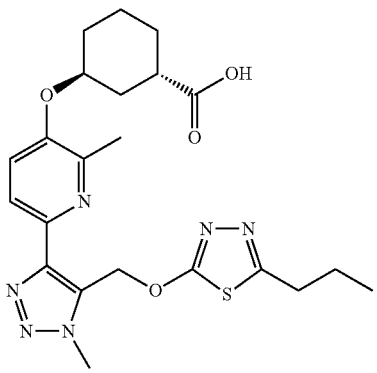<br>(1S,3S)-3-((2-methyl-6-(1-methyl-5-(((5-propyl-1,3,4-oxadiazol-3-yl)oxy)methyl)-1H-1,2,3-triazol-4-yl)pyridin-3-yl)oxy)cyclohexane-1-carboxylic acid | LCMS, [M + H]$^+$ = 473.1;<br>$^1$H NMR (500 MHz, DMSO-d$_6$) δ 7.80 (d, J = 8.5 Hz, 1H), 7.45 (d, J = 8.5 Hz, 1H), 5.60 (s, 2H), 4.75 (s, 1H), 4.07 (s, 3H), 2.65-2.57 (m, 1H), 2.40 (s, 3H), 2.03-1.38 (m, 12H), 0.78 (t, J = 7.4 Hz, 3H);<br>hLPA$_1$ IC$_{50}$ = 97 nM. | Example 5<br>150° C. 2 h |
| 133 | 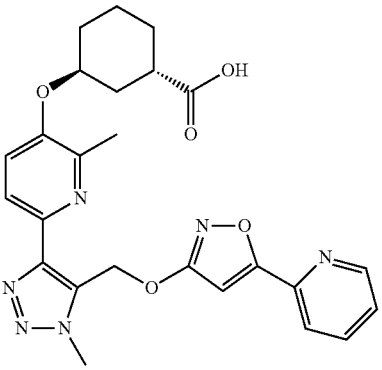<br>(1S,3S)-3-((2-methyl-6-(1-methyl-5-(((5-(pyridin-2-yl)isoxazol-3-yl)oxy)methyl)-1H-1,2,3-triazol-4-yl)pyridin-3-yl)oxy)cyclohexane-1-carboxylic acid | LCMS, [M + H]$^+$ = 491.1;<br>$^1$H NMR (500 MHz, DMSO-d$_6$) δ 8.69 (d, J = 4.7 Hz, 1H), 7.99 (t, J = 7.8 Hz, 1H), 7.90 (dd, J = 14.5, 8.2 Hz, 2H), 7.51 (dd, J = 7.3, 5.1 Hz, 1H), 7.48 (d, J = 8.6 Hz, 1H), 6.90 (s, 1H), 6.00 (s, 2H), 4.77 (s, 1H), 4.15 (s, 3H), 2.65-2.56 (m, 1H), 2.34 (s, 3H), 2.04-1.41 (m, 8H);<br>hLPA$_1$ IC$_{50}$ = 208 nM. | Example 5<br>180° C. 6 h |
| 134 | 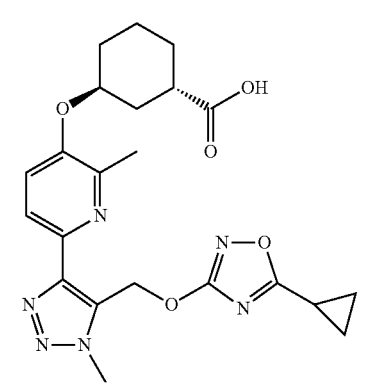<br>(1S,3S)-3-((6-(5-(((5-cyclopropyl-1,2,4-oxadiazol-3-yl)oxy)methyl)-1-methyl-1H-1,2,3-triazol-4-yl)-2-methylpyridin-3-yl)oxy)cyclohexane-1-carboxylic acid | LCMS, [M + H]$^+$ = 455.4;<br>$^1$H NMR (400 MHz, CDCl$_3$) δ 8.00 (d, J = 8.6 Hz, 1H), 7.54 (d, J = 8.7 Hz, 1H), 5.86 (s, 2H), 4.80 (s, 1H), 4.23 (s, 3H), 2.96-2.87 (m, 1H), 2.63 (s, 3H), 2.18-1.61 (m, 9H), 1.28-1.15 (m, 4H);<br>hLPA$_1$ IC$_{50}$ = 25 nM. | Example 5<br>160° C. 2 h |

Example 135. (1S,3S)-3-((6-(5-(((1-Isobutyl-1H-1,2,4-triazol-3-yl)oxy)methyl)-1-methyl-1H-1,2,3-triazol-4-yl)-2-methylpyridin-3-yl)oxy)cyclohexane-1-carboxylic acid

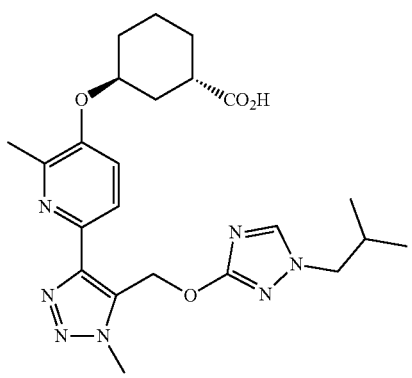 [SMILES: Cc1nc(-c2nnn(C)c2COc2ncn(CC(C)C)n2)ccc1O[C@H]1CCC[C@H](C(=O)O)C1]

135A. 1-Isobutyl-3-nitro-1H-1,2,4-triazole

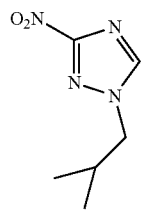

To a suspension of 3-nitro-1H-1,2,4-triazole (1 g, 8.77 mmol) in EtOH (20 mL) in a 40 mL scintillation vial was added NaH (0.88 g of a 60% dispersion in oil, 21.9 mmol). The suspension was stirred for 30 min, after which 1-bromo-2-methylpropane (2.86 mL, 26.3 mmol) was added. The reaction was heated at 70° C. overnight, then was cooled to RT and concentrated in vacuo. The residue was dissolved in EtOAc (100 mL) and washed with 1.0 M aq. $KH_2PO_4$, water and brine, dried ($Na_2SO_4$) and concentrated in vacuo. The crude yellow oily product was chromatographed (80 g $SiO_2$, continuous gradient from 0-50% EtOAc in hexanes) to give the title compound (240 mg, 1.41 mmol, 16% yield) as a clear oil. $^1$H NMR (500 MHz, $CDCl_3$) δ 8.13 (s, 1H), 4.10 (d, J=7.2 Hz, 2H), 2.41-2.28 (m, 1H), 1.01 (d, J=6.6 Hz, 6H). LCMS, $[M+H]^+$=171.2.

Example 135

A solution of Intermediate 12 (20 mg, 0.06 mmol) in THF (0.4 mL) was added dropwise to a mixture of 1-isobutyl-3-nitro-1H-1,2,4-triazole (15 mg, 0.09 mmol) and NaH (5 mg of a 60% oil dispersion, 0.12 mmol) in THF (0.4 mL) at RT. The reaction mixture was stirred at RT for 15 h, then was concentrated in vacuo. The residue was taken up in EtOAc (2 mL)/water (1 mL), and adjusted to pH~5 with 1N aq. HCl. The mixture was extracted with EtOAc (3×2 mL); the combined organic extracts were dried ($MgSO_4$) and concentrated in vacuo. The crude product was purified via preparative LC/MS: Column: XBridge C18, 200 mm×19 mm, 5-μm particles; Mobile Phase A: 5:95 $MeCN:H_2O$ with 0.1% TFA; Mobile Phase B: 95:5 $MeCN:H_2O$ with 0.1% TFA; Gradient: a 0-min hold at 9% B, 9-49% B over 20 min, then a 4-min hold at 100% B; Flow Rate: 20 mL/min; Column Temperature: 25 C. Fraction collection was triggered by MS signals. Fractions containing the desired product were combined to give the title compound (14 mg, 0.02 mmol, 35% yield) as a white solid. LCMS, $[M+H]^+$=469.9. $^1$H NMR (500 MHz, DMSO-$d_6$) δ 8.20 (s, 1H), 7.85 (br d, J=8.5 Hz, 1H), 7.47 (br d, J=8.5 Hz, 1H), 5.90 (s, 2H), 4.79-4.74 (m, 1H), 4.12 (s, 3H), 3.80 (br d, J=6.7 Hz, 2H), 2.67-2.57 (m, 1H), 2.33 (s, 3H), 2.06-1.41 (m, 9H), 0.81 (br d, J=6.7 Hz, 6H). $hLPA_1$ $IC_{50}$=32 nM.

Example 136. (1S,3S)-3-((6-(5-(((2-Isobutyl-2H-tetrazol-5-yl)oxy)methyl)-1-methyl-1H-1,2,3-triazol-4-yl)-2-methylpyridin-3-yl)oxy)cyclohexane-1-carboxylic acid

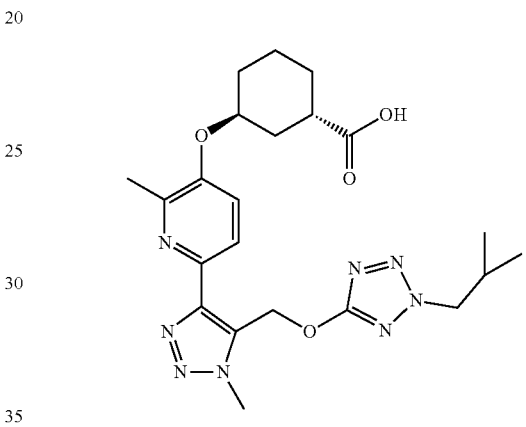

136A. 2-Isobutyl-5-(methylthio)-2H-tetrazole; 136B. 1-Isobutyl-5-(methylthio)-1H-tetrazole

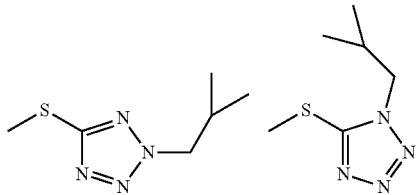

To a solution of 5-(methylthio)-1H-tetrazole (500 mg, 4.31 mmol) in DCM (30 mL) were added 2-methylpropan-1-ol (0.80 mL, 8.61 mmol), $Ph_3P$ (2.0 g, 7.75 mmol), $Et_3N$ (0.90 mL, 6.46 mmol), followed by DIAD (1.52 mL, 7.75 mmol). The reaction mixture was stirred at RT overnight, then was concentrated in vacuo. The residue was chromatographed (120 g $SiO_2$; continuous gradient from 0% to 20% EtOAc in hexanes over 25 min, then at 20% EtOAc/hexane for 10 min) to give Example 126A (502 mg, 2.91 mmol, 68% yield) as a colorless oil: LCMS, $[M+H]^+$=173.2. $^1$H NMR (500 MHz, $CDCl_3$) δ 4.40 (d, J=7.2 Hz, 2H), 2.70 (s, 3H), 2.45-2.32 (m, 1H), 0.99 (d, J=6.6 Hz, 6H) and Example 126B (400 mg, 2.32 mmol, 54% yield) as a colorless oil: LCMS, $[M+H]^+$=173.2. $^1$H NMR (500 MHz, $CDCl_3$) δ 4.04 (d, J=7.2 Hz, 2H), 2.84 (s, 3H), 2.38-2.22 (m, 1H), 0.99 (d, J=6.6 Hz, 6H).

136C. 2-Isobutyl-5-(methyl sulfonyl)-2H-tetrazole

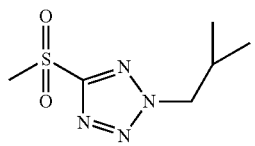

A mixture of 136A (150 mg, 0.87 mmol), Bu₄NBr (14 mg, 0.04 mmol), 10% aq. HOAc (5 mL) and CHCl₃ (5 mL) was stirred the solution became homogeneous, after which KMnO₄ (275 mg, 1.74 mmol) was added. The reaction mixture was stirred for 10 h at RT; the phases were separated and the organic layer was washed with water (5 mL) and brine (5 mL), dried (Na₂SO₄) and concentrated in vacuo to give the crude title compound (170 mg, 96% yield) as a dark brown color oil, which was used in the next step without further purification. $^1$H NMR (500 MHz, CDCl₃) δ 4.58 (d, J=7.2 Hz, 2H), 3.41 (s, 3H), 2.54-2.35 (m, 1H), 1.03 (d, J=6.9 Hz, 7H).

Example 136

A solution of Intermediate 12 (15 mg, 0.04 mmol), 136C (11 mg, 0.05 mmol) and NaOH (9 mg, 0.22 mmol) in MeCN (1 mL) was stirred at RT overnight, then was concentrated in vacuo. The residue was diluted with H₂O (5 mL), and the mixture was adjusted with 1N aq. HCl to pH ~5 and extracted with EtOAc (3×5 mL). The combined organic extracts were washed with brine (2 mL), dried (MgSO₄) and concentrated in vacuo. The crude product was purified by preparative LC/MS: Column: XBridge C18, 200 mm×19 mm, 5-µm particles; Mobile Phase A: 5:95 MeCN:H₂O with 0.1% TFA; Mobile Phase B: 95:5 MeCN:H₂O with 0.1% TFA; Gradient: a 0-min hold at 21% B, 21-61% B over 20 min, then a 4-min hold at 100% B; Flow Rate: 20 mL/min; Column Temperature: 25 C. Fraction collection was triggered by MS signals. Fractions containing the desired product were combined and dried via centrifugal evaporation to give the title compound (14 mg, 47% yield) were obtained as a colorless oil. LCMS, [M+H]⁺=470.9. $^1$H NMR (500 MHz, DMSO-d₆) δ 7.88 (d, J=8.6 Hz, 1H), 7.49 (d, J=8.7 Hz, 1H), 6.08 (s, 2H), 4.82-4.74 (m, 1H), 4.35 (d, J=7.1 Hz, 2H), 4.16 (s, 3H), 2.67-2.57 (m, 1H), 2.28 (s, 3H), 2.05-1.40 (m, 9H), 0.86 (d, J=6.6 Hz, 6H). hLPA₁ IC₅₀=20 nM.

The Examples in the following table were synthesized by the procedures described for the preparation of the Examples as indicated.

| Ex # | Structure & Name | Analytical & Biological Data | Method |
|---|---|---|---|
| 137 | (1S,3S)-3-((6-(5-(((5-isopropyl-1,2,4-thiadiazol-3-yl)amino)methyl)-1-methyl-1H-1,2,3-triazol-4-yl)pyridin-3-yl)oxy)cyclohexane-1-carboxylic acid | LCMS, [M + H]⁺ = 458.4; $^1$H NMR (500 MHz, DMSO-d₆) δ 8.38 (d, J = 2.1 Hz, 1H), 7.98 (d, J = 8.9 Hz. 1H), 7.59 (br t, J = 5.6 Hz, 1H), 7.54 (dd, J = 8.9, 2.4 Hz, 1H), 4.89 (br d, J = 5.8 Hz, 2H), 4.80-4.73 (m, 1H), 4.13 (s, 3H), 3.26-3.16 (m, 1H), 2.69-2.59 (m, 1H), 2.01-1.47 (m, 8H), 1.24 (d, J = 6.7 Hz, 6H); hLPA₁ IC₅₀ = 320 nM. | Example 2 |
| 138 | (1S,3S)-3-((2-methyl-6-(1-methyl-5-(((5-propyloxazol-2-yl)amino)methyl)-1H-1,2,3-triazol-4-yl)pyridin-3-yl)oxy)cyclohexane-1-carboxylic acid | LCMS, [M + H]⁺ = 455.1; $^1$H NMR (500 MHz, DMSO-d₆) δ 7.74 (br d, J = 8.2 Hz, 1H), 7.44 (br d, J = 8.5 Hz, 1H), 6.59 (br s, 1H), 4.80-4.63 (m, 3H), 3.99 (s. 3H), 2.55-2.47 (m, 1H), 2.35-2.26 (m, 5H), 1.99-1.28 (m, 10H), 0.74 (br t, J = 7.3 Hz, 3H); hLPA₁ IC₅₀ = 36 nM. | Example 1 |

-continued

| Ex # | Structure & Name | Analytical & Biological Data | Method |
|---|---|---|---|
| 139 | 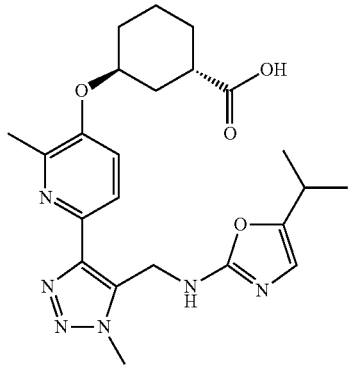<br>(1S,3S)-3-((6-(5-(((5-isopropyloxazol-2-yl)amino)methyl)-1-methyl-1H-1,2,3-triazol-4-yl)-2-methylpyridin-3-yl)oxy)cyclohexane-1-carboxylic acid | LCMS, [M + H]$^+$ = 455.2; $^1$H NMR (500 MHz, DMSO-d$_6$) δ 7.83 (br d, J = 8.5 Hz, 1H), 7.47 (br d, J = 8.5 Hz, 1H), 6.32 (s, 1H), 4.84-4.73 (m, 3H), 4.10 (s, 3H), 2.70-2.56 (m, 2H), 2.42 (s, 3H), 2.04-1.40 (m, 8H), 1.03 (br d, J = 6.7 Hz, 6H); hLPA$_1$ IC$_{50}$ = 38 nM. | Example 1 |
| 140 | 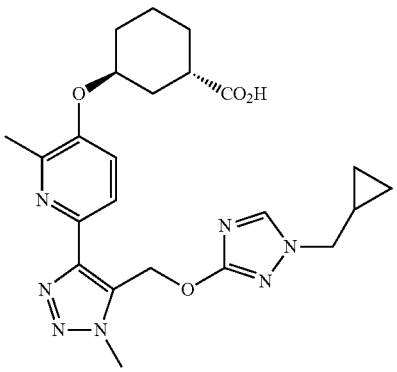<br>(1S,3S)-3-((6-(5-(((1-(cyclopropyl-methyl)-1H-1,2,4-triazol-3-yl)oxy)methyl)-1-methyl-1H-1,2,3-triazol-4-yl)-2-methylpyridin-3-yl)oxy)cyclohexane-1-carboxylic acid | LCMS, [M + H]$^+$ = 468.4; $^1$H NMR (500 MHz, DMSO-d$_6$) δ 8.18 (s, 1H), 7.82 (br d, J = 8.5 Hz, 1H), 7.45 (br d, J = 8.5 Hz, 1H), 5.87 (s, 2H), 4.78-4.72 (m, 1H), 4.11 (s, 3H), 3.84-3.72 (m, 2H), 2.65-2.56 (m, 1H), 2.32 (s, 3H), 2.04-1.38 (m, 8H), 1.20-1.09 (m, 1H), 0.52-0.45 (m, 2H), 0.32-0.25 (m, 2H); hLPA$_1$ IC$_{50}$ = 57 nM. | Example 135 |
| 141 | 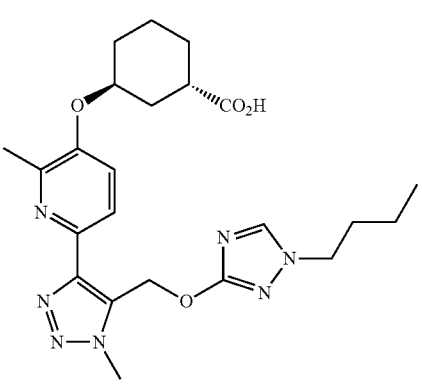<br>(1S,3S)-3-((6-(5-(((1-butyl-1H-1,2,4-triazol-3-yl)oxy)methyl)-1-methyl-1H-1,2,3-triazol-4-yl)-2-methyl-pyridin-3-yl)oxy)cyclohexane-1-carboxylic acid | LCMS, [M + H]$^+$ = 470.3; $^1$H NMR (500 MHz, DMSO-d$_6$) δ 8.22 (br s, 1H), 7.93-7.78 (m, 1H), 7.48 (br d, J = 7.6 Hz, 1H), 5.90 (br s, 2H), 4.81-4.73 (m, 1H), 4.12 (s, 3H), 3.99 (br t, J = 6.9 Hz, 2H), 2.66-2.56 (m, 1H), 2.33 (br s, 3H), 2.06-1.42 (m, 8H), 1.30-1.13 (m, 4H), 0.86 (br t, J = 7.2 Hz, 3H); hLPA$_1$ IC$_{50}$ = 71 nM. | Example 135 |

| Ex # | Structure & Name | Analytical & Biological Data | Method |
|---|---|---|---|
| 142 | 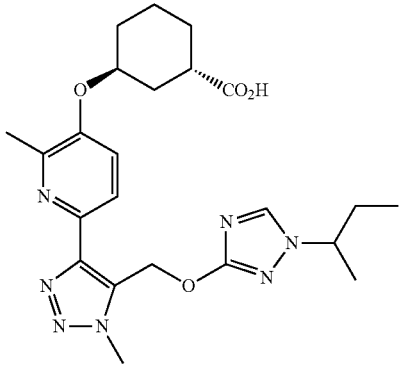<br>(1S,3S)-3-((6-(5-(((1-(sec-butyl)-1H-1,2,4-triazol-3-yl)oxy)methyl)-1-methyl-1H-1,2,3-triazol-4-yl)-2-methylpyridin-3-yl)oxy)cyclohexane-1-carboxylic acid (mixture of diastereomers at CH$_3$) | LCMS, [M + H]$^+$ = 470.5; $^1$H NMR (500 MHz, DMSO-d$_6$) δ 8.17 (s, 1H), 7.82 (br d, J = 8.2 Hz, 1H), 7.45 (br d, J = 8.5 Hz, 1H), 5.89 (s, 2H), 4.79-4.73 (m, 1H), 4.11 (s, 3H), 3.73 (m, 1H), 2.66-2.58 (m, 1H), 2.32 (s, 3H), 2.05-1.42 (m, 10H), 1.27 (br d, J = 6.4 Hz, 3H), 0.63 (br t, J = 7.2 Hz, 3H); hLPA$_1$ IC$_{50}$ = 509 nM. | Example 135 |
| 143 | 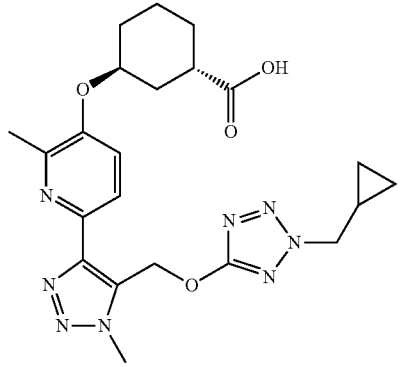<br>(1S,3S)-3-((6-(5-(((2-cyclopropyl methyl)-2H-tetrazol-5-yl)oxy)methyl)-1-methyl-1H-1,2,3-triazol-4-yl)-2-methylpyridin-3-yl)oxy) cyclohexane-1-carboxylic acid | LCMS, [M + H]$^+$ = 469.1; $^1$H NMR (500 MHz, DMSO-d$_6$) δ 7.87 (d, J = 8.5 Hz, 1H), 7.49 (d, J = 8.5 Hz, 1H), 6.07 (d, J = 1.2 Hz, 2H), 4.79-4.73 (m, 1H), 4.39 (d, J = 7.6 Hz, 2H), 4.16 (s, 3H), 2.60-2.55 (m, 1H), 2.27 (s, 3H), 1.99-1.46 (m, 8H), 1.35-1.24 (m, 1H), 0.60-0.53 (m, 2H), 0.44-0.38 (m, 2H); hLPA$_1$ IC$_{50}$ = 24 nM. | Example 136 |
| 144 | 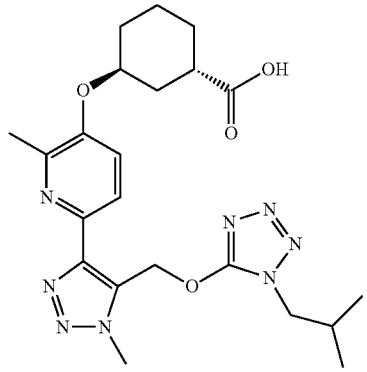<br>(1S,3S)-3-((6-(5-(((1-isobutyl-1H-tetrazol-5-yl)oxy)methyl)-1-methyl-1H-1,2,3-triazol-4-yl)-2-methyl-pyridin-3-yl)oxy)cyclohexane-1-carboxylic acid | LCMS, [M + H]$^+$ = 471.1; $^1$H NMR (500 MHz, DMSO-d$_6$) δ 7.84 (d. J = 8.5 Hz, 1H), 7.45 (d, J = 8.5 Hz, 1H), 6.11 (s, 2H), 4.76-4.70 (m, 1H), 4.15 (s, 3H), 3.81 (d, J = 7.0 Hz, 2H), 2.57-2.53 (m, 1H), 2.22 (s, 3H), 1.98-1.38 (m, 9H), 0.66 (dd, J = 6.7, 2.7 Hz, 6H); hLPA$_1$ IC$_{50}$ = 94 nM. | Example 136 |

| Ex # | Structure & Name | Analytical & Biological Data | Method |
|---|---|---|---|
| 145 | 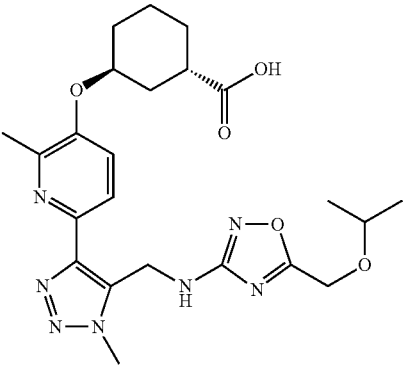<br>(1S,3S)-3-((6-(5-(((5-isopro-poxymethyl)-1,2,4-oxadiazol-3-yl)amino)methyl)-1-methyl-1H-1,2,3-triazol-4-yl)-2-methyl-pyridin-3-yl)oxy)cyclohexane-1-carboxylic acid, bis TFA salt | LCMS, [M + H]$^+$ = 486.2; $^1$H NMR (500 MHz, DMSO-$d_6$) δ 7.87 (d, J = 8.5 Hz, 1H), 7.53 (d, J = 8.8 Hz, 1H), 4.86-4.76 (m, 3H), 4.57 (s, 2H), 4.11 (s, 3H), 3.69 (quin, J = 6.1 Hz, 1H), 2.68-2.58 (m, 1H), 2.45 (s, 3H), 2.08-1.98 (m, 1H), 1.93-1.75 (m, 3H), 1.71-1.44 (m, 4H), 1.11 (d, J = 6.1 Hz, 6H). 29 of 31 protons found; hLPA$_1$ IC$_{50}$ = 31 nM. | Example 42 |
| 146 | 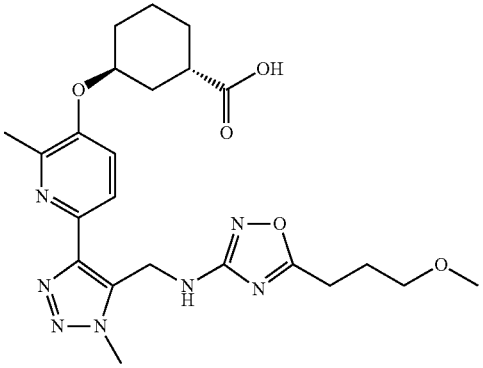<br>(1S,3S)-3-((6-(5-(((5-(3-methoxy-propyl)-1,2,4-oxadiazol-3-yl)amino)methyl)-1-methyl-1H-1,2,3-triazol-4-yl)-2-methyl-pyridin-3-yl)oxy) cyclohexane-1-carboxylic acid | LCMS, [M + H]$^+$ = 486.1; $^1$H NMR (500 MHz, DMSO-$d_6$) δ 7.86 (d, J = 8.5 Hz, 1H), 7.50 (d, J = 8.9 Hz, 1H), 7.25 (t, J = 5.8 Hz, 1H), 4.85-4.75 (m, 3H), 4.11 (s, 3H), 3.21 (s, 3H), 2.75 (t, J = 7.5 Hz, 2H), 2.69-2.60 (m, 1H), 2.44 (s, 3H), 2.07-1.97 (m, 1H), 1.93-1.73 (m, 5H), 1.71-1.44 (m, 4H). 28 of 31 protons found; hLPA$_1$ IC$_{50}$ = 103 nM. | Example 42 |
| 147 | 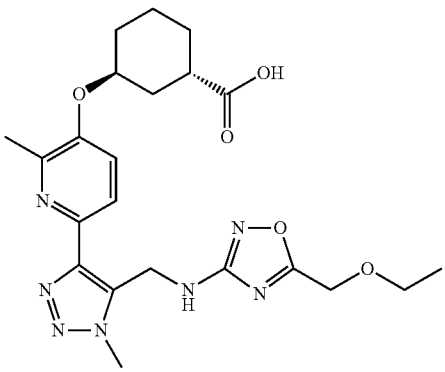<br>(1S,3S)-3-((6-(5-(((5-(ethoxy-methyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 472.2; $^1$H NMR (500 MHz, DMSO-$d_6$) δ 7.87 (d, J = 8.5 Hz, 1H), 7.53 (d, J = 8.8 Hz, 1H), 4.88-4.75 (m, 3H), 4.58 (s, 2H), 4.11 (s, 3H), 3.54 (q, J = 7.1 Hz, 2H), 2.68-2.60 (m, 1H), 2.45 (s, 3H), 2.07-1.99 (m, 1H), 1.91-1.75 (m, 3H), 1.70-1.45 (m, 4H), 1.13 (t, J = 7.0 Hz, 3H). 27 of 29 protons found; hLPA$_1$ IC$_{50}$ = 45 nM. | Example 42 |

| Ex # | Structure & Name | Analytical & Biological Data | Method |
|---|---|---|---|
| 148 | (1S,3S)-3-((6-(5-(((5-(1-fluoro-cyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]⁺ = 486.2; ¹H NMR (500 MHz, DMSO-d₆) δ 7.87 (d, J = 8.5 Hz, 1H), 7.68-7.44 (m, 2H), 4.87 (s, 2H), 4.83-4.64 (m, 1H), 4.12 (s, 3H), 2.69-2.55 (m, 5H), 2.44 (s, 3H), 2.08-1.44 (m, 10H); 27 of 28 protons found; hLPA₁ IC₅₀ = 19 nM. | Example 42 |
| 149 | (1S,3S)-3-((6-(5-(((1-(sec-butyl)-1H-1,2,4-triazol-3-yl)amino)methyl)-1-methyl-1H-1,2,3-triazol-4-yl)-2-methylpyridin-3-yl)oxy) cyclohexane-1-carboxylic acid, 2 TFA salt (diastereomeric mixture) | LCMS, [M + H]⁺ = 469.2; ¹H NMR (500 MHz, DMSO-d₆) δ 8.18 (s, 1H), 7.87 (br d, J = 8.5 Hz, 1H), 7.55 (br d, J = 8.9 Hz, 1H), 4.84-4.77 (m, 1H), 4.67 (s, 2H), 4.17 (s, 3H), 4.13-4.05 (m, 1H), 2.70-2.60 (m, 1H), 2.49 (s, 3H), 2.08-1.98 (m, 1H), 1.92-1.74 (m, 3H), 1.72-1.45 (m, 6H), 1.30 (br d, J = 6.7 Hz, 3H), 0.64 (br t, J = 7.2 Hz, 3H); 30 of 32 protons found; hLPA₁ IC₅₀ = 221 nM. | Example 42 |
| 150 | (1S,3S)-3-((6-(5-(((1-butyl-1H-1,2,4-triazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]⁺ = 469.2; ¹H NMR (500 MHz, DMSO-d₆) δ 7.99 (s, 1H), 7.85 (br d, J = 8.2 Hz, 1H), 7.50 (br d, J = 8.5 Hz, 1H), 4.80-4.75 (m, 1H), 4.66-4.60 (m, 2H), 4.16 (s, 3H), 3.91-3.85 (m, 2H), 2.69-2.58 (m, 1H), 2.47 (s, 3H), 2.10-1.95 (m, 1H), 1.93-1.72 (m, 3H), 1.69-1.44 (m, 4H), 1.30-1.20 (m, 2H), 1.20-1.04 (m, 2H), 0.83 (br t, J = 7.2 Hz, 3H). 30 of 32 protons found; hLPA₁ IC₅₀ = 68.2 nM. | Example 42 |

| Ex # | Structure & Name | Analytical & Biological Data | Method |
|---|---|---|---|
| 151 | (1S,3S)-3-((2-methyl-6-(1-methyl-5-(((5-(tetrahydrofuran-3-yl)-1,2,4-oxadiazol-3-yl)amino)methyl)-1H-1,2,3-triazol-4-yl)pyridin-3-yl)oxy)cyclohexane-1-carboxylic acid, 2 TFA salt (diastereomeric mixture) | LCMS, [M + H]$^+$ = 484.1; $^1$H NMR (500 MHz, DMSO-d$_6$) δ 7.87 (d, J = 8.5 Hz, 1H), 7.53 (d, J = 8.5 Hz, 1H), 4.80 (s, 3H), 4.11 (s, 3H), 4.00-3.93 (m, 1H), 3.84-3.71 (m, 3H), 3.66-3.58 (m, 1H), 2.69-2.60 (m, 1H), 2.45 (s, 3H), 2.33-2.22 (m, 1H), 2.13-1.98 (m, 2H), 1.92-1.75 (m, 3H), 1.70-1.46 (m, 4H). 27 of 29 protons found; hLPA$_1$ IC$_{50}$ = 114 nM. | Example 42 |
| 152 | (1S,3S)-3-((6-(5-(((1-(cyclopropylmethyl)-1H-1,2,4-triazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 467.2; $^1$H NMR (500 MHz, DMSO-d$_6$) δ 8.28 (s, 1H), 7.91 (d, J = 8.5 Hz, 1H), 7.62 (d, J = 8.5 Hz, 1H), 4.86-4.81 (m, 1H), 4.68 (s, 2H), 4.19 (s, 3H), 3.80 (d, J = 7.2 Hz, 2H), 2.71-2.59 (m, 1H), 2.09-1.99 (m, 1H), 1.93-1.76 (m, 3H), 1.72-1.46 (m, 4H), 1.23-1.12 (m, 1H), 0.55-0.48 (m, 2H), 0.35-0.28 (m, 2H). 25 of 30 protons found; hLPA$_1$ IC$_{50}$ = 179 nM. | Example 42 |
| 153 | (1S,3S)-3-((6-(5-(((5-(3,3-difluoro cyclobutyl)-1,2,4-oxadiazol-3-yl)amino) methyl)-1-methyl-1H-1,2,3-triazol-4-yl)-2-methylpyridin-3-yl)oxy) cyclohexane-1-carboxylic acid, 2 TFA salt | LCMS, [M + H]$^+$ = 504.5; $^1$H NMR (500 MHz, DMSO-d$_6$) δ 7.86 (br d, J = 8.5 Hz, 1H), 7.50 (br d, J = 8.5 Hz, 1H), 4.87-4.73 (m, 3H), 4.11 (s, 3H), 3.65-3.52 (m, 1H), 3.14-3.01 (m, 2H), 2.96-2.79 (m, 2H), 2.69-2.59 (m, 1H), 2.44 (s, 3H), 2.07-1.97 (m, 1H), 1.91-1.75 (m, 3H), 1.68-1.45 (m, 4H). 25 of 27 protons found; hLPA$_1$ IC$_{50}$ = 46.1 nM. | Example 42 |

| Ex # | Structure & Name | Analytical & Biological Data | Method |
|---|---|---|---|
| 154 | 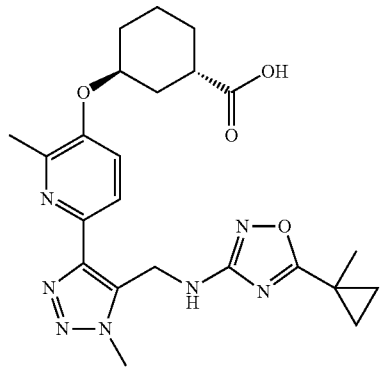<br>(1S,3S)-3-((2-methyl-6-(1-methyl-5-(((5-(1-methyl-cyclopropyl)-1,2,4-oxadiazol-3-yl)amino)methyl)-1H-1,2,3-triazol-4-yl)pyridin-3-yl)oxy) cyclohexane-1-carboxylic acid, 2 TFA salt | LCMS, [M + H]$^+$ = 468; $^1$H NMR (500 MHz, DMSO-d$_6$) δ 7.84 (br d, J = 8.5 Hz, 1H), 7.49 (br d, J = 8.5 Hz, 1H), 4.82-4.69 (m, 3H), 4.09 (s, 3H), 2.69-2.58 (m, 1H), 2.43 (s, 3H), 2.07-1.97 (m, 1H), 1.91-1.73 (m, 3H), 1.68-1.44 (m, 4H), 1.38 (s, 3H), 1.20-1.12 (m, 2H), 1.01-0.92 (m, 2H). 27 of 29 protons found; hLPA$_1$ IC$_{50}$ = 441 nM. | Example 42 |
| 155 | 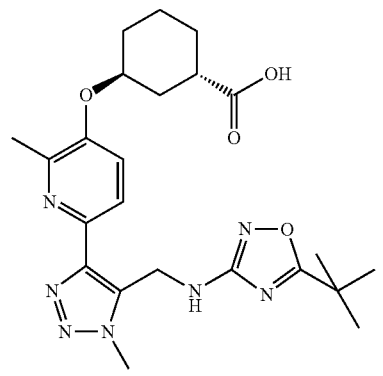<br>(1S,3S)-3-((6-(5-(((5-(tert-butyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 470.3; $^1$H NMR (500 MHz, DMSO-d$_6$) δ 7.85 (br d, J = 8.5 Hz, 1H), 7.52 (br d, J = 8.5 Hz, 1H), 4.84-4.70 (m, 3H), 4.11 (s, 3H), 2.68-2.59 (m, 1H), 2.44 (s, 3H), 2.06-1.98 (m, 1H), 1.91-1.72 (m, 3H), 1.69-1.43 (m, 4H), 1.27 (s, 9H). 29 of 31 protons found; hLPA$_1$ IC$_{50}$ = 85 nM. | Example 42 |
| 156 | 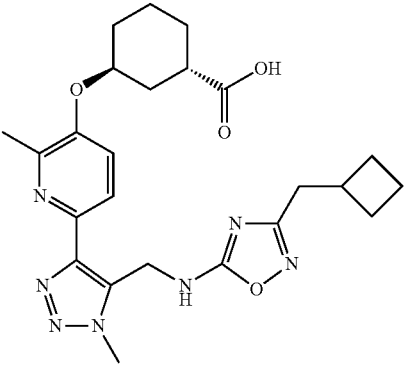<br>(1S,3S)-3-((6-(5-(((3-(cyclobutyl methyl)-1,2,4-oxadiazol-5-yl)amino)methyl)-1-methyl-1H-1,2,3-triazol-4-yl)-2-methyl-pyridin-3-yl)oxy) cyclohexane-1-carboxylic acid, bis TFA salt | LCMS, [M − H]$^-$ = 480.3; $^1$H NMR (500 MHz, DMSO-d$_6$) δ 8.61-8.47 (m, 1H), 7.84 (br d, J = 8.2 Hz, 1H), 7.48 (br d, J = 8.9 Hz, 1H), 4.99 (br d, J = 4.6 Hz, 2H), 4.77 (br s, 1H), 4.09 (s, 3H), 2.67-2.58 (m, 1H), 2.39 (s, 3H), 2.06-1.92 (m, 4H), 1.90-1.72 (m, 5H), 1.71-1.44 (m, 6H). 28 of 31 protons found; hLPA$_1$ IC$_{50}$ = 29 nM. | Example 43 |

| Ex # | Structure & Name | Analytical & Biological Data | Method |
|---|---|---|---|
| 157 | (1S,3S)-3-((6-(5-(((3-isobutyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 470.3; $^1$H NMR (500 MHz, DMSO-d$_6$) δ 8.56 (t, J = 5.2 Hz, 1H), 7.86 (d, J = 8.5 Hz, 1H), 7.51 (d, J = 8.8 Hz, 1H), 5.08-4.98 (m, 2H), 4.82-4.76 (m, 1H), 4.11 (s, 3H), 2.68-2.60 (m, 1H), 2.42 (s, 3H), 2.32 (d, J = 7.2 Hz, 2H), 2.07-1.91 (m, 2H), 1.91-1.75 (m, 3H), 1.70-1.45 (m, 4H), 0.90 (d, J = 6.6 Hz, 6H). 30 of 31 protons found; hLPA$_1$ IC$_{50}$ = 53 nM. | Example 43 |
| 158 | (1S,3S)-3-((6-(5-(((3-isopentyl-1,2,4-oxadiazol-5-yl)amino)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 484.3; $^1$H NMR (500 MHz, CDCl$_3$) δ 8.00 (d, J = 8.8 Hz, 1H), 7.59 (d, J = 8.8 Hz, 1H), 4.87 (s, 2H), 4.84-4.76 (m, 1H), 4.24 (s, 3H), 2.95-2.86 (m, 1H), 2.68 (s, 3H), 2.60-2.53 (m, 2H), 2.12-2.06 (m, 2H), 2.02-1.89 (m, 2H), 1.87-1.75 (m, 3H), 1.74-1.50 (m, 4H), 0.92 (d, J = 6.6 Hz, 6H). 31 of 33 protons found; hLPA$_1$ IC$_{50}$ = 21 nM. | Example 43 |

Example 159. (1S,3S)-3-((2-Methyl-6-(1-methyl-5-(((5-((E)-prop-1-en-1-yl)-1,2,4-oxadiazol-3-yl)amino)methyl)-1H-1,2,3-triazol-4-yl)pyridin-3-yl)oxy)cyclohexane-1-carboxylic acid, bis TFA salt To a solution of Example 162 (43 mg, 0.089 mmol; prepared from 5-(2-fluoropropyl)-1,2,4-oxadiazol-3-amine according to the procedure described for the synthesis of Example 42) in THF (2 mL)/water (1 mL) was added 2M aq. LiOH (0.23 mL, 0.46 mmol). The reaction mixture was stirred at RT for 18 h; the pH was adjusted with 1N aq. HCl to ~4. The mixture was extracted with EtOAc (3×5 mL). The combined organic layers were washed with brine (2 mL), dried (MgSO$_4$) and concentrated in vacuo. The crude product was purified by preparative HPLC (Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min) to give the title compound (5.5 mg, 8.8%). LCMS, [M+H]$^+$=454.3. $^1$H NMR (500 MHz, CD$_3$OD) δ 8.05 (d, J=8.8 Hz, 1H), 7.95 (d, J=8.8 Hz, 1H), 7.07-6.99 (m, 1H), 6.32 (dd, J=15.8, 1.8 Hz, 1H), 4.97 (br s, 1H), 4.74 (s, 2H), 4.25 (s, 3H), 2.87-2.79 (m, 1H), 2.72 (s, 3H), 2.18-2.10 (m, 1H), 2.07-1.93 (m, 6H), 1.86-1.65 (m, 4H).

245

Example 160. (3 S)-3-((6-(5-(((5-Isopentyl-1,2,4-oxadiazol-3-yl)amino)methyl)-1-methyl-1H-1,2,3-triazol-4-yl)-2-methylpyridin-3-yl)oxy)-1-methylcyclohexane-1-carboxylic acid, bis TFA salt (diastereomeric mixture)

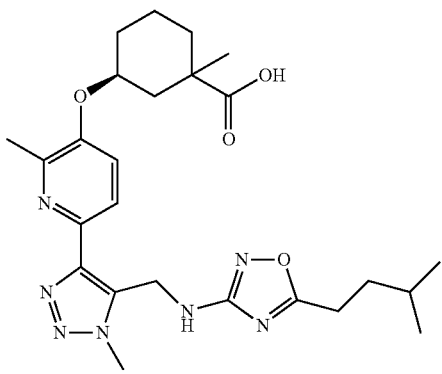 [SMILES: Cc1nc(-c2nnn(C)c2CNc2noc(CCC(C)C)n2)ccc1O[C@H]1CCCC(C)(C(=O)O)C1]

To a 0° C. solution of Example 69 (32 mg, 0.044 mmol) in THF (2 mL) was added iodomethane (5.5 μL, 0.088 mmol) and NaHMDS (1M in THF, 0.13 mL, 0.132 mmol). The reaction was stirred at 0° C. for 2 h, then was quenched with satd aq. NH₄Cl and extracted with EtOAc. The organic layer was washed with brine, dried (Na₂SO₄) and concentrated in vacuo. The residue was dissolved in THF (2 mL)/water (1 mL), and 2M aq. LiOH (0.098 mL, 0.195 mmol) was added. The reaction was stirred at RT for 18 h, after which MeOH (1 mL) and 2M aq. LiOH (98 μL, 0.195 mmol) were added. The reaction was stirred at 50° C. for 5 h, then was cooled to RT. The pH was adjusted with 1N aq. HCl to pH 4; the mixture was extracted with EtOAc (3×5 mL). The combined organic layers were washed with brine (2 mL), dried (MgSO₄) and concentrated in vacuo. The crude product was purified by preparative HPLC (Column: Sunfire Prep C18 OBD 5u 30×100 mm; Mobile Phase A: 10% MeCN-90% H₂O-0.1% TFA; Mobile Phase B: 90% MeCN-10% H₂O-0.1% TFA; Gradient: 20-100% B over 12 min; Flow: 40 mL/min) to give the title compound (9 mg, 32%). LCMS, [M+H]⁺=498.3. ¹H NMR (500 MHz, CD₃OD) δ 8.13-8.05 (m, 2H), 4.74-4.63 (m, 3H), 4.25 (s, 3H), 2.81-2.72 (m, 2H), 2.69 (s, 3H), 2.67-2.55 (m, 1H), 2.27-2.16 (m, 2H), 1.92-1.83 (m, 1H), 1.66-1.47 (m, 5H), 1.35-1.24 (m, 5H), 0.94 (d, J=6.3 Hz, 6H).

246

Example 161. (1 S,3S)-3-((6-(5-(((5-Isopentyl-1,2,4-oxadiazol-3-yl)(methyl)amino)methyl)-1-methyl-1H-1,2,3-triazol-4-yl)-2-methylpyridin-3-yl)oxy)cyclohexane-1-carboxylic acid, 2 TFA salt

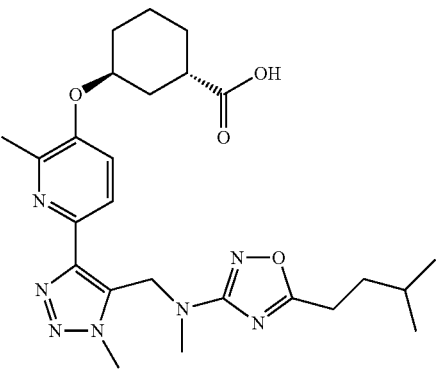 [SMILES: Cc1nc(-c2nnn(C)c2CN(C)c2noc(CCC(C)C)n2)ccc1O[C@H]1CCC[C@H](C(=O)O)C1]

161A. Methyl (1 S,3S)-3-((2-methyl-6-(1-methyl-5-((methylamino)methyl)-1H-1,2,3-triazol-4-yl)pyridin-3-yl)oxy)cyclohexane-1-carboxylate

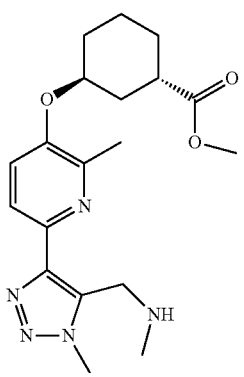 [SMILES: CNCc1c(-c2ccc(O[C@H]3CCC[C@H](C(=O)OC)C3)c(C)n2)nnn1C]

To a solution of Intermediate 8 (325 mg, 0.91 mmol) in MeOH (3.6 mL) was added MeNH₂·HCl (92 mg, 1.36 mmol). The reaction was stirred for 20 min at RT, after which NaBH₃CN (85 mg, 1.36 mmol) was added. The reaction mixture was stirred at RT for 2 h, then was partitioned between EtOAc and 1.0 M aq. K₂HPO₄. The aqueous layer was extracted with EtOAc (2×). The combined organic layers were washed with brine, dried (Na₂SO₄) and concentrated in vacuo. The viscous yellow oily product was chromatographed (SiO₂; continuous gradient from 0-10% MeOH/DCM) to give the title compound (180 mg, 53%) as a clear, colorless oil. LCMS, [M+H]⁺=374.2. ¹H NMR (500 MHz, CD₃OD) δ 7.89 (d, J=8.8 Hz, 1H), 7.47 (d, J=8.5 Hz, 1H), 4.84-4.79 (m, 1H), 4.16 (s, 3H), 4.09 (s, 2H), 3.70 (s, 3H), 2.89-2.82 (m, 1H), 2.53 (s, 3H), 2.46 (s, 3H), 2.19-2.09 (m, 1H), 2.01-1.90 (m, 3H), 1.82-1.61 (m, 4H).

Example 161

A solution of Example 161A (20 mg, 0.054 mmol), 3-chloro-5-isopentyl-1,2,4-oxadiazole (18.70 mg, 0.107 mmol) and iPr₂NEt (0.028 mL, 0.161 mmol) in EtOH (1 mL) was heated at 100° C. for 30 min in a microwave reactor, then was cooled to RT. Additional 3-chloro-5-isopentyl-1,2,4-oxadiazole (18.7 mg, 0.107 mmol) was added and the reaction was heated at 100° C. for another 2 h in a microwave reactor, then was cooled to RT and concentrated in vacuo. The residue was dissolved in THF (2 mL)/water (1 mL) and 2M aq. LiOH (0.135 mL, 0.270 mmol) was added. The reaction was stirred at RT for 18 h, then at 50° C. for 1 h, then was cooled to RT. The pH was adjusted with 1N aq. HCl to ~4; the mixture was extracted with EtOAc (3×5 mL). The combined organic layers were washed with brine, dried (MgSO₄) and concentrated in vacuo. The crude product was purified by preparative HPLC: Column: Sunfire Prep C18 OBD 5u 30×100 mm; Mobile Phase A: 10% MeCN-90% H₂O-0.1% TFA; Mobile Phase B: 90% MeCN-10% H₂O-0.1% TFA; Gradient: 20-100% B over 12 min; Flow: 40 mL/min. Fractions containing the desired product were combined and dried via centrifugal evaporation to give the title compound (7.5 mg, 18%). LCMS, [M+H]⁺=498.4. ¹H NMR (500 MHz, CD₃OD) δ 8.04-7.97 (m, 2H), 5.05-4.96 (m, 3H), 4.19 (s, 3H), 2.98 (s, 3H), 2.87-2.77 (m, 3H), 2.70 (s, 3H), 2.19-2.10 (m, 1H), 2.08-1.92 (m, 3H), 1.88-1.57 (m, 7H), 0.96 (d, J=6.3 Hz, 6H).

Example 162. (1S,3S)-3-((6-(5-(((5-(2-Fluoropropyl)-1,2,4-oxadiazol-3-yl)amino) methyl)-1-methyl-1H-1,2,3-triazol-4-yl)-2-methylpyridin-3-yl)oxy) cyclohexane-1-carboxylic acid, 2 TFA salt (diastereomeric mixture)

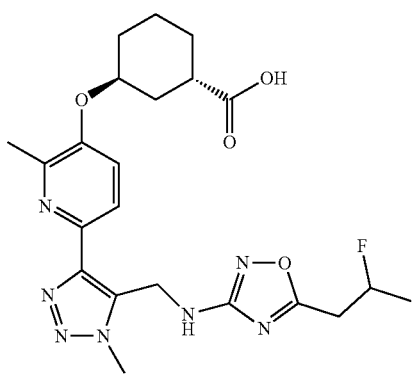 [SMILES: Cc1nc(-c2nnn(C)c2CNc2noc(CC(C)F)n2)ccc1O[C@H]1CCC[C@H](C(=O)O)C1]

162A. tert-Butyl (1 S,3 S)-3-((6-(5-(hydroxymethyl)-1-methyl-1H-1,2,3-triazol-4-yl)-2-methylpyridin-3-yl)oxy)cyclohexane-1-carboxylate

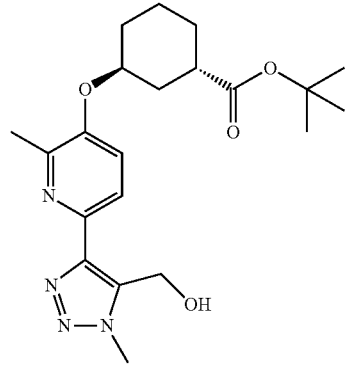 [SMILES: Cc1nc(-c2nnn(C)c2CO)ccc1O[C@H]1CCC[C@H](C(=O)OC(C)(C)C)C1]

A mixture of Intermediate 12 (250 mg, 0.72 mmol) and tert-butyl (Z)—N,N'-diisopropyl carbamimidate (434 mg, 2.17 mmol) in t-BuOH/THF (5 mL each) was stirred at RT for 18 h. The reaction mixture was filtered and the filtrate was concentrated in vacuo. The crude product was chromatographed (24 g SiO₂; continuous gradient from 0-100% EtOAc in hexane) to give the title compound (210 mg, 72%) as a white solid. LCMS, [M+H]⁺=403.1.

162B. tert-Butyl (1 S,3S)-3-((6-(5-formyl-1-methyl-1H-1,2,3-triazol-4-yl)-2-methylpyridin-3-yl)oxy) cyclohexane-1-carboxylate

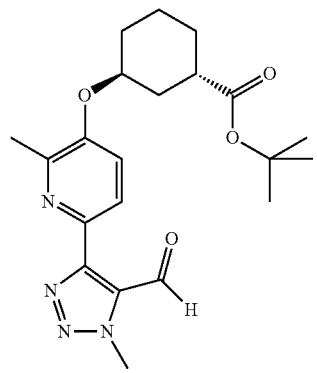 [SMILES: Cc1nc(-c2nnn(C)c2C=O)ccc1O[C@H]1CCC[C@H](C(=O)OC(C)(C)C)C1]

To the solution of 162A (0.21 g, 0.522 mmol) in DCM (2.6 mL) was added NaHCO₃ (219 mg, 2.61 mmol) and Dess-Martin periodinane (0.266 g, 0.63 mmol). The reaction was stirred at RT for 1 h, then was filtered through Celite®; the filter cake was washed with EtOAc. The combined filtrates were washed with satd aq. NaHCO₃, water and brine, dried (Na₂SO₄) and concentrated in vacuo. The crude product was chromatographed (12 g SiO₂; continuous gradient from 0-100% EtOAc in hexanes) to give the title compound (180 mg, 86%) as a white solid. LCMS, [M+H]⁺=401.1.

162C. tert-Butyl (1S,3S)-3-((6-(5-(((5-(2-fluoropropyl)-1,2,4-oxadiazol-3-yl)amino) methyl)-1-methyl-1H-1,2,3-triazol-4-yl)-2-methylpyridin-3-yl)oxy)cyclohexane-1-carboxylate (diastereomeric mixture)

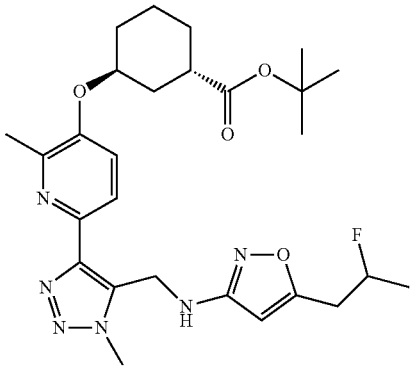 [SMILES: Cc1nc(-c2nnn(C)c2CNc2cc(CC(C)F)on2)ccc1O[C@H]1CCC[C@H](C(=O)OC(C)(C)C)C1]

A sealed tube containing a solution of 162B (30 mg, 0.075 mmol), 5-(2-fluoro-propyl)-1,2,4-oxadiazol-3-amine (11 mg, 0.075 mmol, prepared from 5-allyl-1,2,4-oxadiazol-3-amine according to the procedure described for the synthesis of 5-(3-fluoro-butyl)-1,2,4-oxadiazol-3-amine) and HOAc (21 μL, 0.38 mmol) in MeOH (1.5 mL) was stirred at 65° C. for 2 h. The reaction was cooled to RT; NaBH$_3$CN (9.4 mg, 0.15 mmol) was added. The reaction was stirred at RT for 2 h, then satd aq. NaHCO$_3$ was added. The mixture was extracted with EtOAc. The organic layer was dried (Na$_2$SO$_4$) and concentrated in vacuo. The crude product was used in the next step without further purification.

Example 162

A solution of 162C in DCM (1 mL) and TFA (0.40 mL, 5.2 mmol) was stirred at RT for 18 h, then was concentrated in vacuo. The crude material was purified by preparative LC/MS (Column: XBridge C18, 200 mm×19 mm, 5-μm particles; Mobile Phase A: 5:95 MeCN:H$_2$O with 0.1% TFA; Mobile Phase B: 95:5 MeCN:H$_2$O with 0.1% TFA; Gradient: a 0-min hold at 15% B, 15-55% B over 20 min, then a 4-min hold at 100% B; Flow Rate: 20 mL/min; Column Temperature: 25° C.) to give the title compound (2 mg, 4%). LCMS, [M+H]$^+$=474.2. $^1$H NMR (500 MHz, DMSO-d$_6$) δ 7.85 (br d, J=8.2 Hz, 1H), 7.49 (br d, J=8.5 Hz, 1H), 5.14-4.95 (m, 1H), 4.81-4.75 (m, 3H), 4.10 (s, 3H), 3.19-3.04 (m, 2H), 2.66-2.59 (m, 1H), 2.42 (s, 3H), 2.05-1.96 (m, 1H), 1.91-1.74 (m, 3H), 1.68-1.44 (m, 4H), 1.41-1.31 (m, 3H).

Example 163. (1 S,3 S)-3-((6-(5-(((5-(3-(Fluoromethyl)cyclobutyl)-1,2,4-oxadiazol-3-yl)amino) methyl)-1-methyl-1H-1,2,3-triazol-4-yl)-2-methylpyridin-3-yl)oxy) cyclohexane-1-carboxylic acid, 2 TFA salt (diastereomer A)

Example 164. (1 S,3 S)-3-((6-(5-(((5-(3-(Fluoromethyl)cyclobutyl)-1,2,4-oxadiazol-3-yl)amino) methyl)-1-methyl-1H-1,2,3-triazol-4-yl)-2-methylpyridin-3-yl)oxy) cyclohexane-1-carboxylic acid, 2 TFA salt (diastereomer B)

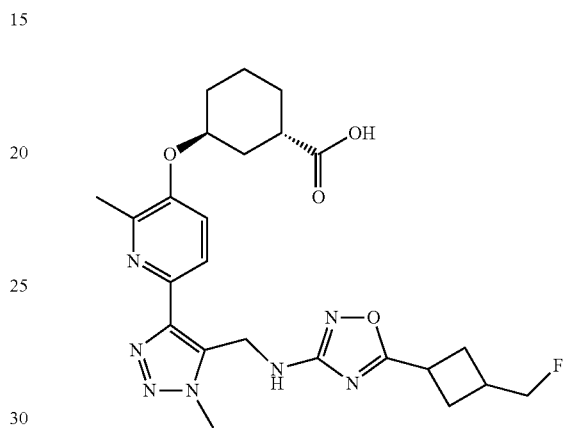

163A. 5-(3-((4,4,5,5-Tetramethyl-1,3,2-dioxaborolan-2-yl)methyl)cyclobutyl)-1,2,4-oxadiazol-3-amine

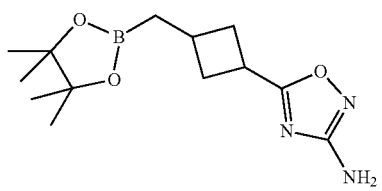 [SMILES: CC1(C)OB(CC2CC(c3nc(N)no3)C2)OC1(C)C]

A flask containing chloro(1,5-cyclooctadiene)iridium(I) dimer (15 mg, 0.022 mmol) and 1,3-bis(diphenylphosphino)propane (18 mg, 0.044 mmol) was flushed with Ar. DCM (5 mL), pinacol borane (1.0 mL, 7.34 mmol), and 5-(3-methylenecyclobutyl)-1,2,4-oxadiazol-3-amine (222 mg, 1.47 mmol) were added. The reaction mixture was stirred at RT for 3 days, then was quenched with water; the mixture was stirred for 30 min at RT until gas evolution ceased. The aqueous layer was extracted with DCM (2×). The combined organic layers were washed with brine, dried (Na$_2$SO$_4$) and concentrated in vacuo. The crude product was chromatographed (12 g SiO$_2$, continuous gradient from 0-100% EtOAc in hexanes) to give the title compound (80 mg, 20%) as a brown solid. LCMS, [M+H]$^+$=280.0.

163B. Methyl (1 S,3 S)-3-((2-methyl-6-(1-methyl-5-(((5-(3-((4,4,5,5-tetramethyl-1,3,2-dioxaboro-1an-2-yl)methyl)cyclobutyl)-1,2,4-oxadiazol-3-yl)amino)methyl)-1H-1,2,3-triazol-4-yl)pyridin-3-yl)oxy)cyclohexane-1-carboxylate (diastereomeric mixture)

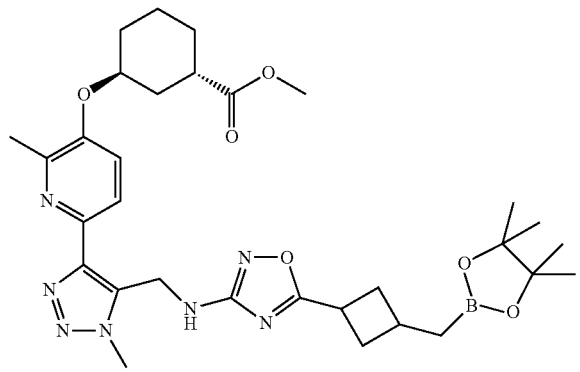

163B (40 mg, 51%) was prepared from 163A according to the procedure described for the synthesis of Example 42. LCMS, [M+H]$^+$=622.3.

163C. Methyl (1 S,3 S)-3-((6-(5-(((5-(3-(hydroxymethyl)cyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylate (diastereomeric mixture)

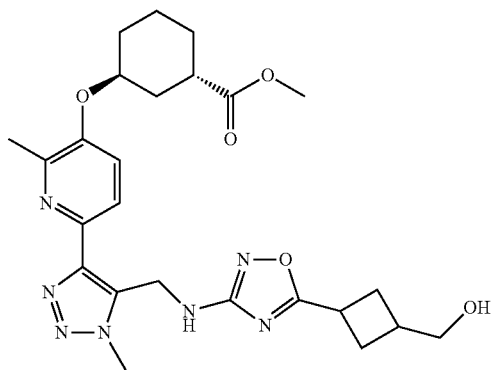 [SMILES: COC(=O)[C@H]1CCC[C@H](Oc2ccc(-c3nnn(C)c3CNc3noc(C4CC(CO)C4)n3)nc2C)C1]

To a 0° C. solution of 163B (40 mg, 0.064 mmol) in THF (1 mL) was added a solution of sodium perborate tetrahydrate (39.6 mg, 0.257 mmol) in water (1 mL). The reaction was allowed to warm to RT and stirred at RT for 18 h, then was quenched with water. The aqueous layer was extracted with EtOAc (2×). The combined organic layers were washed with brine, dried (MgSO$_4$) and concentrated in vacuo to give the title compound (29 mg, 88%) as a colorless solid. LCMS, [M+H]$^+$=512.5. This material was used in the next step without further purification.

163D. Methyl (1 S,3 S)-3-((6-(5-(((5-(3-(fluoromethyl)cyclobutyl)-1,2,4-oxadiazol-3-yl)amino)methyl)-1-methyl-1H-1,2,3-triazol-4-yl)-2-methylpyridin-3-yl)oxy) cyclohexane-1-carboxylate, 2 TFA salt (diastereomeric mixture)

To a 0° C. solution of 163C (29 mg, 0.057 mmol), DMAP (0.69 mg, 5.67 µmol) and TEA (17 µL, 0.125 mmol) in DCM (0.57 mL) was added p-tolenesulfonyl chloride (13 mg, 0.068 mmol). The reaction solution was allowed to warm to RT and stirred at RT for 18 h, then was concentrated in vacuo. The residue was dissolved in Bu$_4$NF (1.0 M in THF, 0.57 mL, 0.57 mmol). The reaction was stirred at RT for 3 days, then was partitioned between water and EtOAc. The organic layer was washed with brine, dried (Na$_2$SO$_4$) and concentrated in vacuo. The crude product was purified by preparative HPLC (Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min.) to give the title compound (18 mg, 43%) as a colorless solid. LCMS, [M+H]$^+$=514.2.

Examples 163 and 164

Examples 163 and 164 were prepared from intermediate 163D according to the procedure described for the synthesis of Example 41. The diastereomeric mixture (12 mg) was separated by preparative chromatography: Column: chiral AD 25×3 cm ID, 5 µm; Flow rate: 85.0 mL/min; Mobile Phase: 65/35 CO$_2$/MeOH w 0.1% DEA; Detector Wavelength: 256 nm; Injection: 1000 uL injection of 12 mg sample in 12 mL to give two diastereomers.

Example 163. First eluting isomer (diastereomer A): (3.1 mg, 18%). LCMS, [M+H]$^+$=500.3. $^1$H NMR (500 MHz, DMSO-d$_6$) δ 7.86 (d, J=8.6 Hz, 1H), 7.48 (d, J=8.6 Hz, 1H), 7.15 (br t, J=5.8 Hz, 1H), 4.84-4.72 (m, 3H), 4.42-4.28 (m, 2H), 4.11 (s, 3H), 3.66-3.46 (m, 1H), 2.77-2.63 (m, 2H), 2.48-2.32 (m, 5H), 2.15-1.98 (m, 3H), 1.93-1.77 (m, 3H), 1.70-1.48 (m, 4H).

Example 164. Second eluting isomer (diastereomer B): (2.3 mg, 13%). LCMS, [M+H]$^+$=500.2. $^1$H NMR (500 MHz, DMSO-d$_6$) δ 7.87 (d, J=8.6 Hz, 1H), 7.49 (d, J=8.6 Hz, 1H), 7.18 (br t, J=5.7 Hz, 1H), 4.84-4.75 (m, 3H), 4.56-4.43 (m, 2H), 4.12 (s, 3H), 3.69-3.59 (m, 1H), 2.78-2.63 (m, 2H), 2.46 (s, 3H), 2.42-2.22 (m, 4H), 2.07-1.99 (m, 1H), 1.94-1.76 (m, 3H), 1.73-1.49 (m, 4H).

Example 207. (1S,3S)-3-((2-Methyl-6-(1-methyl-5-((5-phenyl-1H-1,2,4-triazol-1-yl) methyl)-1H-1,2,3-triazol-4-yl)pyridin-3-yl)oxy)cyclohexane-1-carboxylic acid, 2 TFA salt

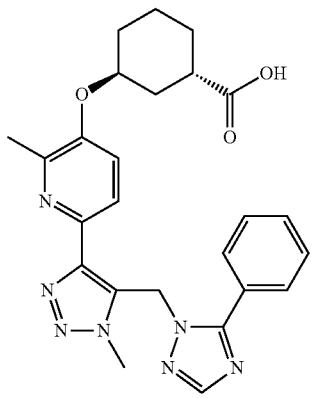 [SMILES: Cc1nc(-c2nnn(C)c2Cn2ncnc2-c2ccccc2)ccc1O[C@H]1CCC[C@H](C(=O)O)C1]

Example 208. (1S,3S)-3-((2-Methyl-6-(1-methyl-5-((3-phenyl-1H-1,2,4-triazol-1-yl) methyl)-1H-1,2,3-triazol-4-yl)pyridin-3-yl)oxy)cyclohexane-1-carboxylic acid, 2 TFA salt

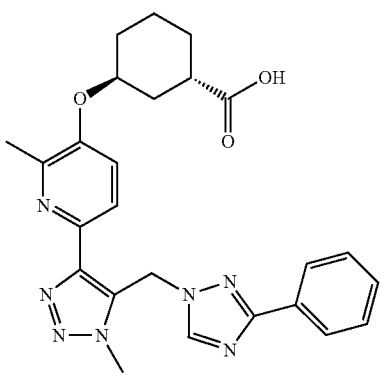 [SMILES: Cc1nc(-c2nnn(C)c2Cn2cnc(-c3ccccc3)n2)ccc1O[C@H]1CCC[C@H](C(=O)O)C1]

207A and 208A

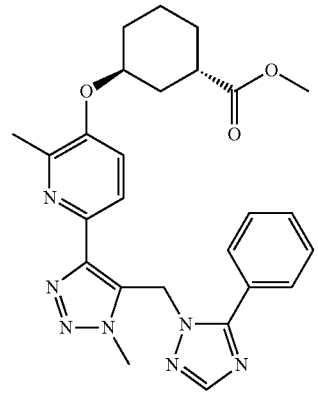

207A

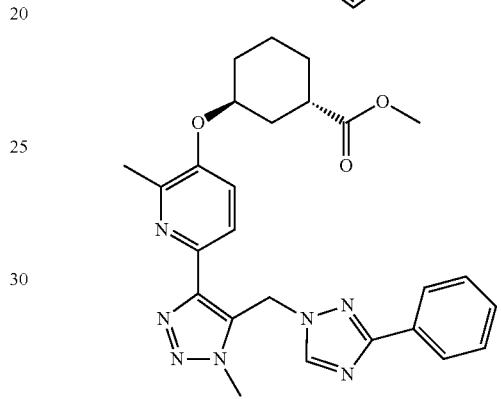

208A

To a solution of 3-phenyl-1H-1,2,4-triazole (27 mg, 0.18 mmol) in THF (1.40 mL) was added 1.0 M NaHMDS in THF (142 µL; 0.14 mmol). The reaction was stirred at RT for 1 h, after which Intermediate 5 (60 mg, 0.14 mmol) was added. The reaction was stirred at RT for 1 h (became a suspension), then was quenched with satd aq. NH$_4$Cl. The mixture was partitioned between EtOAc and water; the aqueous layer was extracted with EtOAc. The combined organic layers dried (Na$_2$SO$_4$) and concentrated in vacuo. The clear colorless residue was purified by reverse phase chromatography (Sunfire, 5µ C18 OBD 30×100 mm column; detection at 220 nm; flow rate=40 mL/min; continuous gradient from 30% B to 100% B over 10 min+5 min hold time at 100% B, where A=90:10:0.1 H$_2$O:MeOH:TFA and B=90:10:0.1 MeOH:H$_2$O:TFA). The first eluting regioisomer was 207A, 2 TFA (11.4 mg, 11%, clear, colorless residue). The second eluting regioisomer was 208A, 2 TFA (43 mg, 43%, clear, colorless residue).

Example 207

A solution of 207A (11.4 mg, 0.016 mmol) in THF (0.10 mL) and 1.0 M aq. LiOH (80 µL, 0.080 mmol) was stirred at RT for 16 h, then was concentrated in vacuo. The residue was dissolved in 1:1 MeCN/water and acidified with TFA. Purification by reverse phase chromatography (Sunfire, 5µ C18 OBD 30×100 mm column; detection at 220 nm; flow rate=40 mL/min; continuous gradient from 10% B to 100% B over 10 min+2 min hold time at 100% B, where A=90:10:0.1 H$_2$O:MeCN:TFA and B=90:10:0.1 MeCN:H$_2$O:TFA) gave the title compound (1.5 mg, 13%) as a white solid.

LCMS, [M+H]⁺=474.2. ¹H NMR (400 MHz, CDCl₃) δ 8.06 (s, 1H), 7.87 (d, J=8.6 Hz, 1H), 7.61-7.56 (m, 2H), 7.54-7.49 (m, 1H), 7.48-7.39 (m, 3H), 6.21-6.09 (m, 2H), 4.78-4.71 (m, 1H), 4.07 (s, 3H), 2.94-2.77 (m, 1H), 2.28 (s, 3H), 2.14-1.61 (m, 8H). 26 of 27 protons found, missing the carboxylic acid proton. hLPA₁ IC₅₀=213 nM.

Example 208

A solution of 208A (43.4 mg, 0.061 mmol) in THF (0.40 mL) and 1.0 M LiOH (0.20 mL, 0.20 mmol) was stirred at RT for 16 h, then was concentrated in vacuo. The residue was dissolved in 1:1 MeCN/water and acidified with TFA. Purification by reverse phase chromatography (Sunfire, 5µ C18 OBD 30×100 mm column; detection at 220 nm; flow rate=40 mL/min; continuous gradient from 10% B to 100% B over 10 min+2 min hold time at 100% B, where A=90:10:0.1 H₂O:MeCN:TFA and B=90:10:0.1 MeCN:H₂O:TFA) gave the title compound (24.2 mg, 57%) as a white solid. LCMS, [M+H]⁺=474.2. ¹H NMR (500 MHz, DMSO-d₆) δ 8.72 (s, 1H), 7.98-7.94 (m, 2H), 7.89 (d, J=8.5 Hz, 1H), 7.51 (d, J=8.8 Hz, 1H), 7.48-7.38 (m, 3H), 6.13-6.01 (m, 2H), 4.82-4.77 (m, 1H), 4.30 (s, 3H), 2.71-2.60 (m, 1H), 2.54 (s, 3H), 2.08-1.98 (m, 1H), 1.92-1.74 (m, 3H), 1.71-1.46 (m, 4H). 26 of 27 protons found, missing carboxylic acid proton. hLPA₁ IC₅₀=370 nM.

The Examples in the following table were synthesized according to procedures described for the preparation of the Examples as indicated.

| Ex. # | Structure & Name | Analytical & Biology Data | Method |
|---|---|---|---|
| 165 | 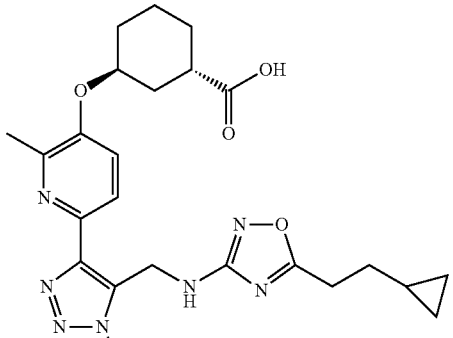<br>(1S,3S)-3-({6-[5-(2-Cyclo-propylethyl)-1,2,4-oxadiazol-3-yl]amino}methyl)-1-methyl-1H-1,2,3-triazol-4-yl]-2-methylpyridin-3-yl}oxy)cyclohexane-1-carboxylic acid, bis TFA salt | LCMS, [M + H]⁺ = 482.2; ¹H NMR (500 MHz, DMSO-d₆) δ 7.86 (br d, J = 8.5 Hz, 1H), 7.52 (br d, J = 8.5 Hz, 1H), 4.80-4.74 (m, 3H), 4.10 (s, 3H), 2.77 (br t, J = 7.3 Hz, 2H), 2.65-2.60 (m, 1H), 2.44 (s, 3H), 2.07-1.98 (m, 1H), 1.90-1.74 (m, 3H), 1.68-1.45 (m, 6H), 0.73-0.63 (m, 1H), 0.39-0.31 (m, 2H), 0.04--0.04 (m, 2H); hLPA₁ IC₅₀ = 6 nM. | Example 72 |
| 166 | 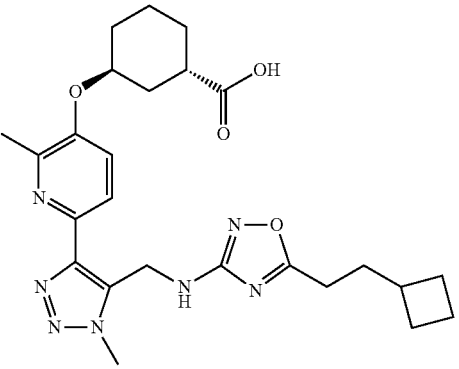<br>(1S,3S)-3-({6-[5-({[5-(2-Cyclobutylethyl)-1,2,4-oxadiazol-3-yl]amino}methyl)-1-methyl-1H-1,2,3-triazol-4-yl]-2-methylpyridin-3-yl}oxy)cyclohexane-1-carboxylic acid, 2 TFA salt | LCMS, [M + H]⁺ = 496.1; ¹H NMR (500 MHz, DMSO-d₆) δ 7.86 (d, J = 8.5 Hz, 1H), 7.48 (d, J = 8.7 Hz, 1H), 4.80-4.73 (m, 3H), 4.10 (s, 3H), 2.69-2.57 (m, 3H), 2.45 (s, 3H), 2.28-2.19 (m, 1H), 2.08-1.92 (m, 3H), 1.89-1.70 (m, 7H), 1.70-1.49 (m, 6H); hLPA₁ IC₅₀ = 5 nM. | Example 72 |

| Ex. # | Structure & Name | Analytical & Biology Data | Method |
|---|---|---|---|
| 167 | (1S,3S)-3-({6-[5-({[5-(3-fluoro-butyl)-1,2,4-oxadiazol-3-yl]amino}methyl)-1-methyl-1H-1,2,3-triazol-4-yl]-2-methylpyridin-3-yl}oxy)cyclohexane-1-carboxylic acid, 2 TFA salt (diastereomeric mixture) | LCMS, [M + H]$^+$ = 488.2; $^1$H NMR (500 MHz, DMSO-d$_6$) δ 7.82 (br d, J = 8.2 Hz, 1H), 7.47 (br d, J = 8.5 Hz, 1H), 4.80-4.58 (m, 4H), 3.91 (br s, 3H), 2.78 (br t, J = 7.3 Hz, 2H), 2.64-2.57 (m, 1H), 2.42 (s, 3H), 2.04-1.71 (m, 6H), 1.64-1.40 (m, 4H), 1.28-1.17 (m, 3H); hLPA$_1$ IC$_{50}$ = 16 nM. | Example 71 |
| 168 | (1S,3S)-3-({2-Methyl-6-[1-methyl-5-({[3-(propan-2-yl)-1,2-oxazol-5-yl]amino}methyl)-1H-1,2,3-triazol-4-yl]pyridin-3-yl}oxy)cyclohexane-1-carboxylic acid, 2 TFA salt | LCMS, [M + H]$^+$ = 455; $^1$H NMR (500 MHz, DMSO-d$_6$) δ 7.84 (d, J = 8.5 Hz, 1H), 7.48 (d, J = 8.6 Hz. 1H), 4.96 (s, 1H), 4.87 (s, 2H), 4.80-4.74 (m, 1H), 4.06 (s, 3H), 2.74-2.60 (m, 2H), 2.44 (s, 3H), 2.06-1.96 (m, 1H), 1.91-1.75 (m, 3H), 1.69-1.45 (m, 4H), 1.02 (d, J = 6.9 Hz, 6H); hLPA$_1$ IC$_{50}$ = 84 nM. | Example 42 |
| 169 | (1S,3S)-3-{[6-(5-{[(5-tert-Butyl-1,2-oxazol-3-yl)amino]methyl}-1-methyl-1H-1,2,3-triazol-4-yl)-2-methylpyridin-3-yl]oxy}cyclo-hexane-1-carboxylic acid | LCMS, [M + H]$^+$ = 469.2; $^1$H NMR (500 MHz, DMSO-d$_6$) δ 7.86 (d, J = 8.6 Hz, 1H), 7.49 (br d, J = 8.5 Hz, 1H), 6.42 (br t, J = 5.9 Hz, 1H), 5.67 (s, 1H), 4.81-4.68 (m, 3H), 4.12 (s, 3H), 2.70-2.60 (m, 1H), 2.47 (s, 3H), 2.07-1.98 (m, 1H), 1.92-1.78 (m, 3H), 1.73-1.48 (m, 4H), 1.19 (s, 9H); hLPA$_1$ IC$_{50}$ = 63 nM. | Example 42 |

| Ex. # | Structure & Name | Analytical & Biology Data | Method |
|---|---|---|---|
| 170 | (1S,3S)-3-({2-Methyl-6-[1-methyl-5-({[5-(2-methylbutyl)-1,2,4-oxadiazol-3-yl]amino}methyl)-1H-1,2,3-triazol-4-yl]pyridin-3-yl}oxy)cyclohexane-1-carboxylic acid, 2 TFA salt (diastereomeric mixture) | LCMS, [M + H]$^+$ = 484.4; $^1$H NMR (500 MHz, DMSO-d$_6$) δ 7.86 (br d, J = 8.5 Hz, 1H), 7.50 (d, J = 8.5 Hz, 1H), 4.82-4.74 (m, 3H), 4.10 (s, 3H), 2.72-2.60 (m, 2H), 2.57-2.53 (m, 1H), 2.43 (s, 3H), 2.07-1.98 (m, 1H), 1.91-1.74 (m, 4H), 1.68-1.45 (m, 4H), 1.34-1.28 (m, 1H), 1.21-1.15 (m, 1H), 0.88-0.82 (m, 6H); hLPA$_1$ IC$_{50}$ = 18 nM. | Example 203 |
| 171 | (1S,3S)-3-({2-Methyl-6-[1-methyl-5-({[5-(pentan-2-yl)-1,2,4-oxadiazol-3-yl]amino}methyl)-1H-1,2,3-triazol-4-yl]pyridin-3-yl}oxy)cyclohexane-1-carboxylic acid, 2 TFA salt (diastereomeric mixture) | LCMS, [M + H]$^+$ = 484.4; $^1$H NMR (500 MHz, DMSO-d$_6$) δ 7.85 (br d, J = 8.5 Hz, 1H), 7.49 (d, J = 8.5 Hz, 1H), 4.80-4.75 (m, 3H), 4.10 (s, 3H), 2.97-2.92 (m, 1H), 2.67-2.59 (m, 1H), 2.43 (s, 3H), 2.08-1.98 (m, 1H), 1.91-1.74 (m, 3H), 1.68-1.45 (m, 6H), 1.28-1.15 (m, 5H), 0.83 (t, J = 7.3 Hz, 3H); hLPA$_1$ IC$_{50}$ = 12 nM. | Example 203 |
| 172 | (1S,3S)-3-({6-[5-({[5-(2-methoxyethyl)-1,2,4-oxadiazol-3-yl]amino}methyl)-1-methyl1H-1,2,3-triazol-4-yl]-2-methylpyridin-3-yl}oxy)cyclo-hexane-1-carboxylic acid, 2 TFA salt | LCMS, [M + H]$^+$ = 472.3; $^1$H NMR (400 MHz, CD$_3$OD) δ 8.05 (d, J = 8.6 Hz, 1H), 7.96 (d, J = 8.8 Hz, 1H), 5.00-4.94 (m, 1H), 4.72 (s, 2H), 4.25 (s, 3H), 3.74 (t, J = 6.2 Hz, 2H), 3.32 (s, 3H), 3.01 (t, J = 6.2 Hz, 2H), 2.87-2.78 (m, 1H), 2.72 (s, 3H), 2.18-2.09 (m, 1H), 2.07-1.91 (m, 3H), 1.87-1.64 (m, 4H); hLPA$_1$ IC$_{50}$ = 120 nM. | Example 203 |

| Ex. # | Structure & Name | Analytical & Biology Data | Method |
|---|---|---|---|
| 173 | 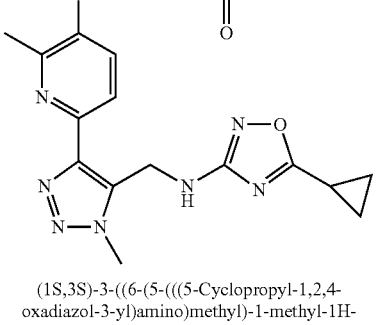<br>(1S,3S)-3-((6-(5-(((5-Cyclopropyl-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]⁺ = 453.9; ¹H NMR (500 MHz, DMSO-d₆) δ 7.85 (br d, J = 8.5 Hz, 1H), 7.50 (d, J = 8.9 Hz, 1H), 4.80-4.74 (m, 3H), 4.09 (s, 3H), 2.64 (br t, J = 10.2 Hz, 1H), 2.43 (s, 3H), 2.13-2.07 (m, 1H), 2.06-1.98 (m, 1H), 1.93-1.75 (m, 3H), 1.70-1.45 (m, 4H), 1.16-1.09 (m, 2H), 1.00-0.92 (m, 2H); hLPA₁ IC₅₀ = 266 nM. | Example 69 |
| 174 | 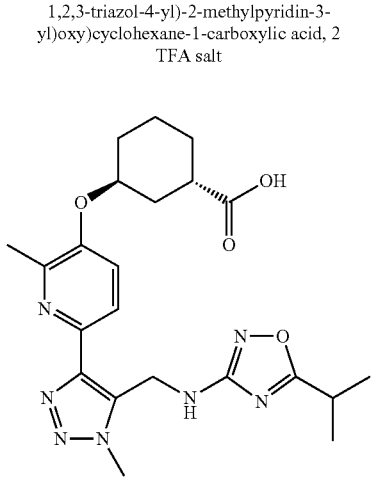<br>(1S,3S)-3-((6-(5-(((5-Isopropyl-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]⁺ = 456.0; ¹H NMR (500 MHz, DMSO-d₆) δ 7.86 (br d, J = 8.2 Hz, 1H), 7.50 (br d, J = 8.5 Hz, 1H), 4.82-4.75 (m, 3H), 4.11 (s, 3H), 3.10-3.01 (m, 1H), 2.67-2.60 (m, 1H), 2.44 (s, 3H), 2.08-1.99 (m, 1H), 1.91-1.75 (m, 3H), 1.69-1.45 (m, 4H), 1.23 (d, J = 7.0 Hz, 6H); hLPA₁ IC₅₀ = 223 nM. | Example 69 |
| 175 | 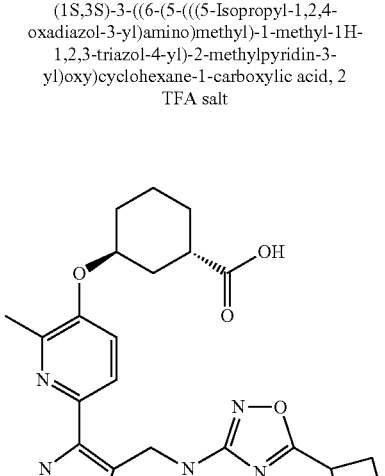<br>(1S,3S)-3-((6-(5-(((5-Cyclobutyl-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]⁺ = 468.4; ¹H NMR (500 MHz, DMSO-d₆) δ 7.87 (d, J = 8.5 Hz, 1H), 7.53 (br d, J = 8.5 Hz, 1H), 4.82-4.75 (m, 3H), 4.11 (s, 3H), 3.66-3.57 (m, 1H), 2.68-2.60 (m, 1H), 2.45 (s, 3H), 2.34-2.19 (m, 4H), 2.06-1.98 (m, 2H), 1.93-1.75 (m, 4H), 1.70-1.45 (m, 4H); hLPA₁ IC₅₀ = 20.0 nM. | Example 69 |

| Ex. # | Structure & Name | Analytical & Biology Data | Method |
|---|---|---|---|
| 176 | (1S,3S)-3-((6-(5-(((5-Cyclopentyl-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 482.4; $^1$H NMR (500 MHz, DMSO-d$_6$) δ 7.86 (d, J = 8.5 Hz, 1H), 7.54 (d, J = 8.9 Hz, 1H), 4.81-4.74 (m, 3H), 4.10 (s, 3H), 3.20-3.15 (m, 1H), 2.65-2.60 (m, 1H), 2.44 (s, 3H), 2.04-1.94 (m, 3H), 1.88-1.76 (m, 3H), 1.73-1.44 (m, 10H); hLPA$_1$ IC$_{50}$ = 25.4 nM. | Example 69 |
| 177 | (1S,3S)-3-((2-Methyl-6-(1-methyl-5-(((5-(4,4,4-trifluorobutyl)-1,2,4-oxadiazol-3-yl)amino)methyl)-1H-1,2,3-triazol-4-yl)pyridin-3-yl)oxy)cyclohexane-1-carboxylic acid, 2 TFA salt | LCMS, [M + H]$^+$ = 524.2; $^1$H NMR (500 MHz, CD$_3$OD) δ 8.13-8.00 (m, 2H), 5.05-4.96 (m, 1H), 4.73 (s, 2H), 4.25 (s, 3H), 2.91-2.81 (m, 3H), 2.75 (s, 3H), 2.40-2.21 (m, 2H), 2.20-2.11 (m, 1H), 2.08-1.93 (m, 5H), 1.87-1.67 (m, 4H); hLPA$_1$ IC$_{50}$ = 9.1 nM. | Example 72 |
| 178 | (1S,3S)-3-((6-(5-(((5-(sec-Butyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt (diastereomeric mixture) | LCMS, [M + H]$^+$ = 470.1; $^1$H NMR (500 MHz, DMSO-d$_6$) δ 7.86 (br d, J = 5.1 Hz, 1H), 7.49 (d, J = 8.6 Hz, 1H), 4.78 (br s, 3H), 4.11 (s, 3H), 2.93-2.83 (m, 1H), 2.70-2.61 (m, 1H), 2.44 (s, 3H), 2.07-1.98 (m, 1H), 1.91-1.76 (m, 3H), 1.72-1.47 (m, 6H), 1.21 (d, J = 6.6 Hz, 3H), 0.87-0.79 (m, 3H); hLPA$_1$ IC$_{50}$ = 27.4 nM. | Example 69 |

| Ex. # | Structure & Name | Analytical & Biology Data | Method |
|---|---|---|---|
| 179 | 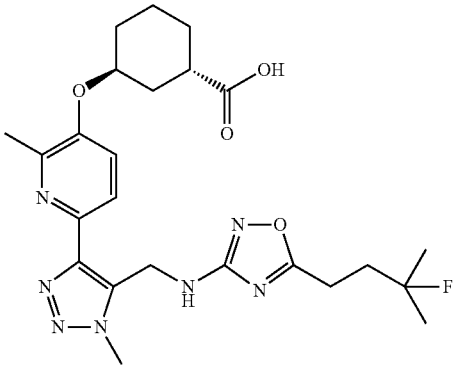<br>(1S,3S)-3-((6-(5-(((5-(3-Fluoro-3-methylbutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, $[M + H]^+$ = 502.3;<br>$^1$H NMR (500 MHz, CD$_3$OD) δ 8.06 (d, J = 8.8 Hz, 1H), 8.00-7.96 (m, 1H), 5.01-4.95 (m, 1H), 4.73 (s, 2H), 4.25 (s, 3H), 2.92-2.81 (m, 3H), 2.73 (s, 3H), 2.17-1.95 (m, 6H), 1.86-1.66 (m, 4H), 1.37 (d, J = 21.2 Hz, 6H);<br>hLPA$_1$ IC$_{50}$ = 43.5 nM. | Example 200 |
| 180 | 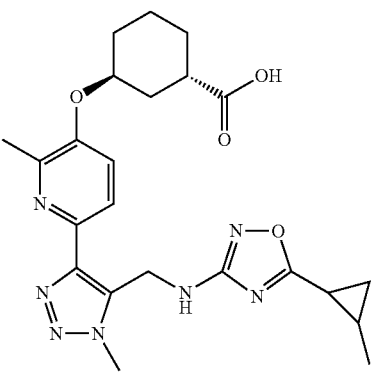<br>(1S,3S)-3-((2-Methyl-6-(1-methyl-5-(((5-(2-methylcyclopropyl)-1,2,4-oxadiazol-3-yl)amino)methyl)-1H-1,2,3-triazol-4-yl)pyridin-3-yl)oxy) cyclohexane-1-carboxylic acid, 2 TFA salt (diastereomeric mixture) | LCMS, $[M + H]^+$ = 468.1;<br>$^1$H NMR (500 MHz, DMSO-d$_6$) δ 7.84 (br d, J = 8.2 Hz, 1H), 7.49 (br d, J = 8.9 Hz, 1H), 4.80-4.72 (m, 3H), 4.08 (s, 3H), 2.66-2.60 (m, 1H), 2.43 (s, 3H), 2.02 (br d, J = 12.5 Hz, 1H), 1.89-1.75 (m, 4H), 1.69-1.45 (m, 4H), 1.40-1.32 (m, 1H), 1.11 (br d, J = 5.8 Hz, 4H), 1.02-0.94 (m, 1H);<br>hLPA$_1$ IC$_{50}$ = 42.1 nM. | Example 72 |
| 181 | 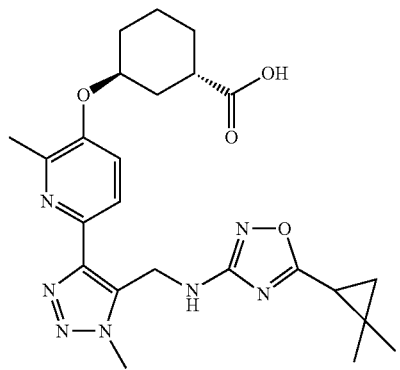<br>(1S,3S)-3-((6-(5-(((5-(2,2-Dimethylcyclopropyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 1$^{st}$ eluting isomer | LCMS, $[M + H]^+$ = 482.2;<br>$^1$H NMR (500 MHz, DMSO-d$_6$) δ 7.84 (br d, J = 8.5 Hz, 1H), 7.49 (br d, J = 8.9 Hz, 1H), 4.79-4.74 (m, 3H), 4.08 (s, 3H), 2.66-2.59 (m, 1H), 2.42 (s, 3H), 2.05-1.92 (m, 2H), 1.88-1.73 (m, 3H), 1.68-1.43 (m, 4H), 1.17 (s, 3H), 1.11 (br dd, J = 8.1, 4.4 Hz, 1H), 1.06-0.97 (m, 4H);<br>hLPA$_1$ IC$_{50}$ = 24.1 nM. | Example 72 |

| Ex. # | Structure & Name | Analytical & Biology Data | Method |
|---|---|---|---|
| 182 | 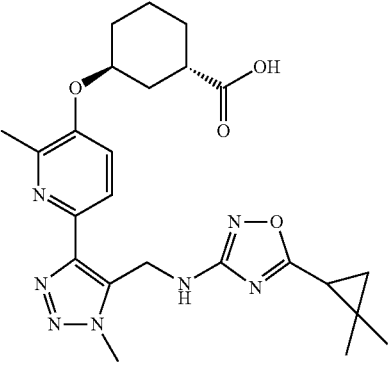<br>(1S,3S)-3-((6-(5-(((5-(2,2-Dimethylcyclopropyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 2$^{nd}$ eluting isomer | LCMS, $[M + H]^+$ = 482.1; $^1$H NMR (500 MHz, DMSO-$d_6$) δ 7.86 (d, J = 8.5 Hz, 1H), 7.50 (d, J = 8.6 Hz, 1H), 4.83-4.72 (m, 3H), 4.10 (s, 3H), 2.71-2.61 (m, 1H), 2.45 (s, 3H), 2.07-1.99 (m, 1H), 1.95 (br dd, J = 8.4, 5.7 Hz, 1H), 1.91-1.75 (m, 3H), 1.71-1.49 (m, 4H), 1.19 (s, 3H), 1.17-1.09 (m, 1H), 1.09-1.01 (m, 4H); hLPA$_1$ IC$_{50}$ = 17 nM. | Example 72 |
| 183 | 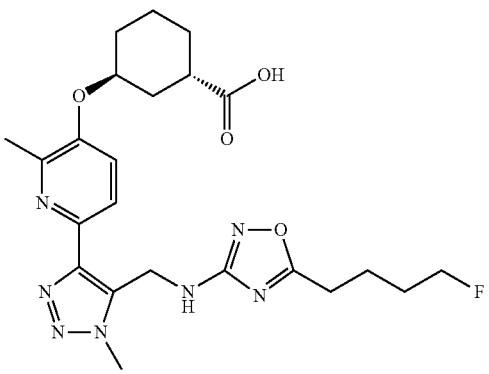<br>(1S,3S)-3-((6-(5-(((5-(4-Fluorobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, $[M + H]^+$ = 488.3; $^1$H NMR (400 MHz, CD$_3$OD) δ 8.08 (d, J = 8.8 Hz, 1H), 8.02 (d, J = 8.8 Hz, 1H), 5.02-4.96 (m, 1H), 4.72 (s, 2H), 4.45 (td, J = 47.3, 5.7 Hz, 2H), 4.25 (s, 3H), 2.87-2.79 (m, 3H), 2.74 (s, 3H), 2.19-2.10 (m, 1H), 2.08-1.94 (m, 3H), 1.91-1.66 (m, 8H); hLPA$_1$ IC$_{50}$ = 32 nM. | Example 163 |
| 184 | 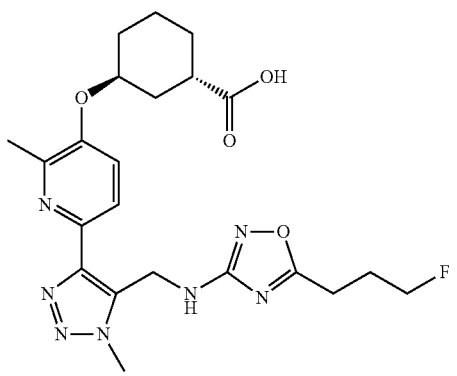<br>(1S,3S)-3-((6-(5-(((5-(3-Fluorobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, $[M + H]^+$ = 474.2; $^1$H NMR (400 MHz, CD$_3$OD) δ 8.11-8.06 (m, 1H), 8.03-7.99 (m, 1H), 5.02-4.96 (m, 1H), 4.73 (s, 2H), 4.50 (td, J = 47.1, 5.7 Hz, 2H), 4.25 (s, 3H), 2.92-2.80 (m, 3H), 2.74 (s, 3H), 2.21-1.93 (m, 6H), 1.88-1.66 (m, 4H); hLPA$_1$ IC$_{50}$ = 74 nM. | Example 163 |

| Ex. # | Structure & Name | Analytical & Biology Data | Method |
|---|---|---|---|
| 185 | 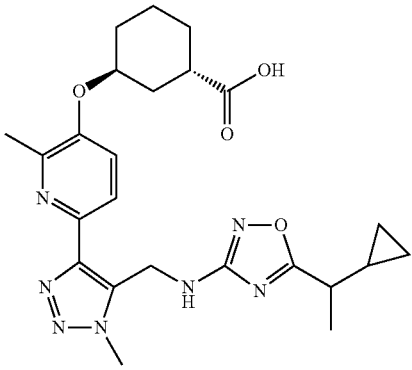<br>(1S,3S)-3-((6-(5-(((5-(1-Cyclopropylethyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, (diastereomer mixture) | LCMS, [M + H]$^+$ = 482.2; $^1$H NMR (500 MHz, DMSO-d$_6$) δ 7.85 (d, J = 8.5 Hz, 1H), 7.48 (d, J = 8.6 Hz, 1H), 4.82-4.74 (m, 3H), 4.11 (s, 3H), 2.65 (br t, J = 10.3 Hz, 1H), 2.44 (s, 3H), 2.37-2.25 (m, 1H), 2.12-1.96 (m, 1H), 1.92-1.74 (m, 3H), 1.69-1.47 (m, 4H), 1.28 (d, J = 7.0 Hz, 3H), 0.95 (dt, J = 8.5, 4.4 Hz, 1H), 0.55-0.40 (m, 2H), 0.24 (ddt, J = 13.6, 9.2, 4.4 Hz, 2H); hLPA$_1$ IC$_{50}$ = 24 nM. | Example 203 |
| 186 | 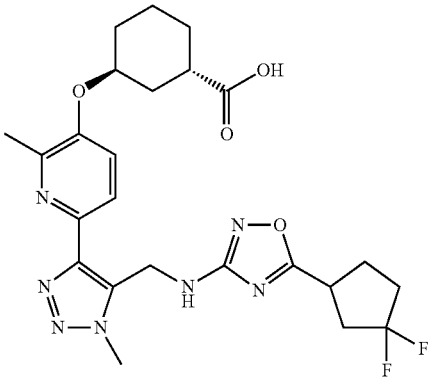<br>(1S,3S)-3-((6-(5-(((5-(3,3-Difluorocyclopentyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt (diastereomeric mixture) | LCMS, [M + H]$^+$ = 518.2; $^1$H NMR (500 MHz, CD$_3$OD) δ 8.02 (br d, J = 8.5 Hz, 1H), 7.84 (br d, J = 8.8 Hz, 1H), 4.96-4.91 (m, 1H), 4.74 (s, 2H), 4.25 (s, 3H), 3.55 (quin, J = 8.3 Hz, 1H), 2.87-2.79 (m, 1H), 2.68 (s, 3H), 2.66-2.51 (m, 1H), 2.42 (qd, J = 15.2, 8.1 Hz, 1H), 2.33-1.93 (m, 8H), 1.86-1.64 (m, 4H); hLPA$_1$ IC$_{50}$ = 79 nM. | Example 203 |
| 187 | 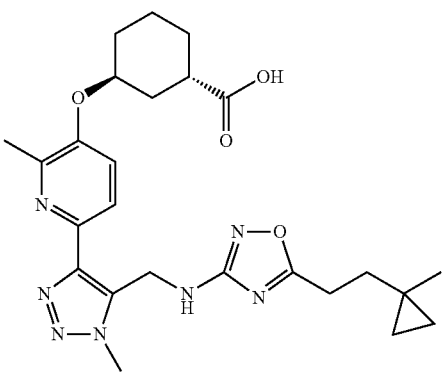<br>(1S,3S)-3-((2-Methyl-6-(1-methyl-5-(((5-(2-(1-methylcyclopropyl)ethyl)-1,2,4-oxadiazol-3-yl)amino)methyl)-1H-1,2,3-triazol-4-yl)pyridin-3-yl)oxy)cyclohexane-1-carboxylic acid, 2 TFA salt | LCMS, [M + H]$^+$ = 496.0; $^1$H NMR (500 MHz, DMSO-d$_6$) δ 7.85 (br d, J = 8.5 Hz, 1H), 7.50 (br d, J = 8.5 Hz, 1H), 4.82-4.71 (m, 3H), 4.09 (s, 3H), 2.79-2.70 (m, 2H), 2.66-2.59 (m, 1H), 2.43 (s, 3H), 2.07-1.95 (m, 1H), 1.90-1.73 (m, 3H), 1.67-1.43 (m, 6H), 0.97 (s, 3H), 0.24-0.14 (m, 4H); hLPA$_1$ IC$_{50}$ = 31 nM. | Example 203 |

| Ex. # | Structure & Name | Analytical & Biology Data | Method |
|---|---|---|---|
| 188 | 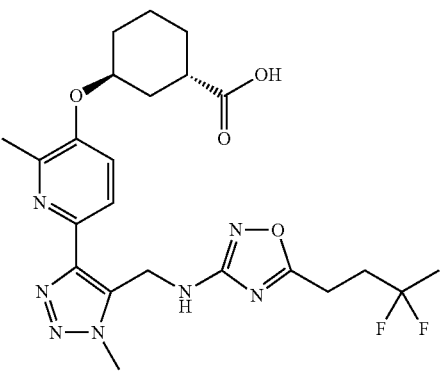<br>(1S,3S)-3-((6-(5-(((5-(3,3-Difluorobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 506.2; $^1$H NMR (500 MHz, DMSO-d$_6$) δ 7.84 (br d, J = 8.5 Hz, 1H), 7.48 (br d, J = 8.5 Hz, 1H), 4.76 (br s, 3H), 4.08 (s, 3H), 2.87 (br t, J = 7.8 Hz, 2H), 2.65-2.58 (m, 1H), 2.42 (s, 3H), 2.29 (tt, J = 16.1, 7.9 Hz, 2H), 2.05-1.97 (m, 1H), 1.89-1.73 (m, 3H), 1.67-1.42 (m, 7H); hLPA$_1$ IC$_{50}$ = 42 nM. | Example 203 |
| 189 | 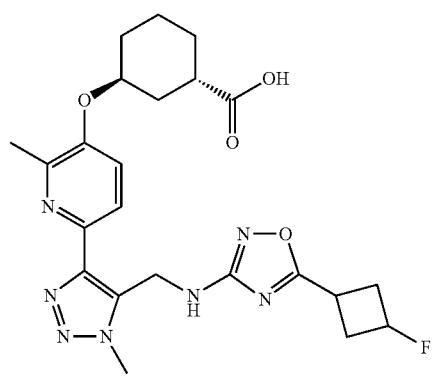<br>(1S,3S)-3-((6-(5-(((5-(3-Fluorocyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 1st eluting isomer | LCMS, [M + H]$^+$ = 486.2; $^1$H NMR (500 MHz, DMSO-d$_6$) δ 7.85 (br d, J = 8.5 Hz, 1H), 7.49 (br d, J = 8.5 Hz, 1H), 5.15-4.96 (m, 1H), 4.82-4.75 (m, 3H), 4.10 (s, 3H), 3.15 (quin, J = 8.5 Hz, 1H), 2.76 (br s, 2H), 2.66-2.60 (m, 1H), 2.45-2.33 (m, 5H), 2.07-1.99 (m, 1H), 1.91-1.74 (m, 3H), 1.69-1.44 (m, 4H); hLPA$_1$ IC$_{50}$ = 74 nM. | Example 203 |
| 190 | 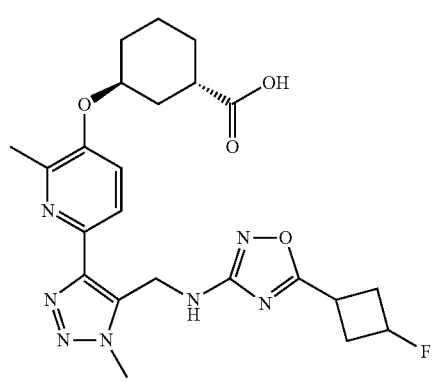<br>(1S,3S)-3-((6-(5-(((5-(3-Fluorocyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA, 2$^{nd}$ eluting isomer | LCMS, [M + H]$^+$ = 486.4; $^1$H NMR (500 MHz, DMSO-d$_6$) δ 7.85 (br d, J = 8.2 Hz, 1H), 7.50 (br d, J = 8.5 Hz, 1H), 5.33-5.11 (m, 1H), 4.81-4.76 (m, 3H), 4.10 (s, 3H), 3.70-3.58 (m, 1H), 2.67-2.56 (m, 5H), 2.44 (s, 3H), 2.02 (br d, J = 12.8 Hz, 1H), 1.90-1.73 (m, 3H), 1.70-1.43 (m, 4H); hLPA$_1$ IC$_{50}$ = 55 nM. | Example 203 |

| Ex. # | Structure & Name | Analytical & Biology Data | Method |
|---|---|---|---|
| 191 | 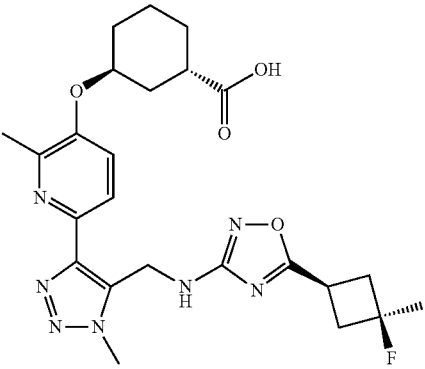<br>(1S,3S)-3-((6-(5-(((5-((1S,3R)-3-Fluoro-3-methylcyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 500.1; $^1$H NMR (500 MHz, DMSO-d$_6$) δ 7.85 (br d, J = 8.5 Hz, 1H), 7.49 (br d, J = 8.9 Hz, 1H), 7.30 (br t, J = 5.5 Hz, 1H), 4.83-4.76 (m, 3H), 4.10 (s, 3H), 2.93 (q, J = 7.3 Hz, 1H), 2.68-2.60 (m, 1H), 2.56-2.52 (m, 4H), 2.43 (s, 3H), 2.08-1.98 (m, 1H), 1.90-1.75 (m, 3H), 1.68-1.39 (m, 7H); hLPA$_1$ IC$_{50}$ = 112 nM. | Example 42 |
| 192 | 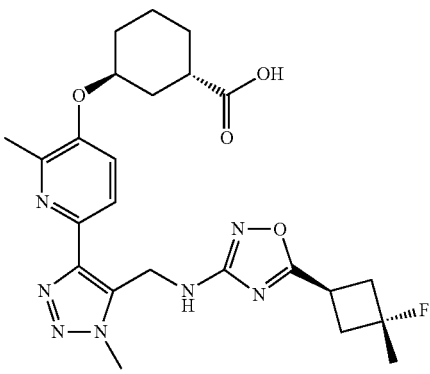<br>(1S,3S)-3-((6-(5-(((5-((1R,3S)-3-Fluoro-3-methylcyclobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt | LCMS, [M + H]$^+$ = 500.4; $^1$H NMR (500 MHz, DMSO-d$_6$) δ 7.86 (br d, J = 8.5 Hz, 1H), 7.51 (br d, J = 8.9 Hz, 1H), 4.83-4.75 (m, 3H), 4.10 (s, 3H), 3.74-3.64 (m, 1H), 2.78-2.59 (m, 3H), 2.46-2.36 (m, 5H), 2.06-1.98 (m, 1H), 1.90-1.74 (m, 3H), 1.69-1.36 (m, 7H); hLPA$_1$ IC$_{50}$ = 52 nM. | Example 42 |

| Ex. # | Structure & Name | Analytical & Biology Data | Method |
|---|---|---|---|
| 193 | 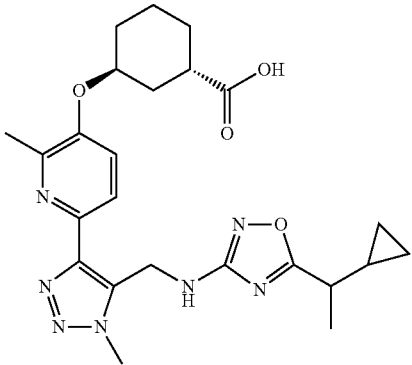<br>(1S,3S)-3-((6-(5-(((5-(1-cyclopropyl ethyl)-1,2,4-oxadiazol-3-yl)amino) methyl)-1-methyl-1H-1,2,3-triazol-4-yl)-2-methylpyridin-3-yl)oxy)cyclohexane-1-carboxylic acid, 2 TFA salt, 1st eluting isomer (chiral preparative chromatography: Column: OX 25 X 2 cm ID, 5 μm; Flow rate: 50.0 mL/min; Mobile Phase: 85/15 $CO_2$/MeOH; Detector Wavelength: 278 nm; Injection: 1 mL injection of 60 mg sample in 20 mL MeOH) | LCMS, $[M + H]^+$ = 482.1; $^1$H NMR (500 MHz, DMSO-$d_6$) δ 7.84 (br d, J = 8.5 Hz, 1H), 7.50 (br d, J = 8.5 Hz, 1H), 7.25 (br t, J = 5.6 Hz, 1H), 4.80-4.74 (m, 3H), 4.11 (s, 3H), 2.63-2.57 (m, 1H), 2.43 (s, 3H), 2.32-2.26 (m, 1H), 2.01-1.95 (m, 1H), 1.87-1.76 (m, 3H), 1.68-1.44 (m, 4H), 1.27 (br d, J = 7.0 Hz, 3H), 0.96-0.90 (m, 1H), 0.52-0.42 (m, 2H), 0.27-0.19 (m, 2H); hLPA$_1$ IC$_{50}$ = 33 nM. | Example 42 |
| 194 | 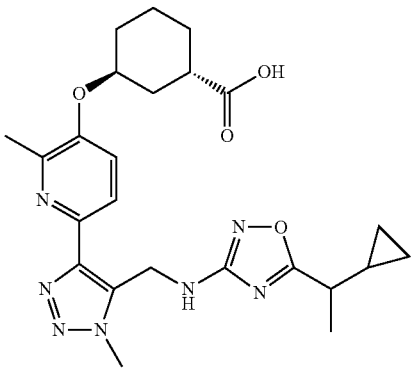<br>(1S,3S)-3-((6-(5-(((5-(1-Cyclopropylethyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 2nd eluting isomer | LCMS, $[M + H]^+$ = 482.1; $^1$H NMR (500 MHz, DMSO-$d_6$) δ 7.84 (br d, J = 8.5 Hz, 1H), 7.50 (br d, J = 8.9 Hz, 1H), 7.25 (br t, J = 5.6 Hz, 1H), 4.81-4.73 (m, 3H), 4.11 (s, 3H), 2.61-2.55 (m, 1H), 2.42 (s, 3H), 2.33-2.25 (m, 1H), 2.00-1.91 (m, 1H), 1.86-1.74 (m, 3H), 1.67-1.46 (m, 4H), 1.27 (br d, J = 7.0 Hz, 3H), 0.98-0.89 (m, 1H), 0.53-0.40 (m, 2H), 0.28-0.18 (m, 2H); hLPA$_1$ IC$_{50}$ = 25 nM. | Example 42 |

| Ex. # | Structure & Name | Analytical & Biology Data | Method |
|---|---|---|---|
| 195 | 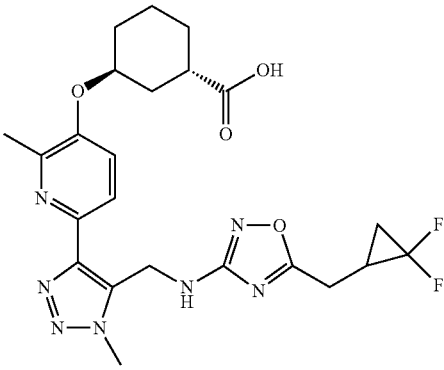<br>(1S,3S)-3-((6-(5-(((5-((2,2-Difluorocyclopropyl)methyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt,<br>1st eluting isomer (chiral preparative chromatography: Column: Chiral AD, 30 x 250 mm, 5 micron; Flow rate: 100 mL/min; Mobile Phase: 83% $CO_2$/17% iPrOH; w/0.1% DEA; Detector Wavelength: 220 nm; Injection: 750 μL 12.8 mg dissolved on 3 mL MeOH) | LCMS, $[M + H]^+$ = 504.4; $^1$H NMR (500 MHz, DMSO-$d_6$) δ 7.84 (br d, J = 8.2 Hz, 1H), 7.50 (br d, J = 8.2 Hz, 1H), 7.33 (br t, J = 5.2 Hz, 1H), 4.81-4.72 (m, 3H), 4.10 (s, 3H), 3.00-2.86 (m, 2H), 2.60-2.54 (m, 1H), 2.42 (s, 3H), 2.09-1.90 (m, 2H), 1.87-1.44 (m, 8H), 1.39-1.29 (m, 1H); hLPA$_1$ IC$_{50}$ = 25 nM. | Example 162 |
| 196 | 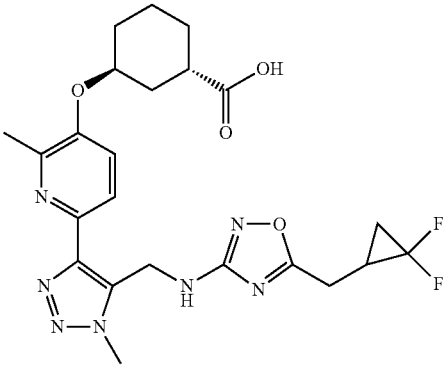<br>(1S,3S)-3-((6-(5-(((5-((2,2-Difluorocyclopropyl)methyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 2$^{nd}$ eluting isomer | LCMS, $[M + H]^+$ = 504.4; $^1$H NMR (500 MHz, DMSO-$d_6$) δ 7.83 (br d, J = 8.5 Hz, 1H), 7.49 (br d, J = 8.5 Hz, 1H), 7.32 (br t, J = 5.5 Hz, 1H), 4.81-4.71 (m, 3H), 4.09 (s, 3H), 2.99-2.85 (m, 2H), 2.55-2.51 (m, 1H), 2.41 (s, 3H), 2.09-1.89 (m, 2H), 1.85-1.43 (m, 8H), 1.39-1.29 (m, 1H); hLPA$_1$ IC$_{50}$ = 28 nM. | Example 162 |

| Ex. # | Structure & Name | Analytical & Biology Data | Method |
|---|---|---|---|
| 197 | (1S,3S)-3-((2-Methyl-6-(1-methyl-5-(((5-(2-methylpentan-2-yl)-1,2,4-oxadiazol-3-yl)amino)methyl)-1H-1,2,3-triazol-4-yl)pyridin-3-yl)oxy)cyclohexane-1-carboxylic acid, 2 TFA salt | LCMS, [M + H]$^+$ = 498.3; $^1$H NMR (500 MHz, DMSO-d$_6$) δ 7.84 (br d, J = 8.5 Hz, 1H), 7.49 (br d, J = 8.5 Hz, 1H), 4.79-4.73 (m, 3H), 4.10 (s, 3H), 2.65-2.58 (m, 1H), 2.42 (s, 3H), 2.04-1.98 (m, 1H), 1.90-1.73 (m, 3H), 1.68-1.43 (m, 6H), 1.23 (s, 6H), 1.12-1.04 (m, 2H), 0.79 (br t, J = 7.2 Hz, 3H); hLPA$_1$ IC$_{50}$ = 42 nM. | Example 203 |
| 198 | (1S,3S)-3-((2-Methyl-6-(1-methyl-5-(((5-(3-methylcyclobutyl)-1,2,4-oxadiazol-3-yl)amino)methyl)-1H-1,2,3-triazol-4-yl)pyridin-3-yl)oxy)cyclohexane-1-carboxylic acid, 1st isomer to elute (chiral preparative chromatography: Column: Chiral AD, 30 x 250 mm. 5 micron; Flow rate: 100 mL/min; Mobile Phase: 80% CO$_2$/20% IPA w/0.1% DEA: Detector Wavelength: 220 nm; Injection: 750 μL 20.3 mg dissolved in 3 mL MeOH) | LCMS, [M + H]$^+$ = 482.2; $^1$H NMR (500 MHz, DMSO-d$_6$) δ 7.84 (br d, J = 8.5 Hz, 1H), 7.48 (br d, J = 8.5 Hz, 1H), 7.23-7.19 (m, 1H), 4.79-4.74 (m, 3H), 4.09 (s, 3H), 2.65-2.59 (m, 1H), 2.45-2.35 (m, 6H), 2.04-1.97 (m, 1H), 1.87-1.75 (m, 5H), 1.68-1.44 (m, 4H), 1.01 (br d, J = 6.1 Hz, 3H), one proton from cyclobutane —CH— not seen due to water suppression; hLPA$_1$ IC$_{50}$ = 28 nM. | Example 42 |

| Ex. # | Structure & Name | Analytical & Biology Data | Method |
|---|---|---|---|
| 199 | 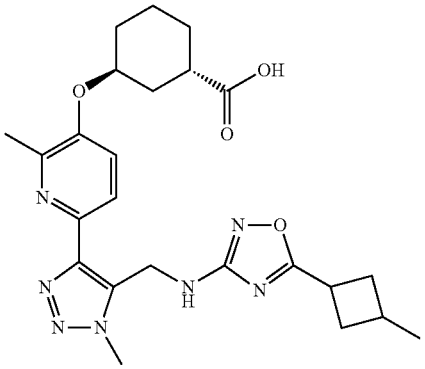<br>(1S,3S)-3-((2-Methyl-6-(1-methyl-5-(((5-(3-methylcyclobutyl)-1,2,4-oxadiazol-3-yl)amino)methyl)-1H-1,2,3-triazol-4-yl)pyridin-3-yl)oxy) cyclohexane-1-carboxylic acid,<br>2nd isomer to elute | LCMS, [M + H]$^+$ = 481.9;<br>$^1$H NMR (500 MHz, DMSO-d$_6$) δ 7.85 (br d, J = 8.5 Hz, 1H), 7.49 (br d, J = 8.5 Hz, 1H), 7.24 (br t, J = 5.5 Hz, 1H), 4.81-4.74 (m, 3H), 4.11 (s, 3H), 3.53-3.41 (m, 1H), 2.66-2.59 (m, 1H), 2.48-2.40 (m, 4H), 2.40-2.29 (m, 2H), 2.06-1.94 (m, 3H), 1.90-1.74 (m, 3H), 1.68-1.43 (m, 4H), 1.11 (br d, J = 6.7 Hz, 3H);<br>hLPA$_1$ IC$_{50}$ = 33 nM. | Example 42 |
| 200 | 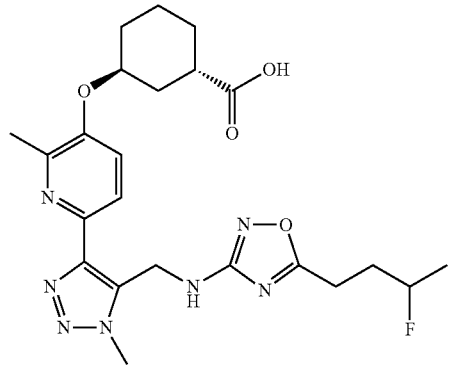<br>(1S,3S)-3-((6-(5-(((5-(3-Fluorobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt,<br>1$^{st}$ eluting isomer (chiral preparative chromatography: Column: Chiral AD, 30 x 250 mm. 5 micron; Flow rate: 100 mL/min; Mobile Phase: 75% CO$_2$/25% IPA w/0.1% DEA; Detector Wavelength: 220 nm; Injection: 500 μL 21.3 mg dissolved in 3 mL MeOH) | LCMS, [M + H]$^+$ = 488.1;<br>$^1$H NMR (500 MHz, DMSO-d$_6$) δ 7.85 (br d, J = 8.5 Hz, 1H), 7.50 (br d, J = 8.5 Hz, 1H), 7.26 (br t, J = 5.5 Hz, 1H), 4.81-4.63 (m, 4H), 4.10 (s, 3H), 2.86-2.77 (m, 2H), 2.68-2.59 (m, 1H), 2.43 (s, 3H), 2.07-1.73 (m, 6H), 1.68-1.45 (m, 4H), 1.32- 1.22 (m, 3H);<br>hLPA$_1$ IC$_{50}$ = 31 nM. | Example 191 |

| Ex. # | Structure & Name | Analytical & Biology Data | Method |
|---|---|---|---|
| 201 | 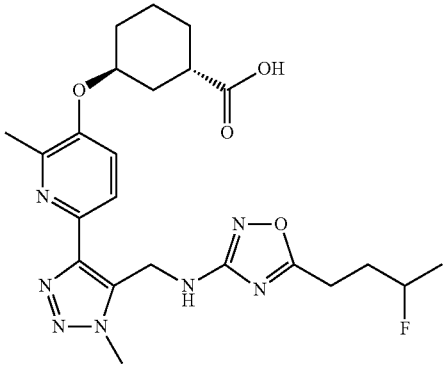<br>(1S,3S)-3-((6-(5-(((5-(3-Fluorobutyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, 2 TFA salt, 2$^{nd}$ eluting isomer | LCMS, [M + H]$^+$ = 488.3; $^1$H NMR (500 MHz, DMSO-d$_6$) δ 7.85 (br d, J = 8.5 Hz, 1H), 7.49 (br d, J = 8.9 Hz, 1H), 7.26 (br t, J = 5.6 Hz, 1H), 4.84-4.61 (m, 4H), 4.10 (s, 3H), 2.86-2.73 (m, 2H), 2.68-2.59 (m, 1H), 2.43 (s, 3H), 2.08-1.74 (m, 6H), 1.69-1.44 (m, 4H), 1.32-1.21 (m, 3H); hLPA$_1$ IC$_{50}$ = 32 nM. | Example 191 |
| 202 | 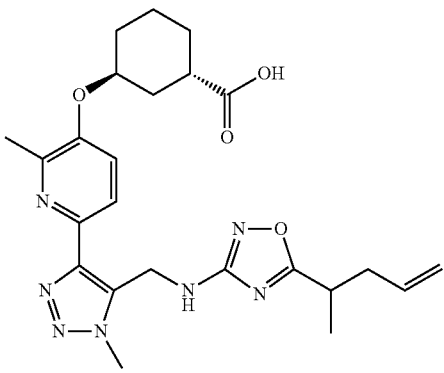<br>(1S,3S)-3-((2-Methyl-6-(1-methyl-5-(((5-(pent-4-en-2-yl)-1,2,4-oxadiazol-3-yl)amino)methyl)-1H-1,2,3-triazol-4-yl)pyridin-3-yl)oxy)cyclohexane-1-carboxylic acid, 2 TFA salt (diastereomeric mixture) | LCMS, [M + H]$^+$ = 482.3; $^1$H NMR (500 MHz, DMSO-d$_6$) δ 7.86 (d, J = 8.5 Hz, 1H), 7.50 (d, J = 8.7 Hz, 1H), 7.26 (br t, J = 5.5 Hz, 1H), 5.75-5.66 (m, 1H), 5.07-4.99 (m, 2H), 4.83-4.76 (m, 3H), 4.11 (s, 3H), 3.11-3.03 (m, 1H), 2.70-2.59 (m, 1H), 2.46-2.37 (m, 4H), 2.37-2.25 (m, 1H), 2.07-1.99 (m, 1H), 1.91-1.75 (m, 3H), 1.69-1.45 (m, 4H), 1.21 (d, J = 7.0 Hz, 3H); hLPA$_1$ IC$_{50}$ = 8.4 nM. | Example 203 |
| 203 | 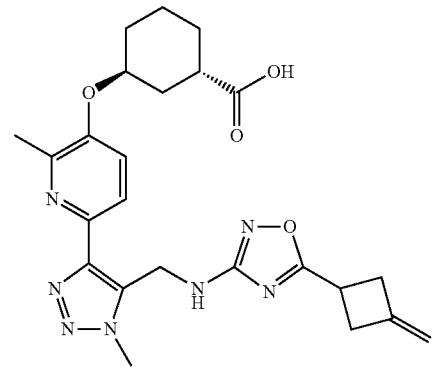<br>(1S,3S)-3-((2-Methyl-6-(1-methyl-5-(((5-(3-methylenecyclobutyl)-1,2,4-oxadiazol-3-yl)amino)methyl)-1H-1,2,3-triazol-4-yl)pyridin-3-yl)oxy)cyclohexane-1-carboxylic acid, 2 TFA salt | LCMS, [M + H]$^+$ = 480.1; $^1$H NMR (500 MHz, DMSO-d$_6$) δ 7.90-7.83 (m, 1H), 7.54 (br d, J = 8.7 Hz, 1H), 4.87-4.73 (m, 5H), 4.11 (s, 3H), 3.13-3.01 (m, 2H), 2.97-2.85 (m, 3H), 2.69-2.59 (m, 1H), 2.44 (br s, 3H), 2.08-1.94 (m, 1H), 1.91-1.75 (m, 3H), 1.68-1.44 (m, 4H); hLPA$_1$ IC$_{50}$ = 11.5 nM. | Example 42 |

| Ex. # | Structure & Name | Analytical & Biology Data | Method |
|---|---|---|---|
| 204 | 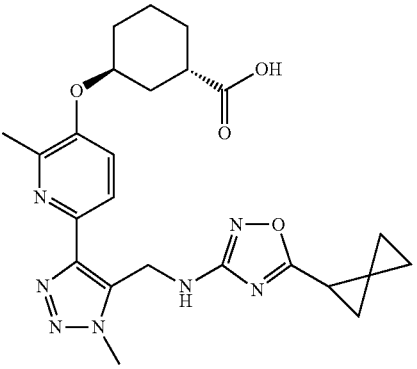<br>(1S,3S)-3-((2-Methyl-6-(1-methyl-5-(((5-(spiro[2.2]pentan-1-yl)-1,2,4-oxadiazol-3-yl)amino)methyl)-1H-1,2,3-triazol-4-yl)pyridin-3-yl)oxy)cyclohexane-1-carboxylic acid, 2 TFA salt, 1st eluting isomer | LCMS, [M + H]$^+$ = 480.2; $^1$H NMR (500 MHz, DMSO-d$_6$) δ 7.84 (d, J = 8.5 Hz, 1H), 7.49 (d, J = 8.5 Hz, 1H), 7.19 (t, J = 6.0 Hz, 1H), 4.79 .4.74 (m, 3H), 4.09 (s, 3H), 2.67-2.59 (m, 1H), 2.48-2.45 (m, 1H), 2.42 (s, 3H), 2.05-1.98 (m, 1H), 1.90-1.75 (m, 3H), 1.68-1.41 (m, 6H), 1.02-0.88 (m, 3H), 0.79-0.73 (m, 1H); hLPA$_1$ IC$_{50}$ = 18.1 nM. | Example 203 |
| 205 | 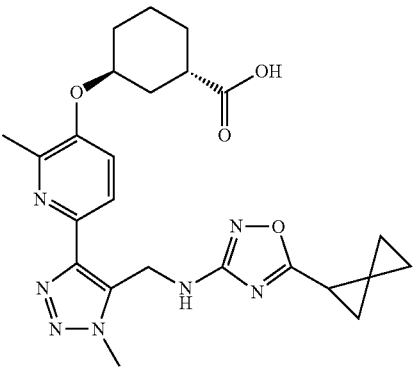<br>(1S,3S)-3-((2-Methyl-6-(1-methyl-5-(((5-(spiro[2.2]pentan-1-yl)-1,2,4-oxadiazol-3-yl)amino)methyl)-1H-1,2,3-triazol-4-yl)pyridin-3-yl)oxy)cyclohexane-1-carboxylic acid, 2 TFA salt, 2nd eluting isomer | LCMS, [M + H]$^+$ = 480.2; $^1$H NMR (500 MHz, DMSO-d$_6$) δ 7.84 (d, J = 8.5 Hz, 1H), 7.48 (d, J = 8.9 Hz, 1H), 7.19 (t, J = 5.8 Hz, 1H), 4.79-4.74 (m, 3H), 4.09 (s, 3H), 2.67-2.59 (m, 1H), 2.48-2.45 (m, 1H), 2.42 (s, 3H), 2.04-1.98 (m, 1H), 1.89-1.74 (m, 3H), 1.69-1.40 (m, 6H), 1.03-0.88 (m, 3H), 0.79-0.74 (m, 1H); hLPA$_1$ IC$_{50}$ = 24.0 nM. | Example 203 |
| 206 | 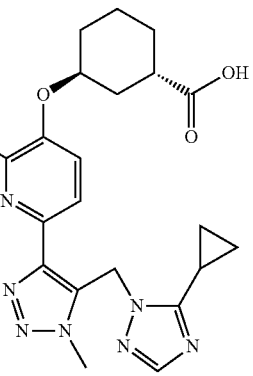<br>(1S,3S)-3-((6-(5-((5-cyclopropyl-1H-1,2,4-triazol-1-yl)methyl)-1-methyl-1H-1,2,3-triazol-4-yl)-2-methylpyridin-3-yl)oxy)cyclo-hexane-1-carboxylic acid, bis TFA salt | LCMS, [M + H]$^+$ = 438.3; $^1$H NMR (500 MHz, DMSO-d$_6$) δ 7.87 (br d, J = 8.2 Hz, 1H), 7.71 (s, 1H), 7.49 (br d, J = 8.5 Hz, 1H). 6.13 (s, 2H), 4.81-4.74 (m, 1H), 4.13 (s, 3H), 2.68-2.58 (m, 1H), 2.44-2.31 (m. 4H), 2.08-1.94 (m, 1H), 1.93-1.71 (m, 3H), 1.68-1.41 (m, 4H), 0.99-0.80 (m, 4H). 26 of 27 protons found; hLPA$_1$ IC$_{50}$ = 1,090 nM. | Examples 207, 208 |

| Ex. # | Structure & Name | Analytical & Biology Data | Method |
|---|---|---|---|
| 209 | 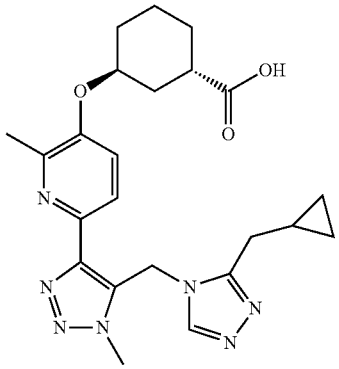<br>(1S,3S)-3-((6-(5-((3-(cyclopropyl methyl)-4H-1,2,4-triazol-4-yl)methyl)-1-methyl-1H-1,2,3-triazol-4-yl)-2-methylpyridin-3-yl)oxy)cyclohexane-1-carboxylic acid, bis TFA salt | LCMS, [M + H]$^+$ = 452.1;<br>$^1$H NMR (500 MHz, DMSO-d$_6$) δ 8.55 (s, 1H), 7.89 (d, J = 8.5 Hz, 1H), 7.51 (d, J = 8.8 Hz, 1H), 5.99-5.94 (m, 2H), 4.82-4.76 (m, 1H), 4.20 (s, 3H), 2.69-2.61 (m, 1H), 2.49 (d, J = 6.9 Hz, 2H), 2.07-1.99 (m, 1H), 1.92-1.74 (m, 3H), 1.71-1.45 (m, 4H), 1.05-0.94 (m, 1H), 0.44-0.37 (m, 2H), 0.17-0.10 (m, 2H);<br>hLPA$_1$ IC$_{50}$ = 2,080 nM. | Examples 207, 208 |
| 210 | 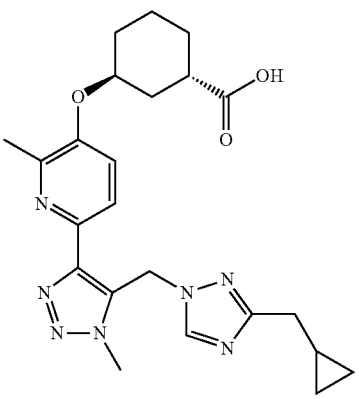<br>(1S,3S)-3-((6-(5-((3-(cyclopropylmethyl)-1H-1,2,4-triazol-1-yl)methyl)-1-methyl-1H-1,2,3-triazol-4-yl)-2-methyl-pyridin-3-yl)oxy)cyclo-hexane-1-carboxylic acid, bis TFA salt | LCMS, [M + H]$^+$ = 452.1;<br>$^1$H NMR (500 MHz, DMSO-d$_6$) δ 8.55 (s, 1H), 7.89 (d, J = 8.5 Hz, 1H), 7.51 (d, J = 8.8 Hz, 1H), 5.99-5.94 (m, 2H), 4.82-4.76 (m, 1H), 4.20 (s, 3H), 2.69-2.61 (m, 1H), 2.49 (d, J = 6.9 Hz, 2H), 2.07-1.99 (m, 1H), 1.92-1.74 (m, 3H), 1.71-1.45 (m, 4H), 1.05-0.94 (m, 1H), 0.44-0.37 (m, 2H), 0.17-0.10 (m, 2H). 25 of 29 protons found;<br>hLPA$_1$ IC$_{50}$ = 191 nM. | Examples 207, 208 |

Example 211. (1S,3S)-3-((6-(5-(((1-(3,5-difluorophenyl)-1H-1,2,4-triazol-3-yl)amino)methyl)-1-methyl-1H-1,2,3-triazol-4-yl)-2-methylpyridin-3-yl)oxy)cyclohexane-1-carboxylic acid

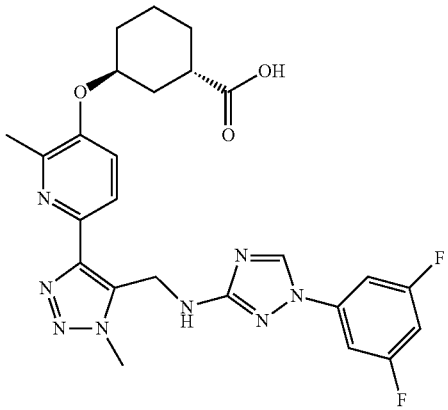 [SMILES: Cc1nc(-c2nnn(C)c2CNc2ncn(-c3cc(F)cc(F)c3)n2)ccc1O[C@H]1CCC[C@H](C(=O)O)C1]

211A.
1-(3,5-difluorophenyl)-3-nitro-1H-1,2,4-triazole

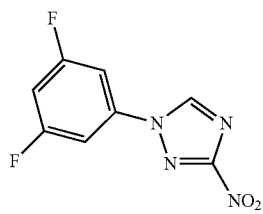

A mixture of 3-nitro-1H-1,2,4-triazole (570 mg, 5.00 mmol), (3,5-difluorophenyl)boronic acid (789 mg, 5.00 mmol), Cu(OAc)$_2$ (1089 mg, 6.00 mmol), pyridine (4.0 ml, 50.0 mmol), and 4A molecular sieves (1 g) in DCM (5 mL) was stirred under air at RT for 4 days, then was filtered. The filtrate was concentrated in vacuo. The residue was dissolved in EtOAc (5 mL) and washed with 1N aq. HCl and water; the organic layer was concentrated in vacuo. The residue was chromatographed (12 g SiO$_2$; continuous gradient from 0% to 50% EtOAc in hexane over 10 min) to give the title compound (300 mg, 1.33 mmol, 26.5% yield) as a white solid. $^1$H NMR (400 MHz, CDCl$_3$) δ 8.70 (s, 1H), 7.45-7.35 (m, 2H), 7.01 (tt, J=8.5, 2.2 Hz, 1H); $^{19}$F NMR (377 MHz, CDCl$_3$) δ −104.41 (s, F).

211B.
1-(3,5-difluorophenyl)-1H-1,2,4-triazol-3-amine

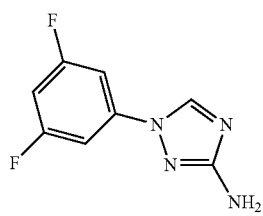 [SMILES: O=[N+]([O-])c1ncn(-c2cc(F)cc(F)c2)n1]

A mixture of Example 211A (300 mg, 1.33 mmol) and 10% Pd—C (14 mg, 0.013 mmol) in MeOH (10 mL) was stirred under an atmosphere of H$_2$ at 50 psi for 18 h, then was filtered and concentrated in vacuo to give the title compound (250 mg, 1.27 mmol, 96% yield) as a white solid. $^1$H NMR (400 MHz, CD$_3$CN) δ 8.42 (s, 1H), 7.44-7.22 (m, 2H), 6.90 (tt, J=9.2, 2.4 Hz, 1H), 5.38-3.45 (m, 2H); $^{19}$F NMR (377 MHz, CD$_3$CN) δ 109.53 (s, F); ESI-MS m/z 197.2 [M+1]$^+$.

Example 211

A mixture of Intermediate 2 (31 mg, 0.069 mmol), Example 211B (27 mg, 0.137 mmol) and DIPEA (0.04 mL, 0.206 mmol) in DMF (1 mL) was heated in a microwave reactor at 150° C. for 15 min, then was cooled to RT and concentrated in vacuo. A mixture of the crude product with 1N aq. NaOH (0.3 mL) in THF (1 mL) and MeOH (0.5 mL) was stirred at RT for 3 days, then was concentrated in vacuo. The residue was purified by preparative HPLC(Sunfire C18 30×100 mm column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the title compound (27 mg, 0.036 mmol, 51.7% yield) as an oil. LCMS, [M+H]$^+$=525.2; $^1$H NMR (400 MHz, CDCl$_3$) δ 8.29 (s, 1H), 7.99 (d, J=8.8 Hz, 1H), 7.39 (d, J=8.6 Hz, 1H), 7.11 (dd, J=7.7, 2.2 Hz, 2H), 6.78 (tt, J=8.6, 2.3 Hz, 1H), 4.78 (s, 2H), 4.73 (br s, 1H), 4.30 (s, 3H), 2.94-2.85 (m, 1H), 2.65 (s, 3H), 2.17-1.60 (m, 8H); $^{19}$F NMR (377 MHz, CDCl$_3$) δ −106.31 (s, F); hLPA$_1$ IC$_{50}$=45 nM.

Example 212. (1S,3S)-3-((6-(5-(((5-(cyclopropoxymethyl)-1,2,4-oxadiazol-3-yl)amino)methyl)-1-methyl-1H-1,2,3-triazol-4-yl)-2-methylpyridin-3-yl)oxy)cyclohexane-1-carboxylic acid

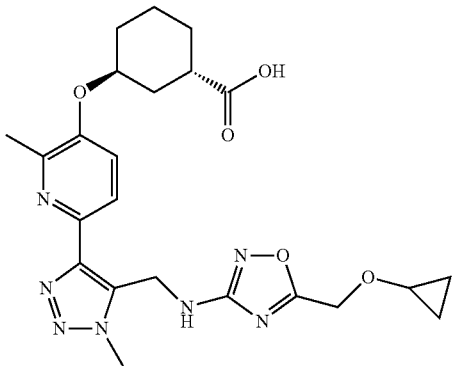 [SMILES: Cc1nc(-c2nnn(C)c2CNc2noc(COC3CC3)n2)ccc1O[C@H]1CCC[C@H](C(=O)O)C1]

212A. 2-cyclopropoxyacetic acid

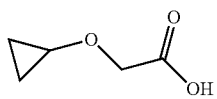

To a 0° C. solution of cyclopropanol (1.10 mL, 17.3 mmol) in THF (5 mL) was added NaH (1.44 g of a 60% dispersion in oil, 36.0 mmol). The reaction was stirred for 2 h at RT, after which BrCH$_2$CO$_2$H (2.0 g, 14.4 mmol) was added and the reaction was stirred at RT for 20 h, after which a white solid was formed. Water (30 mL) was added carefully and the mixture was stirred until a clear solution was obtained. The solution was extracted with Et$_2$O (2×). The aqueous layer was acidified with conc. HCl (1.80 mL, 21.6 mmol) to pH=1 and extracted with Et$_2$O (3×5 mL). The combined organic extracts were dried (MgSO$_4$) and concentrated in vacuo to give the title compound (1.30 g, 11.2 mmol, 78% yield) as a light yellow liquid. $^1$H NMR (400 MHz, CDCl$_3$) δ 4.17 (s, 2H), 3.56-3.50 (m, 1H), 0.72-0.67 (m, 2H), 0.58-0.51 (m, 2H).

212B. 2-cyclopropoxyacetyl chloride

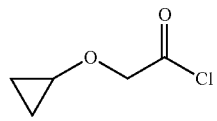

To a solution of Example 212A (1.30 g, 11.2 mmol) in DCM (5 mL) at RT was added DMF (43 µL, 0.56 mmol), followed by 2.0 M oxalyl chloride in DCM (5.6 mL, 11.2 mmol). The reaction was stirred at RT for 2 h to give the title compound in DCM, which was used in the next step without further purification.

212C. N-cyano-2-cyclopropoxyacetamide

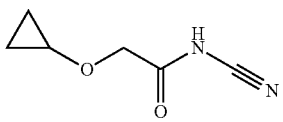

To a 0° C. suspension of sodium hydrogen cyanamide (2.85 g, 44.6 mmol) in THF (22.3 mL) was added dropwise a solution of Example 212B (1.50 g, 11.2 mmol) in DCM (5 mL). The reaction was stirred at RT overnight, then was concentrated in vacuo. The yellow solid residue was dissolved in water (20 mL) and the pH of the solution was adjusted to ~6.5 with 10% aq. HCl. The aq. solution was extracted with EtOAc (2×20 mL). The aqueous layer was acidified to pH 1.5 with 10% aq. HCl and extracted with CH$_2$Cl$_2$ (3×10 mL). The combined CH$_2$Cl$_2$ extracts were dried (Na$_2$SO$_4$) and concentrated in vacuo to give the title compound (0.32 g, 2.28 mmol, 20.5% yield) as a light yellow oil, which was used in the next step without further purification.

212D.
5-(cyclopropoxymethyl)-1,2,4-oxadiazol-3-amine

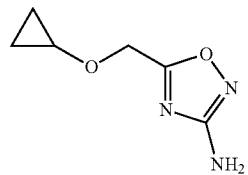 [SMILES: Nc1noc(COC2CC2)n1]

To a solution of Example 212C (320 mg, 2.283 mmol) in EtOH (10 mL) were added NH$_2$OH·HCl (238 mg, 3.43 mmol) and pyridine (0.74 mL, 9.13 mmol). The reaction was stirred at RT for 3 days, then was concentrated in vacuo. The yellow solid residue was dissolved in water (10 mL) and was extracted with DCM (5×5 mL). The combined organic extracts were dried (Na$_2$SO$_4$) and concentrated in vacuo. The crude oil was purified by preparative HPLC (C18 30×100 mm column; detection at 220 nm; flow rate=40 mL/min; continuous gradient from 30% B to 100% B over 10 min+2 min hold time at 100% B, where A=90:10:0.1 H$_2$O:MeCN:TFA and B=90:10:0.1 MeCN:H$_2$O:TFA) to the title compound (28 mg, 0.104 mmol, 4.56% yield) as a white solid (TFA salt). $^1$H NMR (500 MHz, CDCl$_3$) δ 4.64 (s, 4H), 3.55 (tt, J=5.9, 2.9 Hz, 1H), 0.76-0.67 (m, 2H), 0.60-0.48 (m, 2H); LCMS, [M+H]$^+$=156.1.

Example 212

A solution of Intermediate 8 (30 mg, 0.084 mmol), Example 212D (28 mg, 0.10 mmol), and AcOH (17 µL, 0.29 mmol) in MeOH (1 mL) was stirred at 65° C. for 2 h, then was cooled to RT, after which NaBH$_3$CN (10.52 mg, 0.167 mmol) was added. The reaction was stirred at RT for 1 h, then was concentrated in vacuo. The residue was stirred with 1N aq. NaOH (0.2 mL) in THF (1 mL) at RT for 2 h, then was concentrated in vacuo. The residue was purified by preparative HPLC (Sunfire C18 30×100 mm column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) to give the title compound (31 mg, 0.043 mmol, 51.5% yield) as a clear oil. $^1$H NMR (500 MHz, CDCl$_3$) δ 8.07 (d, J=8.5 Hz, 1H), 7.82 (br d, J=8.8 Hz, 1H), 4.86 (br s, 1H), 4.73 (s, 2H), 4.63 (s, 2H), 4.26 (s, 3H), 3.52 (tt, J=6.0, 2.8 Hz, 1H), 2.90 (br s, 1H), 2.76 (s, 3H), 2.20-1.64 (m, 8H), 0.72-0.65 (m, 2H), 0.58-0.52 (m, 2H); LCMS, [M+H]$^+$=483.3; hLPA$_1$ IC$_{50}$=34 nM.

The following Examples were prepared according to the procedures previously described for the synthesis of Example 212.

| Ex # | Structure & Name | Analytical & Biological Data |
|---|---|---|
| 213 | 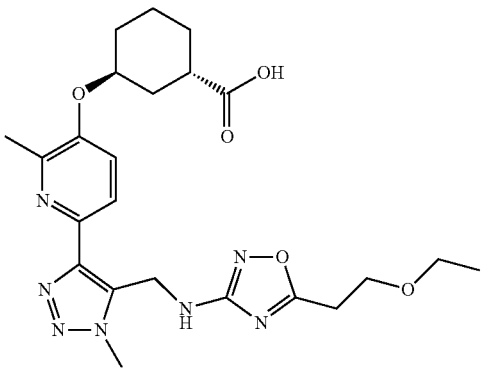 [SMILES: CCOCCc1nc(NCc2c(-c3ccc(O[C@H]4CCC[C@H](C(=O)O)C4)c(C)n3)nnn2C)no1]<br>(1S,3S)-3-((6-(5-(((5-(2-ethoxy-ethyl)-1,2,4-oxadiazol-3-yl)amino) methyl)-1-methyl-1H-1,2,3-triazol-4-yl)-2-methylpyridin-3-yl)oxy)cyclohexane-1-carboxylic acid | LCMS, [M + H]$^+$ = 486.2;<br>$^1$H NMR (500 MHz, CDCl$_3$) δ 8.07 (br d, J = 8.8 Hz, 1H), 7.77 (br d, J = 8.8 Hz, 1H), 4.84 (br s, 1H), 4.71 (s, 2H), 4.26 (s, 3H), 3.81 (t, J = 6.5 Hz, 2H), 3.53 (q, J = 6.9 Hz, 2H), 3.03 (t, J = 6.5 Hz, 2H), 2.95-2.84 (m, 1H), 2.74 (s, 3H), 2.18-1.64 (m, 9H), 1.19 (t, J = 6.9 Hz, 3H);<br>hLPA$_1$ IC$_{50}$ = 98 nM. |
| 214 | 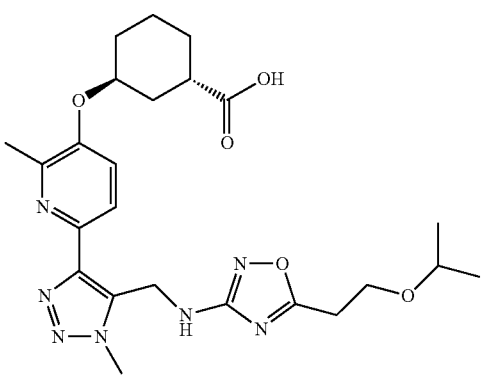 [SMILES: Cc1nc(-c2nnn(C)c2CNc2noc(CCOC(C)C)n2)ccc1O[C@H]1CCC[C@H](C(=O)O)C1]<br>(1S,3S)-3-((6-(5-(((5-(2-isopro-poxyethyl)-1,2,4-oxadiazol-3-yl) amino)methyl)-1-methyl-1H-1,2,3-triazol-4-yl)-2-methylpyridin-3-yl) oxy)cyclohexane-1-carboxylic acid | LCMS, [M + H]$^+$ = 500.2;<br>$^1$H NMR (500 MHz, CDCl$_3$) δ 8.11 (d, J = 8.8 Hz, 1H), 7.95 (d, J = 9.1 Hz, 1H), 4.89 (br s, 1H), 4.71 (s, 2H), 4.25 (s, 3H), 3.81 (t, J = 6.5 Hz, 2H), 3.63 (dt, J = 12.3, 6.1 Hz, 1H), 3.02 (t, J = 6.3 Hz, 2H), 2.94-2.84 (m, 1H), 2.79 (s, 3H), 2.23-2.08 (m, 1H), 2.08-2.00 (m, 1H), 1.99-1.77 (m, 5H), 1.70 (br s, 1H), 1.15 (d, J = 6.3 Hz, 6H);<br>hLPA$_1$ IC$_{50}$ = 246 nM. |

Example 215. (1 S,3 S)-3-((6-(5-(((5-((R)-1-methoxypropyl)-1,2,4-oxadiazol-3-yl)amino) methyl)-1-methyl-1H-1,2,3-triazol-4-yl)-2-methylpyridin-3-yl)oxy)cyclohexane-1-carboxylic acid

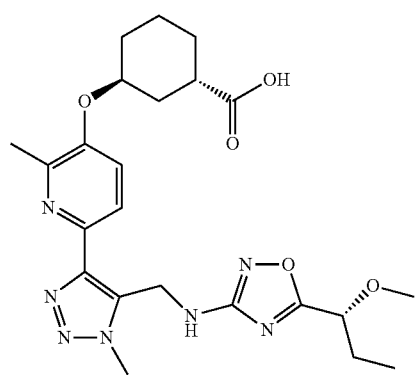

215A. (R)-5-(1-methoxypropyl)-1,2,4-oxadiazol-3-amine

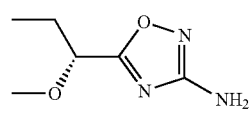

215B. (S)-5-(1-methoxypropyl)-1,2,4-oxadiazol-3-amine

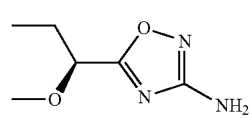

The enantiomers Example 215A (213 mg, 1.36 mmol, 42.6% yield, first eluting peak) and 215B (234 mg, 1.489 mmol, 46.8% yield, 2$^{nd}$ eluting peak) were obtained from (±)-5-(1-methoxypropyl)-1,2,4-oxadiazol-3-amine (500 mg, 3.18 mmol) by chiral SFC separation (Instrument: PIC Solution SFC Prep-200; Column: Chiralpak AD-H, 21×250 mm, 5 μm; Mobile Phase: 10% MeOH/90% CO$_2$; Flow Conditions: 45 mL/min, 150 Bar, 40° C.; Detector Wavelength: 226 nm; Injection Details: 0.4 mL of ~25 mg/mL in MeOH). The absolute stereochemistry of these 2 compounds are arbitrarily assigned.

215A: [α]$^{24}_{589\ nm}$: +92° (1%, MeOH); $^1$H NMR (400 MHz, CDCl$_3$) δ 4.44 (br s, 2H), 4.30 (t, J=6.6 Hz, 1H), 3.44 (s, 3H), 2.02-1.87 (m, 2H), 1.00 (t, J=7.5 Hz, 3H).

215B: [α]$^{24}_{589\ nm}$: −91° (1%, MeOH); $^1$H NMR (400 MHz, CDCl$_3$) δ 4.44 (br s, 2H), 4.30 (t, J=6.6 Hz, 1H), 3.44 (s, 3H), 2.02-1.87 (m, 2H), 1.00 (t, J=7.5 Hz, 3H).

Example 215

A solution of Intermediate 8 (30 mg, 0.084 mmol), Example 215A (20 mg, 0.13 mmol), and AcOH (14 μL, 0.25 mmol) in MeOH (1 mL) was stirred at 65° C. for 2 h, then was cooled to RT. NaBH$_3$CN (10.5 mg, 0.167 mmol) was added. The reaction mixture was stirred at RT for 1 h, then was concentrated in vacuo. The residue was added to 1N aq. NaOH (0.2 mL) in THF (1 mL); the reaction was stirred at RT for 2 h, then was concentrated in vacuo. The crude product was purified by preparative HPLC (Sunfire C18 30×100 mm column; detection at 220 nm; flow rate=40 mL/min; continuous gradient from 0% B to 100% B over 10 min+2 min hold time at 100% B, where A=90:10:0.1 H$_2$O: MeCN:TFA and B=90:10:0.1 MeCN:H$_2$O:TFA) to give the title compound (30 mg, 0.042 mmol, 49.7% yield) as a clear oil. The absolute stereochemistry of the oxadiazole chiral center was not determined, and is arbitrarily assigned. LCMS, [M+H]$^+$=486.3; $^1$H NMR (500 MHz, CDCl$_3$) δ 8.10 (d, J=8.8 Hz, 1H), 7.88 (d, J=8.8 Hz, 1H), 4.87 (br s, 1H), 4.73 (s, 2H), 4.32-4.22 (m, 4H), 3.39 (s, 3H), 2.92-2.84 (m, 1H), 2.77 (s, 3H), 2.19-2.09 (m, 1H), 2.04 (br dd, J=9.1, 4.1 Hz, 1H), 1.99-1.74 (m, 7H), 1.74-1.62 (m, 1H), 0.97 (t, J=7.4 Hz, 3H); hLPA$_1$ IC$_{50}$=154 nM.

Example 216. (1 S,3 S)-3-((6-(5-(((5-((S)-1-methoxypropyl)-1,2,4-oxadiazol-3-yl)amino) methyl)-1-methyl-1H-1,2,3-triazol-4-yl)-2-methylpyridin-3-yl)oxy)cyclohexane-1-carboxylic acid

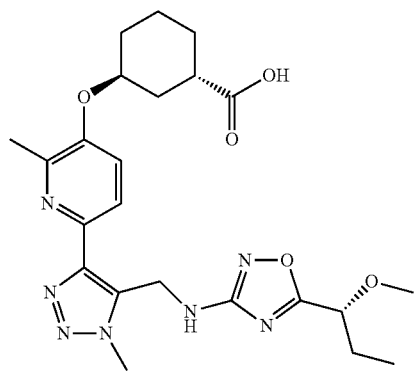

Example 216 was synthesized from Example 215B according to the procedures described for the preparation of Example 215 from Example 215A. LCMS, [M+H]$^+$=486.3; $^1$H NMR (500 MHz, CDCl$_3$) δ 8.10 (d, J=8.8 Hz, 1H), 7.88 (d, J=8.8 Hz, 1H), 4.87 (br s, 1H), 4.73 (s, 2H), 4.32-4.22 (m, 4H), 3.39 (s, 3H), 2.92-2.84 (m, 1H), 2.77 (s, 3H), 2.19-2.09 (m, 1H), 2.04 (br dd, J=9.1, 4.1 Hz, 1H), 1.99-1.74 (m, 7H), 1.74-1.62 (m, 1H), 0.97 (t, J=7.4 Hz, 3H); hLPA$_1$ IC$_{50}$=121 nM.

The following Examples were prepared according to the procedures previously described for the synthesis of Example 215.

| Ex # | Structure & Name | Analytical & Biological Data |
|---|---|---|
| 217 | 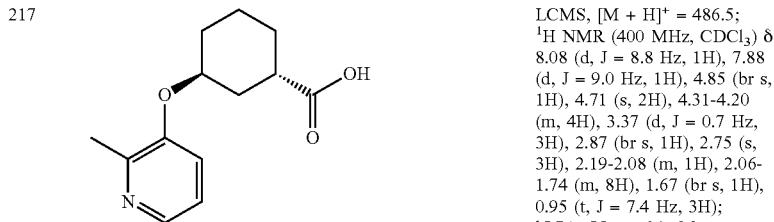<br>(1S,3S)-3-((6-(5-(((5-(1-methoxy-propyl)-1,2,4-oxadiazol-3-yl)amino) methyl)-1-methyl-1H-1,2,3-triazol-4-yl)-2-methylpyridin-3-yl)oxy) cyclo-hexane-1-carboxylic acid<br>Mixture of 2 diastereomers | LCMS, [M + H]$^+$ = 486.5; $^1$H NMR (400 MHz, CDCl$_3$) δ 8.08 (d, J = 8.8 Hz, 1H), 7.88 (d, J = 9.0 Hz, 1H), 4.85 (br s, 1H), 4.71 (s, 2H), 4.31-4.20 (m, 4H), 3.37 (d, J = 0.7 Hz, 3H), 2.87 (br s, 1H), 2.75 (s, 3H), 2.19-2.08 (m, 1H), 2.06-1.74 (m, 8H), 1.67 (br s, 1H), 0.95 (t, J = 7.4 Hz, 3H); hLPA$_1$ IC$_{50}$ = 84 nM. |

| Ex # | Structure & Name | Analytical & Biological Data |
|---|---|---|
| 218 | (1S,3S)-3-((2-methyl-6-(1-methyl-5-(((5-(1-propoxyethyl)-1,2,4-oxadiazol-3-yl)amino)methyl)-1H-1,2,3-triazol-4-yl)pyridin-3-yl)oxy) cyclohexane-1-carboxylic acid<br>Mixture of 2 diastereomers | LCMS, [M + H]⁺ = 500.3;<br>$^1$H NMR (400 MHz, CDCl$_3$) δ 8.08 (d, J = 8.8 Hz, 1H), 7.89 (d, J = 9.0 Hz, 1H), 4.86 (br s, 1H), 4.70 (s, 2H), 4.57 (q, J = 6.6 Hz, 1H), 4.23 (s, 3H), 3.49-3.38 (m, 2H), 2.87 (br s, 1H), 2.76 (s, 3H), 2.21-2.08 (m, 1H), 2.05-1.74 (m, 6H), 1.72-1.48 (m, 6H), 0.89 (t, J = 7.4 Hz, 3H);<br>hLPA$_1$ IC$_{50}$ = 35 nM. |
| 219 | (1S,3S)-3-((2-methyl-6-(1-methyl-5-(((5-((R)-1-propoxyethyl)-1,2,4-oxadiazol-3-yl)amino)methyl)-1H-1,2,3-triazol-4-yl)pyridin-3-yl)oxy) cyclohexane-1-carboxylic acid<br>Diastereomer #1; stereochemistry of the α-methoxy oxadiazole stereocenter is arbitrarily assigned | LCMS, [M + H]⁺ = 500.3;<br>$^1$H NMR (500 MHz, CDCl$_3$) δ 8.06 (d, J = 8.8 Hz, 1H), 7.76 (d, J = 8.8 Hz, 1H), 4.83 (br s, 1H), 4.71 (s, 2H), 4.56 (q, J = 6.9 Hz, 1H), 4.25 (s, 3H), 3.50-3.38 (m, 2H), 2.92-2.85 (m, 1H), 2.73 (s, 3H), 2.16-1.76 (m, 7H), 1.71-1.63 (m, 1H), 1.59 (sxt, J = 7.2 Hz, 2H), 1.53 (d, J = 6.6 Hz, 3H), 0.90 (t, J = 7.4 Hz, 3H);<br>hLPA$_1$ IC$_{50}$ = 63 nM. |
| 220 | 5-((S)-1-propoxyethyl)-1,2,4-oxadiazol-3-yl)amino)methyl)-1H-1,2,3-triazol-4-yl)pyridin-3-yl)oxy) cyclohexane-1-carboxylic acid<br>Diastereomer #2; stereochemistry of the α-methoxy oxadiazole stereocenter is arbitrarily assigned | LCMS, [M + H]⁺ = 500.3;<br>$^1$H NMR (500 MHz, CDCl$_3$) δ 8.06 (d, J = 8.8 Hz, 1H), 7.76 (d, J = 8.8 Hz, 1H), 4.83 (br s, 1H), 4.71 (s, 2H), 4.56 (q, J = 6.9 Hz, 1H), 4.25 (s, 3H), 3.50-3.38 (m, 2H), 2.92-2.85 (m, 1H), 2.73 (s, 3H), 2.16-1.76 (m, 7H), 1.71-1.63 (m, 1H), 1.59 (sxt, J = 7.2 Hz, 2H), 1.53 (d, J = 6.6 Hz, 3H), 0.90 (t, J = 7.4 Hz, 3H);<br>hLPA$_1$ IC$_{50}$ = 160 nM. |

| Ex # | Structure & Name | Analytical & Biological Data |
|---|---|---|
| 221 | 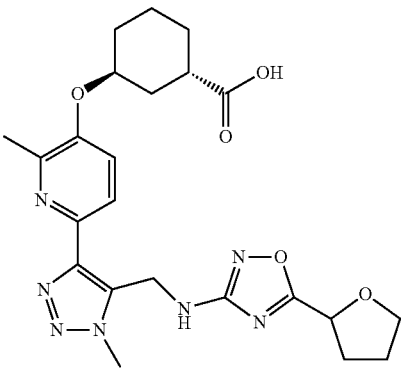 [SMILES: Cc1nc(-c2nnn(C)c2CNc2noc(C3CCCO3)n2)ccc1O[C@H]1CCC[C@H](C(=O)O)C1]<br>(1S,3S)-3-((2-methyl-6-(1-methyl-5-(((5-(tetrahydrofuran-2-yl)-1,2,4-oxadiazol-3-yl)amino)methyl)-1H-1,2,3-triazol-4-yl)pyridin-3-yl)oxy) cyclohexane-1-carboxylic acid<br>Mixture of 2 diastereomers | LCMS, [M + H]$^+$ = 484.2;<br>$^1$H NMR (400 MHz, CDCl$_3$) δ 8.03 (d, J = 8.8 Hz, 1H), 7.69 (d, J = 8.8 Hz, 1H), 5.00 (dd, J = 8.0, 5.2 Hz, 1H), 4.81 (br s, 1H), 4.69 (s, 2H), 4.23 (s, 3H), 4.05-3.88 (m, 2H), 2.86 (br d, J = 4.2 Hz, 1H), 2.69 (s, 3H), 2.40-2.27 (m, 1H), 2.22-1.60 (m, 11H);<br>hLPA$_1$ IC$_{50}$ = 221 nM. |
| 222 | 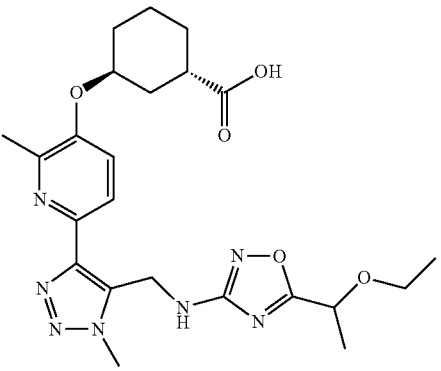 [SMILES: CCOC(C)c1nc(NCc2c(-c3ccc(O[C@H]4CCC[C@H](C(=O)O)C4)c(C)n3)nnn2C)no1]<br>(1S,3S)-3-((6-(5-(((5-(1-ethoxyethyl)-1,2,4-oxadiazol-3-yl)amino)methyl)-1-methyl-1H-1,2,3-triazol-4-yl)-2-methylpyridin-3-yl)oxy)cyclohexane-1-carboxylic acid<br>Mixture of 2 diastereomers | LCMS, [M + H]$^+$ = 486.2;<br>$^1$H NMR (400 MHz, CDCl$_3$) δ 8.06 (d, J = 8.8 Hz, 1H), 7.76 (d, J = 9.0 Hz, 1H), 4.83 (br s, 1H), 4.70 (s, 2H), 4.57 (q, J = 6.8 Hz, 1H), 4.24 (s, 3H), 3.61-3.47 (m, 2H), 2.93-2.82 (m, 1H), 2.72 (s, 3H), 2.17-1.60 (m, 8H), 1.52 (d, J = 6.8 Hz, 3H), 1.20 (td, J = 7.0, 0.7 Hz, 3H);<br>hLPA$_1$ IC$_{50}$ = 92 nM. |
| 223 | 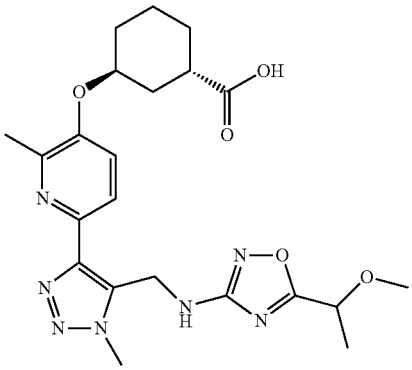<br>(1S,3S)-3-((6-(5-(((5-(1-methoxy-ethyl)-1,2,4-oxadiazol-3-yl)amino) methyl)-1-methyl-1H-1,2,3-triazol-4-yl)-2-methylpyridin-3-yl) oxy)cyclohexane-1-carboxylic acid<br>Mixture of 2 diastereomers | LCMS, [M + H]$^+$ = 472.5;<br>$^1$H NMR (400 MHz, CDCl$_3$) δ 8.07 (d, J = 8.8 Hz, 1H), 7.85 (d, J = 9.0 Hz, 1H), 4.85 (br s, 1H), 4.71 (s, 2H), 4.48 (q, J = 6.8 Hz, 1H), 4.23 (s, 3H), 3.38 (s, 3H), 2.92-2.83 (m, 1H), 2.75 (s, 3H), 2.18-1.97 (m, 2H), 1.96-1.74 (m, 5H), 1.73-1.61 (m, 1H), 1.52 (d, J = 6.6 Hz, 3H);<br>hLPA$_1$ IC$_{50}$ = 466 nM. |

| Ex # | Structure & Name | Analytical & Biological Data |
|---|---|---|
| 224 | 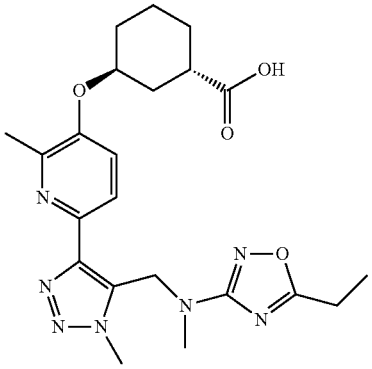 [SMILES: CCc1nc(N(C)Cc2c(-c3ccc(O[C@H]4CCC[C@H](C(=O)O)C4)c(C)n3)nnn2C)no1]<br>(1S,3S)-3-((6-(5-(((5-ethyl-1,2,4-oxadiazol-3-yl)(methyl)amino) methyl)-1-methyl-1H-1,2,3-triazol-4-yl)-2-methylpyridin-3-yl)oxy)cyclohexane-1-carboxylic acid | LCMS, [M + H]$^+$ = 456.4;<br>$^1$H NMR (500 MHz, DMSO-d$_6$) δ 7.84 (br d, J = 8.9 Hz, 1H), 7.47 (d, J = 8.5 Hz, 1H), 5.13 (s, 2H), 4.77 (br s, 1H), 4.00 (s, 3H), 2.85-2.72 (m, 5H), 2.67-2.57 (m, 1H), 2.01 (br d, J = 13.7 Hz, 1H), 1.89-1.72 (m, 3H), 1.66-1.42 (m, 4H), 1.22 (t, J = 7.6 Hz, 3H), (One CH$_3$— are not observed due to water-suppression);<br>hLPA$_1$ IC$_{50}$ = 2715 nM. |
| 225 | 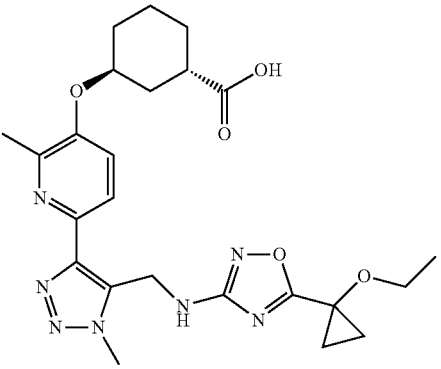 [SMILES: CCOC1(c2nc(NCc3c(-c4ccc(O[C@H]5CCC[C@H](C(=O)O)C5)c(C)n4)nnn3C)no2)CC1]<br>(1S,3S)-3-((6-(5-(((5-(1-ethoxy-cyclopropyl)-1,2,4-oxadiazol-3-yl)amino)methyl)-1-methyl-1H-1,2,3-triazol-4-yl)-2-methylpyridin-3-yl)oxy)cyclohexane-1-carboxylic acid | LCMS, [M + H]$^+$ = 498.3;<br>$^1$H NMR (400 MHz, CDCl$_3$) δ 8.10 (d, J = 8.8 Hz, 1H), 7.98 (d, J = 9.0 Hz, 1H), 4.88 (br s, 1H), 4.67 (s, 2H), 4.21 (s, 3H), 3.64 (q, J = 7.0 Hz, 2H), 2.91-2.82 (m, 1H), 2.78 (s, 3H), 2.20-2.08 (m, 1H), 2.06-1.97 (m, 1H), 1.96-1.61 (m, 6H), 1.49-1.35 (m, 4H), 1.18 (t, J = 7.0 Hz, 3H);<br>hLPA$_1$ IC$_{50}$ = 1316 nM. |
| 226 | 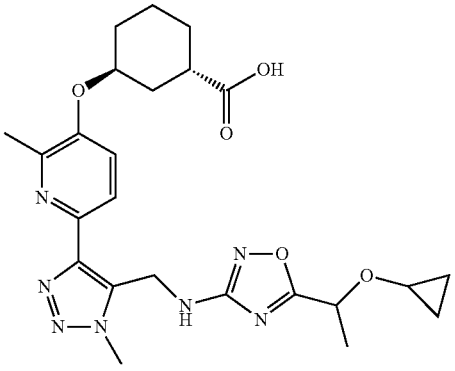<br>(1S,3S)-3-((6-(5-(((5-(1-cyclopro-poxyethyl)-1,2,4-oxadiazol-3-yl) amino)methyl)-1-methyl-1H-1,2,3-triazol-4-yl)-2-methylpyridin-3-yl) oxy)cyclohexane-1-carboxylic acid<br>Mixture of 2 diastereomers | LCMS, [M + H]$^+$ = 498.3;<br>$^1$H NMR (400 MHz, CDCl$_3$) δ 8.08 (br d, J = 8.4 Hz, 1H), 7.86 (br d, J = 8.8 Hz, 1H), 4.86 (br s, 1H), 4.76-4.66 (m, 3H), 4.24 (s, 3H), 3.41 (br d, J = 2.2 Hz, 1H), 2.88 (br s, 1H), 2.76 (s, 3H), 2.22-1.75 (m, 8H), 1.68 (br s, 1H), 1.52 (br d, J = 6.8 Hz, 3H), 0.65-0.46 (m, 4H);<br>hLPA$_1$ IC$_{50}$ = 123 nM. |

Example 227. (1S,3S)-3-((6-(5-((5-(3,3-difluorobutyl)-1,2,4-oxadiazol-3-yl)methyl)-1-methyl-1H-1,2,3-triazol-4-yl)-2-methylpyridin-3-yl)oxy)cyclohexane-1-carboxylic acid

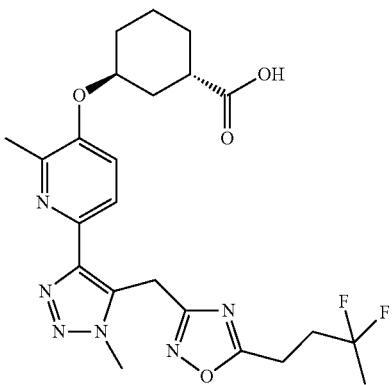 [SMILES: Cc1nc(-c2nnn(C)c2Cc2noc(CCC(C)(F)F)n2)ccc1O[C@H]1CCC[C@H](C(=O)O)C1]

227A. Methyl (1S,3S)-3-((6-(5-((Z)-2-amino-2-(hydroxyimino)ethyl)-1-methyl-1H-1,2,3-triazol-4-yl)-2-methylpyridin-3-yl)oxy)cyclohexane-1-carboxylate

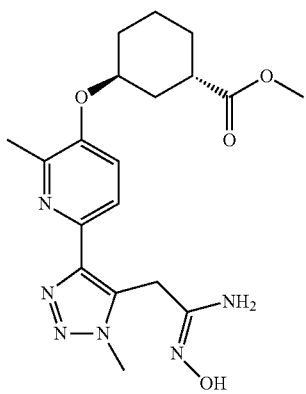

A solution of methyl (1S,3S)-3-((6-(5-(cyanomethyl)-1-methyl-1H-1,2,3-triazol-4-yl)-2-methylpyridin-3-yl)oxy)cyclohexane-1-carboxylate (synthesized from Intermediate 5 by displacement with NaCN analogous to the synthesis of Intermediate 3A from Intermediate 2; 102 mg, 0.28 mmol), NH$_2$OH·HCl (24 mg, 0.35 mmol) and NaHCO$_3$ (29.0 mg, 0.35 mmol) in EtOH (2 mL) was heated to 75° C. for 18 h, then was cooled to RT and concentrated in vacuo to give the title compound as white solid (120 mg, 90% purity, 97% yield) LCMS(+) MS=403.1, $^1$H NMR (CDCl$_3$) δ: 8.62-9.11 (m, 2H), 7.92 (d, J=8.6 Hz, 1H), 7.57 (d, J=8.8 Hz, 1H), 4.83 (br s, 1H), 4.23 (s, 2H), 4.16 (s, 3H), 3.74 (s, 3H), 2.86 (dt, J=8.8, 4.6 Hz, 1H), 2.61 (s, 3H), 1.87-2.20 (m, 4H), 1.60-1.85 (m, 4H).

227B. Methyl (1S,3S)-3-((6-(5-((Z)-2-(4,4-difluoropentanamido)-2-(hydroxyimino)ethyl)-1-methyl-1H-1,2,3-triazol-4-yl)-2-methylpyridin-3-yl)oxy)cyclohexane-1-carboxylate

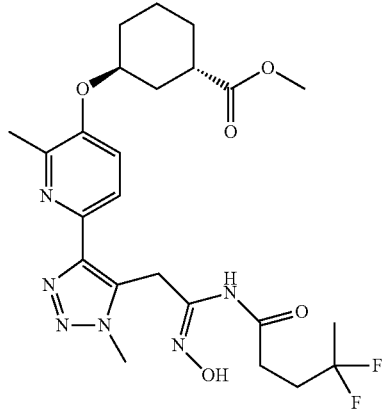 [SMILES: COC(=O)[C@H]1CCC[C@H](Oc2ccc(-c3nnn(C)c3C/C(=N/O)NC(=O)CCC(C)(F)F)nc2C)C1]

To a mixture of 227A (18 mg, 0.045 mmol), 4,4-difluoropentanoic acid (6.2 mg, 0.045 mmol) and DIEA (8 μL, 0.045 mmol) in MeCN (1.5 mL) was added HATU (17.0 mg, 0.045 mmol). The reaction mixture was stirred at RT 18 h, then was concentrated in vacuo. The crude product was chromatographed (SiO$_2$; continuous gradient from 0% to 15% MeOH in DCM over 20 min) to give the title compound (20 mg, 0.038 mmol, 86% yield) LCMS(+) MS=523.0, $^1$H NMR (CDCl$_3$) δ: 8.12-8.45 (m, 1H), 7.86 (d, J=8.6 Hz, 1H), 7.22 (d, J=8.6 Hz, 1H), 4.92-5.39 (m, 1H), 4.57-4.73 (m, 1H), 4.09 (s, 3H), 3.84 (s, 2H), 3.63 (s, 3H), 2.75-2.81 (m, 1H), 2.53-2.60 (m, 2H), 2.43 (s, 3H), 2.06-2.29 (m, 5H), 1.81-1.97 (m, 3H), 1.60-1.63 (m, 2H), 1.33-1.43 (m, 3H).

227C. Methyl (1S,3S)-3-((6-(5-((5-(3,3-difluorobutyl)-1,2,4-oxadiazol-3-yl)methyl)-1-methyl-1H-1,2,3-triazol-4-yl)-2-methylpyridin-3-yl)oxy)cyclohexane-1-carboxylate

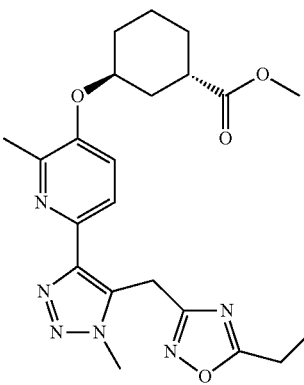

To a mixture of 227B (20 mg, 0.038 mmol) in toluene (1.5 mL) and HOAc (50 μL) was heated at 105° C.; for 6 h, then was cooled to RT and concentrated in vacuo. The crude product was chromatographed (SiO$_2$; continuous gradient from 0% to 100% EtOAc in hexanes over 20 min) to give the title compound (14 mg, 0.028 mmol, 72.5% yield) as a colorless oil. MS(+) MS=505.0; $^1$H NMR (CDCl$_3$) δ: 7.98 (d, 1H), 7.19 (d, 1H), 4.87 (s, 2H), 4.67-4.72 (m, 1H), 4.10 (s, 3H), 3.70 (s, 3H), 3.02-3.13 (m, 2H), 2.83 (s, 3H), 2.48 (s, 3H), 1.87-2.04 (m, 4H), 1.65 (d, 5H), 1.29 (br s, 2H).

Example 227

To a solution of 227C (14 mg, 0.028 mmol) in THF was added 2M aq. LiOH (0.069 mL, 0.14 mmol). The reaction mixture was stirred at RT 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-µm particles; Guard Column: Waters XBridge C18, 19×10 mm, 5-µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound as the TFA salt. (5.2 mg, 0.086 mmol, 31% yield) LCMS(+) MS=491.0; $^1$H NMR (CDCl$_3$) δ: 8.01 (d, 1H), 7.72 (br d, 1H), 7.58-7.64 (m, 1H), 4.84 (br s, 1H), 4.55 (s, 2H), 4.18 (s, 3H), 3.05-3.13 (m, 2H), 2.93 (br d, 1H), 2.73 (s, 3H), 2.29-2.47 (m, 2H), 2.10 (br s, 2H), 1.89-2.01 (m, 2H), 1.77-1.89 (m, 3H), 1.67 (m, 3H); hLPA$_1$ IC$_{50}$=2 nM The Examples listed in the following table were prepared by using the same synthetic sequence and the same intermediates as described for the synthesis of Example 227.

| Ex # | Structure & Name | Analytical & Biological Data |
| --- | --- | --- |
| 228 | 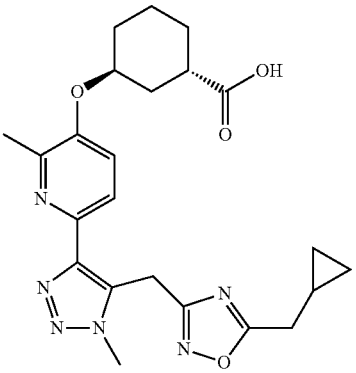 [SMILES: Cc1nc(-c2nnn(C)c2Cc2noc(CC3CC3)n2)ccc1O[C@H]1CCC[C@H](C(=O)O)C1]<br>(1S,3S)-3-((6-(5-((5-(cyclopropyl methyl)-1,2,4-oxadiazol-3-yl) methyl)-1-methyl-1H-1,2,3-triazol-4-yl)-2-methylpyridin-3-yl)oxy)cyclohexane-1-carboxylic acid | LCMS, [M + H]$^+$ = 453.0;<br>$^1$H NMR (CDCl$_3$) δ: 9.63-10.87 (m, 1H), 8.04 (d, 1H), 7.68 (d, 1H), 4.82 (br s, 1H), 4.57 (s, 2H), 4.18 (s, 3H), 2.89 (br s, 1H), 2.78 (d, 2H), 2.70 (s, 3H), 2.04-2.12 (m, 2H), 1.88-2.01 (m, 2H), 1.73-1.86 (m, 3H), 1.58-1.72 (m, 1H), 1.07-1.19 (m, 1H), 0.58-0.69 (m, 2H), 0.24-0.33 (m, 2H);<br>hLPA$_1$ IC$_{50}$ = 19 nM. |
| 229 | 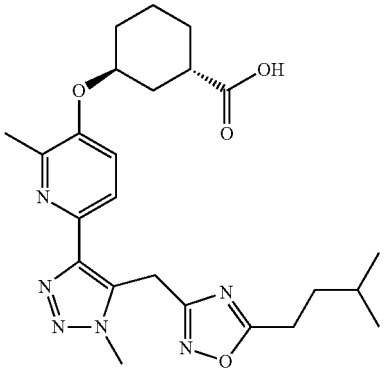 [SMILES: Cc1nc(-c2nnn(C)c2Cc2noc(CCC(C)C)n2)ccc1O[C@H]1CCC[C@H](C(=O)O)C1]<br>(1S,3S)-3-((6-(5-((5-isopentyl-1,2,4-oxadiazol-3-yl)methyl)-1-methyl-1H-1,2,3-triazol-4-yl)-2-methylpyridin-3-yl)oxy)cyclohexane-1-carboxylic acid | LCMS, [M + H]$^+$ = 469.2;<br>$^1$H NMR (CDCl$_3$) δ: 8.61-8.63 (m, 1H), 8.45 (br s, 1H), 8.03 (d, J = 8.8 Hz, 1H), 7.72 (d, J = 8.8 Hz, 1H), 4.83 (br s, 1H), 4.54 (s, 2H), 4.17 (s, 3H), 2.79-2.99 (m, 3H), 2.71 (s, 3H), 2.02-2.20 (m, 2H), 1.74-2.01 (m, 5H), 1.63-1.72 (m, 3H), 0.95 (d, J = 6.4 Hz, 6H);<br>hLPA$_1$ IC$_{50}$ = 11 nM. |

| Ex # | Structure & Name | Analytical & Biological Data |
|---|---|---|
| 230 | 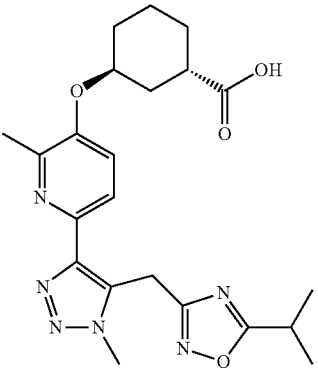 [SMILES: Cc1nc(-c2nnn(C)c2Cc2noc(C(C)C)n2)ccc1O[C@H]1CCC[C@H](C(=O)O)C1]<br>(1S,3S)-3-((6-(5-((5-isopropyl-1,2,4-oxadiazol-3-yl)methyl)-1-methyl-1H-1,2,3-triazol-4-yl)-2-methylpyridin-3-yl)oxy)cyclohexane-1-carboxylic acid | LCMS, $[M + H]^+$ = 441.1;<br>$^1$H NMR (400 MHz, CDCl$_3$)<br>δ = 9.30 (br s, 1H), 8.10 (d, J = 8.8 Hz, 1H), 7.87 (d, J = 9.0 Hz, 1H), 4.87 (br s, 1H), 4.44 (s, 2H), 4.20 (s, 3H), 3.21 (spt, J = 7.0 Hz, 1H), 2.94-2.84 (m, 1H), 2.78 (s, 3H), 2.22-2.00 (m, 2H), 1.99-1.76 (m, 5H), 1.69 (br d, J = 6.2 Hz, 1H), 1.38 (d, J = 7.0 Hz, 6H);<br>hLPA$_1$ IC$_{50}$ = 95 nM. |
| 231 | 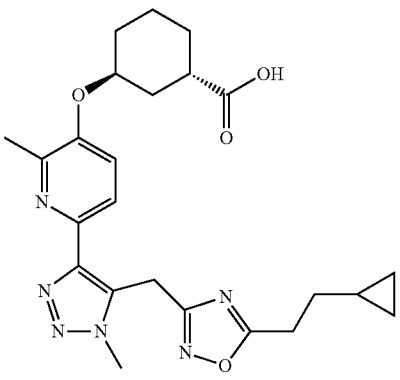 [SMILES: Cc1nc(-c2nnn(C)c2Cc2noc(CCC3CC3)n2)ccc1O[C@H]1CCC[C@H](C(=O)O)C1]<br>(1S,3S)-3-((6-(5-((5-(2-cyclopropyl ethyl)-1,2,4-oxadiazol-3-yl)methyl)-1-methyl-1H-1,2,3-triazol-4-yl)-2-methylpyridin-3-yl)oxy)cyclohexane-1-carboxylic acid | LCMS, $[M + H]^+$ = 467.2.1;<br>$^1$H NMR (CDCl$_3$) δ: 7.98 (d, 1H), 7.71 (d, 1H), 7.52 (br s, 1H), 4.78 (br s, 1H), 4.44 (s, 2H), 4.12 (s, 3H), 2.91 (m, 2H), 2.79-2.87 (m, 1H), 2.67 (s, 3H), 1.96-2.15 (m, 2H), 1.69-1.95 (m, 5H), 1.62 (m, 3H), 0.58-0.75 (m, 1H), 0.36-0.45 (m, 2H), −0.07-0.08 (m, 2H);<br>hLPA$_1$ IC$_{50}$ = 15 nM. |
| 232 | 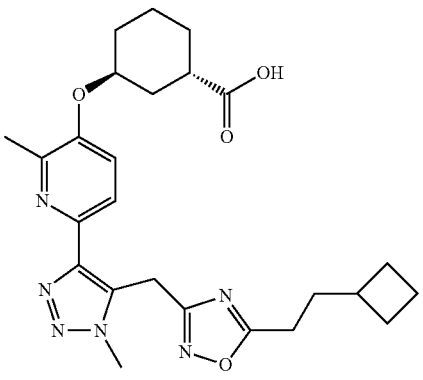 [SMILES: Cc1nc(-c2nnn(C)c2Cc2noc(CCC3CCC3)n2)ccc1O[C@H]1CCC[C@H](C(=O)O)C1]<br>(1S,3S)-3-((6-(5-((5-(2-cyclobutyl ethyl)-1,2,4-oxadiazol-3-yl)methyl)-1-methyl-1H-1,2,3-triazol-4-yl)-2-methylpyridin-3-yl)oxy)cyclohexane-1-carboxylic acid | LCMS, $[M + H]^+$ = 481.1;<br>$^1$H NMR (CDCl$_3$) δ: 8.03 (d, 1H), 7.73 (d, 1H), 7.54 (br s, 1H), 4.83 (br s, 1H), 4.53 (s, 2H), 4.18 (s, 3H), 2.86-2.94 (m, 1H), 2.68-2.82 (m, 5H), 2.22-2.37 (m, 1H), 1.75-2.17 (m, 13H), 1.54-1.74 (m, 3H);<br>hLPA$_1$ IC$_{50}$ = 8 nM. |

| Ex # | Structure & Name | Analytical & Biological Data |
|---|---|---|
| 233 | 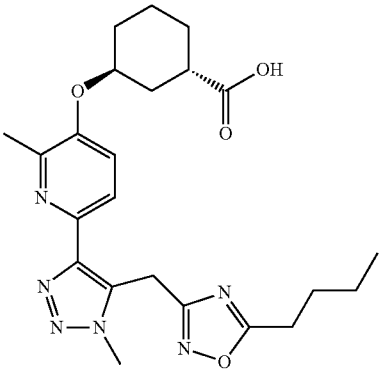 [SMILES: CCCCc1nc(Cc2c(-c3ccc(O[C@H]4CCC[C@H](C(=O)O)C4)c(C)n3)nnn2C)no1]<br>(1S,3S)-3-((6-(5-((5-butyl-1,2,4-oxadiazol-3-yl)methyl)-1-methyl-1H-1,2,3-triazol-4-yl)-2-methylpyridin-3-yl)oxy)cyclohexane-1-carboxylic acid | LCMS, [M + H]$^+$ = 455.2;<br>$^1$H NMR (CDCl$_3$) δ: 10.07 (br s, 1H), 8.08 (d, 1H), 7.86 (d, 1H), 4.87 (br s, 1H), 4.45 (s, 2H), 4.18 (s, 3H), 2.88 (m, 3H), 2.77 (s, 3H), 2.01-2.21 (m, 2H), 1.64-2.00 (m, 8H), 1.41 (m, 2H), 0.95 (m, 3H);<br>hLPA$_1$ IC$_{50}$ = 8 nM. |
| 234 | 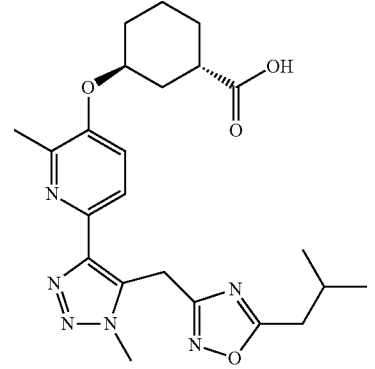 [SMILES: Cc1nc(-c2nnn(C)c2Cc2noc(CC(C)C)n2)ccc1O[C@H]1CCC[C@H](C(=O)O)C1]<br>(1S,3S)-3-((6-(5-((5-isobutyl-1,2,4-oxadiazol-3-yl)methyl)-1-methyl-1H-1,2,3-triazol-4-yl)-2-methylpyridin-3-yl)oxy)cyclohexane-1-carboxylic acid | LCMS, [M + H]$^+$ = 455.1;<br>$^1$H NMR (CDCl$_3$) δ: 10.53 (br s, 1H), 8.09 (d, J = 8.8 Hz, 1H), 7.89 (d, J = 9.0 Hz, 1H), 4.88 (br s, 1H), 4.44 (s, 2H), 4.20 (s, 3H), 2.86-2.95 (m, 1H), 2.74-2.82 (m, 5H), 2.04-2.30 (m, 3H), 1.75-2.02 (m, 5H), 1.69 (br d, J = 6.4 Hz, 1H), 1.00 (d, J = 6.6 Hz, 6H);<br>hLPA$_1$ IC$_{50}$ = 52 nM. |
| 235 | 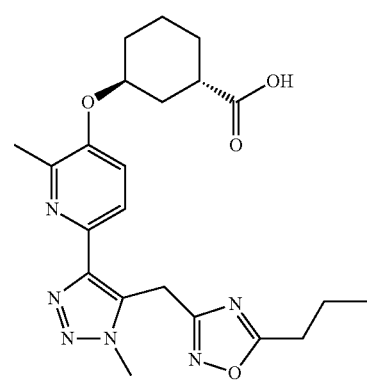 [SMILES: CCCc1nc(Cc2c(-c3ccc(O[C@H]4CCC[C@H](C(=O)O)C4)c(C)n3)nnn2C)no1]<br>(1S,3S)-3-((2-methyl-6-(1-methyl-5-((5-propyl-1,2,4-oxadiazol-3-yl)methyl)-1H-1,2,3-triazol-4-yl)pyridin-3-yl)oxy)cyclohexane-1-carboxylic acid | LCMS, [M + H]$^+$ = 441.1;<br>$^1$H NMR (CDCl$_3$) δ: 10.63 (br s, 1H), 8.11 (d, J = 8.8 Hz, 1H), 7.90 (d, J = 8.8 Hz, 1H), 4.89 (br s, 1H), 4.43 (s, 2H), 4.19 (s, 3H), 2.82-2.97 (m, 3H), 2.79 (s, 3H), 2.03-2.28 (m, 2H), 1.77-2.00 (m, 7H), 1.70 (br s, 1H), 1.02 (t, J = 7.5 Hz, 3H);<br>hLPA$_1$ IC$_{50}$ = 59 nM. |

| Ex # | Structure & Name | Analytical & Biological Data |
|---|---|---|
| 236 | 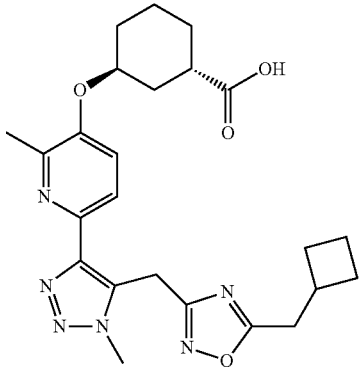 [SMILES: Cc1nc(-c2nnn(C)c2Cc2noc(CC3CCC3)n2)ccc1O[C@H]1CCC[C@H](C(=O)O)C1]<br>(1S,3S)-3-((6-(5-(((5-(cyclobutyl-methyl)-1,2,4-oxadiazol-3-yl) methyl)-1-methyl-1H-1,2,3-triazol-4-yl)-2-methylpyridin-3-yl)oxy) cyclohexane-1-carboxylic acid | LCMS, $[M + H]^+$ = 467.1;<br>$^1$H NMR (CDCl$_3$) δ: 10.78 (br s, 1H), 8.09 (d, J = 8.8 Hz, 1H), 7.88 (d, J = 8.8 Hz, 1H), 4.88 (br s, 1H), 4.43 (s, 2H), 4.18 (s, 3H), 2.97 (d, J = 7.7 Hz, 2H), 2.84-2.93 (m, 1H), 2.70-2.82 (m, 4H), 2.01-2.29 (m, 4H), 1.57-1.98 (m, 10H);<br>hLPA$_1$ IC$_{50}$ = 28 nM. |
| 237 | 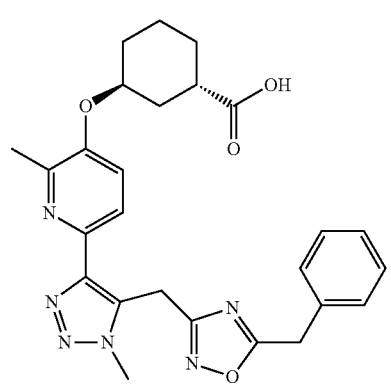 [SMILES: Cc1nc(-c2nnn(C)c2Cc2noc(Cc3ccccc3)n2)ccc1O[C@H]1CCC[C@H](C(=O)O)C1]<br>(1S,3S)-3-((6-(5-(((5-benzyl-1,2,4-oxadiazol-3-yl)methyl)-1-methyl-1H-1,2,3-triazol-4-yl)-2-methylpyridin-3-yl)oxy)cyclohexane-1-carboxylic acid | LCMS, $[M + H]^+$ = 489.0;<br>$^1$H NMR (CDCl$_3$) δ: 10.04-10.92 (m, 1H), 8.09 (d, J = 8.8 Hz, 1H), 7.91 (s, 1H), 7.32-7.37 (m, 3H), 7.30 (s, 1H), 7.28 (br s, 1H), 4.88 (br s, 1H), 4.39 (s, 2H), 4.23 (s, 2H), 4.17 (s, 3H), 2.81-2.94 (m, 1H), 2.69 (s, 3H), 2.05-2.20 (m, 2H), 1.77-2.00 (m, 5H), 1.70 (br s, 1H);<br>hLPA$_1$ IC$_{50}$ = 8 nM. |
| 238 | 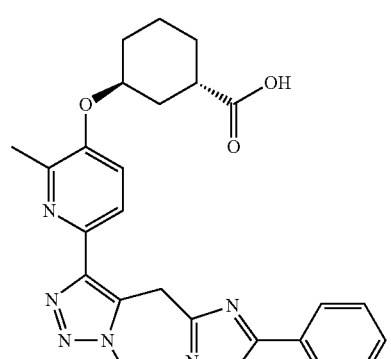<br>(1S,3S)-3-((2-methyl-6-(1-methyl-5-((5-phenyl-1,2,4-oxadiazol-3-yl) methyl)-1H-1,2,3-triazol-4-yl) pyridin-3-yl)oxy)cyclohexane-1-carboxylic acid | LCMS, $[M + H]^+$ = 475.0;<br>$^1$H NMR (CDCl$_3$) δ: 7.92-7.99 (m, 3H), 7.60 (d, J = 8.8 Hz, 1H), 7.49-7.56 (m, 1H), 7.39-7.47 (m, 2H), 4.71 (br s, 1H), 4.55 (s, 2H), 4.14 (s, 3H), 2.80 (br d, J = 3.7 Hz, 1H), 2.61 (s, 3H), 1.92-2.12 (m, 2H), 1.77-1.91 (m, 2H), 1.64-1.77 (m, 3H), 1.49-1.62 (m, 1H);<br>hLPA$_1$ IC$_{50}$ = 161 nM. |

| Ex # | Structure & Name | Analytical & Biological Data |
|---|---|---|
| 239 | 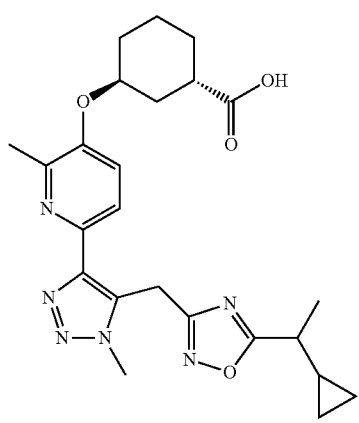 [SMILES: Cc1nc(-c2nnn(C)c2Cc2noc(C(C)C3CC3)n2)ccc1O[C@H]1CCC[C@H](C(=O)O)C1]<br>(1S,3S)-3-((6-(5-((5-(1-cyclopropyl-ethyl)-1,2,4-oxadiazol-3-yl)methyl)-1-methyl-1H-1,2,3-triazol-4-yl)-2-methylpyridin-3-yl)oxy)cyclohexane-1-carboxylic acid; mixture of diastereomers | LCMS, [M + H]$^+$ = 467.2;<br>$^1$H NMR (DMSO-d$_6$) δ: 7.59 (d, J = 8.5 Hz, 1H), 7.21 (d, J = 8.9 Hz, 1H), 4.57 (s, 2H), 4.51 (br s, 1H), 3.82 (s, 2H), 2.32-2.40 (m, 1H), 2.30 (s, 1H), 2.22-2.25 (m, 1H), 2.11 (s, 3H), 1.74 (br d, J = 12.5 Hz, 1H), 1.47-1.64 (m, 3H), 1.18-1.42 (m, 4H), 1.08 (d, J = 7.0 Hz, 3H), 0.62-0.81 (m, 1H), 0.14-0.36 (m, 2H), −0.09-0.06 (m, 2H);<br>hLPA$_1$ IC$_{50}$ = 28 nM. |
| 240 | 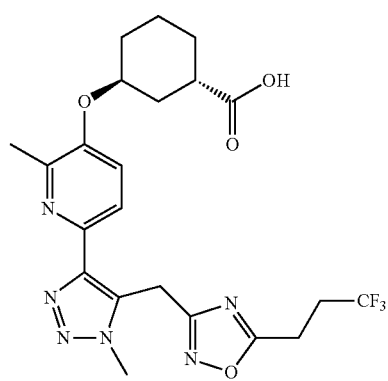 [SMILES: Cc1nc(-c2nnn(C)c2Cc2noc(CCC(F)(F)F)n2)ccc1O[C@H]1CCC[C@H](C(=O)O)C1]<br>(1S,3S)-3-((2-methyl-6-(1-methyl-5-((5-(3,3,3-trifluoropropyl)-1,2,4-oxadiazol-3-yl)methyl)-1H-1,2,3-triazol-4-yl)pyridin-3-ypoxy)cyclohexane-1-carboxylic acid | LCMS, [M + H]$^+$ = 495.0;<br>$^1$H NMR (DMSO-d$_6$) δ: 7.85 (d, J = 8.5 Hz, 1H), 7.46 (d, J = 8.5 Hz, 1H), 4.87 (s, 2H), 4.76 (br s, 1H), 4.04 (s, 3H), 3.12-3.25 (m, 2H), 2.72-2.87 (m, 2H), 2.58-2.68 (m, 1H), 2.38 (s, 3H), 2.00 (br d, J = 13.7 Hz, 1H), 1.73-1.91 (m, 3H), 1.41-1.70 (m, 4H);<br>hLPA$_1$ IC$_{50}$ = 61 nM. |

Example 241. (1S,3S)-3-((6-(5-((3-isopentyl-1,2,4-oxadiazol-5-yl)methyl)-1-methyl-1H-1,2,3-triazol-4-yl)-2-methylpyridin-3-yl)oxy)cyclohexane-1-carboxylic acid

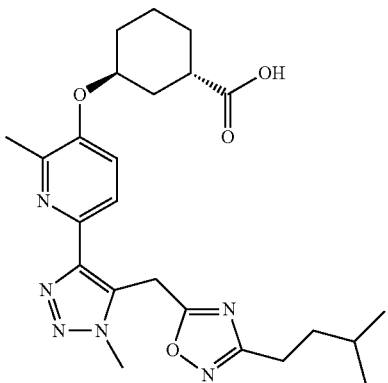 [SMILES: Cc1nc(-c2nnn(C)c2Cc2nc(CCC(C)C)no2)ccc1O[C@H]1CCC[C@H](C(=O)O)C1]

241A. 2-(4-(5-(((1S,3S)-3-(methoxycarbonyl)cyclohexyl)oxy)-6-methylpyridin-2-yl)-1-methyl-1H-1,2,3-triazol-5-yl)acetic acid

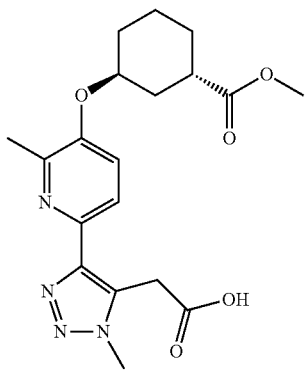

To a RT mixture of Example 73B (80 mg, 0.22 mmol), 2M 2-methyl-2-butene in THF (859 µL, 1.72 mmol), and NaH$_2$PO$_4$ (129 mg, 1.07 mmol) in t-BuOH (2 mL)/water (0.5 mL) was added NaClO$_2$ (48.6 mg, 0.43 mmol). The reaction mixture was stirred at RT for 18 h, then was poured into brine and extracted with EtOAc (3×5 mL). The combined organic extracts were washed with brine (5 mL), dried (Na$_2$SO$_4$) and concentrated in vacuo to give the title compound (72 mg, 0.19 mmol, 86% yield). LCMS(+) MS=389.1.

241B. Methyl (1S,3S)-3-((6-(5-(2-((E)-N'-hydroxy-4-methylpentanimidamido)-2-oxoethyl)-1-methyl-1H-1,2,3-triazol-4-yl)-2-methyl pyridin-3-yl)oxy)cyclohexane-1-carboxylate

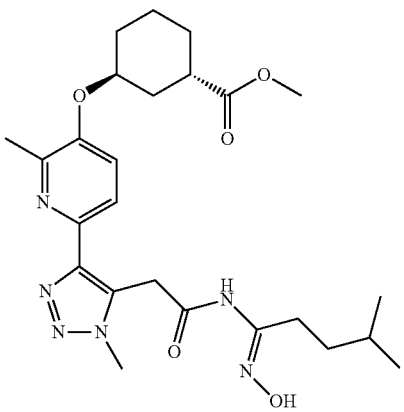 [SMILES: COC(=O)[C@H]1CCC[C@H](Oc2ccc(-c3nnn(C)c3CC(=O)N/C(CCC(C)C)=N/O)nc2C)C1]

To a mixture of 241A (15 mg, 0.039 mmol), (Z)—N'-hydroxy-4-methylpentan-imidamide (5 mg, 0.039 mmol) and iPr$_2$NEt (14 µL, 0.077 mmol) in MeCN (2 mL) was added HATU (14.7 mg, 0.039 mmol). The reaction mixture was stirred at RT for 18 h, then was concentrated in vacuo. The crude product was chromatographed (SiO$_2$; continuous gradient from 0% to 100% EtOAc in hexane over 20 min) to give the title compound (12 mg, 0.024 mmol, 62.1% yield). LCMS [M+H]$^+$=501.1.

241C. Methyl (1S,3S)-3-((6-(5-((3-isopentyl-1,2,4-oxadiazol-5-yl)methyl)-1-methyl-1H-1,2,3-triazol-4-yl)-2-methylpyridin-3-yl)oxy)cyclohexane-1-carboxylate

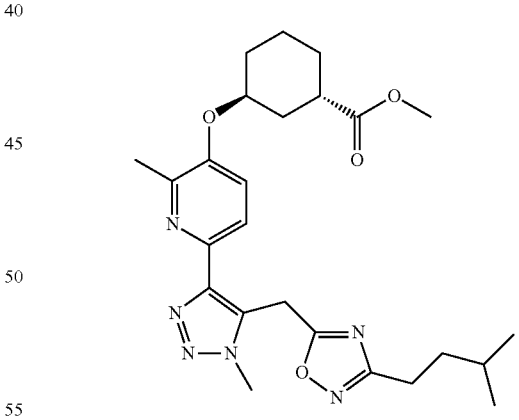

A mixture of Example 241B (12 mg, 0.024 mmol) in toluene (1 mL)/HOAc (0.05 mL) was heated at 100° C. for 18 h, then was concentrated in vacuo. The crude product was chromatographed (SiO$_2$; continuous gradient from 0% to 100% EtOAc in hexanes over 20 min) to give title compound (6 mg, 0.012 mmol, 52% yield), $^1$H NMR (CDCl$_3$) δ: 8.00 (d, J=8.1 Hz, 1H), 7.20 (d, J=8.6 Hz, 1H), 4.99 (d, J=2.2 Hz, 2H), 4.67-4.73 (m, 1H), 4.12 (s, 3H), 3.71 (s, 3H), 2.78-2.90 (m, 1H), 2.66-2.73 (m, 2H), 2.46 (s, 3H), 2.10-2.21 (m, 1H), 1.85-2.07 (m, 3H), 1.70-1.82 (m, 1H), 1.60 (br d, J=4.6 Hz, 4H), 1.53-1.58 (m, 1H), 0.93 (d, J=6.6 Hz, 6H).

Example 241

To a solution of 241C (6 mg, 0.012 mmol) in THF (1 mL) was added 2M aq. LiOH (31 µL, 0.062 mmol). The reaction mixture was stirred at RT for 18 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-µm particles; Guard Column: Waters XBridge C18, 19×10 mm, 5 µm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound as TFA salt (3.5 mg, 0.006 mmol, 47.4% yield). LCMS, [M+H]$^+$=469.1; $^1$H NMR (CDCl$_3$) δ: 7.96 (d, J=8.6 Hz, 1H), 7.68 (d, J=8.8 Hz, 1H), 4.82 (br s, 1H), 4.74 (s, 2H), 4.18 (s, 3H), 2.92 (br d, J=3.7 Hz, 1H), 2.71 (br d, J=7.7 Hz, 2H), 2.68 (s, 3H), 2.05-2.17 (m, 2H), 1.90-2.04 (m, 2H), 1.77-1.89 (m, 3H), 1.69 (br d, J=5.7 Hz, 1H), 1.59 (dd, J=7.4, 4.5 Hz, 3H), 0.94 (d, J=6.2 Hz, 6H); hLPA$_1$ IC$_{50}$=33 nM.

The Examples listed in the following table were prepared by using the same synthetic sequence and the same intermediates as described for the synthesis of Example 241.

| Ex # | Structure & Name | Analytical & Biological Data |
|---|---|---|
| 242 | 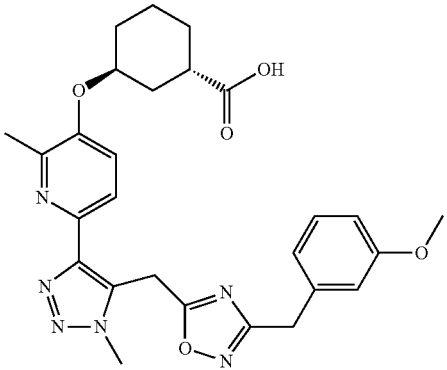<br>(1S,3S)-3-((6-(5-((3-(3-methoxy-benzyl)-1,2,4-oxadiazol-5-yl) methyl)-1-methyl-1H-1,2,3-triazol-4-yl)-2-methylpyridin-3-yl)oxy) cyclohexane-1-carboxylic acid | LCMS, [M + H]$^+$ = 519.1; $^1$H NMR (CDCl$_3$) δ: 7.91 (d, J = 8.8 Hz, 1H), 7.48 (d, J = 8.8 Hz, 1H), 7.18-7.26 (m, 1H), 6.78-6.93 (m, 3H), 4.80 (d, J = 1.3 Hz, 2H), 4.76 (br d, J = 4.8 Hz, 1H), 4.12 (s, 3H), 4.00 (s, 2H), 3.79 (s, 3H), 2.86-2.96 (m, 1H), 2.56 (s, 3H), 1.88-2.16 (m, 4H), 1.64-1.83 (m, 4H); hLPA$_1$ IC$_{50}$ = 2015 nM. |
| 243 | 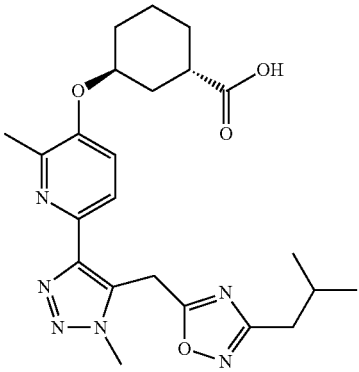 [SMILES: Cc1nc(-c2nnn(C)c2Cc2nc(CC(C)C)no2)ccc1O[C@H]1CCC[C@H](C(=O)O)C1]<br>(1S,3S)-3-((6-(5-((3-isobutyl-1,2,4-oxadiazol-5-yl)methyl)-1-methyl-1H-1,2,3-triazol-4-yl)-2-methylpyridin-3-yl)oxy)cyclohexane-1-carboxylic acid | LCMS, [M + H]$^+$ = 455.1; $^1$H NMR (CDCl$_3$) δ: 7.95 (d, J = 8.8 Hz, 1H), 7.56 (d, J = 8.6 Hz, 1H), 5.32 (s, 1H), 4.80 (br d, J = 0.7 Hz, 3H), 4.17 (s, 3H), 2.92 (br dd, J = 8.5, 4.1 Hz, 1H), 2.63 (s, 3H), 2.57 (d, J = 7.0 Hz, 2H), 1.89-2.20 (m, 5H), 1.64-1.86 (m, 4H), 0.95 (d, J = 6.6 Hz, 6H); hLPA$_1$ IC$_{50}$ = 58 nM. |

| Ex # | Structure & Name | Analytical & Biological Data |
|---|---|---|
| 244 | 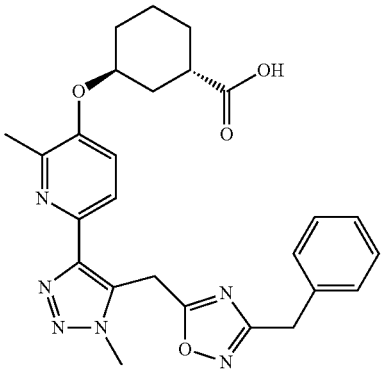 [SMILES: Cc1nc(-c2nnn(C)c2Cc2nc(Cc3ccccc3)no2)ccc1O[C@H]1CCC[C@H](C(=O)O)C1]<br>(1S,3S)-3-((6-(5-((3-benzyl-1,2,4-oxadiazol-5-yl)methyl)-1-methyl-1H-1,2,3-triazol-4-yl)-2-methylpyridin-3-yl)oxy)cyclohexane-1-carboxylic acid | LCMS, [M + H]$^+$ = 489.1;<br>$^1$H NMR (CDCl$_3$) δ: 7.82 (br d, J = 4.4 Hz, 1H), 7.52 (d, J = 8.8 Hz, 1H), 7.30-7.36 (m, 2H), 7.29-7.30 (m, 1H), 7.27-7.27 (m, 1H), 7.24-7.27 (m, 1H), 4.77 (s, 3H), 4.12 (s, 3H), 4.03 (s, 2H), 2.83-2.97 (m, 1H), 2.58 (s, 3H), 1.87-2.15 (m, 4H), 1.61-1.85 (m, 4H);<br>hLPA$_1$ IC$_{50}$ = 40 nM. |
| 245 | 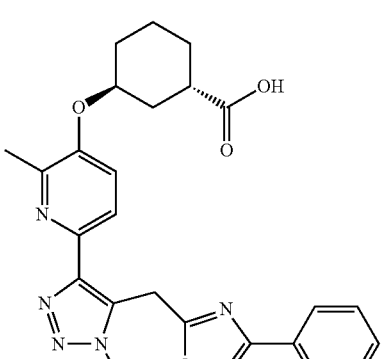<br>(1S,3S)-3-((2-methyl-6-(1-methyl-5-((3-phenyl-1,2,4-oxadiazol-5-yl) methyl)-1H-1,2,3-triazol-4-yl) pyridin-3-yl)oxy)cyclohexane-1-carboxylic acid | LCMS, [M + H]$^+$ = 475.1;<br>$^1$H NMR (CDCl$_3$) δ: 7.99-8.05 (m, 2H), 7.97 (d, J = 8.6 Hz, 1H), 7.41-7.56 (m, 4H), 4.96 (d, J = 3.5 Hz, 2H), 4.65-4.81 (m, 1H), 4.23 (s, 3H), 2.87-2.92 (m, 1H), 2.59 (s, 3H), 1.86-2.20 (m, 4H), 1.61-1.84 (m, 4H);<br>hLPA$_1$ IC$_{50}$ = 79 nM. |
| 246 | 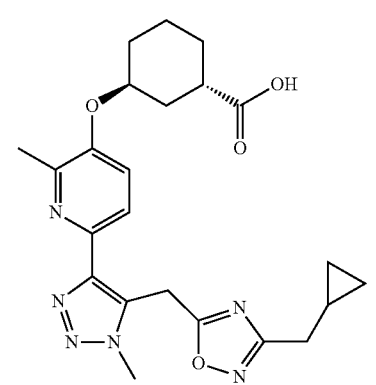 [SMILES: Cc1nc(-c2nnn(C)c2Cc2nc(CC3CC3)no2)ccc1O[C@H]1CCC[C@H](C(=O)O)C1]<br>(1S,3S)-3-((6-(5-((3-(cyclopropyl-methyl)-1,2,4-oxadiazol-5-yl) methyl)-1-methyl-1H-1,2,3-triazol-4-yl)-2-methylpyridin-3-yl)oxy) cyclohexane-1-carboxylic acid | LCMS, [M + H]$^+$ = 453.1;<br>$^1$H NMR (CDCl$_3$) δ: 7.73 (d, J = 8.8 Hz, 1H), 7.43 (d, J = 8.8 Hz, 1H), 4.59 (br d, J = 4.0 Hz, 1H), 4.51 (s, 2H), 3.95 (s, 3H), 2.60-2.73 (m, 1H), 2.44 (s, 3H), 2.37 (d, J = 7.0 Hz, 2H), 1.82-1.89 (m, 2H), 1.64-1.81 (m, 2H), 1.40-1.63 (m, 4H), 0.75-0.92 (m, 1H), 0.27-0.40 (m, 2H), −0.06-0.07 (m, 2H);<br>hLPA$_1$ IC$_{50}$ = 40 nM. |

| Ex # | Structure & Name | Analytical & Biological Data |
|---|---|---|
| 247 | 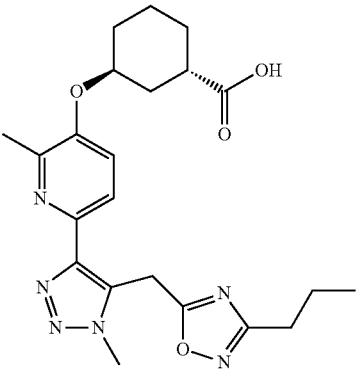 [SMILES: CCCc1noc(Cc2c(-c3ccc(O[C@H]4CCC[C@H](C(=O)O)C4)c(C)n3)nnn2C)n1]<br>(1S,3S)-3-((2-methyl-6-(1-methyl-5-((3-propyl-1,2,4-oxadiazol-5-yl) methyl)-1H-1,2,3-triazol-4-yl) pyridin-3-yl)oxy)cyclohexane-1-carboxylic acid | LCMS, $[M + H]^+$ = 441.1;<br>$^1$H NMR (CDCl$_3$) δ: 7.84-8.02 (m, 1H), 7.47-7.58 (m, 1H), 4.82-4.85 (m, 2H), 4.74-4.81 (m, 1H), 4.17 (s, 3H), 2.88-2.95 (m, 1H), 2.68 (t, J = 7.5 Hz, 2H), 2.61 (s, 3H), 1.89-2.17 (m, 4H), 1.65-1.85 (m, 6H), 0.97 (t, J = 7.5 Hz);<br>hLPA$_1$ IC$_{50}$ = 82 nM. |
| 248 | 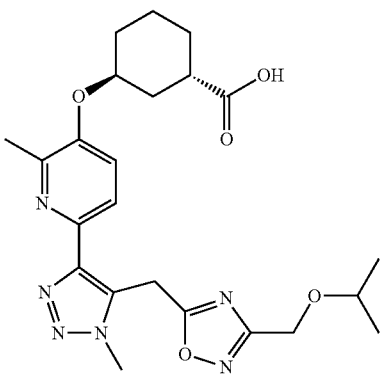 [SMILES: Cc1nc(-c2nnn(C)c2Cc2nc(COC(C)C)no2)ccc1O[C@H]1CCC[C@H](C(=O)O)C1]<br>(1S,3S)-3-((6-(5-((3-(isopropoxy-methyl)-1,2,4-oxadiazol-5-yl) methyl)-1-methyl-1H-1,2,3-triazol-4-yl)-2-methylpyridin-3-yl)oxy) cyclohexane-1-carboxylic acid | LCMS, $[M + H]^+$ = 471.1;<br>$^1$H NMR (CDCl$_3$) δ: 8.05 (d, J = 8.8 Hz, 1H), 7.84 (d, J = 8.8 Hz, 1H), 4.86 (br s, 1H), 4.72 (s, 2H), 4.52 (s, 2H), 4.18 (s, 3H), 3.78 (spt, J = 6.1 Hz, 1H), 2.84-2.94 (m, 1H), 2.77 (s, 3H), 2.02-2.30 (m, 2H), 1.61-2.00 (m, 6H), 1.24 (d, J = 5.9 Hz, 6H);<br>hLPA$_1$ IC$_{50}$ = 61 nM. |
| 249 | 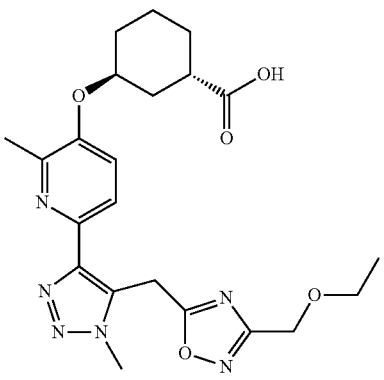<br>(1S,3S)-3-((6-(5-((3-(ethoxymethyl)-1,2,4-oxadiazol-5-yl)methyl)-1-methyl-1H-1,2,3-triazol-4-yl)-2-methylpyridin-3-yl)oxy)cyclohexane-1-carboxylic acid | LCMS, $[M + H]^+$ = 471.1;<br>$^1$H NMR (CDCl$_3$) δ: 8.02 (d, J = 8.8, 1H), 7.74 (d, J = 8.8 Hz, 1H), 4.83 (br s, 1H), 4.71 (s, 2H), 4.58 (s, 2H), 4.17 (s, 3H), 3.67 (q, J = 7.0 Hz, 2H), 2.84-2.94 (m, 1H), 2.72 (s, 3H), 1.61-2.20 (m, 8H), 1.27 (t, J = 6.9 Hz, 3H);<br>hLPA$_1$ IC$_{50}$ = 76 nM. |

Example 250. (1 S,3 S)-3-((6-(5-((5-(cyclopropylmethyl)-2H-tetrazol-2-yl)methyl)-1-methyl-1H-1,2,3-triazol-4-yl)pyridin-3-yl)oxy)cyclohexane-1-carboxylic acid

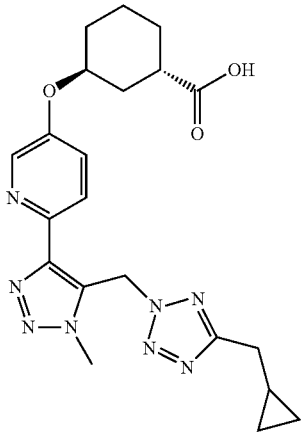 [SMILES: Cn1nnc(-c2ccc(O[C@H]3CCC[C@H](C(=O)O)C3)cn2)c1Cn1nnc(CC2CC2)n1]

250A. Isopropyl (1 S,3 S)-3-((6-(5-((5-(cyclopropylmethyl)-2H-tetrazol-2-yl)methyl)-1-methyl-1H-1,2,3-triazol-4-yl)pyridin-3-yl)oxy)cyclohexane-1-carboxylate

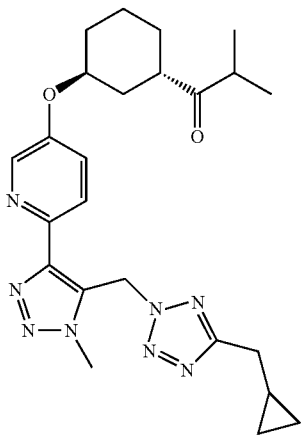 [SMILES: CC(C)C(=O)[C@H]1CCC[C@H](Oc2ccc(-c3nnn(C)c3Cn3nnc(CC4CC4)n3)nc2)C1]

250B. Isopropyl (1 S,3 S)-3-((6-(5-((5-(cyclopropylmethyl)-1H-tetrazol-1-yl)methyl)-1-methyl-1H-1,2,3-triazol-4-yl)pyridin-3-yl)oxy)cyclohexane-1-carboxylate

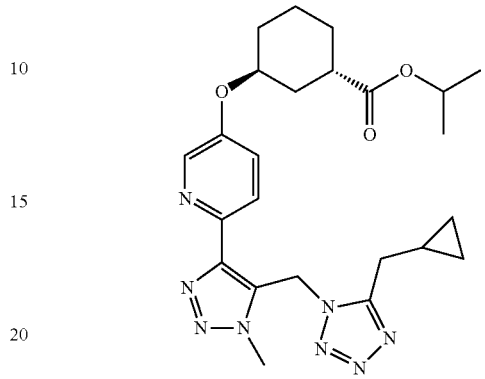

To a solution of Intermediate 1 (20 mg, 0.053 mmol) and $Et_3N$ (37 μL, 0.267 mmol) in in DCM (534 μL) was added a 1:1 mixture of 5-(cyclopropylmethyl)-2H-tetrazole and 5-(cyclo-propyl-methyl)-1H-tetrazole (33 mg, 0.27 mmol) and $Ph_3P$ (70 mg, 0.27 mmol), followed by diisopropyl (E)-diazene-1,2-dicarboxylate (54 mg, 0.27 mmol). The reaction mixture was stirred at RT for 5 h, then was filtered and concentrated in vacuo. The product was chromatographed ($SiO_2$; continuous gradient from 0% to 100% EtOAc in hexanes over 20 min) to give the two isomeric tetrazole products. The first isomer to elute was Example 250A (9 mg, 0.019 mmol, 35.1%); $[M+H]^+$=481.2 $^1$H NMR ($CDCl_3$) δ: 8.10 (d, J=2.4 Hz, 1H), 7.93 (d, J=8.8 Hz, 1H), 7.11 (dd, J=8.7, 3.0 Hz, 1H), 6.34 (s, 2H), 4.74-4.88 (m, 1H), 4.48 (tt, J=5.3, 2.9 Hz, 1H), 3.92 (s, 3H), 2.58 (dt, J=9.0, 4.7 Hz, 1H), 2.53 (d, J=7.0 Hz, 2H), 1.72-1.87 (m, 2H), 1.62-1.71 (m, 2H), 1.33-1.57 (m, 5H), 1.03 (dd, J=6.4, 2.0 Hz, 6H), 0.26-0.40 (m, 2H), −0.02-0.04 (m, 2H). The second isomer to elute was Example 250B (11 mg, 0.023 mmol, 42.9%); $[M+H]^+$=481.2 $^1$H NMR ($CDCl_3$) δ: 8.06 (d, J=2.9 Hz, 1H), 8.01 (d, J=8.8 Hz, 1H), 7.19 (dd, J=8.8, 2.9 Hz, 1H), 6.08 (s, 2H), 4.76-4.91 (m, 1H), 4.52 (br d, J=3.1 Hz, 1H), 4.06 (s, 3H), 2.73 (d, J=7.0 Hz, 2H), 2.57-2.67 (m, 1H), 1.84 (br dd, J=7.6, 2.5 Hz, 2H), 1.69 (td, J=6.2, 3.6 Hz, 2H), 1.49-1.60 (m, 3H), 1.40 (ddd, J=9.2, 6.2, 3.3 Hz, 1H), 1.06 (dd, J=6.2, 1.1 Hz, 6H), 0.79-0.93 (m, 1H), 0.31-0.42 (m, 2H), −0.04-0.04 (m, 2H).

Example 250

To a solution of Example 250A (9 mg, 0.019 mmol) in THF/MeOH (0.5 mL each) was added 2M aq. LiOH (0.047 mL, 0.094 mmol). The reaction mixture was heated at 50° C. for 1 h, then was cooled to RT and concentrated in vacuo. The residue was dissolved in $H_2O$ (1 mL), and the pH was adjusted with 1N aq. HCl to ~3 and extracted with EtOAc (2×1 mL). The combined organic extracts were washed with brine (1 mL), dried ($MgSO_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:$H_2O$ with 0.1% TFA; Mobile Phase B: 95:5 MeCN:$H_2O$ with 0.1% TFA; Gradient: 50-90% B over 20 min, then a 5-min hold at 100% B; Flow:

20 mL/min. Fractions containing the desired product were combined and concentrated in vacuo by centrifugal evaporation to give the title compound as the TFA salt. (7 mg, 0.013 mmol, 64.3% yield) LCMS, [M+H]$^+$=439.0; $^1$H $^1$H NMR (CDCl$_3$) δ: 8.65 (d, J=2.8 Hz, 1H), 8.27 (d, J=8.8 Hz, 1H), 7.84 (dd, J=8.9, 2.9 Hz, 1H), 6.27 (s, 2H), 4.80-4.97 (m, 1H), 4.29 (s, 3H), 2.92-3.06 (m, 1H), 2.79 (d, J=7.2 Hz, 2H), 2.15-2.25 (m, 1H), 2.01-2.12 (m, 1H), 1.75-1.97 (m, 4H), 1.61-1.74 (m, 1H), 1.01-1.21 (m, 1H), 0.54-0.66 (m, 2H), 0.20-0.31 (m, 2H), NOE observed between protons at 86.27 and 84.3. hLPA$_1$ IC$_{50}$=44 nM.

Example 251. (1S,3S)-3-((6-(5-(((5-(cyclopropylmethyl)-1H-tetrazol-1-yl)methyl)-1-methyl-1H-1,2,3-triazol-4-yl)pyridin-3-yl)oxy)cyclohexane-1-carboxylic acid

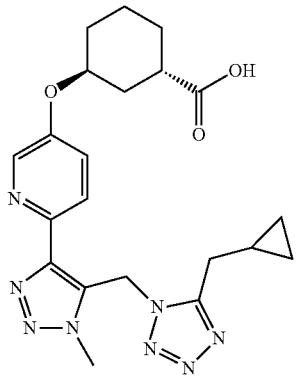 [SMILES: Cn1nnc(-c2ccc(O[C@H]3CCC[C@H](C(=O)O)C3)cn2)c1Cn1nnnc1CC1CC1]

To a solution of Example 250B (12 mg, 0.023 mmol) in THF/MeOH (0.5 mL each) was added 2M aq. LiOH (0.062 mL, 0.13 mmol). The reaction mixture was heated at 50° C. for 1 h, then was cooled to RT and concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound as the TFA salt (11.4 mg, 0.021 mmol, 90% yield). LCMS, [M+H]$^+$=439.0; $^1$H NMR (CDCl$_3$) δ: 8.32 (d, J=2.8 Hz, 1H), 8.19 (d, J=8.8 Hz, 1H), 7.47 (dd, J=8.9, 2.9 Hz, 1H), 6.25 (s, 2H), 4.72-4.80 (m, 1H), 4.32 (s, 3H), 2.98 (d, J=6.9 Hz, 2H), 2.90-2.95 (m, 1H), 1.89-2.16 (m, 4H), 1.72-1.86 (m, 2H), 1.63-1.72 (m, 1H), 1.01-1.13 (m, 1H), 0.56-0.70 (m, 2H), 0.20-0.26 (m, 2H), NOE observed between protons at 86.25, 84.32, 82.98. hLPA$_1$ IC$_{50}$=125 nM.

The Examples listed in the following table were prepared using same synthetic sequence and the same intermediates as described for the synthesis of Examples 250 or 251.

| Ex # | Structure & Name | Analytical & Biological Data | Method |
|---|---|---|---|
| 252 | (1S,3S)-3-((6-(1-methyl-5-((5-propyl-2H-tetrazol-2-yl)methyl)-1H-1,2,3-triazol-4-yl)pyridin-3-yl)oxy)cyclohexane-1-carboxylic acid | LCMS, [M + H]$^+$ = 427.1; $^1$H NMR (DMSO-d$_6$) δ: 8.27 (br s, 1H), 8.02 (br d, 1H), 7.54 (br d, 1H), 6.54 (s, 2H), 4.76 (br s, 1H), 4.10 (s, 3H), 2.74 (br m, 2H), 2.58-2.66 (m, 1H), 1.85-1.97 (m, 2H), 1.70-1.82 (m, 2H), 1.45-1.69 (m, 6H), 0.85 (m, 3H); hLPA$_1$ IC$_{50}$ = 531 nM. | Example 250 |

| Ex # | Structure & Name | Analytical & Biological Data | Method |
|---|---|---|---|
| 253 | (1S,3S)-3-((6-(1-methyl-5-((5-propyl-1H-tetrazol-1-yl)methyl)-1H-1,2,3-triazol-4-yl)pyridin-3-yl)oxy)cyclohexane-1-carboxylic acid | LCMS, [M + H]$^+$ = 427.1; $^1$H NMR (DMSO-d$_6$) δ: 8.27 (br s, 1H), 8.03 (br d, 1H), 7.56 (br d, 1H), 6.15 (s, 2H), 4.77 (br s, 1H), 4.18 (s, 3H), 2.99 (b rm, 2H), 2.60-2.76 (m, 1H), 1.90-1.99 (m, 1H), 1.60-1.88 (m, 7H), 1.46-1.58 (m, 2H), 0.91 (br m, 3H); hLPA$_1$ IC$_{50}$ = 264 nM. | Example 251 |
| 254 | (1S,3S)-3-((6-(5-((5-isobutyl-2H-tetrazol-2-yl)methyl)-1-methyl-1H-1,2,3-triazol-4-yl)pyridin-3-yl)oxy)cyclohexane-1-carboxylic acid | LCMS, [M + H]$^+$ = 441.1; $^1$H NMR (DMSO-d$_6$) δ: 8.25 (br s, 1H), 8.02 (br d, 1H), 7.53 (br d, 1H), 6.53 (s, 2H), 4.76 (br s, 1H), 4.10 (s, 3H), 2.65 (br d, 3H), 1.89-2.00 (m, 2H), 1.70-1.85 (m, 3H), 1.45-1.68 (m, 4H), 0.83 (br d, 6H); hLPA$_1$ IC$_{50}$ = 288 nM. | Example 250 |
| 255 | (1S,3S)-3-((6-(5-((5-isobutyl-1H-tetrazol-1-yl)methyl)-1-methyl-1H-1,2,3-triazol-4-yl)pyridin-3-yl)oxy)cyclohexane-1-carboxylic acid | LCMS, [M + H]$^+$ = 441.1; $^1$H NMR (DMSO-d$_6$) δ: 8.28 (br d, J = 2.1 Hz, 1H), 8.04 (br d, J = 8.8 Hz, 1H), 7.57 (br dd, J = 8.5, 2.4 Hz, 1H), 6.18 (s, 2H), 4.78 (br s, 1H), 4.18 (s, 3H), 2.91 (br d, J = 7.0 Hz, 2H), 2.63-2.72 (m, 1H), 2.06 (dt, J = 13.3, 6.8 Hz, 1H), 1.90-1.98 (m, 1H), 1.72-1.89 (m, 3H), 1.65 (br d, J = 9.2 Hz, 2H), 1.45-1.58 (m, 2H), 0.88 (br d, J = 6.7 Hz, 6H); hLPA$_1$ IC$_{50}$ = 237 nM. | Example 251 |

-continued

| Ex # | Structure & Name | Analytical & Biological Data | Method |
|---|---|---|---|
| 256 | (1S,3S)-3-((6-(5-((5-butyl-1H-tetrazol-1-yl)methyl)-1-methyl-1H-1,2,3-triazol-4-yl)pyridin-3-yl)oxy)cyclohexane-1-carboxylic acid | LCMS, [M + H]$^+$ = 441.1; $^1$H NMR (DMSO-d$_6$) δ: 8.27 (br s, 1H), 8.03 (br d, J = 8.8 Hz, 1H), 7.57 (br d, J = 8.9 Hz, 1H), 6.16 (s, 2H), 4.76 (br s, 1H), 4.17 (s, 3H), 2.99 (br t, J = 7.6 Hz, 2H), 2.57-2.67 (m, 1H), 1.88 (br s, 2H), 1.45-1.81 (m, 8H), 1.25-1.33 (m, 2H), 0.86 (br t, J = 7.3 Hz, 3H); hLPA$_1$ IC$_{50}$ = 111 nM. | Example 251 |
| 257 | (1S,3S)-3-((6-(5-((5-butyl-2H-tetrazol-2-yl)methyl)-1-methyl-1H-1,2,3-triazol-4-yl)pyridin-3-yl)oxy)cyclohexane-1-carboxylic acid | LCMS, [M + H]$^+$ = 441.1; $^1$H NMR (CDCl$_3$) δ: 8.59 (d, J = 2.6 Hz, 1H), 8.22 (d, J = 8.8 Hz, 1H), 7.75 (dd, J = 8.8, 2.6 Hz, 1H), 6.42 (s, 2H), 4.83 (br s, 1H), 4.26 (s, 3H), 2.92-3.03 (m, 1H), 2.81-2.90 (m, 2H), 2.12-2.27 (m, 1H), 2.08 (br t, J = 5.1 Hz, 1H), 1.78-1.99 (m, 5H), 1.59-1.76 (m, 3H), 1.37 (dq, J = 14.9, 7.4 Hz, 2H), 0.93 (t, J = 7.4 Hz, 3H); hLPA$_1$ IC$_{50}$ = 12.5 nM. | Example 250 |
| 258 | (1S,3S)-3-((6-(5-((5-cyclopentyl-1H-tetrazol-1-yl)methyl)-1-methyl-1H-1,2,3-triazol-4-yl)pyridin-3-yl)oxy)cyclohexane-1-carboxylic acid | LCMS, [M + H]$^+$ = 453.1; $^1$H NMR (DMSO-d$_6$) δ: 8.23 (br s, 1H), 8.02 (br d, J = 8.5 Hz, 1H), 7.56 (br d, J = 7.3 Hz, 1H), 6.18 (s, 2H), 4.76 (br s, 1H), 4.17 (s, 3H), 3.53 (br s, 1H), 2.59-2.73 (m, 1H), 1.99 (br s, 2H), 1.81-1.94 (m, 2H), 1.75 (br s, 6H), 1.46-1.67 (m, 6H); hLPA$_1$ IC$_{50}$ = 433 nM. | Example 251 |

-continued

| Ex # | Structure & Name | Analytical & Biological Data | Method |
|---|---|---|---|
| 259 | 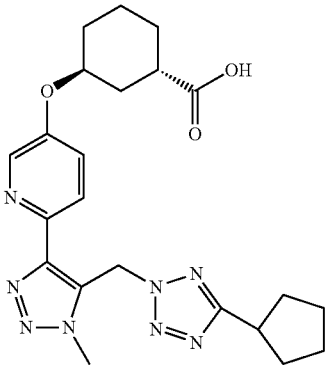 [SMILES: Cn1nnc(-c2ccc(O[C@H]3CCC[C@H](C(=O)O)C3)cn2)c1Cn1nnc(C2CCCC2)n1]<br>(1S,3S)-3-((6-(5-((5-cyclopentyl-2H-tetrazol-2-yl)methyl)-1-methyl-1H-1,2,3-triazol-4-yl)pyridin-3-yl)oxy)cyclohexane-1-carboxylic acid | LCMS, $[M + H]^+$ = 453.1;<br>$^1$H NMR (CDCl$_3$) δ: 8.57 (d, J = 2.9 Hz, 1H), 8.20 (d, J = 8.8 Hz, 1H), 7.69 (dd, J = 8.9, 2.8 Hz, 1H), 6.36 (s, 2H), 4.82 (br s, 1H), 4.26 (s, 3H), 3.26-3.44 (m, 1H), 2.89-3.06 (m, 1H), 2.04-2.35 (m, 4H), 1.89-2.02 (m, 2H), 1.73-1.87 (m, 7H), 1.60-1.72 (m, 3H);<br>hLPA$_1$ IC$_{50}$ = 31 nM. | Example 250 |

Example 260. (1 S,3 S)-3-((6-(5-((4-Isobutyl-2H-1,2,3-triazol-2-yl)methyl)-1-methyl-1H-1,2,3-triazol-4-yl)-2-methylpyridin-3-yl)oxy)cyclohexane-1-carboxylic acid

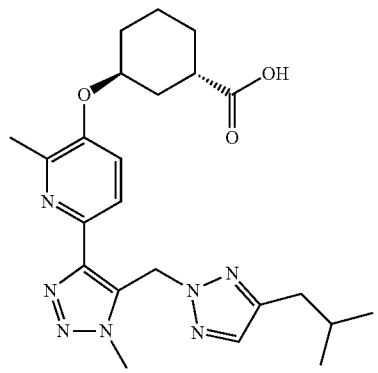 [SMILES: Cc1nc(-c2nnn(C)c2Cn2ncc(CC(C)C)n2)ccc1O[C@H]1CCC[C@H](C(=O)O)C1]

260A. (4-Isobutyl-2H-1,2,3-triazol-2-yl)methanol

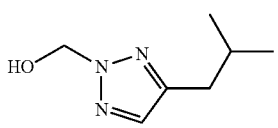

260B. (4-isobutyl-1H-1,2,3-triazol-1-yl)methanol

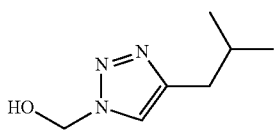

A mixture of paraformaldehyde (9.88 g, 122 mmol), glacial HOAc (1.05 mL, 18.26 mmol), and 1,4-dioxane (10 mL) was stirred at RT for 15 min, after which NaN$_3$ (1.19 g, 18.26 mmol) and 4-methylpent-1-yne (1.43 mL, 12.17 mmol) were successively added. After 10 min at RT, sodium ascorbate (4.82 g, 24.35 mmol) was added, followed by a solution of CuSO$_4$.5H$_2$O (1.52 g, 6.09 mmol) in H$_2$O (8 mL). The reaction mixture was stirred for 18 h at RT, then was diluted with H$_2$O (10 mL) and extracted with CHCl$_3$ (3×25 mL). The combined organic extracts were filtered through Celite® to remove solids, dried (MgSO$_4$) and concentrated in vacuo to give a mixture of the two title compounds (1.26 g, 67% yield). The crude products were used in the next step without further purification. LCMS, $[M+H]^+$=156.2.

260C. 4-Isobutyl-2H-1,2,3-triazole

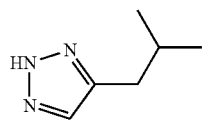

A mixture of 260A and 260B (100 mg, 0.64 mmol) and activated MnO$_2$ (0.56 g, 6.44 mmol) in CHCl$_3$ (2.5 mL) was stirred at reflux for 20 h, then was cooled to RT. The mixture was filtered through Celite®, which was washed with CHCl$_3$:MeOH (1:1). The combined filtrates were concentrated in vacuo to give the title compound (75 mg, 93% yield) as a yellowish oil. $^1$H NMR (400 MHz, CDCl$_3$) δ 7.49 (s, 1H), 2.62 (d, J=7.0 Hz, 2H), 2.11-1.86 (m, 1H), 0.95 (d, J=6.6 Hz, 6H)

260D. Methyl (1 S,3 S)-3-((6-(5-((4-isobutyl-2H-1,2,3-triazol-2-yl)methyl)-1-methyl-1H-1,2,3-triazol-4-yl)-2-methylpyridin-3-yl)oxy)cyclohexane-1-carboxylate

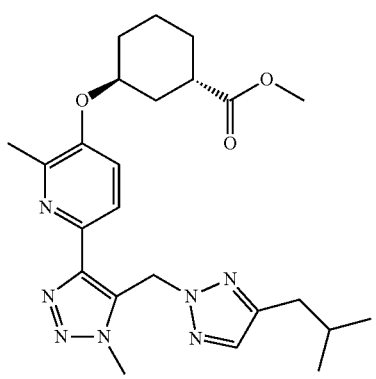 [SMILES: COC(=O)[C@H]1CCC[C@H](Oc2ccc(-c3nnn(C)c3Cn3ncc(CC(C)C)n3)nc2C)C1]

260E. Methyl (1 S,3 S)-3-((6-(5-((4-isobutyl-1H-1,2,3-triazol-1-yl)methyl)-1-methyl-1H-1,2,3-triazol-4-yl)-2-methylpyridin-3-yl)oxy)cyclohexane-1-carboxylate

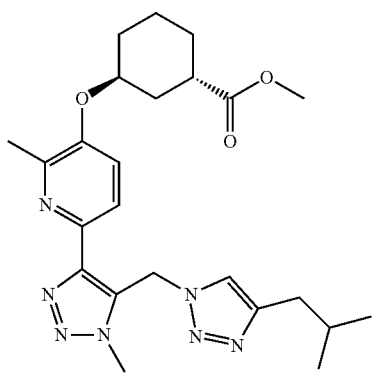 [SMILES: COC(=O)[C@H]1CCC[C@H](Oc2ccc(-c3nnn(C)c3Cn3cc(CC(C)C)nn3)nc2C)C1]

260F. Methyl (1 S,3 S)-3-((6-(5-((5-isobutyl-1H-1,2,3-triazol-1-yl)methyl)-1-methyl-1H-1,2,3-triazol-4-yl)-2-methylpyridin-3-yl)oxy)cyclohexane-1-carboxylate

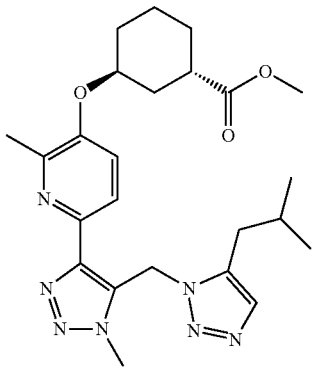 [SMILES: COC(=O)[C@H]1CCC[C@H](Oc2ccc(-c3nnn(C)c3Cn3nncc3CC(C)C)nc2C)C1]

A solution of Intermediate 5 (30 mg, 0.07 mmol), 260C (9.76 mg, 0.08 mmol) and iPr$_2$NEt (0.02 mL, 0.11 mmol) in ClCH$_2$CH$_2$Cl (0.4 mL) was heated at 100° C. for 1 h in a microwave reactor, then was cooled to RT and concentrated in vacuo. The residue was chromatographed (12 g SiO$_2$; continuous gradient from 0% to 70% EtOAc in hexanes over 15 min, then at 70% EtOAc/hexane for 10 min) to give 260D (4.6 mg, 14% yield) as a colorless oil and a mixture of 260E and 260F (8.2 mg, 25% yield) as a colorless oil.

Example 260

A mixture of Example 260D (4.6 mg, 9.84 μmol) and LiOH·H$_2$O (2 mg, 0.05 mmol) in THF (0.8 mL)/H$_2$O (0.4 mL) was stirred at RT overnight, then was concentrated in vacuo; the pH was adjusted with 1N aq. HCl to ~5 and extracted with EtOAc (3×5 mL). The combined organic extracts were washed with brine (2 mL), dried (MgSO$_4$) and concentrated in vacuo. The crude product was purified by preparative LC/MS: Column: XBridge C18, 200 mm×19 mm, 5-μm particles; Mobile Phase A: 5:95 MeCN:H$_2$O with 10 mM aq. NH$_4$OAc; Mobile Phase B: 95:5 MeCN:H$_2$O with 10 mM aq. NH$_4$OAc; Gradient: a 0-min hold at 25% B, 25-65% B over 20 min, then a 4-min hold at 100% B; Flow Rate: 20 mL/min; Column Temperature: 25 C. Fraction collection was triggered by MS signals. Fractions containing the desired product were combined and dried via centrifugal evaporation. The title compound (3.2 mg, 69% yield) was obtained as a colorless oil. LCMS, [M+H]$^+$=454.3. $^1$H NMR (500 MHz, DMSO-d$_6$) δ 7.84 (br d, J=8.5 Hz, 1H), 7.52 (s, 1H), 7.45 (br d, J=8.5 Hz, 1H), 6.28 (s, 2H), 4.79-4.73 (m, 1H), 4.01 (s, 3H), 2.65-2.56 (m, 1H), 2.43 (br d, J=7.0 Hz, 2H), 2.40 (s, 3H), 2.03-1.43 (m, 9H), 0.81 (br d, J=6.7 Hz, 6H). hLPA$_1$ IC$_{50}$=35 nM.

The following Examples were synthesized according to the general procedures described for the preparation for Example 260.

| Ex # | Structure & Name | Analytical & Biological Data |
| --- | --- | --- |
| 261 | (1S,3S)-3-((6-(5-((5-isobutyl-1H-1,2,3-triazol-1-yl)methyl)-1-methyl-1H-1,2,3-triazol-4-yl)-2-methyl-pyridin-3-yl)oxy)cyclohexane-1-carboxylic acid | LCMS, [M + H]$^+$ = 453.9; $^1$H NMR (400 MHz, CDCl$_3$) δ 8.00 (br d, J = 8.8 Hz, 1H), 7.64-7.57 (m, 2H), 6.12 (s, 2H), 4.85-4.77 (m, 1H), 4.11 (s, 3H), 2.96-2.83 (m, 1H), 2.65 (s, 3H), 2.53 (d, J = 7.3 Hz, 2H), 2.13-1.64 (m, 9H), 0.84 (d, J = 6.6 Hz, 5H); hLPA$_1$ IC$_{50}$ = 115 nM. |
| 262 | (1S,3S)-3-((6-(5-((4-isobutyl-1H-1,2,3-triazol-1-yl)methyl)-1-methyl-1H-1,2,3-triazol-4-yl)-2-methylpyridin-3-yl)oxy)cyclohexane-1-carboxylic acid | LCMS, [M + H]$^+$ = 454.4; $^1$H NMR (400 MHz, CDCl$_3$) δ 8.03 (d, J = 8.4 Hz, 1H), 7.88 (s, 1H), 7.45 (d, J = 8.8 Hz, 1H), 6.15 (s, 2H), 4.82-4.76 (m, 1H), 4.19 (s, 3H), 2.96-2.87 (m, 1H), 2.62-2.56 (m, 5H), 2.19-1.65 (m, 9H), 0.90 (d, J = 6.6 Hz, 6H); hLPA$_1$ IC$_{50}$ = 86 nM. |
| 263 | (1S,3S)-3-((6-(5-((5-(cyclopropyl-methyl)-1H-1,2,3-triazol-1-yl)-methyl)-1-methyl-1H-1,2,3-triazol-4-yl)-2-methylpyridin-3-yl)oxy)-cyclohexane-1-carboxylic acid | LCMS, [M + H]$^+$ = 452.2; $^1$H NMR (500 MHz, DMSO-d$_6$) δ 7.83 (d, J = 8.7 Hz, 1H), 7.54 (s, 1H), 7.47 (d, J = 8.6 Hz, 1H), 6.17 (s, 2H), 4.75-4.69 (m, 1H), 4.03 (s, 3H), 2.57-2.51 (m, 3H), 2.40 (s, 3H), 1.96-1.45 (m, 8H), 0.89-0.80 (m, 1H), 0.45-0.37 (m, 2H), 0.02--0.04 (m, 2H); hLPA$_1$ IC$_{50}$ = 41 nM. |

| Ex # | Structure & Name | Analytical & Biological Data |
|---|---|---|
| 264 | 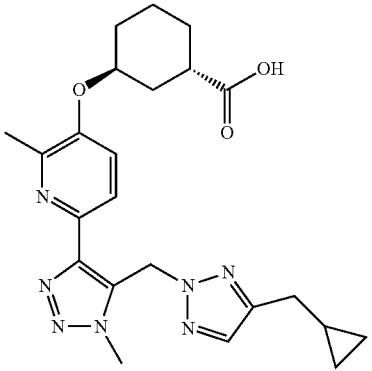 [SMILES: Cc1nc(-c2nnn(C)c2Cn2ncc(CC3CC3)n2)ccc1O[C@H]1CCC[C@H](C(=O)O)C1]<br>(1S,3S)-3-((6-(5-((4-(cyclopropyl-methyl)-2H-1,2,3-triazol-2-yl)methyl)-1-methyl-1H-1,2,3-triazol-4-yl)-2-methylpyridin-3-yl)oxy)cyclohexane-1-carboxylic acid | LCMS, [M + H]$^+$ = 452.2;<br>$^1$H NMR (500 MHz, DMSO-d$_6$) δ 7.73 (br d, J = 8.2 Hz, 1H), 7.47 (s, 1H), 7.34 (br d, J = 8.5 Hz, 1H), 6.18 (s, 2H), 4.68-4.61 (m, 1H), 3.92 (s, 3H), 2.53-2.41 (m, 3H), 2.30 (s, 3H), 1.92-1.30 (m, 8H), 0.87-0.76 (m, 1H), 0.31 (br d, J = 7.0 Hz, 2H), 0.01 (br d, J = 4.3 Hz, 2H);<br>hLPA$_1$ IC$_{50}$ = 14 nM. |
| 265 | 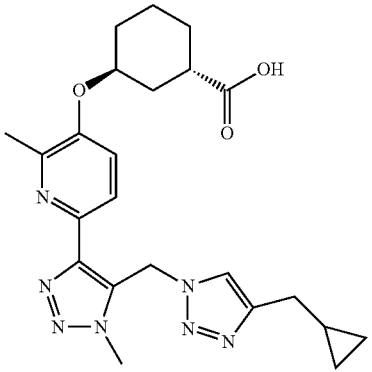<br>(1S,3S)-3-((6-(5-((4-(cyclopropyl-methyl)-1H-1,2,3-triazol-1-yl)methyl)-1-methyl-1H-1,2,3-triazol-4-yl)-2-methylpyridin-3-yl)oxy)cyclohexane-1-carboxylic acid | LCMS, [M + H]$^+$ = 452.1;<br>$^1$H NMR (500 MHz, DMSO-d$_6$) δ 7.85 (s, 1H), 7.75 (d, J = 8.5 Hz, 1H), 7.38 (br d, J = 8.7 Hz, 1H), 6.02 (s, 2H), 4.67-4.60 (m, 1H), 4.00 (s, 3H), 2.52-2.40 (m, 3H), 2.36 (s, 3H), 1.89-1.36 (m, 8H), 0.86-0.76 (m, 1H), 0.32-0.26 (m, 2H), 0.02--0.04 (m, 2H);<br>hLPA$_1$ IC$_{50}$ = 40 nM. |
| 266 | 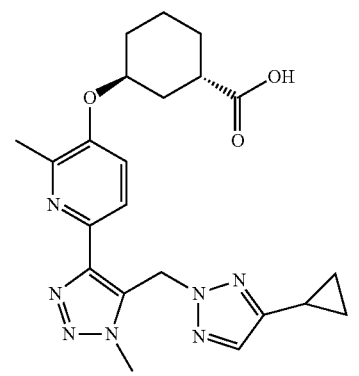 [SMILES: Cc1nc(-c2nnn(C)c2Cn2ncc(C3CC3)n2)ccc1O[C@H]1CCC[C@H](C(=O)O)C1]<br>(1S,3S)-3-((6-(5-((4-cyclopropyl-2H-1,2,3-triazol-2-yl)methyl)-1-methyl-1H-1,2,3-triazol-4-yl)-2-methyl-pyridin-3-yl)oxy)cyclohexane-1-carboxylic acid | LCMS, [M + H]$^+$ = 437.9;<br>$^1$H NMR (500 MHz, DMSO-d$_6$) δ 7.85 (d, J = 8.5 Hz, 1H), 7.48-7.43 (m, 2H), 6.25 (s, 2H), 4.79-4.74 (m, 1H), 4.04 (s, 3H), 2.70-2.62 (m, 1H), 2.44 (s, 3H), 2.09-1.47 (m, 9H), 0.94-0.88 (m, 2H), 0.70-0.63 (m, 2H);<br>hLPA$_1$ IC$_{50}$ = 90 nM. |

| Ex # | Structure & Name | Analytical & Biological Data |
|---|---|---|
| 267 | 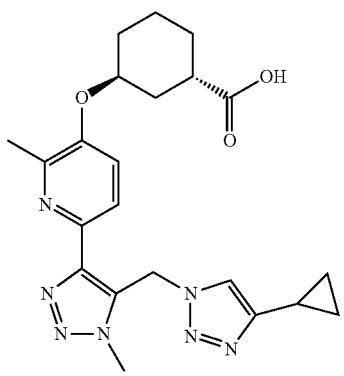 [SMILES: Cc1nc(-c2nnn(C)c2Cn2cc(C3CC3)nn2)ccc1O[C@H]1CCC[C@H](C(=O)O)C1]<br>(1S,3S)-3-((6-(5-((4-cyclopropyl-1H-1,2,3-triazol-1-yl)methyl)-1-methyl-1H-1,2,3-triazol-4-yl)-2-methylpyridin-3-yl)oxy)cyclohexane-1-carboxylic acid | LCMS, [M + H]$^+$ = 438.1;<br>$^1$H NMR (500 MHz, DMSO-d$_6$) δ 7.89 (d, J = 8.6 Hz, 1H), 7.86 (s, 1H), 7.49 (d, J = 8.4 Hz, 1H), 6.15 (s, 2H), 4.81-4.75 (m, 1H), 4.11 (s, 3H), 2.71-2.63 (m, 1H), 2.49 (s, 3H), 2.10-1.46 (m, 9H), 0.91-0.82 (m, 2H), 0.72-0.62 (m, 2H);<br>hLPA$_1$ IC$_{50}$ = 2215 nM. |
| 268 | 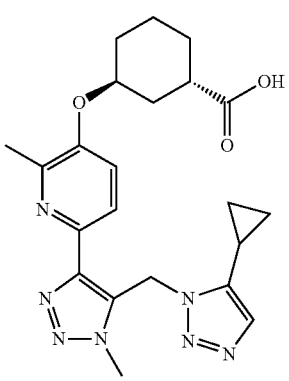 [SMILES: Cc1nc(-c2nnn(C)c2Cn2nncc2C2CC2)ccc1O[C@H]1CCC[C@H](C(=O)O)C1]<br>(1S,3S)-3-((6-(5-((5-cyclopropyl-1H-1,2,3-triazol-1-yl)methyl)-1-methyl-1H-1,2,3-triazol-4-yl)-2-methyl-pyridin-3-yl)oxy)cyclohexane-1-carboxylic acid | LCMS, [M + H]$^+$ = 438.1;<br>$^1$H NMR (500 MHz, DMSO-d$_6$) δ 7.89 (d, J = 8.5 Hz, 1H), 7.51 (d, J = 8.9 Hz, 1H), 7.39 (s, 1H), 6.35 (s, 2H), 4.82-4.77 (m, 1H), 4.04 (s, 3H), 2.67-2.58 (m, 1H), 2.42 (s, 3H), 2.07-1.46 (m, 9H), 0.82-0.76 (m, 2H), 0.65-0.58 (m, 2H);<br>hLPA$_1$ IC$_{50}$ = 301 nM. |

Example 269. (1S,3S)-3-((2-methyl-6-(1-methyl-5-((4-propyl-1H-1,2,3-triazol-1-yl)methyl)-1H-1,2,3-triazol-4-yl)pyridin-3-yl)oxy)cyclohexane-1-carboxylic acid

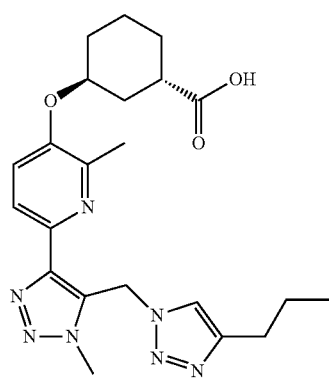 [SMILES: CCCc1cn(Cc2c(-c3ccc(O[C@H]4CCC[C@H](C(=O)O)C4)c(C)n3)nnn2C)nn1]

269A. Methyl (1S,3S)-3-((6-(5-((4-bromo-2H-1,2,3-triazol-2-yl)methyl)-1-methyl-1H-1,2,3-triazol-4-yl)-2-methylpyridin-3-yl)oxy)cyclohexane-1-carboxylate

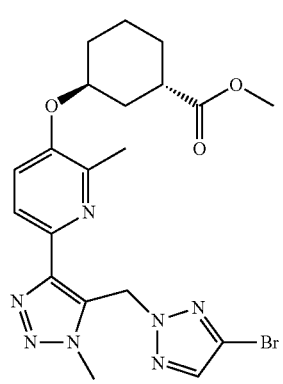 [SMILES: COC(=O)[C@H]1CCC[C@H](Oc2ccc(-c3nnn(C)c3Cn3ncc(Br)n3)nc2C)C1]

269B. Methyl (1S,3S)-3-((6-(5-((4-bromo-1H-1,2,3-triazol-1-yl)methyl)-1-methyl-1H-1,2,3-triazol-4-yl)-2-methylpyridin-3-yl)oxy)cyclohexane-1-carboxylate

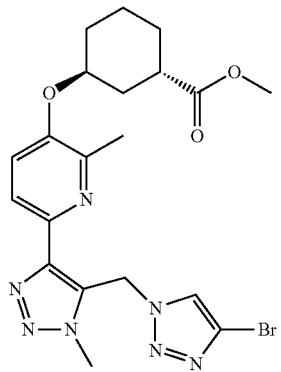 [SMILES: COC(=O)[C@H]1CCC[C@H](Oc2ccc(-c3nnn(C)c3Cn3cc(Br)nn3)nc2C)C1]

A solution of Intermediate 5 (100 mg, 0.24 mmol), 4-bromo-2H-1,2,3-triazole (53 mg, 0.35 mmol) and iPr₂NEt (62 μL, 0.35 mmol) in 1,2-dichloroethane (1.5 mL) was heated at 100° C. for 1 h in a microwave reactor, then was cooled to RT and concentrated in vacuo. The residue was chromatographed (12 g SiO₂, continuous gradient from 0-100% EtOAc in hexanes over 13 min) to give 269A (early eluting isomer, 30 mg, 0.061 mmol, 25.9% yield) and 269B (later eluting isomer, 70 mg, 0.143 mmol, 60.4% yield) as colorless oils. The regiochemistry of 269B was determined by NOE $^1$H NMR analysis.

269A, LCMS, [M+H]$^+$=490.0. $^1$H NMR (500 MHz, CDCl$_3$) δ 8.00 (d, J=8.5 Hz, 1H), 7.56 (s, 1H), 7.21 (d, J=8.6 Hz, 1H), 6.39 (s, 2H), 4.71 (dq, J=5.0, 2.5 Hz, 1H), 4.12 (s, 3H), 3.71 (s, 3H), 2.85 (tt, J=10.5, 3.9 Hz, 1H), 2.52 (s, 3H), 2.21-1.57 (m, 8H).

269B, LCMS, [M+H]$^+$=490.0. $^1$H NMR (500 MHz, CDCl$_3$) δ 8.11 (s, 1H), 8.07 (d, J=8.5 Hz, 1H), 7.29 (d, J=2.0 Hz, 1H), 6.24 (s, 2H), 4.76 (dq, J=5.9, 3.5, 2.9 Hz, 1H), 4.21 (s, 3H), 3.72 (s, 3H), 2.86 (tt, J=10.4, 3.9 Hz, 1H), 2.56 (s, 3H), 2.21-1.60 (m, 8H).

269C. Methyl (1S,3S)-3-((2-methyl-6-(1-methyl-5-((4-((E)-prop-1-en-1-yl)-1H-1,2,3-triazol-1-yl)methyl)-1H-1,2,3-triazol-4-yl)pyridin-3-yl)oxy)cyclohexane-1-carboxylate

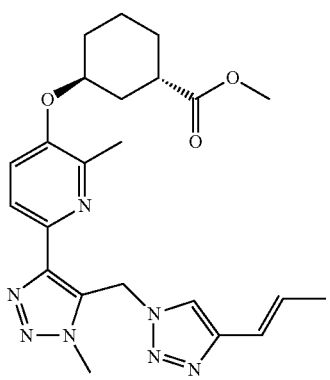 [SMILES: C/C=C/c1cn(Cc2c(-c3ccc(O[C@H]4CCC[C@H](C(=O)OC)C4)c(C)n3)nnn2C)nn1]

A mixture of 269B (24 mg, 0.049 mmol), (E)-4,4,5,5-tetramethyl-2-(prop-1-en-1-yl)-1,3,2-dioxaborolane (33 mg, 0.20 mmol), PdCl$_2$(dppf)-CH$_2$Cl$_2$-adduct (2 mg, 2.5 μmol), and K$_3$PO$_4$ (31 mg, 0.15 mmol) in 1,4-dioxane (1 mL) was degassed and refilled with N$_2$ (3×). The reaction mixture was heated at 50° C. for 15 h, then was cooled to RT. The mixture was diluted with Et$_2$O (5 mL) and filtered through Celite®. The filtrate was concentrated in vacuo. The residue was chromatographed (12 g SiO$_2$, continuous gradient from 0-100% EtOAc in hexane over 12 min) to give the title compound (10 mg, 0.022 mmol, 45% yield). LCMS, [M+H]$^+$=452.1.

Example 269

A mixture of compound 269C (10 mg, 0.022 mmol) and 10% Pd/carbon (2 mg) in MeOH (1 mL) was stirred under 1 atm of H$_2$ for 14 h. The mixture was filtered, and the filtrate was concentrated in vacuo to give the crude methyl (1S,3S)-3-((2-methyl-6-(1-methyl-5-((4-propyl-1H-1,2,3-triazol-1-yl)methyl)-1H-1,2,3-triazol-4-yl)pyridin-3-yl)oxy)cyclohexane-1-carboxylate (10 mg, 0.022 mmol, 100% yield) as a slightly colored oil. LCMS, [M+H]$^+$=454.0. The crude methyl ester was dissolved in THF (0.5 mL) and water (0.5 mL). LiOH·H$_2$O (9 mg, 0.22 mmol) was added and the reaction mixture was stirred at RT for 5 h. The pH of the mixture was adjusted to ~5 with 1N aq. HCl, then was extracted with EtOAc (3×2 mL). The combined organic extracts were dried (MgSO$_4$) and concentrated in vacuo. The residue was dissolved in DMF and purified via preparative LC/MS: Column: XBridge C18, 200 mm×19 mm, 5-μm particles; Mobile Phase A: 5:95 MeCN:H$_2$O with 0.1% TFA; Mobile Phase B: 95:5 MeCN:H$_2$O with 0.1% TFA; Gradient: a 0-min hold at 18% B, 18-58% B over 20 min, then a 4-min hold at 100% B; Flow Rate: 20 mL/min; Column Temperature: 25° C. Fraction collection was triggered by MS signals. Fractions containing the desired product were combined and dried via centrifugal evaporation to give the title compound (TFA salt, 8.5 mg, 57.2% yield; LCMS purity=99%). LC/MS[M+H]$^+$=440.5; $^1$H NMR (500 MHz, DMSO-d$_6$) δ 7.94 (s, 1H), 7.88 (d, J=8.6 Hz, 1H), 7.50 (d, J=8.7 Hz, 1H), 6.16 (s, 2H), 4.78 (s, 1H), 4.13 (s, 3H), 2.62 (t, J=10.8 Hz, 1H), 2.57-2.52 (m, 2H), 2.47 (s, 3H), 2.06-1.45 (m, 10H), 0.85 (t, J=7.4 Hz, 3H); hLPA$_1$ IC$_{50}$=76 nM.

Example 270. (1S,3S)-3-((2-methyl-6-(1-methyl-5-((4-propyl-2H-1,2,3-triazol-2-yl)methyl)-1H-1,2,3-triazol-4-yl)pyridin-3-yl)oxy)cyclohexane-1-carboxylic acid

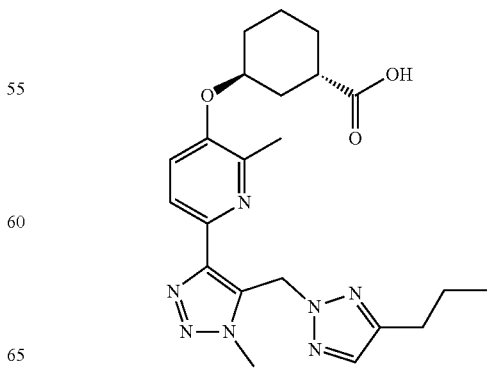

The title compound was synthesized from Intermediate 269A following the same sequence as for the preparation of Example 269. LCMS, [M+H]⁺=440.1. ¹H NMR (500 MHz, DMSO-$d_6$) δ 7.84 (d, J=8.5 Hz, 1H), 7.54 (s, 1H), 7.48 (d, J=8.7 Hz, 1H), 6.28 (s, 2H), 4.74 (s, 1H), 4.03 (s, 3H), 2.40 (s, 3H), 1.99-1.42 (m, 10H), 0.85 (t, J=7.3 Hz, 3H). (The propyl —CH₂-off the triazole and α-proton of the carboxylic acid are not observed due to water-suppression). hLPA₁ IC₅₀=61 nM.

Example 271. (1S,3 S)-3-((2-methyl-6-(1-methyl-5-((4-(prop-1-en-2-yl)-2H-1,2,3-triazol-2-yl) methyl)-1H-1,2,3-triazol-4-yl)pyridin-3-yl)oxy)cyclohexane-1-carboxylic acid

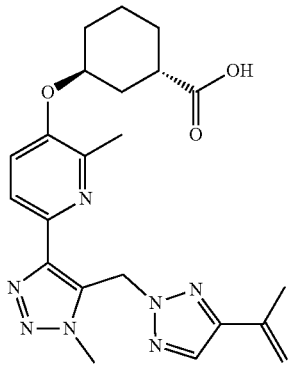 [SMILES: C=C(C)c1cnn(Cc2c(-c3ccc(O[C@H]4CCC[C@H](C(=O)O)C4)c(C)n3)nnn2C)n1]

271A. Methyl (1 S,3 S)-3-((2-methyl-6-(1-methyl-5-((4-(prop-1-en-2-yl)-2H-1,2,3-triazol-2-yl) methyl)-1H-1,2,3-triazol-4-yl)pyri din-3-yl)oxy) cyclohexane-1-carboxylate

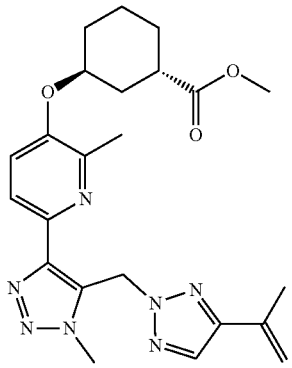 [SMILES: C=C(C)c1cnn(Cc2c(-c3ccc(O[C@H]4CCC[C@H](C(=O)OC)C4)c(C)n3)nnn2C)n1]

A mixture of 269A (24 mg, 0.049 mmol), 4,4,5,5-tetramethyl-2-(prop-1-en-2-yl)-1,3,2-dioxaborolane (21 mg, 0.12 mmol), PdCl₂(dppf)-CH₂Cl₂-adduct (2 mg, 2.5 μmol), and K₃PO₄ (31 mg, 0.15 mmol) in 1,4-dioxane (1 mL) was degassed and refilled with N₂ (3×). The reaction mixture was heated at 70° C. for 24 h, then was cooled to RT. The mixture was diluted with Et₂O (5 mL) and filtered through Celite®. The filtrate was concentrated in vacuo. The residue was chromatographed (12 g SiO₂, continuous gradient from 0-100% EtOAc in hexane over 12 min) to give the title compound (16 mg, 0.035 mmol, 72.4% yield). LCMS, [M+H]⁺=452.4. ¹H NMR (400 MHz, CDCl₃) δ 8.01 (d, J=8.5 Hz, 1H), 7.63 (s, 1H), 7.20 (d, J=8.6 Hz, 1H), 6.37 (s, 2H), 5.55 (t, J=1.1 Hz, 1H), 5.15 (t, J=1.5 Hz, 1H), 4.71 (dt, J=5.2, 2.4 Hz, 1H), 4.10 (s, 3H), 3.71 (s, 3H), 2.85 (tt, J=10.4, 3.8 Hz, 1H), 2.54 (s, 3H), 2.17 (dd, J=13.9, 4.5 Hz, 1H), 2.12 (t, J=1.3 Hz, 3H), 2.05-1.55 (m, 7H).

Example 271

To a solution of 271A (3.5 mg, 7.8 μmol) in THF/water (0.5 mL each) was added LiOH·H₂O (3 mg, 0.07 mmol). The reaction mixture was stirred for 16 h at RT; the pH was adjusted to ~5 with 1N aq. HCl. The mixture was extracted with EtOAc (3×2 mL). The combined organic extracts were dried (MgSO₄) and concentrated in vacuo. The crude product was dissolved in DMF and purified via preparative LC/MS: Column: XBridge C18, 200 mm×19 mm, 5-μm particles; Mobile Phase A: 5:95 MeCN:H₂O with 0.1% TFA; Mobile Phase B: 95:5 MeCN:H₂O with 0.1% TFA; Gradient: a 0-min hold at 18% B, 18-58% B over 20 min, then a 4-min hold at 100% B; Flow Rate: 20 mL/min; Column Temperature: 25° C. Fraction collection was triggered by MS signals. Fractions containing the desired product were combined and dried via centrifugal evaporation to give the title compound (2.2 mg, 42.6% yield; LCMS purity=100%). LCMS, [M+H]⁺=438.2. ¹H NMR (500 MHz, DMSO-$d_6$) δ 7.92 (s, 1H), 7.85 (d, J=8.5 Hz, 1H), 7.46 (d, J=8.7 Hz, 1H), 6.31 (s, 2H), 5.57 (s, 1H), 5.14 (s, 1H), 4.76 (s, 1H), 4.10 (s, 3H), 2.65-2.58 (m, 1H), 2.41 (s, 3H), 2.08-1.40 (m, 11H). hLPA₁ IC₅₀=136 nM.

Example 272. (1S,3S)-3-((6-(5-((4-isopropyl-2H-1,2,3-triazol-2-yl)methyl)-1-methyl-1H-1,2,3-triazol-4-yl)-2-methylpyridin-3-yl)oxy)cyclohexane-1-carboxylic acid

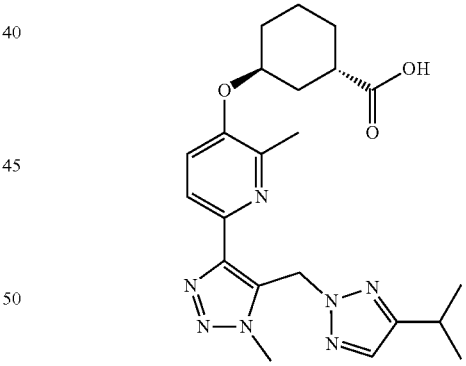

The title compound was synthesized from 269A using the same sequence used for the preparation of Example 271. The compound was purified by preparative LC/MS: Column: Phenomenex Luna 5u C18 30×250 mm; Solvent A: 10% MeCN-90% H₂O-0.1% TFA; Solvent B: 90% MeCN-10% H₂O-0.1% TFA; Gradient: 0-100% B over min; Flow Rate: 40 mL/min; Column Temperature: 25° C. UV detection Wavelength: 220 nm. Fractions were collected and concentrated to give the title compound (11 mg, 0.016 mmol, 56.9% yield; 99% purity by LC/MS) as a colorless oil. LCMS, [M+H]⁺=440.4. ¹H NMR (400 MHz, CDCl₃) δ 8.33 (d, J=8.4 Hz, 1H), 7.94 (d, J=8.6 Hz, 1H), 7.46 (s, 1H), 5.89 (s, 2H), 4.91 (s, 1H), 4.28 (s, 3H), 3.04 (dt, J=13.9, 7.0 Hz, 1H), 2.91 (br s, 1H), 2.82 (s, 3H), 2.03 (s, 8H), 1.29 (d, J=6.9 Hz, 6H). hLPA$_1$ IC$_{50}$=35 nM.

Example 273. (1 S,3S)-3-((2-methyl-6-(1-methyl-5-((4-phenyl-2H-1,2,3-triazol-2-yl)methyl)-1H-1,2,3-triazol-4-yl)pyridin-3-yl)oxy)cyclohexane-1-carboxylic acid

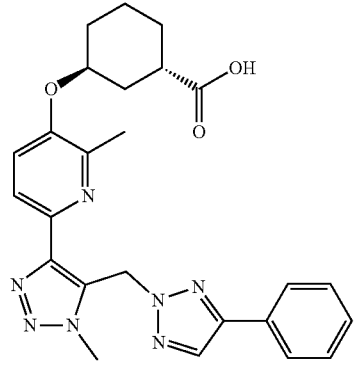 [SMILES: Cc1nc(-c2nnn(C)c2Cn2ncc(-c3ccccc3)n2)ccc1O[C@H]1CCC[C@H](C(=O)O)C1]

To a solution of 4-phenyl-2H-1,2,3-triazole (10 mg, 0.071 mmol) in THF (0.5 mL) was added NaH (6 mg of a 60% dispersion in mineral oil; 0.14 mmol). The mixture was stirred for 5 min, after which Intermediate 5 (15 mg, 0.035 mmol) was added. The reaction mixture was stirred for 72 h at RT, after which THF/water (0.5 mL each) and LiOH·H$_2$O (2 mg, 0.05 mmol) were added. The reaction was stirred at RT for 4 h, then was concentrated in vacuo. The residue was taken up in EtOAc (2 mL)/water (1 mL), and adjusted to pH~5 with 1N aq. HCl. The mixture was extracted with EtOAc (3×2 mL); the combined organic extracts were dried (MgSO$_4$) and concentrated in vacuo. The residue was dissolved in DMF and purified via preparative LC/MS: Column: XBridge C18, 200 mm×19 mm, 5-μm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 15% B, 15-55% B over 25 min, then a 4-min hold at 100% B; Flow Rate: 20 mL/min; Column Temperature: 25° C. Fraction collection was triggered by MS signals. Fractions containing the desired product were combined and dried via centrifugal evaporation to give the title compound (1.3 mg, 8% yield; 100% purity by LCMS) as a colorless oil (1.3 mg of the other regioisomer was also isolated). LCMS, [M+H]$^+$=474.2. $^1$H NMR (500 MHz, DMSO-d$_6$) δ 8.20 (s, 1H), 7.87 (d, J=8.5 Hz, 1H), 7.79 (d, J=7.6 Hz, 2H), 7.51 (d, J=8.6 Hz, 1H), 7.45 (t, J=7.6 Hz, 2H), 7.37 (t, J=7.4 Hz, 1H), 6.41 (s, 2H), 4.73 (s, 1H), 4.15 (s, 3H), 2.66-2.62 (m, 1H), 2.44 (s, 3H), 1.94-1.48 (m, 8H). hLPA$_1$ IC$_{50}$=57 nM.

Example 274. (1 S,3 S)-3-((6-(5-((5-cyclopropyl-3-imino-1,2,4-thiadiazol-2(3H)-yl)methyl)-1-methyl-1H-1,2,3-triazol-4-yl)-2-methylpyridin-3-yl)oxy)cyclohexane-1-carboxylic acid

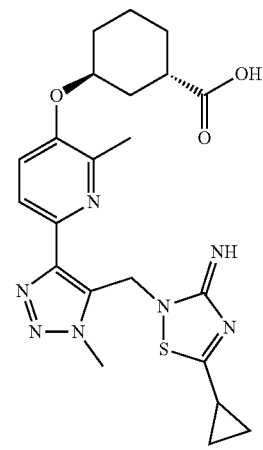 [SMILES: Cc1nc(-c2nnn(C)c2Cn2sc(C3CC3)nc2=N)ccc1O[C@H]1CCC[C@H](C(=O)O)C1]

A mixture of Intermediate 5 (16 mg, 0.038 mmol), 5-cyclopropyl-1,2,4-thiadiazol-3-amine hydrochloride (13 mg, 0.075 mmol) and iPr$_2$NEt (7 μL, 0.038 mmol) in DMF (0.5 mL) was heated in a microwave reactor at 130° C. for 30 min, then was cooled to RT and concentrated in vacuo. The residue was dissolved in THF/water (0.5 mL each). LiOH·H$_2$O (8 mg, 0.19 mmol) was added and the reaction was stirred at RT for 5 h, then was diluted with EtOAc (2 mL)/water (1 mL). The pH was adjusted to ~5 with 1N aq. HCl. The mixture was extracted with EtOAc (3×2 mL); the combined organic extracts were dried (MgSO$_4$) and concentrated in vacuo. The crude product was dissolved in DMF and purified via preparative LC/MS: Column: XBridge C18, 19×200 mm, 5-μm particles; Mobile Phase A: 5:95 MeCN:H$_2$O with 10 mM aq. NH$_4$OAc; Mobile Phase B: 95:5 MeCN:H$_2$O with 10 mM NH$_4$OAc; Gradient: 5-45% B over 20 min, then 4-min hold at 100% B; Flow: 20 mL/min. Fractions containing the desired product were combined and dried via centrifugal evaporation to give the title compound (5.5 mg, 30% yield; 96% purity by LCMS) as a colorless oil. LCMS, [M+H]$^+$=470.3. $^1$H NMR (500 MHz, DMSO-d$_6$) δ 7.81 (d, J=8.5 Hz, 1H), 7.46 (d, J=8.6 Hz, 1H), 5.54 (s, 2H), 4.76 (s, 1H), 4.05 (s, 3H), 2.66-2.59 (m, 1H), 2.44 (s, 3H), 2.04-1.46 (m, 9H), 0.88 (td, J=6.9, 4.3 Hz, 2H), 0.64-0.58 (m, 2H). hLPA$_1$ IC$_{50}$=1000 nM.

Example 275. (1S,3S)-3-((6-(5-((5-Butyl-1,2,4-oxadiazol-3-yl)amino)-1-methyl-1H-1,2,3-triazol-4-yl)-2-methylpyridin-3-yl)oxy)cyclohexane-1-carboxylic acid, 2 TFA salt

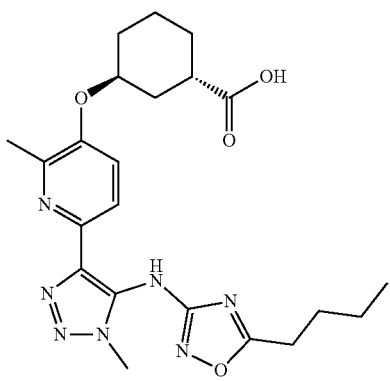 [SMILES: CCCCc1nc(Nc2c(-c3ccc(O[C@H]4CCC[C@H](C(=O)O)C4)c(C)n3)nnn2C)no1]

275A. Methyl (1S,3S)-3-((6-(5-((imino(methylthio)methyl)amino)-1-methyl-1H-1,2,3-triazol-4-yl)-2-methylpyridin-3-yl)oxy)cyclohexane-1-carboxylate

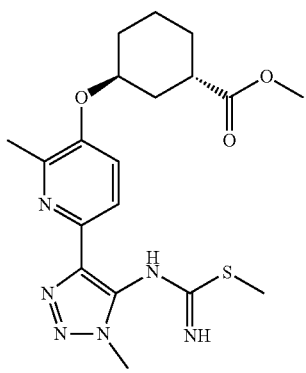

A mixture of Intermediate 18 (170 mg, 0.49 mmol) and 1,1'-thiocarbonyldi-2(1H)-pyridone (343 mg, 1.48 mmol) in DCM (6.5 mL) was stirred at RT for 18 h, then was concentrated in vacuo. 2M ammonia in MeOH (6.2 mL, 12.4 mmol) was added and the reaction was stirred at RT for 4 h, then was concentrated in vacuo. The residue was dissolved in EtOH (2.5 mL) and MeI (0.092 mL, 1.48 mmol) was added. The mixture was heated in a sealed tube at 50° C. for 2 h, then was cooled to RT and concentrated in vacuo. The residue was dissolved in EtOAc, washed with satd aq. NaHCO$_3$ (2×) and brine, dried (Na$_2$SO$_4$) and concentrated in vacuo. The crude product was chromatographed (12 g SiO$_2$, continuous gradient from 0-100% EtOAc in hexane) to give the title compound (143 mg, 69%) as a white solid. LCMS, [M+H]$^+$=419.1; $^1$H NMR (500 MHz, CDCl$_3$) δ 7.85 (d, J=8.5 Hz, 1H), 7.23 (d, J=8.5 Hz, 1H), 6.18 (br s, 2H), 4.73-4.67 (m, 1H), 3.89 (s, 3H), 3.71 (s, 3H), 2.84 (tt, J=10.4, 3.9 Hz, 1H), 2.57 (s, 3H), 2.46 (s, 3H), 2.21-2.11 (m, 1H), 2.03-1.87 (m, 3H), 1.82-1.56 (m, 4H).

275B. Methyl (1S,3S)-3-((6-(5-(3-hydroxyguanidino)-1-methyl-1H-1,2,3-triazol-4-yl)-2-methylpyridin-3-yl)oxy)cyclohexane-1-carboxylate

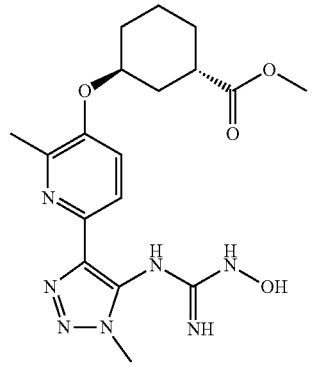

A mixture of 275A, iPr$_2$NEt (0.36 mL, 2.1 mmol) and NH$_2$OH·HCl (71 mg, 1.02 mmol) in MeOH (3 mL) was heated in a microwave reactor at 140° C. for 1 h, then was cooled to RT and concentrated in vacuo. The crude product was chromatographed (12 g SiO$_2$, continuous gradient from 0-10% MeOH in DCM) to give the title compound (163 mg, 118%) as a brown solid. LCMS, [M+H]$^+$=404.1. $^1$H NMR (500 MHz, CD$_3$OD) δ 7.88 (d, J=8.5 Hz, 1H), 7.50 (d, J=8.8 Hz, 1H), 4.86-4.81 (m, 1H), 4.05 (s, 3H), 3.70 (s, 3H), 2.89-2.79 (m, 1H), 2.54 (s, 3H), 2.18-2.04 (m, 1H), 2.04-1.90 (m, 4H), 1.83-1.62 (m, 5H).

275C. Methyl (1S,3S)-3-((6-(5-((Z)-2-hydroxy-3-pentanoylguanidino)-1-methyl-1H-1,2,3-triazol-4-yl)-2-methylpyridin-3-yl)oxy)cyclohexane-1-carboxylate

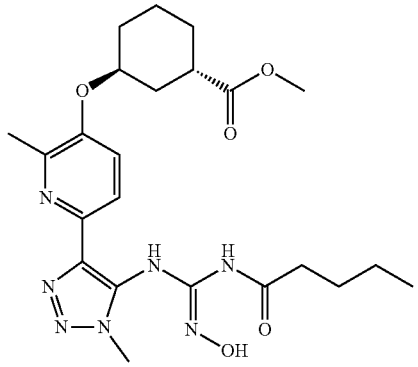 [SMILES: CCCCC(=O)N/C(=N\O)Nc1c(-c2ccc(O[C@H]3CCC[C@H](C(=O)OC)C3)c(C)n2)nnn1C]

To a solution of 275B (70 mg, 0.17 mmol), pentanoic acid (18 mg, 0.17 mmol) and iPr$_2$NEt (36 μL, 0.21 mmol) in MeCN (1 mL) was added HATU (79 mg, 0.21 mmol). The reaction mixture was stirred at RT for 18 h, then was concentrated in vacuo. The crude product was chromatographed (4 g SiO$_2$, continuous gradient from 0-100% EtOAc in hexane) to give the title compound (32 mg, 38%) as a white solid. LCMS, [M+H]$^+$=488.3.

275D. Methyl (1S,3S)-3-((6-(5-((5-butyl-1,2,4-oxadiazol-3-yl)amino)-1-methyl-1H-1,2,3-triazol-4-yl)-2-methylpyridin-3-yl)oxy)cyclohexane-1-carboxylate, 2 TFA salt

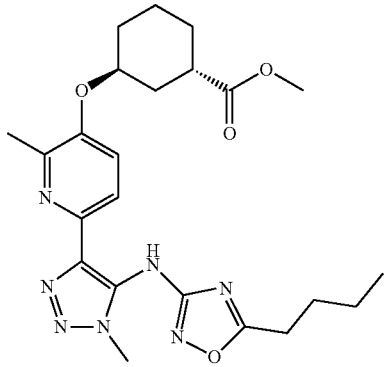 [SMILES: CCCCc1nc(Nc2c(-c3ccc(O[C@H]4CCC[C@H](C(=O)OC)C4)c(C)n3)nnn2C)no1]

A mixture of 275C (32 mg, 0.066 mmol) and HOAc (0.75 µL, 0.013 mmol) in toluene (2 mL) was heated in a sealed tube at 110° C. for 18 h, then was cooled to RT and concentrated in vacuo. The crude material was purified by preparative HPLC: Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min) to give the title compound (12 mg, 26%) as a white solid. LCMS, [M+H]$^+$=470.2. $^1$H NMR (500 MHz, CD$_3$OD) δ 7.80 (s, 2H), 4.97-4.88 (m, 1H), 4.06 (s, 3H), 3.70 (s, 3H), 2.88-2.75 (m, 3H), 2.62 (s, 3H), 2.16-2.07 (m, 1H), 2.02-1.89 (m, 3H), 1.81-1.62 (m, 6H), 1.38 (dq, J=15.0, 7.5 Hz, 2H), 0.95 (t, J=7.4 Hz, 3H).

Example 275

To a solution of 275D (12 mg, 0.017 mmol) in THF (2 mL)/water (1 mL) was added 2M aq. LiOH (0.043 mL, 0.086 mmol). The reaction mixture was stirred at RT for 18 h; the pH was adjusted with 1N aq. HCl to ~4. The mixture was extracted with EtOAc (3×5 mL). The combined organic layers were washed with brine, dried (MgSO$_4$), and concentrated in vacuo. The crude product was purified by preparative HPLC: Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min to give the title compound (2.5 mg, 22%) as a white solid. LCMS, [M+H]$^+$=456.1. $^1$H NMR (500 MHz, CD$_3$OD) δ 7.84-7.78 (m, 2H), 4.97-4.89 (m, 1H), 4.06 (s, 3H), 2.83-2.77 (m, 3H), 2.62 (s, 3H), 2.15-2.06 (m, 1H), 2.04-1.90 (m, 3H), 1.82-1.63 (m, 6H), 1.43-1.33 (m, 2H), 0.95 (t, J=7.4 Hz, 3H). hLPA$_1$ IC$_{50}$=18 nM.

Example 276. (1S,3S)-3-((6-(5-((5-(Cyclopropylmethyl)-1,3,4-oxadiazol-2-yl)amino)-1-methyl-1H-1,2,3-triazol-4-yl)-2-methylpyridin-3-yl)oxy)cyclohexane-1-carboxylic acid, 2 TFA salt

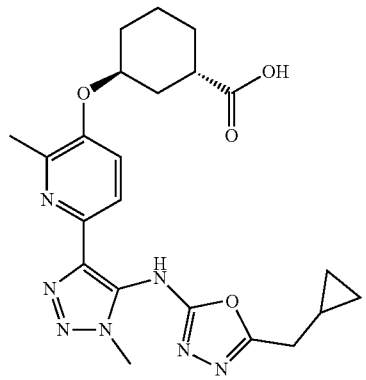 [SMILES: Cc1nc(-c2nnn(C)c2Nc2nnc(CC3CC3)o2)ccc1O[C@H]1CCC[C@H](C(=O)O)C1]

276A. Methyl (1S,3S)-3-((6-(5-(2-(2-cyclopropylacetyl)hydrazine-1-carboxamido)-1-methyl-1H-1,2,3-triazol-4-yl)-2-methylpyridin-3-yl)oxy)cyclohexane-1-carboxylate

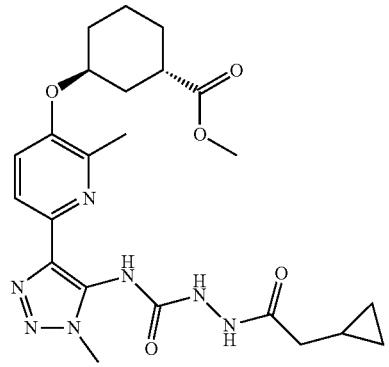 [SMILES: COC(=O)[C@H]1CCC[C@H](Oc2ccc(-c3nnn(C)c3NC(=O)NNC(=O)CC3CC3)nc2C)C1]

To a 0° C. mixture of Intermediate 18 (30 mg, 0.087 mmol) and NaHCO$_3$ (0.022 g, 0.26 mmol) in DCM/MeCN (1 mL each) was added 20% phosgene in toluene (0.14 mL, 0.26 mmol). The reaction mixture was stirred at 0° C. for 30 min, then was concentrated in vacuo. The residue was dissolved in DCM/MeCN (1 mL each), and to this solution (cooled to 0° C.) were added 2-cyclopropylacetohydrazide (0.030 g, 0.26 mmol) and Et$_3$N (0.024 mL, 0.17 mmol). The resulting cloudy mixture was stirred at 0° C. for 30 min, at RT for 18 h, and at 65° C. for 36 h, then was cooled to RT and concentrated in vacuo. The crude product was chromatographed (4 g SiO$_2$, continuous gradient from 0-100% EtOAc in hexanes) to give the title compound (13 mg, 31%) as a white solid. LCMS, [M+H]$^+$=486.2. $^1$H NMR (400 MHz, CDCl$_3$) δ 9.02 (br s, 1H), 8.29 (br s, 2H), 7.83 (d, J=8.6 Hz, 1H), 7.17 (d, J=8.8 Hz, 1H), 4.70-4.62 (m, 1H), 3.98 (s, 3H), 3.69 (s, 3H), 2.90-2.70 (m, 1H), 2.43 (s, 3H), 2.33-2.07 (m, 3H), 2.02-1.81 (m, 3H), 1.79-1.55 (m, 4H), 1.13-0.89 (m, 1H), 0.65-0.54 (m, 2H), 0.28-0.14 (m, 2H).

276B. Methyl (1S,3S)-3-((6-(5-((5-(cyclopropylmethyl)-1,3,4-oxadiazol-2-yl)amino)-1-methyl-1H-1,2,3-triazol-4-yl)-2-methylpyridin-3-yl)oxy)cyclohexane-1-carboxylate, 2 TFA salt

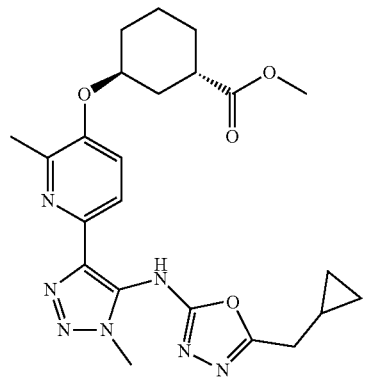 [SMILES: COC(=O)[C@H]1CCC[C@H](Oc2ccc(-c3nnn(C)c3Nc3nnc(CC4CC4)o3)nc2C)C1]

A mixture of 276A (13 mg, 0.027 mmol), Et$_3$N (11 μL, 0.080 mmol) and 2,4,6-tripropyl-1,3,5,2,4,6-trioxatriphosphorinane-2,4,6-trioxide (50% in EtOAc, 0.048 mL, 0.080 mmol) in MeCN (1 mL) was heated at 100° C. for 30 min, then at 135° C. for 30 min in a microwave reactor, then was cooled to RT and concentrated in vacuo. The crude product was purified by preparative HPLC (Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min) to give the title compound (3 mg, 16%) as a white solid. LCMS, [M+H]$^+$=468.1. $^1$H NMR (500 MHz, CD$_3$OD) δ 7.90 (d, J=8.8 Hz, 1H), 7.80 (d, J=8.8 Hz, 1H), 4.95-4.91 (m, 1H), 4.00 (s, 3H), 3.73-3.67 (m, 3H), 2.90-2.80 (m, 1H), 2.67-2.50 (m, 5H), 2.18-2.05 (m, 1H), 2.03-1.89 (m, 3H), 1.84-1.61 (m, 4H), 0.95-0.86 (m, 1H), 0.54-0.47 (m, 2H), 0.24-0.16 (m, 2H).

Example 276. (1S,3S)-3-((6-(5-((5-(Cyclopropylmethyl)-1,3,4-oxadiazol-2-yl)amino)-1-methyl-1H-1,2,3-triazol-4-yl)-2-methylpyridin-3-yl)oxy)cyclohexane-1-carboxylic acid, 2 TFA salt

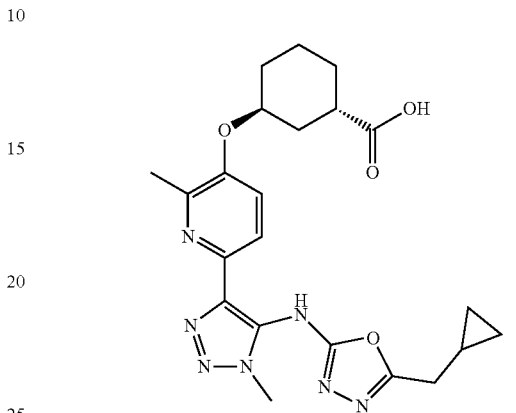

The title compound (1.7 mg, 53%, white solid) was prepared from 276B according to the procedure described for the synthesis of Example 275. LCMS, [M+H]$^+$=454.1. $^1$H NMR (500 MHz, CD$_3$OD) δ 7.88 (d, J=8.8 Hz, 1H), 7.76 (d, J=8.8 Hz, 1H), 5.10-4.93 (m, 1H), 4.00 (s, 3H), 3.56-3.46 (m, 1H), 2.84-2.74 (m, 1H), 2.58-2.49 (m, 5H), 2.15-2.05 (m, 1H), 2.05-1.87 (m, 3H), 1.82-1.63 (m, 4H), 0.94-0.85 (m, 1H), 0.55-0.45 (m, 2H), 0.23-0.15 (m, 2H). hLPA$_1$ IC$_{50}$=446 nM.

The following example was synthesized according to the procedures as indicated.

| Ex # | Structure & Name | Analytical & Biology Data | Method |
|---|---|---|---|
| 277 | ![structure] (1S,3S)-3-{[6-(5-{[5-(Cyclopropylmethyl)-1,2,4-oxadiazol-3-yl]amino}-1-methyl-1H-1,2,3-triazol-4-yl)-2-methylpyridin-3-yl]oxy}cyclohexane-1-carboxylic acid, bis TFA salt | LCMS, [M + H]$^+$ = 454.3; $^1$H NMR (400 MHz, CD$_3$OD) δ 7.81-7.74 (m, 2H), 4.90-4.85 (m, 1H), 4.04 (s, 3H), 2.83-2.74 (m, 1H), 2.70 (d, J = 7.0 Hz, 2H), 2.59 (s, 3H), 2.13-2.04 (m, 1H), 2.02-1.86 (m, 3H), 1.81-1.61 (m, 4H), 1.13-1.01 (m, 1H), 0.61-0.53 (m, 2H), 0.29-0.20 (m, 2H); hLPA$_1$ IC$_{50}$ = 33 nM. | Example 275 |

| Ex # | Structure & Name | Analytical & Biology Data | Method |
|---|---|---|---|
| 278 | (1S,3S)-3-((6-(5-(((5-(2-cyclobutyl ethyl)-1,2,4-oxadiazol-3-yl)amino) methyl)-1-methyl-1H-1,2,3-triazol-4-yl)-5-fluoro-2-methylpyridin-3-yl) oxy)cyclohexane-1-carboxylic acid | LCMS, [M + H]$^+$ = 514; $^1$H NMR (500 MHz, DMSO-d$_6$) δ 7.56 (d, J = 12.2 Hz, 1H), 7.15 (t, J = 5.5 Hz, 1H), 4.79 (br s, 1H), 4.64 (br d, J = 5.5 Hz, 2H), 4.11 (s, 3H), 2.61-2.56 (m, 3H), 2.37 (s, 3H), 2.28-2.16 (m, 1H), 1.99-1.91 (m, 3H), 1.81-1.53 (m, 13H); hLPA$_1$ IC$_{50}$ = 30 nM. | Example 42, intermediate 20 |
| 279 | (1S,3S)-3-((6-(5-(((5-(2-cyclopropyl-ethyl)-1,2,4-oxadiazol-3-yl)amino) methyl)-1-methyl-1H-1,2,3-triazol-4-yl)-5-fluoro-2-methylpyridin-3-yl) oxy)cyclohexane-1-carboxylic acid | LCMS, [M + H]$^+$ = 500; $^1$H NMR (500 MHz, DMSO-d$_6$) δ 7.55 (d, J = 12.2 Hz, 1H), 7.14 (br t, J = 5.6 Hz, 1H), 4.78 (br s, 1H), 4.63 (br d, J = 5.5 Hz, 2H), 4.10 (s, 3H), 2.74 (t, J = 7.5 Hz, 2H), 2.61-2.55 (m, 1H), 2.36 (s, 3H), 1.96-1.76 (m, 4H), 1.67-1.47 (m, 6H), 0.75-0.63 (m, 1H), 0.36 (m, 2H), 0.00 (m, 2H); hLPA$_1$ IC$_{50}$ = 51 nM. | Example 42; intermediate 20 |
| 280 | (1S,3S)-3-((6-(5-(((5-butyl-1,2,4-oxadiazol-3-yl)amino)methyl)-1-methyl-1H-1,2,3-triazol-4-yl)-5-fluoro-2-methylpyridin-3-yl)oxy) cyclohexane-1-carboxylic acid | LCMS, [M + H]$^+$ = .488; $^1$H NMR (500 MHz, DMSO-d$_6$) δ 7.54 (d, J = 12.2 Hz, 1H), 7.16 (br t, J = 5.5 Hz, 1H), 4.81 (br s, 1H), 4.64 (br d, J = 5.5 Hz, 2H), 4.11 (s, 3H), 2.68 (t, J = 7.5 Hz, 2H), 2.63 (m, 1H), 2.37 (s, 3H), 2.05-1.98 (m, 1H), 1.90-1.78 (m, 3H), 1.68-1.50 (m, 6H), 1.30 (m, 2H), 0.86 (t, J = 7.3 Hz, 3H); hLPA$_1$ IC$_{50}$ = 143 nM. | Example 42; intermediate 20 |

| Ex # | Structure & Name | Analytical & Biology Data | Method |
|---|---|---|---|
| 281 | 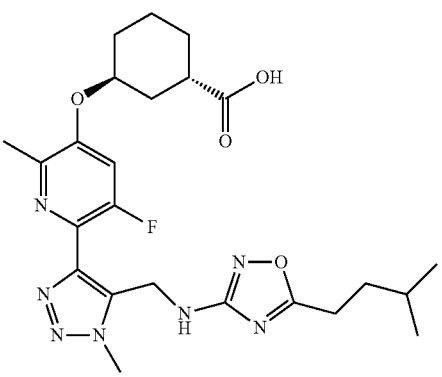 [SMILES: Cc1nc(-c2nnn(C)c2CNc2noc(CCC(C)C)n2)c(F)cc1O[C@H]1CCC[C@H](C(=O)O)C1]<br>(1S,3S)-3-((5-fluoro-6-(5-(((5-isopentyl-1,2,4-oxadiazol-3-yl)amino)methyl)-1-methyl-1H-1,2,3-triazol-4-yl)-2-methylpyridin-3-yl)oxy)cyclohexane-1-carboxylic acid | LCMS, $[M + H]^+$ = 502;<br>$^1$H NMR (500 MHz, DMSO-$d_6$) δ 7.51 (d, J = 12.2 Hz, 1H), 7.13 (t, J = 5.3 Hz, 1H), 4.79 (br s, 1H), 4.62 (d, J = 5.5 Hz, 2H), 4.10 (s, 3H), 2.68-2.62 (m, 3H), 2.36 (s, 3H), 2.00 (m, 1H), 1.89-1.76 (m, 3H), 1.66-1.45 (m, 7H), 0.84 (d, J = 5.5 Hz, 6H);<br>hLPA$_1$ IC$_{50}$ = 67 nM. | Example 42 |
| 282 | 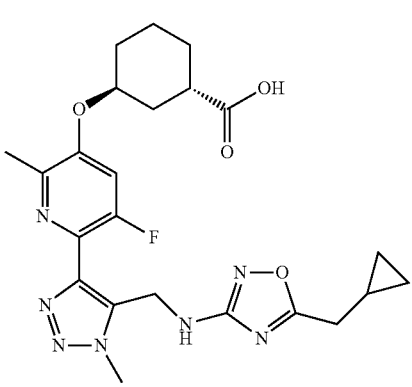 [SMILES: Cc1nc(-c2nnn(C)c2CNc2noc(CC3CC3)n2)c(F)cc1O[C@H]1CCC[C@H](C(=O)O)C1]<br>(1S,3S)-3-((6-(5-(((5-(cyclopropylmethyl)-1,2,4-oxadiazol-3-yl)amino)methyl)-1-methyl-1H-1,2,3-triazol-4-yl)-5-fluoro-2-methylpyridin-3-yl)oxy)cyclohexane-1-carboxylic acid | LCMS, $[M + H]^+$ = 486;<br>$^1$H NMR (500 MHz, DMSO-$d_6$) δ 7.53 (d, J = 12.2 Hz, 1H), 7.18 (br t, J = 5.5 Hz, 1H), 4.80 (br s, 1H), 4.64 (d, J = 5.5 Hz, 2H), 4.11 (s, 3H), 2.64 (m, 1H), 2.60 (d, J = 7.0 Hz, 2H), 2.37 (s, 3H), 2.01 (m, 1H), 1.88-1.76 (m, 3H), 1.67-1.46 (m, 4H), 1.05-0.93 (m, 1H), 0.48 (m, 2H), 0.18 (m, 2H);<br>hLPA$_1$ IC$_{50}$ = 236 nM. | Example 42; intermediate 20 |
| 283 | 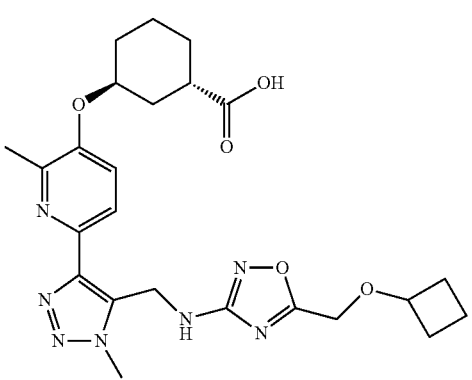 [SMILES: Cc1nc(-c2nnn(C)c2CNc2noc(COC3CCC3)n2)ccc1O[C@H]1CCC[C@H](C(=O)O)C1]<br>(1S,3S)-3-((6-(5-(((5-(cyclobutoxymethyl)-1,2,4-oxadiazol-3-yl)amino)methyl)-1-methyl-1H-1,2,3-triazol-4-yl)-2-methylpyridin-3-yl)oxy)cyclohexane-1-carboxylic acid, TFA salt | LCMS, $[M + H]^+$ = 498;<br>$^1$H NMR (500 MHz, DMSO-$d_6$) δ 7.86 (d, J = 8.5 Hz, 1H), 7.51 (d, J =8.7 Hz, 1H), 4.83-4.77 (m, 3H), 4.47 (s, 2H), 4.10 (s, 3H), 4.01 (m, 1H), 2.66-2.59 (m, 1H), 2.10 (m, 2H), 2.02 (m, 1H), 1.90-1.75 (m, 5H), 1.66-1.39 (m, 6H);<br>hLPA$_1$ IC$_{50}$ = 19 nM. | Example 285 |

| Ex # | Structure & Name | Analytical & Biology Data | Method |
|---|---|---|---|
| 284 | 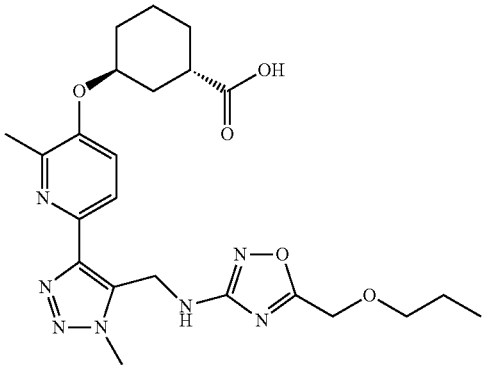 [SMILES: CCCOCc1nc(NCc2c(-c3ccc(O[C@H]4CCC[C@H](C(=O)O)C4)c(C)n3)nnn2C)no1]<br>(1S,3S)-3-((2-methyl-6-(1-methyl-5-(((5-(propoxymethyl)-1,2,4-oxadiazol-3-yl)amino)methyl)-1H-1,2,3-triazol-4-yl)pyridin-3-yl)oxy)cyclohexane-1-carboxylic acid, TFA salt | LCMS, [M + H]$^+$ = 486;<br>$^1$H NMR (500 MHz, DMSO-d$_6$)<br>δ 7.86 (d, J = 8.9 Hz, 1H), 7.50 (d, J = 8.5 Hz, 1H), 4.83-4.76 (m, 3H), 4.57 (s, 2H), 4.10 (s, 3H), 2.63 (m, 1H), 2.05-1.99 (m, 1H), 1.90-1.74 (m, 3H), 1.68-1.46 (m, 6H), 0.85 (t, J = 7.3 Hz, 3H);<br>hLPA$_1$ IC$_{50}$ = 24 nM. | Example 285 |

Example 285. (1 S,3 S)-3-((6-(5-(((5-isopentyl-1,2,4-oxadiazol-3-yl)amino)methyl)-1-methyl-1H-1,2,3-triazol-4-yl)pyridin-3-yl)oxy)cyclohexane-1-carboxylic acid

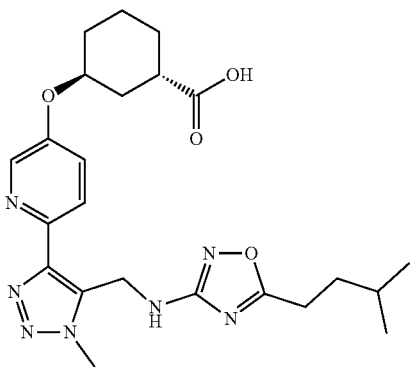 [SMILES: CC(C)CCc1nc(NCc2c(-c3ccc(O[C@H]4CCC[C@H](C(=O)O)C4)cn3)nnn2C)no1]

To a solution of Intermediate 21 (32 mg, 0.093 mmol), 5-isopentyl-1,2,4-oxadiazol-3-amine (14.4 mg, 0.093 mmol) in MeOH (1 mL) was added HOAc (0.027 mL, 0.46 mmol). The reaction was heated at 65° C. for 2 h, then was cooled to RT, after which NaBH$_3$CN (12 mg, 0.19 mmol) was added. The reaction was stirred at RT for 18 h; satd aq. NaHCO$_3$ was then added. The aqueous layer was extracted with EtOAc. The organic layer was washed with brine, dried (MgSO$_4$) and concentrated in vacuo; product LCMS [M+H]$^+$=484.2. The residue was dissolved in THF/MeOH (0.5 mL each) and 2M aq. LiOH (0.13 mL, 0.25 mmol) was added. The reaction mixture was stirred at RT for 3 h, then was concentrated in vacuo. The residue was dissolved in H$_2$O (1 mL), and the pH was adjusted with 1N aq. HCl to ~3 and extracted with EtOAc (2×1 mL). The combined organic extracts were washed with brine (1 mL), dried (MgSO$_4$) and concentrated in vacuo. The crude product was purified by preparative LC/MS: Column: Waters XBridge C18, 19×200 mm, 5-μm particles; Guard Column: Waters XBridge C18, 19×10 mm, 5-μm particles; Mobile Phase A: 5:95 MeCN:H$_2$O with 0.1% TFA; Mobile Phase B: 95:5 MeCN:H$_2$O with 0.1% TFA; Gradient: 50-90% B over 20 min, then a 5-min hold at 100% B; Flow: 20 mL/min. Fractions containing the desired product were combined and concentrated in vacuo by centrifugal evaporation to give the title compound (bis-TFA salt) as a colorless solid (18.5 mg, 0.026 mmol, 41.9% yield). LCMS, [M+H]$^+$=470.2; $^1$H NMR (400 MHz, CDCl$_3$) δ 8.34 (br d, J=1.8 Hz, 1H), 8.09 (br d, J=8.8 Hz, 1H), 7.37 (dd, J=8.8, 2.4 Hz, 1H), 4.67 (br s, 1H), 4.60 (s, 3H), 4.21 (s, 3H), 2.84 (dq, J=8.8, 4.4 Hz, 1H), 2.68-2.58 (m, 2H), 2.11-1.79 (m, 4H), 1.78-1.48 (m, 7H), 0.84 (d, J=6.4 Hz, 6H); hLPA$_1$ IC$_{50}$=93 nM.

The Examples listed in the following table were prepared by using same synthetic sequence and the same intermediates as described for the synthesis of Example 285 (and also as described in the synthetic sequence shown in Scheme 1).

| Ex # | Structure & Name | Analytical & Biological Data |
|---|---|---|
| 286 | 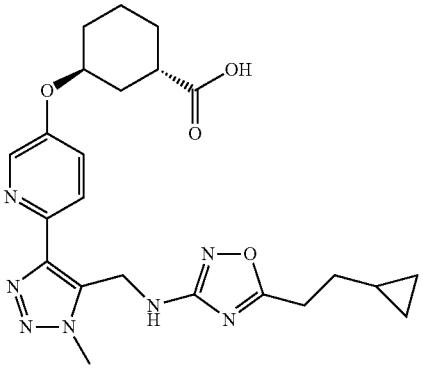 [SMILES: Cn1nnc(-c2ccc(O[C@H]3CCC[C@H](C(=O)O)C3)cn2)c1CNc1noc(CCC2CC2)n1]<br><br>(1S,3S)-3-((6-(5-(((5-(2-cyclopropyl-ethyl)-1,2,4-oxadiazol-3-yl)amino)methyl)-1-methyl-1H-1,2,3-triazol-4-yl)pyridin-3-yl)oxy)cyclohexane-1-carboxylic acid | LCMS, $[M + H]^+ = 468.3$;<br>$^1$H NMR (400 MHz, CDCl$_3$) δ 8.37 (br s, 1H), 8.12 (br d, J = 8.6 Hz, 1H), 7.54-7.31 (m, 1H), 5.78 (br s, 1H), 4.70 (br s, 1H), 4.62 (s, 2H), 4.23 (s, 3H), 2.86 (dq, J = 8.8, 4.3 Hz, 1H), 2.76 (t, J = 7.6 Hz, 2H), 2.15-1.82 (m, 4H), 1.81-1.50 (m, 6H), 0.79-0.57 (m, 1H), 0.43-0.30 (m, 2H), −0.01 (d, J = 5.3 Hz, 2H);<br>hLPA$_1$ IC$_{50}$ = 10 nM. |
| 287 | 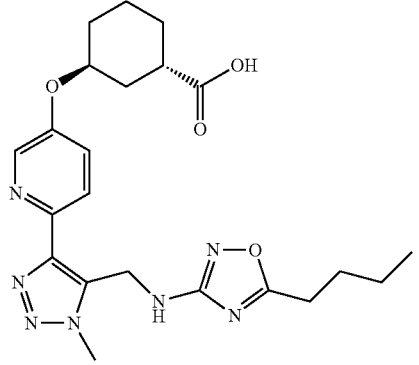<br><br>(1S,3S)-3-((6-(5-(((5-butyl-1,2,4-oxadiazol-3-yl)amino)methyl)-1-methyl-1H-1,2,3-triazol-4-yl)pyridin-3-yl)oxy)cyclohexane-1-carboxylic acid | LCMS, $[M + H]^+ = 456.2$;<br>$^1$H NMR (CDCl$_3$) δ: 8.54 (br s, 1H), 8.21 (br d, J = 9.0 Hz, 1H), 7.64 (br d, J = 8.8 Hz, 1H), 4.79 (br d, J = 2.6 Hz, 1H), 4.72 (s, 2H), 4.30 (s, 3H), 2.74 (br t, J = 7.6 Hz, 2H), 1.52-2.27 (m, 10H), 1.20-1.50 (m, 3H), 0.95 (br t, J = 7.2 Hz, 3H);<br>hLPA$_1$ IC$_{50}$ = 124 nM. |
| 288 | 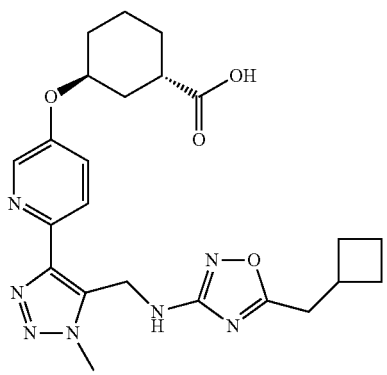 [SMILES: Cn1nnc(-c2ccc(O[C@H]3CCC[C@H](C(=O)O)C3)cn2)c1CNc1noc(CC2CCC2)n1]<br><br>(1S,3S)-3-((6-(5-(((5-(cyclobutylmethyl)-1,2,4-oxadiazol-3-yl)amino)methyl)-1-methyl-1H-1,2,3-triazol-4-yl)pyridin-3-yl)oxy)cyclohexane-1-carboxylic acid | LCMS, $[M + H]^+ = 468.1$;<br>$^1$H NMR (400 MHz, CDCl$_3$) δ 8.44 (d, J = 2.6 Hz, 1H), 8.11 (d, J = 8.8 Hz, 1H), 7.51 (dd, J = 8.8, 2.9 Hz, 1H), 6.22 (br s, 1H), 4.78-4.66 (m, 1H), 4.64 (s, 2H), 4.23 (s, 3H), 2.87 (tt, J = 8.5, 4.3 Hz, 1H), 2.77-2.72 (m, 2H), 2.65 (dt, J = 15.3, 7.8 Hz, 1H), 2.22-1.48 (m, 14H);<br>hLPA$_1$ IC$_{50}$ = 34.1 nM. |

| Ex # | Structure & Name | Analytical & Biological Data |
|---|---|---|
| 289 | 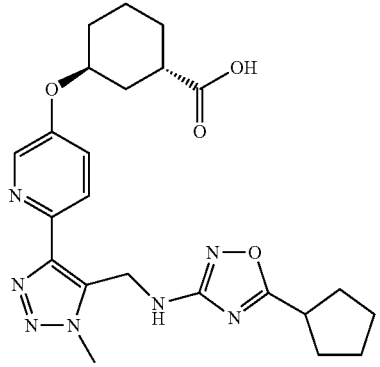 [SMILES: Cn1nnc(-c2ccc(O[C@H]3CCC[C@H](C(=O)O)C3)cn2)c1CNc1noc(C2CCCC2)n1]<br>(1S,3S)-3-((6-(5-(((5-cyclopentyl-1,2,4-oxadiazol-3-yl)amino)methyl)-1-methyl-1H-1,2,3-triazol-4-yl)pyridin-3-yl)oxy)cyclohexane-1-carboxylic acid | LCMS, [M + H]$^+$ = 468.1;<br>$^1$H NMR (DMSO-d$_6$) δ: 8.37 (br s, 1H), 8.00 (br d, J = 8.6 Hz, 1H), 7.53 (dd, J = 8.7, 2.4 Hz, 1H), 6.91-7.26 (m, 1H), 4.77 (br d, J = 4.5 Hz, 3H), 4.12 (s, 3H), 3.05-3.35 (m, 1H), 2.69 (br s, 1H), 1.99 (br d, J = 8.6 Hz, 3H), 1.47-1.92 (m, 13H);<br>hLPA$_1$ IC$_{50}$ = 50.7 nM. |
| 290 | 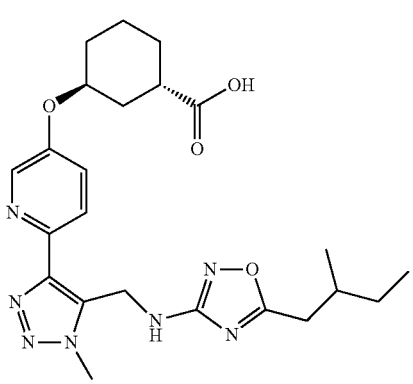 [SMILES: CCC(C)Cc1nc(NCc2c(-c3ccc(O[C@H]4CCC[C@H](C(=O)O)C4)cn3)nnn2C)no1]<br>(1S,3S)-3-((6-(1-methyl-5-(((5-(2-methylbutyl)-1,2,4-oxadiazol-3-yl)amino)methyl)-1H-1,2,3-triazol-4-yl)pyridin-3-yl)oxy)cyclohexane-1-carboxylic acid, racemate | LCMS, [M + H]$^+$ = 470.2;<br>$^1$H NMR (400 MHz, CDCl$_3$) δ 8.62 (d, J = 2.9 Hz, 1H), 8.26 (d, J = 9.0 Hz, 1H), 7.89 (dd, J = 9.0, 2.9 Hz, 1H), 7.77 (br s, 1H), 4.85 (br s, 1H), 4.75 (s, 2H), 4.29 (s, 3H), 3.01-2.85 (m, 1H), 2.74 (dd, J = 15.0, 6.2 Hz, 1H), 2.65-2.51 (m, 1H), 2.30-2.11 (m, 1H), 2.10-1.99 (m, 1H), 1.98-1.75 (m, 6H), 1.73-1.61 (m, 1H), 1.46-1.33 (m, 1H), 1.33-1.19 (m, 1H), 0.99-0.87 (m, 6H);<br>hLPA$_1$ IC$_{50}$ = 37.3 nM. |
| 291 | 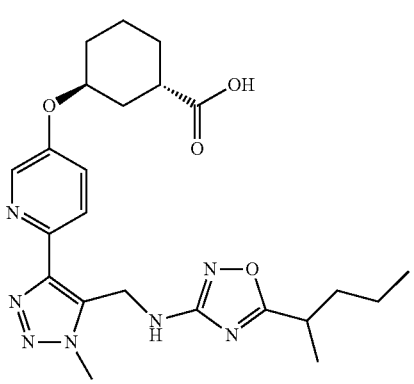 [SMILES: CCCC(C)c1nc(NCc2c(-c3ccc(O[C@H]4CCC[C@H](C(=O)O)C4)cn3)nnn2C)no1]<br>(1S,3S)-3-((6-(1-methyl-5-(((5-(pentan-2-yl)-1,2,4-oxadiazol-3-yl)amino)methyl)-1H-1,2,3-triazol-4-yl)pyridin-3-yl)oxy)cyclohexane-1-carboxylic acid, racemate | LCMS, [M + H]$^+$ = 470.1;<br>$^1$H NMR (400 MHz, CDCl$_3$) δ 8.54 (d, J = 2.9 Hz, 1H), 8.20 (d, J = 9.0 Hz, 1H), 7.65 (dd, J = 9.0, 2.9 Hz, 1H), 6.17 (br s, 1H), 4.80 (br d, J = 3.5 Hz, 1H), 4.73 (s, 2H), 4.31 (s, 3H), 3.04-2.87 (m, 2H), 2.16-2.05 (m, 2H), 2.00-1.86 (m, 2H), 1.86-1.47 (m, 6H), 1.31 (d, J = 7.0 Hz, 5H), 0.91 (t, J = 7.4 Hz, 3H);<br>hLPA$_1$ IC$_{50}$ = 59.4 nM. |

| Ex # | Structure & Name | Analytical & Biological Data |
|---|---|---|
| 292 | (1S,3S)-3-((6-(1-methyl-5-(((5-(4,4,4-trifluorobutyl)-1,2,4-oxadi-azol-3-yl)amino)methyl)-1H-1,2,3-triazol-4-yl)pyridin-3-yl)oxy)cyclohexane-1-carboxylic acid | LCMS, [M + H]$^+$ = 510.2; $^1$H NMR (DMSO-d$_6$) δ 8.36 (d, J = 2.1 Hz, 1H), 7.99 (d, J = 8.5 Hz, 1H), 7.54 (dd, J = 8.7, 2.3 Hz, 1H), 7.20 (br t, J = 5.6 Hz, 1H), 4.77 (br d, J = 5.8 Hz, 3H), 4.10 (s, 3H), 2.82 (br t, J = 7.5 Hz, 2H), 2.65 (br d, J = 3.4 Hz, 1H), 2.25-2.40 (m, 2H), 1.92-2.03 (m, 1H), 1.73-1.90 (m, 5H), 1.66 (br d, J = 9.5 Hz, 2H), 1.44-1.59 (m, 2H); hLPA$_1$ IC$_{50}$ = 48.7 nM. |
| 293 | (1S,3S)-3-((6-(5-(((5-isopropyl-1,2,4-oxadiazol-3-yl)amino)methyl)-1-methyl-1H-1,2,3-triazol-4-yl)pyridin-3-yl)oxy)cyclohexane-1-carboxylic acid | LCMS, [M + H]$^+$ = 442.0; $^1$H NMR (DMSO-d$_6$) δ: 8.37 (d, J = 2.6 Hz, 1H), 8.00 (d, J = 8.8 Hz, 1H), 7.53 (dd, J = 8.8, 2.8 Hz, 1H), 7.05 (br t, J = 5.8 Hz, 1H), 4.78 (br d, J = 5.6 Hz, 3H), 4.12 (s, 3H), 3.05 (dt, J = 13.9, 6.9 Hz, 1H), 2.66-2.75 (m, 1H), 1.95-2.05 (m, 1H), 1.75-1.93 (m, 3H), 1.69 (br d, J = 8.2 Hz, 2H), 1.56 (br d, J = 10.7 Hz, 2H), 1.23 (d, J = 6.9 Hz, 6H); hLPA$_1$ IC$_{50}$ = 613 nM. |
| 294 | (1S,3S)-3-((6-(5-(((5-(2-cyclobutyl-ethyl)-1,2,4-oxadiazol-3-yl)amino)methyl)-1-methyl-1H-1,2,3-triazol-4-yl)pyridin-3-yl)oxy)cyclohexane-1-carboxylic acid | LCMS, [M + H]$^+$ = 482.2; $^1$H NMR (400 MHz, CDCl$_3$) δ 8.60 (d, J = 2.2 Hz, 1H), 8.23 (d, J = 9.0 Hz, 1H), 7.79 (dd, J = 9.0, 2.6 Hz, 1H), 6.92-6.53 (m, 1H), 4.82 (br s, 1H), 4.74 (s, 2H), 4.29 (s, 3H), 3.02-2.88 (m, 1H), 2.73-2.60 (m, 2H), 2.37-2.21 (m, 1H), 2.20-1.99 (m, 4H), 1.98-1.75 (m, 9H), 1.73-1.53 (m, 3H); hLPA$_1$ IC$_{50}$ = 33.4 nM. |

The following examples were synthesized according to the procedures described for the preparation of Examples 105 and 106.

| Ex # | Structure & Name | Analytical & Biology Data |
|---|---|---|
| 295 | (1S,3S)-3-{[6-(5-{[5-(cyclobutyl-methyl)-2H-1,2,3,4-tetrazol-2-yl]methyl}-1-methyl-1H-1,2,3-triazol-4-yl)-2-methylpyridin-3-yl]oxy} cyclohexane-1-carboxylic acid | LCMS, (M + H)$^+$ = 467.1; $^1$H NMR (500 MHz, DMSO-d$_6$) δ 7.85 (br d, J = 8.5 Hz, 1H), 7.45 (br d, J = 8.9 Hz, 1H), 6.49 (s, 2H), 4.75 (br s, 1H), 4.13 (s, 3H), 2.85 (br d, J = 7.3 Hz, 2H), 2.65-2.56 (m, 2H), 2.35 (s, 3H), 2.03-1.44 (m, 14H); hLPA$_1$ IC$_{50}$ = 102 nM. |
| 296 | (1S,3S)-3-{[6-(5-{[5-(2-cyclopropyl-ethyl)-2H-1,2,3,4-tetrazol-2-yl]methyl}-1-methyl-1H-1,2,3-triazol-4-yl)-2-methylpyridin-3-yl]oxy} cyclohexane-1-carboxylic acid | LCMS, (M + H)$^+$ = 467.4; $^1$H NMR (500 MHz, DMSO-d$_6$) δ 7.85 (br d, J = 8.5 Hz, 1H), 7.45 (br d, J = 8.9 Hz, 1H), 6.50 (s, 2H), 4.76 (br s, 1H), 4.13 (s, 3H), 2.84 (br t, J = 7.5 Hz, 2H), 2.66-2.56 (m, 1H), 2.36 (s, 3H), 2.02-1.96 (m, 1H), 1.88-1.72 (m, 3H), 1.64-1.44 (m, 6H), 0.67-0.60 (m, 1H), 0.28 (br d, J = 7.6 Hz, 2H),-0.06 (br d, J = 4.3 Hz, 2H); hLPA$_1$ IC$_{50}$ = 96 nM. |
| 297 | (1S,3S)-3-({2-methyl-6-[1-methyl-5-({5-[(2R)-oxolan-2-yl]-2H-1,2,3,4-tetrazol-2-yl}methyl)-1H-1,2,3-triazol-4-yl]pyridin-3-yl}oxy) cyclohexane-1-carboxylic acid | LCMS, (M + H)$^+$ = 469; $^1$H NMR (500 MHz, DMSO-d$_6$) δ 7.88 (br d, J = 8.5 Hz, 1H), 7.49 (br d, J = 8.5 Hz, 1H), 6.39 (br d, J = 15.3 Hz, 1H), 6.25 (br d, J = 15.3 Hz, 1H), 5.41 (br t, J = 6.6 Hz, 1H), 4.77 (br s, 1H), 4.12 (s, 3H), 3.85-3.76 (m, 2H), 2.63-2.57 (m, 1H), 2.37 (s, 3H), 2.31-2.23 (m, 1H), 2.07-1.91 (m, 3H), 1.87-1.73 (m, 3H), 1.65-1.44 (m, 4H); hLPA$_1$ IC$_{50}$ = 92 nM. |

-continued

| Ex # | Structure & Name | Analytical & Biology Data |
|---|---|---|
| 298 | 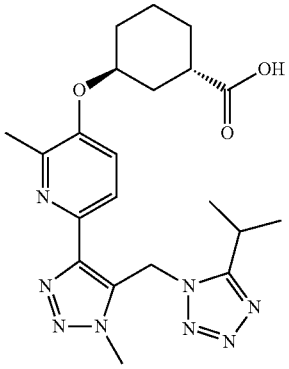 [SMILES: Cc1nc(-c2nnn(C)c2Cn2nnnc2C(C)C)ccc1O[C@H]1CCC[C@H](C(=O)O)C1]<br>(1S,3S)-3-{[2-methyl-6-(1-methyl-5-{[5-(propan-2-yl)-1H-1,2,3,4-tetrazol-1-yl]methyl}-1H-1,2,3-triazol-4-yl)pyridin-3-yl]oxy}cyclohexane-1-carboxylic acid | LCMS, (M + H)$^+$ = 441.4;<br>$^1$H NMR (500 MHz, DMSO-d$_6$) δ 7.89 (br d, J = 8.5 Hz, 1H), 7.51 (br d, J = 8.5 Hz, 1H), 6.29 (s, 2H), 4.79 (br s, 1H), 4.15 (s, 3H), 3.56-3.47 (m, 1H), 2.66-2.56 (m, 1H), 2.41 (s, 3H), 2.04-1.97 (m, 1H), 1.88-1.74 (m, 3H), 1.66-1.46 (m, 4H), 1.21 (br t, J = 5.8 Hz, 6H);<br>hLPA$_1$ IC$_{50}$ = 96 nM. |
| 299 | 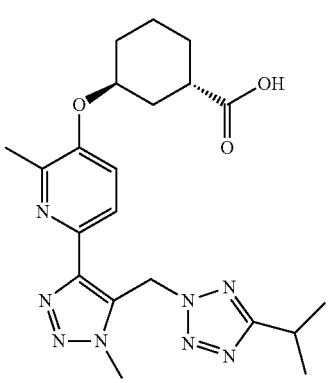 [SMILES: Cc1nc(-c2nnn(C)c2Cn2nnc(C(C)C)n2)ccc1O[C@H]1CCC[C@H](C(=O)O)C1]<br>(1S,3S)-3-{[2-methyl-6-(1-methyl-5-{[5-(propan-2-yl)-2H-1,2,3,4-tetrazol-2-yl]methyl}-1H-1,2,3-triazol-4-yl)pyridin-3-yl]oxy}cyclohexane-1-carboxylic acid | LCMS, (M + H)$^+$ = 441.2;<br>$^1$H NMR (500 MHz, DMSO-d$_6$) δ 7.84 (d, J = 8.6 Hz, 1H), 7.44 (d, J = 8.6 Hz, 1H), 6.47 (s, 2H), 4.74 (br s, 1H), 4.14 (s, 3H), 3.20-3.09 (m, 1H), 2.67-2.59 (m, 1H), 2.37 (s, 3H), 2.02-1.95 (m, 1H), 1.90-1.74 (m, 3H), 1.67-1.44 (m, 4H), 1.25 (d, J = 7.0 Hz, 6H);<br>hLPA$_1$ IC$_{50}$ = 99 nM. |
| 300 | 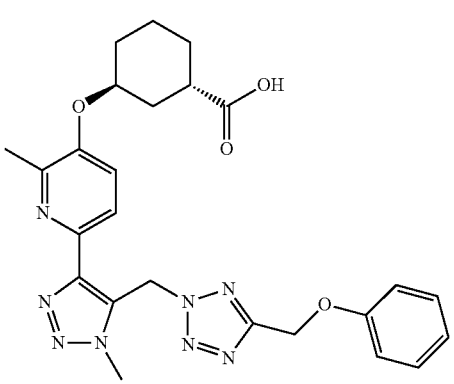 [SMILES: Cc1nc(-c2nnn(C)c2Cn2nnc(COc3ccccc3)n2)ccc1O[C@H]1CCC[C@H](C(=O)O)C1]<br>(1S,3S)-3-{[2-methyl-6-(1-methyl-5-{[5-(phenoxymethyl)-2H-1,2,3,4-tetrazol-2-yl]methyl}-1H-1,2,3-triazol-4-yl)pyridin-3-yl]oxy}cyclohexane-1-carboxylic acid | LCMS, (M + H)$^+$ = 505.3;<br>$^1$H NMR (500 MHz, DMSO-d$_6$) δ 7.86 (br d, J = 8.5 Hz, 1H), 7.45 (br d, J = 8.5 Hz, 1H), 7.30-7.21 (m, 2H), 7.02-6.90 (m, 3H), 6.57 (s, 2H), 5.30 (s, 2H), 4.75 (br s, 1H), 4.14 (s, 3H), 2.64-2.56 (m, 1H), 2.33 (s, 3H), 2.03-1.94 (m, 1H), 1.88-1.72 (m, 3H), 1.64-1.43 (m, 4H);<br>hLPA$_1$ IC$_{50}$ = 98 nM. |

| Ex # | Structure & Name | Analytical & Biology Data |
|---|---|---|
| 301 | (1S,3S)-3-({6-[5-({5-[(3,5-dimethyl-1H-pyrazol-1-yl)methyl]-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, (M + H)⁺ = 506.9; ¹H NMR (500 MHz, DMSO-d₆) δ 7.88 (br d, J = 8.5 Hz, 1H), 7.48 (br d, J = 8.5 Hz, 1H), 6.40 (s, 2H), 5.82 (s, 1H), 5.67 (s, 2H), 4.76 (br s, 1H), 4.04 (s, 3H), 2.62-2.56 (m, 1H), 2.34 (s, 3H), 2.18 (s, 3H), 1.99 (s, 3H), 1.89 (s, 1H), 1.85-1.71 (m, 3H), 1.63-1.43 (m, 4H); hLPA₁ IC₅₀ = 963 nM. |
| 302 | (1S,3S)-3-{[2-methyl-6-(1-methyl-5-{[5-(propoxymethyl)-2H-1,2,3,4-tetrazol-2-yl]methyl}-1H-1,2,3-triazol-4-yl)pyridin-3-yl]oxy}cyclohexane-1-carboxylic acid | LCMS, (M + H)⁺ = 471.3; ¹H NMR (500 MHz, DMSO-d₆) δ 7.85 (br d, J = 8.2 Hz, 1H), 7.44 (br d, J = 8.5 Hz, 1H), 6.53 (s, 2H), 4.74 (br s, 1H), 4.61 (s, 2H), 4.15 (s, 3H), 3.38-3.30 (m, 1H), 2.63-2.56 (m, 1H), 2.34 (s, 3H), 2.01-1.93 (m, 1H), 1.86-1.70 (m, 4H), 1.61-1.42 (m, 6H), 0.76 (br t, J = 7.3 Hz, 3H); hLPA₁ IC₅₀ = 63 nM. |
| 303 | (1S,3S)-3-({2-methyl-6-[1-methyl-5-({5-[(3-methyl-1H-pyrazol-1-yl)methyl]-1H-1,2,3,4-tetrazol-1-yl}methyl)-1H-1,2,3-triazol-4-yl]pyridin-3-yl}oxy)cyclohexane-1-carboxylic acid | LCMS, (M + H)⁺ = 493.1; ¹H NMR (500 MHz, DMSO-d₆) δ 7.89 (br d, J = 8.9 Hz, 1H), 7.72 (s, 1H), 7.48 (br d, J = 8.5 Hz, 1H), 6.40 (br s, 2H), 6.05 (s, 1H), 5.80 (s, 2H), 4.76 (br s, 1H), 4.06 (s, 3H), 2.64-2.57 (m, 1H), 2.30 (s, 3H), 2.08 (s, 3H), 2.03-1.94 (m, 1H), 1.87-1.72 (m, 3H), 1.63-1.42 (m, 4H); hLPA₁ IC₅₀ = 951 nM. |

| Ex # | Structure & Name | Analytical & Biology Data |
|---|---|---|
| 304 | (1S,3S)-3-{[2-methyl-6-(1-methyl-5-{[5-(phenoxymethyl)-1H-1,2,3,4-tetrazol-1-yl]methyl}-1H-1,2,3-triazol-4-yl)pyridin-3-yl]oxy}cyclohexane-1-carboxylic acid | LCMS, (M + H)+ = 505; $^1$H NMR (500 MHz, DMSO-$d_6$) δ 7.80 (br d, J = 8.5 Hz, 1H), 7.35 (br d, J = 8.9 Hz, 1H), 7.26-7.20 (m, 2H), 6.98-6.92 (m, 1H), 6.84 (br d, J = 7.9 Hz, 2H), 6.46 (s, 2H), 5.46 (s, 2H), 4.69 (br s, 1H), 4.09 (s, 3H), 2.63-2.55 (m, 1H), 2.28 (s, 3H), 2.00-1.93 (m, 1H), 1.87-1.80 (m, 1H), 1.79-1.71 (m, 2H), 1.63-1.42 (m, 4H); hLPA$_1$ IC$_{50}$ = 124 nM. |
| 305 | (1S,3S)-3-{[2-methyl-6-(1-methyl-5-{[5-(propoxymethyl)-1H-1,2,3,4-tetrazol-1-yl]methyl}-1H-1,2,3-triazol-4-yl)pyridin-3-yl]oxy}cyclohexane-1-carboxylic acid | LCMS, (M + H)+ = 471.2; $^1$H NMR (500 MHz, DMSO-$d_6$) δ 7.87 (br d, J = 8.5 Hz, 1H), 7.47 (br d, J = 8.5 Hz, 1H), 6.32 (s, 2H), 4.82 (s, 2H), 4.76 (br s, 1H), 4.07 (s, 3H), 3.29 (br t, J = 6.6 Hz, 2H), 2.62-2.56 (m, 1H), 2.36 (s, 3H), 2.02-1.94 (m, 1H), 1.87-1.72 (m, 3H), 1.63-1.39 (m, 6H), 0.76 (br t, J = 7.3 Hz, 3H); hLPA$_1$ IC$_{50}$ = 243 nM. |
| 306 | (1S,3S)-3-{[6-(5-{[5-(cyclopropyl-methyl)-1H-1,2,3,4-tetrazol-1-yl]methyl}-1-methyl-1H-1,2,3-triazol-4-yl)-2-ethylpyridin-3-yl]oxy}cyclohexane-1-carboxylic acid | LCMS, (M + H)+ = 467.3; $^1$H NMR (500 MHz, DMSO-$d_6$) δ 7.89 (d, J = 8.5 Hz, 1H), 7.51 (br d, J = 8.5 Hz, 1H), 6.28 (s, 2H), 4.79 (br s, 1H), 4.08 (s, 3H), 2.84-2.72 (m, 4H), 2.64-2.57 (m, 1H), 2.04-1.97 (m, 1H), 1.90-1.74 (m, 3H), 1.67-1.43 (m, 4H), 1.13 (t, J = 7.5 Hz, 3H), 1.04-0.95 (m, 1H), 0.44 (br d, J = 7.9 Hz, 2H), 0.08 (br d, J = 4.6 Hz, 2H); hLPA$_1$ IC$_{50}$ = 205 nM. |

| Ex # | Structure & Name | Analytical & Biology Data |
|---|---|---|
| 307 | 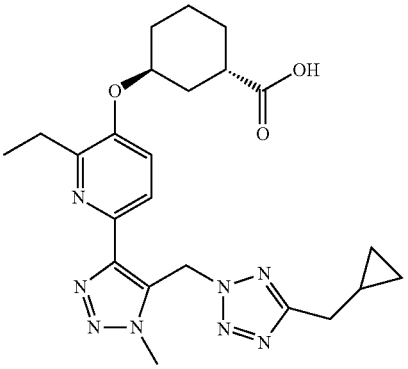 [SMILES: CCc1nc(-c2nnn(C)c2Cn2nnc(CC3CC3)n2)ccc1O[C@H]1CCC[C@H](C(=O)O)C1]<br>(1S,3S)-3-{[6-(5-{[5-(cyclopropyl-methyl)-2H-1,2,3,4-tetrazol-2-yl]methyl}-1-methyl-1H-1,2,3-triazol-4-yl)-2-ethylpyridin-3-yl]oxy}cyclohexane-1-carboxylic acid | LCMS, (M + H)$^+$ = 467;<br>$^1$H NMR (500 MHz, DMSO-d$_6$) δ 7.88 (br d, J = 8.5 Hz, 1H), 7.47 (br d, J = 8.9 Hz, 1H), 6.58 (s, 2H), 4.77 (br s, 1H), 4.16 (s, 3H), 2.80-2.70 (m, 4H), 2.64-2.57 (m, 1H), 2.03-1.97 (m, 1H), 1.89-1.73 (m, 3H), 1.64-1.44 (m, 4H), 1.19 (br t, J = 7.5 Hz, 3H), 1.06-0.98 (m, 1H), 0.43 (br d, J = 7.9 Hz, 2H), 0.16 (br d, J = 4.6 Hz, 2H);<br>hLPA$_1$ IC$_{50}$ = 32 nM. |
| 308 | 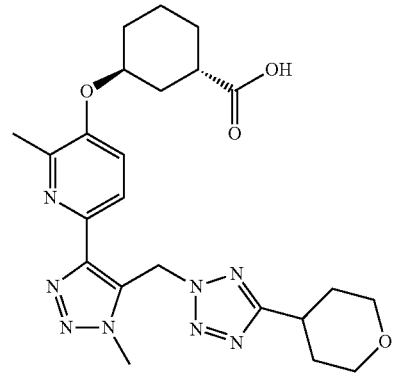 [SMILES: Cc1nc(-c2nnn(C)c2Cn2nnc(C3CCOCC3)n2)ccc1O[C@H]1CCC[C@H](C(=O)O)C1]<br>(1S,3S)-3-{[2-methyl-6-(1-methyl-5-{[5-(oxan-4-yl)-2H-1,2,3,4-tetrazol-2-yl]methyl}-1H-1,2,3-triazol-4-yl)pyridin-3-yl]oxy}cyclohexane-1-carboxylic acid | LCMS, (M + H)$^+$ = 483.1;<br>$^1$H NMR (500 MHz, DMSO-d$_6$) δ 7.85 (d, J = 8.5 Hz, 1H), 7.44 (d, J = 8.6 Hz, 1H), 6.50 (s, 2H), 4.74 (br s, 1H), 4.14 (s, 3H), 3.88-3.80 (m, 2H), 3.50-3.41 (m, 1H), 3.19-3.12 (m, 1H), 2.65-2.57 (m, 1H), 2.37 (s, 3H), 2.02-1.95 (m, 1H), 1.90-1.45 (m, 11H);<br>hLPA$_1$ IC$_{50}$ = 714 nM. |
| 309 | 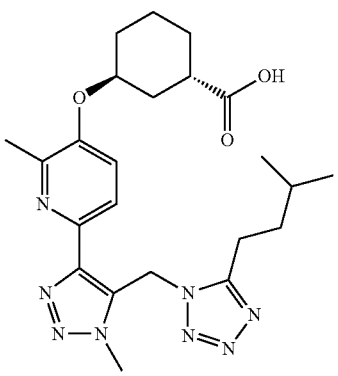 [SMILES: Cc1nc(-c2nnn(C)c2Cn2nnnc2CCC(C)C)ccc1O[C@H]1CCC[C@H](C(=O)O)C1]<br>(1S,3S)-3-{[2-methyl-6-(1-methyl-5-{[5-(3-methylbutyl)-1H-1,2,3,4-tetrazol-1-yl]methyl}-1H-1,2,3-triazol-4-yl)pyridin-3-yl]oxy}cyclohexane-1-carboxylic acid | LCMS, (M + H)$^+$ = 469.1;<br>$^1$H NMR (500 MHz, DMSO-d$_6$) δ 7.90 (d, J = 8.5 Hz, 1H), 7.50 (d, J = 8.9 Hz, 1H), 6.32 (s, 2H), 4.78 (br s, 1H), 4.09 (s, 3H), 2.84-2.77 (m, 2H), 2.64-2.57 (m, 1H), 2.41 (s, 3H), 2.03-1.97 (m, 1H), 1.89-1.73 (m, 3H), 1.65-1.37 (m, 7H), 0.75 (d, J = 6.4 Hz, 6H);<br>hLPA$_1$ IC$_{50}$ = 191 nM. |

| Ex # | Structure & Name | Analytical & Biology Data |
|---|---|---|
| 310 | 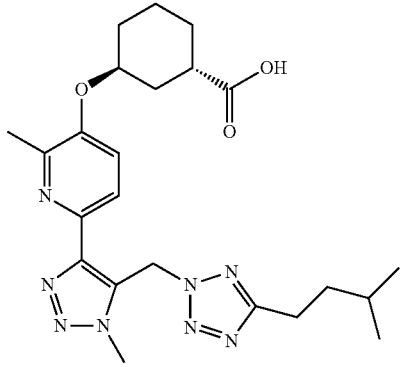 [SMILES: Cc1nc(-c2nnn(C)c2Cn2nnc(CCC(C)C)n2)ccc1O[C@H]1CCC[C@H](C(=O)O)C1]<br>(1S,3S)-3-{[2-methyl-6-(1-methyl-5-{[5-(3-methylbutyl)-2H-1,2,3,4-tetrazol-2-yl]methyl}-1H-1,2,3-triazol-4-yl)pyridin-3-yl]oxy}cyclohexane-1-carboxylic acid | LCMS, (M + H)$^+$ = 469.3;<br>$^1$H NMR (500 MHz, DMSO-d$_6$) δ 7.85 (br d, J = 8.5 Hz, 1H), 7.46 (d, J = 8.5 Hz, 1H), 6.49 (s, 2H), 4.76 (br s, 1H), 4.13 (s, 3H), 2.76 (br t, J = 7.5 Hz, 2H), 2.64-2.56 (m, 1H), 2.36 (s, 3H), 2.03-1.96 (m, 1H), 1.89-1.73 (m, 3H), 1.64-1.42 (m, 7H), 0.84 (d, J = 6.1 Hz, 6H);<br>hLPA$_1$ IC$_{50}$ = 24 nM. |
| 311 | 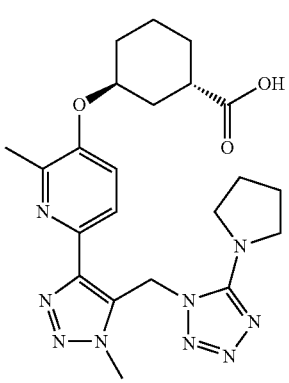 [SMILES: Cc1nc(-c2nnn(C)c2Cn2nnnc2N2CCCC2)ccc1O[C@H]1CCC[C@H](C(=O)O)C1]<br>(1S,3S)-3-{[2-methyl-6-(1-methyl-5-{[5-(pyrrolidin-1-yl)-1H-1,2,3,4-tetrazol-1-yl]methyl}-1H-1,2,3-triazol-4-yl)pyridin-3-yl]oxy}cyclohexane-1-carboxylic acid | LCMS, (M + H)$^+$ = 468.2;<br>$^1$H NMR (500 MHz, DMSO-d$_6$) δ 7.83 (br d, J = 8.5 Hz, 1H), 7.46 (br d, J = 8.5 Hz, 1H), 6.07 (br d, J = 6.4 Hz, 2H), 4.73 (br s, 1H), 4.10 (s, 3H), 3.65-3.58 (m, 1H), 2.32 (s, 3H), 1.99-1.86 (m, 6H), 1.83-1.72 (m, 3H), 1.63-1.43 (m, 4H);<br>hLPA$_1$ IC$_{50}$ = 605 nM. |
| 312 | 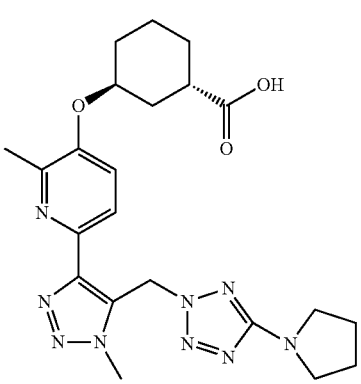 [SMILES: Cc1nc(-c2nnn(C)c2Cn2nnc(N3CCCC3)n2)ccc1O[C@H]1CCC[C@H](C(=O)O)C1]<br>(1S,3S)-3-{[2-methyl-6-(1-methyl-5-{[5-(pyrrolidin-1-yl)-2H-1,2,3,4-tetrazol-2-yl]methyl}-1H-1,2,3-triazol-4-yl)pyridin-3-yl]oxy}cyclohexane-1-carboxylic acid | LCMS, (M + H)$^+$ = 468.1;<br>$^1$H NMR (500 MHz, DMSO-d$_6$) δ 7.85 (d, J = 8.5 Hz, 1H), 7.46 (br d, J = 8.5 Hz, 1H), 6.35 (br d, J = 1.8 Hz, 2H), 4.76 (br s, 1H), 4.13 (s, 3H), 3.32-3.25 (m, 3H), 2.65-2.57 (m, 1H), 2.40 (s, 3H), 2.01-1.95 (m, 1H), 1.91-1.73 (m, 8H), 1.65-1.44 (m, 4H);<br>hLPA$_1$ IC$_{50}$ = 234 nM. |

| Ex # | Structure & Name | Analytical & Biology Data |
|---|---|---|
| 313 | 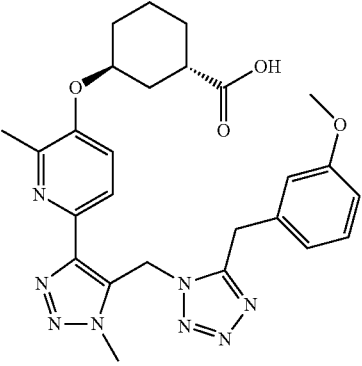 [SMILES: COc1cccc(Cc2nnnn2Cc2c(-c3ccc(O[C@H]4CCC[C@H](C(=O)O)C4)c(C)n3)nnn2C)c1]<br>(1S,3S)-3-({6-[5-({5-[(3-methoxy-phenyl)methyl]-1H-1,2,3,4-tetrazol-1-yl}methyl)-1-methyl-1H-1,2,3-triazol-4-yl]-2-methylpyridin-3-yl}oxy)cyclohexane-1-carboxylic acid | LCMS, (M + H)$^+$ = 519.1;<br>$^1$H NMR (500 MHz, DMSO-d$_6$) δ 7.86 (d, J = 8.5 Hz, 1H), 7.49 (d, J = 8.5 Hz, 1H), 7.17 (t, J = 7.9 Hz, 1H), 6.80 (br d, J = 7.9 Hz, 1H), 6.68-6.58 (m, 2H), 6.32 (br d, J = 6.1 Hz, 2H), 4.75 (br s, 1H), 4.40 (s, 2H), 4.07 (s, 3H), 3.68 (s, 3H), 2.57-2.53 (m, 1H), 2.31 (s, 2H), 2.00-1.93 (m, 1H), 1.86-1.75 (m, 3H), 1.65-1.47 (m, 4H);<br>hLPA$_1$ IC$_{50}$ = 277 nM. |
| 314 | 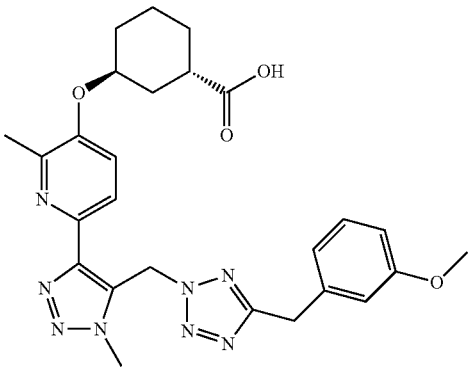<br>(1S,3S)-3-({6-[5-({5-[(3-methoxy-phenyl)methyl]-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, (M + H)$^+$ = 519.1;<br>$^1$H NMR (500 MHz, DMSO-d$_6$) δ 7.85 (d, J = 8.2 Hz, 1H), 7.44 (d, J = 8.5 Hz, 1H), 7.16 (t, J = 7.6 Hz, 1H), 6.80-6.73 (m, 3H), 6.50 (s, 2H), 4.75 (br s, 1H), 4.16-4.11 (m, 5H), 3.67 (s, 3H), 2.62-2.57 (m, 1H), 2.30 (s, 3H), 2.02-1.96 (m, 1H), 1.89-1.72 (m, 3H), 1.65-1.44 (m, 4H);<br>hLPA$_1$ IC$_{50}$ = 12 nM. |
| 315 | 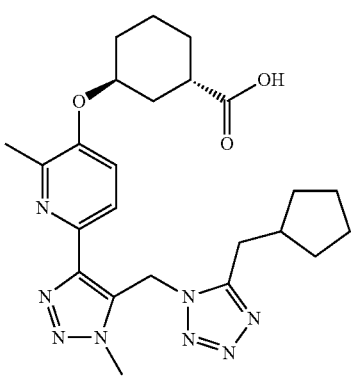 [SMILES: Cc1nc(-c2nnn(C)c2Cn2nnnc2CC2CCCC2)ccc1O[C@H]1CCC[C@H](C(=O)O)C1]<br>(1S,3S)-3-{[6-(5-{[5-(cyclopentyl-methyl)-1H-1,2,3,4-tetrazol-1-yl]methyl}-1-methyl-1H-1,2,3-triazol-4-yl)-2-methylpyridin-3-yl]oxy}cyclohexane-1-carboxylic acid | LCMS, (M + H)$^+$ = 480.9;<br>$^1$H NMR (500 MHz, DMSO-d$_6$) δ 7.89 (d, J = 8.5 Hz, 1H), 7.51 (d, J = 8.9 Hz, 1H), 6.32 (s, 2H), 4.79 (br s, 1H), 4.12 (s, 3H), 2.96-2.89 (m, 1H), 2.84 (d, J = 7.3 Hz, 2H), 2.66-2.58 (m, 1H), 2.42 (s, 3H), 2.17-2.09 (m, 1H), 2.04-1.98 (m, 1H), 1.90-1.74 (m, 3H), 1.66-1.38 (m, 11H);<br>hLPA$_1$ IC$_{50}$ = 154 nM. |

Example 316. (1S,3S)-3-((6-(5-((5-(2-cyclopropylethoxy)-2H-tetrazol-2-yl)methyl)-1-methyl-1H-1,2,3-triazol-4-yl)-2-methylpyridin-3-yl)oxy)cyclohexane-1-carboxylic acid

316B. (1S,3S)-3-((2-methyl-6-(1-methyl-5-((5-(methylsulfonyl)-2H-tetrazol-2-yl)methyl)-1H-1,2,3-triazol-4-yl)pyridin-3-yl)oxy)cyclohexane-1-carboxylic acid

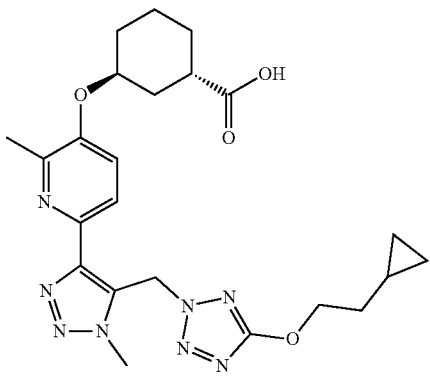 [SMILES: Cc1nc(-c2nnn(C)c2Cn2nnc(OCCC3CC3)n2)ccc1O[C@H]1CCC[C@H](C(=O)O)C1]

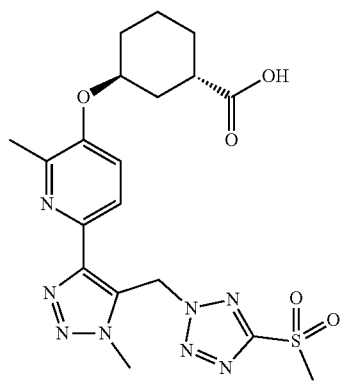

316A. Methyl (1S,3S)-3-((2-methyl-6-(1-methyl-5-((5-(methylthio)-2H-tetrazol-2-yl)methyl)-1H-1,2,3-triazol-4-yl)pyridin-3-yl)oxy)cyclohexane-1-carboxylate To a solution of 316A (0.360 g, 0.785 mmol) in THF (3 mL) and MeOH (1 mL) was added 4M aq. LiOH (0.981 mL, 23.9 mmol). The reaction was stirred at RT for 2 h, after which oxone (0.531 g, 0.864 mmol) and water/MeOH (1 mL each) were added. The reaction was stirred overnight at RT, then was filtered; the filtrate was concentrated in vacuo. The residue was purified by preparative HPLC: Phenomenex Axia Luna column (30×75 mm); 0-100% B over 15 min, then 3 min B hold @ 40 mL/min; Solvent A=10% MeCN, 90% $H_2O$, 0.10% TFA; Solvent B=90% MeCN, 10% $H_2O$, 0.10% TFA) to give the title compound as a colorless viscous oil (0.211 g, 56%). LCMS, $[M+H]^+$=477.2.

Example 316

To a RT solution of 316B (15 mg, 0.031 mmol) and 2-cyclopropylethan-1-ol (0.008 mg, 0.094 mmol) in THF (0.32 mL) was added 0.5 M KN(TMS)$_2$ in toluene (0.264 mL, 0.132 mmol) dropwise. The reaction was stirred overnight at RT, then was partitioned between DCM and 1N aq. HCl, and the resulting mixture was stirred at RT for 15 min. The pH was adjusted to ~3-4 with 1N aq. HCl. The organic layer was dried (Na$_2$SO$_4$) and concentrated in vacuo. The crude product was purified by preparative LC/MS: Column: XBridge C18, 200 mm×19 mm, 5-µm particles; Mobile Phase A: 5:95 MeCN:H$_2$O:10 mM aq. NH$_4$OAc; Mobile Phase B: 95:5 MeCN:H$_2$O:10 mM aq. NH$_4$OAc; Gradient: a 0-min hold at 15% B, 15-55% B over 20 min, then a 4-min hold at 100% B; Flow Rate: 20 mL/min; Column Temperature: 25 C. Fraction collection was triggered by MS signals. Fractions containing the desired product were combined and dried via centrifugal evaporation. The title compound was obtained as a colorless viscous oil (10 mg, 62%). LCMS, $[M+H]^+$=483.32. $^1$H NMR (500 MHz, DMSO-d$_6$) δ 7.86 (d, J=8.5 Hz, 1H), 7.46 (d, J=8.5 Hz, 1H), 6.41 (s, 2H), 4.76 (br s, 1H), 4.31 (t, J=6.6 Hz, 2H), 4.14 (s, 3H), 2.64-2.58 (m, 1H), 2.38 (s, 3H), 1.99 (br d, J=12.5 Hz, 1H), 1.84 (br d, J=11.3 Hz, 1H), 1.81-1.73 (m, 2H), 1.58 (q, J=6.6 Hz, 4H), 1.55-1.42 (m, 2H), 0.72 (br d, J=7.0 Hz, 1H), 0.39-0.34 (m, 2H), 0.06-0.02 (m, 2H). hLPA$_1$ IC$_{50}$=22 nM.

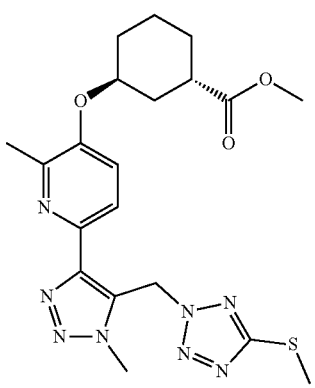

A mixture of Intermediate 5 (1.80 g, 4.25 mmol), 5-(methylthio)-2H-tetrazole (1.09 g, 9.35 mmol), and iPr$_2$NEt (3.0 mL, 17.0 mmol) in 1,4-dioxane (10 mL) was heated at 100° C. for 1 h in a microwave reactor, then was cooled to RT and concentrated in vacuo. The residue was chromatographed (80 g SiO$_2$, continuous gradient from 0-100% EtOAc in hexane over 15 min, 60 mL/min) to give the title compound as a colorless viscous oil (1.14 g, 59%). LCMS, $[M+H]^+$=459.1.

The following Examples were synthesized according to the procedures described for the preparation of the Examples as specified in the table.

| Ex # | Structure & Name | Analytical & Biological Data | Method |
|---|---|---|---|
| 317 | (1S,3S)-3-((6-(5-((3-benzyl-1H-pyrazol-1-yl)methyl)-1-methyl-1H-1,2,3-triazol-4-yl)-2-methylpyridin-3-yl)oxy)cyclo-hexane-1-carboxylic acid | LCMS, [M + H]$^+$ = 487.1; $^1$H NMR (500 MHz, DMSO-d$_6$) δ 7.74 (br s, 1H), 7.52-7.44 (m, 1H), 7.30-7.14 (m, 6H), 7.00 (br d, J = 7.0 Hz, 1H), 6.06-5.85 (m, 4H), 4.78 (br s, 1H), 4.12 (s, 2H), 4.10-4.04 (m, 1H), 3.99 (s, 1H), 3.83 (s, 1H), 3.54 (br s, 1H), 2.70-2.60 (m, 1H), 2.04 (br s, 1H), 1.93-1.72 (m, 3H), 1.68-1.44 (m, 4H); hLPA$_1$ IC$_{50}$ = 63 nM. | Example 80 |
| 318 | (1S,3S)-3-((6-(5-((5-ethyl-2H-tetrazol-2-yl)methyl)-1-methyl-1H-1,2,3-triazol-4-yl)-2-methylpyridin-3-yl)oxy)cyclo-hexane-1-carboxylic acid | LCMS, [M + H]$^+$ = 427.0; $^1$H NMR (500 MHz, DMSO-d$_6$) δ 7.87 (d, J = 8.5 Hz, 1H), 7.46 (d, J = 8.6 Hz, 1H), 6.52 (s, 2H), 4.76 (br s, 1H), 4.15 (s, 3H), 2.81 (q, J = 7.6 Hz, 2H), 2.70-2.60 (m, 1H), 2.40 (s, 3H), 2.01 (br d, J = 13.6 Hz, 1H), 1.92-1.75 (m, 3H), 1.71-1.45 (m, 4H), 1.24 (t, J = 7.6 Hz, 3H); hLPA$_1$ IC$_{50}$ = 414 nM. | Examples 105, 106 |
| 319 | (1S,3S)-3-((6-(5-((5-cyclopropyl-1H-tetrazol-1-yl)methyl)-1-methyl-1H-1,2,3-triazol-4-yl)-2-methylpyridin-3-yl)oxy)cyclo-hexane-1-carboxylic acid | LCMS, [M + H]$^+$ = 439.0; $^1$H NMR (500 MHz, DMSO-d$_6$) δ 7.89 (br d, J = 8.5 Hz, 1H), 7.49 (br d, J = 8.5 Hz, 1H), 6.32 (s, 2H), 4.77 (br s, 1H), 4.14 (s, 3H), 2.92 (br d, J = 5.5 Hz, 2H), 2.38 (s, 3H), 2.06-1.41 (m, 8H), 1.08 (br d, J = 8.2 Hz, 2H), 0.99 (br s, 2H); hLPA$_1$ IC$_{50}$ = 673 nM. | Examples 105, 106 |

| Ex # | Structure & Name | Analytical & Biological Data | Method |
|---|---|---|---|
| 320 | 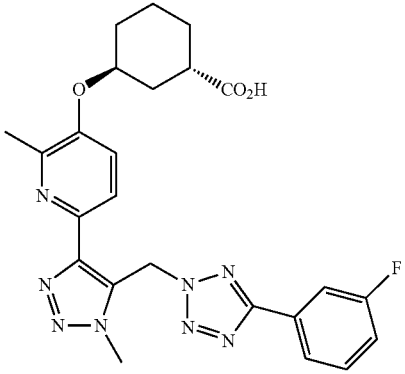 [SMILES: Cc1nc(-c2nnn(C)c2Cn2nnc(-c3cccc(F)c3)n2)ccc1O[C@H]1CCC[C@H](C(=O)O)C1]<br>(1S,3S)-3-((6-(5-(((5-(3-fluoro-phenyl)-2H-tetrazol-2-yl)methyl)-1-methyl-1H-1,2,3-triazol-4-yl)-2-methylpyridin-3-yl)oxy)cyclo-hexane-1-carboxylic acid | LCMS, $[M + H]^+$ = 493.2; $^1$H NMR (500 MHz, DMSO-$d_6$) δ 7.91-7.83 (m, 2H), 7.76 (br d, J = 9.5 Hz, 1H), 7.60 (q, J = 7.7 Hz, 1H), 7.47 (d, J = 8.5 Hz, 1H), 7.38 (br t, J = 7.6 Hz, 1H), 6.62 (s, 2H), 4.75 (br s, 1H), 4.24 (s, 3H), 2.65-2.56 (m, 1H), 2.37 (s, 3H), 1.98 (br d, J = 13.4 Hz, 1H), 1.88-1.71 (m, 3H), 1.66-1.42 (m, 4H); hLPA$_1$ IC$_{50}$ = 58 nM. | Examples 105, 106 |
| 321 | 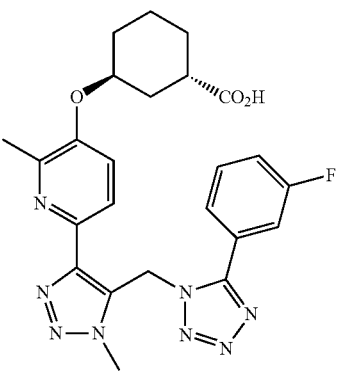 [SMILES: Cc1nc(-c2nnn(C)c2Cn2nnnc2-c2cccc(F)c2)ccc1O[C@H]1CCC[C@H](C(=O)O)C1]<br>(1S,3S)-3-((6-(5-(((5-(3-fluoro-phenyl)-1H-tetrazol-1-yl)methyl)-1-methyl-1H-1,2,3-triazol-4-yl)-2-methylpyridin-3-yl)oxy)cyclo-hexane-1-carboxylic acid | LCMS, $[M + H]^+$ = 493.0; $^1$H NMR (500 MHz, DMSO-$d_6$) δ 7.76 (d, J = 8.5 Hz, 1H), 7.70-7.56 (m, 3H), 7.45 (br t, J = 7.9 Hz, 1H), 7.38 (d, J = 8.5 Hz, 1H), 6.40 (s, 2H), 4.71 (br s, 1H), 4.19-4.08 (m, 3H), 2.61-2.55 (m, 1H), 2.00-1.79 (m, 5H), 1.79-1.67 (m, 2H), 1.62-1.37 (m, 4H); hLPA$_1$ IC$_{50}$ = 428 nM. | Examples 105, 106 |
| 322 | 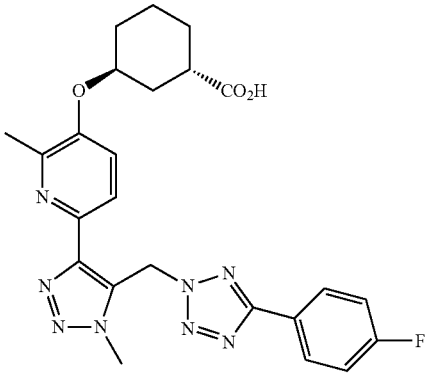 [SMILES: Cc1nc(-c2nnn(C)c2Cn2nnc(-c3ccc(F)cc3)n2)ccc1O[C@H]1CCC[C@H](C(=O)O)C1]<br>(1S,3S)-3-((6-(5-(((5-(4-fluoro-phenyl)-2H-tetrazol-2-yl)methyl)-1-methyl-1H-1,2,3-triazol-4-yl)-2-methylpyridin-3-yl)oxy)cyclo-hexane-1-carboxylic acid | LCMS, $[M + H]^+$ = 492.9; $^1$H NMR (500 MHz, DMSO-$d_6$) δ 8.05 (br t, J = 6.9 Hz, 2H), 7.87 (d, J = 8.5 Hz, 1H), 7.45 (br d, J = 8.7 Hz, 1H), 7.36 (br t, J = 8.8 Hz, 2H), 6.60 (s, 2H), 4.74 (br s, 1H), 4.23 (s, 3H), 2.62 (br t, J = 10.1 Hz, 1H), 2.38 (s, 3H), 1.99 (br d, J = 13.5 Hz, 1H), 1.90-1.72 (m, 3H), 1.70-1.43 (m, 4H); hLPA$_1$ IC$_{50}$ = 243 nM. | Examples 105, 106 |

| Ex # | Structure & Name | Analytical & Biological Data | Method |
|---|---|---|---|
| 323 | (1S,3S)-3-((6-(5-((5-(4-fluoro-phenyl)-1H-tetrazol-1-yl)methyl)-1-methyl-1H-1,2,3-triazol-4-yl)-2-methylpyridin-3-yl)oxy)cyclo-hexane-1-carboxylic acid | LCMS, [M + H]⁺ = 493.2; ¹H NMR (500 MHz, DMSO-$d_6$) δ 7.88 (br t, J = 6.9 Hz, 2H), 7.76 (d, J = 8.2 Hz, 1H), 7.46-7.35 (m, 3H), 6.37 (s, 2H), 4.70 (br s, 1H), 4.15 (s, 3H), 2.55 (s, 1H), 2.00-1.67 (m, 7H), 1.62-1.37 (m, 4H); hLPA₁ IC₅₀ = 414 nM. | Examples 105, 106 |
| 324 | (1S,3S)-3-((6-(5-((5-(4-chloro-benzyl)-2H-tetrazol-2-yl)methyl)-1-methyl-1H-1,2,3-triazol-4-yl)-2-methylpyridin-3-yl)oxy)cyclo-hexane-1-carboxylic acid | LCMS, [M + H]⁺ = 523.1 ¹H NMR (500 MHz, DMSO-$d_6$) δ 7.85 (d, J = 8.5 Hz, 1H), 7.47 (br d, J = 8.5 Hz, 1H), 7.33 (d, J = 8.2 Hz, 2H), 7.24 (br d, J = 8.2 Hz, 2H), 6.54-6.45 (m, 2H), 4.75 (br s, 1H), 4.20 (s, 2H), 4.14 (s, 3H), 2.28 (s, 3H), 1.95 (br d, J = 13.1 Hz, 1H), 1.87-1.72 (m, 3H), 1.67-1.43 (m, 4H), 1 proton is in water suppression area; hLPA₁ IC₅₀ = 38 nM. | Examples 105, 106 |
| 325 | (1S,3S)-3-((6-(5-((5-(4-chloro-benzyl)-1H-tetrazol-1-yl)methyl)-1-methyl-1H-1,2,3-triazol-4-yl)-2-methylpyridin-3-yl)oxy)cyclo-hexane-1-carboxylic acid | LCMS, [M + H]⁺ = 523.2; ¹H NMR (500 MHz, DMSO-$d_6$) δ 7.85 (d, J = 8.5 Hz, 1H), 7.47 (d, J = 8.9 Hz, 1H), 7.31 (d, J = 8.2 Hz, 2H), 7.09 (br d, J = 8.2 Hz, 2H), 6.36-6.24 (m, 2H), 4.76 (br s, 1H), 4.43 (s, 2H), 4.09 (s, 3H), 2.61 (br t, J = 10.4 Hz, 1H), 2.30 (s, 3H), 2.00 (br d, J = 13.7 Hz, 1H), 1.89-1.71 (m, 3H), 1.67-1.42 (m, 4H); hLPA₁ IC₅₀ = 167 nM. | Examples 105, 106 |

| Ex # | Structure & Name | Analytical & Biological Data | Method |
|---|---|---|---|
| 326 | (1S,3S)-3-((2-methyl-6-(1-methyl-5-((5-(p-tolyloxy)-2H-tetrazol-2-yl)methyl)-1H-1,2,3-triazol-4-yl)pyridin-3-yl)oxy)cyclohexane-1-carboxylic acid | LCMS, $[M + H]^+$ = 505.3; $^1$H NMR (500 MHz, DMSO-$d_6$) δ 7.87 (d, J = 8.6 Hz, 1H), 7.46 (d, J = 8.6 Hz, 1H), 7.20 (br d, J = 8.3 Hz, 2H), 7.08 (br d, J = 8.4 Hz, 2H), 6.45 (s, 2H), 4.76 (br s, 1H), 4.15 (s, 3H), 2.70-2.60 (m, 1H), 2.36 (s, 3H), 2.30 (s, 3H), 2.01 (br d, J = 13.3 Hz, 1H), 1.91-1.75 (m, 3H), 1.69-1.44 (m, 4H); hLPA$_1$ IC$_{50}$ = 23 nM. | Example 316 |
| 327 | (1S,3S)-3-((6-(5-((5-isobutyl-2H-tetrazol-2-yl)methyl)-1-methyl-1H-1,2,3-triazol-4-yl)-2-methylpyridin-3-yl)oxy)cyclohexane-1-carboxylic acid | LCMS, $[M + H]^+$ = 455.1; $^1$H NMR (500 MHz, DMSO-$d_6$) δ 7.85 (d, J = 8.2 Hz, 1H), 7.46 (d, J = 8.5 Hz, 1H), 6.50 (s, 2H), 4.76 (br s, 1H), 4.14 (s, 3H), 2.71-2.57 (m, 3H), 2.36 (s, 3H), 2.06-1.71 (m, 5H), 1.67-1.43 (m, 4H), 0.83 (d, J = 6.7 Hz, 6H); hLPA$_1$ IC$_{50}$ = 28 nM. | Examples 105, 106 |
| 328 | (1S,3S)-3-((6-(5-((5-isobutyl-1H-tetrazol-1-yl)methyl)-1-methyl-1H-1,2,3-triazol-4-yl)-2-methylpyridin-3-yl)oxy)cyclohexane-1-carboxylic acid | LCMS, $[M + H]^+$ = 455.2; $^1$H NMR (500 MHz, DMSO-$d_6$) δ 7.89 (d, J = 8.5 Hz, 1H), 7.52 (d, J = 8.5 Hz, 1H), 6.31 (s, 2H), 4.79 (br s, 1H), 4.12 (s, 3H), 2.76 (d, J = 7.3 Hz, 2H), 2.60 (br t, J = 10.4 Hz, 1H), 2.43 (s, 3H), 2.07-1.93 (m, 2H), 1.90-1.72 (m, 3H), 1.67-1.42 (m, 4H), 0.77 (d, J = 6.4 Hz, 6H); hLPA$_1$ IC$_{50}$ = 118 nM. | Examples 105, 106 |

| Ex # | Structure & Name | Analytical & Biological Data | Method |
|---|---|---|---|
| 329 | 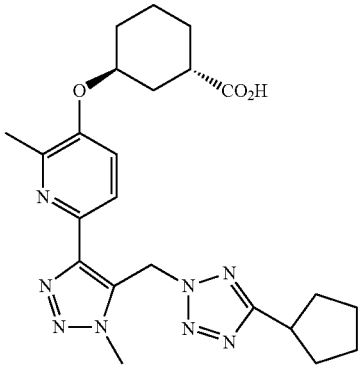 [SMILES: Cc1nc(-c2nnn(C)c2Cn2nnc(C3CCCC3)n2)ccc1O[C@H]1CCC[C@H](C(=O)O)C1]<br>(1S,3S)-3-((6-(5-((5-cyclopentyl-2H-tetrazol-2-yl)methyl)-1-methyl-1H-1,2,3-triazol-4-yl)-2-methylpyridin-3-yl)oxy)cyclo-hexane-1-carboxylic acid | LCMS, $[M + H]^+$ = 467.0;<br>$^1$H NMR (500 MHz, DMSO-$d_6$) δ 7.86 (d, J = 8.6 Hz, 1H), 7.46 (d, J = 8.6 Hz, 1H), 6.50 (s, 2H), 4.76 (br s, 1H), 4.15 (s, 3H), 2.73-2.60 (m, 1H), 2.39 (s, 3H), 2.01 (br d, J = 8.1 Hz, 3H), 1.91-1.44 (m, 14H);<br>hLPA$_1$ IC$_{50}$ = 14 nM. | Examples 105, 106 |
| 330 | 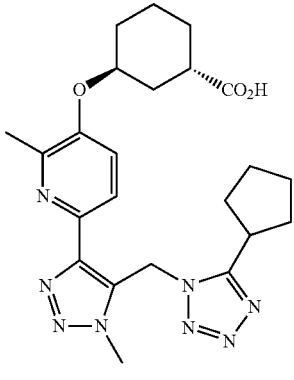 [SMILES: Cc1nc(-c2nnn(C)c2Cn2nnnc2C2CCCC2)ccc1O[C@H]1CCC[C@H](C(=O)O)C1]<br>(1S,3S)-3-((6-(5-((5-cyclopentyl-1H-tetrazol-1-yl)methyl)-1-methyl-1H-1,2,3-triazol-4-yl)-2-methylpyridin-3-yl)oxy)cyclo-hexane-1-carboxylic acid | LCMS, $[M + H]^+$ = 467.3;<br>$^1$H NMR (500 MHz, DMSO-$d_6$) δ 7.89 (d, J = 8.5 Hz, 1H), 7.52 (d, J = 8.9 Hz, 1H), 6.30 (s, 2H), 4.79 (br s, 1H), 4.14 (s, 3H), 2.58 (br d, J = 10.7 Hz, 1H), 2.41 (s, 3H), 1.98 (br d, J = 12.8 Hz, 1H), 1.91-1.41 (m, 16H);<br>hLPA$_1$ IC$_{50}$ = 385 nM. | Examples 105, 106 |
| 331 | 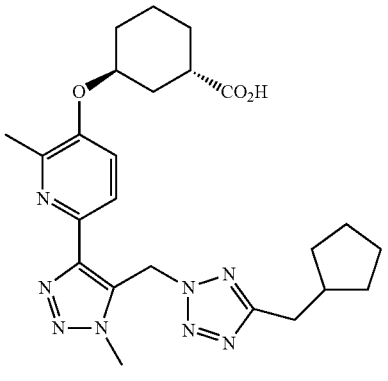 [SMILES: Cc1nc(-c2nnn(C)c2Cn2nnc(CC3CCCC3)n2)ccc1O[C@H]1CCC[C@H](C(=O)O)C1]<br>(1S,3S)-3-((6-(5-((5-(cyclopentyl-methyl)-2H-tetrazol-2-yl)methyl)-1-methyl-1H-1,2,3-triazol-4-yl)-2-methylpyridin-3-yl)oxy)cyclohexane-1-carboxylic acid | LCMS, $[M + H]^+$ = 480.9;<br>$^1$H NMR (500 MHz, DMSO-$d_6$) δ 7.85 (d, J = 8.6 Hz, 1H), 7.44 (d, J = 8.7 Hz, 1H), 6.54-6.45 (m, 2H), 4.75 (br s, 1H), 4.14 (s, 3H), 2.77 (d, J = 7.3 Hz, 2H), 2.68-2.59 (m, 1H), 2.37 (s, 3H), 2.15 (dt, J = 15.1, 7.5 Hz, 1H), 2.00 (br d, J = 13.6 Hz, 1H), 1.90-1.74 (m, 3H), 1.67-1.40 (m, 10H), 1.20-1.09 (m, 2H);<br>hLPA$_1$ IC$_{50}$ = 7 nM. | Examples 105, 106 |

| Ex # | Structure & Name | Analytical & Biological Data | Method |
|---|---|---|---|
| 332 | 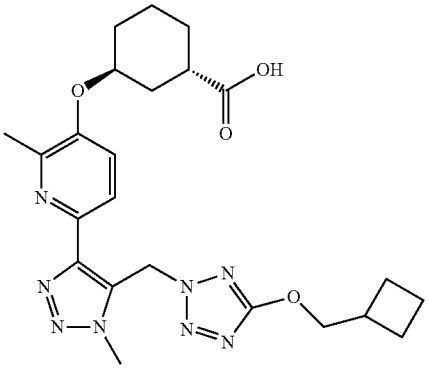 [SMILES: Cc1nc(-c2nnn(C)c2Cn2nnc(OCC3CCC3)n2)ccc1O[C@H]1CCC[C@H](C(=O)O)C1]<br>(1S,3S)-3-{[6-(5-{[5-(cyclobutyl-methoxy)-2H-1,2,3,4-tetrazol-2-yl]methyl}-1-methyl-1H-1,2,3-triazol-4-yl)-2-methylpyridin-3-yl]oxy} cyclohexane-1-carboxylic acid | LCMS, [M + H]$^+$ = 482.9; $^1$H NMR (500 MHz, DMSO-d$_6$) δ 7.85 (d, J = 8.9 Hz, 1H), 7.46 (d, J = 8.9 Hz, 1H), 6.39 (s, 2H), 4.76 (br s, 1H), 4.23 (d, J = 6.7 Hz, 2H), 4.14 (s, 3H), 2.71-2.57 (m, 2H), 2.37 (s, 3H), 1.98 (br d, J = 7.6 Hz, 3H), 1.88-1.72 (m, 7H), 1.63-1.54 (m, 2H), 1.54-1.44 (m, 2H);<br>hLPA$_1$ IC$_{50}$ = 30 nM. | Example 316 |
| 333 | 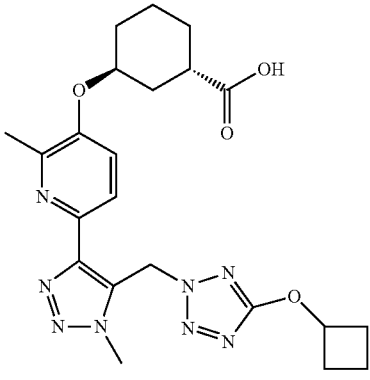 [SMILES: Cc1nc(-c2nnn(C)c2Cn2nnc(OC3CCC3)n2)ccc1O[C@H]1CCC[C@H](C(=O)O)C1]<br>(1S,3S)-3-[(6-{5-[(5-cyclobutoxy-2H-1,2,3,4-tetrazol-2-yl)methyl]-1-methyl-1H-1,2,3-triazol-4-yl}-2-methylpyridin-3-yl)oxy]cyclo-hexane-1-carboxylic acid | LCMS, [M + H]$^+$ = 469.3; $^1$H NMR (500 MHz, DMSO-d$_6$) δ 7.85 (d, J = 8.5 Hz, 1H), 7.48 (d, J = 8.9 Hz, 1H), 6.40 (d, J = 2.4 Hz, 2H), 4.92 (t, J = 7.2 Hz, 1H), 4.75 (br s, 1H), 4.15 (s, 3H), 2.58 (br s, 1H), 2.40-2.36 (m, 3H), 2.36-2.29 (m, 2H), 2.11-2.02 (m, 2H), 1.96 (br d, J = 13.1 Hz, 1H), 1.85-1.72 (m, 4H), 1.64-1.46 (m, 5H);<br>hLPA$_1$ IC$_{50}$ = 48 nM. | Example 316 |
| 334 | 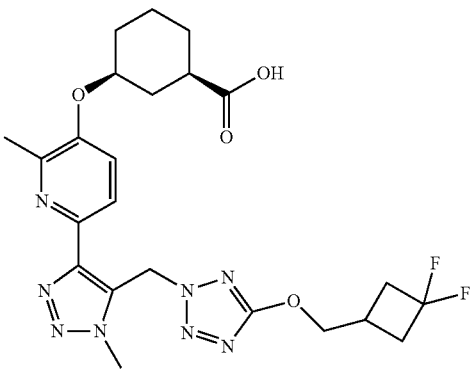 [SMILES: Cc1nc(-c2nnn(C)c2Cn2nnc(OCC3CC(F)(F)C3)n2)ccc1O[C@H]1CCC[C@@H](C(=O)O)C1]<br>(1R,3S)-3-({6-[5-({5-[(3,3-difluoro-cyclobutyl)methoxy]-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, [M + H]$^+$ = 519.2; $^1$H NMR (500 MHz, DMSO-d$_6$) δ 7.84 (d, J = 8.9 Hz, 1H), 7.49 (d, J = 8.5 Hz, 1H), 6.39 (s, 2H), 4.39 (br s, 1H), 4.32 (d, J = 6.1 Hz, 2H), 4.13 (s, 3H), 2.68-2.52 (m, 3H), 2.47-2.36 (m, 3H), 2.32 (s, 3H), 2.21 (br d, J = 12.5 Hz, 1H), 2.01 (br d, J = 12.2 Hz, 1H), 1.82 (br t, J = 14.3 Hz, 2H), 1.45-1.23 (m, 4H);<br>hLPA$_1$ IC$_{50}$ = 258 nM. | Example 316 |

| Ex # | Structure & Name | Analytical & Biological Data | Method |
|---|---|---|---|
| 335 | (1R,3S)-3-[(6-{5-[(5-cyclobutoxy-2H-1,2,3,4-tetrazol-2-yl)methyl]-1-methyl-1H-1,2,3-triazol-4-yl}-2-methylpyridin-3-yl)oxy]cyclo-hexane-1-carboxylic acid | LCMS, [M + H]$^+$ = 469.3; $^1$H NMR (500 MHz, DMSO-d$_6$) δ 7.84 (d, J = 8.5 Hz, 1H), 7.49 (d, J = 8.5 Hz, 1H), 6.37 (s, 2H), 4.90 (t, J = 7.3 Hz, 1H), 4.38 (br s, 1H), 4.14 (s, 3H), 2.47-2.35 (m, 1H), 2.31 (s, 5H), 2.21 (br d, J = 13.1 Hz, 1H), 2.09-1.99 (m, 3H), 1.86-1.70 (m, 3H), 1.62-1.52 (m, 1H), 1.47-1.34 (m, 2H) 1.34-1.20 (m, 2H); hLPA$_1$ IC$_{50}$ = 405 nM. | Example 316 |
| 336 | (1S,3S)-3-{[6-(5-{[5-(cyclopentyl-oxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 483.3; $^1$H NMR (500 MHz, DMSO-d$_6$) δ 7.84 (d, J = 8.5 Hz, 1H), 7.53 (br d, J = 8.9 Hz, 1H), 6.45-6.36 (m, 2H), 5.10-5.06 (m, 1H), 4.71 (br s, 1H), 2.47-2.39 (m, 1H), 2.36 (s, 3H), 1.91-1.82 (m, 3H), 1.79 (br s, 1H), 1.76-1.61 (m, 7H), 1.57 (br s, 4H), 1.50 (br s, 1H); Triazole-CH$_3$ missing in $^1$H NMR due to water suppression; hLPA$_1$ IC$_{50}$ = 67 nM. | Example 316 |
| 337 | (1R,3S)-3-{[6-(5-{[5-(cyclopentyl oxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 483.3; $^1$H NMR (500 MHz, DMSO-d$_6$) δ 7.83 (d, J = 8.2 Hz, 1H), 7.49 (d, J = 8.9 Hz, 1H), 6.39-6.34 (m, 2H), 5.06 (br s, 1H), 4.35 (br s, 1H), 4.14 (s, 3H), 2.32 (s, 4H), 2.21 (br d, J = 11.9 Hz, 1H), 2.01 (br d, J = 11.0 Hz, 1H), 1.89-1.76 (m, 4H), 1.74-1.53 (m, 6H), 1.37 (q, J = 11.6 Hz, 2H), 1.32-1.19 (m, 2H); hLPA$_1$ IC$_{50}$ = 546 nM. | Example 316 |

| Ex # | Structure & Name | Analytical & Biological Data | Method |
| --- | --- | --- | --- |
| 338 | 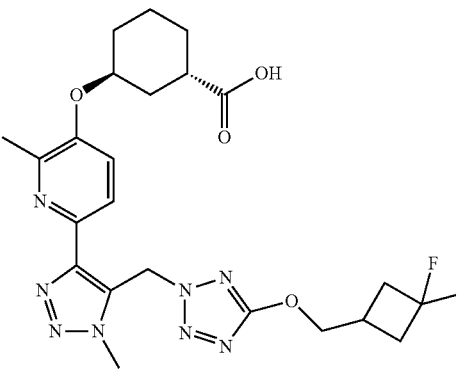<br>(1S,3S)-3-({6-[5-({5-[(3,3-difluoro-cyclobutyl)methoxyl-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, $[M + H]^+$ = 519.2; $^1$H NMR (500 MHz, DMSO-$d_6$) δ 7.86 (d, J = 8.5 Hz, 1H), 7.47 (d, J = 8.9 Hz, 1H), 6.43 (s, 2H), 4.76 (br s, 1H), 4.34 (d, J = 6.4 Hz, 2H), 4.14 (s, 3H), 2.70-2.57 (m, 4H), 2.48-2.36 (m, 5H), 1.99 (br d, J = 13.4 Hz, 1H), 1.87-1.74 (m, 3H), 1.65-1.55 (m, 2H), 1.51 (br d, J = 15.9 Hz, 2H); hLPA$_1$ IC$_{50}$ = 43 nM. | Example 316 |
| 339 | 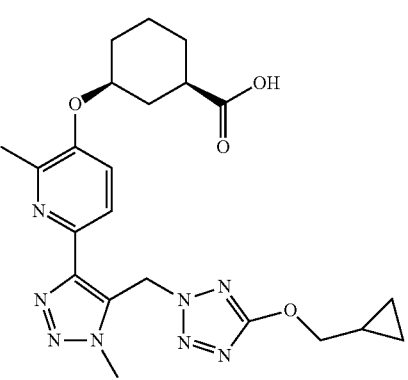 [SMILES: Cc1nc(-c2nnn(C)c2Cn2nnc(OCC3CC3)n2)ccc1O[C@H]1CCC[C@@H](C(=O)O)C1]<br>(1R,3S)-3-{[6-(5-{[5-(cyclopropyl-methoxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, $[M + H]^+$ = 469; $^1$H NMR (500 MHz, DMSO-$d_6$) δ 7.83 (br d, J = 8.2 Hz, 1H), 7.49 (br d, J = 8.5 Hz, 1H), 6.37 (s, 2H), 4.38 (br s, 1H), 4.16-4.11 (m, 3H), 4.11-4.05 (m, 2H), 2.48-2.39 (m, 1H), 2.32 (s, 3H), 2.21 (br d, J = 12.2 Hz, 1H), 2.00 (br s, 1H), 1.91-1.69 (m, 2H), 1.46-1.23 (m, 4H), 1.19 (br s, 1H), 0.51 (br d, J = 7.6 Hz, 2H), 0.29 (br d, J = 4.3 Hz, 2H); hLPA$_1$ IC$_{50}$ = 192 nM. | Example 316 |
| 340 | 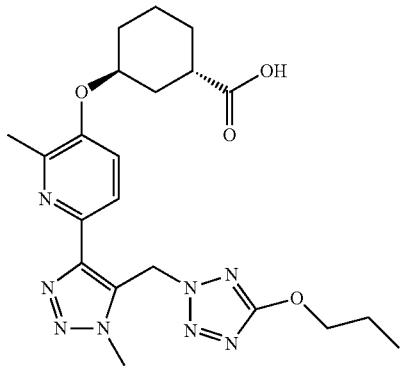 [SMILES: CCCOc1nnn(Cc2c(-c3ccc(O[C@H]4CCC[C@H](C(=O)O)C4)c(C)n3)nnn2C)n1]<br>(1S,3S)-3-[(2-methyl-6-{1-methyl-5-[(5-propoxy-2H-1,2,3,4-tetrazol-2-yl)methyl]-1H-1,2,3-triazol-4-yl}pyridin-3-yl)oxylcyclohexane-1-carboxylic acid | LCMS, $[M + H]^+$ = 457.22; $^1$H NMR (500 MHz, DMSO-$d_6$) δ 7.85 (d, J = 8.5 Hz, 1H), 7.45 (d, J = 8.5 Hz, 1H), 6.38 (s, 2H), 4.75 (br s, 1H), 4.21 (t, J = 6.4 Hz, 2H), 4.13 (s, 3H), 2.67-2.55 (m, 1H), 2.37 (s, 3H), 1.98 (br d, J = 14.3 Hz, 1H), 1.84 (br d, J = 10.4 Hz, 1H), 1.80-1.65 (m, 4H), 1.62-1.50 (m, 3H), 1.47 (br s, 1H), 0.89 (t, J = 7.5 Hz, 3H); hLPA$_1$ IC$_{50}$ = 97 nM. | Example 316 |

| Ex # | Structure & Name | Analytical & Biological Data | Method |
|---|---|---|---|
| 341 | (3S)-3-[(6-{5-[(5-cyclopropoxy-2H-1,2,3,4-tetrazol-2-yl)methyl]-1-methyl-1H-1,2,3-triazol-4-yl}-2-methylpyridin-3-yl)oxy]cyclo-hexane-1-carboxylic acid | LCMS, [M + H]$^+$ = 455.2; $^1$H NMR (500 MHz, DMSO-d$_6$) δ 7.86 (d, J = 8.5 Hz, 1H), 7.47 (d, J = 8.9 Hz, 1H), 6.46-6.39 (m, 2H), 4.76 (br s, 1H), 4.27-4.23 (m, 1H), 4.15 (s, 3H), 2.61 (br t, J = 10.1 Hz, 1H), 2.39 (s, 3H), 2.00 (br d, J = 14.0 Hz, 1H), 1.85 (br d, J = 12.5 Hz, 1H), 1.81-1.73 (m, 2H), 1.64-1.42 (m, 4H), 0.74 (d, J = 4.6 Hz, 4H); hLPA$_1$ IC$_{50}$ = 81 nM. | Example 316 |
| 342 | (1S,3S)-3-{[6-(5-{[5-(benzyloxy)-2H-1,2,3,4-tetrazol-2-yl]methyl}-1-methyl-1H-1,2,3-triazol-4-yl)-2-methylpyridin-3-yl]oxy}cyclo-hexane-1-carboxylic acid | LCMS, [M + H]$^+$ = 505.3; $^1$H NMR (500 MHz, DMSO-d$_6$) δ 7.86 (br d, J = 8.4 Hz, 1H), 7.46 (br d, J = 8.8 Hz, 1H), 7.40 (br s, 2H), 7.37-7.31 (m, 3H), 6.42 (br s, 2H), 5.33 (br s, 2H), 4.75 (br s, 1H), 4.13 (s, 2H), 2.59 (br s, 1H), 2.36 (br s, 3H), 1.98 (br d, J = 13.7 Hz, 1H), 1.84 (br d, J = 10.6 Hz, 1H), 1.80-1.71 (m, 2H), 1.64-1.43 (m, 4H); hLPA$_1$ IC$_{50}$ = 11 nM. | Example 316 |
| 343 | (1S,3S)-3-[(6-{5-[(5-methane-sulfonyl-2H-1,2,3,4-tetrazol-2-yl)methyl]-1-methyl-1H-1,2,3-triazol-4-yl}-2-methylpyridin-3-yl)oxy]cyclohexane-1-carboxylic acid | LCMS, [M + H]$^+$ = 477.1; $^1$H NMR (500 MHz, DMSO-d$_6$) δ 7.87 (d, J = 8.5 Hz, 1H), 7.45 (d, J = 8.5 Hz, 1H), 6.68-6.60 (m, 2H), 4.74 (br s, 1H), 4.19 (s, 3H), 3.47 (s, 3H), 2.95-2.85 (m, 1H), 2.63-2.55 (m, 1H), 2.31 (s, 3H), 1.98 (br d, J = 14.0 Hz, 1H), 1.83 (br d, J = 11.3 Hz, 1H), 1.80-1.70 (m, 2H), 1.63-1.49 (m, 2H), 1.46 (br d, J = 9.5 Hz, 1H); hLPA$_1$ IC$_{50}$ = 1100 nM. | Example 316 |

| Ex # | Structure & Name | Analytical & Biological Data | Method |
|---|---|---|---|
| 344 | (1S,3S)-3-{[2-methyl-6-(1-methyl-5-{[5-(2-methylpropoxy)-2H-1,2,3,4-tetrazol-2-yl]methyl}-1H-1,2,3-triazol-4-yl)pyridin-3-yl]oxy}cyclohexane-1-carboxylic acid | LCMS, [M + H]$^+$ = 471.2; $^1$H NMR (500 MHz, DMSO-d$_6$) δ 7.85 (d, J = 8.4 Hz, 1H), 7.45 (br d, J = 8.7 Hz, 1H), 6.38 (br s, 2H), 4.75 (br s, 1H), 4.13 (s, 3H), 4.04 (d, J = 6.6 Hz, 2H), 2.59 (br s, 1H), 2.36 (s, 3H), 2.09-1.93 (m, 2H), 1.82 (br s, 1H), 1.80-1.70 (m, 2H) 1.63-1.49 (m, 3H), 1.47 (br s, 1H), 0.93-0.86 (m, 7H); hLPA$_1$ IC$_{50}$ = 25 nM. | Example 316 |
| 345 | (1S,3S)-3-[(6-{5-[(5-butoxy-2H-1,2,3,4-tetrazol-2-yl)methyl]-1-methyl-1H-1,2,3-triazol-4-yl}-2-methylpyridin-3-yl)oxy]cyclo-hexane-1-carboxylic acid | LCMS, [M + H]$^+$ = 471.1; $^1$H NMR (500 MHz, DMSO-d$_6$) δ 7.85 (d, J = 8.5 Hz, 1H), 7.45 (d, J = 8.2 Hz, 1H), 6.39 (s, 2H), 4.75 (br s, 1H), 4.26 (t, J = 6.4 Hz, 2H), 4.14 (s, 2H), 2.60 (br s, 2H), 2.48-2.30 (m, 3H), 1.99 (br d, J = 14.3 Hz, 1H), 1.84 (br d, J = 10.7 Hz, 1H), 1.81-1.71 (m, 2H), 1.69-1.50 (m, 5H), 1.47 (br d, J = 10.7 Hz, 1H), 1.41-1.28 (m, 2H), 0.86 (t, J = 7.5 Hz, 3H); hLPA$_1$ IC$_{50}$ = 32 nM. | Example 316 |
| 346 | (1S,3S)-3-{[2-methyl-6-(1-methyl-5-{[5-(propan-2-yloxy)-2H-1,2,3,4-tetrazol-2-yl]methyl}-1H-1,2,3-triazol-4-yl)pyridin-3-yl]oxy}cyclohexane-1-carboxylic acid | LCMS, [M + H]$^+$ = 457.3; $^1$H NMR (500 MHz, DMSO-d$_6$) δ 7.85 (d, J = 8.5 Hz, 1H), 7.45 (d, J = 8.9 Hz, 1H), 6.38 (s, 2H), 4.83 (dt, J = 12.3, 6.2 Hz, 1H), 4.75 (br s, 1H), 4.14 (s, 3H), 2.65-2.56 (m, 1H), 2.43-2.30 (m, 3H), 1.99 (br d, J = 14.6 Hz, 1H), 1.84 (br d, J = 11.6 Hz, 1H), 1.80-1.68 (m, 2H), 1.65-1.54 (m, 2H), 1.52 (br s, 1H), 1.47 (br d, J = 12.2 Hz, 1H), 1.28 (d, J = 6.1 Hz, 6H); hLPA$_1$ IC$_{50}$ = 49 nM. | Example 316 |

| Ex # | Structure & Name | Analytical & Biological Data | Method |
|---|---|---|---|
| 347 | 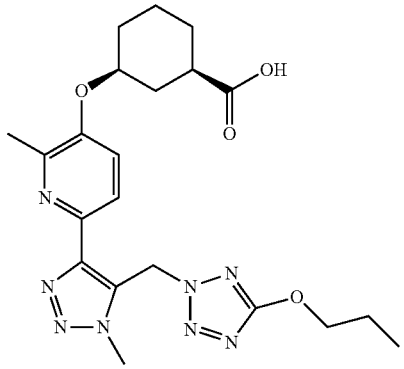 [SMILES: CCCOc1nnn(Cc2c(-c3ccc(O[C@H]4CCC[C@@H](C(=O)O)C4)c(C)n3)nnn2C)n1]<br>(1R,3S)-3-[(2-methyl-6-{1-methyl-5-[(5-propoxy-2H-1,2,3,4-tetrazol-2-yl)methyl]-1H-1,2,3-triazol-4-yl}pyridin-3-yl)oxy]cyclohexane-1-carboxylic acid | LCMS, [M + H]$^+$ = 457.3; $^1$H NMR (500 MHz, DMSO-d$_6$) δ 7.85 (d, J = 8.5 Hz, 1H), 7.55-7.45 (m, 1H), 6.41 (s, 2H), 4.40 (br t, J = 10.4 Hz, 1H), 4.22 (t, J = 6.4 Hz, 2H), 4.14 (s, 3H), 2.43 (br t, J = 11.7 Hz, 1H), 2.33 (s, 3H), 2.24 (br d, J = 11.6 Hz, 1H), 2.03 (br d, J = 10.7 Hz, 1H), 1.88-1.66 (m, 4H), 1.47-1.24 (m, 4H), 0.91 (t, J = 7.3 Hz, 3H); hLPA$_1$ IC$_{50}$ = 270 nM. | Example 316 |
| 348 | 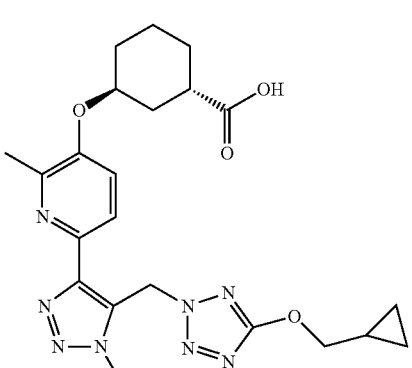<br>(1S,3S)-3-{[6-(5-{[5-(cyclopropyl-methoxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 469.4; $^1$H NMR (500 MHz, DMSO-d$_6$) δ 7.85 (d, J = 8.5 Hz, 1H), 7.46 (d, J = 8.9 Hz, 1H), 6.40 (s, 2H), 4.76 (br s, 1H), 4.18-4.06 (m, 5H), 2.60 (br s, 1H), 2.42-2.32 (m, 3H), 1.99 (br d, J = 14.0 Hz, 1H), 1.84 (br d, J = 11.0 Hz, 1H), 1.81-1.69 (m, 2H), 1.65-1.50 (m, 3H), 1.48 (br s, 1H), 1.27-1.07 (m, 1H), 0.52 (br d, J = 7.6 Hz, 2H), 0.30 (br d, J = 4.9 Hz, 2H); hLPA$_1$ IC$_{50}$ = 26 nM. | Example 316 |
| 349 | 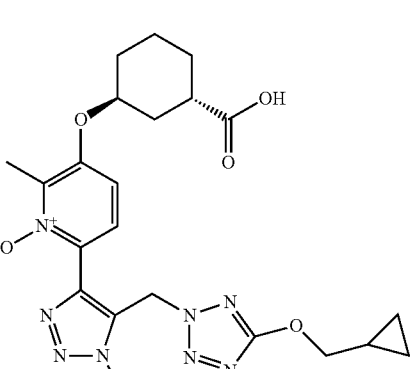<br>3-{[(1S,3S)-3-carboxycyclohexyl]oxy}-6-(5-{[5-(cyclopropyl-methoxy)-2H-1,2,3,4-tetrazol-2-yl]methyl}-1-methyl-1H-1,2,3-triazol-4-yl)-2-methylpyridin-1-ium-1-olate | LCMS, [M + H]$^+$ = 485.4; $^1$H NMR (500 MHz, DMSO-d$_6$) δ 7.55 (d, J = 8.9 Hz, 1H), 7.23 (d, J = 9.2 Hz, 1H), 6.32 (s, 2H), 4.82 (br s, 1H), 4.16 (s, 3H), 3.97 (d, J = 7.3 Hz, 2H), 2.78-2.57 (m, 1H), 2.36 (s, 3H), 2.02 (br d, J = 14.0 Hz, 1H), 1.92-1.72 (m, 3H), 1.67-1.45 (m, 4H), 1.14 (br d, J = 7.6 Hz, 1H), 0.57-0.43 (m, 2H), 0.26 (br d, J = 4.9 Hz, 2H); hLPA$_1$ IC$_{50}$ = 304 nM. | Example 316 |

| Ex # | Structure & Name | Analytical & Biological Data | Method |
|---|---|---|---|
| 350 | 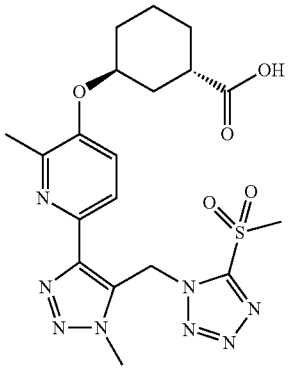<br>(1S,3S)-3-[(6-{5-[(5-methanesul-fonyl-1H-1,2,3,4-tetrazol-1-yl) methyl]-1-methyl-1H-1,2,3-triazol-4-yl}-2-methylpyridin-3-yl)oxy]cyclohexane-1-carboxylic acid | $^1$H NMR (500 MHz, CDCl$_3$) δ 7.96 (d, J = 8.8 Hz, 1H), 7.49 (d, J = 8.8 Hz, 1H), 6.57-6.49 (m, 2H), 4.79 (br s, 1H), 4.25 (s, 3H), 3.55 (s, 5H), 2.96-2.85 (m, 1H), 2.61 (s, 3H), 2.15-1.98 (m, 3H), 1.98-1.90 (m, 1H), 1.85-1.66 (m, 4H);<br>hLPA$_1$ IC$_{50}$ = 1238 nM. | Example 316 |
| 351 | 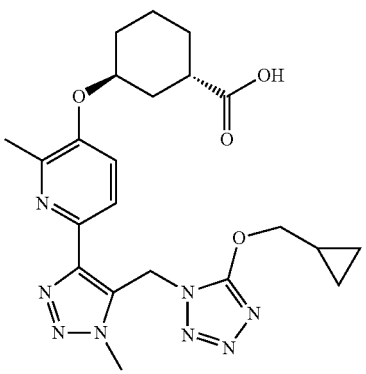 [SMILES: Cc1nc(-c2nnn(C)c2Cn2nnnc2OCC2CC2)ccc1O[C@H]1CCC[C@H](C(=O)O)C1]<br>(1S,3S)-3-{[6-(5-{[5-(cyclopropyl-methoxy)-1H-1,2,3,4-tetrazol-1-yl]methyl}-1-methyl-1H-1,2,3-triazol-4-yl)-2-methylpyridin-3-yl]oxy}cyclohexane-1-carboxylic acid | LCMS, [M + H]$^+$ = 469.3;<br>$^1$H NMR (500 MHz, DMSO-d$_6$) δ 7.83 (d, J = 8.5 Hz, 1H), 7.49 (t, J = 7.3 Hz, 1H), 6.03-5.96 (m, 2H), 4.73 (br s, 1H), 4.26 (d, J = 7.3 Hz, 1H), 4.14 (d, J = 1.5 Hz, 3H), 2.47-2.32 (m, 4H), 1.99-1.91 (m, 1H), 1.91-1.70 (m, 5H), 1.64-1.55 (m, 2H), 1.52 (br s, 2H), 0.54-0.48 (m, 2H), 0.33-0.29 (m, 2H);<br>hLPA$_1$ IC$_{50}$ = 152 nM. | Example 316 |
| 352 | 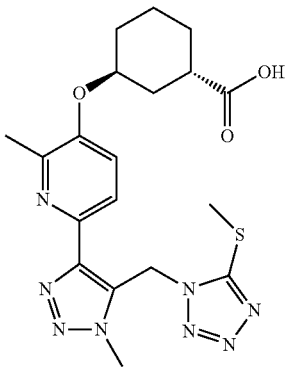 [SMILES: CSc1nnnn1Cc1c(-c2ccc(O[C@H]3CCC[C@H](C(=O)O)C3)c(C)n2)nnn1C]<br>(1S,3S)-3-{[2-methyl-6-(1-methyl-5-{[5-(methylsulfanyl)-1H-1,2,3,4-tetrazol-1-yl]methyl}-1H-1,2,3-triazol-4-yl)pyridin-3-yl]oxy}cyclohexane-1-carboxylic acid | LCMS, [M + H]$^+$ = 445.1;<br>$^1$H NMR (500 MHz, DMSO-d$_6$) δ 7.84 (d, J = 8.5 Hz, 1H), 7.43 (d, J = 8.9 Hz, 1H), 6.06 (s, 2H), 4.73 (br s, 1H), 4.10 (s, 2H), 2.68 (s, 3H), 2.60-2.52 (m, 2H), 2.34 (s, 3H), 1.95 (br s, 1H), 1.75 (br d, J = 11.0 Hz, 3H), 1.62-1.41 (m, 4H);<br>hLPA$_1$ IC$_{50}$ = 580 nM. | Example 316 |

| Ex # | Structure & Name | Analytical & Biological Data | Method |
| --- | --- | --- | --- |
| 353 | (1S,3S)-3-{[2-methyl-6-(1-methyl-5-{[5-(methylsulfanyl)-2H-1,2,3,4-tetrazol-2-yl]methyl}-1H-1,2,3-triazol-4-yl)pyridin-3-yl]oxy}cyclohexane-1-carboxylic acid | LCMS, $[M + H]^+$ = 445.2; $^1$H NMR (500 MHz, DMSO-$d_6$) δ 7.85 (d, J = 8.5 Hz, 1H), 7.46 (d, J = 8.5 Hz, 1H), 6.50 (s, 2H), 4.75 (br s, 1H), 4.16 (s, 3H), 2.59 (s, 4H), 2.36 (s, 3H), 1.99 (br d, J = 13.4 Hz, 1H), 1.84 (br d, J = 12.5 Hz, 1H), 1.77 (br d, J = 12.2 Hz, 2H), 1.60 (br d, J = 9.8 Hz, 2H), 1.50 (br d, J = 18.6 Hz, 2H); hLPA$_1$ IC$_{50}$ = 800 nM. | Example 316 |
| 354 | (1S,3S)-3-[(6-{5-[(5-cyclobutyl-1H-1,2,3,4-tetrazol-1-yl)methyl]-1-methyl-1H-1,2,3-triazol-4-yl}-2-methylpyridin-3-yl)oxy]cyclo-hexane-1-carboxylic acid | LCMS, $[M + H]^+$ = 453.2; $^1$H NMR (500 MHz, DMSO-$d_6$) δ 7.87 (d, J = 8.3 Hz, 1H), 7.50 (d, J = 8.6 Hz, 1H), 6.17 (s, 2H), 4.76 (br s, 1H), 4.09 (s, 3H), 4.00-3.86 (m, 1H), 2.61 (br s, 1H), 2.43 (s, 3H), 2.35-2.19 (m, 4H), 2.01-1.88 (m, 3H), 1.87-1.75 (m, 3H), 1.64 (br d, J = 9.5 Hz, 2H), 1.54 (br d, J = 7.7 Hz, 2H); hLPA$_1$ IC$_{50}$ = 226 nM. | Example 316 |
| 355 | (1S,3S)-3-[(6-{5-[(5-cyclobutyl-2H-1,2,3,4-tetrazol-2-yl)methyl]-1-methyl-1H-1,2,3-triazol-4-yl}-2-methylpyridin-3-yl)oxy]cyclohexane-1-carboxylic acid | LCMS, $[M + H]^+$ = 453.2; $^1$H NMR (500 MHz, DMSO-$d_6$) δ 7.85 (d, J = 8.3 Hz, 1H), 7.44 (d, J = 8.4 Hz, 1H), 6.50 (s, 2H), 4.74 (br s, 1H), 4.14 (s, 3H), 3.78-3.65 (m, 1H), 2.63 (br s, 1H), 2.43-2.31 (m, 5H), 2.28-2.14 (m, 2H), 2.12-1.97 (m, 2H), 1.92 (br d, J = 5.0 Hz, 1H), 1.88-1.73 (m, 3H), 1.63 (br d, J = 10.4 Hz, 2H), 1.53 (br d, J = 11.5 Hz, 2H); hLPA$_1$ IC$_{50}$ = 32 nM. | Example 316 |

| Ex # | Structure & Name | Analytical & Biological Data | Method |
|---|---|---|---|
| 356 | (1S,3S)-3-{[6-(5-{[5-(cyclobutyl-methyl)-1H-1,2,3,4-tetrazol-1-yl]methyl}-1-methyl-1H-1,2,3-triazol-4-yl)-2-methylpyridin-3-yl]oxy}cyclohexane-1-carboxylic acid | LCMS, [M + H]$^+$ = 467; $^1$H NMR (500 MHz, DMSO-d$_6$) δ 7.89 (d, J = 8.5 Hz, 1H), 7.51 (d, J = 8.5 Hz, 1H), 6.29 (s, 2H), 4.79 (br s, 1H), 4.13 (s, 3H), 2.98 (d, J = 7.6 Hz, 2H), 2.65-2.56 (m, 1H), 2.44 (s, 3H), 2.01 (br d, J = 14.3 Hz, 2H), 1.95-1.82 (m, 3H), 1.82-1.67 (m, 4H), 1.65-1.44 (m, 6H); hLPA$_1$ IC$_{50}$ = 146 nM. | Example 316 |
| 357 | (1S,3S)-3-{[6-(5-{[5-(2-cyclopropylethyl)-1H-1,2,3,4-tetrazol-1-yl]methyl}-1-methyl-1H-1,2,3-triazol-4-yl)-2-methylpyridin-3-yl]oxy}cyclohexane-1-carboxylic acid | LCMS, [M + H]$^+$ = 467.2; $^1$H NMR (500 MHz, DMSO-d$_6$) δ 7.89 (br d, J = 8.5 Hz, 1H), 7.52 (br d, J = 8.9 Hz, 1H), 6.29 (br s, 2H), 4.76 (br s, 1H), 4.11 (s, 3H), 3.02-2.93 (m, 2H), 2.58-2.55 (m, 1H), 2.41 (s, 3H), 1.91 (br s, 1H), 1.80 (br d, J = 11.9 Hz, 3H), 1.61 (br d, J = 8.5 Hz, 2H), 1.53 (q, J = 7.2 Hz, 4H), 0.59 (br s, 1H), 0.30 (br d, J = 7.6 Hz, 2H), −0.09 (br d, J = 4.3 Hz, 2H); hLPA$_1$ IC$_{50}$ = 332 nM. | Example 316 |

Example 362. (1S,3S)-3-((6-(5-(((5-(butylamino)-2H-tetrazol-2-yl)methyl)-1-methyl-1H-1,2,3-triazol-4-yl)-2-methylpyridin-3-yl)oxy)cyclohexane-1-carboxylic acid 362A. Methyl (1 S,3 S)-3-((6-(5-(((5-amino-2H-tetrazol-2-yl)methyl)-1-methyl-1H-1,2,3-triazol-4-yl)-2-methylpyridin-3-yl)oxy)cyclohexane-1-carboxylate

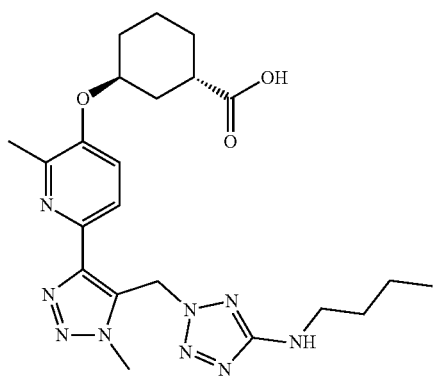 [SMILES: CCCCNc1nnn(Cc2c(-c3ccc(O[C@H]4CCC[C@H](C(=O)O)C4)c(C)n3)nnn2C)n1]

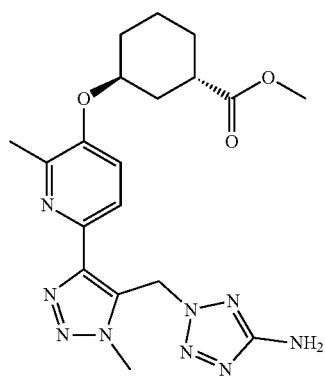

A mixture of Intermediate 5 (200 mg, 0.472 mmol), 2H-tetrazol-5-amine (48 mg, 0.567 mmol), and Cs₂CO₃ (185 mg, 0.567 mmol) in MeCN (4.7 mL) was stirred at RT overnight, then was partially concentrated in vacuo. The mixture was partitioned between DCM and 50% satd aq. NH₄Cl and stirred at RT for 15 min. The organic layer was separated, dried (Na₂SO₄) and concentrated in vacuo. The residue was chromatographed (12 g SiO₂; continuous gradient from 0-25% MeOH in DCM over 20 min, 30 mL/min) to give the title compound as a white foam (204 mg, 100%). LCMS, [M+H]⁺=428.3.

362B. Methyl (1 S,3 S)-3-((6-(5-((5-(butyl amino)-2H-tetrazol-2-yl)methyl)-1-methyl-1H-1,2,3-triazol-4-yl)-2-methylpyridin-3-yl)oxy)cyclohexane-1-carboxylate

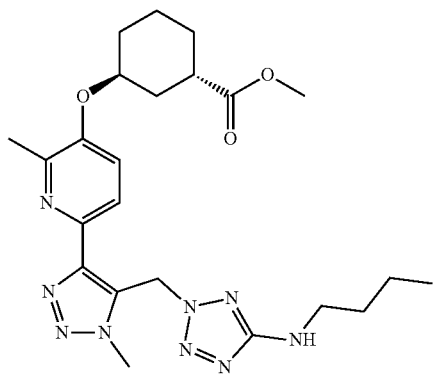 [SMILES: CCCCNc1nnn(Cc2c(-c3ccc(O[C@H]4CCC[C@H](C(=O)OC)C4)c(C)n3)nnn2C)n1]

A mixture of 362A (40 mg, 0.094 mmol), 1-bromobutane (15 mg, 0.103 mmol), Bu₄NI (3 mg, 0.009 mmol), and Cs₂CO₃ (0.037 g, 0.112 mmol) in MeCN (0.94 mL) was stirred at RT overnight, then was partially concentrated in vacuo. The residue was partitioned between DCM and 50% satd aq. NH₄Cl and stirred at RT for 15 min. The organic layer was separated, dried (Na₂SO₄) and concentrated in vacuo. The residue was chromatographed (12 g SiO₂; continuous gradient from 0-100% EtOAc in hexane over 10 min, 30 mL/min) to give the title compound as a colorless viscous oil (17 mg, 39%). LCMS, [M+H]⁺=484.2.

Example 362

To a RT solution of 362B (5 mg, 0.010 mmol) in THF/MeOH (0.16 mL/0.05 mL) was added 2M aq. LiOH (50 μL, 0.10 mmol). The reaction was stirred overnight at RT, then was partitioned between DCM and 1N aq. HCl. The mixture was stirred for 15 min at RT; the pH was adjusted to 3-4 with 1N aq. HCl. The organic layer was dried (Na₂SO₄), then was concentrated in vacuo. The crude product was purified by preparative LC/MS (Column: XBridge C18, 200 mm×19 mm, 5-μm particles; Mobile Phase A: 5:95 MeCN:H₂O with 10-mM aq. NH₄OAc; Mobile Phase B: 95:5 MeCN:H₂O with 10-mM aq. NH₄OAc; Gradient: a 0-min hold at 15% B, 15-55% B over 20 min, then a 4-min hold at 100% B; Flow Rate: 20 mL/min; Column Temperature: 25 C. Fraction collection was triggered by MS signals; fractions containing desired product were combined and dried via centrifugal evaporation) to give the title compound as a colorless viscous oil (2 mg, 33%). LCMS, [M+H]⁺=470.4; ¹H NMR (500 MHz, DMSO-d₆) δ 7.90 (d, J=8.5 Hz, 1H), 7.57 (d, J=8.9 Hz, 1H), 7.45 (t, J=5.5 Hz, 1H), 5.93-5.85 (m, 2H), 4.79 (br s, 1H), 4.07 (s, 3H), 3.29-3.23 (m, 2H), 2.62-2.52 (m, 1H), 2.48-2.45 (m, 3H), 1.96 (br d, J=14.0 Hz, 1H), 1.84-1.75 (m, 3H), 1.62 (br d, J=8.9 Hz, 2H), 1.52 (br d, J=15.6 Hz, 2H), 1.39 (quin, J=7.2 Hz, 2H), 1.13-1.05 (m, 2H), 0.73 (t, J=7.3 Hz, 3H); hLPA₁ IC₅₀=316 nM.

Example 384. (1S,3S)-3-((6-(5-(((2-(4-chlorophenyl)-2H-tetrazol-5-yl)amino)methyl)-1-methyl-1H-1,2,3-triazol-4-yl)-2-methylpyridin-3-yl)oxy)cyclohexane-1-carboxylic acid

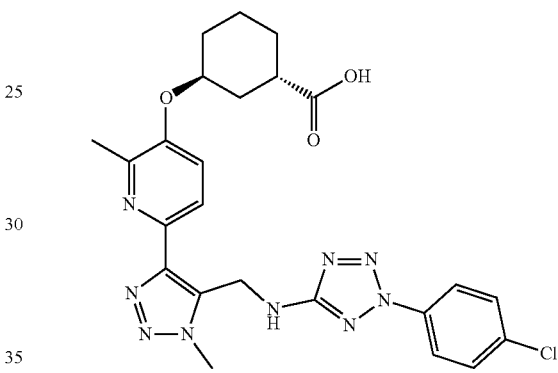

384A. 2-trityl-2H-tetrazol-5-amine

A mixture of 2H-tetrazol-5-amine (5.00 g, 58.8 mmol), trityl chloride (19.7 g, 70.5 mmol), DMAP (0.36 g, 2.94 mmol), and iPr₂NEt (15.4 mL, 88.0 mmol) in DCM (294 mL) was stirred at RT for 7 days. The solid product was filtered off and dried in vacuo to give the title compound as a white solid (12.1 g, 63%). ¹H NMR (400 MHz, CDCl₃) δ 7.39-7.27 (m, 9H), 7.24-7.11 (m, 6H), 4.36 (br s, 2H).

384B. Methyl (1S,3S)-3-((2-methyl-6-(1-methyl-5-(((2-trityl-2H-tetrazol-5-yl)amino)methyl)-1H-1,2,3-triazol-4-yl)pyridin-3-yl)oxy)cyclohexane-1-carboxylate

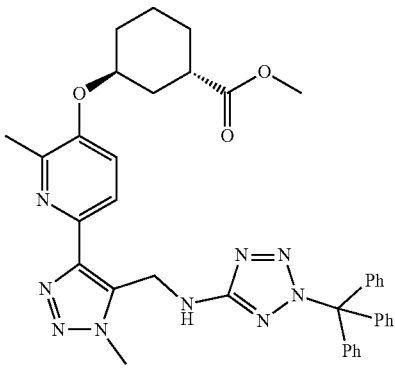 [SMILES: COC(=O)[C@H]1CCC[C@H](Oc2ccc(-c3nnn(C)c3CNc3nnn(C(c4ccccc4)(c4ccccc4)c4ccccc4)n3)nc2C)C1]

To a RT solution of Intermediate 8 (500 mg, 1.40 mmol), 348A (695 mg, 1.50 mmol), and NaBH(OAc)$_3$ (591 mg, 2.79 mmol) in DCE (14 mL) was added HOAc (16 μL, 0.279 mmol). The reaction mixture was stirred overnight at RT, then was partitioned between DCM and 50% satd aq. NaHCO$_3$. The mixture was stirred at RT for 15 min. The organic layer was dried (Na$_2$SO$_4$) and concentrated in vacuo. The residue was chromatographed (40 g SiO$_2$; continuous gradient from 0-100% EtOAc in hexane over 20 min, 40 mL/min) to give the title compound as a colorless viscous oil (0.703 g, 75%). LCMS, [M+H]$^+$=670.4.

384C. Methyl (1S,3S)-3-((6-(5-(((2H-tetrazol-5-yl)amino)methyl)-1-methyl-1H-1,2,3-triazol-4-yl)-2-methylpyridin-3-yl)oxy)cyclohexane-1-carboxylate

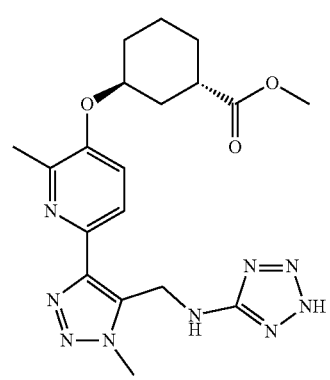

To a RT solution of LJK4 (0.700 g, 1.05 mmol) and Et$_3$SiH (0.501 mL, 3.14 mmol) in DCM (9.4 mL) was added TFA (1 mL). The reaction mixture was stirred at RT for 2 h, then was concentrated in vacuo. The residue was chromatographed (24 g SiO$_2$; continuous gradient from 0-50% MeOH in DCM over 20 min, 30 mL/min) to give the title compound as a colorless viscous oil (0.442 g, 99%). LCMS, [M+H]$^+$=428.2.

384D. Methyl (1S,3S)-3-((6-(5-(((2-(4-chlorophenyl)-2H-tetrazol-5-yl)amino)methyl)-1-methyl-1H-1,2,3-triazol-4-yl)-2-methylpyridin-3-yl)oxy)cyclohexane-1-carboxylate

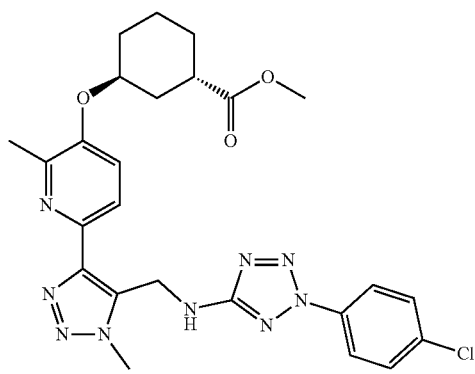 [SMILES: COC(=O)[C@H]1CCC[C@H](Oc2ccc(-c3nnn(C)c3CNc3nnn(-c4ccc(Cl)cc4)n3)nc2C)C1]

To a RT solution of LJK5 (20 mg, 0.047 mmol), (4-chlorophenyl)boronic acid (9 mg, 0.056 mmol), and pyridine (15 μL, 0.19 mmol) in DCM (0.23 mL) was added Cu(OAc)$_2$ (10 mg, 0.056 mmol). The reaction mixture was stirred overnight at RT, then was filtered through Celite®; the filtrate was concentrated in vacuo. The residue was chromatographed (12 g SiO$_2$; continuous gradient from 0-100% EtOAc in hexane over 10 min, 30 mL/min) to give the title compound as a colorless viscous oil (12 mg, 47%). LCMS, [M+H]$^+$=538.2.

Example 384

To a RT solution of 384C (11 mg, 0.020 mmol) in THF/MeOH (0.30 mL/0.10 mL) was added 2M aq. LiOH (0.10 mL, 0.20 mmol). The reaction was stirred overnight at RT, then was partitioned between DCM and 1N aq. HCl; the resulting mixture was stirred for 15 min at RT. The pH was adjusted to 3-4 with 1N aq. HCl. The separated organic layer was dried (Na$_2$SO$_4$) and concentrated in vacuo. The crude product was purified by preparative LC/MS (Column: XBridge C18, 200 mm×19 mm, 5-μm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 15% B, 15-55% B over 20 min, then a 4-min hold at 100% B; Flow Rate: 20 mL/min; Column Temperature: 25 C. Fraction collection was triggered by MS signals; fractions containing desired product were combined and dried via centrifugal evaporation) to give the title compound as a colorless viscous oil (5 mg, 49%). LCMS, [M+H]$^+$=524.3; $^1$H NMR (500 MHz, DMSO-d$_6$) δ 7.85 (d, J=8.5 Hz, 1H), 7.61 (d, J=8.9 Hz, 2H), 7.51-7.47 (m, 4H), 4.93 (br d, J=5.8 Hz, 2H), 4.76 (br s, 1H), 4.17 (s, 3H), 2.61-2.55 (m, 1H), 2.11 (s, 3H), 1.97 (br d, J=12.5 Hz, 1H), 1.85-1.75 (m, 3H), 1.64-1.48 (m, 4H); hLPA$_1$ IC$_{50}$=41 nM.'

Example 388. (1 S,3 S)-3-((6-(5-(((2-isobutyl-2H-tetrazol-5-yl)amino)methyl)-1-methyl-1H-1,2,3-triazol-4-yl)-2-methylpyridin-3-yl)oxy)cyclohexane-1-carboxylic acid

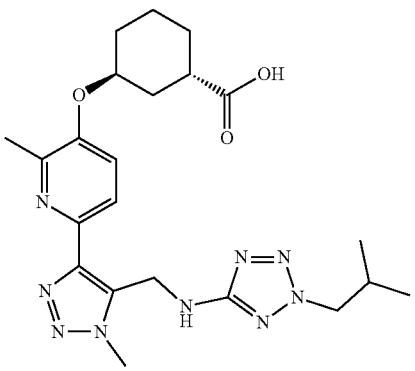 [SMILES: Cc1nc(-c2nnn(C)c2CNc2nnn(CC(C)C)n2)ccc1O[C@H]1CCC[C@H](C(=O)O)C1]

388A. Methyl (1 S,3 S)-3-((6-(5-(((2-isobutyl-2H-tetrazol-5-yl)amino)methyl)-1-methyl-1H-1,2,3-triazol-4-yl)-2-methylpyridin-3-yl)oxy)cyclohexane-1-carboxylate

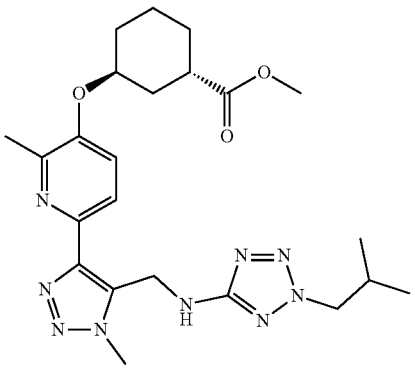 [SMILES: COC(=O)[C@H]1CCC[C@H](Oc2ccc(-c3nnn(C)c3CNc3nnn(CC(C)C)n3)nc2C)C1]

To a RT solution of 384C (14 mg, 0.033 mmol), isobutanol (4 mg, 0.049 mmol), and Ph₃P (13 mg, 0.049 mmol) was added DEAD dropwise (10% solution in DCM, 77 μL, 0.049 mmol). The reaction mixture was stirred overnight at RT, then was concentrated in vacuo. The residue was chromatographed (12 g SiO₂; continuous gradient from 0-100% EtOAc in hexane over 15 min, 30 mL/min) to give the title compound as a colorless viscous oil (6 mg, 37%). LCMS, [M+H]⁺=484.1.

Example 388

To a RT solution of 388A (5 mg, 0.010 mmol) in THF/MeOH (0.16 mL/0.05 mL) was added 2M aq. LiOH (52 μL, 0.103 mmol). The reaction was stirred overnight at RT, then was partitioned between DCM and 1N aq. HCl, and the resulting mixture was stirred for 15 min at RT. The pH was adjusted to 3-4 with 1N aq. HCl. The separated organic layer was dried (Na₂SO₄) and concentrated in vacuo. The residue was purified by preparative LC/MS (Column: XBridge C18, 200 mm×19 mm, 5-μm particles; Mobile Phase A: 5:95 MeCN:H₂O with 10-mM aq. NH₄OAc; Mobile Phase B: 95:5 MeCN:H₂O with 10-mM aq. NH₄OAc; Gradient: a 0-min hold at 15% B, 15-55% B over 20 min, then a 4-min hold at 100% B; Flow Rate: 20 mL/min; Column Temperature: 25 C. Fraction collection was triggered by MS signals; fractions containing desired product were combined and dried via centrifugal evaporation) to give the title compound as a colorless viscous oil (0.005 g, 93%). LCMS, [M+H]⁺=469.9; ¹H NMR (500 MHz, DMSO-d₆) δ 7.84 (d, J=8.5 Hz, 1H), 7.49 (d, J=8.9 Hz, 1H), 7.13 (br t, J=6.1 Hz, 1H), 4.83 (br d, J=5.8 Hz, 2H), 4.77 (br s, 1H), 4.19 (d, J=7.3 Hz, 2H), 4.11 (s, 3H), 2.67-2.57 (m, 1H), 2.42 (s, 3H), 2.15-1.95 (m, 2H), 1.94-1.82 (m, 1H), 1.82-1.71 (m, 2H), 1.68-1.52 (m, 3H), 1.49 (br d, J=10.4 Hz, 1H), 0.80 (d, J=6.7 Hz, 6H).

Example 400. (1 S,3 S)-3-((6-(5-((2-(2-cyclopropylethyl)-2H-tetrazol-5-yl)methyl)-1-methyl-1H-1,2,3-triazol-4-yl)-2-methylpyridin-3-yl)oxy)cyclohexane-1-carboxylic acid

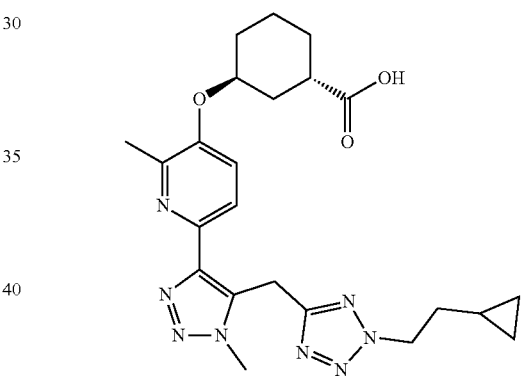

400A. Methyl (1 S,3S)-3-((6-(5-(cyanomethyl)-1-methyl-1H-1,2,3-triazol-4-yl)-2-methylpyridin-3-yl)oxy)cyclohexane-1-carboxylate

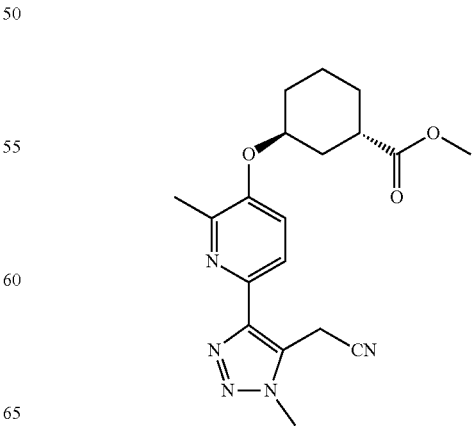

To a solution of Intermediate 5 (1.10 g, 2.60 mmol) in MeCN (10 mL) was added NaCN (0.127 g, 2.60 mmol) in DMSO (10 mL) portionwise. The reaction mixture was stirred at 0° C.; for 30 min, then was partitioned between EtOAc and water. The aqueous phase was extracted with EtOAc (3×20 mL). The combined organic extracts were concentrated in vacuo. The crude product was chromatographed (SiO$_2$; continuous gradient from 0% to 100% EtOAc in hexanes over 20 min) to give the title compound as white solid (0.864 g, 2.34 mmol, 90% yield). LCMS, [M+H]$^+$=370.2; $^1$H NMR (400 MHz, CDCl$_3$) δ 8.28-7.77 (m, 1H), 7.23 (d, J=8.8 Hz, 1H), 4.79-4.55 (m, 3H), 4.20 (s, 3H), 3.72 (s, 3H), 3.06-2.72 (m, 1H), 2.53 (s, 3H), 2.25-2.08 (m, 1H), 2.03-1.59 (m, 7H).

400B. Methyl (1 S,3 S)-3-((6-(5-((2H-tetrazol-5-yl)methyl)-1-methyl-1H-1,2,3-triazol-4-yl)-2-methylpyridin-3-yl)oxy)cyclohexane-1-carboxylate

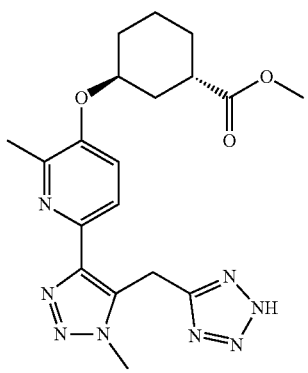

A mixture of Intermediate 400A (230 mg, 0.623 mmol), TMSN$_3$ (717 mg, 6.23 mmol), and Bu$_2$SnO (0.310 g, 1.24 mmol) in toluene (12.5 mL) was heated at 90° C., overnight, then was cooled to RT and concentrated in vacuo. The residue was chromatographed (12 g SiO$_2$; continuous gradient from 0-25% MeOH in DCM over 20 min, 30 mL/min) to give the title compound as a white foam (201 mg, 79%). LCMS, M+H]$^+$=413.2.

400C. Methyl (1 S,3S)-3-((6-(5-((2-(2-cyclopropylethyl)-2H-tetrazol-5-yl)methyl)-1-methyl-1H-1,2,3-triazol-4-yl)-2-methylpyridin-3-yl)oxy)cyclohexane-1-carboxylate

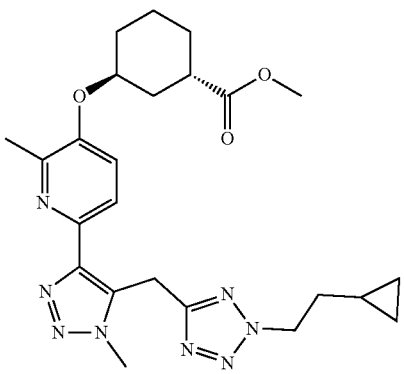 [SMILES: COC(=O)[C@H]1CCC[C@H](Oc2ccc(-c3nnn(C)c3Cc3nnn(CCC4CC4)n3)nc2C)C1]

To a RT solution of 400B (20 mg, 0.048 mmol), 2-cyclopropylethan-1-ol (8 mg, 0.097 mmol), and Ph$_3$P (25 mg, 0.097 mmol) was added DEAD dropwise (10% solution in DCM, 0.150 mL, 0.097 mmol). The reaction was stirred at RT overnight, then was concentrated in vacuo. The residue was chromatographed (12 g SiO$_2$; continuous gradient from 0-100% EtOAc in hexane over 15 min, 30 mL/min) to give the title compound (as an inseparable mixture with Ph$_3$PO; 100% yield assumed). This material was used in the next step without further purification.

Example 400

To a RT solution of 400C (23 mg, 0.048 mmol) in THF/MeOH (0.72 mL/0.24 mL) was added 2M aq. LiOH (0.24 mL, 0.48 mmol). The reaction was stirred at RT overnight, then was partitioned between DCM and 1N aq. HCl, and the resulting mixture was stirred for 15 min at RT. The pH was adjusted to 3-4 with 1N aq. HCl; the organic layer was dried (Na$_2$SO$_4$), then was concentrated in vacuo. The crude product was purified by preparative LC/MS (Column: XBridge C18, 200 mm×19 mm, 5-μm particles; Mobile Phase A: 5:95 MeCN:H$_2$O with 10-mM aq. NH$_4$OAc; Mobile Phase B: 95:5 MeCN:H$_2$O with 10-mM aq. NH$_4$OAc; Gradient: a 0-min hold at 15% B, 15-55% B over 20 min, then a 4-min hold at 100% B; Flow Rate: 20 mL/min; Column Temperature: 25 C. Fraction collection was triggered by MS signals; fractions containing desired product were combined and dried via centrifugal evaporation) to give the title compound as a colorless viscous oil (11 mg, 46%, 2 steps). LCMS, [M+H]$^+$=457.4. $^1$H NMR (500 MHz, DMSO-d$_6$) δ 7.81 (d, J=8.5 Hz, 1H), 7.43 (br d, J=8.5 Hz, 1H), 4.94 (s, 2H), 4.73 (br s, 1H), 4.62 (t, J=6.7 Hz, 2H), 4.03 (s, 3H), 2.59 (br s, 1H), 2.32 (s, 3H), 1.98 (br d, J=12.2 Hz, 1H), 1.83 (br s, 1H), 1.80-1.68 (m, 4H), 1.63-1.45 (m, 4H), 0.50 (br s, 1H), 0.23-0.19 (m, 2H), −0.16 (br d, J=4.6 Hz, 2H). hLPA$_1$ IC$_{50}$=129 nM.

The Examples in the following table were synthesized according to the procedures described for the preparation of the Examples indicated.

| Ex # | Structure & Name | Analytical & Biology Data | Method |
|---|---|---|---|
| 358 | 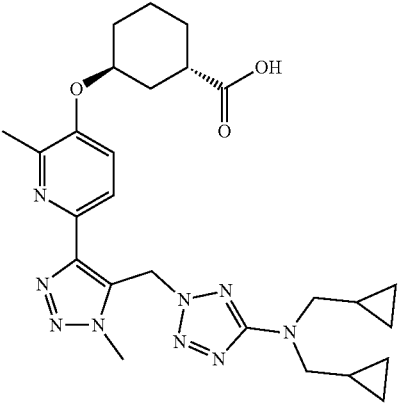 [SMILES: Cc1nc(-c2nnn(C)c2Cn2nnc(N(CC3CC3)CC3CC3)n2)ccc1O[C@H]1CCC[C@H](C(=O)O)C1]<br><br>(1S,3S)-3-((6-(5-((5-(bis(cyclo-propylmethyl)amino)-2H-tetrazol-2-yl)methyl)-1-methyl-1H-1,2,3-triazol-4-yl)-2-methylpyridin-3-yl)oxy)cyclohexane-1-carboxylic acid | LCMS, [M + H]$^+$ = 522.4; $^1$H NMR (500 MHz, DMSO-d$_6$) δ 7.86 (br d, J = 8.5 Hz, 1H), 7.48 (br d, J = 8.8 Hz, 1H), 6.19 (s, 2H), 4.77 (br s, 1H), 3.95 (s, 3H), 3.17 (br d, J = 7.1 Hz, 5H), 2.67-2.56 (m, 1H), 2.39 (s, 3H), 1.99 (br d, J = 13.8 Hz, 1H), 1.85 (br d, J = 11.3 Hz, 1H), 1.81-1.68 (m, 2H), 1.65-1.50 (m, 3H), 1.48 (br s, 1H), 0.90 (br s, 2H), 0.35 (br d, J = 7.7 Hz, 4H), 0.05 (br d, J = 4.2 Hz, 4H);<br>hLPA$_1$ IC$_{50}$ = 949 nM. | Example 362 |
| 359 | 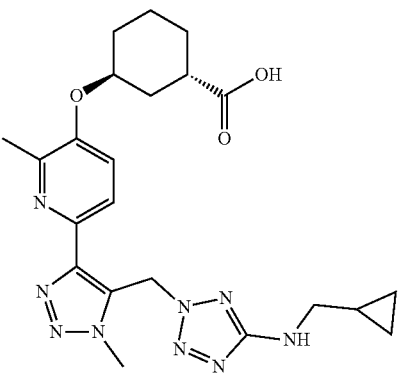 [SMILES: Cc1nc(-c2nnn(C)c2Cn2nnc(NCC3CC3)n2)ccc1O[C@H]1CCC[C@H](C(=O)O)C1]<br><br>(1S,3S)-3-((6-(5-((5-((cyclopropyl methyl)amino)-2H-tetrazol-2-yl)methyl)-1-methyl-1H-1,2,3-triazol-4-yl)-2-methylpyridin-3-yl)oxy)cyclohexane-1-carboxylic acid | LCMS, [M + H]$^+$ = 468.1; $^1$H NMR (500 MHz, DMSO-d$_6$) δ 7.90 (br d, J = 8.5 Hz, 1H), 7.56 (d, J = 7.9 Hz, 1H), 7.51 (t, J = 6.1 Hz, 1H), 5.94-5.87 (m, 2H), 4.78 (br s, 1H), 4.07 (s, 3H), 3.17-3.10 (m, 3H), 2.62-2.54 (m, 1H), 2.47 (s, 3H), 1.94 (br s, 1H), 1.79 (br d, J = 11.6 Hz, 4H), 1.64-1.44 (m, 4H), 0.91 (br s, 1H), 0.27 (br d, J = 7.9 Hz, 2H), 0.04 (br d, J = 4.3 Hz, 2H);<br>hLPA$_1$ IC$_{50}$ = 428 nM. | Example 362 |
| 360 | 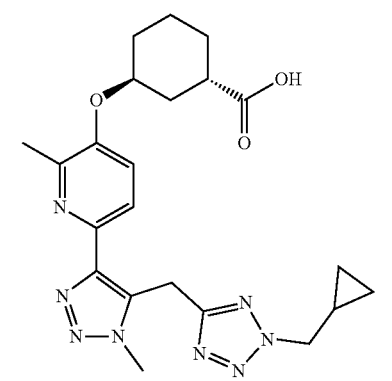 [SMILES: Cc1nc(-c2nnn(C)c2Cc2nnn(CC3CC3)n2)ccc1O[C@H]1CCC[C@H](C(=O)O)C1]<br><br>(1S,3S)-3-((6-(5-((2-(cyclopropyl-methyl)-2H-tetrazol-5-yl)methyl)-1-methyl-1H-1,2,3-triazol-4-yl)-2-methylpyridin-3-yl)oxy)cyclo-hexane-1-carboxylic acid | LCMS, [M + H]$^+$ = 453.4; $^1$H NMR (500 MHz, DMSO-d$_6$) δ 7.82 (d, J = 8.5 Hz, 1H), 7.43 (d, J = 8.5 Hz, 1H), 4.95 (s, 2H), 4.74 (br s, 1H), 4.46 (d, J = 7.3 Hz, 2H), 4.04 (s, 3H), 2.66-2.56 (m, 1H), 2.34 (s, 3H), 1.98 (br d, J = 14.3 Hz, 1H), 1.84 (br d, J = 10.4 Hz, 1H), 1.80-1.72 (m, 2H), 1.63-1.43 (m, 4H), 1.26 (br d, J = 7.6 Hz, 1H), 0.54-0.48 (m, 2H), 0.37 (br d, J = 4.9 Hz, 2H);<br>hLPA$_1$ IC$_{50}$ = 92 nM. | Example 400 |

| Ex # | Structure & Name | Analytical & Biology Data | Method |
|---|---|---|---|
| 361 | (1S,3S)-3-((6-(5-((5-(butyl(methyl)amino)-2H-tetrazol-2-yl)methyl)-1-methyl-1H-1,2,3-triazol-4-yl)-2-methylpyridin-3-yl)oxy)cyclo-hexane-1-carboxylic acid | LCMS, [M + H]⁺ = 484.2; ¹H NMR (500 MHz, DMSO-d₆) δ 7.85 (d, J = 8.5 Hz, 1H), 7.47 (d, J = 8.9 Hz, 1H), 6.08 (s, 2H), 4.75 (br s, 1H), 4.04 (s, 3H), 3.28 (br t, J = 7.5 Hz, 1H), 3.00 (s, 3H), 2.62-2.55 (m, 1H), 2.35 (s, 3H), 1.96 (br d, J = 13.1 Hz, 1H), 1.85-1.73 (m, 3H), 1.63-1.45 (m, 6H), 1.25-1.17 (m, 2H), 0.85 (t, J = 7.3 Hz, 3H); hLPA₁ IC₅₀ = 228 nM. | Example 362 |
| 362 | (1S,3S)-3-((6-(5-((5-(butylamino)-2H-tetrazol-2-yl)methyl)-1-methyl-1H-1,2,3-triazol-4-yl)-2-methyl-pyridin-3-yl)oxy)cyclohexane-1-carboxylic acid | LCMS, [M + H]⁺ = 470.4; ¹H NMR (500 MHz, DMSO-d₆) δ 7.90 (d, J = 8.5 Hz, 1H), 7.57 (d, J = 8.9 Hz, 1H), 7.45 (t, J = 5.5 Hz, 1H), 5.93-5.85 (m, 2H), 4.79 (br s, 1H), 4.07 (s, 3H), 3.29-3.23 (m, 2H), 2.62-2.52 (m, 1H), 2.48-2.45 (m, 3H), 1.96 (br d, J = 14.0 Hz, 1H), 1.84-1.75 (m, 3H), 1.62 (br d, J = 8.9 Hz, 2H), 1.52 (br d, J = 15.6 Hz, 2H), 1.39 (quin, J = 7.2 Hz, 2H), 1.13-1.05 (m, 2H), 0.73 (t, J = 7.3 Hz, 3H); hLPA₁ IC₅₀ = 316 nM. | Example 362 |
| 363 | (1S,3S)-3-((6-(5-((5-(dibutylamino)-2H-tetrazol-2-yl)methyl)-1-methyl-1H-1,2,3-triazol-4-yl)-2-methyl-pyridin-3-yl)oxy)cyclohexane-1-carboxylic acid | LCMS, [M + H]⁺ = 526.5; ¹H NMR (500 MHz, DMSO-d₆) δ 7.85 (d, J = 8.9 Hz, 1H), 7.47 (d, J = 8.9 Hz, 1H), 6.13 (s, 2H), 4.75 (br s, 1H), 3.94 (s, 3H), 3.22-3.16 (m, 4H), 2.61-2.52 (m, 1H), 2.37 (s, 3H), 1.95 (br d, J = 13.4 Hz, 1H), 1.84-1.73 (m, 3H), 1.58 (br d, J = 7.0 Hz, 2H), 1.50 (br d, J = 19.8 Hz, 2H), 1.39 (quin, J = 7.6 Hz, 4H), 1.11 (sxt, J = 7.4 Hz, 4H), 0.77 (t, J = 7.5 Hz, 6H); hLPA₁ IC₅₀ = 229 nM. | Example 362 |

| Ex # | Structure & Name | Analytical & Biology Data | Method |
|---|---|---|---|
| 364 | 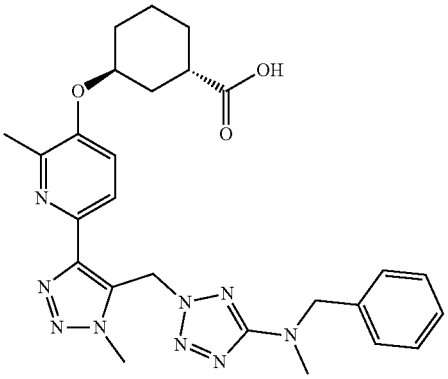 [SMILES: Cc1nc(-c2nnn(C)c2Cn2nnc(N(C)Cc3ccccc3)n2)ccc1O[C@H]1CCC[C@H](C(=O)O)C1]<br>(1S,3S)-3-((6-(5-((5-(benzyl (methyl)amino)-2H-tetrazol-2-yl)methyl)-1-methyl-1H-1,2,3-triazol-4-yl)-2-methylpyridin-3-yl)oxy)cyclohexane-1-carboxylic acid | LCMS, [M + H]⁺ = 518.42; ¹H NMR (500 MHz, DMSO-d₆) δ 7.82 (d, J = 8.4 Hz, 1H), 7.42 (d, J = 8.7 Hz, 1H), 7.30-7.18 (m, 5H), 6.10 (s, 2H), 4.73 (br s, 1H), 4.50 (s, 2H), 4.03 (s, 1H), 3.84 (br s, 1H), 2.97-2.87 (m, 3H), 2.61-2.54 (m, 1H), 2.26 (s, 3H), 1.96 (br d, J = 13.5 Hz, 1H), 1.82 (br d, J = 12.4 Hz, 1H), 1.78-1.67 (m, 2H), 1.60-1.48 (m, 3H), 1.44 (br s, 1H); hLPA₁ IC₅₀ = 273 nM. | Example 362 |
| 365 | 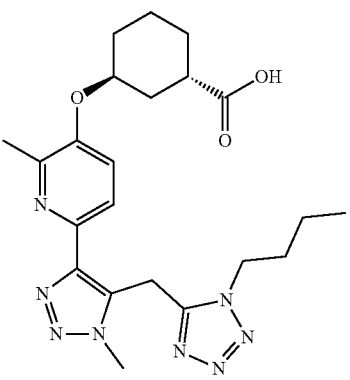 [SMILES: CCCCn1nnnc1Cc1c(-c2ccc(O[C@H]3CCC[C@H](C(=O)O)C3)c(C)n2)nnn1C]<br>(1S,3S)-3-((6-(5-((1-butyl-1H-tetrazol-5-yl)methyl)-1-methyl-1H-1,2,3-triazol-4-yl)-2-methylpyridin-3-yl)oxy)cyclohexane-1-carboxylic acid | LCMS, [M + H]⁺ = 455.24; ¹H NMR (500 MHz, DMSO-d₆) δ 7.87 (d, J = 8.5 Hz, 1H), 7.51-7.44 (m, 1H), 5.04 (s, 2H), 4.74 (br s, 1H), 4.43 (t, J = 7.2 Hz, 2H), 4.02 (s, 3H), 2.61-2.53 (m, 1H), 2.38-2.31 (m, 3H), 1.95 (br d, J = 14.3 Hz, 1H), 1.85-1.67 (m, 4H), 1.59 (br d, J = 8.5 Hz, 2H), 1.50 (br d, J = 12.8 Hz, 2H), 1.39 (br d, J = 11.0 Hz, 1H), 1.30-1.10 (m, 3H), 0.85-0.78 (m, 3H); hLPA₁ IC₅₀ = 322 nM. | Example 400 |
| 366 | 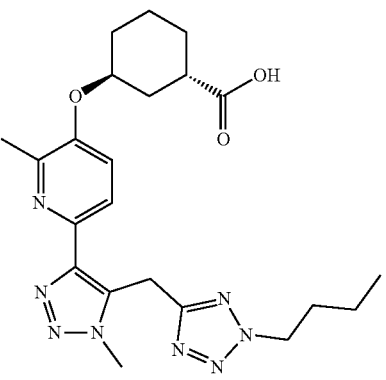 [SMILES: CCCCn1nnc(Cc2c(-c3ccc(O[C@H]4CCC[C@H](C(=O)O)C4)c(C)n3)nnn2C)n1]<br>(1S,3S)-3-((6-(5-((2-butyl-2H-tetrazol-5-yl)methyl)-1-methyl-1H-1,2,3-triazol-4-yl)-2-methylpyridin-3-yl)oxy)cyclohexane-1-carboxylic acid | LCMS, [M + H]⁺ = 455.3; ¹H NMR (500 MHz, DMSO-d₆) δ 7.81 (d, J = 8.5 Hz, 1H), 7.42 (d, J = 8.9 Hz, 1H), 4.92 (s, 2H), 4.72 (br s, 1H), 4.55 (t, J = 6.9 Hz, 2H), 4.02 (s, 3H), 2.62-2.54 (m, 1H), 2.31 (s, 3H), 1.96 (br d, J = 13.1 Hz, 1H), 1.89 (s, 1H), 1.85-1.71 (m, 5H), 1.62-1.43 (m, 4H), 1.13 (sxt, J = 7.4 Hz, 2H), 0.79 (t, J = 7.3 Hz, 3H); hLPA₁ IC₅₀ = 43 nM. | Example 400 |

-continued

| Ex # | Structure & Name | Analytical & Biology Data | Method |
|---|---|---|---|
| 367 | 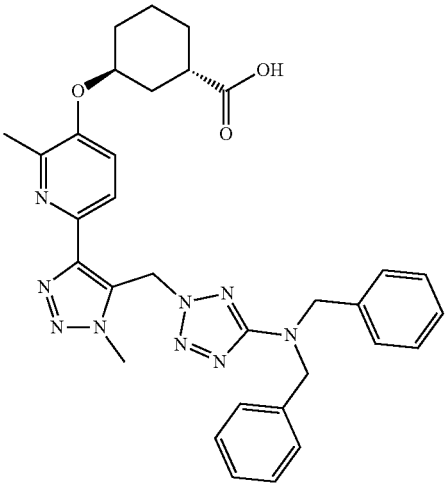 [SMILES: Cc1nc(-c2nnn(C)c2Cn2nnc(N(Cc3ccccc3)Cc3ccccc3)n2)ccc1O[C@H]1CCC[C@H](C(=O)O)C1]<br>(1S,3S)-3-((6-(5-((5-(dibenzyl-amino)-2H-tetrazol-2-yl)methyl)-1-methyl-1H-1,2,3-triazol-4-yl)-2-methylpyridin-3-yl)oxy)cyclo-hexane-1-carboxylic acid | LCMS, $[M + H]^+$ = 594.4; $^1$H NMR (500 MHz, DMSO-$d_6$) δ 7.87 (d, J = 8.9 Hz, 1H), 7.51 (d, J = 8.9 Hz, 1H), 7.29-7.20 (m, 6H), 7.14-7.07 (m, 4H), 6.31 (d, J = 2.4 Hz, 2H), 4.76 (br s, 1H), 3.90 (s, 1H), 3.81 (s, 3H), 2.58-2.53 (m, 1H), 2.30 (s, 3H), 1.92 (br s, 2H), 1.84-1.69 (m, 3H), 1.60 (br d, J = 11.3 Hz, 2H), 1.52 (br s, 3H); hLPA$_1$ IC$_{50}$ = 1584 nM. | Example 362 |
| 368 | 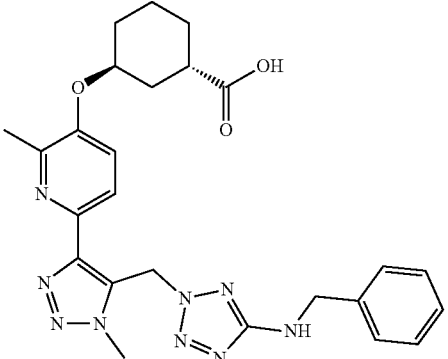<br>(1S,3S)-3-((6-(5-((5-(benzylamino)-2H-tetrazol-2-yl)methyl)-1-methyl-1H-1,2,3-triazol-4-yl)-2-methyl-pyridin-3-yl)oxy)cyclohexane-1-carboxylic acid | LCMS, $[M + H]^+$ = 504.12; $^1$H NMR (500 MHz, DMSO-$d_6$) δ 8.10 (br t, J = 5.3 Hz, 1H), 7.87 (d, J = 8.5 Hz, 1H), 7.55 (br d, J = 8.2 Hz, 1H), 7.23-7.14 (m, 5H), 6.03-5.88 (m, 2H), 4.72 (br s, 1H), 4.49 (d, J = 5.5 Hz, 2H), 4.08 (s, 3H), 2.47-2.36 (m, 1H), 2.26 (s, 3H), 1.84 (br s, 2H), 1.73 (br s, 2H), 1.61 (br d, J = 10.4 Hz, 1H), 1.54 (br d, J = 9.2 Hz, 3H); hLPA$_1$ IC$_{50}$ = 1023 nM. | Example 362 |
| 369 | 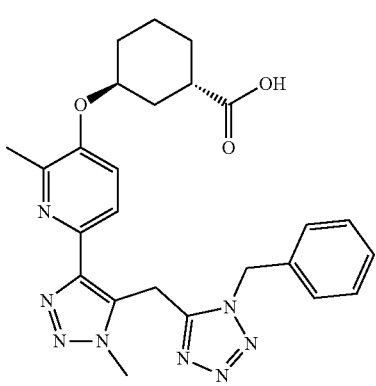 [SMILES: Cc1nc(-c2nnn(C)c2Cc2nnnn2Cc2ccccc2)ccc1O[C@H]1CCC[C@H](C(=O)O)C1]<br>(1S,3S)-3-((6-(5-((1-benzyl-1H-tetrazol-5-yl)methyl)-1-methyl-1H-1,2,3-triazol-4-yl)-2-methylpyridin-3-yl)oxy)cyclohexane-1-carboxylic acid | LCMS, $[M + H]^+$ = 489.4; $^1$H NMR (500 MHz, DMSO-$d_6$) δ 7.82 (br d, J = 8.6 Hz, 1H), 7.43 (br d, J = 8.7 Hz, 1H), 7.34 (br s, 3H), 7.19 (br s, 2H), 5.78 (br s, 2H), 5.05 (br s, 2H), 4.71 (br s, 1H), 3.98 (s, 3H), 2.83 (br s, 1H), 2.16-2.07 (m, 3H), 1.93 (br s, 1H), 1.80 (br s, 1H), 1.75 (br s, 2H), 1.57 (br s, 2H), 1.51 (br s, 2H); hLPA$_1$ IC$_{50}$ = 123 nM. | Example 400 |

| Ex # | Structure & Name | Analytical & Biology Data | Method |
|---|---|---|---|
| 370 | (1S,3S)-3-((2-ethyl-6-(5-((4-isobutyl-1H-1,2,3-triazol-1-yl)methyl)-1-methyl-1H-1,2,3-triazol-4-yl) pyridin-3-yl)oxy)cyclohexane-1-carboxylic acid | LCMS, [M + H]$^+$ = 468.21; $^1$H NMR (500 MHz, DMSO-d$_6$) δ 7.90 (d, J = 8.6 Hz, 1H), 7.79 (s, 1H), 7.49 (d, J = 8.7 Hz, 1H), 6.21 (s, 2H), 4.78 (br s, 1H), 4.07 (s, 3H), 2.90-2.78 (m, 2H), 2.63 (br t, J = 10.3 Hz, 1H), 2.47-2.41 (m, 2H), 2.02 (br d, J = 13.5 Hz, 1H), 1.88 (br s, 1H), 1.85-1.77 (m, 3H), 1.69-1.48 (m, 4H), 1.25-1.18 (m, 3H), 0.82 (d, J = 6.6 Hz, 6H); hLPA$_1$ IC$_{50}$ = 66 nM. | Example 79 |
| 371 | (1S,3S)-3-((2-ethyl-6-(5-((4-isopropyl-1H-1,2,3-triazol-1-yl)methyl)-1-methyl-1H-1,2,3-triazol-4-yl)pyridin-3-yl)oxy)cyclohexane-1-carboxylic acid | LCMS, [M + H]$^+$ = 454.2; $^1$H NMR (500 MHz, DMSO-d$_6$) δ 7.89 (d, J = 8.5 Hz, 1H), 7.83 (s, 1H), 7.52 (br d, J = 8.6 Hz, 1H), 6.18 (s, 2H), 4.76 (br s, 1H), 4.09 (s, 3H), 2.97-2.80 (m, 3H), 1.94 (br s, 1H), 1.90-1.74 (m, 4H), 1.71-1.59 (m, 2H), 1.55 (br s, 2H), 1.26-1.11 (m, 9H); hLPA$_1$ IC$_{50}$ = 1541 nM. | Example 79 |
| 372 | (1S,3S)-3-((2-ethyl-6-(1-methyl-5-((4-propyl-1H-1,2,3-triazol-1-yl)methyl)-1H-1,2,3-triazol-4-yl)pyridin-3-yl)oxy)cyclohexane-1-carboxylic acid | LCMS, [M + H]$^+$ = 454.2; $^1$H NMR (500 MHz, DMSO-d$_6$) δ 7.90 (d, J = 8.6 Hz, 1H), 7.80 (s, 1H), 7.51 (d, J = 8.7 Hz, 1H), 6.21 (s, 2H), 4.77 (br s, 1H), 4.08 (s, 3H), 2.91-2.73 (m, 2H), 2.63-2.52 (m, 3H), 1.98 (br d, J = 13.5 Hz, 1H), 1.90-1.75 (m, 3H), 1.65 (br d, J = 9.8 Hz, 2H), 1.55 (dq, J = 14.7, 7.3 Hz, 4H), 1.21 (t, J = 7.5 Hz, 3H), 0.85 (t, J = 7.3 Hz, 3H); hLPA$_1$ IC$_{50}$ = 303 nM. | Example 79 |

| Ex # | Structure & Name | Analytical & Biology Data | Method |
|---|---|---|---|
| 373 | 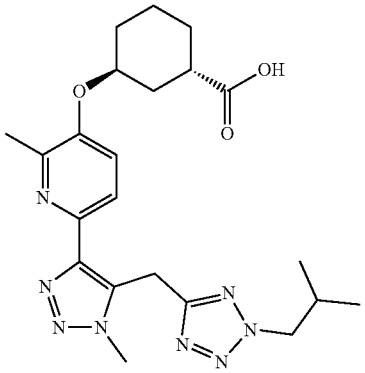 [SMILES: Cc1nc(-c2nnn(C)c2Cc2nnn(CC(C)C)n2)ccc1O[C@H]1CCC[C@H](C(=O)O)C1]<br>(1S,3S)-3-((6-(5-((2-isobutyl-2H-tetrazol-5-yl)methyl)-1-methyl-1H-1,2,3-triazol-4-yl)-2-methylpyridin-3-yl)oxy)cyclohexane-1-carboxylic acid | LCMS, [M + H]$^+$ = 455.5; $^1$H NMR (500 MHz, DMSO-$d_6$) δ 7.81 (br d, J = 8.5 Hz, 1H), 7.43 (d, J = 8.5 Hz, 1H), 4.92 (s, 2H), 4.73 (br s, 1H), 4.39 (d, J = 7.0 Hz, 2H), 4.02 (s, 3H), 2.64-2.55 (m, 1H), 2.31 (s, 3H), 2.18-2.02 (m, 1H), 1.98 (br d, J = 13.1 Hz, 1H), 1.84 (br d, J = 11.9 Hz, 1H), 1.80-1.71 (m, 2H), 1.63-1.43 (m, 4H), 0.77 (d, J = 6.7 Hz, 6H);<br>hLPA$_1$ IC$_{50}$ = 136 nM. | Example 400 |
| 374 | 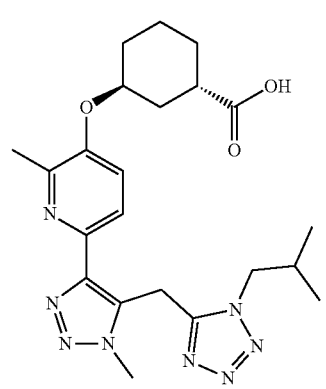 [SMILES: Cc1nc(-c2nnn(C)c2Cc2nnnn2CC(C)C)ccc1O[C@H]1CCC[C@H](C(=O)O)C1]<br>(1S,3S)-3-((6-(5-((1-isobutyl-1H-tetrazol-5-yl)methyl)-1-methyl-1H-1,2,3-triazol-4-yl)-2-methylpyridin-3-yl)oxy)cyclohexane-1-carboxylic acid | LCMS, [M + H]$^+$ = 455.5; $^1$H NMR (500 MHz, DMSO-$d_6$) δ 7.87 (br d, J = 8.5 Hz, 1H), 7.48 (d, J = 8.5 Hz, 1H), 5.05 (s, 2H), 4.76 (br s, 1H), 4.27 (br d, J = 7.3 Hz, 2H), 4.02 (s, 3H), 2.65-2.55 (m, 1H), 2.34 (s, 3H), 2.16-2.04 (m, 1H), 1.99 (br d, J = 13.4 Hz, 1H), 1.84 (br d, J = 11.6 Hz, 1H), 1.80-1.72 (m, 2H), 1.63-1.50 (m, 3H), 1.47 (br d, J = 9.5 Hz, 1H), 0.79 (br d, J = 6.4 Hz, 6H);<br>hLPA$_1$ IC$_{50}$ = 207 nM. | Example 400 |
| 375 | 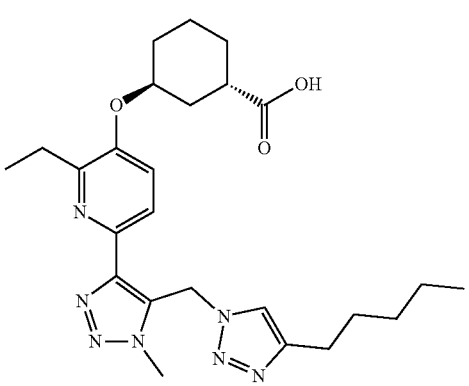 [SMILES: CCCCCc1cn(Cc2c(-c3ccc(O[C@H]4CCC[C@H](C(=O)O)C4)c(CC)n3)nnn2C)nn1]<br>(1S,3S)-3-((2-ethyl-6-(1-methyl-5-((4-pentyl-1H-1,2,3-triazol-1-yl)methyl)-1H-1,2,3-triazol-4-yl)pyridin-3-yl)oxy)cyclohexane-1-carboxylic acid | LCMS, [M + H]$^+$ = 482.4; $^1$H NMR (500 MHz, DMSO-$d_6$) δ 8.71 (s, 1H), 7.89 (br d, J = 8.5 Hz, 1H), 7.48 (br d, J = 8.9 Hz, 1H), 6.25 (s, 2H), 4.76 (br s, 1H), 4.13 (s, 3H), 3.55 (br s, 2H), 2.98 (s, 1H), 2.90 (br t, J = 7.2 Hz, 2H), 2.80 (q, J = 7.3 Hz, 2H), 2.59 (br s, 1H), 2.06-1.92 (m, 1H), 1.83 (br s, 1H), 1.81-1.69 (m, 2H), 1.64-1.53 (m, 4H), 1.48 (br s, 2H), 1.21 (br s, 2H), 1.13 (br t, J = 7.3 Hz, 3H), 0.86 (br t, J = 7.3 Hz, 3H);<br>hLPA$_1$ IC$_{50}$ = 585 nM. | Example 79 |

| Ex # | Structure & Name | Analytical & Biology Data | Method |
|---|---|---|---|
| 376 | (1S,3S)-3-((6-(5-(((2-ethyl-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 442.3; $^1$H NMR (500 MHz, DMSO-d$_6$) δ 7.84 (d, J = 8.7 Hz, 1H), 7.49 (d, J = 8.8 Hz, 1H), 4.88-4.71 (m, 3H), 4.39 (d, J = 7.2 Hz, 1H), 4.43-4.33 (m, 1H), 4.12 (s, 3H), 2.61 (br t, J = 10.6 Hz, 1H), 2.45-2.41 (m, 3H), 2.09-1.93 (m, 1H), 1.85 (br d, J = 12.7 Hz, 1H), 1.81-1.69 (m, 2H), 1.65-1.43 (m, 5H), 1.37 (t, J = 7.3 Hz, 4H); hLPA$_1$ IC$_{50}$ = 2108 nM. | Example 388 |
| 377 | (1S,3S)-3-((6-(5-(((cyclopropyl-methyl)(2-(cyclopropylmethyl)-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 522.5; $^1$H NMR (500 MHz, DMSO-d$_6$) δ 7.77 (br d, J = 8.6 Hz, 1H), 7.44 (d, J = 8.8 Hz, 1H), 5.13 (s, 2H), 4.75 (br s, 1H), 4.02 (s, 3H), 3.89 (br d, J = 7.2 Hz, 2H), 3.04 (d, J = 6.9 Hz, 2H), 2.66-2.57 (m, 1H), 2.36 (s, 3H), 1.99 (br d, J = 12.7 Hz, 1H), 1.92-1.81 (m, 1H), 1.81-1.70 (m, 2H), 1.65-1.51 (m, 3H), 1.48 (br s, 1H), 0.98 (br d, J = 12.5 Hz, 2H), 0.38-0.25 (m, 4H), 0.15 (br s, 2H), −0.08 (q, J = 4.7 Hz, 2H); hLPA$_1$ IC$_{50}$ = 1238 nM. | Example 388 |
| 378 | (1S,3S)-3-((6-(5-(((1-(cyclopropyl methyl)-1H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 468.2; $^1$H NMR (500 MHz, DMSO-d$_6$) δ 7.89-7.82 (m, 1H), 7.49 (d, J = 8.9 Hz, 1H), 4.98 (br s, 2H), 4.77 (br s, 1H), 4.11 (s, 3H), 3.94 (br d, J = 6.8 Hz, 2H), 2.60 (br s, 1H), 2.37 (s, 3H), 2.00 (br d, J = 13.3 Hz, 1H), 1.92-1.81 (m, 1H), 1.81-1.69 (m, 2H), 1.65-1.50 (m, 3H), 1.47 (br d, J = 11.8 Hz, 1H), 1.03 (br s, 1H), 0.36 (br d, J = 8.1 Hz, 2H), 0.20 (br d, J = 3.0 Hz, 2H); hLPA$_1$ IC$_{50}$ = 300 nM. | Example 388 |

| Ex # | Structure & Name | Analytical & Biology Data | Method |
|---|---|---|---|
| 379 | (1R,3S)-3-((6-(5-(((2-(4-methoxy-phenyl)-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 520.4; hLPA$_1$ IC$_{50}$ = 2076 nM. | Example 384 |
| 380 | (1S,3S)-3-((2-methyl-6-(1-methyl-5-(((2-(m-tolyl)-2H-tetrazol-5-yl)amino)methyl)-1H-1,2,3-triazol-4-yl)pyridin-3-yl)oxy)cyclohexane-1-carboxylic acid | LCMS, [M + H]$^+$ = 504.32; $^1$H NMR (500 MHz, DMSO-d$_6$) δ 7.86 (d, J = 8.5 Hz, 1H), 7.53-7.33 (m, 4H), 7.19 (br d, J = 7.6 Hz, 1H), 7.12 (s, 1H), 4.85 (br d, J = 6.1 Hz, 2H), 4.75 (br s, 1H), 4.20 (s, 3H), 2.62-2.54 (m, 1H), 2.22 (s, 3H), 2.04-1.95 (m, 4H), 1.85 (br d, J = 11.6 Hz, 1H), 1.81-1.72 (m, 2H), 1.63-1.43 (m, 4H); hLPA$_1$ IC$_{50}$ = 183 nM. | Example 384 |
| 381 | (1S,3S)-3-((2-methyl-6-(1-methyl-5-(((2-(o-tolyl)-2H-tetrazol-5-yl)amino)methyl)-1H-1,2,3-triazol-4-yl)pyridin-3-yl)oxy)cyclohexane-1-carboxylic acid | LCMS, [M + H]$^+$ = 504.3; $^1$H NMR (500 MHz, DMSO-d$_6$) δ 7.84 (d, J = 8.5 Hz, 1H), 7.50-7.47 (m, 2H), 7.37-7.29 (m, 3H), 7.20 (d, J = 7.6 Hz, 1H), 4.81 (br d, J = 6.4 Hz, 2H), 4.74 (br s, 1H), 4.18 (s, 3H), 1.94 (br d, J = 13.7 Hz, 1H), 1.87-1.74 (m, 7H), 1.65 (s, 3H), 1.63-1.46 (m, 4H); hLPA$_1$ IC$_{50}$ = 313 nM. | Example 384 |

| Ex # | Structure & Name | Analytical & Biology Data | Method |
|---|---|---|---|
| 382 | (1S,3S)-3-((6-(5-(((2-butyl-2H-tetrazol-5-yl)amino)methyl)-1-methyl-1H-1,2,3-triazol-4-yl)-2-methylpyridin-3-yl)oxy)cyclo-hexane-1-carboxylic acid | LCMS, [M + H]⁺ = 470.3; ¹H NMR (500 MHz, DMSO-d₆) δ 7.84 (br d, J = 8.5 Hz, 1H), 7.74-7.60 (m, 1H), 5.00 (br s, 2H), 4.74-4.62 (m, 1H), 4.11 (s, 3H), 4.03 (br t, J = 6.9 Hz, 2H), 2.36 (s, 3H), 1.63 (br s, 4H), 1.59 (s, 3H), 1.57-1.43 (m, 4H), 1.27-1.08 (m, 3H), 0.75 (t, J = 7.3 Hz, 3H); hLPA₁ IC₅₀ = 521 nM. | Example 388 |
| 383 | (1S,3S)-3-((6-(5-(((2-(4-methoxy-phenyl)-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]⁺ = 520.2; ¹H NMR (500 MHz, DMSO-d₆) δ 7.86 (d, J = 8.6 Hz, 1H), 7.50 (d, J = 8.7 Hz, 1H), 7.41-7.35 (m, 1H), 7.35-7.27 (m, 2H), 7.04 (d, J = 8.9 Hz, 3H), 4.86 (br d, J = 6.0 Hz, 2H), 4.77 (br s, 1H), 4.19 (s, 2H), 3.80 (s, 2H), 2.65-2.55 (m, 1H), 2.07-1.98 (m, 4H), 1.85 (br d, J = 12.0 Hz, 1H), 1.81-1.70 (m, 2H), 1.64-1.52 (m, 3H), 1.50 (br s, 1H), 1.25 (br d, J = 6.1 Hz, 1H); hLPA₁ IC₅₀ = 513 nM. | Example 384 |
| 384 | (1S,3S)-3-((6-(5-(((2-(4-chloro-phenyl)-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]⁺ = 524.3; ¹H NMR (500 MHz, DMSO-d₆) δ 7.85 (d, J = 8.5 Hz, 1H), 7.61 (d, J = 8.9 Hz, 2H), 7.51-7.47 (m, 4H), 4.93 (br d, J = 5.8 Hz, 2H), 4.76 (br s, 1H), 4.17 (s, 3H), 2.61-2.55 (m, 1H), 2.11 (s, 3H), 1.97 (br d, J = 12.5 Hz, 1H), 1.85-1.75 (m, 3H), 1.64-1.48 (m, 4H); hLPA₁ IC₅₀ = 41 nM. | Example 384 |

| Ex # | Structure & Name | Analytical & Biology Data | Method |
|---|---|---|---|
| 385 | (1S,3S)-3-((2-methyl-6-(1-methyl-5-(((2-(p-tolyl)-2H-tetrazol-5-yl)amino)methyl)-1H-1,2,3-triazol-4-yl)pyridin-3-yl)oxy)cyclohexane-1-carboxylic acid | LCMS, [M + H]$^+$ = 504.2; $^1$H NMR (500 MHz, DMSO-$d_6$) δ 7.86 (d, J = 8.9 Hz, 1H), 7.49 (d, J = 8.9 Hz, 1H), 7.41 (br t, J = 6.0 Hz, 1H), 7.31 (br d, J = 8.2 Hz, 2H), 7.24 (d, J = 8.2 Hz, 2H), 4.85 (br d, J = 6.1 Hz, 2H), 4.76 (br s, 1H), 4.19 (s, 3H), 2.58 (br s, 2H), 2.36 (s, 3H), 2.03 (s, 3H), 1.98 (br s, 1H), 1.85 (br d, J = 10.4 Hz, 1H), 1.81-1.69 (m, 2H), 1.65-1.52 (m, 3H), 1.50 (br s, 1H); hLPA$_1$ IC$_{50}$ = 158 nM. | Example 384 |
| 386 | (1S,3S)-3-((6-(5-(((2-(cyclopropyl-methyl)-2H-tetrazol-5-yl)amino)methyl)-1-methyl-1H-1,2,3-triazol-4-yl)-2-methylpyridin-3-yl)oxy)cyclohexane-1-carboxylic acid | LCMS, [M + H]$^+$ = 468.3; $^1$H NMR (500 MHz, DMSO-$d_6$) δ 7.84 (d, J = 8.5 Hz, 1H), 7.48 (d, J = 8.5 Hz, 1H), 7.12 (br t, J = 6.1 Hz, 1H), 4.82 (br d, J = 6.1 Hz, 2H), 4.76 (br s, 1H), 4.23 (d, J = 7.3 Hz, 2H), 4.13 (s, 2H), 2.62 (br t, J = 10.5 Hz, 1H), 2.47-2.37 (m, 3H), 2.00 (br d, J = 13.7 Hz, 1H), 1.85 (br d, J = 12.2 Hz, 1H), 1.81-1.71 (m, 2H), 1.67-1.56 (m, 2H), 1.53 (br s, 1H), 1.48 (br d, J = 10.1 Hz, 1H), 1.33-1.12 (m, 1H), 0.54-0.46 (m, 2H), 0.33 (br d, J = 4.9 Hz, 2H); hLPA$_1$ IC$_{50}$ = 26 nM. | Example 384 |
| 387 | (1S,3S)-3-((2-methyl-6-(1-methyl-5-(((2-propyl-2H-tetrazol-5-yl)amino)methyl)-1H-1,2,3-triazol-4-yl)pyridin-3-yl)oxy)cyclohexane-1-carboxylic acid | LCMS, [M + H]$^+$ = 456.2; $^1$H NMR (500 MHz, DMSO-$d_6$) δ 7.85 (d, J = 8.5 Hz, 1H), 7.50 (d, J = 8.9 Hz, 1H), 7.14 (br t, J = 5.8 Hz, 1H), 4.84 (br d, J = 6.1 Hz, 2H), 4.78 (br s, 1H), 4.34 (t, J = 6.7 Hz, 2H), 4.13 (s, 3H), 2.67-2.60 (m, 1H), 2.47-2.40 (m, 3H), 2.02 (br d, J = 12.8 Hz, 1H), 1.89-1.75 (m, 5H), 1.67-1.57 (m, 2H), 1.55 (br s, 1H), 1.49 (br d, J = 11.6 Hz, 1H), 0.78 (t, J = 7.3 Hz, 3H); hLPA$_1$ IC$_{50}$ = 285 nM. | Example 388 |

| Ex # | Structure & Name | Analytical & Biology Data | Method |
|---|---|---|---|
| 388 | 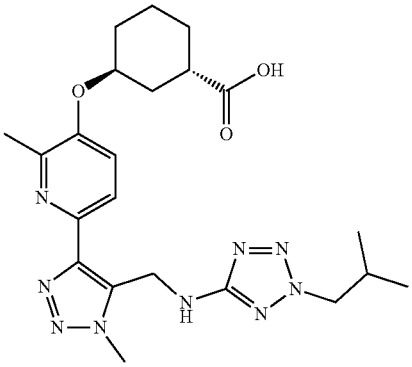 [SMILES: Cc1nc(-c2nnn(C)c2CNc2nnn(CC(C)C)n2)ccc1O[C@H]1CCC[C@H](C(=O)O)C1]<br>(1S,3S)-3-((6-(5-(((2-isobutyl-2H-tetrazol-5-yl)amino)methyl)-1-methyl-1H-1,2,3-triazol-4-yl)-2-methylpyridin-3-yl)oxy)cyclo-hexane-1-carboxylic acid | LCMS, [M + H]$^+$ = 469.9; $^1$H NMR (500 MHz, DMSO-$d_6$) δ 7.84 (d, J = 8.5 Hz, 1H), 7.49 (d, J = 8.9 Hz, 1H), 7.13 (br t, J = 6.1 Hz, 1H), 4.83 (br d, J = 5.8 Hz, 2H), 4.77 (br s, 1H), 4.19 (d, J = 7.3 Hz, 2H), 4.11 (s, 3H), 2.67-2.57 (m, 1H), 2.42 (s, 3H), 2.15-1.95 (m, 2H), 1.94-1.82 (m, 1H), 1.82-1.71 (m, 2H), 1.68-1.52 (m, 3H), 1.49 (br d, J = 10.4 Hz, 1H), 0.80 (d, J = 6.7 Hz, 6H); hLPA$_1$ IC$_{50}$ = 43 nM. | Example 388 |
| 389 | 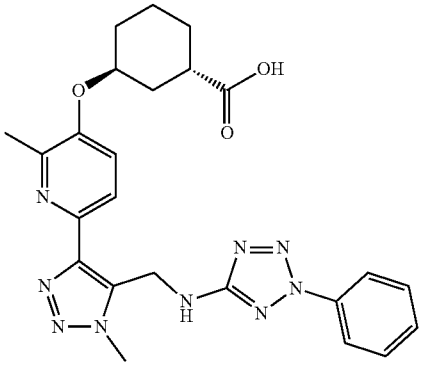 [SMILES: Cc1nc(-c2nnn(C)c2CNc2nnn(-c3ccccc3)n2)ccc1O[C@H]1CCC[C@H](C(=O)O)C1]<br>(1S,3S)-3-((2-methyl-6-(1-methyl-5-(((2-phenyl-2H-tetrazol-5-yl)amino)methyl)-1H-1,2,3-triazol-4-yl)pyridin-3-yl)oxy)cyclohexane-1-carboxylic acid | LCMS, [M + H]$^+$ = 490.2; $^1$H NMR (500 MHz, DMSO-$d_6$) δ 7.85 (d, J = 8.5 Hz, 1H), 7.59-7.50 (m, 4H), 7.50-7.45 (m, 1H), 7.45-7.38 (m, 2H), 4.88 (br d, J = 5.8 Hz, 2H), 4.73 (br s, 1H), 4.21 (s, 3H), 2.05 (s, 3H), 1.87 (br d, J = 16.5 Hz, 2H), 1.79 (br d, J = 11.6 Hz, 2H), 1.73 (br s, 1H), 1.66-1.46 (m, 4H); hLPA$_1$ IC$_{50}$ = 84 nM. | Example 384 |
| 390 | 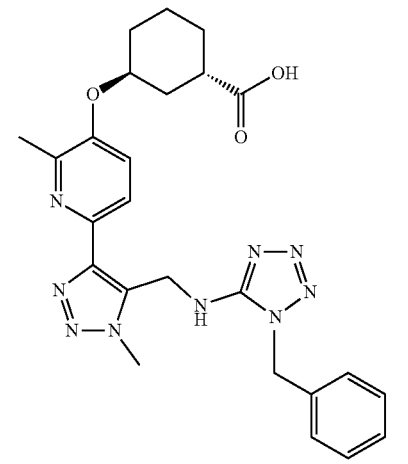<br>(1S,3S)-3-((6-(5-(((1-benzyl-1H-tetrazol-5-yl)amino)methyl)-1-methyl-1H-1,2,3-triazol-4-yl)-2-methylpyridin-3-yl)oxy)cyclo-hexane-1-carboxylic acid | LCMS, [M + H]$^+$ = 504.4; $^1$H NMR (500 MHz, DMSO-$d_6$) δ 7.84 (br d, J = 8.2 Hz, 1H), 7.47 (br d, J = 8.9 Hz, 1H), 7.18 (br d, J = 5.5 Hz, 4H), 7.04-6.99 (m, 2H), 5.36 (s, 2H), 5.02-4.98 (m, 2H), 4.77 (br s, 1H), 4.05 (s, 3H), 2.61 (br s, 1H), 2.29 (s, 3H), 2.07-1.94 (m, 1H), 1.91-1.72 (m, 3H), 1.71-1.36 (m, 5H); hLPA$_1$ IC$_{50}$ = 375 nM. | Example 388 |

| Ex # | Structure & Name | Analytical & Biology Data | Method |
|---|---|---|---|
| 391 | 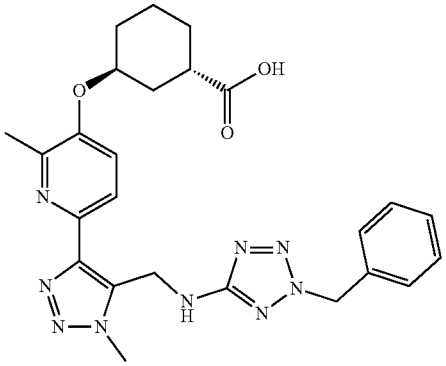 [SMILES: Cc1nc(-c2nnn(C)c2CNc2nnn(Cc3ccccc3)n2)ccc1O[C@H]1CCC[C@H](C(=O)O)C1]<br>(1S,3S)-3-((6-(5-(((2-benzyl-2H-tetrazol-5-yl)amino)methyl)-1-methyl-1H-1,2,3-triazol-4-yl)-2-methylpyridin-3-yl)oxy)cyclo-hexane-1-carboxylic acid | LCMS, [M + H]$^+$ = 504.1; $^1$H NMR (500 MHz, CDCl$_3$) δ 8.06 (d, J = 8.5 Hz, 1H), 7.42-7.36 (m, 3H), 7.33-7.29 (m, 2H), 7.29-7.26 (m, 1H), 5.55 (s, 2H), 4.73 (s, 3H), 4.14 (s, 3H), 2.98-2.88 (m, 1H), 2.59 (s, 3H), 2.21-2.12 (m, 1H), 2.07-1.93 (m, 3H), 1.86-1.76 (m, 1H), 1.75-1.65 (m, 3H), 0.07-0.03 (m, 1H); hLPA$_1$ IC$_{50}$ = 23 nM. | Example 388 |
| 392 | 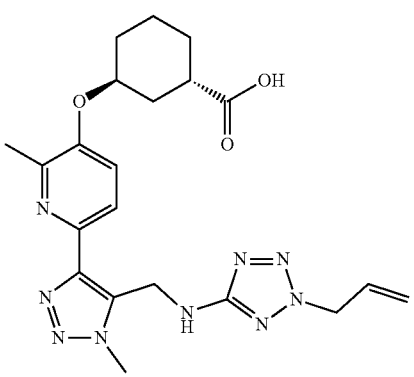 [SMILES: C=CCn1nnc(NCc2c(-c3ccc(O[C@H]4CCC[C@H](C(=O)O)C4)c(C)n3)nnn2C)n1]<br>(1S,3S)-3-((6-(5-(((2-allyl-2H-tetrazol-5-yl)amino)methyl)-1-methyl-1H-1,2,3-triazol-4-yl)-2-methylpyridin-3-yl)oxy)cyclo-hexane-1-carboxylic acid | LCMS, [M + H]$^+$ = 454.2; $^1$H NMR (500 MHz, DMSO-d$_6$) δ 7.84 (br d, J = 8.6 Hz, 1H), 7.54-7.45 (m, 1H), 5.97 (qd, J = 11.1, 6.0 Hz, 1H), 5.27 (br d, J = 10.3 Hz, 1H), 5.20 (br d, J = 17.1 Hz, 1H), 5.02 (br d, J = 6.0 Hz, 2H), 4.81 (s, 2H), 4.75 (br s, 1H), 4.11 (s, 3H), 2.64 (br t, J = 10.4 Hz, 1H), 2.44 (s, 3H), 2.01 (br d, J = 17.7 Hz, 1H), 1.91-1.74 (m, 3H), 1.69-1.57 (m, 2H), 1.57-1.46 (m, 2H); hLPA$_1$ IC$_{50}$ = 167 nM. | Example 388 |
| 393 | 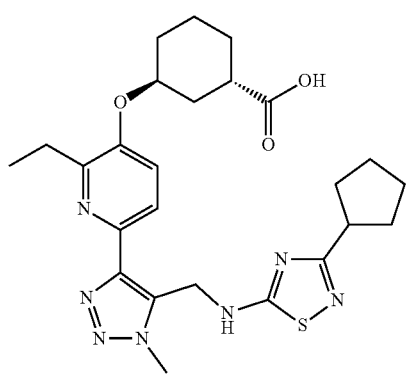 [SMILES: CCc1nc(-c2nnn(C)c2CNc2nc(C3CCCC3)ns2)ccc1O[C@H]1CCC[C@H](C(=O)O)C1]<br>(1S,3S)-3-((6-(5-(((3-cyclopentyl-1,2,4-thiadiazol-5-yl)amino)methyl)-1-methyl-1H-1,2,3-triazol-4-yl)-2-ethylpyridin-3-yl)oxy)cyclohexane-1-carboxylic acid | LCMS, [M + H]$^+$ = 511.9; $^1$H NMR (500 MHz, DMSO-d$_6$) δ 7.84 (d, J = 8.5 Hz, 1H), 7.47 (d, J = 8.9 Hz, 1H), 5.12 (br d, J = 5.2 Hz, 2H), 4.76 (br s, 1H), 4.12 (s, 3H), 3.01-2.97 (m, 1H), 2.81 (q, J = 7.3 Hz, 2H), 2.63-2.56 (m, 1H), 2.00 (br d, J = 13.1 Hz, 1H), 1.89-1.75 (m, 5H), 1.69-1.57 (m, 6H), 1.57-1.49 (m, 4H), 1.20 (t, J = 7.5 Hz, 3H); hLPA$_1$ IC$_{50}$ = 35 nM. | Example 44 |

| Ex # | Structure & Name | Analytical & Biology Data | Method |
|---|---|---|---|
| 394 | 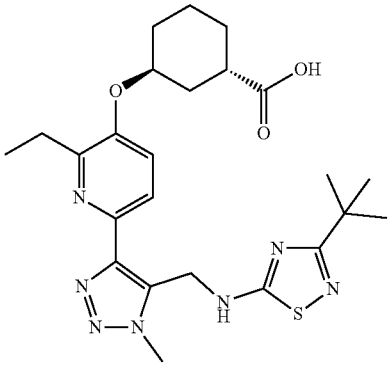 [SMILES: CCc1nc(-c2nnn(C)c2CNc2nc(C(C)(C)C)ns2)ccc1O[C@H]1CCC[C@H](C(=O)O)C1]<br>(1S,3S)-3-((6-(5-(((3-(tert-butyl)-1,2,4-thiadiazol-5-yl)amino)methyl)-1-methyl-1H-1,2,3-triazol-4-yl)-2-ethylpyridin-3-yl)oxy)cyclohexane-1-carboxylic acid | LCMS, [M + H]$^+$ = 500.4; $^1$H NMR (500 MHz, DMSO-d$_6$) δ 7.84 (d, J = 8.5 Hz, 1H), 7.47 (d, J = 8.5 Hz, 1H), 5.18-5.11 (m, 2H), 4.78 (br s, 1H), 4.14 (s, 3H), 2.82 (q, J = 7.3 Hz, 2H), 2.63-2.55 (m, 1H), 2.01 (br d, J = 13.4 Hz, 1H), 1.87-1.75 (m, 3H), 1.65-1.53 (m, 3H), 1.50 (br s, 1H), 1.25-1.19 (m, 3H), 1.19-1.13 (m, 9H); hLPA$_1$ IC$_{50}$ = 66 nM. | Example 44 |
| 395 | 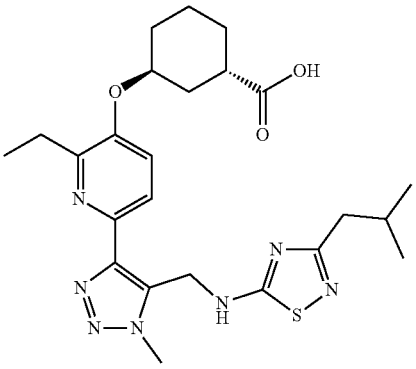 [SMILES: CCc1nc(-c2nnn(C)c2CNc2nc(CC(C)C)ns2)ccc1O[C@H]1CCC[C@H](C(=O)O)C1]<br>(1S,3S)-3-((2-ethyl-6-(5-(((3-isobutyl-1,2,4-thiadiazol-5-yl)amino)methyl)-1-methyl-1H-1,2,3-triazol-4-yl)pyridin-3-yl)oxy)cyclohexane-1-carboxylic acid | LCMS, [M + H]$^+$ = 500.3; $^1$H NMR (500 MHz, DMSO-d$_6$) δ 7.84 (d, J = 8.5 Hz, 1H), 7.46 (d, J = 8.9 Hz, 1H), 5.10 (br d, J = 4.9 Hz, 2H), 4.76 (br s, 1H), 4.11 (s, 3H), 2.80 (q, J = 7.3 Hz, 2H), 2.65-2.56 (m, 1H), 2.40 (d, J = 7.0 Hz, 2H), 2.05-1.94 (m, 2H), 1.85 (br d, J = 11.3 Hz, 1H), 1.81-1.71 (m, 2H), 1.65-1.51 (m, 3H), 1.48 (br s, 1H), 1.26-1.13 (m, 3H), 0.83 (d, J = 6.4 Hz, 6H); hLPA$_1$ IC$_{50}$ = 22 nM. | Example 44 |
| 396 | 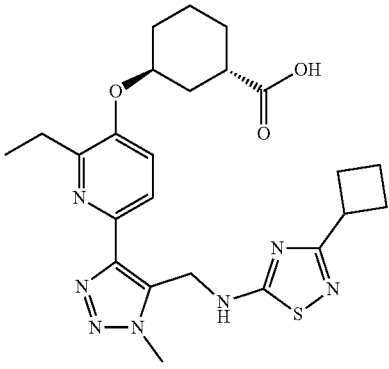 [SMILES: CCc1nc(-c2nnn(C)c2CNc2nc(C3CCC3)ns2)ccc1O[C@H]1CCC[C@H](C(=O)O)C1]<br>(1S,3S)-3-((6-(5-(((3-cyclobutyl-1,2,4-thiadiazol-5-yl)amino)methyl)-1-methyl-1H-1,2,3-triazol-4-yl)-2-ethylpyridin-3-yl)oxy)cyclohexane-1-carboxylic acid | LCMS, [M + H]$^+$ = 498.04; $^1$H NMR (500 MHz, DMSO-d$_6$) δ 7.85 (d, J = 8.5 Hz, 1H), 7.48 (d, J = 8.5 Hz, 1H), 5.14 (br d, J = 5.2 Hz, 2H), 4.77 (br s, 1H), 4.14 (s, 3H), 2.95-2.88 (m, 1H), 2.82 (q, J = 7.3 Hz, 2H), 2.61 (br t, J = 10.5 Hz, 1H), 2.21-2.14 (m, 4H), 2.06-1.98 (m, 1H), 1.95-1.82 (m, 2H), 1.82-1.74 (m, 3H), 1.65-1.45 (m, 4H), 1.21 (t, J = 7.5 Hz, 3H); hLPA$_1$ IC$_{50}$ = 33 nM. | Example 44 |

-continued

| Ex # | Structure & Name | Analytical & Biology Data | Method |
|---|---|---|---|
| 397 | 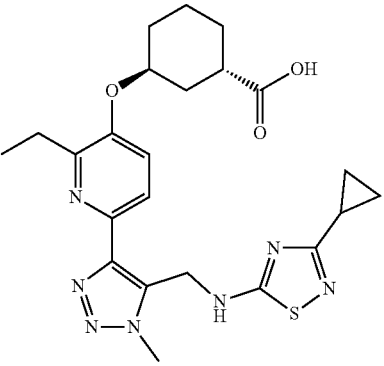 [SMILES: CCc1nc(-c2nnn(C)c2CNc2nc(C3CC3)ns2)ccc1O[C@H]1CCC[C@H](C(=O)O)C1]<br>(1S,3S)-3-((6-(5-(((3-cyclopropyl-1,2,4-thiadiazol-5-yl)amino)methyl)-1-methyl-1H-1,2,3-triazol-4-yl)-2-ethylpyridin-3-yl)oxy)cyclohexane-1-carboxylic acid | LCMS, $[M + H]^+$ = 484.3;<br>$^1$H NMR (500 MHz, DMSO-$d_6$) δ 7.84 (d, J = 8.5 Hz, 1H), 7.47 (d, J = 8.9 Hz, 1H), 5.09 (br d, J = 5.2 Hz, 2H), 4.78 (br s, 1H), 4.10 (s, 3H), 2.82 (q, J = 7.3 Hz, 2H), 2.61 (br t, J = 10.7 Hz, 1H), 2.06-1.99 (m, 1H), 1.92-1.82 (m, 2H), 1.82-1.74 (m, 2H), 1.65-1.45 (m, 4H), 1.21 (t, J = 7.5 Hz, 3H), 0.85-0.77 (m, 2H), 0.76-0.72 (m, 2H);<br>hLPA$_1$ IC$_{50}$ = 931 nM. | Example 44 |
| 398 | 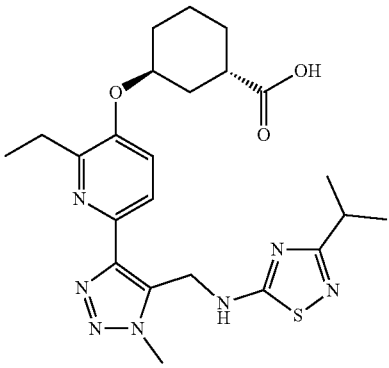 [SMILES: CCc1nc(-c2nnn(C)c2CNc2nc(C(C)C)ns2)ccc1O[C@H]1CCC[C@H](C(=O)O)C1]<br>(1S,3S)-3-((2-ethyl-6-(5-(((3-isopropyl-1,2,4-thiadiazol-5-yl)amino)methyl)-1-methyl-1H-1,2,3-triazol-4-yl)pyridin-3-yl)oxy)cyclohexane-1-carboxylic acid | LCMS, $[M + H]^+$ = 486.4;<br>$^1$H NMR (500 MHz, DMSO-$d_6$) δ 8.56 (br s, 1H), 7.84 (d, J = 8.5 Hz, 1H), 7.47 (d, J = 8.5 Hz, 1H), 5.12 (br d, J = 5.2 Hz, 2H), 4.77 (br s, 1H), 4.14 (s, 3H), 2.88-2.78 (m, 3H), 2.60 (br t, J = 10.4 Hz, 1H), 2.06-1.97 (m, 1H), 1.90-1.82 (m, 1H), 1.82-1.73 (m, 2H), 1.66-1.52 (m, 3H), 1.48 (br d, J = 9.5 Hz, 1H), 1.21 (t, J = 7.5 Hz, 3H), 1.14 (d, J = 6.7 Hz, 6H);<br>hLPA$_1$ IC$_{50}$ = 59 nM. | Example 44 |
| 399 | 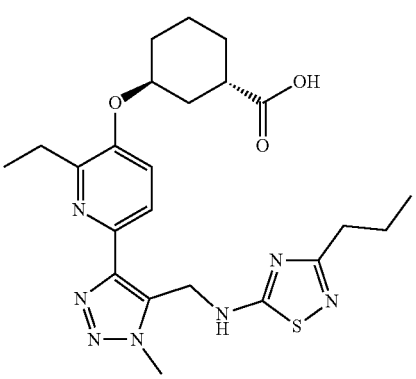 [SMILES: CCCc1nsc(NCc2c(-c3ccc(O[C@H]4CCC[C@H](C(=O)O)C4)c(CC)n3)nnn2C)n1]<br>(1S,3S)-3-((2-ethyl-6-(1-methyl-5-(((3-propyl-1,2,4-thiadiazol-5-yl)amino)methyl)-1H-1,2,3-triazol-4-yl)pyridin-3-yl)oxy)cyclohexane-1-carboxylic acid | LCMS, $[M + H]^+$ = 486.3;<br>$^1$H NMR (500 MHz, DMSO-$d_6$) δ 7.85 (d, J = 8.5 Hz, 1H), 7.47 (d, J = 8.5 Hz, 1H), 5.11 (br d, J = 4.6 Hz, 2H), 4.77 (br s, 1H), 4.12 (s, 3H), 2.81 (q, J = 7.3 Hz, 2H), 2.60 (br t, J = 10.7 Hz, 1H), 2.01 (br d, J = 13.4 Hz, 1H), 1.85 (br d, J = 13.1 Hz, 1H), 1.82-1.74 (m, 2H), 1.65-1.53 (m, 6H), 1.48 (br d, J = 8.9 Hz, 1H), 1.22-1.16 (m, 3H), 0.85 (t, J = 7.3 Hz, 3H);<br>hLPA$_1$ IC$_{50}$ = 73 nM. | Example 44 |

| Ex # | Structure & Name | Analytical & Biology Data | Method |
|---|---|---|---|
| 400 | (1S,3S)-3-{[6-(5-{[2-(2-cyclo-propylethyl)-2H-1,2,3,4-tetrazol-5-yl]methyl}-1-methyl-1H-1,2,3-triazol-4-yl)-2-methylpyridin-3-yl]oxy}cyclohexane-1-carboxylic acid | LCMS, [M + H]$^+$ = 467.4; $^1$H NMR (500 MHz, DMSO-d$_6$) δ 7.81 (d, J = 8.5 Hz, 1H), 7.43 (br d, J = 8.5 Hz, 1H), 4.94 (s, 2H), 4.73 (br s, 1H), 4.62 (t, J = 6.7 Hz, 2H), 4.03 (s, 3H), 2.59 (br s, 1H), 2.32 (s, 3H), 1.98 (br d, J = 12.2 Hz, 1H), 1.83 (br s, 1H), 1.80-1.68 (m, 4H), 1.63-1.45 (m, 4H), 0.50 (br s, 1H), 0.23-0.19 (m, 2H), −0.16 (br d, J = 4.6 Hz, 2H); hLPA$_1$ IC$_{50}$ = 128 nM. | Example 400 |
| 401 | (1S,3S)-3-{[6-(5-{[2-(3-methoxy-propyl)-2H-1,2,3,4-tetrazol-5-yl]methyl}-1-methyl-1H-1,2,3-triazol-4-yl)-2-methylpyridin-3-yl]oxy}cyclohexane-1-carboxylic acid | LCMS, [M + H]$^+$ = 471.4; $^1$H NMR (500 MHz, DMSO-d$_6$) δ 7.81 (d, J = 8.6 Hz, 1H), 7.42 (d, J = 8.8 Hz, 1H), 4.92 (s, 2H), 4.73 (br s, 1H), 4.59 (t, J = 6.9 Hz, 2H), 4.01 (s, 3H), 3.25-3.13 (m, 2H), 3.12-3.08 (m, 3H), 2.60-2.55 (m, 1H), 2.31 (s, 3H), 2.07-1.94 (m, 3H), 1.83 (br d, J = 12.2 Hz, 1H), 1.79-1.67 (m, 2H), 1.63-1.49 (m, 3H), 1.46 (br d, J = 10.9 Hz, 1H); hLPA$_1$ IC$_{50}$ = 1124 nM. | Example 400 |
| 402 | (1S,3S)-3-[(6-{5-[(2-benzyl-2H-1,2,3,4-tetrazol-5-yl)methyl]-1-methyl-1H-1,2,3-triazol-4-yl}-2-methylpyridin-3-yl)oxy]cyclo-hexane-1-carboxylic acid | LCMS, [M + H]$^+$ = 489.1; $^1$H NMR (500 MHz, DMSO-d$_6$) δ 7.78 (br d, J = 8.3 Hz, 1H), 7.40 (br d, J = 8.6 Hz, 1H), 7.30 (br d, J = 3.7 Hz, 3H), 7.20 (br s, 2H), 5.80 (s, 2H), 4.88 (s, 2H), 4.71 (br s, 1H), 3.99 (s, 3H), 2.57-2.55 (m, 1H), 2.20 (s, 3H), 1.95 (br d, J = 13.2 Hz, 1H), 1.82 (br d, J = 10.1 Hz, 1H), 1.75 (br d, J = 10.3 Hz, 2H), 1.56 (br d, J = 6.6 Hz, 2H), 1.51 (br s, 1H), 1.46 (br s, 1H); hLPA$_1$ IC$_{50}$ = 47 nM. | Example 400 |

| Ex # | Structure & Name | Analytical & Biology Data | Method |
|---|---|---|---|
| 403 | 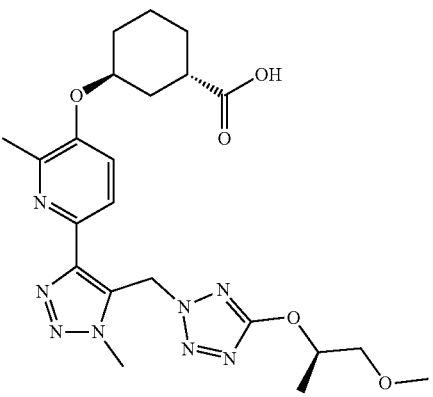<br>(1S,3S)-3-[(6-{5-[(5-{[(2R)-1-methoxypropan-2-yl]oxy}-2H-1,2,3,4-tetrazol-2-yl)methyl]-1-methyl-1H-1,2,3-triazol-4-yl}-2-methylpyridin-3-yl)oxy]cyclo-hexane-1-carboxylic acid | LCMS, [M + H]$^+$ = 487.3; $^1$H NMR (500 MHz, DMSO-$d_6$) δ 7.86 (d, J = 8.5 Hz, 1H), 7.46 (d, J = 8.8 Hz, 1H), 6.40 (s, 2H), 4.98-4.82 (m, 1H), 4.76 (br s, 1H), 4.15 (s, 3H), 3.49 (br s, 1H), 3.21 (s, 3H), 2.60 (br t, J = 10.4 Hz, 1H), 2.38 (s, 3H), 1.99 (br d, J = 13.1 Hz, 1H), 1.85 (br d, J = 11.6 Hz, 1H), 1.81-1.70 (m, 2H), 1.64-1.43 (m, 4H), 1.24 (d, J = 6.3 Hz, 4H); hLPA$_1$ IC$_{50}$ = 250 nM. | Example 316 |
| 404 | 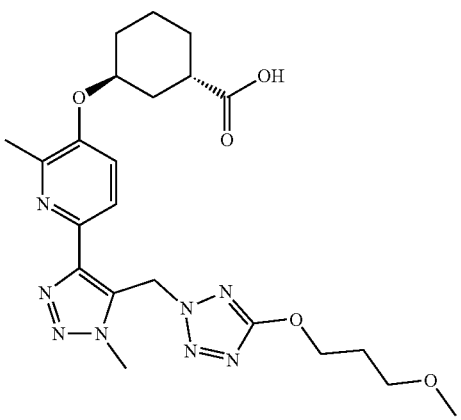<br>(1S,3S)-3-{[6-(5-{[5-(3-methoxy-propoxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 487.3; $^1$H NMR (500 MHz, DMSO-$d_6$) δ 7.86 (d, J = 8.6 Hz, 1H), 7.46 (d, J = 8.7 Hz, 1H), 6.41 (s, 2H), 4.76 (br s, 1H), 4.31 (t, J = 6.4 Hz, 2H), 4.14 (s, 3H), 3.58-3.42 (m, 2H), 3.21-3.16 (m, 3H), 2.60 (br t, J = 10.3 Hz, 1H), 2.38 (s, 3H), 2.02-1.81 (m, 4H), 1.81-1.70 (m, 2H), 1.65-1.54 (m, 2H), 1.54-1.41 (m, 2H); hLPA$_1$ IC$_{50}$ = 365 nM. | Example 316 |
| 405 | 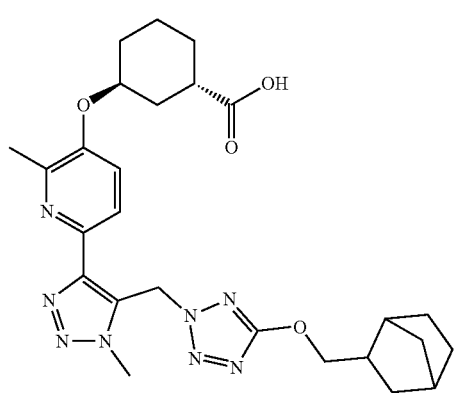 [SMILES: Cc1nc(-c2nnn(C)c2Cn2nnc(OCC3CC4CCC3C4)n2)ccc1O[C@H]1CCC[C@H](C(=O)O)C1]<br>(1S,3S)-3-{[6-(5-{[5-({bicyclo[2.2.1]heptan-2-yl}methoxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 523.4; $^1$H NMR (500 MHz, DMSO-$d_6$) δ 7.85 (d, J = 8.4 Hz, 1H), 7.45 (br d, J = 8.4 Hz, 1H), 6.38 (br s, 2H), 4.75 (br s, 1H), 4.32-4.20 (m, 1H), 4.13 (s, 3H), 2.58 (br d, J = 10.4 Hz, 1H), 2.48-2.31 (m, 3H), 2.23 (br s, 1H), 2.15 (br d, J = 15.5 Hz, 2H), 1.98 (br d, J = 13.8 Hz, 1H), 1.83 (br d, J = 11.1 Hz, 1H), 1.80-1.70 (m, 2H), 1.64 (br s, 1H), 1.62-1.50 (m, 3H), 1.46 (br d, J = 12.9 Hz, 2H), 1.39 (br s, 1H), 1.34-1.21 (m, 3H), 1.10 (br d, J = 7.7 Hz, 1H), 1.04 (br s, 1H), 0.67 (br d, J = 7.4 Hz, 1H); hLPA$_1$ IC$_{50}$ = 47 nM. | Example 316 |

| Ex # | Structure & Name | Analytical & Biology Data | Method |
|---|---|---|---|
| 406 | 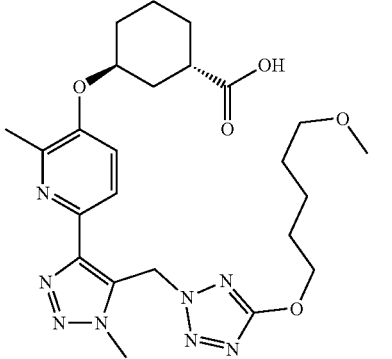<br>(1S,3S)-3-({6-[5-({5-[(5-methoxypentyl)oxy]-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, [M + H]$^+$ = 515; $^1$H NMR (500 MHz, DMSO-d$_6$) δ 7.85 (br d, J = 8.4 Hz, 1H), 7.45 (br d, J = 8.1 Hz, 1H), 6.44-6.31 (m, 2H), 4.75 (br s, 1H), 4.25 (br t, J = 6.4 Hz, 2H), 4.13 (s, 3H), 3.25 (br t, J = 6.3 Hz, 2H), 3.16 (s, 3H), 2.57 (br s, 1H), 2.36 (s, 3H), 1.97 (br d, J = 13.5 Hz, 1H), 1.88 (s, 1H), 1.85-1.72 (m, 3H), 1.72-1.63 (m, 2H), 1.62-1.42 (m, 5H), 1.41-1.20 (m, 2H); hLPA$_1$ IC$_{50}$ = 681 nM. | Example 316 |
| 407 | 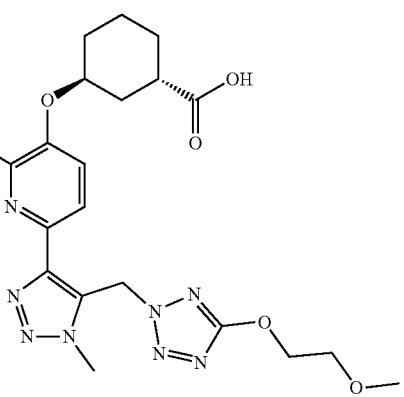<br>(1S,3S)-3-{[6-(5-{[5-(2-methoxy-ethoxy)-2H-1,2,3,4-tetrazol-2-yl]methyl}-1-methyl-1H-1,2,3-triazol-4-yl)-2-methylpyridin-3-yl]oxy}cyclohexane-1-carboxylic acid | LCMS, [M + H]$^+$ = 473.1; $^1$H NMR (500 MHz, DMSO-d$_6$) δ 7.85 (d, J = 8.2 Hz, 1H), 7.46 (br d, J = 8.7 Hz, 1H), 6.41 (br s, 2H), 4.76 (br s, 1H), 4.38 (br d, J = 4.2 Hz, 2H), 4.14 (s, 3H), 3.63-3.60 (m, 2H), 3.23 (s, 3H), 2.60 (br s, 1H), 2.38 (s, 3H), 1.99 (br d, J = 14.0 Hz, 1H), 1.84 (br d, J = 12.7 Hz, 1H), 1.80-1.69 (m, 2H), 1.65-1.54 (m, 2H), 1.52 (br s, 1H), 1.47 (br d, J = 9.6 Hz, 1H); hLPA$_1$ IC$_{50}$ = 142 nM. | Example 316 |
| 408 | 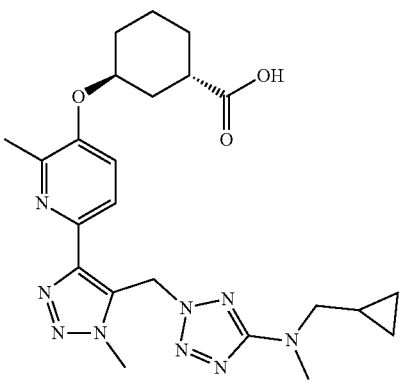 [SMILES: Cc1nc(-c2nnn(C)c2Cn2nnc(N(C)CC3CC3)n2)ccc1O[C@H]1CCC[C@H](C(=O)O)C1]<br>(1S,3S)-3-({6-(5-({5-[(cyclopropyl methyl)(methyl)amino]-2H-1,2,3,4-tetrazol-2-yl}methyl)-1-methyl-1H-1,2,3-triazol-4-yl]-2-methylpyridin-3-yl}oxy)cyclohexane-1-carboxylic acid | LCMS, [M + H]$^+$ = 482.1; $^1$H NMR (500 MHz, DMSO-d$_6$) δ 7.85 (d, J = 8.5 Hz, 1H), 7.46 (d, J = 8.5 Hz, 1H), 6.09 (s, 2H), 4.75 (br s, 1H), 4.05 (s, 3H), 3.17 (d, J = 6.7 Hz, 2H), 3.07 (s, 3H), 2.62-2.55 (m, 1H), 2.36 (s, 3H), 1.97 (br d, J = 13.4 Hz, 1H), 1.85-1.72 (m, 3H), 1.62-1.54 (m, 2H), 1.54-1.44 (m, 2H), 0.99 (br s, 1H), 0.48-0.42 (m, 2H), 0.17 (br d, J = 4.6 Hz, 2H); hLPA$_1$ IC$_{50}$ = 339 nM. | Example 362 |

| Ex # | Structure & Name | Analytical & Biology Data | Method |
|---|---|---|---|
| 409 | 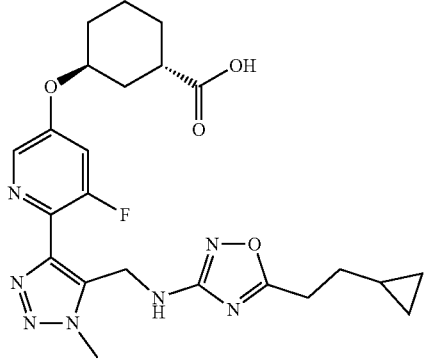 [SMILES: Cn1nnc(-c2ncc(O[C@H]3CCC[C@H](C(=O)O)C3)cc2F)c1CNc1noc(CCC2CC2)n1]<br>(1S,3S)-3-((6-(5-(((5-(2-cyclopropyl ethyl)-1,2,4-oxadiazol-3-yl)amino)methyl)-1-methyl-1H-1,2,3-triazol-4-yl)-5-fluoropyridin-3-yl)oxy)cyclohexane-1-carboxylic acid | LCMS, $[M + H]^+$ = 486; $^1$H NMR (500 MHz, DMSO-$d_6$) δ 8.27 (s, 1H), 7.57 (br d, J = 11.9 Hz, 1H), 7.17 (br t, J = 5.3 Hz, 1H), 4.80 (br s, 1H), 4.62 (br d, J = 5.5 Hz, 2H), 4.11 (s, 3H), 2.73 (br t, J = 7.3 Hz, 2H), 2.70-2.65 (m, 1H), 2.00-1.93 (m, 1H), 1.90-1.76 (m, 3H), 1.72-1.60 (m, 2H), 1.59-1.47 (m, 4H), 0.72-0.63 (m, 1H), 0.36 (br d, J = 7.6 Hz, 2H), 0.01 (br d, J = 4.3 Hz, 2H); hLPA$_1$ IC$_{50}$ = 1920 nM. | Example 42 |
| 410 | 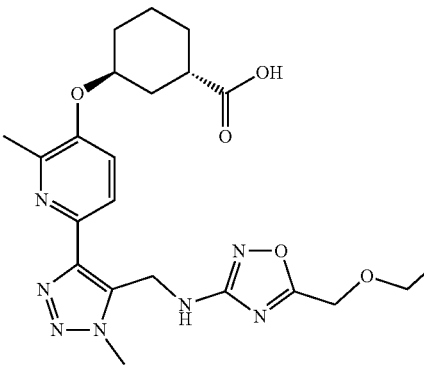<br>(1S,3S)-3-((6-(5-(((5-((4-fluoro-butoxy)methyl)-1,2,4-oxadiazol-3-yl)amino)methyl)-1-methyl-1H-1,2,3-triazol-4-yl)-2-methylpyridin-3-yl)oxy)cyclohexane-1-carboxylic acid | LCMS, $[M + H]^+$ = 518.3; $^1$H NMR (400 MHz, CDCl$_3$) δ 8.04 (d, J = 8.6 Hz, 1H), 7.41 (d, J = 8.8 Hz, 1H), 4.78 (br d, J = 2.6 Hz, 1H), 4.70 (s, 2H), 4.54 (br t, J = 5.7 Hz, 1H), 4.45-4.39 (m, 1H), 4.29 (s, 3H), 3.62 (t, J = 6.2 Hz, 2H), 3.00-2.88 (m, 1H), 2.64 (s, 3H), 2.09-1.89 (m, 5H), 1.88-1.64 (m, 9H); $^{19}$F NMR (377 MHz, CDCl$_3$) δ −218.68 (s, 1F); hLPA$_1$ IC$_{50}$ = 43 nM. | Examples 42 |
| 412 | 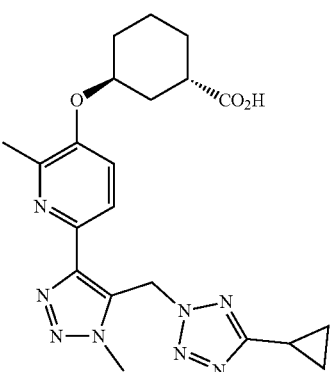<br>(1S,3S)-3-((6-(5-((5-cyclopropyl-2H-tetrazol-2-yl)methyl)-1-methyl-1H-1,2,3-triazol-4-yl)-2-methyl-pyridin-3-yl)oxy)cyclohexane-1-carboxylic acid | LCMS, $[M + H]^+$ = 439.2; $^1$H NMR (500 MHz, DMSO-$d_6$) δ 7.82 (d, J = 8.5 Hz, 1H), 7.45 (br d, J = 8.5 Hz, 1H), 6.47-6.34 (m, 2H), 4.71 (br s, 1H), 4.12 (s, 3H), 2.46 (br d, J = 9.2 Hz, 1H), 2.34 (s, 3H), 2.11 (tt, J = 8.6, 4.7 Hz, 1H), 1.88 (br d, J = 12.8 Hz, 1H), 1.77 (s, 3H), 1.64-1.39 (m, 4H), 1.08-0.99 (m, 2H), 0.82 (t, J = 3.4 Hz, 2H); hLPA$_1$ IC$_{50}$ = 384 nM. | Examples 105, 106 |

Example 411. (1S,3S)-3-((2-methyl-6-(1-methyl-5-((3-phenyl-1,2,4-oxadiazol-5-yl)amino)-1H-1,2,3-triazol-4-yl)pyridin-3-yl)oxy)cyclohexane-1-carboxylic acid, 2 TFA

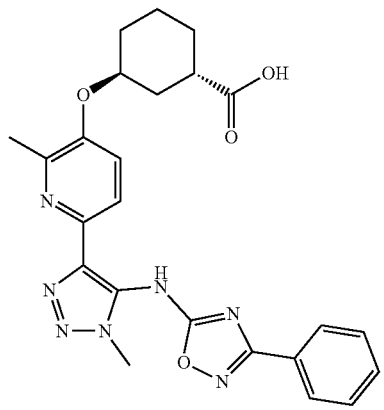 [SMILES: Cc1nc(-c2nnn(C)c2Nc2nc(-c3ccccc3)no2)ccc1O[C@H]1CCC[C@H](C(=O)O)C1]

411A. Methyl (1S,3S)-3-((2-methyl-6-(1-methyl-5-((3-phenyl-1,2,4-oxadiazol-5-yl)amino)-1H-1,2,3-triazol-4-yl)pyridin-3-yl)oxy)cyclohexane-1-carboxylate, 2 TFA

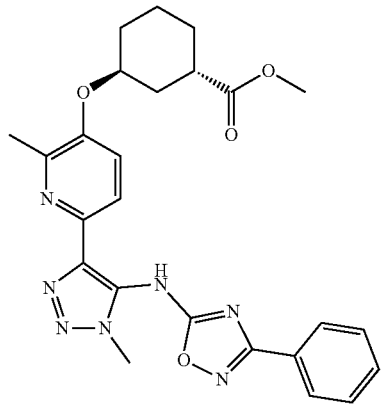 [SMILES: COC(=O)[C@H]1CCC[C@H](Oc2ccc(-c3nnn(C)c3Nc3nc(-c4ccccc4)no3)nc2C)C1]

To a solution of Intermediate 18 (20 mg, 0.058 mmol) in 1,4-dioxane (1 mL) were added 5-chloro-3-phenyl-1,2,4-oxadiazole (10 mg, 0.058 mmol), Zn(OAc)$_2$ (6 mg, 0.035 mmol), 4,5-bis(diphenylphosphino)-9,9-dimethylxanthene (3.7 mg, 6.37 µmol), Pd$_2$(dba)$_3$-CHCl$_3$ adduct (3 mg, 2.90 µmol) and K$_2$CO$_3$ (16 mg, 0.116 mmol). The reaction vessel was evacuated and back-filled with Ar (3×). The reaction mixture was stirred at 100° C. for 18 h, then was cooled to RT and concentrated in vacuo. The crude product was purified by preparative HPLC: Column: Sunfire Prep C18 OBD 5u 30×100 mm; Mobile Phase A: 10% MeCN-90% H$_2$O-0.1% TFA; Mobile Phase B: 90% MeCN-10% H$_2$O-0.1% TFA; Gradient: 20-100% B over 12 min; Flow: 40 mL/min. Fractions containing the desired product were combined and dried via centrifugal evaporation to give the title compound (4 mg, 10%) as a white solid. LCMS, [M+H]$^+$=490.2. $^1$H NMR (500 MHz, CD$_3$OD) δ 7.88-7.82 (m, 3H), 7.64 (d, J=8.8 Hz, 1H), 7.56-7.44 (m, 3H), 4.83- 4.78 (m, 1H), 4.13 (s, 3H), 3.68 (s, 3H), 2.83-2.75 (m, 1H), 2.45 (s, 3H), 2.10-2.02 (m, 1H), 1.97-1.81 (m, 3H), 1.74-1.52 (m, 4H).

Example 411

The title compound (3.1 mg, 79% yield, white solid) was prepared from 411A according to the procedure described for the synthesis of Example 275. LCMS, [M+H]$^+$=476.1. $^1$H NMR (400 MHz, CD$_3$OD) δ 7.87-7.82 (m, 3H), 7.64 (d, J=8.8 Hz, 1H), 7.54-7.43 (m, 3H), 4.83-4.77 (m, 1H), 4.12 (s, 3H), 2.79-2.70 (m, 1H), 2.44 (s, 3H), 2.09-1.99 (m, 1H), 1.97-1.80 (m, 3H), 1.73-1.57 (m, 4H). hLPA$_1$ IC$_{50}$=1440 nM.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. The compound of Formula (IIa) or (IIb):

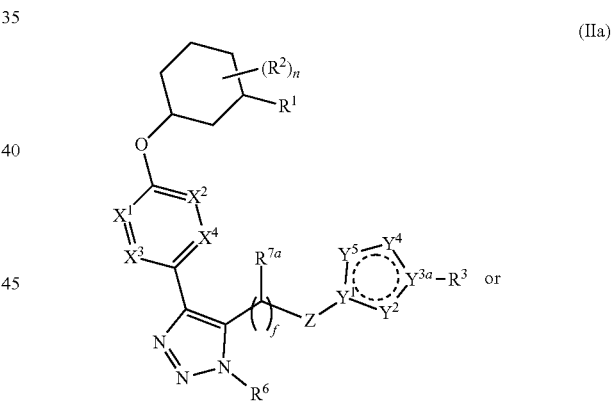

(IIa)

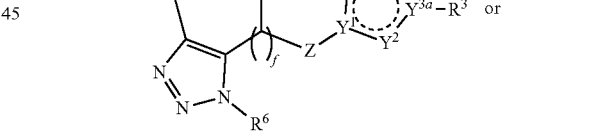

or

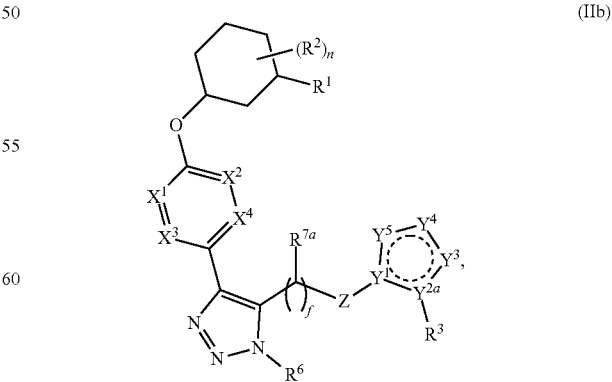

(IIb)

or a stereoisomer, tautomer, or pharmaceutically acceptable salt or solvate thereof, wherein X$^1$, X$^2$, X$^3$, and X$^4$ are each independently CR⁵ or N; provided that no more than two of X¹, X², X³, or X⁴ are N;

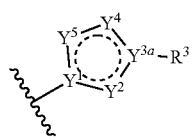

the moiety is

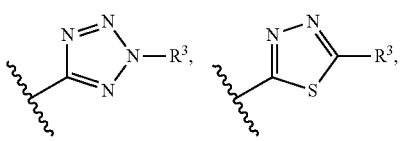

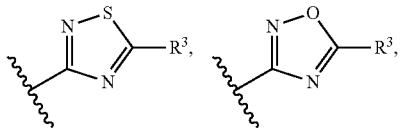

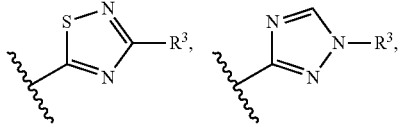

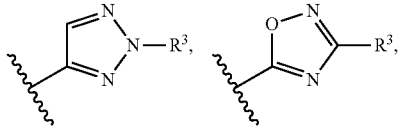

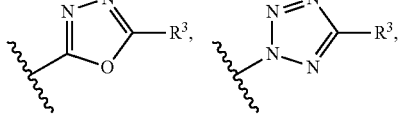

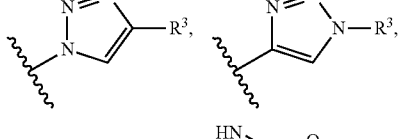

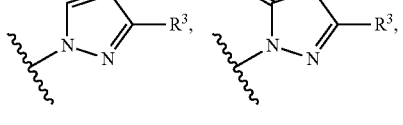

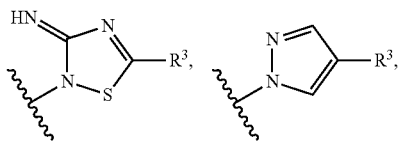

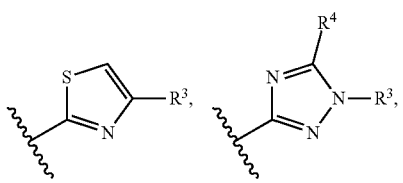

-continued

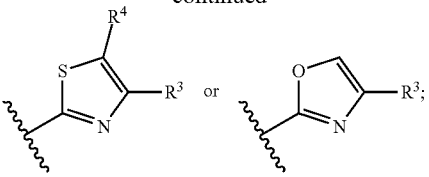

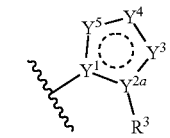

the moiety is

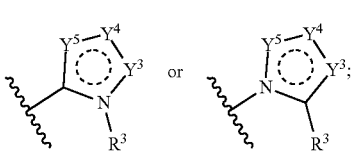

$R^1$ is $(-CH_2)_aR^9$;

a is an integer of 0 or 1;

$R^2$ is each independently halo, cyano, hydroxyl, amino, $C_{1-6}$ alkyl, $C_{3-6}$ cycloalkyl, 4- to 6-membered heterocyclyl, alkylamino, haloalkyl, hydroxyalkyl, aminoalkyl, alkoxy, alkoxyalkyl, haloalkoxyalkyl, or haloalkoxy;

$R^3$ is halo, cyano, hydroxyl, amino, $-OR^a$, $-SR^a$, $-NR^cR^c$, $C_{1-6}$ alkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^4$ is methyl, Cl, or F;

$R^5$ is hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^{7a}$ is each independently hydrogen, halo, cyano, hydroxyl, amino, $C_{1-6}$ alkyl, $C_{3-6}$ cycloalkyl, alkylamino, haloalkyl, hydroxyalkyl, aminoalkyl, alkoxyalkyl, haloalkoxyalkyl, alkoxy, or haloalkoxy;

f is an integer of 0, 1, or 2;

Z is $CH_2$ or $NR^{8b}$; with the proviso that when Z is $NR^{8b}$, $Y^1$ is C;

n is 0 or 1;

$R^6$ is $C_{1-4}$ alkyl;

$R^{8b}$ is hydrogen or $C_{1-4}$ alkyl;

$R^9$ is selected from $-CN$, $-C(O)OR^{10}$, $-C(O)NR^{11a}R^{11b}$,

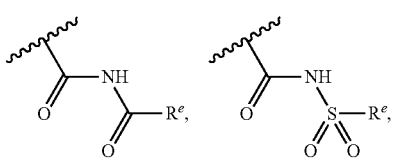

-continued

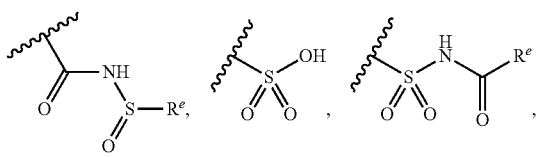

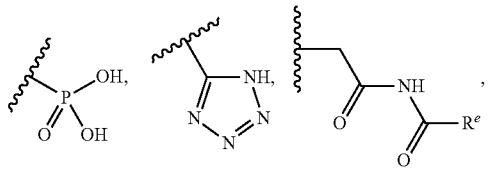

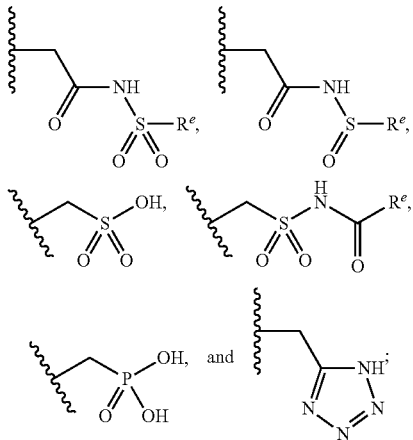

$R^e$ is $C_{1-6}$ alkyl, haloalkyl, hydroxyalkyl, aminoalkyl, alkoxyalkyl, or haloalkoxyalkyl;

$R^{10}$ is hydrogen or $C_{1-10}$ alkyl;

$R^{11a}$ and $R^{11b}$ are each independently hydrogen, $C_{1-6}$ alkyl, $C_{3-6}$ cycloalkyl, 4- to 6-membered heterocyclyl, alkylamino, haloalkyl, hydroxyalkyl, aminoalkyl, alkoxyalkyl, haloalkoxyalkyl, alkoxy, or haloalkoxy;

$R^a$ is selected from $C_{1-6}$ alkyl, $C_{1-6}$ deuterated alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl; and $R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, —$NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety.

2. The compound according to claim 1, wherein $X^1$ is $CR^5$, where $R^5$ is hydrogen or $C_{1-4}$ alkyl.

3. The compound according to claim 2, wherein $X^3$ is N.

4. The compound according to claim 2, wherein

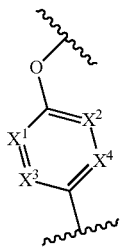

the moiety is selected from

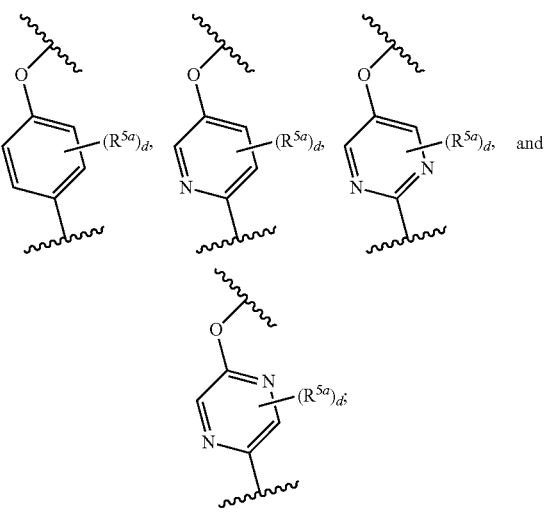

$R^{5a}$ is each independently halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; and d is an integer of 0, 1, or 2.

5. The compound according to claim 4, wherein

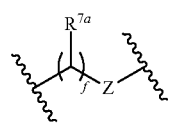

the moiety is

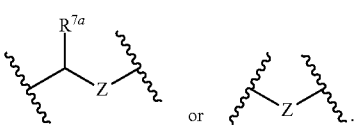

6. The compound according to claim 5, wherein $R^{7a}$ is hydrogen.

7. The compound according to claim 6, wherein $R^1$ is $CO_2H$.

8. The compound according to claim 1, which is represented by Formula (IIa) or (IIIb):

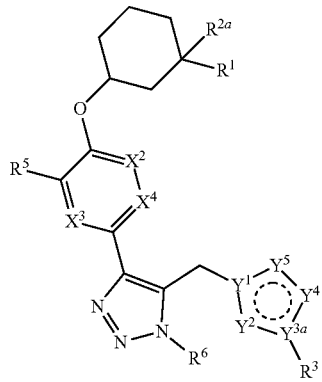
(IIIa)

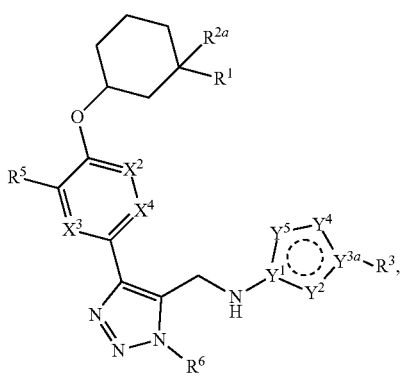
(IIIb)

$Y^1$ and $Y^{3a}$ are each independently selected from C or N;
$Y^2$, $Y^4$, and $Y^5$ are each independently selected from C, $CR^{4a}$, N, S, or O; with the proviso that at least one of $Y^1$, $Y^2$, $Y^{3a}$, $Y^4$, and $Y^5$ is N or $NR^{4b}$; and the dashed circle denotes optional bonds forming an aromatic ring;
$R^{2a}$ is hydrogen, chloro, fluoro, or $C_{1-4}$ alkyl;
$R^{4a}$ is each independently hydrogen, halo, hydroxyl, cyano, —C(O)NH$_2$, —C(O)NHR, C(O)OR, $C_{1-4}$ alkyl, $C_{1-4}$ haloalkyl, $C_{2-6}$ alkoxyalkyl, or $C_{1-4}$ alkoxy;
$R^{4b}$ is each independently hydrogen or $C_{1-4}$ alkyl;
$R^5$ is hydrogen or $C_{1-4}$ alkyl; and
$R^6$ is $C_{1-4}$ alkyl.

9. The compound according to claim 8, wherein the

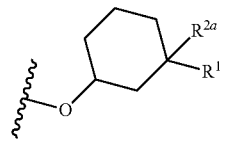

moiety is selected from

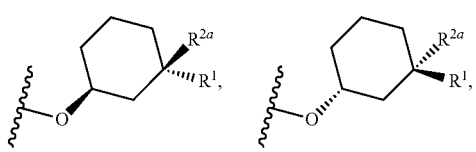

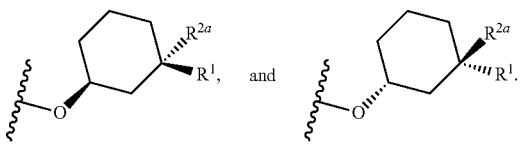

10. The compound according to claim 9, wherein $R^1$ is $CO_2H$.

11. The compound according to claim 10, wherein

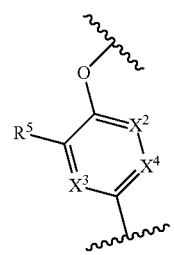

the moiety is

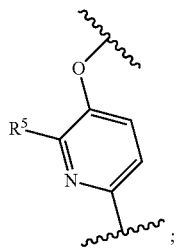

and $R^5$ is hydrogen, methyl, or ethyl.

12. The compound according to claim 1, wherein

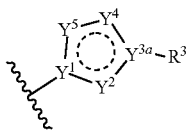

the moiety is

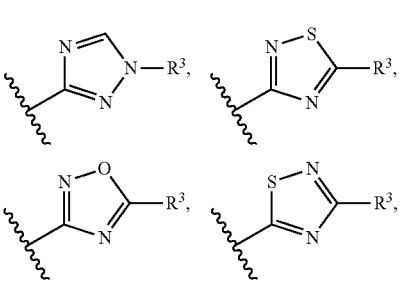

-continued

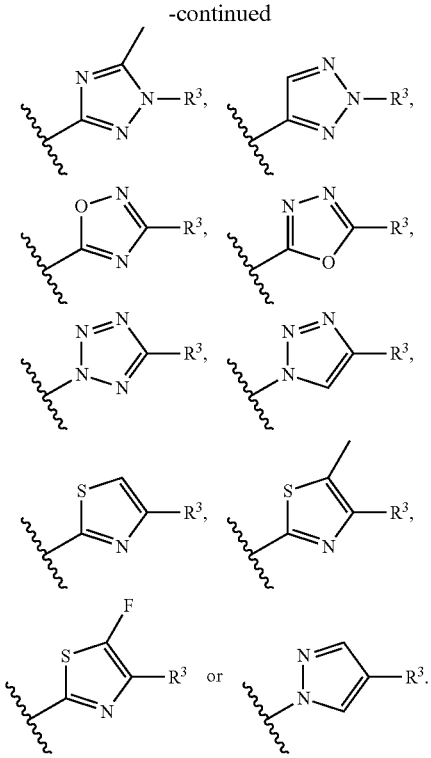

13. The compound according to claim 12, wherein
$R^3$ is halo, cyano, hydroxyl, amino, —$OR^a$, —$SR^a$, —$NR^cR^c$, $C_{1-6}$ alkyl, $C_{1-6}$ deuterated alkyl, $C_{1-6}$ haloalkyl, $C_{1-6}$ heteroalkyl, 6- to 10-membered aryl, arylalkyl, 5- to 10-membered heteroaryl, heteroarylalkyl, 3- to 8-membered carbocyclyl, carbocyclylalkyl, 4- to 8-membered heterocyclyl, or heterocyclylalkyl; wherein the alkyl, heteroalkyl, aryl, heteroaryl, carbocyclyl, heterocyclyl, and $R^a$, by themselves or as part of another group, are each independently substituted with 0 to 5 $R^d$;

$R^a$ is selected from $C_{1-6}$ alkyl, $C_{1-6}$ deuterated alkyl, haloalkyl, hydroxyalkyl, aminoalkyl, alkoxyalkyl, haloalkoxyalkyl, aryl, arylalkyl, heteroaryl, heteroarylalkyl, carbocyclyl, carbocyclylalkyl, heterocyclyl, and heterocyclylalkyl;

$R^b$ is each independently hydrogen or $R^a$;

$R^c$ is each independently $R^b$; or alternatively, two $R^c$, taken together with the nitrogen atom to which they are attached, form a 4- to 7-membered heterocyclyl; and $R^d$ is each independently selected from $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, and —$NR^cR^c$; or alternatively one or two $R^d$ on alkyl, heteroalkyl, aryl, heteroaryl, carbocyclyl, or heterocyclyl, taken together with the atoms to which the $R^d$ is attached, form a cyclic or bridge moiety.

14. The compound according to claim 13, wherein
$R^3$ is $C_{1-6}$ alkyl, $C_{1-6}$ haloalkyl, $C_{1-6}$ alkoxy, $C_{1-6}$ deuterated alkoxy, $C_{1-6}$ haloalkoxy, —S-($C_{1-6}$ alkyl), $C_{3-6}$ cycloalkyl, 4- to 6-membered heterocyclyl, phenyl, (a 5 or 6-membered heteroaryl containing 1 to 3 heteroatoms each of which is independently selected from N, O, and S), -($C_{1-3}$ alkylene)-($C_{3-6}$ cycloalkyl), -($C_{1-3}$ alkylene)-(phenyl), -($C_{1-3}$ alkylene)-(4 to 6-membered heterocyclyl), —O-($C_{3-6}$ cycloalkyl), —O-(4 to 6-membered heterocyclyl), —O-phenyl, —O-(5 or 6-membered heteroaryl containing 1 to 3 heteroatoms each of which is independently selected from N, O, and S), —O-($C_{1-3}$ alkylene)-(phenyl), —O-($C_{1-3}$ alkylene)-($C_{3-6}$ cycloalkyl), —NH-($C_{1-3}$ alkylene)-(phenyl), —NH-($C_{1-6}$ alkyl), —NH-($C_{1-6}$ haloalkyl), —NH-phenyl, —NH-($C_{3-6}$ cycloalkyl), —NH-($C_{1-3}$ alkylene)-($C_{3-6}$ cycloalkyl), and —N($C_{1-6}$ alkyl)$_2$; and the alkyl, alkylene, cycloalkyl, phenyl, heterocyclyl, and heteroaryl, by themselves or as part of another group, are each independently substituted with 0 to 3 $R^d$; and $R^d$ is halo, cyano, hydroxyl, amino, $C_{1-6}$ alkyl, $C_{1-6}$ alkoxy, $C_{3-6}$ cycloalkyl, or 4- to 6-membered heterocyclyl;

$R^{4a}$ is hydrogen, fluoro, chloro, $C_{1-4}$ alkyl, $C_{1-4}$ haloalkyl, $C_{2-6}$ alkoxyalkyl, or $C_{1-4}$ alkoxy; and $R^{4b}$ is hydrogen.

15. A pharmaceutical composition comprising one or more compounds according to claim 1, or a stereoisomer, tautomer, or pharmaceutically acceptable salt or solvate thereof; and a pharmaceutically acceptable carrier or diluent.

16. A method of relieving the disease-state and/or reducing the risk of a disease, disorder, or condition selected from idiopathic pulmonary fibrosis (IPF), non-alcoholic steatohepatitis (NASH), non-alcoholic fatty liver disease (NAFLD), chronic kidney disease, diabetic kidney disease, and systemic sclerosis, in a patient having the disease, disorder, or condition, comprising administering a therapeutically effective amount of a compound or a stereoisomer, a tautomer, or a pharmaceutically acceptable salt or solvate thereof according to claim 1.

17. A pharmaceutical composition comprising one or more compounds according to claim 1, or a stereoisomer, tautomer, or pharmaceutically acceptable salt or solvate thereof; and a pharmaceutically acceptable carrier or diluent.

18. A pharmaceutical composition comprising one or more compounds according to claim 2, or a stereoisomer, tautomer, or pharmaceutically acceptable salt or solvate thereof; and a pharmaceutically acceptable carrier or diluent.

19. A pharmaceutical composition comprising one or more compounds according to claim 3, or a stereoisomer, tautomer, or pharmaceutically acceptable salt or solvate thereof; and a pharmaceutically acceptable carrier or diluent.

20. A pharmaceutical composition comprising one or more compounds according to claim 4, or a stereoisomer, tautomer, or pharmaceutically acceptable salt or solvate thereof; and a pharmaceutically acceptable carrier or diluent.

21. A pharmaceutical composition comprising one or more compounds according to claim 5, or a stereoisomer, tautomer, or pharmaceutically acceptable salt or solvate thereof; and a pharmaceutically acceptable carrier or diluent.

22. A pharmaceutical composition comprising one or more compounds according to claim 6, or a stereoisomer, tautomer, or pharmaceutically acceptable salt or solvate thereof; and a pharmaceutically acceptable carrier or diluent.

23. A pharmaceutical composition comprising one or more compounds according to claim 7, or a stereoisomer, tautomer, or pharmaceutically acceptable salt or solvate thereof; and a pharmaceutically acceptable carrier or diluent.

24. A pharmaceutical composition comprising one or more compounds according to claim 8, or a stereoisomer, tautomer, or pharmaceutically acceptable salt or solvate thereof; and a pharmaceutically acceptable carrier or diluent.

25. A pharmaceutical composition comprising one or more compounds according to claim 9, or a stereoisomer, tautomer, or pharmaceutically acceptable salt or solvate thereof; and a pharmaceutically acceptable carrier or diluent.

26. A pharmaceutical composition comprising one or more compounds according to claim 10, or a stereoisomer, tautomer, or pharmaceutically acceptable salt or solvate thereof; and a pharmaceutically acceptable carrier or diluent.

27. A pharmaceutical composition comprising one or more compounds according to claim 11, or a stereoisomer, tautomer, or pharmaceutically acceptable salt or solvate thereof; and a pharmaceutically acceptable carrier or diluent.

28. A pharmaceutical composition comprising one or more compounds according to claim 12, or a stereoisomer, tautomer, or pharmaceutically acceptable salt or solvate thereof; and a pharmaceutically acceptable carrier or diluent.

29. A pharmaceutical composition comprising one or more compounds according to claim 13, or a stereoisomer, tautomer, or pharmaceutically acceptable salt or solvate thereof; and a pharmaceutically acceptable carrier or diluent.

30. A pharmaceutical composition comprising one or more compounds according to claim 14, or a stereoisomer, tautomer, or pharmaceutically acceptable salt or solvate thereof; and a pharmaceutically acceptable carrier or diluent.

\* \* \* \* \*

UNITED STATES PATENT AND TRADEMARK OFFICE
CERTIFICATE OF CORRECTION

PATENT NO. : 11,319,315 B2  
APPLICATION NO. : 16/772842  
DATED : May 3, 2022  
INVENTOR(S) : Yan Shi et al.

Page 1 of 1

It is certified that error appears in the above-identified patent and that said Letters Patent is hereby corrected as shown below:

In the Claims

Column 456

Line 22-26, Claim 1, " 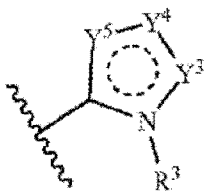 " should read -- 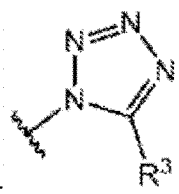 --; and

Line 22-26, Claim 1, " 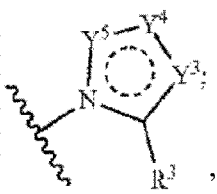 " should read -- 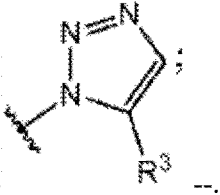 --.

Column 457
Line 37, Claim 1, "$R^{1lb}$" should read -- $R^{11b}$ --; and
Line 60, Claim 1, after "—$SR^a$," insert -- and --.

Signed and Sealed this  
Twelfth Day of July, 2022

Katherine Kelly Vidal  
*Director of the United States Patent and Trademark Office*